US012215100B2

(12) United States Patent
Martín López et al.

(10) Patent No.: US 12,215,100 B2
(45) Date of Patent: Feb. 4, 2025

(54) ANTICANCER COMPOUNDS

(71) Applicant: Pharma Mar, S.A., Madrid (ES)

(72) Inventors: María Jesús Martín López, Madrid (ES); Raquel Rodríguez Acebes, Madrid (ES); Patricia Gema Cruz López, Madrid (ES); Andrés M. Francesch Solloso, Madrid (ES); Maria del Carmen Cuevas Marchante, Madrid (ES)

(73) Assignee: PHARMA MAR, S.A., Madrid (ES)

( * ) Notice: Subject to any disclaimer, the term of this patent is extended or adjusted under 35 U.S.C. 154(b) by 757 days.

(21) Appl. No.: 17/414,946

(22) PCT Filed: Dec. 17, 2019

(86) PCT No.: PCT/EP2019/085544

§ 371 (c)(1),
(2) Date: Jun. 16, 2021

(87) PCT Pub. No.: WO2020/127194

PCT Pub. Date: Jun. 25, 2020

(65) Prior Publication Data

US 2022/0056021 A1 Feb. 24, 2022

(30) Foreign Application Priority Data

Dec. 17, 2018 (EP) .................................... 18382934

(51) Int. Cl.

| | |
|---|---|
| ***C07D 417/12*** | (2006.01) |
| ***C07D 417/14*** | (2006.01) |
| ***C07D 493/14*** | (2006.01) |
| ***C07H 15/26*** | (2006.01) |

(52) U.S. Cl.

CPC ......... *C07D 417/12* (2013.01); *C07D 417/14* (2013.01); *C07D 493/14* (2013.01); *C07H 15/26* (2013.01)

(58) Field of Classification Search

None

See application file for complete search history.

(56) References Cited

FOREIGN PATENT DOCUMENTS

| | | |
|---|---|---|
| WO | WO 2002/066046 | 8/2002 |
| WO | WO 2005/014537 | 2/2005 |
| WO | WO2009054983 | 4/2009 |
| WO | WO 2010/137351 | 12/2010 |

OTHER PUBLICATIONS

Boyd and Paull, "Some Practical Considerations and Applications of the National Cancer Institute In Vitro Anticancer Drug Discovery Screen", Drug Dev. Res. 1995, 34, 91-109.

Deng, L. et al. "Synthesis of 4-methylumbelliferyl α-d-mannopyranosyl-(1-→ 6)-β-d-mannopyranoside and development of a coupled fluorescent assay for GH125 exo-α-1, 6-mannosidases",Bioorg. Med. Chem. 2013, 21, 4839-4845.

Reber J et al., "Total Synthesis of Pyrophen and Campyrones A-C",. Nat. Prod. 2018, 81(2), 292-297.

Singh, S., Asymmetric synthesis of (R)- and (S)-α-methylcysteine, Recent Res. Devel. Organic Chem. 2004, 8, 323-339.

Singh et al. "Efficient Asymmetric Synthesis of (S)- and(R)-N-Fmoc-S-Trityl-α-methylcysteine Using Camphorsultam as a Chiral Auxiliary", J. Org. Chem.2004, 69, 4551-4554.

Umezawa et al., "Total Synthesis of Streptomycin", J. of Antibiotics 1974, 27, 997-999.

Vichai, et al. "Sulforhodamine B colorimetric assay for cytotoxicity screening", Nature Protoc. 2006, 1, 1112-1116.

Yamaguchi, et al. "A New Antibiotic, Althiomycin", J. of Antibiotics 1957, vol. 10, No. 5, 195-200.

Yamada, T. et al. "Establishment of a Human Pancreatic Adenocarcinoma Cell Line (PSN-1) with Amplifications of Both c-myc and Activated c-Ki-ras by a Point Mutation", Biochem. & Biophys. Res. Commun. 1986, vol. 140, No. 1, 167-173.

Astuti et al. "Pyrophen Produced by Endophytic Fungi *Aspergillus* sp Isolated from Piper crocatum Ruiz & Pav Exhibits Cytotoxic Activity and Induces S Phase Arrest in T47D Breast Cancer Cells", Asian Pacific Journal of Cancer Prevention, 17(2), pp. 615-618, 2016.

Office Action for Columbian Patent Application No. NC2021/0009339 dated Nov. 23, 2022.

Reber, Keith P., and Hannah E. Burdge. "Total synthesis of pyrophen and campyrones A-C." Journal of natural products 81.2 (2018): 292-297.

Pessolano, A. A., et al. "Novel nucleophilic substitution of alkyl bromo-2 (1H)-pyridones." Journal of heterocyclic chemistry 22.2 (1985): 265-272.

Registry(STN)[online], CAS Registry No. 2171482-38-3, Jan. 30, 2018, [Search Date: Nov. 15, 2023].

Registry(STN)[online], CAS Registry No. 2091625-99-7, Apr. 18, 2017, [Search Date: Nov. 15, 2023].

Registry(STN)[online], CAS Registry No. 1213526-02-3, Mar. 23, 2010, [Search Date: Nov. 15, 2023].

Registry(STN)[online], CAS Registry No. 1213491-46-3, Mar. 23, 2010, [Search Date: Nov. 15, 2023].

Registry(STN)[online], CAS Registry No. 1259813-57-4, Jan. 19, 2011, [Search Date: Nov. 15, 2023].

Registry(STN)[online], CAS Registry No. 1259809-62-5, Jan. 19, 2011, [Search Date: Nov. 15, 2023].

Japanese Office Action for Application No. 2021-534773 mailed Dec. 18, 2023.

*Primary Examiner* — Patrick T Lewis

(74) *Attorney, Agent, or Firm* — Ballard Spahr LLP

(57) ABSTRACT

Anticancer compounds of formula (I) and derivatives thereof are provided.

(I)

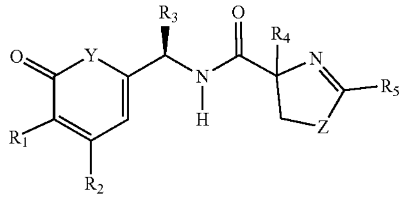

28 Claims, No Drawings

ANTICANCER COMPOUNDS

The present invention relates to new anticancer compounds, their use as anticancer agents, their pharmaceutical compositions and methods for their synthesis.

BACKGROUND OF THE INVENTION

In 1957 Yamaguchi et al. reported the isolation of althiomycin from a *Streptomyces* assigned to *Streptomyces althioticus, n.* sp (Yamaguchi, H et al. J. of Antibiotics A, 1957, 10, 195-200). This paper also disclosed its antibiotic activity against both gram positive and gram negative bacteria.

Its structure was elucidated in 1974 by Umezawa et al. (J. of Antibiotics 1974, 27, 897-899).

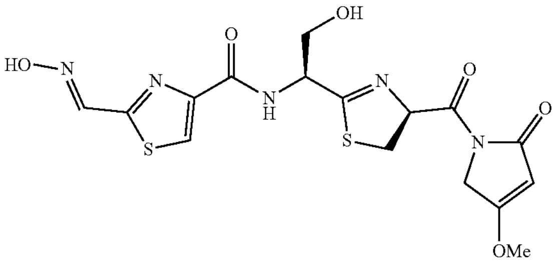

althiomycin

The cytotoxic activity of althiomycin against several gastric and liver cancer cell lines was described in international patent application publication WO2002066046. In particular althiomycin had $IC_{50}$ values in the micro molar range against gastric cancer cell lines SNU-638, SNU-216 and AGS (0.77 μM, 0.77 μM and 0.85 μM, respectively) and against liver cancer cell lines HepG2, Hep3B and SK-HEP-1 (1.43 μM, 0.88 μM and 0.81 μM, respectively).

International patent application publication WO2010137351 discloses compounds A-D, which have blocking activities of T-type calcium channels or voltage sodium channels as the tetrodotoxin-sensitive (TTX-S) blockers such as $Nav_{1.3}$ and $Nav_{1.7}$ with $IC_{50}$ values in the micro molar range. This patent application also discloses the use of these compounds in the treatment of several diseases, including cancer.

A

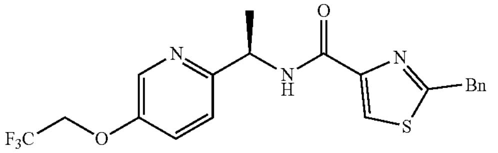

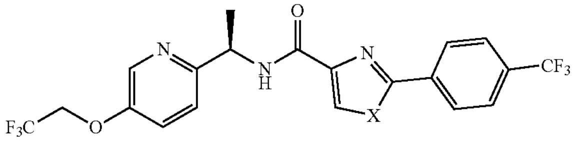

B X=O
C X=S

-continued

D

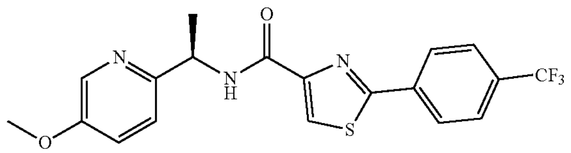

International patent application publication WO2005014537 discloses compounds of general formula:

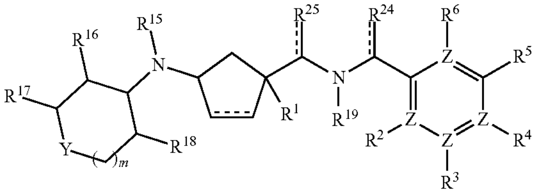

or

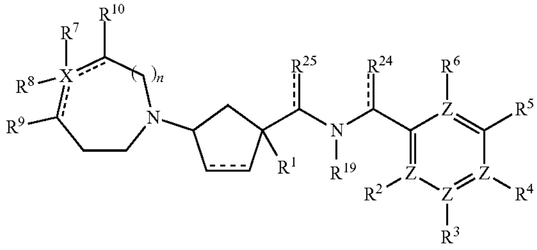

wherein $R^1$-$R^{10}$, $R^{15}$-$R^{19}$, $R^{24}$-$R^{25}$, X, Y, Z, m and n take several meanings;

which are modulators of chemokine receptor activity and their use in the prevention or treatment of inflammatory and immunoregulatory disorders and diseases.

Since cancer is a leading cause of death in animals and humans, efforts have been and continue to be undertaken in order to obtain further anticancer therapies which are both active and safe to be administered to patients suffering from cancer.

SUMMARY OF THE INVENTION

In a first aspect, the present invention is directed to a compound of formula I or a pharmaceutically acceptable salt or ester thereof

I

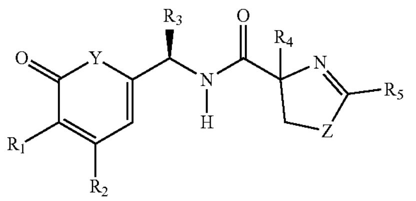

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, —$OSO_2R_b$, —$NR_cR_d$, —$NR_c$(C═O)$R_f$, and —$NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br, and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from —$C(OR_e)_2R_g$, —$C(SR_e)_2R_g$, —$CH(OR_a)R_g$, —CH(O—(C═O)$R_f$)$R_g$, —$CH(NR_cR_d)R_g$, —CH($NR_c$—(C═O)$R_f$)$R_g$, —CH($NR_c$—$OR_h$)$R_g$, —(C═O)$R_g$, —(C═$NR_c$)$R_g$, —(C═N—$OR_h$)$R_g$, —(C═N—O—(C═O)$R_f$)$R_g$, —(C═N—O—(C═O)$OR_a$)$R_g$, —(C═N—O—[(P═O)$(OR_a)_2$])$R_g$, —(C═N—$NR_cR_d$)$R_g$, —(C═O)$OR_a$, —(C═O)$NR_c$—$OR_h$, —(C═O)$NR_cR_d$, —(C═$CH_2$)$R_g$, and —(C═$CH_2$)$OR_a$; or $R_5$ is a

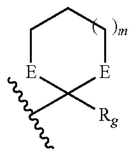

group where m is 0, 1 or 2 and each E group is independently selected from O and S;

Y and Z are independently selected from —O—, —S—, —(NH)—, and —(NProt$^{NH}$)-, where Prot$^{NH}$ is a protecting group for amino;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, —$CH_2O(CH_2CH_2O)_pCH_3$ wherein p is from 1 to about 25 and the optional substituents are one or more substituents $R_x$, and a group of formula:

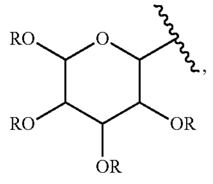

, or

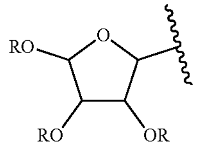

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$ wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $OSO_2OR_y$, $SSR_y$, P(═O)($R_y$)$OR_z$, OP(═O)$(OR_y)_2$, $NR_yR_z$, $NR_y$C(═O)$R_z$, $NR_y$C(═O)$OR_z$, $NR_y$C(═O)$NR_yR_z$, $NR_y$C(═$NR_y$)$NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_y$C(═$NR_y$)$NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings, and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s).

In a further aspect, the present invention is directed to a compound of formula I or a pharmaceutically acceptable salt or ester thereof

I

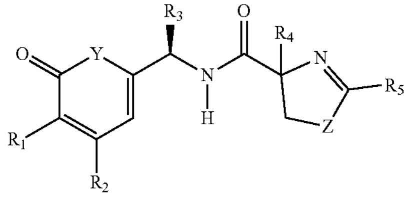

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, —$OSO_2R_b$, —$NR_cR_d$, —$NR_c$(C═O)$R_f$, and —$NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$cycloalkyl-$C_1$-$C_{12}$ alkyl, wherein the optional substituents are one or more substituents $R_x$ and the halogen substituents are one or more substituents independently selected from F, Cl, Br, and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from —$C(OR_e)_2R_g$, —$C(SR_e)_2R_g$, —CH$(OR_a)R_g$, —CH(O—(C═O)$R_f$)$R_g$, —CH($NR_cR_d$)$R_g$, —CH($NR_c$—(C═O)$R_f$)$R_g$, —CH($NR_c$—$OR_h$)$R_g$, —(C═O)$R_g$, —(C═$NR_c$)$R_g$, —(C═N—$OR_h$)$R_g$, —(C═N—O—(C═O)$R_f$)$R_g$, —(C═N—$NR_cR_d$)$R_g$, —(C═O)$OR_a$, —(C═O)$NR_c$—$OR_h$, and —(C═O)$NR_cR_d$; or $R_5$ is a

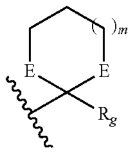

group where m is 0, 1 or 2 and each E group is independently selected from O and S;

Y and Z are independently selected from —O—, —S—, —(NH)—, and —(NProt$^{NH}$)-, where Prot$^{NH}$ is a protecting group for amino;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$ and —$CH_2O(CH_2CH_2O)_pCH_3$ wherein p is from 1 to about 25 and the optional substituents are one or more substituents $R_x$;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$ wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, $S(=O)R_y$, $SO_2R_y$, $SSR_y$, $P(=O)(R_y)OR_z$, $NR_yR_z$, $NR_yCOR_z$, $NR_yC(=O)NR_yR_z$, $NR_yC(=NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC(=NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings, and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s).

In a further aspect of the present invention, there is provided a pharmaceutical composition comprising a compound according to the present invention, or a pharmaceutically acceptable salt or ester thereof, and a pharmaceutically acceptable carrier.

In a yet further aspect of the present invention, there is provided a dosage form comprising a pharmaceutical composition according to the present invention.

In a yet further aspect of the present invention, there is provided a compound, pharmaceutical composition or dosage form according to the present invention for use as a medicament.

In a yet further aspect of the present invention, there is provided a compound, pharmaceutical composition or dosage form according to the present invention for use in the treatment of cancer.

In a yet further aspect of the present invention, there is provided the use of a compound, pharmaceutical composition or dosage form according to the present invention for the manufacture of a medicament, preferably for the treatment of cancer.

In a yet further aspect of the present invention, there is provided a method for the prevention or treatment of cancer, comprising administering an effective amount of a compound according to the present invention, administering an effective amount of a pharmaceutical composition according to the present invention, or administering an effective amount of a dosage form according to the present invention to a patient in need thereof, notably a human.

In a yet further aspect of the present invention, there is provided the use of a compound according to the present invention for the treatment of cancer.

In a yet further aspect of the present invention, there is provided a kit comprising a therapeutically effective amount of a compound according to the present invention and a pharmaceutically acceptable carrier. The kit is preferably for use in the treatment of cancer.

In a yet further aspect of the present invention, there is provided a process for obtaining compounds of formula I or a pharmaceutically acceptable salt or ester thereof, comprising the coupling of a compound of formula II with a compound of formula III in accordance to Scheme I:

Scheme I

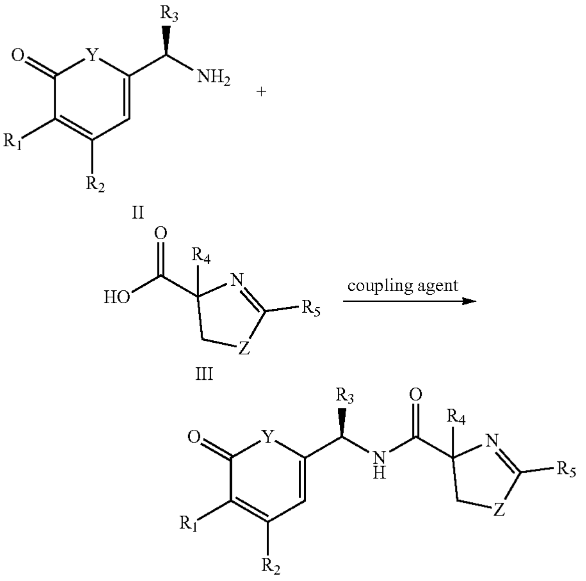

II

III

I wherein $R_1$, $R_2$, $R_3$, $R_4$, $R_5$, Y, and Z are as defined in the compound of formula I or an appropriately protected group as needed.

In a yet further aspect of the present invention, there is provided the use of intermediate compounds of formula II or a salt thereof:

II

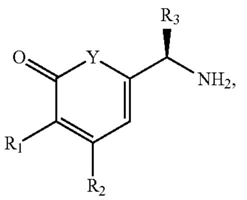

wherein $R_1$, $R_2$, $R_3$, and Y are as defined for compounds of formula I, or an appropriately protected group as needed, in the manufacture of compounds of formula I as defined herein or a pharmaceutically acceptable salt or ester thereof.

In a yet further aspect of the present invention, there are provided intermediate compounds of formula IIa:

IIa

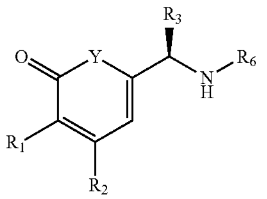

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, —$OSO_2R_b$, —$NR_cR_d$, —$NR_c$(C═O)$R_f$, and —$NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl, and substituted or unsubstituted $C_3$-$C_6$cycloalkyl-$C_1$-$C_{12}$ alkyl, wherein the optional substituents are one or more substituents $R_x$ and the halogen substituents are one or more substituents independently selected from F, Cl, Br, and I;

$R_6$ is selected from hydrogen and a carbamate protecting group for amino;

Y is selected from —O—, —S—, —(NH)—, and —(NProt$^{NH}$)-, where Prot$^{NH}$ is a protecting group for amino, with the proviso that when $R_2$ is hydrogen, then Y is selected from —O— and —S—;

$R_a$ is selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

$R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, and —$CH_2O(CH_2CH_2O)_pCH_3$ wherein p is from 1 to about 25, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $OSO_2OR_y$, $SSR_y$, P(═O)($R_y$)$OR_z$, OP(═O)$(OR_y)_2$, $NR_yR_z$, $NR_y$C(═O)$R_z$, $NR_y$C(═O)$OR_z$, $NR_y$C(═O)$NR_yR_z$, $NR_y$C(═$NR_y$)$NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_y$C(═$NR_y$)$NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

or a salt thereof.

In a yet further aspect of the present invention, there is provided the use of intermediate compounds of formula IIc or a salt thereof:

IIc

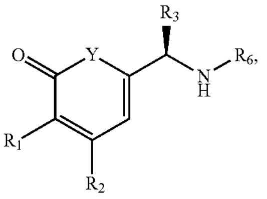

wherein $R_1$, $R_2$, $R_3$, and Y are as defined for compounds of formula I, or an appropriately protected group as needed, and $R_6$ is selected from hydrogen and a carbamate protecting group for amino, in the manufacture of compounds of formula I as defined herein or a pharmaceutically acceptable salt or ester thereof.

In a yet further aspect of the present invention, there is provided the use of intermediate compounds of formula III or a salt thereof:

III

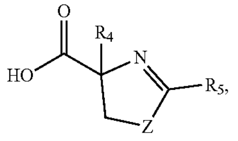

wherein $R_4$, $R_5$, and Z are as defined for the compounds of formula I, or an appropriately protected group as needed, in the manufacture of compounds of formula I as defined herein or a pharmaceutically acceptable salt or ester thereof.

In a yet further aspect of the present invention, there are provided intermediate compounds of formula IIIa:

IIIa

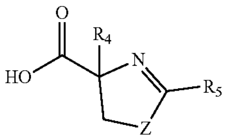

wherein $R_4$ is selected from unsubstituted $C_1$-$C_{12}$ alkyl, unsubstituted $C_2$-$C_{12}$ alkenyl and unsubstituted $C_2$-$C_{12}$ alkynyl;

$R_5$ is selected from —$C(OR_e)_2R_g$, —$C(SR_e)_2R_g$, —$CH(OR_a)R_g$, —CH(O—(C═O)$R_f$)$R_g$, —CH($NR_c$—(C═O)$R_f$)$R_g$, —CH($NR_c$—$OR_h$)$R_g$, —(C═O)$R_g$, —(C═$NR_c$)$R_g$, —(C═N—$OR_h$)$R_g$, —(C═N—O—(C═O)$R_f$)$R_g$, —(C═N—O—(C═O)$OR_a$)$R_g$, —(C═N—O—[(P═O)$(OR_a)_2$])$R_g$, —(C═N—$NR_cR_d$)$R_g$, —(C═O)$OR_a$, —(C═O)$NR_c$—$OR_h$, —(C═O)$NR_cR_d$, —(C═$CH_2$)$R_g$, and —(C═$CH_2$)$OR_a$; or $R_5$ is a

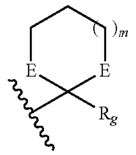

group where m is 0, 1, or 2 and each E group is independently selected from O and S;

Z is selected from —O—, —S—, —(NH)—, and —($NProt^{NH}$)-, where $Prot^{NH}$ is a protecting group for amino;

each group $R_a$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, —$CH_2O(CH_2CH_2O)_pCH_3$ wherein p is from 1 to about 25 and the optional substituents are one or more substituents $R_x$, and a group of formula:

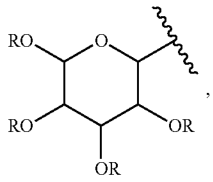

, or

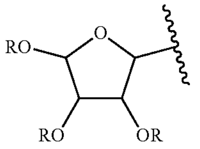

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$, wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $OSO_2OR_y$, $SSR_y$, P(═O)($R_y$)$OR_z$, OP(═O)$(OR_y)_2$, $NR_yR_z$, $NR_y$C(═O)$R_z$, $NR_y$C(═O)$OR_z$, $NR_y$C(═O)$NR_yR_z$, $NR_y$C(═$NR_y$)$NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC(=NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s); or a salt thereof.

In a yet further aspect of the present invention, it is provided the isolation of compound 1 from a sponge of the order Lithistida, family Theonellidae, genus *Discodermia* (du Bocage 1869), and the formation of derivatives from the isolated compound.

In a yet further aspect of the present invention, there is provided purified compound 1.

In a yet further aspect of the present invention, there is provided isolated compound 1.

In a yet further aspect of the present invention, there is provided compound 1 at a purity of above about 80%, above about 90%, above about 95%, above about 98%, above about 99%, above about 99.5% or above about 99.9%.

In a yet further aspect of the present invention, there is provided compound 1 in amorphous form.

In a yet further aspect of the present invention, there is provided compound 1 in crystalline form.

In a further aspect, there is provided a composition comprising compound 1 in crystalline form. In a yet further embodiment, the composition may comprise compound 1 in at least 30% crystalline form, in at least 50% crystalline form, in at least 75% crystalline form, in at least 90% crystalline form, in at least 95% crystalline form, in at least 99% crystalline form, or in about 100% crystalline form.

In a yet further aspect of the present invention, there is provided a pharmaceutically acceptable salt or ester of compound 1.

In a yet further aspect of the present invention, there is provided a solvate of compound 1, for example a hydrate.

In a yet further aspect of the present invention, there is provided a stable composition of compound 1.

In a yet further aspect of the present invention, there is provided a solid pharmaceutical composition (including a tablet, pill, capsule, or granule) or a liquid composition (including a solution, suspension or emulsion) of compound 1 or a pharmaceutically acceptable salt or ester thereof.

In a yet further aspect of the present invention there is provided a pharmaceutical composition adapted for oral, topical or parenteral administration of compound 1 or a pharmaceutically acceptable salt or ester thereof.

DETAILED DESCRIPTION OF PREFERRED EMBODIMENTS

The following embodiments apply to all aspects of the present invention.

In the compounds defined by a Markush formula in this specification, the groups can be selected in accordance with the following guidance:

Alkyl groups may be branched or unbranched, and preferably have from 1 to about 24 carbon atoms. One preferred class of alkyl groups has from 1 to about 12 carbon atoms. One more preferred class of alkyl groups has from 1 to about 8 carbon atoms or from 1 to about 6 carbon atoms. Even more preferred are alkyl groups having 1, 2, 3 or 4 carbon atoms. Methyl, ethyl, n-propyl, isopropyl, n-butyl, t-butyl, sec-butyl and isobutyl are particularly preferred alkyl groups in the compounds of the present invention. As used herein, the term alkyl, unless otherwise stated, refers to both cyclic and noncyclic groups, although cyclic groups will comprise at least three carbon ring members.

Cycloalkylalkyl groups are non-cyclic alkyl groups substituted with a cycloalkyl group. A preferred class of cycloalkylalkyl group has a cycloalkyl moiety with from 3 to about 6 carbon ring atoms and an alkyl moiety with from 1 to about 12 carbon atoms. One more preferred class of cycloalkylalkyl groups has a cycloalkyl moiety with from 3 to about 4 carbon ring atoms and an alkyl moiety with from 1 to about 6 carbon atoms. Cyclopropylmethyl is a particularly preferred cycloalkyl group in the compounds of the present invention.

Preferred alkenyl and alkynyl groups in the compounds of the present invention may be branched or unbranched, have one or more unsaturated linkages and from 2 to about 12 carbon atoms. One more preferred class of alkenyl and alkynyl groups has from 2 to about 8 carbon atoms or from 2 to about 6 carbon atoms. Even more preferred are alkenyl and alkynyl groups having 2, 3 or 4 carbon atoms. The terms alkenyl and alkynyl as used herein refer to both cyclic and noncyclic groups, although cyclic groups will comprise at least three carbon ring members.

Suitable aryl groups in the compounds of the present invention include single and multiple ring compounds, including multiple ring compounds that contain separate and/or fused aryl groups. Typical aryl groups contain from 1 to 3 separated and/or fused rings and from 6 to about 18 carbon ring atoms. Preferably aryl groups contain from 6 to about 14 carbon ring atoms. Specially preferred aryl groups include substituted or unsubstituted phenyl, substituted or unsubstituted naphthyl, substituted or unsubstituted biphenyl, substituted or unsubstituted phenanthryl and substituted or unsubstituted anthryl. The most preferred aryl group is substituted or unsubstituted phenyl.

Suitable heterocyclic groups may be saturated or unsaturated and include heteroaromatic and heteroalicyclic groups, the latter of which may be partially unsaturated, both the aromatic and the alicyclic heterocyclic groups containing from 1 to 3 separated and/or fused rings and from 5 to about 18 ring atoms. Preferably heteroaromatic and heteroalicyclic groups contain from 5 to about 10 ring atoms, more preferably 5, 6 or 7 ring atoms. Suitable heteroaromatic groups in the compounds of the present invention contain one, two or three heteroatoms selected from N, O or S atoms and include, e.g., coumarinyl including 8-coumarinyl, quinolyl including 8-quinolyl, isoquinolyl, pyridyl, pyrazinyl, pyrazolyl, pyrimidinyl, furyl, pyrrolyl, thienyl, thiazolyl, isothiazolyl, triazolyl, tetrazolyl, isoxazolyl, oxazolyl, imidazolyl, indolyl, isoindolyl, indazolyl, indolizinyl, phthalazinyl, pteridinyl, purinyl, oxadiazolyl, thiadiazolyl, furazanyl, pyridazinyl, triazinyl, cinnolinyl, benzimidazolyl, benzofuranyl, benzofurazanyl, benzothiophenyl, benzothiazolyl, benzoxazolyl, quinazolinyl, quinoxalinyl, naphthyridinyl and furopyridyl. Suitable heteroalicyclic groups in the compounds of the present invention contain one, two or three heteroatoms selected from N, O or S atoms and include, e.g., pyrrolidinyl, tetrahydrofuranyl, dihydrofuranyl, tetrahydrothienyl, tetrahydrothiopyranyl, piperidyl, morpholinyl, thiomorpholinyl, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, and quinolizinyl.

Heterocycloalkyl groups are non-cyclic alkyl groups substituted with a heterocyclic group. A preferred class of heterocycloalkyl group has a heterocyclic moiety with from 5 to about 10 ring atoms and 1 or 2 heteroatoms independently selected from O, N and S, and an alkyl moiety with from 1 to about 6 carbon atoms. One more preferred class of cycloalkylalkyl groups has a heterocyclic moiety with from 5 to 6 ring atoms and 1 or 2 heteroatoms independently selected from O and N and an alkyl moiety with from 1 to about 6 carbon atoms. Even more preferred are substituted or unsubstituted morpholino-$C_3$-$C_5$ alkyl and substituted or unsubstituted piperazinyl-$C_3$-$C_5$alkyl. [4$\lambda^2$-morpholine]-$(CH_2)_4$— and [1-methyl-4$\lambda^2$-piperazine]-$(CH_2)_3$ are most preferred heterocycloalkyl groups in the compounds of the present invention.

Suitable monosaccharides include aldoses, a saccharide bearing an aldehyde functional group at the terminal position, and more particularly an aldohexose, a saccharide with 6 carbon atoms, or an aldopentose, a saccharide with 5 carbon atoms, preferably an aldohexose. It will thus be in particular allose, altrose, glucose, mannose, gulose, idose, galactose, talose, ribose, arabinose, xylose or lyxose, in D or L form. The monosaccharide will be preferably in a cyclized form, in particular in a pyranose form, a 6-member ring, or in a furanose form, a 5 member ring. In these cases, the aldehyde functional group borne by the saccharide is in a hemiacetal form, also called a pseudoaldehyde functional group. It is particular preferred the piranose form.

By “monosaccharide residue” is meant, in the context of the present invention, the part of the monosaccharide, as defined above, that is connected to the rest of the molecule via its carbon atom 1 following a condensation reaction between the aldehyde, or pseudoaldehyde, functional group of the monosaccharide and a hydroxy (OH) functional group.

Suitable halogen groups or substituents in the compounds of the present invention include F, Cl, Br and I. Fluorine is the most preferred halogen group in the compounds of the present invention.

The term halogen-substituted group refer to a group substituted with one or more halogen atoms at one or more suitable positions, wherein the halogen atoms at each halogen-substituted group may be the same or different.

The terms “pharmaceutically acceptable salt” and “ester” refers to any pharmaceutically acceptable salt or ester which, upon administration to the patient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts can be carried out by methods known in the art.

For instance, pharmaceutically acceptable salts of compounds provided herein are synthesized from the parent compound, which contains a basic or acidic moiety, by conventional chemical methods. Generally, such salts are, for example, prepared by reacting the free acid or base forms of these compounds with a stoichiometric amount of the appropriate base or acid in water or in an organic solvent or in a mixture of both. Generally, nonaqueous media like ether, ethyl acetate, ethanol, 2-propanol or acetonitrile are preferred. Examples of the acid addition salts include mineral acid addition salts such as, for example, hydrochloride, hydrobromide, hydroiodide, sulfate, nitrate, phosphate, and organic acid addition salts such as, for example, acetate, trifluoroacetate, maleate, fumarate, citrate, oxalate, succinate, tartrate, malate, mandelate, methanesulfonate and p-toluenesulfonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine and basic aminoacids salts.

The compounds of the invention may be in amorphous form or in crystalline form either as free compounds or as solvates (e.g. hydrates) and it is intended that all forms are within the scope of the present invention. Methods of solvation are generally known within the art.

Stereoisomerism about the asymmetric carbons with unspecified stereochemistry is possible, therefore in such cases the asymmetric carbon can have (R) or (S) configuration. All diastereomers generated by a specific configuration of such asymmetric carbons in conjunction with the other asymmetric carbons present in the molecule, and mixtures thereof, are considered within the scope of the present invention. Stereoisomerism about the double bond (geometric isomerism) is also possible, therefore in some cases the molecule could exist as (E)-isomer or (Z)-isomer. If the molecule contains several double bonds, each double bond will have its own stereoisomerism, that could be the same or different than the stereoisomerism of the other double bonds of the molecule. Furthermore, compounds referred to herein may exist as atropoisomers. The single stereoisomers including diastereoisomers, geometric isomers and atropoisomers of the compounds referred to herein, and mixtures thereof fall within the scope of the present invention.

In addition, compounds referred to herein may exist in isotopically-labelled forms. All pharmaceutically acceptable salts, esters and isotopically labelled forms of the compounds referred to herein, and mixtures thereof, are considered within the scope of the present invention.

Protected forms of the compounds disclosed herein are considered within the scope of the present invention. Suitable protecting groups are well known for the skilled person in the art. A general review of protecting groups in organic chemistry is provided by Wuts, P. G. M. and Greene T. W. in Protecting Groups in Organic Synthesis, $4^{th}$ Ed. Wiley-Interscience, and by Kocienski P. J. in Protecting Groups, $3^{rd}$ Ed. Georg Thieme Verlag. These references provide sections on protecting groups for OH and amino groups. All these references are incorporated by reference in their entirety.

Within the scope of the present invention a protecting group for OH is defined to be the O-bonded moiety resulting from the protection of the OH group through the formation of a suitable protected OH group. Examples of such protected OH groups include ethers, silyl ethers, esters, sulfonates, sulfenates and sulfinates, carbonates, and carbamates. In the case of ethers the protecting group for the OH can be selected from methyl, methoxymethyl, methylthiomethyl, (phenyldimethylsilyl)methoxymethyl, benzyloxymethyl, p-methoxybenzyloxymethyl, [(3,4-dimethoxybenzyl)oxy]methyl, p-nitrobenzyloxymethyl, o-nitrobenzyloxymethyl, [(R)-1-(2-nitrophenyl)ethoxy] methyl, (4-methoxy-phenoxy)methyl, guaiacolmethyl, [(p-phenylphenyl)oxy]methyl, t-butoxy-methyl, 4-pentenyloxymethyl, siloxymethyl, 2-methoxyethoxymethyl, 2-cyanoethoxymethyl, bis(2-chloroethoxy)methyl, 2,2,2-trichloroethoxymethyl, 2-(trimethyl-silyl)ethoxymethyl, menthoxymethyl, O-bis(2-acetoxyethoxy)methyl, tetrahydropyranyl, fluorous tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxy-tetrahydrothiopyranyl S,S-dioxide, 1-[(2-chloro-4-methyl)-phenyl]-4-methoxypiperidin-4-yl, 1-(2-fluorophenyl)-4-methoxypiperidin-4-yl, 1-(4-chlorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 2-hydroxyethyl, 2-bromoethyl, 1-[2-(trimethylsilyl)ethoxy]ethyl, 1-methyl-1-methoxyethyl, 1-methyl-1-benzyloxyethyl, 1-methyl-1-benzyloxy-2-fluoroethyl, 1-methyl-1-phenoxyethyl, 2,2,2-trichloroethyl, 1,1-dianisyl-2,2,2-trichloroethyl, 1,1,1,3,3,3-hexafluoro-2-phenylisopropyl, 1-(2-cyanoethoxy)ethyl, 2-trimethylsilylethyl, 2-(benzylthio)ethyl, 2-phenylselenyl) ethyl, t-butyl, cyclohexyl, 1-methyl-1'-cyclopropylmethyl, allyl, prenyl, cinnamyl, 2-phenallyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, p-methoxybenzyl, 3,4-dimethoxybenzyl, 2,6-dimethoxybenzyl, o-nitrobenzyl, p-nitrobenzyl, pentadienylnitrobenzyl, pentadienyl-nitropiperonyl, halobenzyl, 2,6-dichlorobenzyl, 2,4-dichlorobenzyl, 2,6-difluorobenzyl, p-cyanobenzyl, fluorous benzyl, 4-fluorousalkoxybenzyl, trimethylsilylxylyl, p-phenylbenzyl, 2-phenyl-2-propyl, p-acylaminobenzyl, p-azidobenzyl, 4-azido-3-chlorobenzyl, 2-trifluoromethylbenzyl, 4-trifluoromethylbenzyl, p-(methylsulfinyl)benzyl, p-siletanylbenzyl, 4-acetoxybenzyl, 4-(2-trimethylsilyl)ethoxymethoxybenzyl, 2-naphthylmethyl, 2-picolyl, 4-picolyl, 3-methyl-2-picolyl N-oxide, 2-quinolinylmethyl, 6-methoxy-2-(4-methylphenyl-4-quinolinemethyl, 1-pyrenylmethyl, diphenylmethyl, 4-methoxydiphenylmethyl, 4-phenyldiphenylmethyl, p,p'-dinitrobenzhydryl, 5-dibenzosuberyl, triphenylmethyl, tris(4-t-butylphenyl) methyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxy) phenyldiphenylmethyl, 4,4',4"-tris(4,5-dichlorophthalimidophenyl)methyl, 4,4',4"-tris (levulinoyloxyphenyl)methyl, 4,4',4"-tris(benzoyloxyphenyl)methyl, 4,4'-dimethoxy-3"-[N-(imidazolylmethyl)]trityl, 4,4'-dimethoxy-3"-[N-(imidazolylethyl)carbamoyl]trityl, bis(4-methoxyphenyl)-1'-pyrenylmethyl, 4-(17-tetrabenzo[a,c,g,i]fluorenylmethyl)-4, 4"-dimethoxytrityl, 9-anthryl, 9-(9-phenyl)xanthenyl, 9-phenylthioxanthyl, 9-(9-phenyl-10-oxo)anthryl, 1,3-benzodithiolan-2-yl, and 4,5-bis(ethoxycarbonyl)-[1,3]-dioxolan-2-yl, benzisothiazolyl S,S-dioxide. In the case of silyl ethers the protecting group for the OH can be selected from trimethylsilyl, triethylsilyl, triisopropylsilyl, dimethylisopropylsilyl, diethylisopropylsilyl, dimethylthexylsilyl, 2-norbornyldimethylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. In the case of esters the protecting group for the OH together with the oxygen atom of the unprotected OH group to which it is attached form an ester that can be selected from formate, benzoylformate, acetate, chloroacetate, dichloroacetate, trichloroacetate, trichloroacetamidate, trifluoroacetate, methoxyacetate, triphenylmethoxyacetate, phenoxyacetate, p-chlorophenoxyacetate, phenylacetate, diphenylacetate, 3-phenylpropionate, bisfluorous chain type propanoyl, 4-pentenoate, 4-oxopentanoate, 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate, 4-bromobenzoate, 2,5-difluorobenzoate, p-nitrobenzoate, picolinate, nicotinate, 2-(azidomethyl)benzoate, 4-azidobutyrate, (2-azidomethyl)phenylacetate, 2-{[(tritylthio)oxy] methyl}benzoate, 2-{[(4-methoxytritylthio)oxy] methyl}benzoate, 2-{[methyl(trityl-thio)amino] methyl}benzoate, 2-{{[(4-methoxytrityl)thio] methylamino}-methyl}benzoate, 2-(allyl-oxy) phenylacetate, 2-(prenyloxymethyl)benzoate, 6-(levulinyloxymethyl)-3-methoxy-2-nitrobenzoate, 6-(levulinyloxymethyl)-3-methoxy-4-nitrobenzoate, 4-benzyloxybutyrate, 4-trialkylsilyloxybutyrate, 4-acetoxy-2,2-dimethylbutyrate, 2,2-dimethyl-4-pentenoate, 2-iodobenzoate, 4-nitro-4-methylpentanoate, o-(dibromomethyl)benzoate, 2-formylbenzenesulfonate, 4-(methylthiomethoxy)butyrate, 2-(methylthiomethoxymethyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxy) ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethyl-phosphorodiamidate, and 2-chlorobenzoate. In the case of sulfonates, sulfenates and sulfinates the protecting group for the OH together with the oxygen atom of the unprotected OH group to which it is attached form a group that can be selected from sulfate, allylsulfonate, methanesulfonate, benzylsulfonate, tosylate, 2-[(4-nitrophenyl)ethyl]sulfonate, 2-trifluoromethylbenzenesulfonate, 4-monomethoxytritylsulfenate, alkyl 2,4-dinitrophenylsulfenate, and 2,2,5,5-tetramethylpyrrolidin-3-one-1-sulfinate. In the case of carbonates the protecting group for the OH together with the oxygen atom of the unprotected OH group to which it is attached from a carbonate group that can be selected from methyl carbonate, methoxymethyl carbonate, 9-fluorenylmethyl carbonate, ethyl carbonate, bromoethyl carbonate, 2-(methylthiomethoxy)ethyl carbonate, 2,2,2-trichloroethyl carbonate, 1,1-dimethyl-2,2,2-trichloroethyl carbonate, 2-(trimethylsilyl)ethyl carbonate, 2-[dimethyl(2-naphthylmethyl)silyl] ethyl carbonate, 2-(phenylsulfonyl) ethyl carbonate, 2-(triphenylphosphonio)ethyl carbonate, cis-[4-[[(methoxytrityl) sulfenyl]oxy]-tetrahydrofuran-3-yl]oxy carbonate, isobutyl carbonate, t-butyl carbonate, vinyl carbonate, allyl carbonate, cinnamyl carbonate, propargyl carbonate, p-chlorophenyl carbonate, p-nitrophenyl carbonate, 4-ethoxy-1-naphthyl carbonate, 6-bromo-7-hydroxycoumarin-4-ylmethyl carbonate, benzyl carbonate, o-nitrobenzyl carbonate, p-nitrobenzyl carbonate, p-methoxybenzyl carbonate, 3,4-dimethoxybenzyl carbonate, anthraquinon-2-ylmethyl carbonate, 2-dansylethyl carbonate, 2-(4-nitrophenyl)ethyl carbonate, 2-(2,4-dinitrophenyl)ethyl carbonate, 2-(2-nitrophenyl)propyl carbonate, alkyl 2-(3,4-methylenedioxy-6-nitrophenyl) propyl carbonate, 2-cyano-1-phenylethyl carbonate, 2-(2-pyridyl)amino-1-phenylethyl carbonate, 2-[N-methyl-N-(2-pyridyl)]amino-1-phenylethyl carbonate, phenacyl carbonate, 3',5'-dimethoxybenzoin carbonate, methyl dithiocarbonate, and S-benzyl thiocarbonate. And in the case of carbamates the protecting group for the OH together with the oxygen atom of the unprotected OH group to which it is attached form a carbamate that can be selected from dimethylthiocarbamate, N-phenylcarbamate, N-methyl-N-(o-nitrophenyl)carbamate.

Within the scope of the present invention an amino protecting group is defined to be the N-bonded moiety resulting from the protection of the amino group through the formation of a suitable protected amino group. Examples of such protected amino groups include carbamates, ureas, amides, heterocyclic systems, N-alkyl amines, N-alkenyl amines, N-alkynyl amines, N-aryl amines, imines, enamines, N-metal derivatives, N—N derivatives, N—P derivatives, N—Si derivatives, and N—S derivatives. In the case of carbamates the protecting group for the amino group together with the nitrogen atom of the unprotected amino group to which it is attached form a carbamate that can be selected from methylcarbamate, ethylcarbamate, 9-fluorenylmethylcarbamate, 2,6-di-t-butyl-9-fluorenylmethylcarbamate, 2,7-bis(trimethylsilyl)fluorenylmethylcarbamate, 9-(2-sulfo)fluorenylmethylcarbamate, 9-(2,7-dibromo)fluorenylmethylcarbamate, 17-tetrabenzo[a,c,g,i]fluorenylmethylcarbamate, 2-chloro-3-indenylmethylcarbamate, benz[f]inden-3-ylmethylcarbamate, 1,1-dioxobenzo[b]-thiophene-2-ylmethylcarbamate, 2-methylsulfonyl-3-phenyl-1-prop-2-enylcarbamate, 2,7-di-t-butyl-[9-(10,10-dioxo-10,10,10,10-tetrahydrothioxanthyl)]methylcarbamate, 2,2,2-trichloroethylcarbamate, 2-trimethylsilylethylcarbamate, (2-phenyl-2-trimethylsilyl)ethylcarbamate, 2-phenylethylcarbamate, 2-chloroethylcarbamate, 1,1-dimethyl-2-haloethylcarbamate, 1,1-dimethyl-2,2-dibromoethylcarbamate, 1,1-dimethyl-2,2,2-trichloroethylcarbamate, 2-(2'-pyridyl)ethylcarbamate, 2-(4'-pyridyl)ethylcarbamate, 2,2-bis(4'-nitrophenyl)ethylcarbamate, 2-[(2-nitrophenyl)dithio]-1-phenylethylcarbamate, 2-(N,N-dicyclohexylcarboxamido)ethylcarbamate, t-butylcarbamate, $C_8F_{19}CH_2CH_2C(CH_3)_2$-carbamate, 1-adamantylcarbamate, 2-adamantylcarbamate, 1-(1-adamantyl)-1-methylethylcarbamate, 1-methyl-1-(4-byphenylyl)ethylcarbamate, 1-(3,5-di-t-butylphenyl)-1-methylethylcarbamate, triisopropyl-silylcarbamate, vinylcarbamate, allylcarbamate, prenylcarbamate, 1-isopropylallylcarbamate, cinnamylcarbamate, 4-nitrocinnamylcarbamate, 3-(3'-pyridyl)prop-2-enylcarbamate, hexadienylcarbamate, propargylcarbamate, but-2-ynylbiscarbamate, 8-quinolylcarbamate, N-hydroxypiperidinylcarbamate, alkyldithiocarbamate, benzylcarbamate, 3,5-di-t-butylbenzylcarbamate, p-methoxybenzylcarbamate, p-nitrobenzylcarbamate, p-bromobenzylcarbamate, p-chlorobenzylcarbamate, 2,4-dichlorobenzylcarbamate, 4-methylsulfinylbenzylcarbamate, 4-trifluoromethylbenzylcarbamate, $C_8F_{17}CH_2CH_2—C_6H_4—CH_2$-carbamate, $(C_8F_{17}CH_2CH_2)_3Si—C_6H_4—CH_2$-carbamate, 2-naphthylmethylcarbamate, 9-anthrylmethylcarbamate, diphenylmethylcarbamate, 4-phenylacetoxybenzylcarbamate, 4-azidobenzylcarbamate, 4-azido-methoxybenzylcarbamate, m-chloro-p-acyloxybenzylcarbamate, p-(dihydroxyboryl)benzylcarbamate, 5-benzisoxazolylmethylcarbamate, 2-(trifluoromethyl)-6-chromonylmethylcarbamate, 2-methylthioethylcarbamate, 2-methylsulfonylethylcarbamate, 2-(p-toluenesulfonyl)ethylcarbamate, 2-(4-nitrophenylsulfonyl)ethylcarbamate, 2-(2,4-dinitrophenylsulfonyl)ethylcarbamate, 2-(4-trifluoromethylphenylsulfonyl)ethylcarbamate, [2-(1,3-dithianyl)]methylcarbamate, 2-phosphonioethylcarbamate, 2-[phenyl(methyl)sulfonio]ethylcarbamate, 1-methyl-2-(triphenylphosphonio)ethylcarbamate, 1,1-dimethyl-2-cyanoethylcarbamate, 2-dansylethylcarbamate, 2-(4-nitrophenyl)ethylcarbamate, 4-methylthiophenylcarbamate, 2,4-dimethylthiophenylcarbamate, m-nitrophenylcarbamate, 3,5-dimethoxybenzylcarbamate, 1-methyl-1-(3,5-dimethoxyphenyl)ethylcarbamate, α-methylnitropiperonylcarbamate, o-nitrobenzylcarbamate, 3,4-dimethoxy-6-nitrobenzylcarbamate, phenyl(o-nitrophenyl)methylcarbamate, 2-nitrophenylethylcarbamate, 6-nitroveratrylcarbamate, 4-methoxyphenacylcarbamate, 3',5'-dimethoxybenzoincarbamate, 9-xanthenylmethylcarbamate, t-amylcarbamate, 1-methylcyclobutylcarbamate, 1-methylcyclohexylcarbamate, 1-methyl-1-cyclopropylmethylcarbamate, cyclobutylcarbamate, cyclopentylcarbamate, cyclohexylcarbamate, isobutylcarbamate, isobornylcarbamate, cyclopropylmethylcarbamate, p-decyloxybenzylcarbamate, diisopropylmethylcarbamate, 2,2-dimethoxycarbonylvinylcarbamate, o-(N,N-dimethylcarboxamido)benzylcarbamate, 1,1-dimethyl-3-(N,N-dimethylcarboxamido)propylcarbamate, butynylcarbamate, 1,1-dimethylpropynylcarbamate, 2-iodoethylcarbamate, 1-methyl-1-(4'-pyridyl)ethylcarbamate, 1-methyl-1-(p-phenylazophenyl)ethylcarbamate, p-(p-methoxyphenylazo)benzylcarbamate, p-(phenylazo)benzylcarbamate, 2,4,6-trimethylbenzylcarbamate, isonicotinylcarbamate, 4-(trimethylammonium)benzylcarbamate, p-cyanobenzylcarbamate, di(2-pyridyl)methylcarbamate, 2-furanylmethylcarbamate, phenylcarbamate, 2,4,6-tri-t-butylphenylcarbamate, 1-methyl-1-phenylethylcarbamate, and S-benzyl thiocarbamate. In the case of ureas the protecting groups for the amino group can be selected from phenothiazinyl-(10)-carbonyl, N'-p-toluenesulfonylaminocarbonyl, N'-phenylaminothiocarbonyl, 4-hydroxyphenylaminocarbonyl, 3-hydroxytryptaminocarbonyl, and N'-phenyl-aminothiocarbonyl. In the case of amides the protecting group for the amino group together with the nitrogen atom of the unprotected amino group to which it is attached form an amide group that can be selected from formamide, acetamide, chloroacetamide, trichloroacetamide, trifluoroacetamide, phenylacetamide, 3-phenylpropanamide, pent-4-enamide, picolinamide, 3-pyridylcarboxamide, N-benzoylphenylalanyl, benzamide, p-phenylbenzamide, o-nitrophenylacetamide, 2,2-dimethyl-2-(o-nitrophenyl)acetamide, o-nitrophenoxyacetamide, 3-(o-nitrophenyl)propanamide, 2-methyl-2-(o-nitrophenoxy)-propanamide, 3-methyl-3-nitrobutanamide, o-nitrocinnamide, o-nitrobenzamide, 3-(4-t-butyl-2,6-dinitrophenyl)-2,2-dimethylpropanamide, o-benzoyloxymethyl)benzamide, 2-(acetoxymethyl)benzamide, 2-[(t-butyldiphenylsiloxy)methyl]benzamide, 3-(3',6'-dioxo-2',4',5'-trimethylcyclohexa-1',4'-diene)-3,3-dimethylpropionamide, o-hydroxy-trans-cinnamide, 2-methyl-2-(o-phenylazophenoxy)propanamide, 4-chlorobutanamide, acetoacetamide, 3-(p-hydroxyphenyl)propanamide, (N'-dithiobenzyloxycarbonylamino)acetamide, and N-acetylmethionine amide. In the case of heterocyclic systems the protecting group for the amino group together with the nitrogen group of the unprotected amino group to which it is attached form a heterocyclic system that can be selected from 4,5-diphenyl-3-oxazolin-2-one, N-phthalimide, N-dichlorophthalimide, N-tetrachlorophthalimide, N-4-nitrophthalimide, N-thiodiglycoloyl, N-dithiasuccinimide, N-2,3-diphenylmaleimide, N-2,3-dimethylmaleimide, N-2,5-dimethylpyrrole, N-2,5-bis(triisopropylsiloxy)pyrrole, N-1,1,4,4-tetramethyldisilylazacyclopentane adduct, N-1,1,3,3-tetramethyl-1,3-disilaisoindoline, N-diphenylsilyldiethylene, N-5-substituted-1,3-dimethyl-1,3,5-triazacyclohexan-2-one, N-5-substituted-1,3-benzyl-1,3,5-triazacyclohexan-2-one, 1-substituted 3,5-dinitro-4-pyridone, and 1,3,5-dioxazine. In the case of N-alkyl, N-alkenyl, N-alkynyl or N-aryl amines the protecting group for the amino group can be selected from N-methyl, N-t-butyl, N-allyl, N-prenyl, N-cinnamyl, N-phenylallyl, N-propargyl, N-methoxymethyl, N-[2-(trimethylsilyl)ethoxy]methyl, N-3-acetoxypropyl, N-cyanomethyl, N-2-azanorbornenes, N-2,4-dinitrophenyl, o-methoxyphenyl, p-methoxyphenyl, N-benzyl, N-4-methoxybenzyl, N-2,4-dimethoxybenzyl, N-2-hydroxybenzyl, N-9-phenylfluorenyl, N-fluorenyl, N-ferrocenylmethyl, N-2-picolylamine N'-Oxide, N-7-methoxycoumar-4-ylmethyl, N-diphenylmethyl, N-bis(4-methoxyphenyl)methyl, N-5-dibenzosuberyl, N-triphenylmethyl, N-(4-methylphenyl)diphenylmethyl, and N-(4-methoxyphenyl)diphenylmethyl. In the case of imines the protecting group for the amino group can be selected from N-1,1-dimethylthiomethylene, N-benzylidene, N-p-methoxybenzylidene, N-diphenylmethylene, N-[2-pyridyl)mesityl]methylene, N—(N',N'-dimethylaminomethylene), N—(N',N'-dibenzylaminomethylene), N—(N'-t-butylaminomethylene), N',N'-isopropylidene, N-p-nitrobenzylidene, N-salicylidene, N-5-chlorosalicylidene, N-(5-chloro-2-hydroxyphenyl)phenylmethylene, N-cyclohexylidene, and N-t-butylidene. In the case of enamines the protecting group for the amino group can be selected from N-(5,5-dimethyl-3-oxo-1-cyclohexenyl), N-2,7-dichloro-9-fluorenylmethylene, N-1-(4,4-dimethyl-2,6-dioxocyclohexylidene)ethyl, N-(1,3-dimethyl-2,4,6-(1H,3H,5H)-trioxopyrimidine-5-ylidene)methyl, N-4,4,4-trifluoro-3-oxo-1-butenyl, and N-(1-isopropyl-4-nitro-2-oxo-3-pyrrolin-3-yl). In the case of N-metal derivatives the protecting group for the amino group together with the nitrogen atom of the unprotected amino group form a derivative that can be selected from N-borane derivative, N-diphenylborinic acid derivative, N-diethylborinic acid derivative, N-9-borabicyclononane derivative, N-difluoroborinic acid derivative, and 3,5-bis(trifluoromethyl)phenylboronic acid derivative; and also including N-[phenyl(pentacarbonylchromium)]carbenyl, N-[phenyl (pentacarbonyltungsten)]carbenyl, N-[methyl (pentacarbonylchromium)]carbenyl, N-[methyl (pentacarbonyltungsten)]carbenyl, N-copper chelate, N-zinc chelate, and a 18-crown-6-derivative. In the case of N—N derivatives the protecting group for the amino group together with the nitrogen atom of the unprotected amino group to which it is attached form a derivative that can be selected from N-nitro derivative, N-nitroso derivative, N-oxide derivative, azide derivative, triazene derivative, and N-trimethylsilylmethyl-N-benzylhydrazine derivative. In the case of N—P derivatives the protecting group for the amino group together with the nitrogen group of the unprotected amino group to which it is attached form a N—P derivative that can be selected from N-diphenylphosphinamide, dimethylthiophosphinamide, diphenylthiophosphinamide, dialkyl phosphoramidate, dibenzyl phosphoramidate, diphenyl phosphoramidate, and iminotriphenylphosphorane. In the case of N—Si derivatives the protecting group for the amino group can be selected from t-butyldiphenylsilyl and triphenylsilyl. In the case of N—S derivatives the protecting group for the amino group together with the nitrogen atom of the unprotected amino group to which it is attached from a N—S derivative that can be selected from N-sulfenyl or N-sulfonyl derivatives. The N-sulfenyl derivatives can be selected from benzenesulfenamide, 2-nitrobenzenesulfenamide, 2,4-dinitrobenzenesulfenamide, pentachlorobenzenesulfenamide, 2-nitro-4-methoxybenzenesulfenamide, triphenylmethylsulfenamide, 1-(2,2,2)-trifluoro-1,1-diphenyl)ethylsulfenamide, and N-3-nitro-2-pyridinesulfenamide. The N-sulfonyl derivatives can be selected from methanesulfonamide, trifluoromethanesulfonamide, t-butylsulfonamide, benzylsulfonamide, 2-(trimethylsilyl)ethanesulfonamide, p-toluenesulfonamide, benzenesulfonamide, o-anisylsulfonamide, 2-nitrobenzenesulfonamide, 4-nitrobenzenesulfonamide, 2,4-dinitrobenzenesulfonamide, 2-naphthalenesulfonamide, 4-(4',8'-dimethoxynaphthylmethyl)benzenesulfonamide, 2-(4-methylphenyl)-6-methoxy-4-methylsulfonamide, 9-anthracenesulfonamide, pyridine-2-sulfonamide, benzothiazole-2-sulfonamide, phenacylsulfonamide, 2,3,6-trimethyl-4-methoxybenzenesulfonamide, 2,4,6-trimethoxybenzenesulfonamide, 2,6-dimethyl-4-methoxybenzenesulfonamide, pentamethylbenzenesulfonamide, 2,3,5,6-tetramethyl-4-methoxybenzenesulfonamide, 4-methoxybenzenesulfonamide, 2,4,6-trimethylbenzenesulfonamide, 2,6-dimethoxy-4-methylbenzenesulfonamide, 3-methoxy-4-t-butylbenzenesulfonamide, and 2,2,5,7,8-pentamethylchroman-6-sulfonamide.

The mention of these groups should not be interpreted as a limitation of the scope of the invention, since they have been mentioned as a mere illustration of protecting groups for OH and amino, but further groups having said function may be known by the skill person in the art, and they are to be understood to be also encompassed by the present invention.

Suitable coupling agents are well known for the skilled person in the art. Examples of coupling agents are N,N'-dicyclohexylcarbodiimide (DCC), N-(3-dimethylaminopropyl)-N'-ethylcarbodiimide (EDC) and its salts, 1-[3-(dimethylamino)propyl]-3-ethylcarbodiimide methiodide (EDC methiodide), N,N'-diisopropylcarbodiimide, 1-t-butyl-3-ethyl carbodiimide, N-cyclohexyl-N'-(2-morpholinoethyl) carbodiimide metho-p-toluenesulfonate (CMC), N,N'-d-t-butylcarbodiimide, 1,3-Di-p-tolylcarbodiimide, 1,1'-carbonyldiimidazole (CDI), 1,1'-carbonyl-di-(1,2,4-triazole) (CDT), oxalic acid diimidazolide, 2-chloro-1,3-dimethylimidazolidinium chloride (DMC), 2-chloro-1,3-dimethylimidazolidinium tetrafluoroborate (CIB), 2-chloro-1,3-dimethylimidazolidinium hexafluorophosphate (CIP), 2-fluoro-1,3-dimethylimidazolidinium hexafluorophosphate (DFIH), (benzotriazol-1-yloxy)tris(dimethylamino)phosphonium hexafluorophosphate (BOP), (benzotriazol-1-yloxy)tripyrrolidinophosphonium hexafluorophosphate, 7-azabenzotriazol-1-yloxy)tripyrrolidinophosphonium hexafluorophosphate (PyAOP), bromotris(dimethylamino)-phosphonium hexafluorophosphate (BRoP), chlorotripyrrolidinophosphonium hexafluorophosphate (PyClOP), bromotripyrrolidinophosphonium hexafluorophosphate, 3-(diethoxyphosphoryloxy)-1,2,3-benzotriazin-4(3H)-one (DEPBT), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBPyU), O-benzotriazol-1-yl-N,N,N',N'-bis(pentamethylene)uronium hexafluorophosphate (HBPipU), (benzotriazol-1-yloxy)dipiperidinocarbenium tetrafluoroborate (TBPipU), O-(6-chlorobenzotriazol-1-yl)-N,N,N',N'-tetramethyluronium hexafluorophosphate (HCTU), O-(6-chlorobenzotriazol-1-yl)-N,N,N',N'-tetramethyluronium (TCTU), O-(3,4-dihydro-4-oxo-1,2,3-benzotriazin-3-yl)-N,N,N',N'-tetramethyluronium tetrafluoroborate (TDBTU), 0-(2-oxo-1(2H)pyridyl)-N,N,N',N'-tetramethyluronium tetrafluoroborate (TPTU), O-[(ethoxycarbonyl)cyanomethylenamino]-N,N,N',N'-tetramethyluronium hexafluorophosphate (HOTU), O-[(ethoxycarbonyl)cyanomethylenamino]-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl) uronium tetrafluoroborate (TSTU), dipyrrolidino(N-succinimidyloxy)carbenium (HSPyU), and S-(1-oxido-2-pyridyl)-N,N,N',N'-tetramethylthiouronium tetrafluoroborate (TOTT).

To provide a more concise description, some of the quantitative expressions given herein are not qualified with the term "about". It is understood that, whether the term "about" is used explicitly or not, every quantity given herein is meant to refer to the actual given value, and it also meant to refer to the approximation of such given value that would reasonable be inferred based on the ordinary skill in the art, including equivalents and approximations due to experimental and/or measurement conditions for such given value.

Particularly preferred stereochemistry of said compounds of formula I is the following

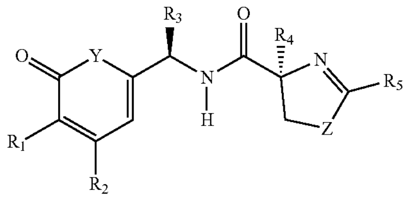

In another embodiment, particularly preferred compounds of formula I are those also having formula Ia or a pharmaceutically acceptable salt or ester thereof Ia

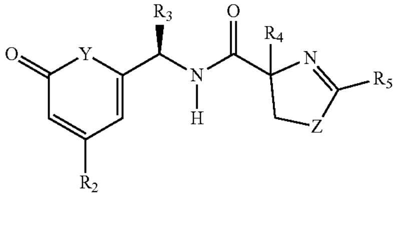

wherein $R_2$, $R_3$, $R_4$, $R_5$, Y, and Z have the same meanings given above.

Particularly preferred stereochemistry of said compounds of formula Ia is the following Ib

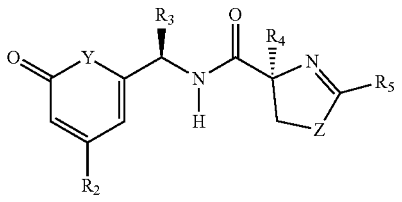

In another embodiment, the compound of formula I, Ia, or Ib is not a natural product, more preferably the compound of formula I, Ia, or Ib is not compound 1 of formula

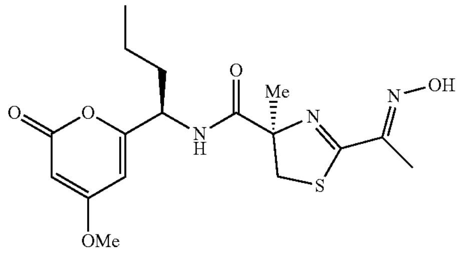 [SMILES: CCC[C@@H](NC(=O)[C@]1(C)CSC(/C(C)=N/O)=N1)c1cc(OC)cc(=O)o1]

In compounds of formula I, particularly preferred $R_1$ is selected from hydrogen, halogen and substituted or unsubstituted $C_2$-$C_6$ alkynyl, being more preferred $R_1$ hydrogen and substituted or unsubstituted $C_2$-$C_6$ alkynyl, wherein the optional substituents are one or more substituents $R_x$; being hydrogen the most preferred $R_1$ group.

In compounds of formula I, Ia and Ib, particularly preferred $R_2$ is hydrogen, substituted or unsubstituted $C_1$-$C_{24}$ alkyl, substituted or unsubstituted $C_2$-$C_{24}$ alkenyl, —$OR_a$, and —$NR_cR_d$, wherein the optional substituents are one or more substituents $R_x$; wherein $R_a$, $R_c$ and $R_d$ are defined herein. Further particularly preferred $R_2$ is hydrogen, substituted or unsubstituted $C_1$-$C_6$ alkyl, substituted or unsubstituted $C_2$-$C_6$ alkenyl, wherein the optional substituents are one or more substituents $R_x$; —$OR_a$, and —$NR_cR_d$; where $R_a$ is selected from hydrogen, a silylether protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_6$alkyl, —$(CH_2CH_2O)_pCH_2CH_3$ where p is from 1 to about 15, and the optional substituents are one or more substituents $R_x$; and $R_c$ and $R_d$ are independently selected from substituted or unsubstituted $C_1$-$C_6$ alkyl wherein the optional substituents are one or more substituents $R_x$. Particularly preferred $R_a$ is hydrogen, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_3$-$C_4$ cycloalkyl-$C_1$-$C_4$alkyl, —$(CH_2CH_2O)_pCH_2CH_3$ where p is from 1 to about 10 and the optional substituents are one or more substituents $R_x$, and a silylether protecting group for OH selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl (TBS), t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1- yl, and fluorous silyl. Particularly preferred $R_c$ and $R_d$ are independently selected from substituted or unsubstituted $C_1$-$C_4$ alkyl wherein the optional substituents are one or more substituents $R_x$. More preferred $R_2$ is hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted vinyl, substituted or unsubstituted allyl, wherein the optional substituents are one or more substituents $R_x$, —$OR_a$, and —$NR_cR_d$ where $R_a$ is selected from hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted n-heptyl, substituted or unsubstituted allyl, substituted or unsubstituted 1-methyl-2-propenyl, substituted or unsubstituted 2-methyl-2-propenyl, substituted or unsubstituted 2-butenyl, substituted or unsubstituted 3-butenyl, substituted or unsubstituted propargyl, substituted or unsubstituted 1-methyl-2-propynyl, substituted or unsubstituted 2-butynyl, substituted or unsubstituted 3-butynyl, substituted or unsubstituted cyclopropylmethyl, substituted or unsubstituted 2-cyclopropylethyl, and —$(CH_2CH_2O)_pCH_2CH_3$ wherein p is from 1 to about 5 and the optional substituents are one or more substituents $R_x$; and $R_c$ and $R_d$ are selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_2$ is hydrogen, methyl, vinyl, allyl, $NEt_2$, and $OR_a$ where $R_a$ is selected from hydrogen, methyl, ethyl, n-butyl, n-heptyl, allyl, propargyl, cyclopropylmethyl, —$(CH_2)_3$NHBoc, —$(CH_2)_3NH_2$, and —$(CH_2CH_2O)_3CH_2CH_3$.

In another embodiment, in compounds of formula I, Ia and Ib, particularly preferred $R_2$ is hydrogen, substituted or unsubstituted $C_1$-$C_{24}$ alkyl, substituted or unsubstituted $C_2$-$C_{24}$ alkenyl, —$OR_a$, and —$NR_cR_d$, wherein the optional substituents are one or more substituents $R_x$; wherein $R_a$, $R_c$ and $R_d$ are defined herein, other than when $R_2$ is —$OR_a$, $R_a$ is not unsubstituted methyl. Further particularly preferred $R_2$ is hydrogen, substituted or unsubstituted $C_1$-$C_6$ alkyl, substituted or unsubstituted $C_2$-$C_6$ alkenyl, wherein the optional substituents are one or more substituents $R_x$, —$OR_a$, and —$NR_cR_d$; where $R_a$ is selected from hydrogen, a silylether protecting group for OH, substituted $C_1$-$C_{12}$ alkyl, unsubstituted $C_2$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_6$alkyl, —$(CH_2CH_2O)_pCH_2CH_3$ where p is from 1 to about 15 and the optional substituents are one or more substituents $R_x$; and $R_c$ and $R_d$ are independently selected from substituted or unsubstituted $C_1$-$C_6$ alkyl wherein the optional substituents are one or more substituents $R_x$. Particularly preferred $R_a$ is hydrogen, substituted or unsubstituted $C_2$-$C_8$ alkyl, substituted or unsubstituted $C_2$-$C_8$ alkenyl, substituted or unsubstituted $C_2$-$C_8$ alkynyl, substituted or unsubstituted $C_3$-$C_4$ cycloalkyl-$C_1$-$C_4$alkyl, —$(CH_2CH_2O)_pCH_2CH_3$ wherein p is from 1 to about 10 and the optional substituents are one or more substituents $R_x$, and a silylether protecting group for OH selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl (TBS), t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. Particularly preferred $R_c$ and $R_d$ are independently selected from substituted or unsubstituted $C_1$-$C_4$ alkyl wherein the optional substituents are one or more substituents $R_x$. More preferred $R_2$ is hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted vinyl, substituted or unsubstituted allyl, wherein the optional substituents are one or more substituents $R_x$, —$OR_a$, and —$NR_cR_d$ where $R_a$ is selected from hydrogen, substituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted n-heptyl, substituted or unsubstituted allyl, substituted or unsubstituted 1-methyl-2-propenyl, substituted or unsubstituted 2-methyl-2-propenyl, substituted or unsubstituted 2-butenyl, substituted or unsubstituted 3-butenyl, substituted or unsubstituted propargyl, substituted or unsubstituted 1-methyl-2-propynyl, substituted or unsubstituted 2-butynyl, substituted or unsubstituted 3-butynyl, substituted or unsubstituted cyclopropylmethyl, substituted or unsubstituted 2-cyclopropylethyl, and —$(CH_2CH_2O)_pCH_2CH_3$ wherein p is from 1 to about 5 and the optional substituents are one or more substituents $R_x$; and $R_c$ and $R_d$ are selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_2$ is hydrogen, methyl, vinyl, allyl, $NEt_2$, and $OR_a$ where $R_a$ is selected from hydrogen, ethyl, n-butyl, n-heptyl, allyl, propargyl, cyclopropylmethyl, —$(CH_2)_3$NH-Boc, —$(CH_2)_3NH_2$, and —$(CH_2CH_2O)_3CH_2CH_3$.

In compounds of formula I, Ia and Ib, particularly preferred $R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I. More preferred $R_3$ is halogen-substituted or unsubstituted methyl, halogen-substituted or unsubstituted ethyl, halogen-substituted or unsubstituted n-propyl, halogen-substituted or unsubstituted isopropyl, halogen-substituted or unsubstituted n-butyl, halogen-substituted or unsubstituted t-butyl, halogen-substituted or unsubstituted isobutyl and halogen-substituted or unsubstituted sec-butyl, wherein the optional substituents are one or more substituents $R_x$ and the halogen substituents are one or more substituents independently selected from F, Cl, Br, and I. Most preferred $R_3$ is n-propyl, 3,3,3-trifluoropropyl, and isobutyl.

In compounds of formula I, Ia and Ib, particularly preferred $R_4$ is hydrogen and substituted or unsubstituted $C_1$-$C_6$ alkyl wherein the optional substituents are one or more substituents $R_x$. More preferred $R_4$ is hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_4$ is hydrogen and methyl.

In compounds of formula I, Ia and Ib, particularly preferred $R_5$ is selected from —$C(OR_e)_2R_g$, —$CH(NR_cR_d)R_g$, —$(C{=}O)R_g$, —$(C{=}NR_c)R_g$, —$(C{=}N{-}OR_h)R_g$, —$(C{=}N{-}O{-}(C{=}O)R_f)R_g$, —$(C{=}N{-}O{-}(C{=}O)OR_a)R_g$, —$(C{=}N{-}O{-}[(P{=}O)(OR_a)_2])R_g$, —$(C{=}N{-}NR_cR_d)R_g$, —$(C{=}CH_2)R_g$, and —$(C{=}CH_2)OR_a$; or $R_5$ is selected from —$CH(OR_a)R_g$, —$CH(NR_cR_d)R_g$, —$(C{=}NR_c)R_g$, —$(C{=}N{-}OR_h)R_g$, —$(C{=}N{-}NR_cR_d)R_g$; or $R_5$ is selected from —$CH(OR_a)R_g$, —$(C{=}NR_c)R_g$, —$(C{=}N{-}OR_h)R_g$;

wherein:

$R_h$ is selected from hydrogen, a protecting group for OH, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted heterocyclo-$C_1C_6$alkyl, —$(CH_2CH_2O)_p$ $CH_2CH_3$ where p is from 1 to about 15 and a substituted or unsubstituted monosaccharide residue of formula:

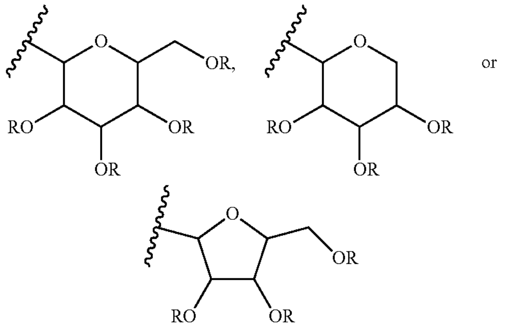

where each R group is, at each occurrence, independently selected from hydrogen, substituted or unsubstituted $C_1$-$C_6$ alkyl group, substituted or unsubstituted —(C=O)—($C_1$-$C_6$)alkyl, and substituted or unsubstituted —(C=O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

$R_g$ is substituted or unsubstituted $C_1$-$C_6$ alkyl, wherein the optional substituents are one or more substituents $R_x$;

$R_c$ and $R_d$ are independently selected from hydrogen and substituted or unsubstituted $C_1$-$C_6$ alkyl, wherein the optional substituents are one or more substituents $R_x$;

$R_a$ is substituted or unsubstituted $C_1$-$C_6$ alkyl, wherein the optional substituents are one or more substituents $R_x$;

$R_e$ is substituted or unsubstituted $C_1$-$C_6$ alkyl, wherein the optional substituents are one or more substituents $R_x$; and $R_f$ is selected from substituted or unsubstituted $C_1$-$C_6$ alkyl, —$CH_2O(CH_2CH_2O)_pCH_3$ where p is from 1 to about 15 and the optional substituents are one or more substituents $R_x$, and a group of formula:

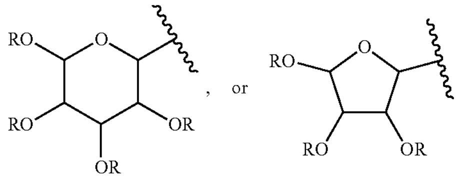

where each R group is, at each occurrence, independently selected from hydrogen, substituted or unsubstituted $C_1$-$C_6$ alkyl group, substituted or unsubstituted —(C=O)—($C_1$-$C_6$)alkyl, and substituted or unsubstituted —(C=O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals.

More preferred $R_h$ is hydrogen, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted heterocyclo-$C_1$-$C_6$alkyl, —$(CH_2CH_2O)_pCH_2CH_3$ where p is from 1 to about 10, and a substituted or unsubstituted monosaccharide residue of formula

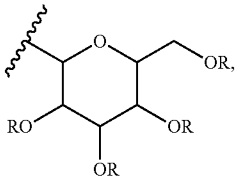

wherein each R group is, at each occurrence, independently selected from hydrogen and substituted or unsubstituted —(C=O)—($C_1$-$C_6$)alkyl; wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

More preferred $R_g$ is substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$.

More preferred $R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$.

More preferred $R_c$ and $R_d$ are independently selected from hydrogen and substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$.

More preferred $R_e$ is substituted or unsubstituted methyl, substituted or unsubstituted ethyl, substituted or n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$.

More preferred $R_f$ is substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, $—CH_2O(CH_2CH_2O)_pCH_3$ where p is from 1 to about 10 and the optional substituents are one or more substituents $R_x$, and a group of formula:

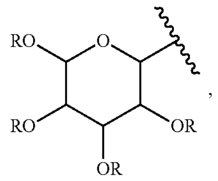

where each R group is, at each occurrence, independently selected from hydrogen, and substituted or unsubstituted $C_1$-$C_6$ alkyl group; or two adjacent OR groups form an isopropylidene ketal or an acetal group selected from methylene-, methoxymethylene-, ethoxymethylene-, ethylidene-, benzylidene-, and p-methoxybenzylidene-acetals.

More preferred $R_5$ is selected from $—CH(NR_cR_d)R_g$, $—(C{=}O)R_g$, $—(C{=}NR_c)R_g$, $—(C{=}N—OR_h)R_g$, $—(C{=}N—O—(C{=}O)R_f)R_g$, $—(C{=}N—O—(C{=}O)OR_a)R_g$, $—(C{=}N—O—[(P{=}O)(OR_a)_2])R_g$, $—(C{=}N—NR_cR_d)R_g$, $—(C{=}CH_2)R_g$, and $—(C{=}CH_2)OR_a$ wherein:

$R_h$ is selected from hydrogen, a protecting group for OH, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted heterocyclo-$C_1$-$C_6$alkyl, $—(CH_2CH_2O)_pCH_2CH_3$ where p is from 1 to about 15, and a substituted or unsubstituted monosaccharide residue of formula:

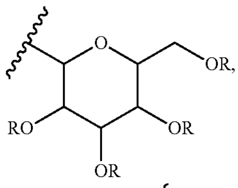

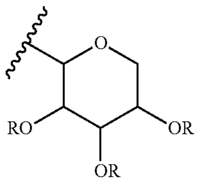

or

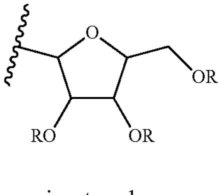

where each R group is, at each occurrence, independently selected from hydrogen, substituted or unsubstituted $C_1$-$C_6$ alkyl group, substituted or unsubstituted $—(C{=}O)—(C_1$-$C_6)$alkyl, and substituted or unsubstituted $—(C{=}O)NH(C_1$-$C_6)$alkyl; wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

$R_g$ is substituted or unsubstituted $C_1$-$C_6$ alkyl, wherein the optional substituents are one or more substituents $R_x$;

$R_a$ is substituted or unsubstituted $C_1$-$C_6$ alkyl, wherein the optional substituents are one or more substituents $R_x$;

$R_c$ and $R_d$ are independently selected from hydrogen and substituted or unsubstituted $C_1$-$C_6$ alkyl, wherein the optional substituents are one or more substituents $R_x$; and $R_f$ is selected from substituted or unsubstituted $C_1$-$C_6$ alkyl and $—CH_2O(CH_2CH_2O)_pCH_3$ where p is from 1 to about 15 and the optional substituents are one or more substituents $R_x$.

Even more preferred $R_5$ is $—CH(NR_cR_d)R_g$, $—(C{=}O)R_g$, $—(C{=}NR_c)R_g$, $—(C{=}N—OR_h)R_g$, $—(C{=}N—O—(C{=}O)R_f)R_g$, $—(C{=}N—O—(C{=}O)OR_a)R_g$, $—(C{=}N—O—[(P{=}O)(OR_a)_2])R_g$, $—(C{=}N—NR_cR_d)R_g$, $—(C{=}CH_2)R_g$, and $—(C{=}CH_2)OR_a$ wherein:

$R_h$ is selected from hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted allyl, substituted or unsubstituted propargyl, substituted or unsubstituted morpholino-n-butyl, substituted or unsubstituted piperazinyl-n-propyl, $—(CH_2CH_2O)_pCH_2CH_3$ where p is from 1 to about 5, and a substituted or unsubstituted monosaccharide residue of formula:

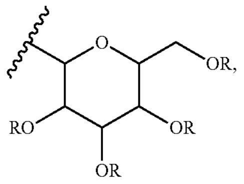

wherein each R group is, at each occurrence, independently selected from hydrogen and substituted or unsubstituted $—(C{=}O)—(C_1$-$C_6)$alkyl; wherein the optional substituents are one or more substituents $R_x$; or two adjacent OR groups may form an isopropylidene ketal;

each $R_g$ group is independently selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$;

$R_a$ is selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$;

$R_c$ and $R_d$ are independently selected from hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$; and $R_f$ is substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, $—CH_2O(CH_2CH_2O)_pCH_3$ where p is from 1 to about 5 and the optional substituents are one or more substituents $R_x$ and a group of formula:

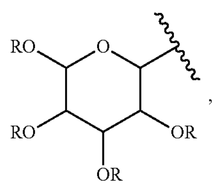

, where each R group is, at each occurrence, hydrogen or two adjacent OR groups form an isopropylidene ketal.

Most preferred $R_5$ is $—CH(NH_2)Me$, —(C═O)Me, $—(C═NR_c)Me$, $—(C═N—OR_h)Me$, $—(C═N—O(C═O)R_f)Me$, $—(C═N—NH_2)Me$, $—(C═N—O—(C═O)OR_a)Me$, $—(C═N—O—[(P═O)(OR_a)_2])Me$, $—(C═CH_2)Me$, or $—(C═CH_2)OR_a$ where $R_a$ is ethyl or benzyl, $R_c$ is $—(CH_2)_3NHBoc$, $R_f$ is $—(CH_2)_5—NHBoc$, $—CH_2O(CH_2CH_2O)_2Me$ or a group of formula:

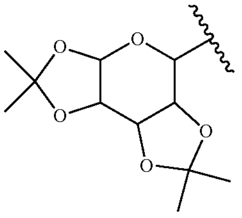

, and $R_h$ is selected from hydrogen, methyl, allyl, propargyl, $—(CH_2)_3NHBoc$, $—(CH_2)_3NH_2$, $—(CH_2)_3SH$, $—(CH_2)_4OH$, $—(CH_2)_4OP(═O)(OH)_2$, $—(CH_2)_4OP(═O)(O^{t}\cdot BU)_2$, $—(CH_2)_4\text{-}[4\lambda^2\text{-morpholine}]$, $—(CH_2)_3\text{-}[1\text{-methyl-}4\lambda^2\text{-piperazine}]$, $—(CH_2CH_2O)_3CH_2CH_3$, and a monosaccharide residue of formula:

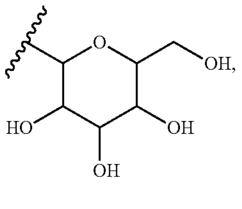

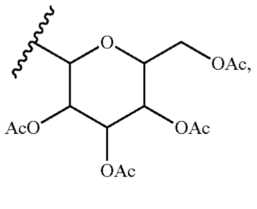

-continued

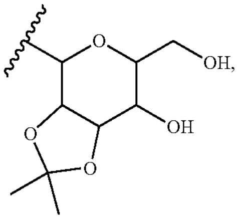

or

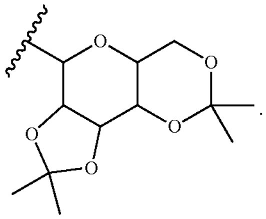

In compounds of formula I, Ia, and Ib particularly preferred Y is —O— or —NH—. Most preferred Y is —O—.

In compounds of formula I, Ia, and Ib particularly preferred Z is —S— or —O—. Most preferred Z is —S—.

In additional preferred embodiments, the preferences described above for the different substituents are combined. The present invention is also directed to such combinations of preferred substitutions in the formula I, Ia or Ib above.

Particularly preferred compounds of formula I, Ia or Ib are compounds:

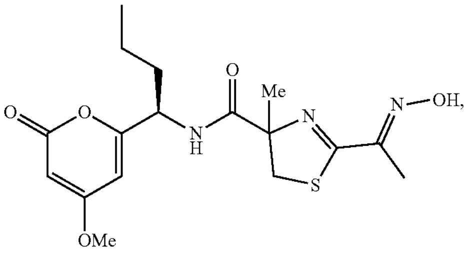

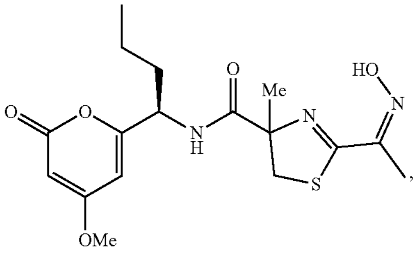

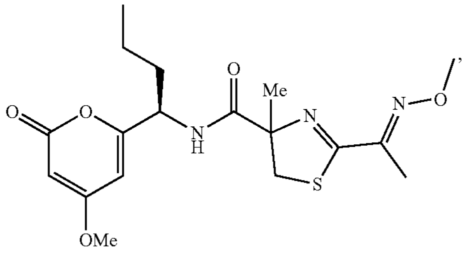

-continued
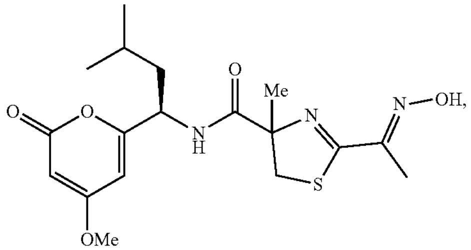
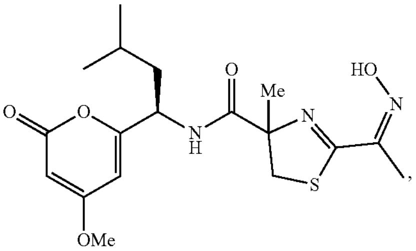
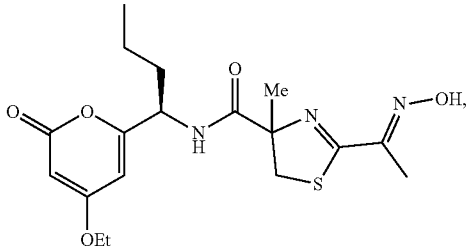
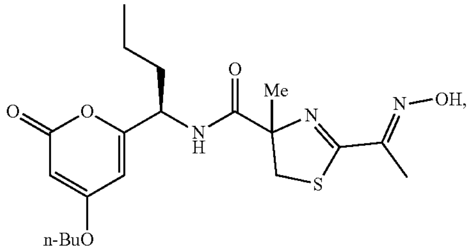
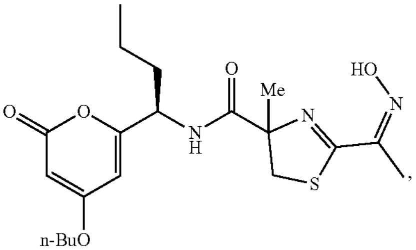
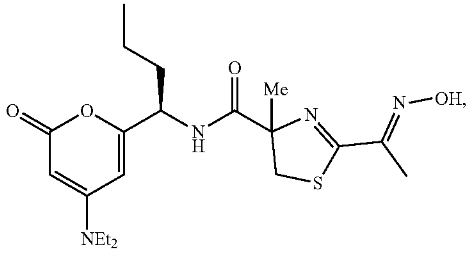
-continued
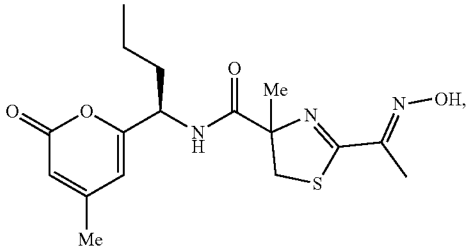
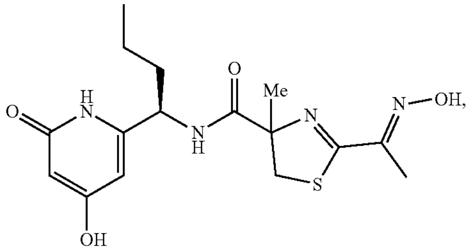
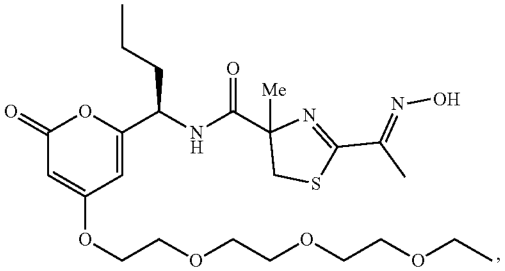
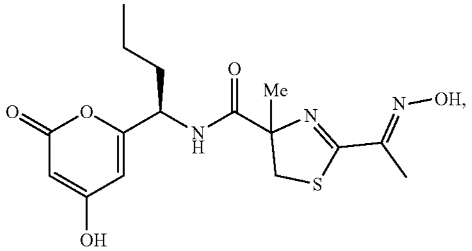
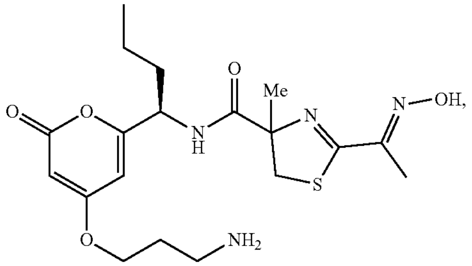
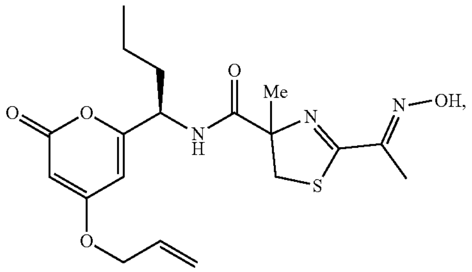

-continued
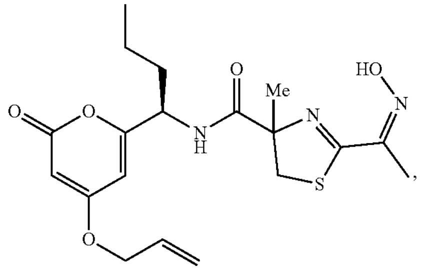
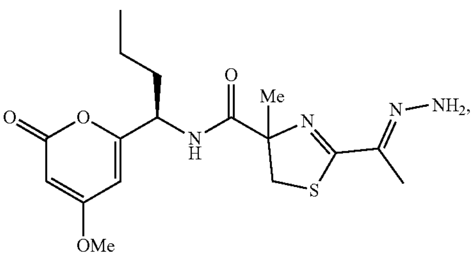
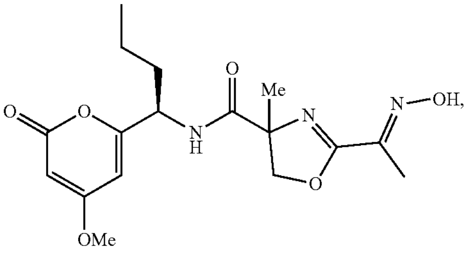
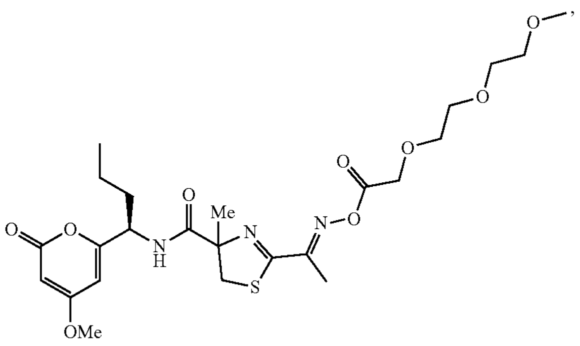
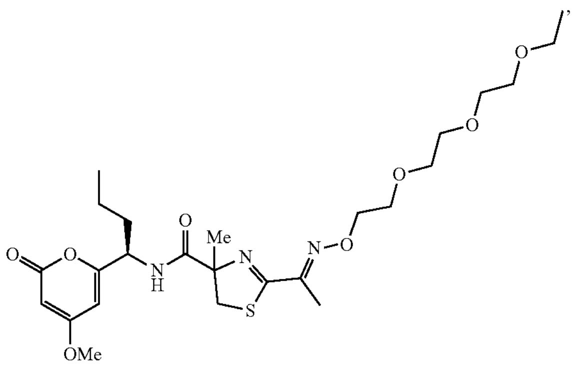
-continued
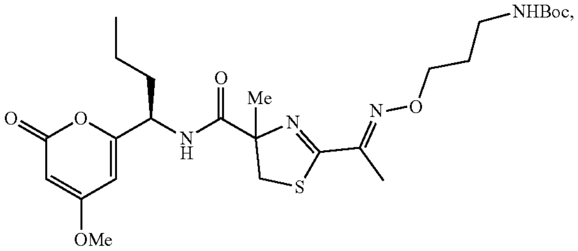
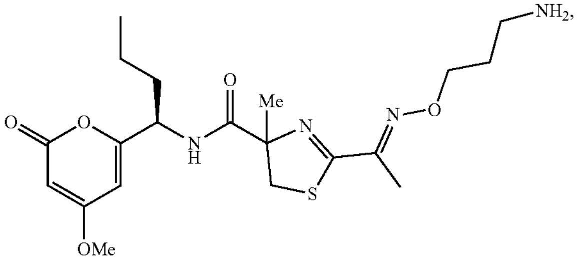
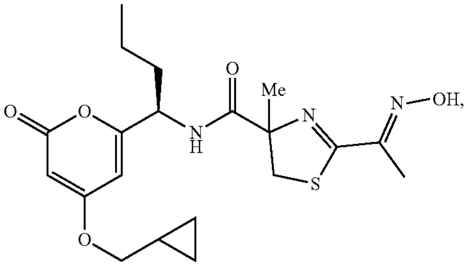
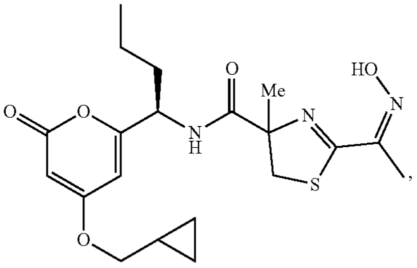
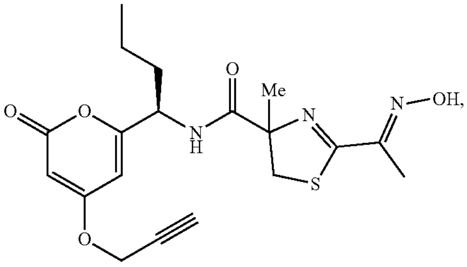
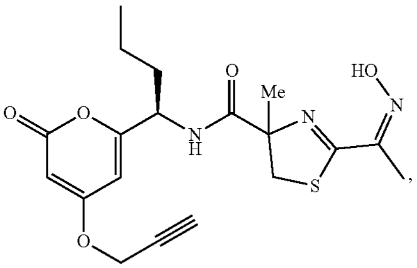

-continued
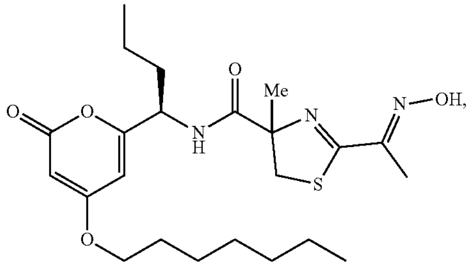
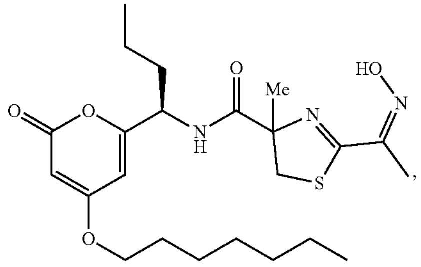
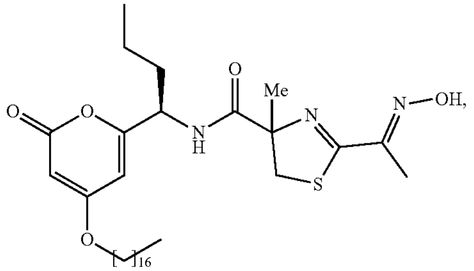
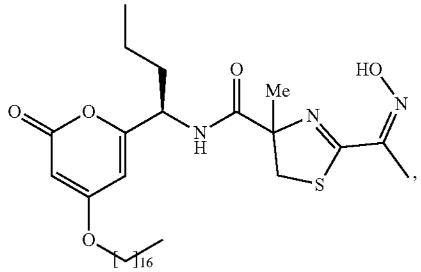
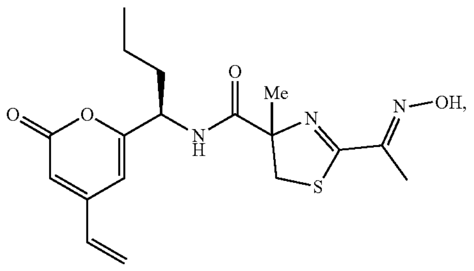
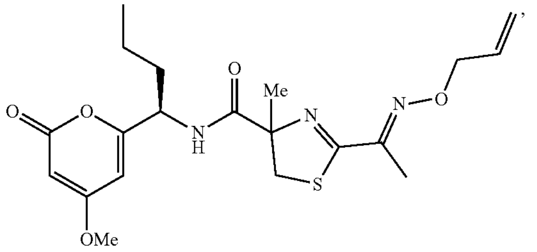
-continued
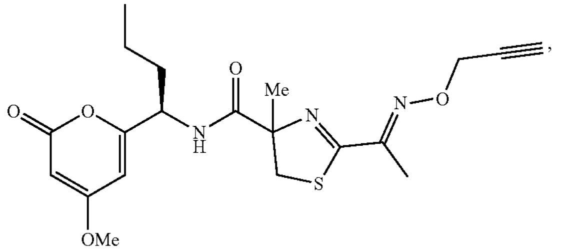
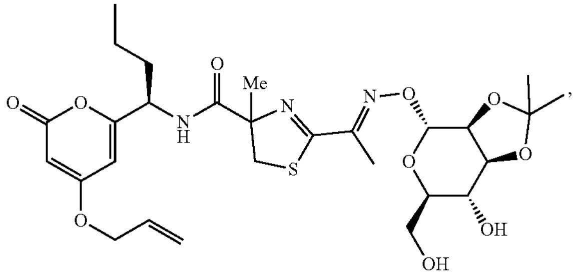
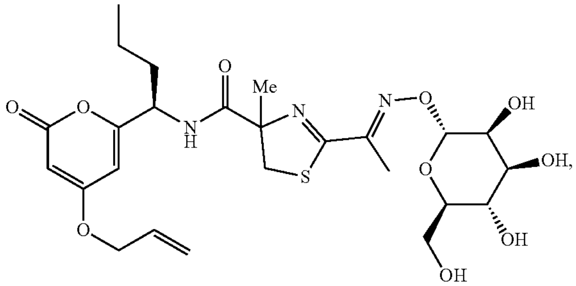
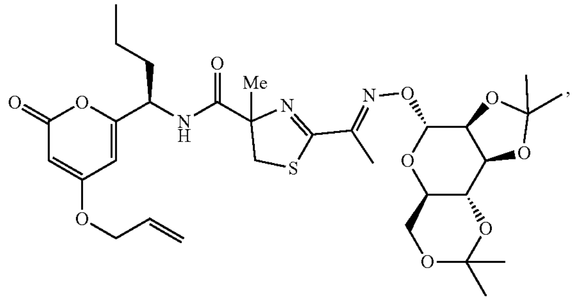
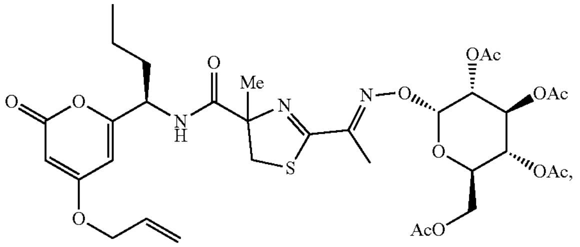
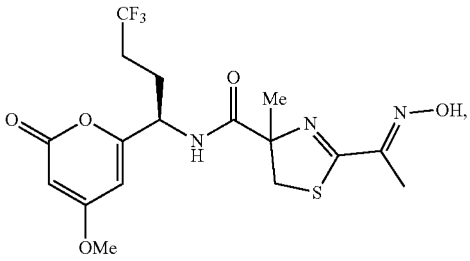

-continued
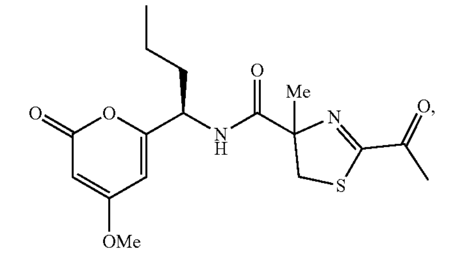
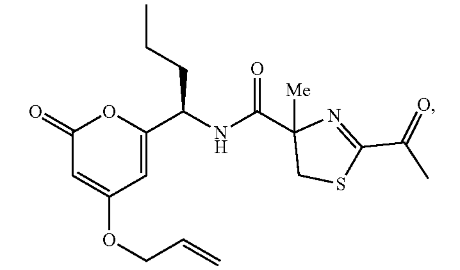
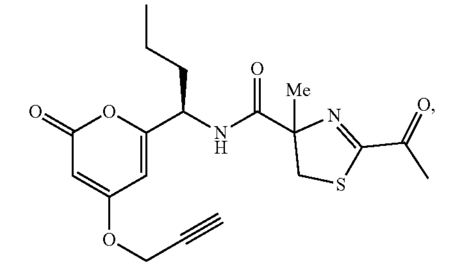
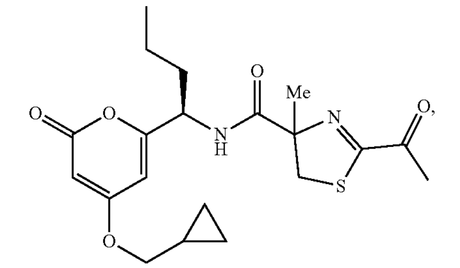
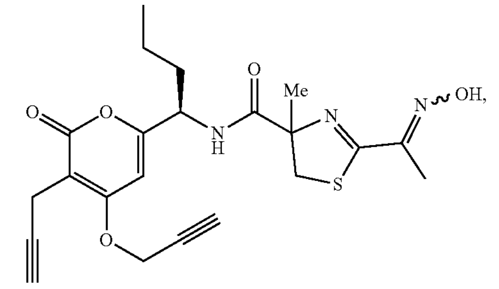
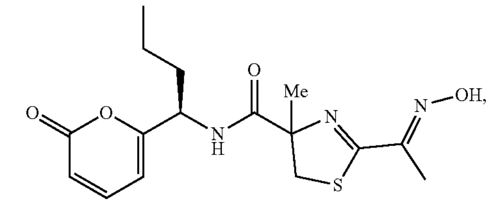
-continued
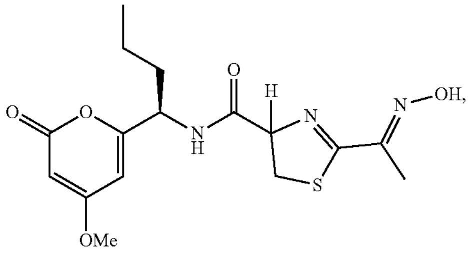
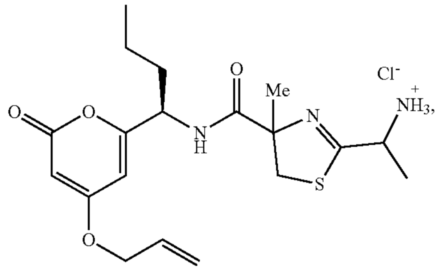
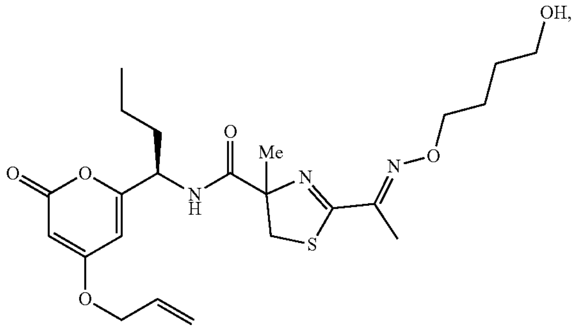
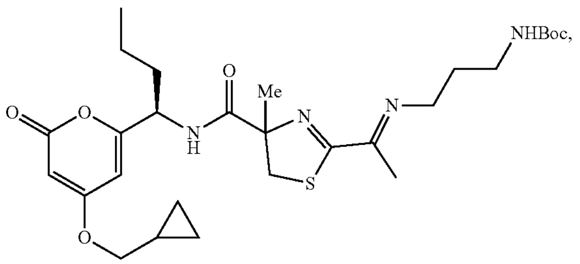
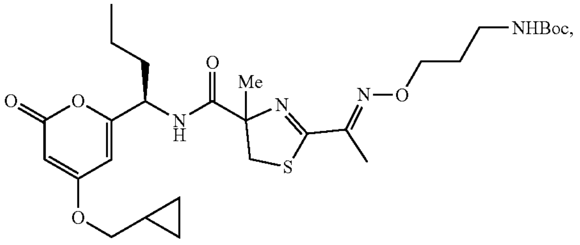
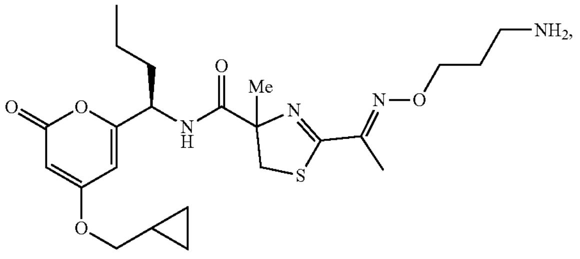

-continued
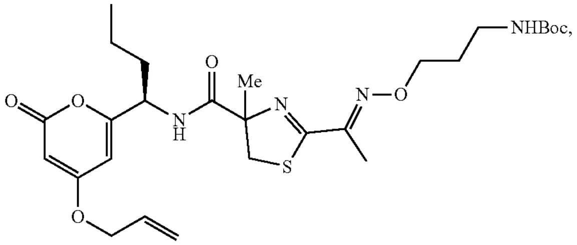
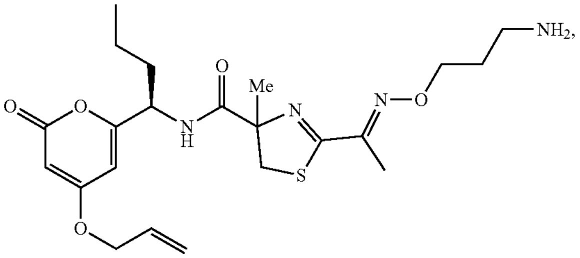
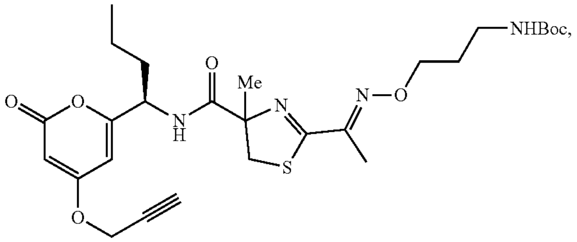
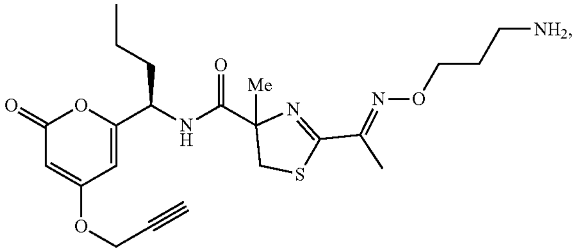
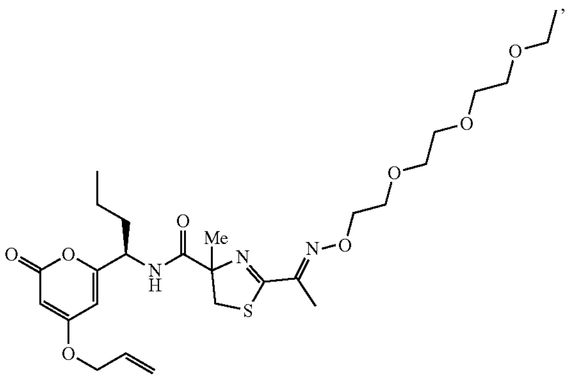
-continued
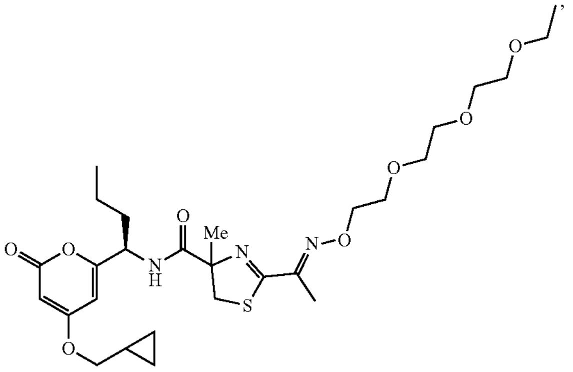
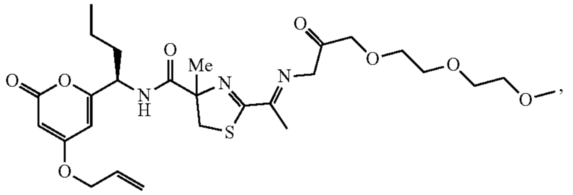
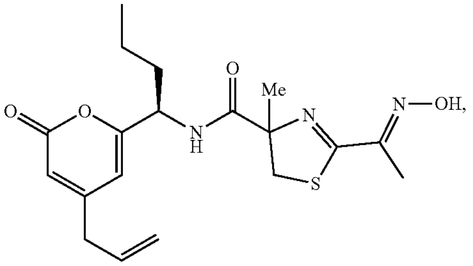
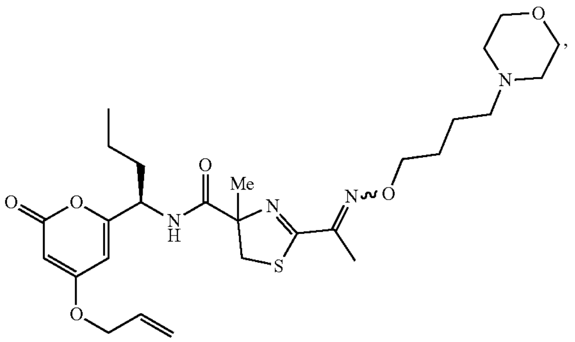
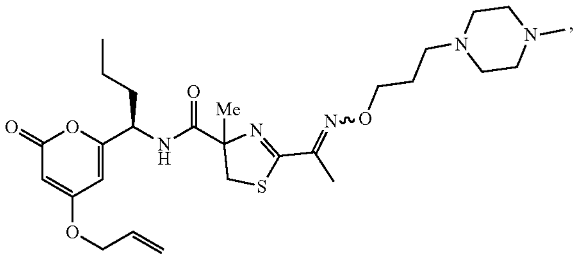
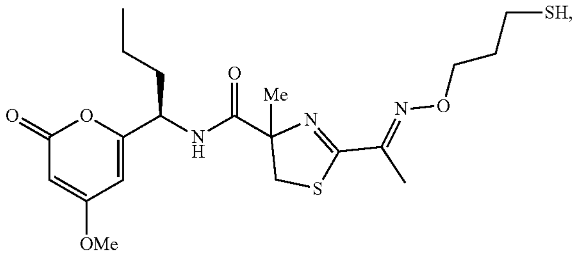

-continued
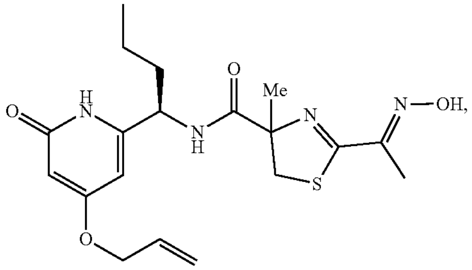
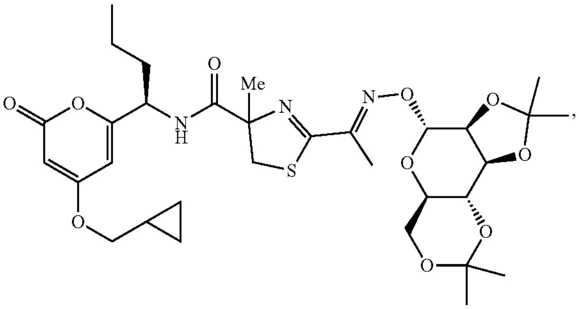
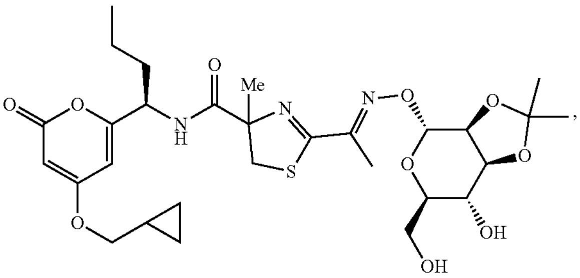
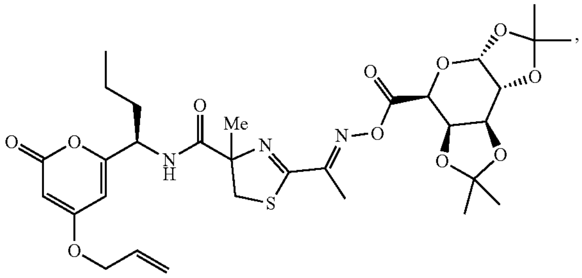
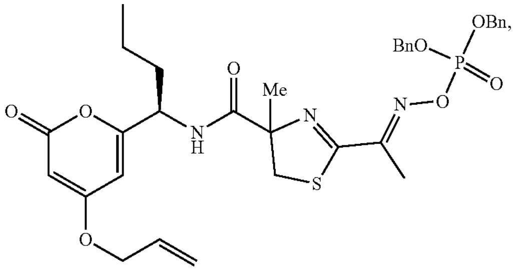
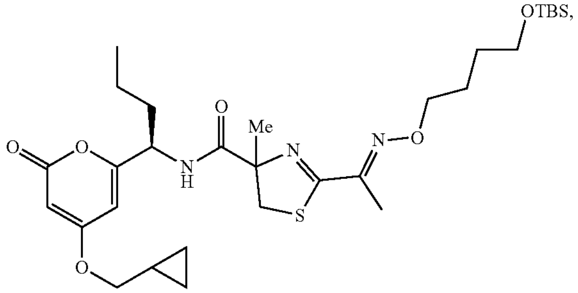
-continued
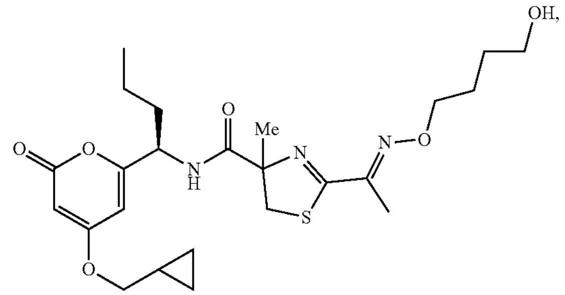
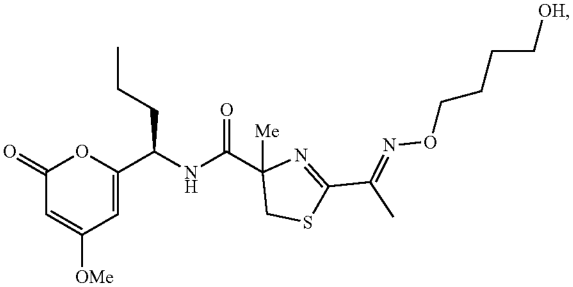
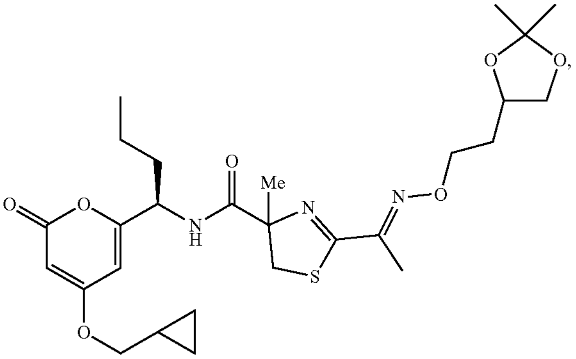
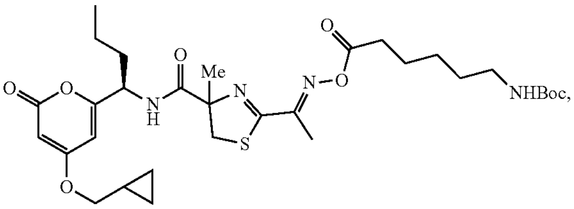
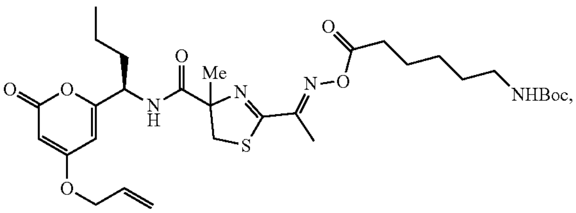
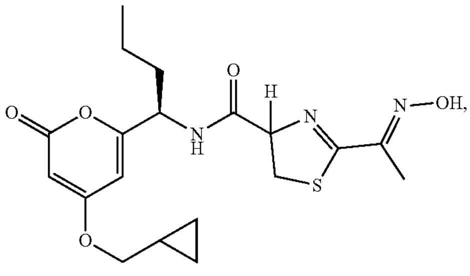

-continued
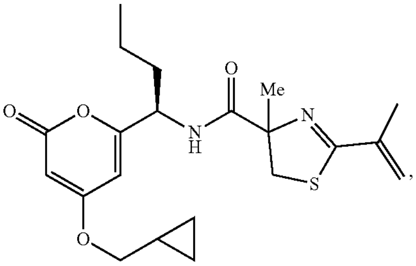
,
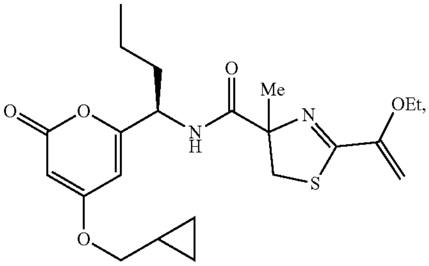
,
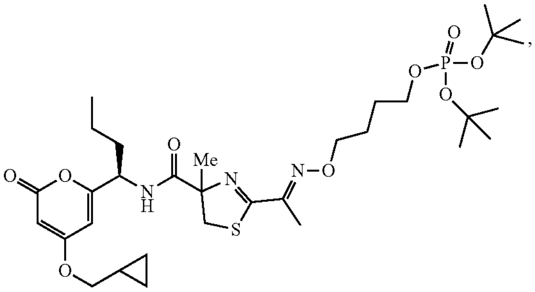
, and
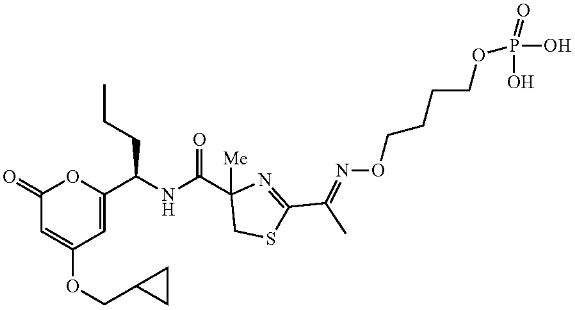
or pharmaceutically acceptable salts or esters thereof.
More preferred compounds of the invention are compounds
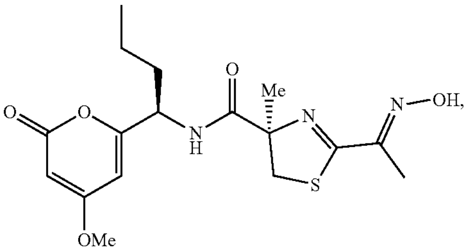
,
-continued
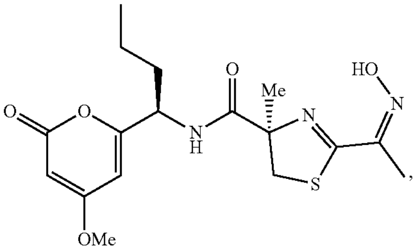
,
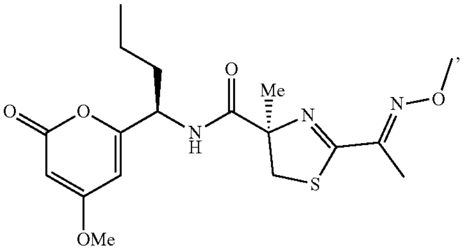
,
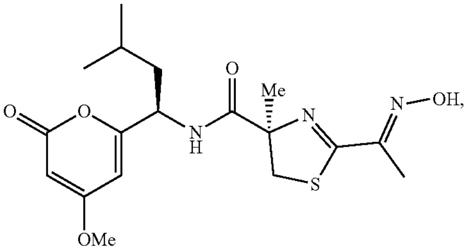
,
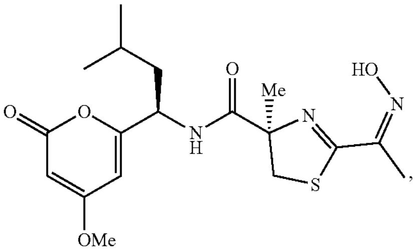
,
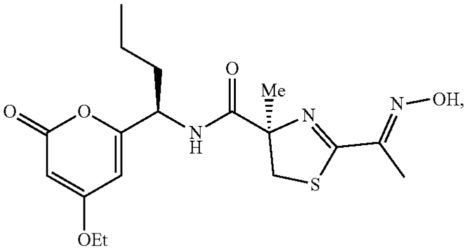
,
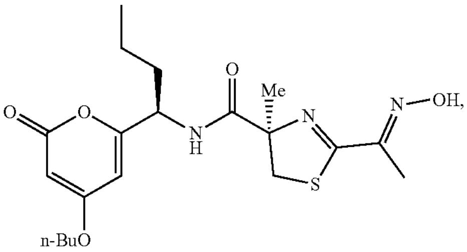
, -continued
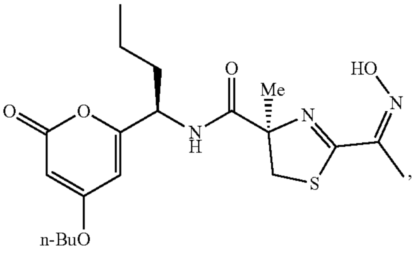
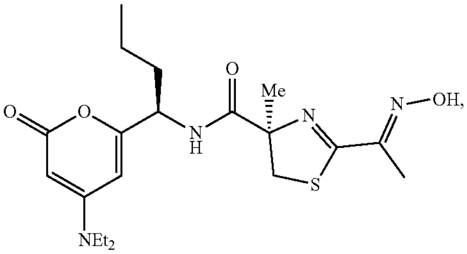
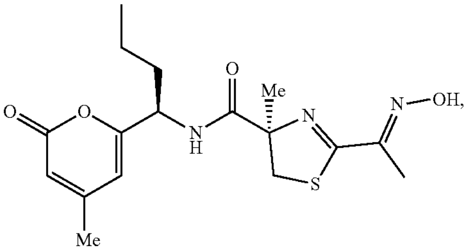
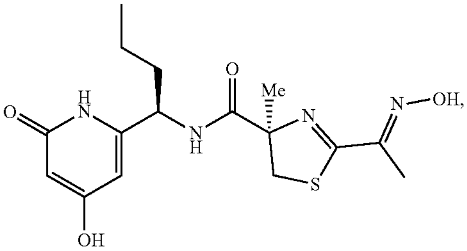
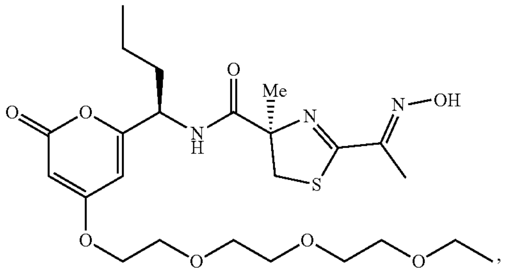
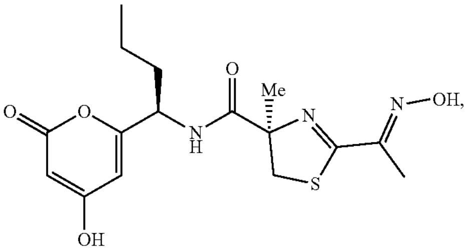
-continued
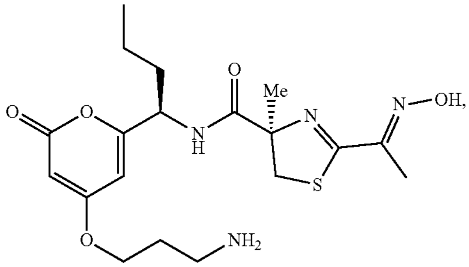
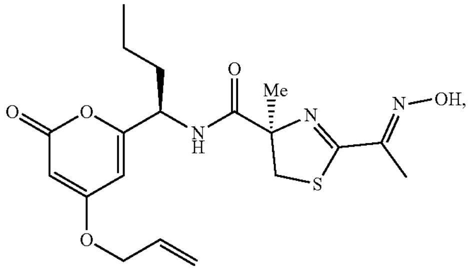
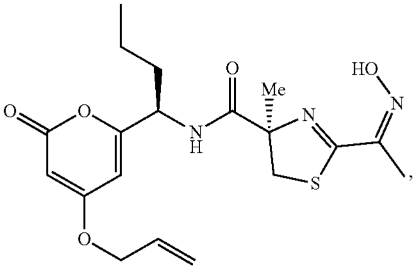
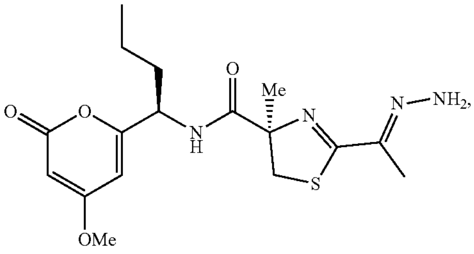
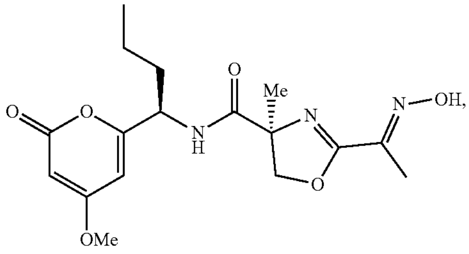
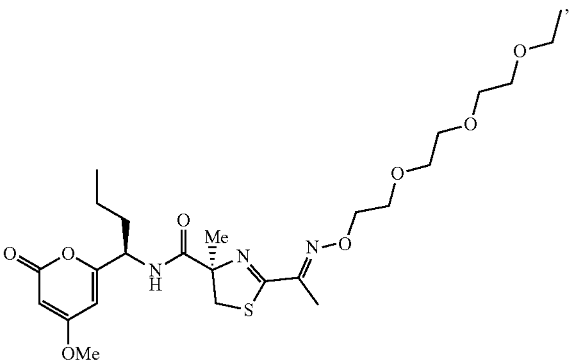

-continued
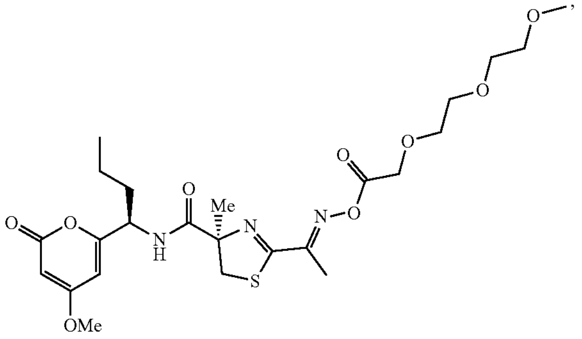
,
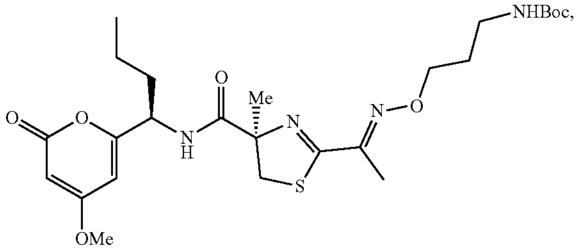
,
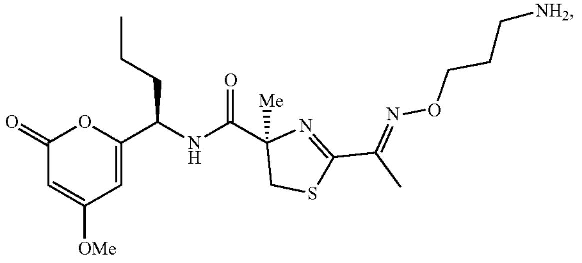
,
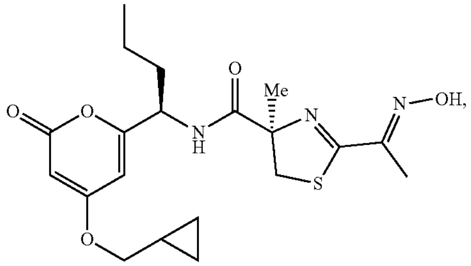
,
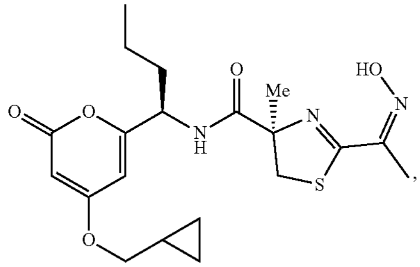
,
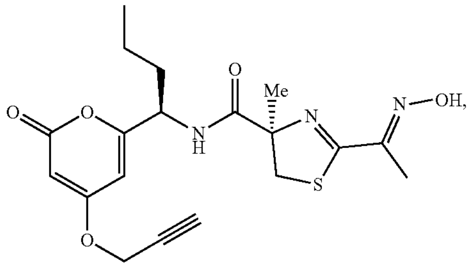
,
-continued
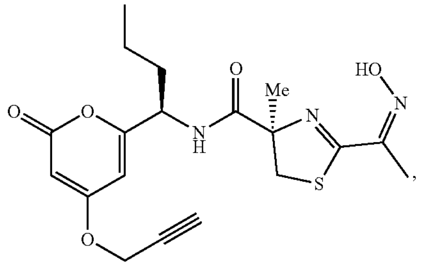
,
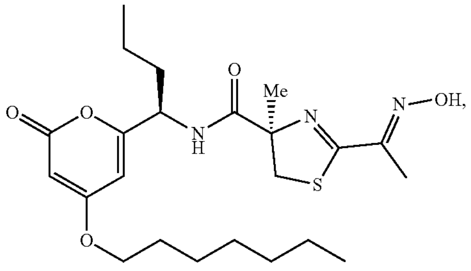
,
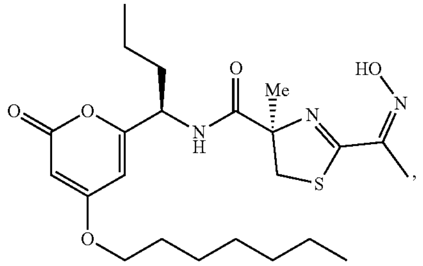
,
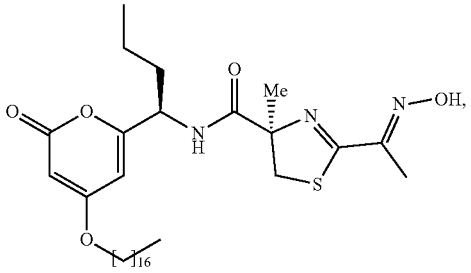
,
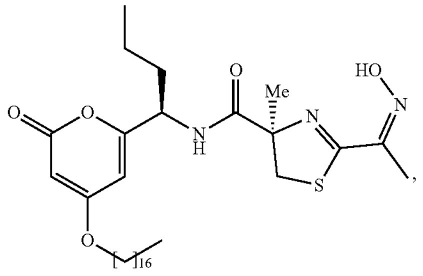
,
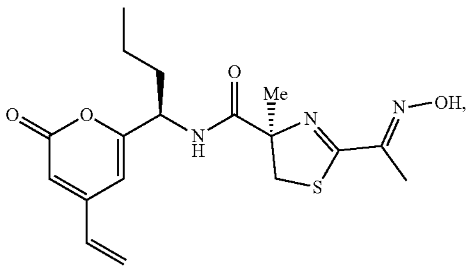
, -continued
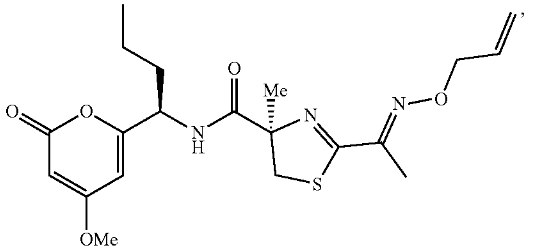
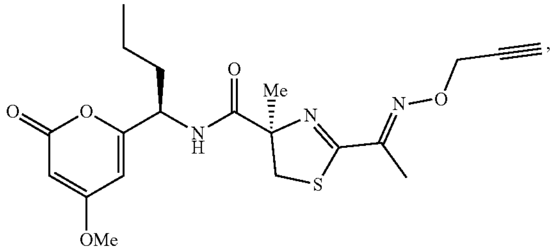
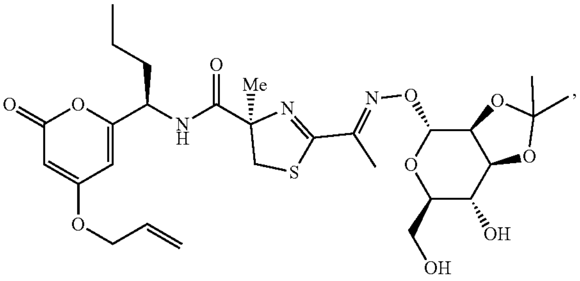
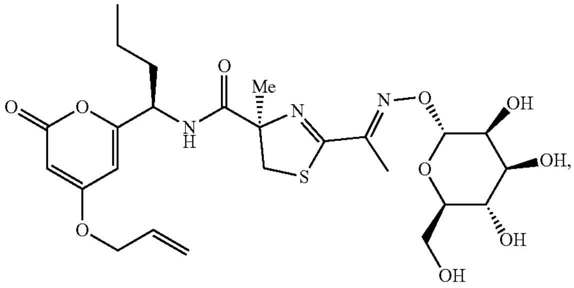
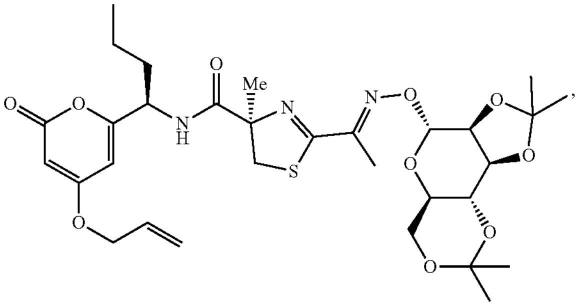
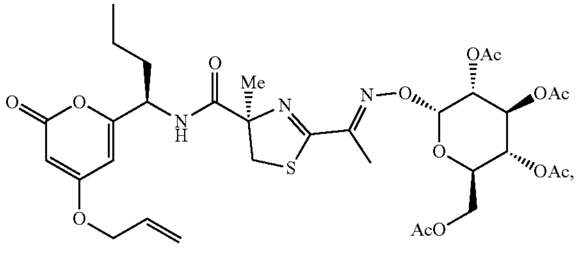
-continued
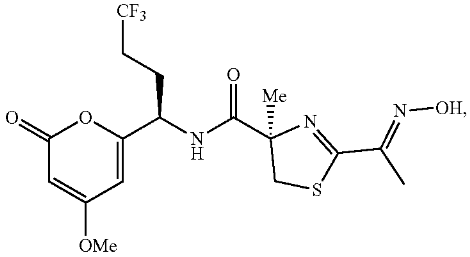
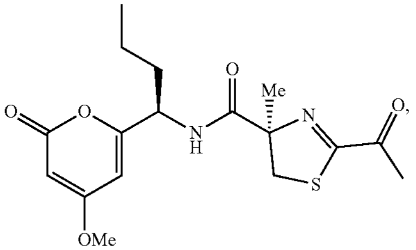
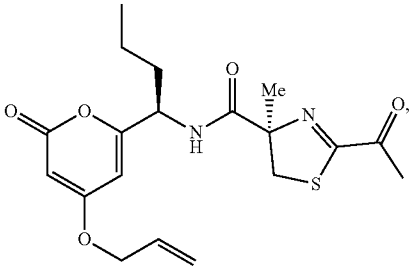
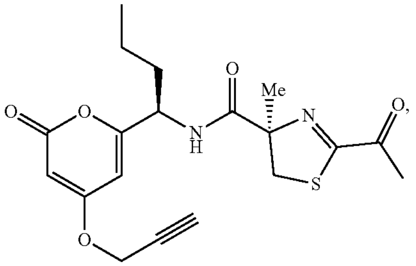
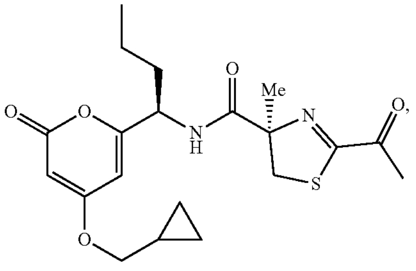
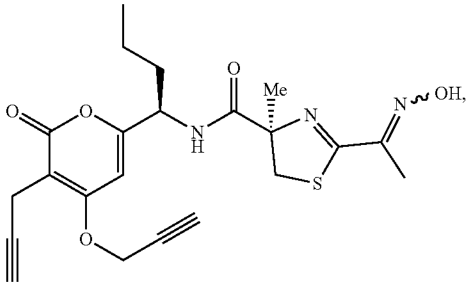

-continued
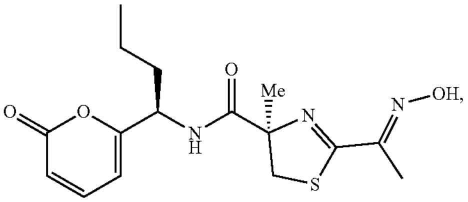
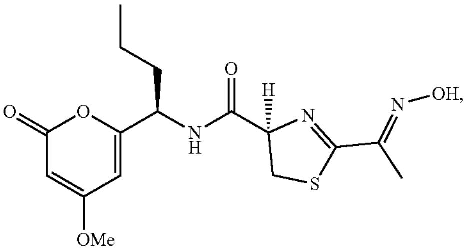
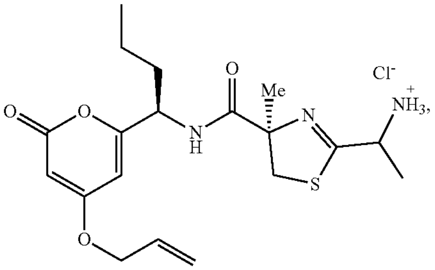
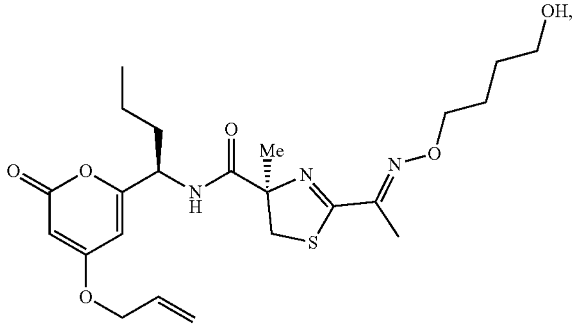
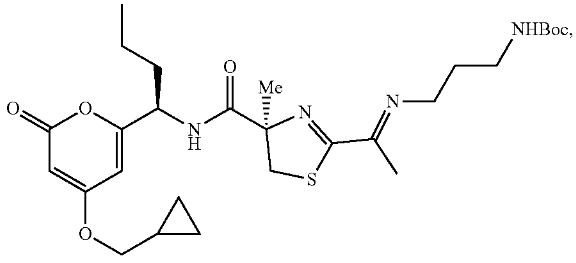
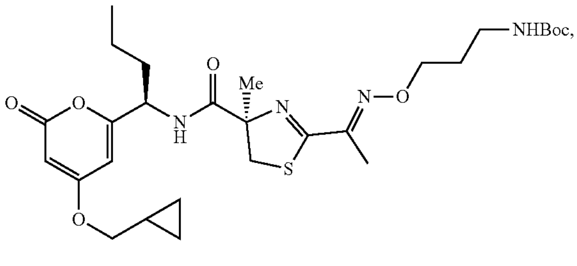
-continued
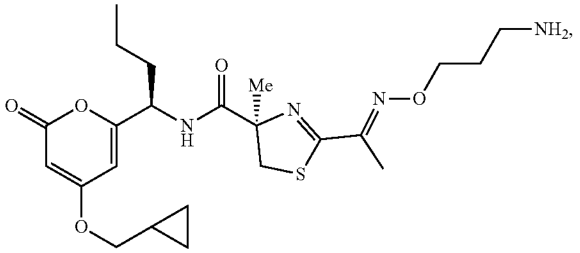
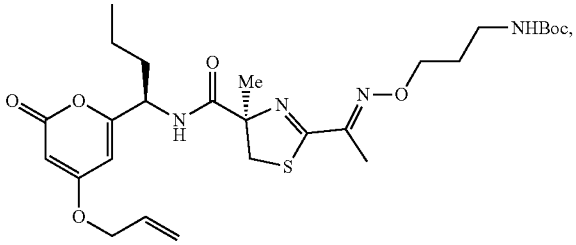
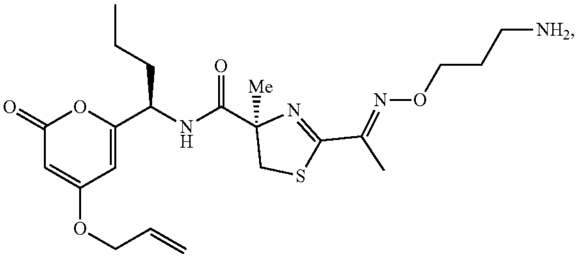
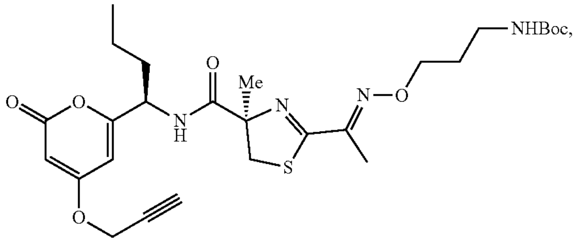
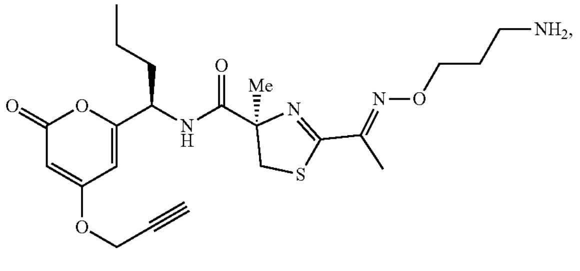
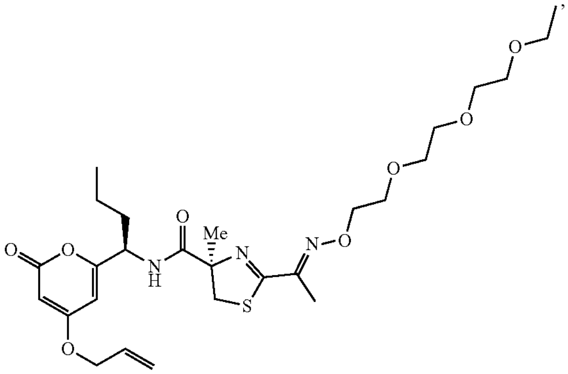

-continued
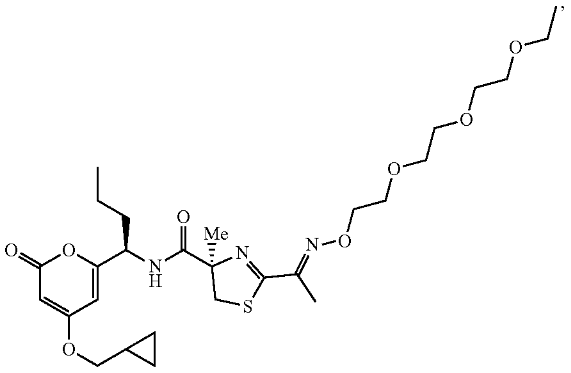
,
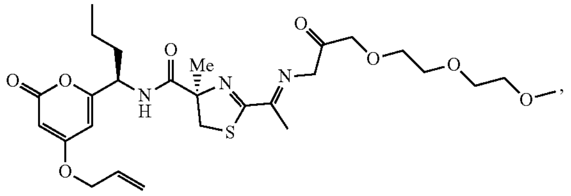
,
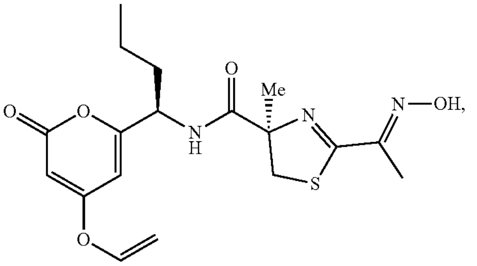
,
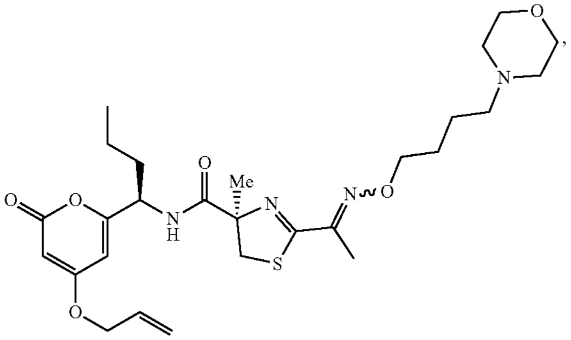
,
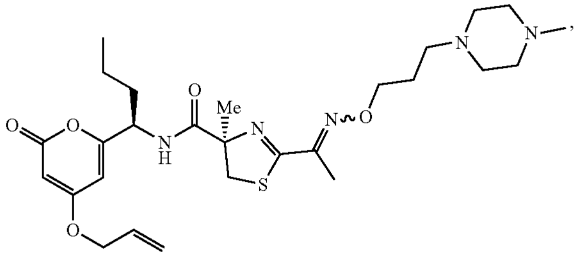
,
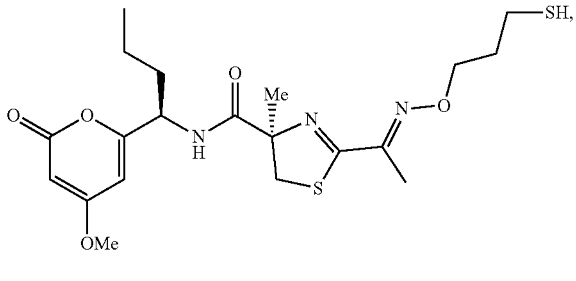
,
-continued
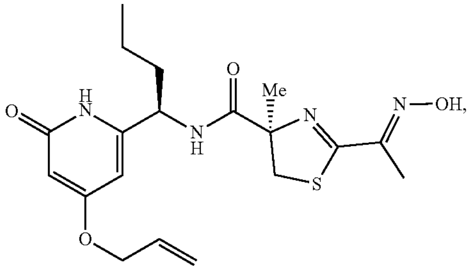
,
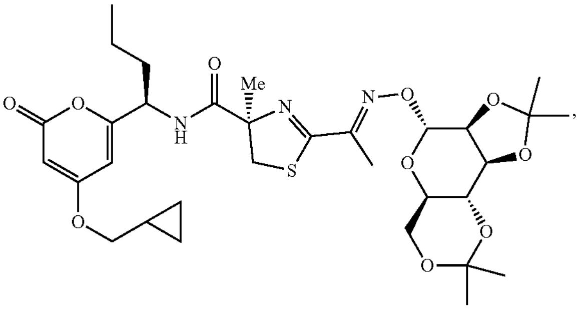
,
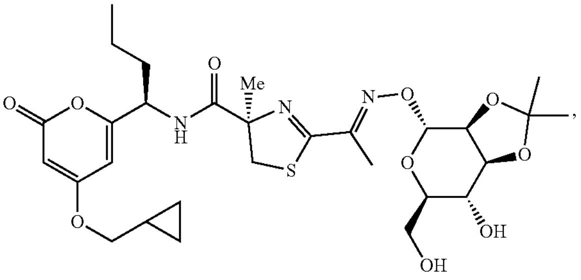
,
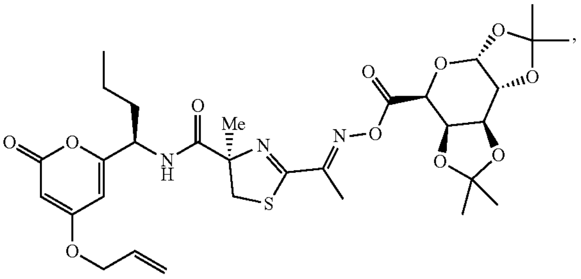
,
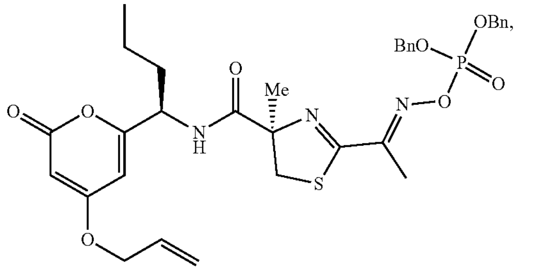
,
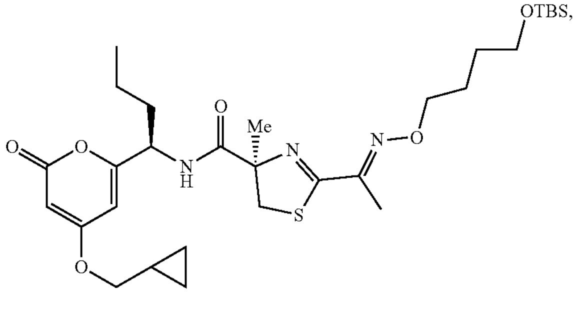
,

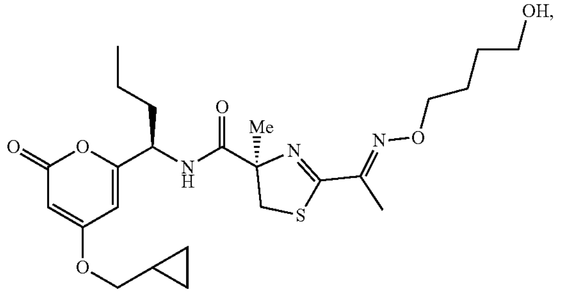
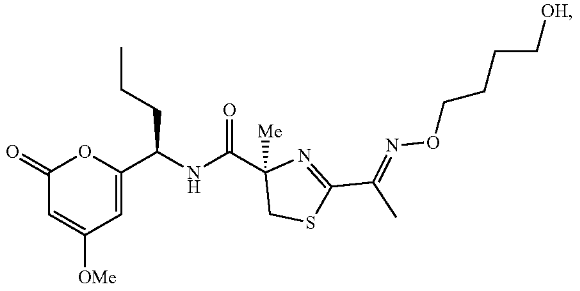
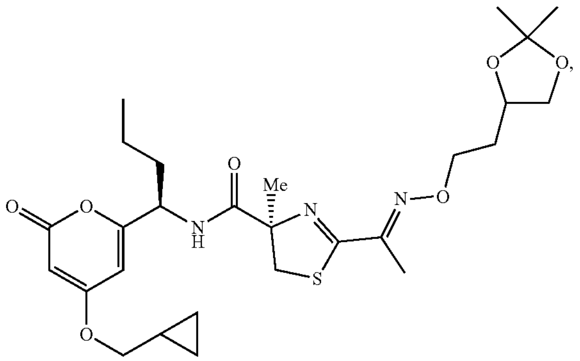
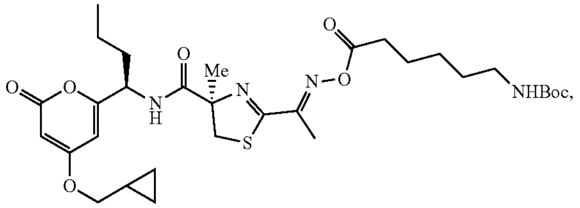
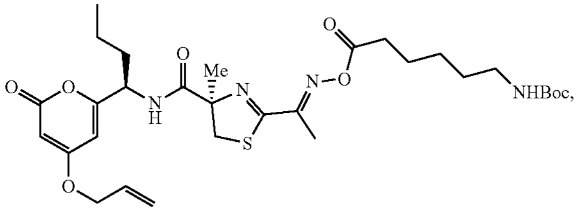
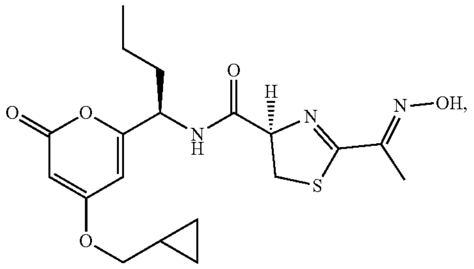
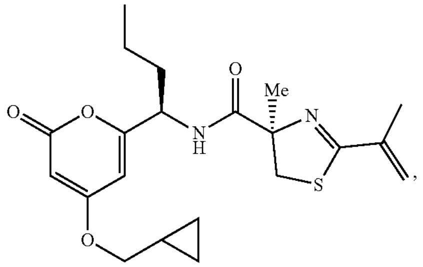
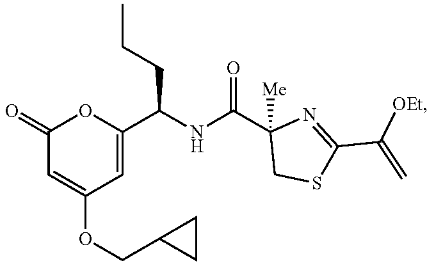
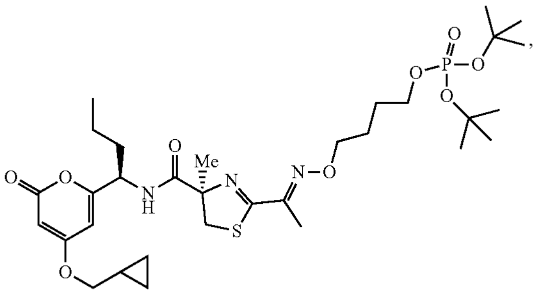
and
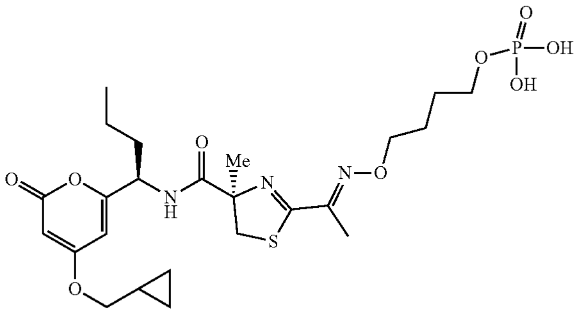
or pharmaceutically acceptable salts or esters thereof.
Even more preferred compounds of the invention are selected from
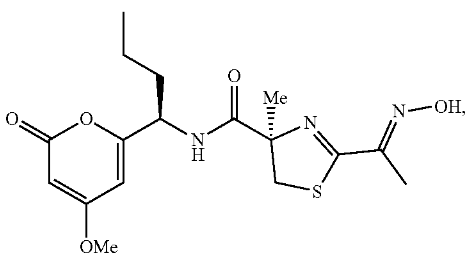

-continued
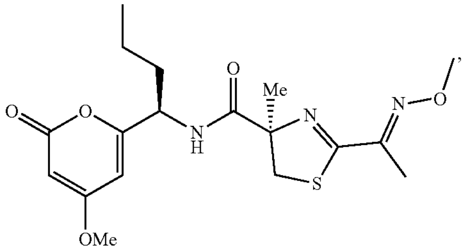
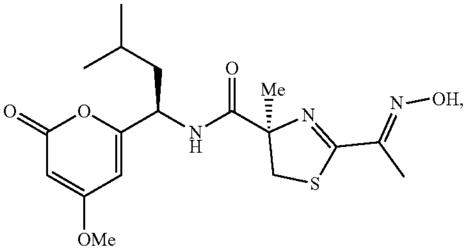
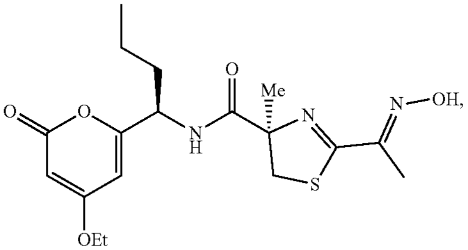
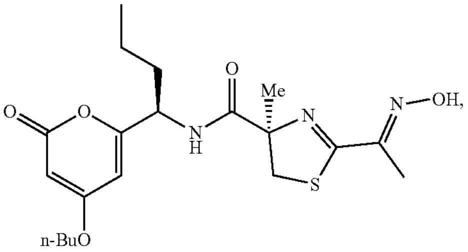
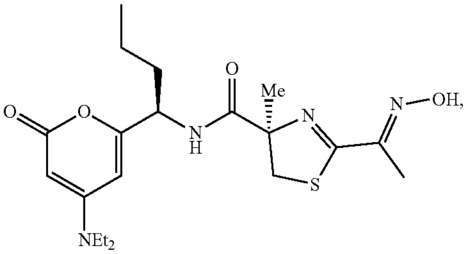
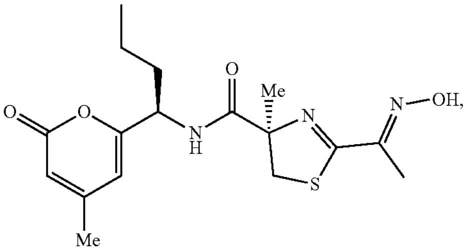
-continued
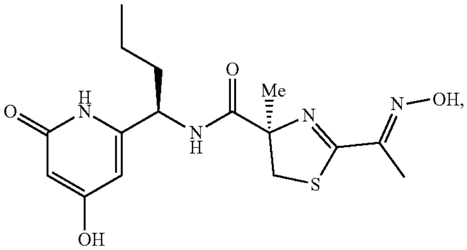
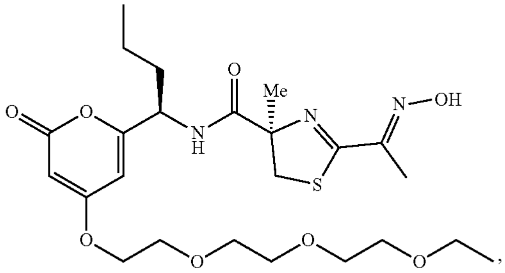
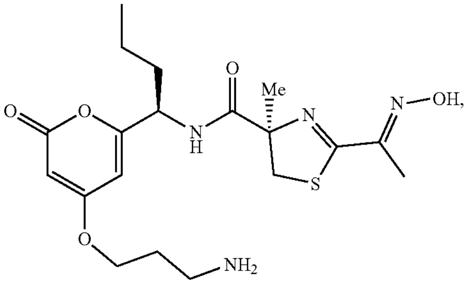
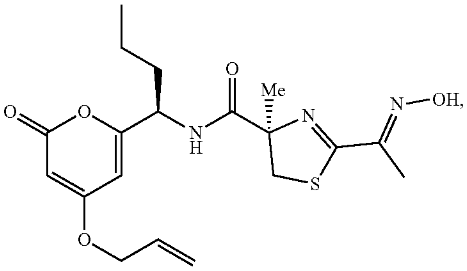
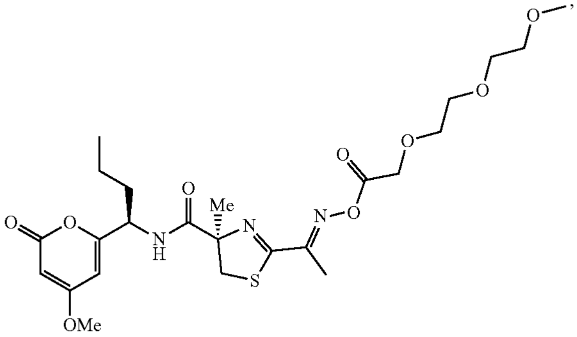

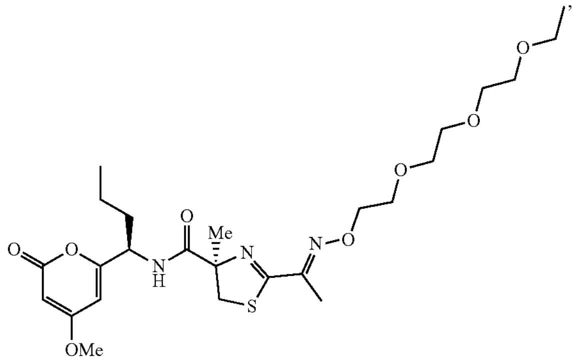,
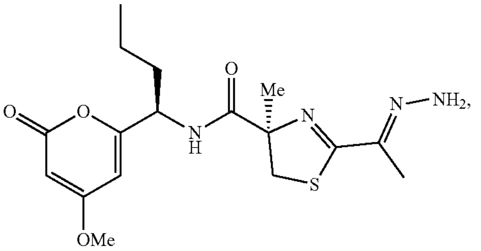,
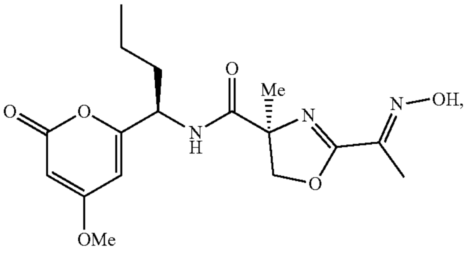,
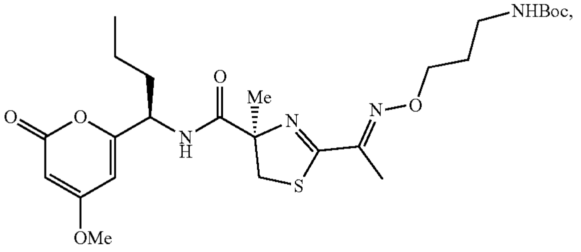,
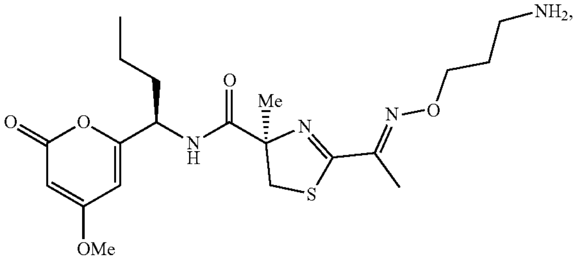,
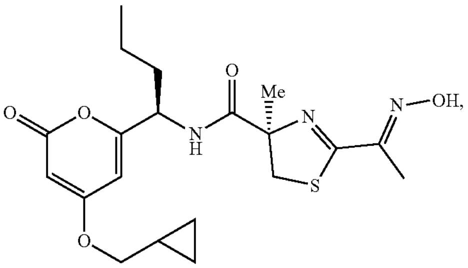,
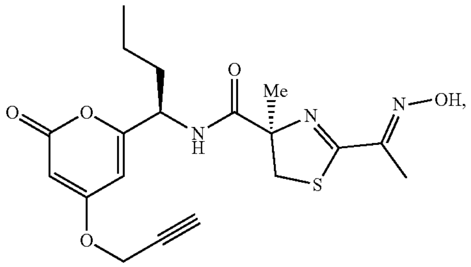,
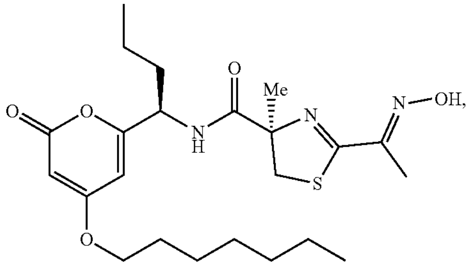,
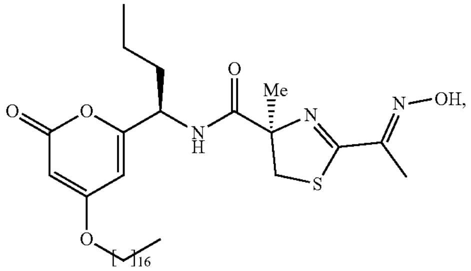,
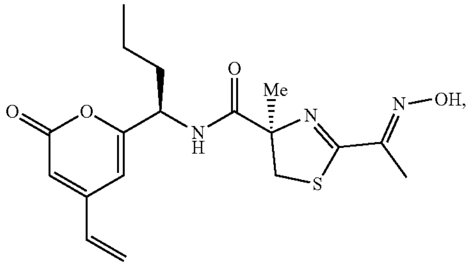,
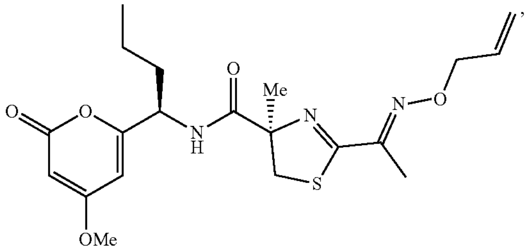,
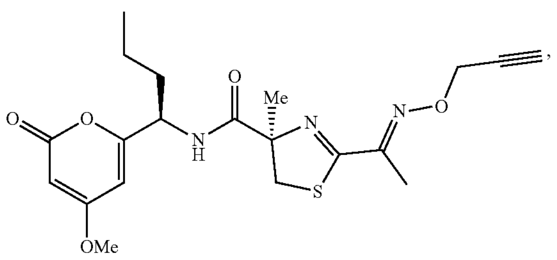, -continued
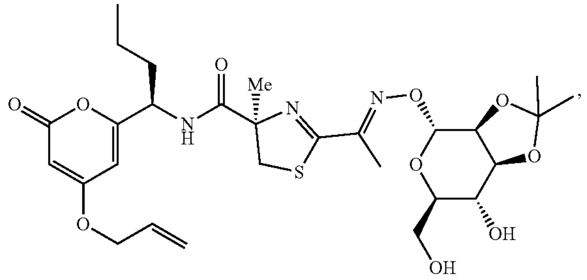
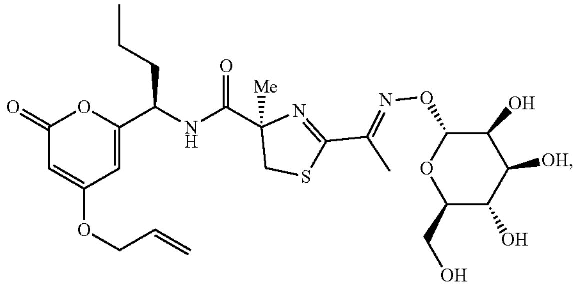
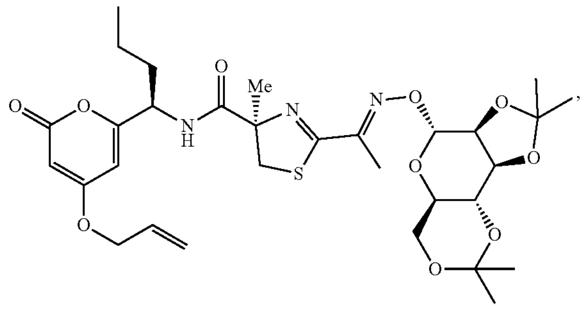
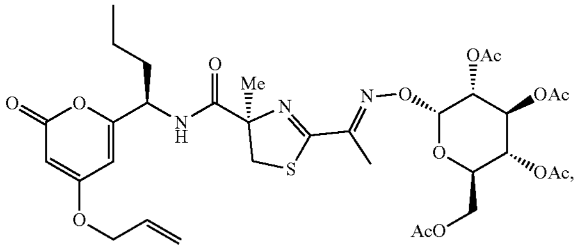
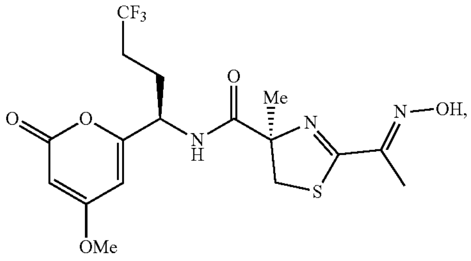
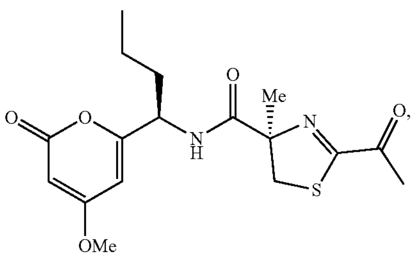
-continued
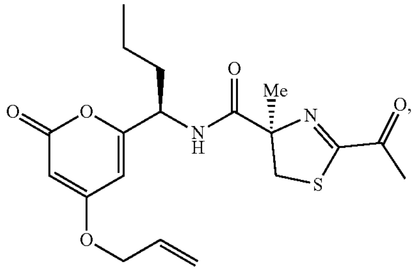
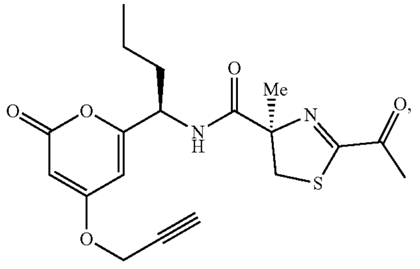
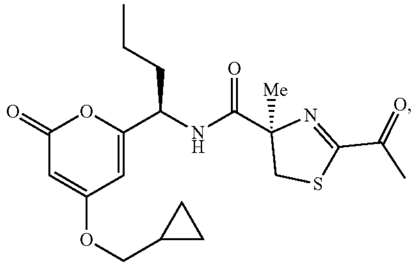
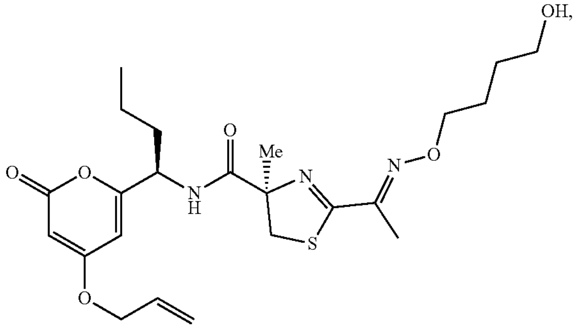
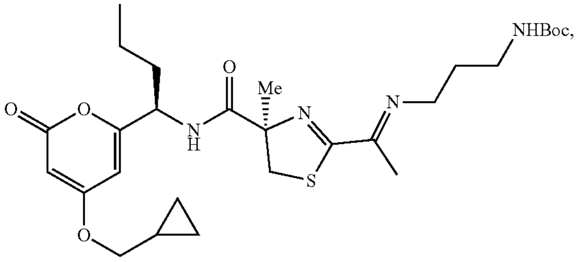
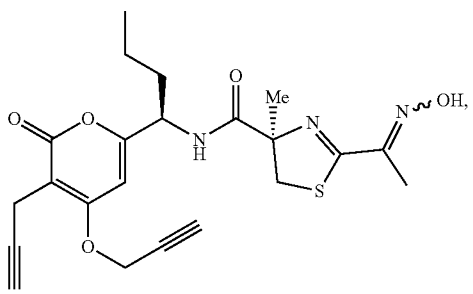

-continued
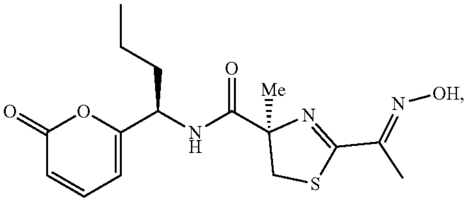
,
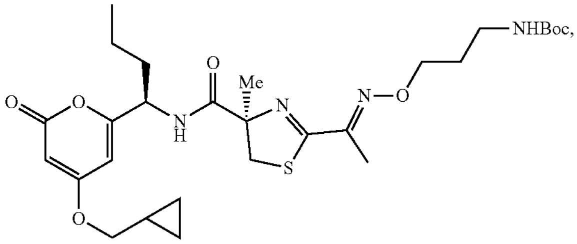
,
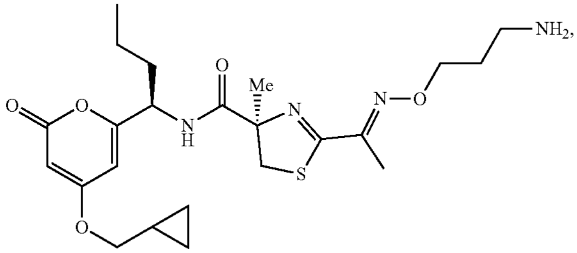
,
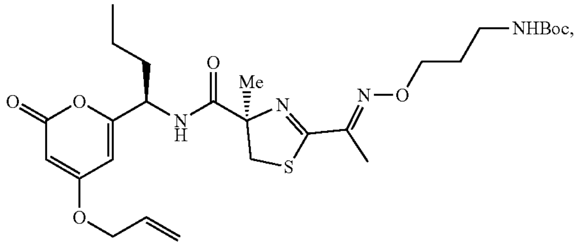
,
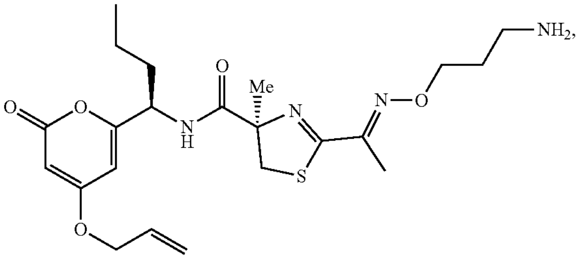
,
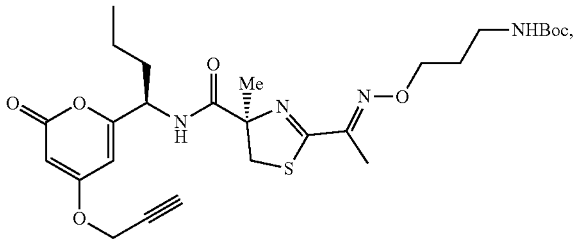
,
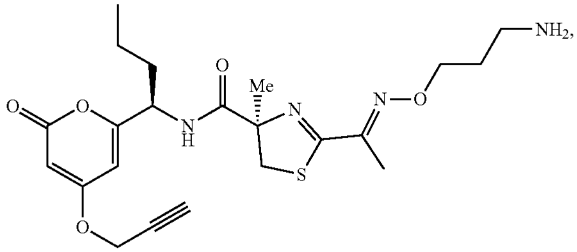
,
-continued
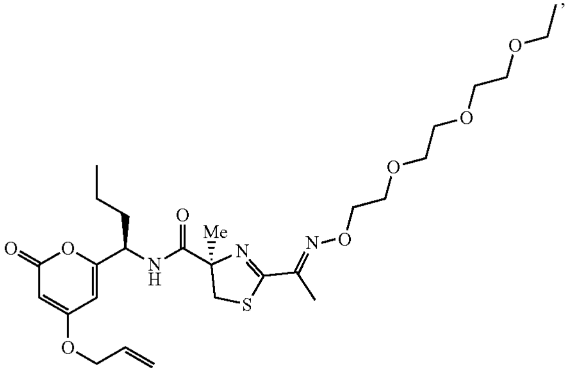
,
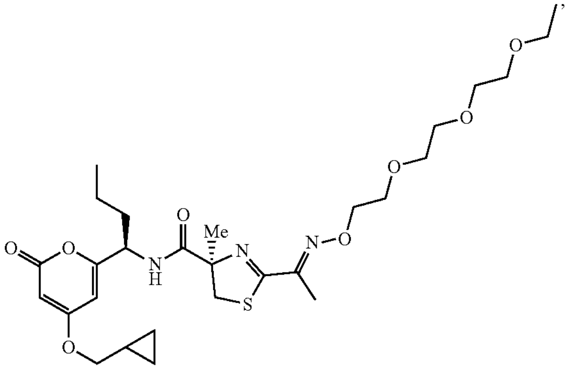
,
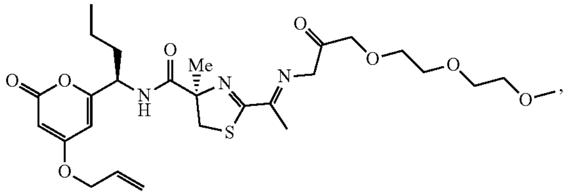
,
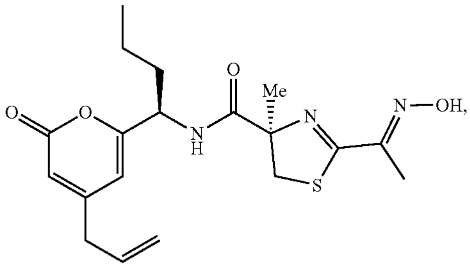
,
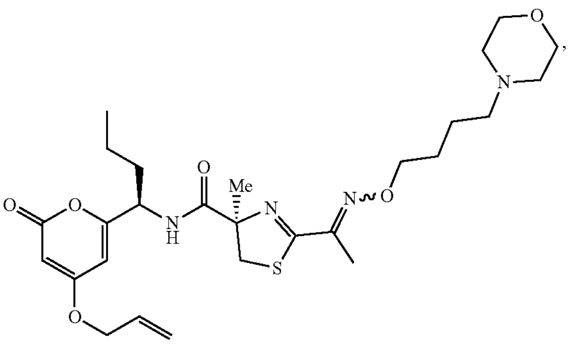
, -continued
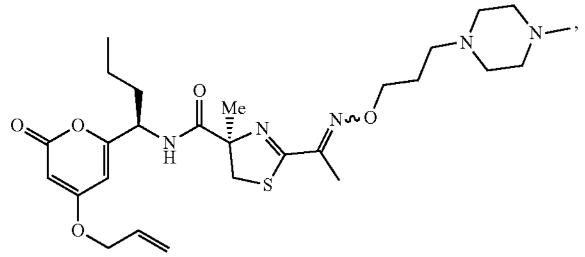
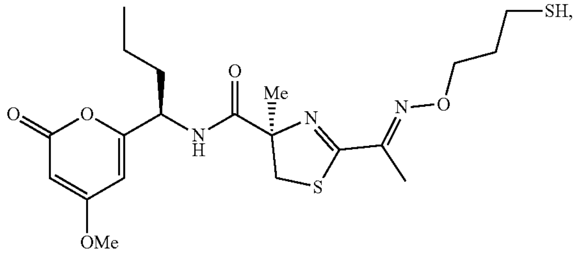
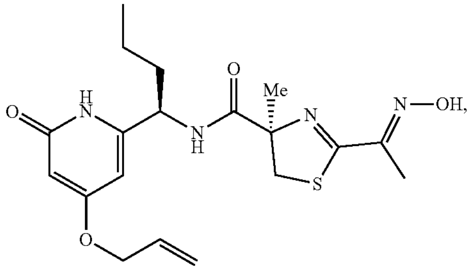
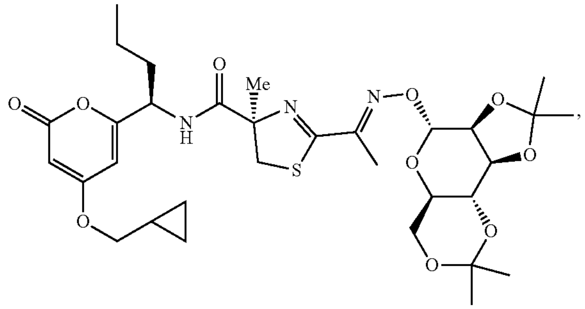
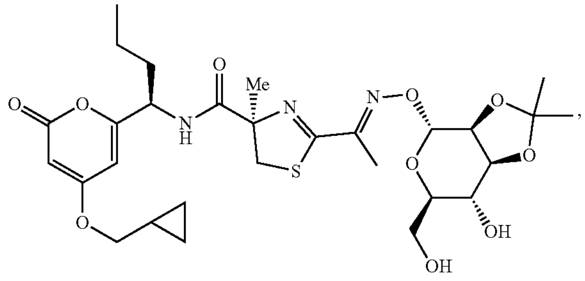
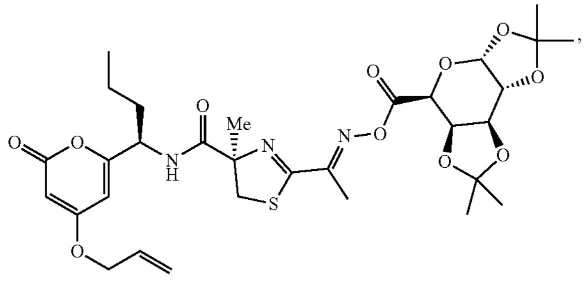
-continued
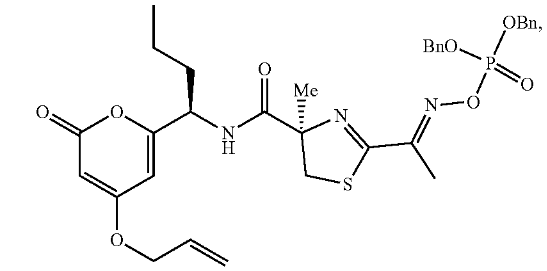
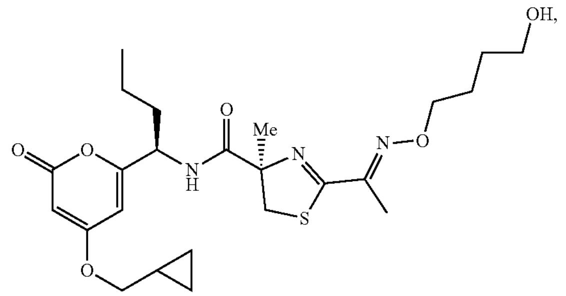
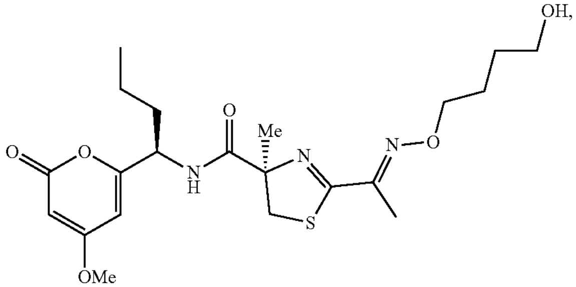
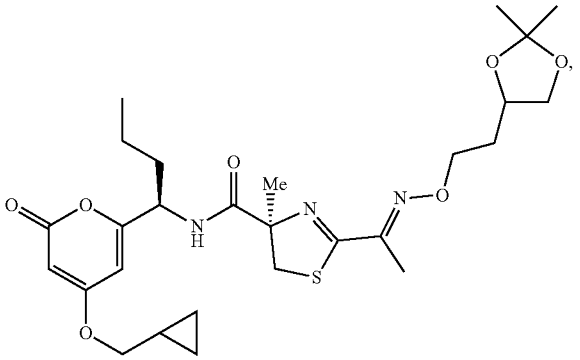
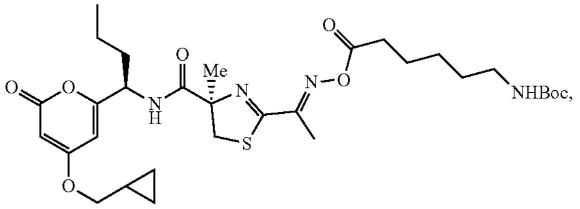
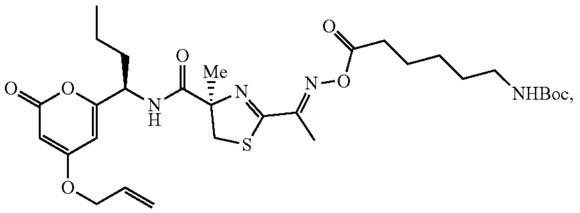

-continued

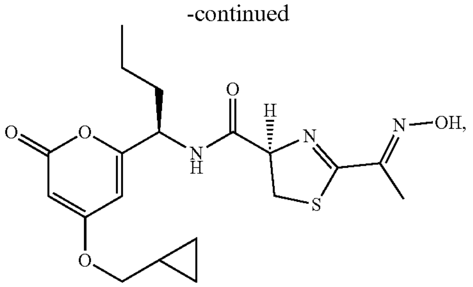

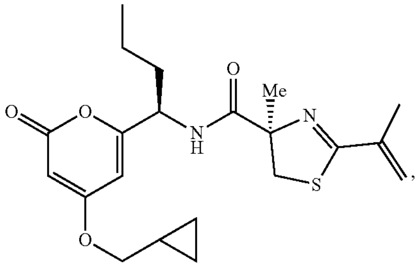

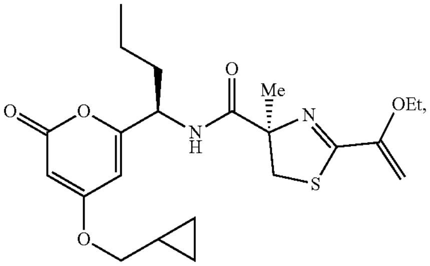

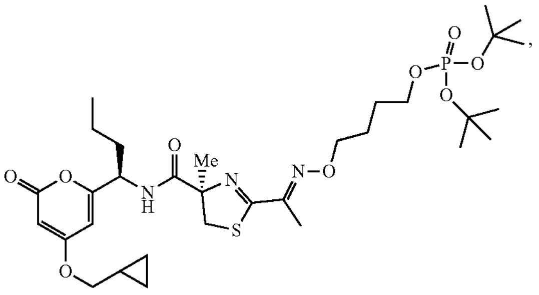

and

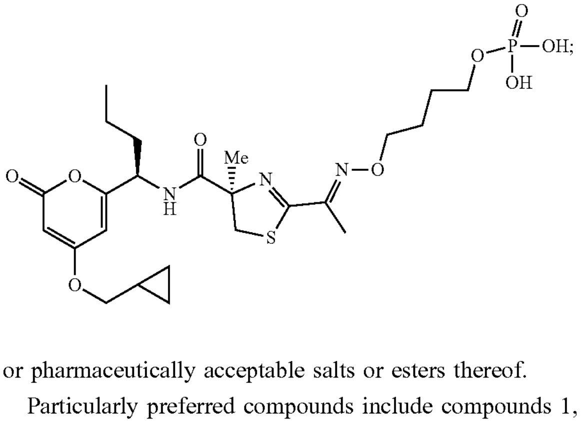

or pharmaceutically acceptable salts or esters thereof.

Particularly preferred compounds include compounds 1, 2, 64, 70, 71, 71a, 72, 72a, 73a, 74, 74a, 75, 75a, 76, 76a, 78, 93, 94, 95, 98, 107, 110, 111, 113, 115, 116, 128, 136, 137, 141, 144, 145, 147, 148, 149, 152, 153, 154, 155, 156, 157, 158, 159, 161, 163, 164, 165, 166, 170, 172, 175, 178, 179, 182, 183, 185, 191, and 192 or pharmaceutically acceptable salts or esters thereof. Further preferred compounds include compounds 71, 74, 74a, 75, 75a, 76, 76a, 113, 115, 149, 153, 154, 156, 158, 161, 163, 170, 179 and 192, or pharmaceutically acceptable salts or esters thereof.

Preferred compounds of formula I further include compounds wherein:

$R_1$ is selected from hydrogen and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

and $R_2$, $R_4$, $R_5$, Y and Z are defined herein.

Further preferred compounds of formula I include compounds wherein:

$R_1$ is selected from hydrogen, and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

$R_4$ is selected from hydrogen and substituted or unsubstituted $C_1$-$C_6$ alkyl; being most preferred hydrogen and methyl.

and $R_2$, $R_5$, Y and Z are defined herein.

Further preferred compounds of formula I include compounds wherein:

$R_1$ is selected from hydrogen, and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

$R_4$ is selected from hydrogen and substituted or unsubstituted $C_1$-$C_6$ alkyl; being most preferred hydrogen and methyl;

Y is O;

and $R_2$, $R_5$, and Z are defined herein.

Further preferred compounds of formula I include compounds wherein:

$R_1$ is selected from hydrogen, and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

$R_4$ is selected from hydrogen and substituted or unsubstituted $C_1$-$C_6$ alkyl; being most preferred hydrogen and methyl;

Y is O;

Z is S;

and $R_2$ and $R_5$ are defined herein.

Further preferred compounds of formula I include compounds wherein:

$R_1$ is selected from hydrogen, and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

$R_4$ is selected from hydrogen and substituted or unsubstituted $C_1$-$C_6$ alkyl; being most preferred hydrogen and methyl;

Y is O;

Z is S;

$R_2$ is selected from hydrogen, methyl, vinyl, allyl, $NEt_2$, and $OR_a$ where $R_a$ is selected from hydrogen, methyl, ethyl, n-butyl, n-heptyl, allyl, propargyl, cyclopropylmethyl, $-(CH_2)_3NHBoc$, $-(CH_2)_3NH_2$, and $-(CH_2CH_2O)_3CH_2CH_3$;

and $R_5$ is defined herein.

Further preferred compounds of formula I include compounds wherein:

$R_1$ is selected from hydrogen, and substituted or unsubstituted $C_2$-$C_6$ alkynyl, wherein the optional substituents are one or more substituents $R_x$; being hydrogen the most preferred $R_1$ group;

$R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected form F, Cl, Br, and I; being most preferred n-propyl, 3,3,3-trifluoropropyl, and isobutyl;

$R_4$ is selected from hydrogen and substituted or unsubstituted $C_1$-$C_6$ alkyl; being most preferred hydrogen and methyl;

Y is O;

Z is S;

$R_5$ is selected from $-CH(NH_2)Me$, $-(C{=}O)Me$, $-(C{=}NR_c)Me$, $-(C{=}N{-}OR_h)Me$, $-(C{=}N{-}O(C{=}O)R_f)Me$, $-(C{=}N{-}NH_2)Me$, $-(C{=}N{-}O{-}(C{=}O)OR_a)Me$, $-(C{=}N{-}O{-}[(P{=}O)(OR_a)_2])Me$, $-(C{=}CH_2)Me$, or $-(C{=}CH_2)OR_a$ where $R_a$ is ethyl or benzyl, $R_c$ is $-(CH_2)_3NHBoc$, $R_f$ is $-(CH_2)_5-NHBoc$, $-CH_2O(CH_2CH_2O)_2Me$ or a group of formula:

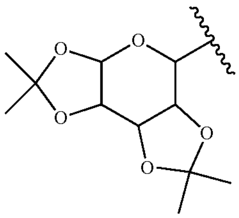

and $R_h$ is selected from hydrogen, methyl, allyl, propargyl, $-(CH_2)_3NHBoc$, $-(CH_2)_3NH_2$, $-(CH_2)_3SH$, $-(CH_2)_4OH$, $-(CH_2)_4OP({=}O)(OH)_2$, $-(CH_2)_4OP({=}O)(O^t.Bu)_2$, $-(CH_2)_4$-[4$\lambda^2$-morpholine], $-(CH_2)_3$-[1-methyl-4$\lambda^2$-piperazine], $-(CH_2CH_2O)_3CH_2CH_3$, and a monosaccharide residue of formula:

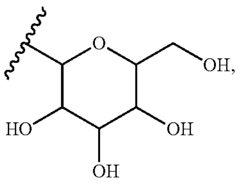

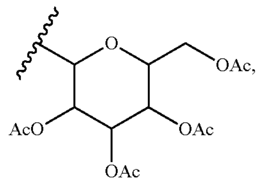

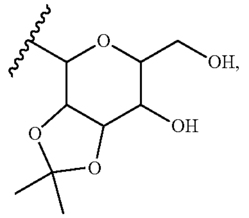

or

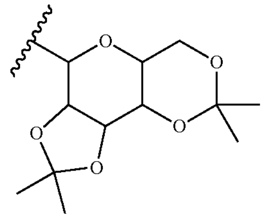

and $R_2$ is defined herein.

Compounds of formula I

I

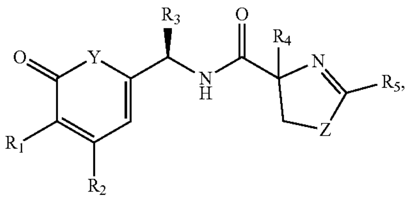

wherein $R_1$, $R_2$, $R_3$, $R_4$, $R_5$, Y, and Z are as defined above, can be obtained synthetically by coupling an amine of formula II with a carboxylic acid of formula III

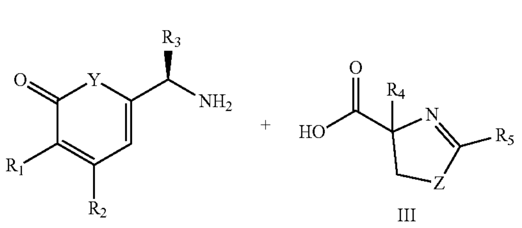

II

III wherein $R_1$, $R_2$, $R_3$, $R_4$, $R_5$, Y, and Z in the compounds of formula II and III are as defined above in the compounds of formula I or an appropriately protected group as needed.

In the process for the manufacture of a compound of formula I, particularly preferred $R_1$, $R_2$, $R_3$, and Y in the intermediates of formula II and particularly preferred $R_4$, $R_5$, and Z in the intermediates of formula III are as defined above in preferred embodiments of compounds of formula I or an appropriately protected group as needed; and particularly preferred $R_5$ is selected from —$C(OR_e)_2R_g$ and a

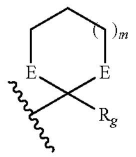

group where m is 0, 1 or 2 and each E group is independently selected from O and S, $R_e$ is substituted or unsubstituted $C_1$-$C_6$ alkyl, wherein the optional substituents are one or more substituents $R_x$, and $R_g$ is selected from hydrogen and substituted or unsubstituted $C_1$-$C_6$ alkyl wherein the optional substituents are one or more substituents $R_x$. More preferred $R_5$ is a —$C(OR_e)_2R_g$ group where $R_g$ and $R_e$ are independently substituted or unsubstituted $C_1$-$C_6$ alkyl wherein the optional substituents are one or more substituents $R_x$. More preferred $R_g$ and $R_e$ are independently substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_5$ is —$C(OEt)_2Me$.

Moreover, when the compound of formula I has a $R_5$ group of formula —$C(OR_e)_2R_g$ this process can further comprise a deprotection step to give a compound of formula I where $R_5$ is —$(C{=}O)R_g$.

Moreover, when the compound of formula I has a $R_5$ group of formula —$(C{=}O)R_g$, the process can further comprise a reaction with hydroxylamine, with an hydrazine, with a primary amine, with a methylenation reagent or with an orthoester to give a compound of formula —$(C{=}N{-}OH)R_g$ or —$(C{=}N{-}NR_cR_d)R_g$, —$(C{=}NR_c)R_g$, —$(C{=}CH_2)Me$, or —$(C{=}CH_2)OR_a$, respectively.

Moreover, when the compound of formula I has a $R_5$ group of formula —$(C{=}N{-}OH)R_g$, the process can further comprise alkylation, acylation, or phosphorylation of the OH group of the oxime to give the corresponding ether, ester or phosphate.

In addition, with this invention there are provided novel intermediates of formula IIa:

IIa

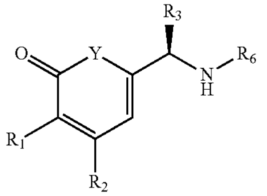

wherein $R_1$, $R_2$, $R_3$, $R_6$ and Y are as defined above in the previous disclosure of intermediates of formula IIa.

In another embodiment, particularly preferred intermediates of formula IIa are those also having formula IIb or a salt thereof IIb

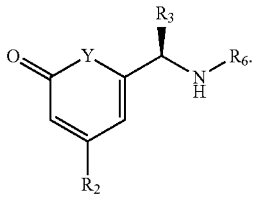

In intermediates of formula IIa, particularly preferred $R_1$ is selected from hydrogen, halogen and substituted or unsubstituted $C_2$-$C_6$ alkynyl, wherein the optional substituents are one or more substituents $R_x$; being hydrogen the most preferred $R_1$ group.

In intermediates of formula IIa, IIb or IIc, particularly preferred $R_2$ is selected from hydrogen, substituted or unsubstituted $C_1$-$C_6$ alkyl, substituted or unsubstituted $C_2$-$C_6$ alkenyl, wherein the optional substituents are one or more substituents $R_x$, —$OR_a$, —$OSO_2R_b$, and —$NR_cR_d$; where $R_a$ is selected from hydrogen, a silylether protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_6$alkyl, and —$(CH_2CH_2O)_pCH_2CH_3$ where p is from 1 to about 15 and the optional substituents are one or more substituents $R_x$; $R_b$ is selected from substituted or unsubstituted $C_1$-$C_6$ alkyl and substituted or unsubstituted aryl, wherein the optional substituents are one or more substituents $R_x$; and $R_c$ and $R_d$ are independently selected from substituted or unsubstituted $C_1$-$C_6$ alkyl wherein the optional substituents are one or more substituents $R_x$. Particularly preferred $R_a$ is selected from hydrogen, substituted or unsubstituted $C_1$-$C_8$ alkyl, substituted or unsubstituted $C_2$-$C_8$ alkenyl, substituted or unsubstituted $C_2$-$C_8$ alkynyl, substituted or unsubstituted $C_3$-$C_4$cycloalkyl-$C_1$-$C_4$ alkyl, —$(CH_2CH_2O)_pCH_2CH_3$ where p is from 1 to about 10 and the optional substituents are one or more substituents $R_x$, and a silyl ether protecting group for OH selected from trimethylsilyl, triethylsilyl, triisopropylsilyl, dimethylisopropylsilyl, diethylisopropylsilyl, dimethylhexylsilyl, 2-norbornyldimethylsilyl, t-butyldimethylsilyl (TBS), t-butyldiphenylsilyl, tribenzylsilyl, tri-p-xylylsilyl, triphenylsilyl, diphenylmethylsilyl, di-t-butylmethylsilyl, bis(t-butyl)-1-pyrenylmethoxysilyl, tris(trimethylsilyl)silyl, (2-hydroxystyryl)dimethylsilyl, (2-hydroxystyryl)diisopropylsilyl, t-butylmethoxyphenylsilyl, t-butoxydiphenylsilyl, 1,1,3,3-tetraisopropyl-3-[2-(triphenylmethoxy)ethoxy]disiloxane-1-yl, and fluorous silyl. Particularly preferred $R_b$ is selected from substituted or unsubstituted $C_1$-$C_6$ alkyl and substituted or unsubstituted phenyl, wherein the optional substituents are one or more substituents $R_x$. Particularly preferred $R_c$ and $R_d$ are independently selected from substituted or unsubstituted $C_1$-$C_4$ alkyl wherein the optional substituents are one or more substituents $R_x$. More preferred $R_2$ is selected from hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted vinyl, substituted or unsubstituted allyl, wherein the optional substituents are one or more substituents $R_x$, —$OR_a$, —$OSO_2R_b$, and —$NR_cR_d$; where $R_a$ is selected from hydrogen, substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, substituted or unsubstituted sec-butyl, substituted or unsubstituted n-heptyl, substituted or unsubstituted allyl, substituted or unsubstituted 1-methyl-2-propenyl, substituted or unsubstituted 2-methyl-2-propenyl, substituted or unsubstituted 2-butenyl, substituted or unsubstituted 3-butenyl, substituted or unsubstituted propargyl, substituted or unsubstituted 1-methyl-2-propynyl, substituted or unsubstituted 2-butynyl, substituted or unsubstituted 3-butynyl, substituted or unsubstituted cyclopropylmethyl, substituted or unsubstituted 2-cyclopropylethyl, and $-(CH_2CH_2O)_pCH_2CH_3$ wherein p is from 1 to about 5 and the optional substituents are one or more substituents $R_x$; $R_b$ is selected from substituted or unsubstituted methyl and substituted or unsubstituted phenyl wherein the optional substituents are one or more substituents $R_x$; and $R_c$ and $R_d$ are independently selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_2$ is selected from hydrogen, methyl, vinyl, allyl, OTosyl, ONs, OTf, $NEt_2$, and $OR_a$ where $R_a$ is hydrogen, methyl, ethyl, n-propyl, n-butyl, n-heptyl, allyl, propargyl, cyclopropylmethyl, $-(CH_2)_3NHBoc$, $-(CH_2)_3NH_2$, and $-(CH_2CH_2O)_3CH_2CH_3$.

In intermediates of formula IIa, Mb or Me, particularly preferred $R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected from F, Cl, Br, and I. Particularly preferred $R_3$ is an halogen substituted or unsubstituted $C_1$-$C_6$ alkyl, wherein the halogen substituents are one or more substituents independently selected from F, Cl, Br, and I. More preferred $R_3$ is selected from halogen-substituted or unsubstituted methyl, halogen-substituted or unsubstituted ethyl, halogen-substituted or unsubstituted n-propyl, halogen-substituted or unsubstituted isopropyl, halogen-substituted or unsubstituted n-butyl, halogen-substituted or unsubstituted t-butyl, halogen-substituted or unsubstituted isobutyl and halogen-substituted or unsubstituted sec-butyl, wherein the halogen substituents are one or more substituents independently selected from F, Cl, Br and I. Most preferred $R_3$ is n-propyl, 3,3,3-trifluoropropyl and isobutyl.

In intermediates of formula IIa, IIb or IIc particularly preferred $R_6$ is hydrogen or t-butoxycarbonyl.

In intermediates of formula IIa, IIb or IIc particularly preferred —Y— is —O— or —NH— with the proviso that when $R_2$ is hydrogen then Y is —O—. Most preferred Y is —O—.

In additional preferred embodiments, the preferences described above for the different substituents are combined. The present invention is also directed to such combinations of preferred substitutions in the formula IIa, IIb or IIc above.

Particularly preferred intermediates of formula IIa, Mb or Me are selected from:

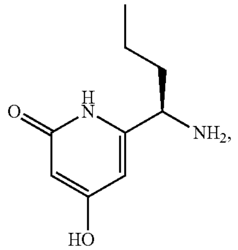,
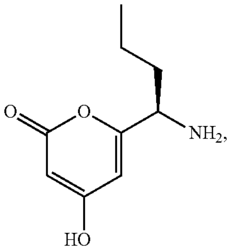,
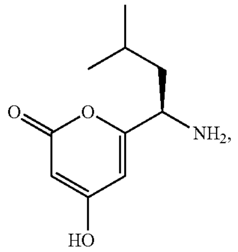,
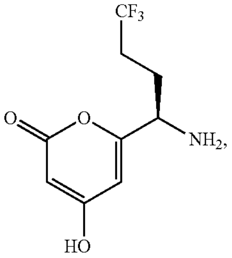,
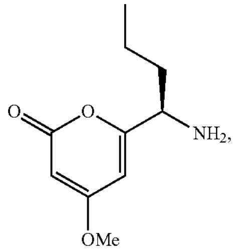,
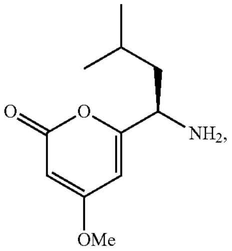,
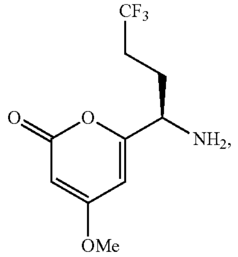,
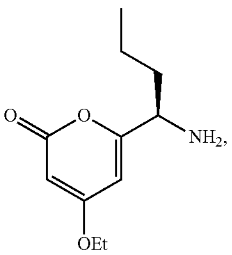,
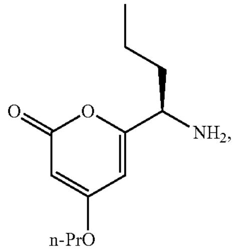,
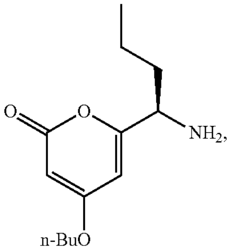,
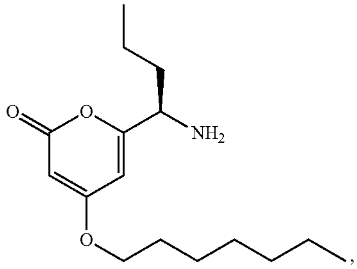, -continued

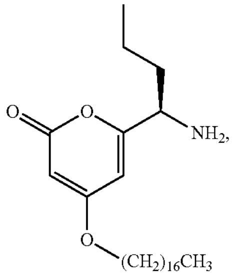,
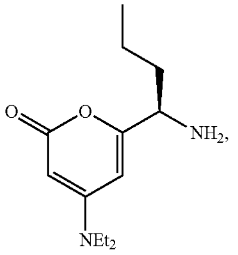,
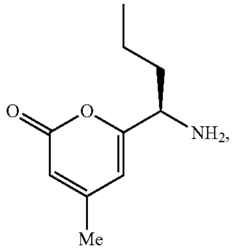,
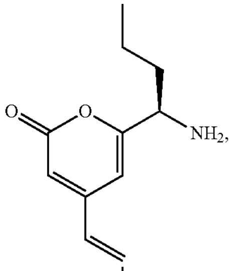,
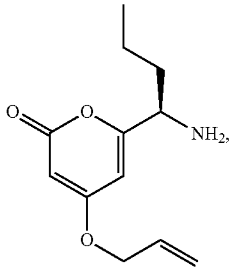,
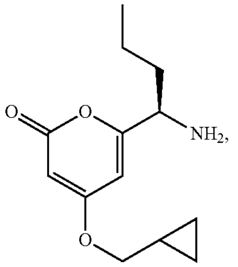,
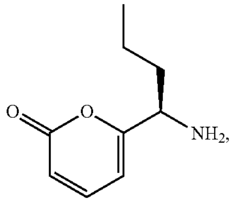,
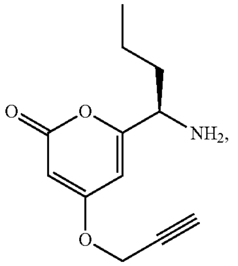,
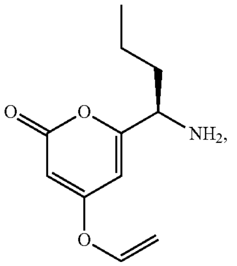, and
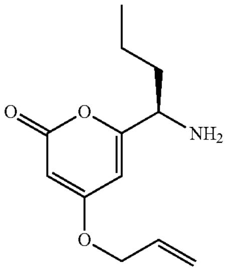

or salts thereof.

In addition, with this invention we provide novel intermediates of formula IIIa

IIIa

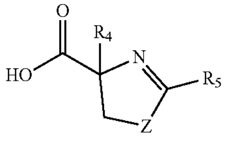

wherein $R_4$, $R_5$ and Z are as defined above in the previous disclosure of intermediates of formula IIIa.

Particularly preferred stereochemistry of said intermediates of formula IIIa is the following IIIb

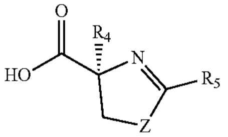

In intermediates of formula IIIa or IIIb, particularly preferred $R_4$ is unsubstituted $C_1$-$C_6$ alkyl. More preferred $R_4$ is selected from unsubstituted methyl, unsubstituted ethyl, unsubstituted n-propyl, unsubstituted isopropyl, unsubstituted n-butyl, unsubstituted t-butyl, unsubstituted isobutyl, and unsubstituted sec-butyl. Most preferred $R_4$ is methyl.

In intermediates of formula IIIa or IIIb, particularly preferred $R_5$ is selected from —$C(OR_e)_2R_g$ and a

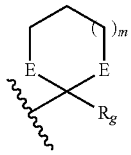

group where m is 0, 1 or 2, and each E group is independently selected from —O— and —S—; where each $R_g$ and $R_e$ groups are, independently, a substituted or unsubstituted $C_1$-$C_6$ alkyl group, wherein the optional substituents are one or more substituents $R_x$. Particularly preferred $R_g$ and $R_e$ are substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Particularly preferred m is 0 or 1 and particularly preferred E is —O—. More preferred $R_5$ is —$C(OR_e)_2R_g$, wherein $R_e$ and $R_g$ are independently selected from substituted or unsubstituted methyl, substituted or unsubstituted ethyl, substituted or unsubstituted n-propyl, substituted or unsubstituted isopropyl, substituted or unsubstituted n-butyl, substituted or unsubstituted t-butyl, substituted or unsubstituted isobutyl, and substituted or unsubstituted sec-butyl, wherein the optional substituents are one or more substituents $R_x$. Most preferred $R_5$ is —$C(OEt)_2Me$.

In intermediates of formula IIIa or IIIb particularly preferred Z group is —O— or —S—. Most preferred Z group is —S—.

In additional preferred embodiments, the preferences described above for the different substituents are combined. The present invention is also directed to such combinations or preferred substitutions in the formula IIIa and IIIb above.

A particularly preferred intermediate of formula IIIa is

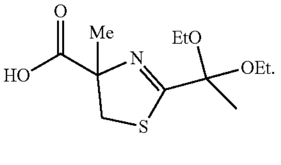 [SMILES: CCOC(C)(OCC)C1=NC(C)(C(=O)O)CS1].

Even more preferred intermediate of formula IIIb is

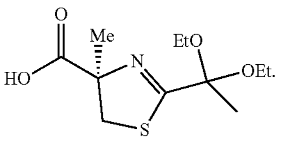

In the present description and definitions, when there are several groups R, $R_a$, $R_c$, $R_d$, $R_e$, $R_f$, R, $R_x$, $R_y$ or $R_z$ present in the compounds of the invention, and unless it is stated explicitly so, it should be understood that they can be each independently different within the given definition, i.e. $R_a$ does not represent necessarily the same group simultaneously in a given compound of the invention.

Compound 1 was originally isolated from a sponge of the order Lithistida, family Theonellidae, genus *Discodermia* (du Bocage 1869). This sponge was collected by hand using Rebreather diving system in Halmahera, Indonesia (2° 16.307' N/127° 44.466' E) at depths ranging between 6 and 73 m. A sample of the specimen was deposited at the Centre for Advanced Studies of Blanes in Girona, Spain, with the reference code HALM-706.

Description: massive irregular sponge, with many fouling organisms, red in color, approximately of 5 cm thick in average, 12×6 cm in diameter. Widely separated and irregularly distributed oscula, which are oval and measure 0.5-0.8 mm across. With smaller round pores, 0.20-0.25 mm in diameter, widely separated and irregularly distributed over the whole surface.

Meaascleres:

Discotriaenes 250-350 μm in diameter with short conical rhabd measuring 87-108 μm long.

Desmas tetraclones are about 300-450 μm in size and 100-110 μm thick.

Microscleres:

Acanthorhabds smaller ones are fusiform, massive, 15-22 μm long and 2-4.5 μm thick.

Skeletal Arrangement:

Surfaces are smooth and covered with a dense crust of ectosomal round to oval discotriaenes.

Desmas form a relatively dense skeleton with meshes about 500-600 μm wide.

Additionally, compounds of the invention can be obtained by total synthesis, or by modifying compound 1 already obtained from the natural source or by further modifying those already modified by using a variety of chemical reactions. Thus, hydroxyl groups can be acylated by standard coupling or acylation procedures, for instance by using acetic acid, acetyl chloride or acetic anhydride in pyridine or the like. Formate groups can be obtained by heating hydroxyl precursors with isocyanates. Flydroxyl groups can be converted into halogen groups through intermediate sulfonates for iodide, bromide or chloride, or directly using a sulfur trifluoride for fluorides; or they can be reduced to hydrogen by reduction of intermediate sulfonates. Flydroxyl groups can also be converted into alkoxy groups by alkylation using an alkyl bromide, iodide or sulfonate, or into amino lower alkoxy groups by using, for instance, a protected 2-bromoethylamine. Amido groups can be alkylated or acylated by standard alkylation or acylation procedures, for instance by using, respectively, KH and methyl iodide or acetyl chloride in pyridine or the like. Ester groups can be hydrolyzed to carboxylic acids or reduced to aldehyde or to alcohol. Carboxylic acids can be coupled with amines to provide amides by standard coupling or acylation procedures. When necessary, appropriate protecting groups can be used on the substituents to ensure that reactive groups are not affected. The procedures and reagent needed to prepare these derivatives are known to the skilled person and can be found in general textbooks such as March's Advanced Organic Chemistry $6^{th}$ Edition 2007, Wiley Interscience.

An important feature of the above described compounds of formula I, Ia or Ib is their bioactivity and in particular their cytotoxic activity against tumor cells. Thus, with this invention we provide pharmaceutical compositions of compounds of formula I, Ia or Ib, or a pharmaceutically acceptable salt or ester thereof that possess cytotoxic activities and their use as anticancer agents. The present invention further provides pharmaceutical compositions comprising a compound of formula I, Ia or Ib, or a pharmaceutically acceptable salt or ester thereof, with a pharmaceutically acceptable carrier or diluent.

Examples of pharmaceutical compositions include any solid (tablets, pills, capsules, granules, etc.) or liquid (solutions, suspensions or emulsions) composition for oral, topical or parenteral administration.

Administration of the compounds of formula I, Ia, or Ib or compositions of the present invention may be by any suitable method, such as intravenous infusion, oral preparations, and intraperitoneal and intravenous administration.

The correct dosage of the compounds will vary according to the particular formulation, the mode of application, and the particular situs, host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compound of the invention have anticancer activity against several cancer types which include, but are not limited to, solid tumours, lung cancer, colon cancer, breast cancer and pancreas cancer.

Thus, in alternative embodiments of the invention, the pharmaceutical composition comprising the compounds of formula I and the kits as defined above is for the treatment of solid tumours, lung cancer, colon cancer, breast cancer and pancreas cancer.

In the present application, by "cancer" it is meant to include tumors, neoplasias and any other malignant disease having as cause malignant tissue or cells.

The term "treating", as used herein, unless otherwise indicated, means reversing, attenuating, alleviating or inhibiting the progress of the disease or condition to which such term applies, or one or more symptoms of such disorder or condition. The term "treatment", as used herein, unless otherwise indicated, refers to the act of treating as "treating" is defined immediately above.

The compounds and compositions according to the present invention can be administered to an animal that has also undergone surgery as treatment for the cancer. In one embodiment of the present invention, the additional method of treatment is radiation therapy.

In a specific embodiment of the present invention, the compound or composition according to the present invention is administered concurrently with radiation therapy. In another specific embodiment, the radiation therapy is administered prior or subsequent to administration of the compound or composition of the present invention, preferably at least an hour, three hours, five hours, 12 hours, a day, a week, a month, more preferably several months (e.g. up to three months) prior or subsequent to administration of a compound or composition of the present invention.

Any radiation therapy protocol can be used depending upon the type of cancer to be treated. For example, but not by way of limitation x-ray radiation can be administered; in particular, high-energy megavoltage (radiation of greater than 1 MeV energy) can be used for deep tumors, and electron beam and orthovoltage x-ray radiation can be used for skin cancers. Gamma-ray emitting radioisotopes, such as radioactive isotopes of radium, cobalt and other elements can also be administered.

EXAMPLES

Example 1: Description of the Marine Organism and Collection Site

A sponge of the genus *Discodermia* du Bocage, 1869 was collected by hand using Rebreather diving system in Halmahera, Indonesia (2° 16.307' N/127° 44.466' E) at depths ranging between 6 and 73 m. The animal material was identified by Dr. María Jesús Uriz (Centre for Advanced Studies of Blanes). A sample of the specimen was deposited at the Centre for Advanced Studies of Blanes in Girona, Spain, with the reference code HALM-706.

Description: massive irregular sponge, with many fouling organisms, red in color, approximately of 5 cm thick in average, 12x6 cm in diameter. Widely separated and irregularly distributed oscula, which are oval and measure 0.5-0.8 mm across. With smaller round pores, 0.20-0.25 mm in diameter, widely separated and irregularly distributed over the whole surface.

Meaascleres:

Discotriaenes 250-350 μm in diameter with short conical rhabd measuring 87-108 μm long.

Desmas tetraclones are about 300-450 μm in size and 100-110 μm thick.

Microscleres:

Acanthorhabds smaller ones are fusiform, massive, 15-22 μm long, 2-4.5 μm thick.

Skeletal Arrangement:

Surfaces are smooth and covered with a dense crust of ectosomal round to oval discotriaenes.

Desmas form a relatively dense skeleton with meshes about 500-600 μm wide.

Example 2: Isolation of Compound 1

The frozen specimen of Example 1 was diced and extracted at room temperature under magnetic stirring, firstly with a mixture of 1:1 $CH_2Cl_2/CH_3OH$ (3×500 mL) and later with $H_2O$ (1×300 mL). Organic and aqueous extracts were evaporated to provide a dry residue of 5.3 g and 213 mg, respectively.

The organic extract was subjected to step gradient VLC on Lichroprep RP-18 from $H_2O$ to $CH_3OH$ and subsequently from $CH_3OH$ to $CH_2Cl_2$. The fraction eluted with $H_2O/CH_3OH$ 1:3 (80.4 mg) was subjected to semipreparative reversed phase HPLC (XBridge C18, 5 μm, 10×150 mm, isocratic $H_2O$+0.04% TFA/$CH_3CN$+0.04% TFA (65:35) for 3 minutes, gradient from 35 to 60% $CH_3CN$+0.04% TFA in 19 minutes and from 65 to 100% $CH_3CN$+0.04% TFA in 3 minutes, UV detection, flow 3 mL/min).

Fraction H5, with a retention time of 14.2 min, was subsequently purified with semipreparative reversed phase HPLC (SymmetryPrep C18, 7 μm, 7.8×150 mm, isocratic $H_2O$+0.04% TFA/$CH_3CN$+0.04% TFA (75:25) for 3 minutes, gradient from 25 to 80% $CH_3CN$+0.04% TFA in 18 min, UV detection, flow 2.8 mL/min) to afford compound 1 (14.1 mg, retention time 11.3 min).

Compound 1: White powder. (+)ESIMS m/z 382.3 $[M+H]^+$, 404.1 $[M+Na]^+$, 785.2 $[2M+Na]^+$, 157.2 $[C_6H_9N_2OS]^+$, 181.2 $[C_{10}H_{13}O_3]^+$; (+)HRESIMS m/z 382.1430 $[M+H]^+$ (cald for $C_{17}H_{24}N_3O_5S$ 382.1431, Δ=0.36 ppm); $^1H$ (500 MHz) and $^{13}C$ NMR (125 MHz) see Table 1.

TABLE 1

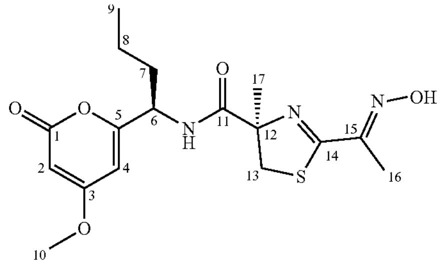

Compound 1

$^1H$ and $^{13}C$ NMR data of Compound 1 in $CD_3OD$ and $CD_3CN$.

| | CD$_3$OD | | CD$_3$CN | |
|---|---|---|---|---|
| No | δ $^{13}C$ | δ $^1H$, m, J (Hz) | δ $^{13}C$ | δ $^1H$, m, J (Hz) |
| 1 | 166.7 | — | 164.5 | — |
| 2 | 88.9 | 5.54, d (2.2) | 88.7 | 5.41, d (2.3) |
| 3 | 173.4 | — | 172.1 | — |
| 4 | 100.8 | 6.04, d (2.1) | 99.7 | 5.89, dd (2.3, 0.5) |
| 5 | 165.2 | — | 165.1 | — |
| 6 | 52.2 | 4.75, m | 51.6 | 4.66, m |
| 7 | 35.3 | 1.85, m | 35.0 | 1.78, m |
| 8 | 20.2 | 1.47, m | 19.8 | 1.42, m |
| | | 1.39, m | | 1.34, m |
| 9 | 13.8 | 0.99, t (7.4) | 13.8 | 0.94, t (7.4) |
| 10 | 57.0 | 3.84, s | 57.1 | 3.78, s |
| 11 | 176.6 | — | 174.8 | — |
| 12 | 85.6 | — | 85.3 | — |
| 13 | 40.6 | 3.54, d (11.5) | 40.7 | 3.54, d (11.6) |
| | | 3.18, d (11.5) | | 3.17, d (11.6) |
| 14 | 170.3 | — | 168.6 | — |
| 15 | 152.8 | — | 153.7 | — |
| 16 | 11.0 | 2.18, s | 11.3 | 2.17, s |
| 17 | 25.0 | 1.53, s | 25.1 | 1.48, s |
| NH | — | 7.84, d (8.7) | — | 7.07, d (85) |
| OH | — | 11.82, s* | — | 9.73, s |

*Assigned from spectrum acquired in $CD_3OH$.

Absolute configuration of the aminoacid residues in compound 1 was determined by Marfey's analysis (Marfey, P. Carlsberg Res. Commun. 1984, 49, 591-596).

0.3 mg of compound 1 were dissolved in 0.5 mL of 6N HCl in a sealed vial and heated at 110° C. for 16 h. The solvent was evaporated under a $N_2$ stream, the residue was dissolved in 50 μL of water, and 0.7 mg of fluorodinitrophenyl-5-L-alaninamide (L-FDAA, Marfey's reagent) in 100 μL of acetone and 40 μL of 1N aqueous $NaHCO_3$ were added. The resulting mixture was heated at 40° C. for 1 h and, after cooling at room temperature, neutralised with 100 μL of 2N HCl. Finally, the mixture was diluted with 700 μL of water and filtrated (45 μm filter) prior to HPLC-MS analysis.

Standards of all stereoisomers of the aminoacid residues present in compound 1 were derivatized in the same manner as the compound hydrolysed. Racemic methyl 4-methyl-2-(pyridin-3-yl)-4,5-dihydrothiazole-4-carboxylate was prepared following the procedure described by Singh et ah in J. Org. Chem. 2004, 69, 4551-4554.

Relative retention times to unreacted L-FDAA of both, the derivative hydrolysed and the derivative aminoacid standards, were determined by reversed phase HPLC-MS: Symmetry C18, 5 μm, 4.6×150 mm, gradient $H_2O$+0.04% TFA/$CH_3CN$+0.04% TFA from 20% to 50% $CH_3CN$+0.04% TFA in 30 min, UV (215 and 350 nm) and (+)ESIMS detection, flow 0.8 mL/min.

Comparison of these retention times unambiguously confirmed the presence in compound 1 of 2-methyl-L-cysteine.

Norvaline residue could not be obtained by simple hydrolysis of compound 1, and therefore the compound was first subjected to an oxidative ozonolysis protocol. To do that, a stream of ozone in $O_2$ was bubbled through a solution of compound 1 (0.3 mg) in $CH_2Cl_2$ (3 mL) for 5 min. The solvent was evaporated under a $N_2$ stream and the residue was dissolved in 2 mL of hydrogen peroxide (35%):formic acid (1:9) at 0° C. and kept for 2 h. Then, the solvent was removed under a stream of $N_2$; the resultant residue was hydrolyzed in acidic conditions and immediately subjected to Marfey's derivatization as described above. Finally, it was analyzed by HPLC-MS in same conditions previously depicted for non-oxidized sample.

Comparison of relative retention times of authentic standards of L- and D-norvaline derivatized following de same procedure with the aminoacid residue of natural sample confirmed the presence of D-norvaline in compound 1.

These results have been confirmed by the total synthesis of compound 1 described in Example 7.

Example 3: Scale-Up of Isolation of Compound 1

A second group of samples of the specimen of Example 1 (926 g) was diced and extracted at room temperature under magnetic stirring, firstly with a mixture of 1:1 $CH_2Cl_2$/$CH_3OH$ (6×500 mL) and later with $H_2O$ (2×300 mL). Organic extract was evaporated to provide three dry residues A (19.5 g), B (16.8 g) and C (10.7 g), while the aqueous extract gave a residue of 2.4 g.

Residues A, B and C were subjected to step gradient VLC on Lichroprep RP-18 from $H_2O$ to $CH_3OH$ and subsequently from $CH_3OH$ to $CH_2Cl_2$. For residue A, fractions eluted with $H_2O/CH_3OH$ 1:3 (172.0 mg), $CH_3OH$ (800.0 mg) and $CH_3OH/CH_2Cl_2$ 1:1 (619.8 mg) contained compound 1. For residues B and C, fractions eluted with $CH_3OH/H_2O$ 1:1 (445.6 mg B, 225.1 mg C), $CH_3OH/H_2O$ 3:1 (286.3 mg B, 149.5 mg C), $CH_3OH$ (2.1 g B, 962.5 mg C) and $CH_3OH/CH_2Cl_2$ 1:1 (3.26 g B, 618.8 mg C) were the ones containing compound 1. All these fractions were subjected to flash chromatography normal phase (12 g Silica column, isocratic n-Hex/EtOAc 70:30 for 8-9 minutes, from 30 to 70% EtOAc in 27-29 minutes, isocratic 70% EtOAc for 6-8 minutes and from 70 to 100% EtOAc in 4-7 minutes, wavelength 254 and 280 nm, flow 30 mL/min) to afford Compound 1 (196 mg, retention time 8-13 min).

Example 4: Methylation of Compound 1

To a solution of Compound 1 (1.4 mg) in anhydrous DMF 1.5 mL) was added $Cs_2CO_3$ (5 mg) and methyl iodide (40 μL). The reaction mixture was stirred at room temperature overnight. Then, the solution was subjected to analytical HPLC (Symmetry C18, 5 μm, 4.6×150 mm, isocratic $H_2O$+0.04% TFA/$CH_3CN$+0.04% TFA (75:25) for 3 minutes, gradient from 25 to 80% $CH_3CN$+0.04% TFA in 18 min, UV detection, flow 1 mL/min) to give Compound 2 (0.5 mg).

Compound 2: White powder. (+)ESIMS m/z 396.2 $[M+H]^+$, 418.1 $[M+Na]^+$; (+)HRESIMS m/z 396.1582 $[M+H]^+$ (cald for $C_{18}H_{26}N_3O_5S$ 396.1588, Δ=1.5 ppm); $^1H$ (500 MHz) see Table 2.

TABLE 2

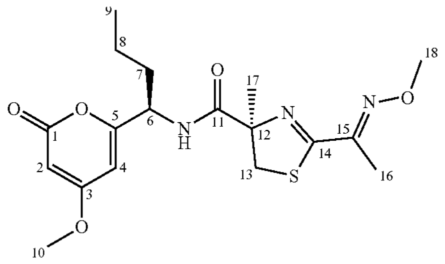

Compound 2

$^1H$ NMR data of compound 2 in $CD_3OH$ and $CDCl_3$.

| No | $CD_3OH$ δ $^1H$, m, J (Hz) | $CDCl_3$ δ $^1H$, m, J (Hz) |
|---|---|---|
| 1 | — | — |
| 2 | 5.54, d (2.2) | 5.43, d (2.2) |
| 3 | — | — |
| 4 | 6.03, dd (2.2, 0.7) | 5.89, d (2.2) |
| 5 | — | — |
| 6 | * | 4.73, q (7.94) |
| 7 | 1.84, m | 1.88, m |
| 8 | 1.47, m | 1.37, m |
| | 1.38 m | |
| 9 | 0.98, t (7.4) | 0.96, t (7.3) |
| 10 | 3.84, s | 3.79, s |
| 11 | — | — |
| 12 | — | — |
| 13 | 3.56, d (11.7) | 3.53, d (11.6) |
| | 3.19, d (11.7) | 3.21, d (11.6) |
| 14 | — | — |
| 15 | — | — |
| 16 | 2.18, s | 2.18, s |
| 17 | 1.52, s | 1.52, s |
| 18 | 3.99, s | 4.03, s |
| NH | 7.84, d (8.8) | 7.11, d (8.8) |

* Overlapped with $H_2O$ signal in $CH_3OH$

Example 5: Synthesis of Intermediates of Formula II

Scheme 2 provides some examples of the synthesis of intermediates of formula II and of some (S)-analogs used to confirm the stereochemistry of compound 1.

Scheme 2

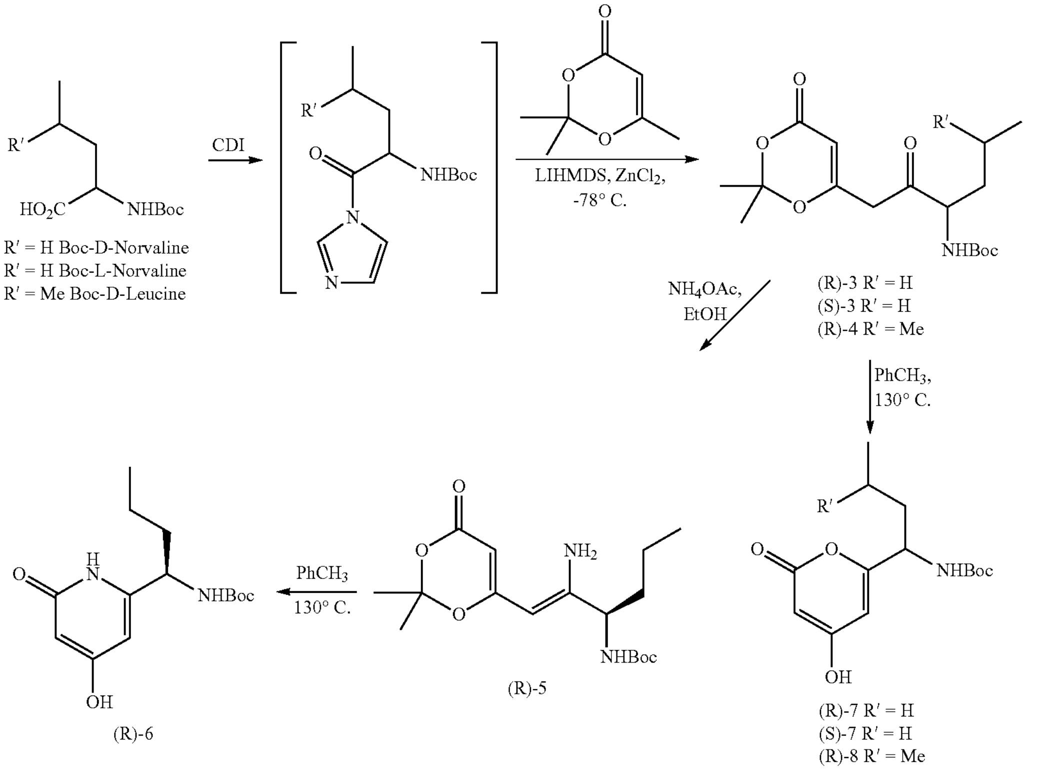

Synthesis of Intermediate (R)-3

(R)-3

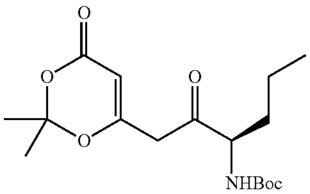

To a solution of Boc-D-norvaline (20 g, 92.0 mmol, commercial chemical from Chem-impex) in 2-Me-THF (368 mL, 4 mL/mmol) under nitrogen atmosphere at 23° C. was added 1,1'-carbonyldiimidazole (CDI) (15.7 g, 96.6 mmol, 1.05 equiv). The reaction mixture was for 2 hours at 23° C. A solution of 2,2,6-trimethyl-4H-1,3-dioxin-4-one (30.55 mL, 230 mmol, 2.5 equiv) in 2-Me-THF (368 mL, 4 mL/mmol) was slowly added to a precooled at −78° C. dilution of LiHMDS (368 mL, 1.0 M in THF, 368 mmol, 4.0 equiv) in 2-Me-THF (368 mL, 4 mL/mmol). The reaction mixture was stirred at −78° C. for 1 hour. $ZnCl_2$ (31.3 g, 230 mmol, 2.5 equiv) was added in one portion and the reaction mixture was stirred at −78° C. for 30 minutes. Finally, the solution of the intermediate previously prepared was added, by cannula, at −78° C. The reaction mixture was stirred at −78° C. for 4 hours. An aqueous saturated solution of $NH_4Cl$ was added and the aqueous layers were extracted with EtOAc. The combined organic layers were dried over anhydrous $NaSO_4$, filtered and concentrated under vacuum. The crude obtained was purified by column chromatography ($CH_2Cl_2$:EtOAc, 9:1) to give pure (R)-3 (12.9 g, 41% yield).

$^1H$ NMR (300 MHz, $CDCl_3$): δ 5.35 (s, 1H), 5.02 (d, J=7.9 Hz, 1H), 4.27 (td, J=7.9, 4.7 Hz, 1H), 3.43 (s, 2H), 1.77 (m, 2H), 1.68 (s, 6H), 1.58-1.28 (m, 2H), 1.43 (s, 9H), 0.94 (t, J=7.2 Hz, 3H).

$^{13}C$ NMR (75 MHz, $CDCl_3$): δ 203.2, 164.5, 160.8, 155.7, 107.4, 97.1, 80.4, 59.8, 43.9, 33.0, 28.5, 25.2, 18.8, 13.9.

MS (ES): m/z 364.3 $[M+Na]^+$.

$R_f$: 0.13 (Hex:EtOAc 4:1).

Synthesis of Analog (S)-3

(S)-3

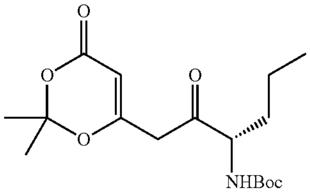

In a first flask, CDI (3.9 g, 24.15 mmol) was added in portions to a solution of Boc-L-norvaline (5.0 g, 23 mmol, commercial chemical from Chem-impex) in 2-Me-THF (92 mL), with gas evolution. This mixture was stirred for 2 h. In another flask, at −78° C. 2,2,6-trimethyl-4H-1,3-dioxin-4-one (7.6 mL, 57 mmol) in 2-Me-THF (92 mL) was added slowly to a solution of LiHMDS (57.5 mL, 1.0 M in THF, 57.5 mmol) in 2-Me-THF (92 mL). After stirring at the same temperature for 1 h, the first mixture was added via canula. The reaction was stirring at −78° C. for 4 h and then quenched with saturated aqueous solution of $NH_4Cl$. Extraction with EtOAc, and dryness of the organic layers over $Na_2SO_4$ gave a crude which was purified by flash chromatography on silica gel (hexane/EtOAc 9/1 to 7/3) to afford (S)-3 (2.0 g, 64% yield).

$^1$H NMR (300 MHz, $CDCl_3$): δ 5.35 (s, 1H), 5.02 (d, J=7.9 Hz, 1H), 4.27 (td, J=7.9, 4.7 Hz, 1H), 3.43 (s, 2H), 1.77 (m, 2H), 1.69 (s, 6H), 1.58-1.28 (m, 2H), 1.43 (s, 9H), 0.94 (t, J=7.2 Hz, 3H).

$^{13}$C NMR (75 MHz, $CDCl_3$): δ 203.2, 164.5, 160.8, 155.7, 107.4, 97.1, 80.4, 59.8, 43.9, 33.0, 28.5, 25.2, 18.8, 13.9.

MS (ES): m/z 364.3 $[M+Na]^+$, 705.2 $[2M+Na]^+$.

$R_f$: 0.5 (Hex:EtOAc 6:4).

Synthesis of Intermediate (R)-4

(R)-4

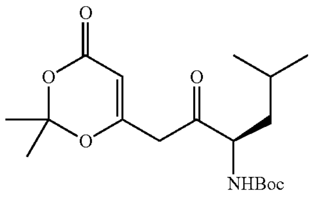

In a first flask, CDI (1.66 g, 10.29 mmol) was added in portions to a solution of Boc-D-leucine (2.27 g, 9.8 mmol) in $Et_2O$ (40 mL), with gas evolution. This mixture was stirred for 2 h. In another flask, at −78° C., a solution of 2,2,6-trimethyl-4H-1,3-dioxin-4-one (4.2 mL, 29.4 mmol) in $Et_2O$ (30 mL) was added slowly to a solution of LiHMDS (29.4 mL, 1.0 M in THF, 29.4 mmol) in $Et_2O$ (29.4 mL). After stirring at the same temperature for 1 h, $ZnCl_2$ (2.67 g, 29.4 mmol) was added in one portion. After 30 min, the first mixture was added via canula. The reaction was stirring at −78° C. for 4 h and then quenched with saturated aqueous solution of $NH_4Cl$. Extraction with EtOAc, and dryness of the organic layers over $Na_2SO_4$ gave a crude which was purified by flash chromatography on silica gel ($CH_2Cl_2$/EtOAc 9/1) to afford pure (R)-4 (0.42 g, 12% yield).

$^1$H NMR (300 MHz, $CDCl_3$): δ 5.35 (s, 1H), 4.87 (d, J=8.0 Hz, 1H), 4.38-4.21 (m, 1H), 3.44 (d, J=3.5 Hz, 2H), 1.70 (s, 6H), 1.55 (m, 2H), 1.44 (s, 9H), 1.37 (m, 1H), 0.96 (d, J=6.5 Hz, 6H).

Synthesis of Intermediate (R)-5

(R)-5

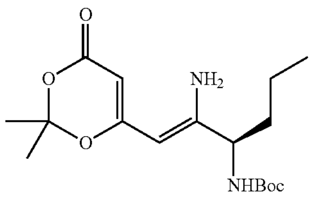

A solution of (R)-3 (330 mg, 0.97 mmol), $NH_4OAc$ (373 mg, 4.85 mmol) in ethanol (4 mL) was stirred at 23° C. for 24 h. After evaporating the solvent, the crude was triturated with EtOAc to NHBoc remove the solids by filtration. The solvent was evaporated to obtain (R)-5 (329 mg, 100% yield).

$^1$H NMR (400 MHz, $CDCl_3$): δ 5.53 (s, 1H), 4.92 (s, 1H), 4.75 (s, 1H), 4.53 (s, 1H), 3.91 (s, 1H), 1.74 (s, 6H), 1.73-1.53 (m, 1H), 1.44 (s, 2H), 1.43 (s, 9H), 1.49-1.31 (m, 1H), 0.94 (t, J=7.3 Hz, 3H).

$^{13}$C NMR (101 MHz, $CDCl_3$): δ 168.0, 162.9, 157.5, 155.9, 105.7, 86.6, 28.4, 25.7, 25.5, 19.5, 13.8.

MS (ES): m/z 341.3 $[M+H]^+$.

Synthesis of Intermediate (R)-6

(R)-6

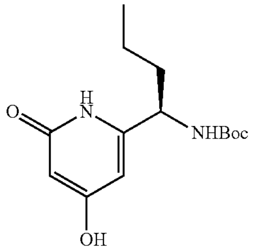

A solution of (R)-5 (329 mg, 0.96 mmol) in toluene (100 mL) was stirred in a bath at 130° C. for 2 h. Evaporation of the solvent under vacuo gave a crude which purified by flash chromatography over silica gel ($CH_2Cl_2/CH_3OH$ 98/2) to give (R)-6 (93 mg, 34% yield).

$^1$H NMR (500 MHz, $CD_3OD$): δ 5.95 (d, J=2.21 Hz, 1H), 5.66 (d, J=2.2 Hz, 1H), 4.36 (s, 1H), 1.71-1.55 (m, 4H), 1.43 (s, 12H), 0.95 (t, J=7.4 Hz, 3H).

$^{13}$C NMR (125 MHz, $CD_3OD$): δ 171.1, 168.0, 157.8, 153.4, 99.2, 80.7, 53.5, 37.7, 32.8, 28.7, 23.7, 20.5, 14.4, 13.9.

MS (ES): m/z 283.3 $[M+H]^+$.

$R_f$: 0.26 ($CH_2Cl_2$:MeOH 9:1).

Synthesis of Intermediate (R)-7

(R)-7

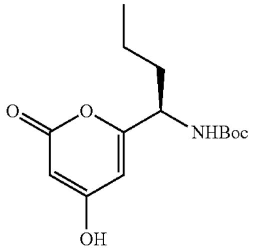

(R)-3 (10.74 g, 31.5 mmol) was dissolved in toluene (315 mL, 10 mL/mmol) and heated in a bath at 130° C. for 30 minutes. Evaporation of the solvent under vacuum afforded (R)-7 crude (8.91 g) that was used in the next step without further purification.

$^1$H NMR (400 MHz, $CDCl_3$): δ 10.50 (s, 1H), 6.09 (d, J=1.8 Hz, 1H), 5.56 (s, 1H), 5.23 (d, J=8.5 Hz, 1H), 4.36 (q, J=7.8 Hz, 1H), 1.78 (s, 1H), 1.67 (s, 1H), 1.43 (s, 9H), 0.92 (t, J=7.3 Hz, 3H).

$^{13}$C NMR (75 MHz, $CDCl_3$): δ 171.6, 166.9, 165.2, 155.8, 129.2, 128.4, 125.5, 100.9, 90.9, 80.9, 53.0, 35.3, 28.5, 19.3, 13.8.

MS (ES): m/z 306.1 $[M+Na]^+$.

$R_f$: 0.35 ($CH_2Cl_2$:MeOH 9:1).

Optical rotation: $[\alpha_D]$ +101.6 (c 0.018, MeOH).

Synthesis of Analog (S)-7

A solution of (S)-3 (700 mg, 2.05 mmol) in toluene (12 mL) was stirred in a bath at 130° C. for 30 min. Evaporation of the solvent under vacuum gave a crude of (S)-7 which was used in the next step without purification.

$^1H$ NMR (300 MHz, $CDCl_3$): δ 6.08 (d, J=2.1 Hz, 1H), 5.56 (d, J=2.0 Hz, 1H), 5.16 (d, J=8.5 Hz, 1H), 4.50-4.27 (m, 1H), 1.90-1.57 (m, 2H), 1.50-1.38 (m, 10H), 1.00-0.81 (m, 3H).

(S)-7

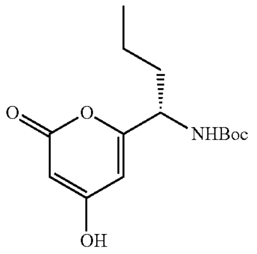

Synthesis of Intermediate (R)-8

(R)-8

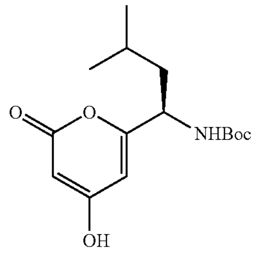

A solution of (R)-4 (400 mg, 1.12 mmol) in toluene (120 mL) was stirred in a bath at 130° C. for 30 min. Evaporation of the solvent under vacuum gave of (R)-8 crude which was used in the next step without purification.

$^1H$ NMR (300 MHz, $CDCl_3$): δ 6.09 (s, 1H), 5.55 (s, 1H), 5.27 (d, J=10.6 Hz, 2H), 4.41 (m, 1H), 1.59 (m, 3H), 1.41 (s, 9H), 0.91 (m, 6H).

MS (ES): m/z 320.3 $[M+Na]^+$.

Scheme 3 provides more examples of the synthesis of intermediates of formula II and of some (S)-analogs used to confirm the stereochemistry of compound 1.

Scheme 3

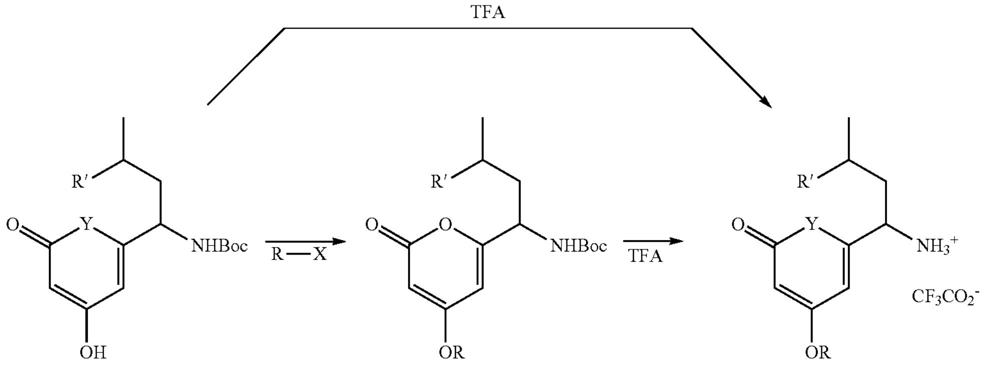

(R)-6 Y = NH, R′ = H
(R)-7 Y = O, R′ = H
(S)-7 Y = O, R′ = H
(R)-8 Y = O, R′ = Me (R)-9 R′ = H, R = Me
(S)-9 R′ = H, R = Me
(R)-10 R′ = Me, R = Me
(R)-11 R′ = H, R = Et
(R)-12 R′ = H, R = n-Pr
(R)-13 R′ = H, R = n-Bu
(R)-14 R′ = H, R = n-heptyl
(R)-15 R′ = H, R = n-heptadecyl
(R)-16 R′ = H, R = allyl
(R)-17 R′ = H, R = propargyl
(R)-18 R′ = H, R = cyclopropylmethyl
(R)-19 R′ = H, R = Ts
(R)-20 R′ = H, R = Ns (R)-21 Y = NH, R′ = H, R = H
(R)-22 Y = O, R′ = H, R = H
(R)-23 Y = O, R′ = H, R = Me
(S)-23 Y = O, R′ = H, R = Me
(R)-24 Y = O, R′ = Me, R = Me
(R)-25 Y = O, R′ = H, R = Et
(R)-26 Y = O, R′ = H, R = n-Pr
(R)-27 Y = O, R′ = H, R = n-Bu
(R)-28 Y = O, R′ = H, R = n-heptyl
(R)-29 Y = O, R′ = H, R = n-heptadecyl
(R)-30 Y = O, R′ = H, R = allyl
(R)-31 Y = O, R′ = H, R = propargyl
(R)-32 Y = O, R′ = H, R = cyclopropylmethyl Synthesis of Intermediate (R)-9

(R)-9

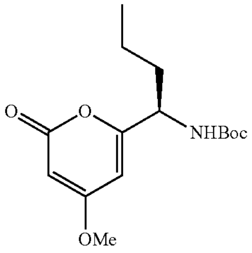

To a solution of (R)-7 (8.92 g, 31.46 mmol) in acetone (314.6 mL, 10 mL/mmol) under nitrogen atmosphere at 23° C. was added $K_2CO_3$ (21.74 g, 157.3 mmol, 5.0 equiv) and dimethyl sulfate (14.9 mL, 157.3 mmol, 5.0 equiv). The reaction mixture was stirred for 2 hours at 23° C., filtered over Celite®, washed with $CH_2Cl_2$, and the solvent was removed under vacuum. The crude obtained was purified by column chromatography (Hexane:EtOAc, from 9:1 to 7:3) to give (R)-9 pure (5.39 g, 60% yield for two steps).

$^1H$ NMR (400 MHz, $CDCl_3$): δ 5.93 (d, J=2.2 Hz, 1H), 5.42 (d, J=2.2 Hz, 1H), 5.30 (s, 1H), 4.88 (d, J=8.8 Hz, 1H), 4.38 (q, J=8.0 Hz, 1H), 3.80 (s, 3H), 1.79 (ddt, J=13.3, 9.3, 6.5 Hz, 1H), 1.70-1.61 (m, 1H), 1.43 (s, 9H), 1.42-1.21 (m, 2H), 0.93 (t, J=7.3 Hz, 3H).

$^{13}C$ NMR (75 MHz, $CDCl_3$): δ 171.3, 164.6, 163.7, 155.1, 103.3, 100.0, 88.5, 56.2, 53.6, 52.7, 35.4, 29.9, 28.5, 19.3, 13.8.

MS (ES): m/z 320.0 $[M+Na]^+$.

$R_f$: 0.3 (Hex:EtOAc 6:4).

Synthesis of Analog (S)-9

(S)-9

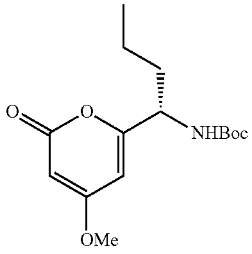

A mixture of (S)-7 (560 mg, 1.98 mmol), acetone (20 mL), $K_2CO_3$ (1.37 g, 9.88 mmol) and dimethyl sulfate (0.94 mL, 9.88 mmol) was stirred at 23° C. for 2 h. Filtration over Celite® and washing with $CH_2Cl_2$ gave a crude which was purified by flash chromatography on silica gel (hexane/EtOAc 8/2 to 6/4) to yield (S)-9 (268 mg, 48% yield for 2 steps).

$^1H$ NMR (300 MHz, $CDCl_3$): δ 5.91 (d, J=2.2 Hz, 1H), 5.40 (dd, J=2.2, 0.6 Hz, 1H), 4.94 (d, J=8.8 Hz, 1H), 4.43-4.24 (m, 1H), 3.77 (d, J=0.6 Hz, 3H), 1.75 (ddd, J=13.4, 9.4, 6.8 Hz, 1H), 1.66-1.56 (m, 1H), 1.39 (d, J=0.6 Hz, 10H), 1.31 (ddd, J=8.7, 4.9, 1.5 Hz, 1H), 0.89 (dd, J=7.7, 7.0 Hz, 3H).

Synthesis of Intermediate (R)-10

(R)-10

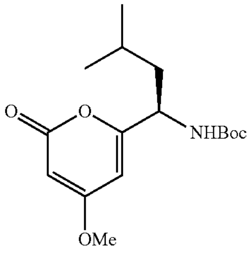

A mixture of (R)-8 (79 mg, 0.26 mmol), acetone (2.6 mL), $K_2CO_3$ (183 g, 1.33 mmol) and dimethyl sulfate (0.13 mL, 1.33 mmol) was stirred at 23° C. for 2 h. Filtration over Celite® and washing with $CH_2Cl_2$ gave a crude which was purified by flash chromatography on silica gel (hexane/EtOAc 8/2 to 6/4) to yield (R)-10 (74 mg, 89% yield for 2 steps).

$^1H$ NMR (300 MHz, $CDCl_3$): δ 5.94 (d, J=2.2 Hz, 1H), 5.41 (d, J=2.2 Hz, 1H), 4.87 (d, J=8.9 Hz, 1H), 4.43 (q, J=7.9 Hz, 1H), 3.78 (s, 3H), 1.61 (m, 3H), 1.41 (s, 9H), 0.97-0.85 (m, 6H).

Synthesis of Intermediate (R)-11

(R)-11

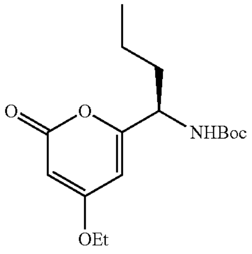

A mixture of (R)-7 (80 mg, 0.28 mmol), $CH_2Cl_2$ (5.6 mL), $Ag_2O$ (130 mg, 0.56 mmol) and iodoethane (0.67 mL, 8.4 mmol) was stirred at 23° C. for 24 h. Filtration over Celite® and washing with $CH_2Cl_2$ gave a crude which was purified by flash chromatography on silica gel (hexane/EtOAc 8/2 to 6/4) to yield (R)-11 (37 mg, 42% yield for 2 steps).

$^1H$ NMR (300 MHz, $CDCl_3$): δ 5.91 (d, J=2.2 Hz, 1H), 5.37 (d, J=2.2 Hz, 1H), 4.92 (d, J=8.9 Hz, 1H), 4.35 (q, J=7.8 Hz, 1H), 3.99 (q, J=7.0 Hz, 2H), 1.76 (dq, J=9.2, 6.8 Hz, 1H), 1.62 (td, J=8.3, 7.4, 3.4 Hz, 1H), 1.40 (s, 9H), 1.45-1.17 (m, 4H), 0.90 (t, J=7.3 Hz, 3H).

Synthesis of Intermediate (R)-12

(R)-12

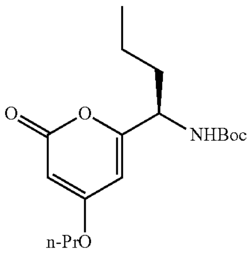

A mixture of (R)-7 (50 mg, 0.176 mmol), acetone (1.8 mL), $K_2CO_3$ (121 mg, 0.88 mmol) and iodopropane (0.2 mL, 1.76 mmol) was stirred at 23° C. for 5 h. Filtration over Celite® and washing with $CH_2Cl_2$ gave a crude which was purified by flash chromatography on silica gel (hexane/EtOAc 8/2 to 6/4) to yield (R)-12 (35 mg, 100% yield for 2 steps).

$^1$H NMR (300 MHz, $CDCl_3$): δ 5.93 (d, J=2.2 Hz, 1H), 5.39 (dd, J=2.3, 0.8 Hz, 1H), 4.98-4.81 (m, 1H), 4.37 (q, J=7.9 Hz, 1H), 3.89 (t, J=6.5 Hz, 2H), 1.79 (m, 4H), 1.42 (s, 9H), 1.40-1.19 (m, 2H), 1.01 (td, J=7.5, 0.8 Hz, 3H), 0.92 (td, J=7.3, 0.8 Hz, 3H).

Synthesis of Intermediate (R)-13

(R)-13

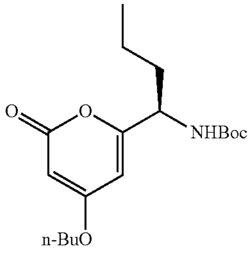

A mixture of (R)-7 (50 mg, 0.176 mmol), acetone (1.8 mL), $K_2CO_3$ (121 mg, 0.88 mmol) and iodobutane (0.16 mL, 1.76 mmol) was stirred at 23° C. for 5 h. Filtration over Celite® and washing with $CH_2Cl_2$ gave a crude which was purified by flash chromatography on silica gel (hexane/EtOAc 8/2 to 6/4) to yield (R)-13 (34 mg, 100% yield for 2 steps).

$^1$H NMR (400 MHz, $CDCl_3$): δ 5.92 (d, J=2.2 Hz, 1H), 5.39 (d, J=2.2 Hz, 1H), 4.88 (d, J=8.9 Hz, 1H), 4.37 (q, J=7.9 Hz, 1H), 3.93 (t, J=6.5 Hz, 2H), 1.86-1.66 (m, 3H), 1.62 (s, 1H), 1.54-1.27 (m, 11H), 0.94 (dt, J=13.8, 7.4 Hz, 6H).

MS (ES): m/z 362.3 $[M+Na]^+$, 701.5 $[2M+Na]^+$.

$R_f$: 0.37 (Hex:EtOAc 7:3).

Synthesis of Intermediate (R)-14

(R)-14

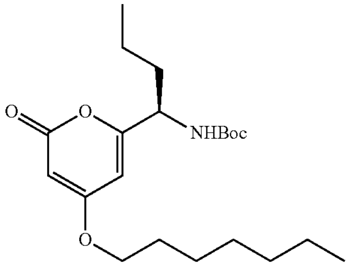

(R)-7 (69 mg) was dissolved in acetone (2.4 mL) and then $Cs_2CO_3$ (119 mg) and 1-bromoheptane (57 μL) were added. This suspension was refluxed for 2 h. Then the reaction mixture was allowed to cool to 23° C., filtered through a plug of Celite® and washed with EtOAc (3×10 mL) and evaporated to dryness. Purification by flash chromatography over silica gel ($CH_2Cl_2$/EtOAc 100:0 to 95:5) yielded (R)-14 (78 mg, 84% yield for 2 steps).

$^1$H NMR (400 MHz, $CDCl_3$): δ 5.92 (d, J=2.2 Hz, 1H), 5.38 (d, J=2.2 Hz, 1H), 4.90 (d, J=8.9 Hz, 1H), 4.36 (q, J=7.8 Hz, 1H), 3.91 (t, J=6.5 Hz, 2H), 1.85-1.68 (m, 3H), 1.71-1.55 (m, 1H), 1.42 (s, 9H), 1.41-1.21 (m, 10H), 0.98-0.83 (m, 6H).

$^{13}$C NMR (100 MHz, $CDCl_3$): δ 170.4, 164.6, 163.3, 154.9, 100.0, 88.6, 80.0, 69.0, 52.5, 35.2, 31.6, 28.8, 28.4, 28.3, 25.7, 22.5, 19.0, 14.0, 13.5.

Synthesis of Intermediate (R)-15

(R)-15

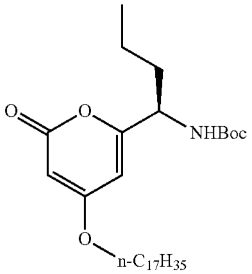

To a solution of (R)-7 (63 mg, 0.222 mmol) in acetone (2.2 mL) was added $Cs_2CO_3$ (109 mg, 0.334 mmol) and 1-bromoheptadecane (106 mg, 0.334 mmol) at 23° C. The reaction mixture was refluxed for 4 h. The reaction mixture was cooed to 23° C., filtrated over Celite® and washed with EtOAc. The crude obtained was purified by flash chromatography on silica gel ($CH_2Cl_2$:EtOAc from 100:0 to 95:5) to field (R)-15 (93 mg, 80% yield).

$^1$H NMR (400 MHz, $CDCl_3$): δ 5.92 (d, J=2.2 Hz, 1H), 5.38 (d, J=2.2 Hz, 1H), 4.90 (d, J=8.9 Hz, 1H), 4.36 (q, J=7.9 Hz, 1H), 3.91 (t, J=6.5 Hz, 2H), 1.83-1.72 (m, 3H), 1.76-1.55 (m, 1H), 1.42 (s, 9H), 1.47-1.22 (m, 30H), 0.96-0.80 (m, 6H).

$^{13}$C NMR (100 MHz, $CDCl_3$): δ 170.4, 164.5, 163.3, 154.9, 100.0, 88.6, 80.0, 69.1, 52.5, 35.2, 31.9, 29.7, 29.6 (×2), 29.5 (×2), 29.3, 29.2 (×2), 28.4, 28.3, 25.8, 22.7, 19.0, 14.1, 13.6.

Synthesis of Intermediate (R)-16

(R)-16

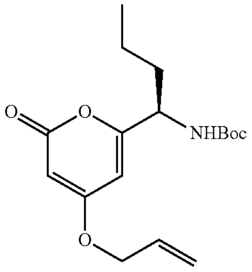

To a solution of (R)-7 (7.05 g, 24.88 mmol) in acetone (250 mL) was added $Cs_2CO_3$ (12.16 g, 37.32 mmol) and allyl bromide (3.23 mL, 37.32 mmol) at 23° C. The reaction mixture was refluxed for 1 h. Filtration over Celite® and washing with EtOAc gave a crude which was purified in an automatic system for flash chromatography on ($SiO_2$, Hex:EtOAc 70:30) to field (R)-16 (5.0 g, 62% yield).

$^1$H NMR (400 MHz, $CDCl_3$): δ 6.03-5.91 (m, 2H), 5.46-5.27 (m, 3H), 4.87 (d, J=9.0 Hz, 1H), 4.50 (d, J=5.5 Hz, 2H), 4.37 (m, 1H), 1.79 (ddt, J=13.4, 9.5, 6.6 Hz, 2H), 1.43 (d, J=0.5 Hz, 9H), 1.33 (td, J=15.1, 7.4 Hz, 2H), 1.00-0.81 (m, 3H).

$^{13}$C NMR (100 MHz, $CDCl_3$): δ 169.8, 164.3, 163.7, 154.9, 130.6, 119.4, 99.8, 89.1, 80.0, 69.5, 52.5, 35.1, 28.3, 19.0, 13.5.

MS (ES+): m/z 346.3 $[M+Na]^+$.

Optical rotation: $[\alpha_D]$ +82.1 (c 0.045, MeOH).

$R_f$: 0.31 (Hex:EtOAc 7:3).

Synthesis of Intermediate (R)-17

(R)-17

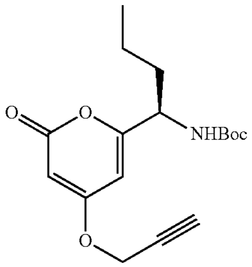

To a solution of (R)-7 (2.88 g, 10.16 mmol) in acetone (102 mL) was added $Cs_2CO_3$ (4.97 g, 15.25 mmol) and propargyl bromide (1.7 mL, 15.25 mmol) at 23° C. The reaction mixture was refluxed for 2 h. The reaction mixture was cooled to 23° C., filtered over Celite® and washed with EtOAc. The crude obtained was purified in an automatic system for flash chromatography on ($SiO_2$, $CH_2Cl_2$:EtOAc from 99:1 to 95:5) to field (R)-17 (2.31 g, 71% yield).

$^1$H NMR (400 MHz, $CDCl_3$): δ 5.96 (d, J=2.2 Hz, 1H), 5.55 (dd, J=2.4, 0.7 Hz, 1H), 4.95 (d, J=8.8 Hz, 1H), 4.66 (d, J=2.5 Hz, 2H), 4.42 (q, J=7.8 Hz, 1H), 2.62 (td, J=2.6, 0.9 Hz, 1H), 1.87-1.71 (m, 1H), 1.74-1.60 (m, 1H), 1.42 (s, 9H), 1.40-1.21 (m, 2H), 0.93 (t, J=7.3 Hz, 3H).

$^{13}$C NMR (100 MHz, $CDCl_3$): δ 168.9, 164.0, 154.9, 99.5, 89.8, 80.1, 77.6, 75.7, 56.4, 52.5, 35.1, 28.3, 19.0, 13.5.

MS (ES+): m/z 344.2 $[M+Na]^+$.

$R_f$: 0.37 (Hex:EtOAc 7:3).

Synthesis of Intermediate (R)-18

(R)-18

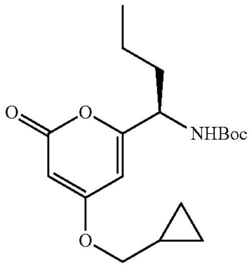

To a solution of (R)-7 (9.9 g, 34.94 mmol) in DMF (800 mL) was added $K_2CO_3$ (9.66 g, 69.89 mmol) at 23° C. The reaction mixture was stirred for 30 min at 23° C. and cyclopropylmethyl bromide (3.7 mL, 38.44 mmol) was added at 23° C. The reaction mixture was stirred overnight at 60° C. The reaction mixture was concentrated under vacuum, diluted with EtOAc, filtrated over Celite® and washed with EtOAc. The crude obtained was purified in an automatic system for flash chromatography ($SiO_2$, Hex: EtOAc 70:30) to field (R)-18 (10.13 g, 86% yield).

$^1$H NMR (400 MHz, $CDCl_3$): δ 5.95 (d, J=2.2 Hz, 1H), 5.34 (d, J=2.2 Hz, 1H), 4.91 (d, J=8.9 Hz, 1H), 4.37 (q, J=7.6 Hz, 1H), 3.75 (dd, J=7.1, 1.3 Hz, 2H), 1.77 (ddt, J=13.3, 9.5, 6.5 Hz, 1H), 1.69-1.53 (m, 1H), 1.41 (s, 9H), 1.46-1.13 (m, 2H), 0.91 (t, J=7.3 Hz, 3H), 0.72-0.59 (m, 2H), 0.39-0.26 (m, 2H).

$^{13}$C NMR (100 MHz, $CDCl_3$): δ 170.2, 164.5, 163.5, 154.9, 99.9, 88.5, 80.0, 73.7, 52.5, 35.1, 28.3, 19.0, 13.5, 9.4, 3.3 (×2).

MS (ES+): m/z 360.2 $[M+Na]^+$.

Optical rotation: $[\alpha_D]$ +82.1 (c 0.046, MeOH).

$R_f$: 0.32 (Hex:EtOAc 7:3).

Synthesis of Intermediate (R)-19

(R)-19

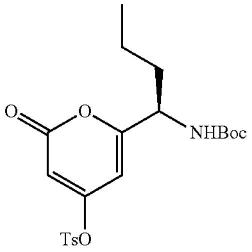

A solution of (R)-7 (37 mg, 0.124 mmol), p-toluenesulfonyl chloride (24 mg, 0.124 mmol) and triethylamine (0.017 mL, 0.124 mmol) in $CH_2Cl_2$ (2 mL) was stirred at 23° C. for 2 h. The reaction mixture was quenched with water and extracted with $CH_2Cl_2$. The organic layers were dried over $Na_2SO_4$ and filtered off to afford (R)-19 (54 mg, 100% yield).

$^1$H NMR (400 MHz, $CDCl_3$): δ 7.85-7.77 (m, 2H), 7.42-7.34 (m, 2H), 6.09 (d, J=2.2 Hz, 1H), 5.90 (d, J=2.2 Hz, 1H), 4.85 (d, J=8.6 Hz, 1H), 4.37 (q, J=7.8 Hz, 1H), 2.46 (s, 3H), 1.75 (ddt, J=13.7, 9.6, 6.3 Hz, 1H), 1.67-1.53 (m, 1H), 1.42 (s, 9H), 1.36-1.18 (m, 2H), 0.91 (t, J=7.3 Hz, 3H).

$^{13}$C NMR (100 MHz, $CDCl_3$): δ 166.0, 162.3, 161.7, 154.8, 146.7, 131.5, 130.3, 128.4, 101.3, 99.5, 80.3, 52.6, 35.0, 28.2, 21.8, 18.9, 13.5.

Synthesis of intermediate (R)-20

(R)-20

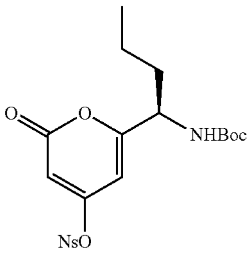

To a solution of (R)-7 (600 mg, 2.12 mmol) in $CH_2Cl_2$ (6 mL) was added N,N-diisopropylethylamine (0.44 mL, 2.54 mmol) at 23° C. The reaction mixture was stirred for 10 min at 23° C. and 4-nitrobenzenesulfonyl chloride (469 mg, 2.12 mmol) was added at 23° C. The reaction mixture was stirred for 24 h at 23° C. and diluted with HCl 1N. The layers were separated and the organic layer was dried over anhydrous $Na_2SO_4$, filtered and concentrated under vacuum. The obtained crude was purified in an automatic system for flash chromatography ($SiO_2$) to yield (R)-20 (791 mg, 80% yield).

$^1H$ NMR (400 MHz, $CDCl_3$): δ 8.60-8.38 (m, 2H), 8.31-8.06 (m, 2H), 6.10 (dd, J=2.0, 1.3 Hz, 1H), 5.96 (d, J=2.3 Hz, 1H), 4.80 (d, J=8.0 Hz, 1H), 4.36 (d, J=8.0 Hz, 1H), 1.63 (d, J=5.9 Hz, 2H), 1.47-1.38 (m, 9H), 1.25 (s, 2H), 0.98-0.89 (m, 3H).

$^{13}C$ NMR (100 MHz, $CDCl_3$): δ 161.3, 151.7, 140.3, 130.0, 125.0, 102.0, 99.3, 80.7, 77.4, 52.9, 35.0, 29.9, 28.4, 19.2, 13.7, 1.2.

MS (ES+): m/z 491.1 $[M+Na]^+$.

$R_f$: 0.55 (Hex:EtOAc 7:3).

Synthesis of Intermediate (R)-21

(R)-21

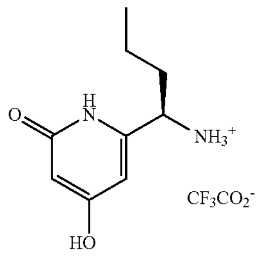

A solution of (R)-6 (31 mg, 0.11 mmol), $CH_2Cl_2$ (1.2 mL) and trifluoroacetic acid (0.34 mL) was stirred at 23° C. for 2 h and then evaporated to dryness. The crude was evaporated three times with toluene to remove trifluoroacetic acid. The crude contained (R)-21 (100% yield) was used in the next step without further purification.

$^1H$ NMR (300 MHz, $CD_3OD$): δ 6.38 (t, J=1.8 Hz, 1H), 5.99 (dd, J=2.4, 1.2 Hz, 1H), 4.21 (td, J=7.5, 1.3 Hz, 1H), 2.06-1.80 (m, 2H), 1.49-1.24 (m, 3H), 0.98 (td, J=7.4, 1.3 Hz, 3H).

MS (ES): m/z 387.2 $[2M+Na]^+$.

Synthesis of Intermediate (R)-22

(R)-22

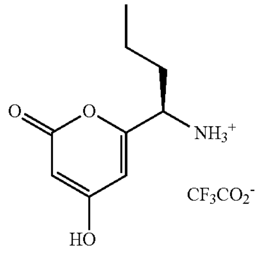

A solution of (R)-7 (19 mg, 0.067 mmol), $CH_2Cl_2$ (0.7 mL) and trifluoroacetic acid (0.2 mL) was stirred at 23° C. for 2 h and then evaporated to dryness. The crude was evaporated three times with toluene to remove trifluoroacetic acid to obtain (R)-22 crude (13 mg, 100% yield) which was used in the next step without further purification.

$^1H$ NMR (300 MHz, $CD_3OD$): δ 6.33 (d, J=1.0 Hz, 1H), 4.92 (s, 1H), 4.36-3.98 (m, 1H), 2.02-1.74 (m, 2H), 1.54-1.18 (m, 2H), 0.99 (td, J=7.3, 1.9 Hz, 3H).

Synthesis of Intermediate (R)-23

(R)-23

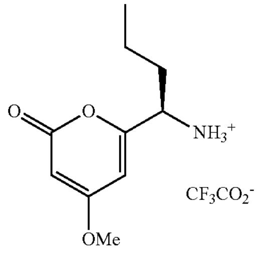

To a solution of (R)-9 (5.39 g, 18.1 mmol) in $CH_2Cl_2$ (202 mL, 37.5 mL/g) at 23° C. was added trifluoroacetic acid (59.3 mL, 11 mL/g). The reaction mixture was stirred for 1.5 hours at 23° C. Evaporation of the solvent under vacuum gave (R)-23 crude that was used in the next step without further purification.

$^1H$ NMR (300 MHz, $CDCl_3$): δ 6.16 (s, 1H), 5.54 (s, 1H), 4.13 (t, J=7.5 Hz, 1H), 3.84 (s, 3H), 1.92 (q, J=7.7 Hz, 2H), 1.29 (m, 2H), 0.93 (t, J=7.3 Hz, 3H), 0.87 (m, 2H).

$^{13}C$ NMR (75 MHz, $CDCl_3$): δ 171.5, 165.4, 157.5, 141.6, 117.7, 104.0, 103.3, 89.8, 56.7, 53.1, 33.2, 29.9, 18.8, 13.3.

Synthesis of Analog (S)-23

(S)-23

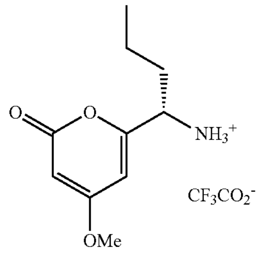

A solution of (S)-9 (253 mg, 0.85 mmol), $CH_2Cl_2$ (9.5 mL) and trifluoroacetic acid (2.8 mL) was stirred at 23° C. for 1 h and then evaporated to dryness. The crude was evaporated three times with toluene to remove trifluoroacetic acid. The crude contained (S)-23 (100% yield) was used in the next step without further purification.

$^1H$ NMR (300 MHz, $CD_3OD$): δ 6.35 (dd, J=2.3, 0.8 Hz, 1H), 5.69 (dd, J=2.3, 0.8 Hz, 1H), 4.26-4.10 (m, 1H), 3.89 (d, J=0.8 Hz, 3H), 2.04-1.76 (m, 2H), 1.47-1.23 (m, 2H), 1.03-0.89 (m, 3H).

Synthesis of intermediate (R)-24

(R)-24

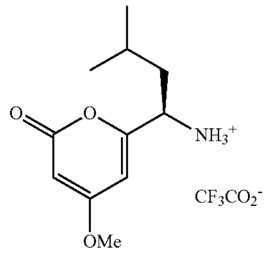

A solution of (R)-10 (74 mg, 0.24 mmol), $CH_2Cl_2$ (9 mL) and trifluoroacetic acid (2.6 mL) was stirred at 23° C. for 1 h and then evaporated to dryness. The crude was evaporated three times with toluene to remove trifluoroacetic acid. The crude contained (R)-24 (100% yield) was used in the next step without further purification.

$^{1}H$ NMR (400 MHz, $CDCl_3$): δ 6.15 (d, J=2.1 Hz, 1H), 5.49 (d, J=2.0 Hz, 1H), 4.07 (dd, J=9.7, 5.8 Hz, 1H), 3.81 (s, 3H), 1.82 (dd, J=9.3, 5.2 Hz, 1H), 1.74-1.60 (m, 1H), 1.56-1.42 (m, 1H), 0.91 (d, J=6.5 Hz, 6H).

Synthesis of Intermediate (R)-25

(R)-25

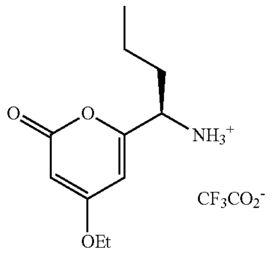

A solution of (R)-11 (37 mg, 0.112 mmol), $CH_2Cl_2$ (4 mL) and trifluoroacetic acid (1.23 mL) was stirred at 23° C. for 1 h and then evaporated to dryness. The crude was evaporated three times with toluene to remove trifluoroacetic acid. The crude contained (R)-25 (100% yield) was used in the next step without further purification.

$^{1}H$ NMR (300 MHz, $CD_3OD$) δ 6.33 (dd, J=2.3, 1.2 Hz, 1H), 5.65 (d, J=1.9 Hz, 1H), 4.14 (dd, J=7.2, 1.2 Hz, 3H), 2.04-1.76 (m, 2H), 1.46-1.24 (m, 4H), 0.98 (td, J=7.3, 1.3 Hz, 3H).

Synthesis of Intermediate (R)-26

(R)-26

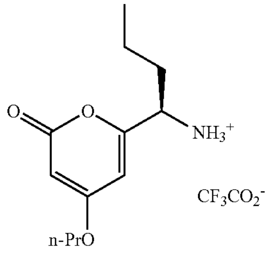

A solution of (R)-12 (35 g, 0.1 mmol), $CH_2Cl_2$ (1.3 mL) and trifluoroacetic acid (0.37 mL) was stirred at 23° C. for 1 h and then evaporated to dryness. The crude was evaporated three times with toluene to remove trifluoroacetic acid. The crude contained (R)-26 (100%) was used in the next step without further purification.

$^{1}H$ NMR (300 MHz, $CD_3OD$) δ 6.06 (dd, J=2.3, 0.7 Hz, 1H), 5.52 (d, J=2.2 Hz, 1H), 4.31 (dd, J=9.2, 5.5 Hz, 1H), 4.00 (t, J=6.4 Hz, 2H), 1.90-1.55 (m, 4H), 1.44 (m, 2H), 1.02 (t, J=7.4 Hz, 3H), 0.95 (t, J=7.3 Hz, 3H).

Synthesis of Intermediate (R)-27

(R)-27

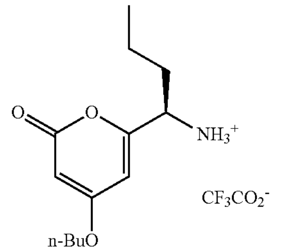

A solution of (R)-13 (34 mg, 0.14 mmol), $CH_2Cl_2$ (1.3 mL) and trifluoroacetic acid (0.37 mL) was stirred at 23° C. for 1 h and then evaporated to dryness. The crude was evaporated three times with toluene to remove trifluoroacetic acid. The crude contained (R)-27 (100%) was used in the next step without further purification.

$^{1}H$ NMR (300 MHz, $CD_3OD$) δ 6.35 (dd, J=2.2, 0.9 Hz, 1H), 5.67 (dd, J=2.3, 0.9 Hz, 1H), 4.16 (ddd, J=9.1, 6.3, 1.0 Hz, 1H), 4.07 (td, J=6.4, 0.9 Hz, 2H), 2.04-1.67 (m, 4H), 1.59-1.22 (m, 4H), 0.98 (tdd, J=7.4, 2.2, 0.8 Hz, 6H).

Synthesis of Intermediate (R)-28

(R)-28

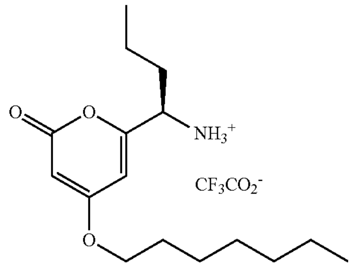

To a solution of (R)-14 (76 mg) in $CH_2Cl_2$ (2.85 mL) was added trifluoroacetic acid (0.84 mL). After being stirred for 2 hours, the mixture was evaporated to dryness and then evaporated with toluene to remove trifluoroacetic acid to obtain (R)-28

$^{1}H$ NMR (400 MHz, $CDCl_3$): δ 6.14 (d, J=2.1 Hz, 1H), 5.50 (d, J=2.1 Hz, 1H), 4.13 (t, J=7.5 Hz, 1H), 3.95 (t, J=6.5 Hz, 2H), 1.91 (q, J=7.7 Hz, 2H), 1.83-1.71 (m, 2H), 1.46-1.19 (m, 10H), 0.93 (t, J=7.3 Hz, 3H), 0.89 (t, J=6.7 Hz, 3H).

$^{13}C$ NMR (100 MHz, $CDCl_3$): δ 170.7, 165.4, 157.2, 104.0, 89.8, 69.9, 52.9, 32.9, 31.6, 28.8, 28.2, 25.6, 22.5, 18.5, 14.0, 13.1.

(R)-29

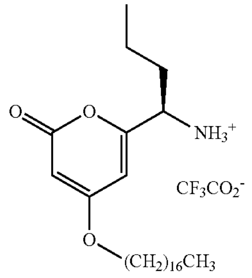

Synthesis of Intermediate (R)-29

A solution of (R)-15 (91 mg, 0.174 mmol) in $CH_2Cl_2$ (3.5 mL) and trifluoroacetic acid (1.0 mL) was stirred at 23° C. for 1 h and then evaporated to dryness. The crude was evaporated three times with toluene to remove trifluoroacetic acid. The crude containing (R)-29 (116 mg, >100%) was used in the next step without further purification.

$^1H$ NMR (400 MHz, $CDCl_3$): δ 6.16 (d, J=2.1 Hz, 1H), 5.52 (d, J=2.1 Hz, 1H), 4.14 (t, J=7.5 Hz, 1H), 3.95 (t, J=6.5 Hz, 2H), 1.92 (q, J=7.5 Hz, 2H), 1.77 (dd, J=8.3, 6.2 Hz, 2H), 1.44-1.21 (m, 32H), 0.93 (t, J=7.3 Hz, 3H), 0.87 (t, J=6.8 Hz, 3H).

$^{13}C$ NMR (100 MHz, $CDCl_3$): δ 170.9, 165.7, 157.1, 104.2, 89.8, 70.0, 53.0, 32.9, 31.9, 29.7 (×2), 29.6, 29.5, 29.4, 29.2, 28.3, 25.6, 22.7, 18.6, 14.1, 13.1.

Synthesis of Intermediate (R)-30

(R)-30

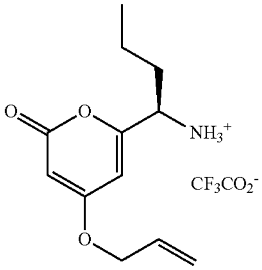

A solution of (R)-16 (5.0 g, 15.46 mmol) in $CH_2Cl_2$ (180 mL) and trifluoroacetic acid (55 mL) was stirred at 23° C. for 2 h and then evaporated to dryness. The crude was evaporated three times with toluene to remove trifluoroacetic acid. The crude containing (R)-30 (5.21 g, 100%) was used in the next step without further purification.

$^1H$ NMR (400 MHz, $CDCl_3$): δ 6.38 (d, J=2.2 Hz, 1H), 5.97-6.07 (m, 1H), 5.68 (d, J=2.2 Hz, 1H), 5.32-5.46 (m, 2H), 4.63 (td, J=5.5, 1.5 Hz, 2H), 4.18 (dd, J=8.9, 6.1 Hz, 1H), 1.99-1.82 (m, 2H), 1.45-1.28 (m, 2H), 0.98 (t, J=7.3 Hz, 3H).

$^{13}C$ NMR (100 MHz, $CDCl_3$): δ 169.8, 163.9, 157.7, 130.9, 118.2, 103.2, 89.9, 69.8, 52.0, 32.7, 18.2, 12.3.

MS (ES+): m/z 224.1 $[M+H]^+$.

Optical rotation: $[\alpha_D]$ −14.3 (c 0.015, MeOH).

Synthesis of intermediate (R)-31

(R)-31

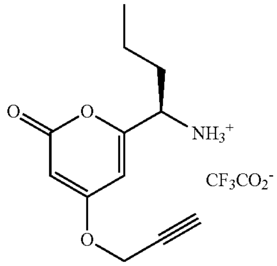

A solution of (R)-17 (2.31 g, 7.18 mmol) in $CH_2Cl_2$ (87 mL) and trifluoroacetic acid (25.4 mL) was stirred at 23° C. for 2 h and then evaporated to dryness. The crude was evaporated three times with toluene to remove trifluoroacetic acid. The crude containing (R)-31 was used in the next step without further purification.

$^1H$ NMR (400 MHz, $CDCl_3$): δ 8.48 (br s, 2H), 6.19 (d, J=2.0 Hz, 1H), 5.67 (d, J=2.1 Hz, 1H), 4.70 (t, J=2.0 Hz, 2H), 4.14 (t, J=7.1 Hz, 1H), 2.66 (t, J=2.3 Hz, 1H), 1.92 (q, J=7.9 Hz, 2H), 1.39-1.26 (m, 2H), 0.93 (t, J=7.3 Hz, 3H).

$^{13}C$ NMR (100 MHz, $CDCl_3$): δ 169.0, 164.6, 157.7, 103.6, 91.2, 78.2, 75.1, 57.0, 52.8, 32.9, 18.5, 13.1.

Synthesis of Intermediate (R)-32

(R)-32

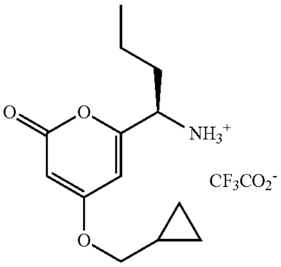

A solution of (R)-18 (8.9 g, 26.44 mmol) in $CH_2Cl_2$ (334 mL) and trifluoroacetic acid (98 mL) was stirred at 23° C. for 2 h and then evaporated to dryness. The crude was evaporated three times with toluene to remove trifluoroacetic acid. The crude containing (R)-32 (13.9 g, >100%) was used in the next step without further purification.

$^1H$ NMR (400 MHz, $CDCl_3$): δ 8.51 (s, 2H), 6.18 (d, J=1.8 Hz, 1H), 5.48 (s, 1H), 4.13 (t, J=7.3 Hz, 1H), 3.80 (d, J=7.2 Hz, 2H), 1.91 (q, J=7.6 Hz, 2H), 1.38-1.18 (m, 2H), 0.92 (t, J=7.3 Hz, 3H), 0.72-0.62 (m, 2H), 0.39-0.30 (m, 2H).

$^{13}C$ NMR (100 MHz, $CDCl_3$): δ 170.6, 157.2, 104.2, 89.8, 74.7, 52.9, 32.8, 18.5, 13.1, 9.2, 3.4, 3.3.

Optical rotation: $[\alpha_D]$ −89 (c 0.037, MeOH).

Scheme 4 provides more examples of the synthesis of intermediates of formula II.

Scheme 4

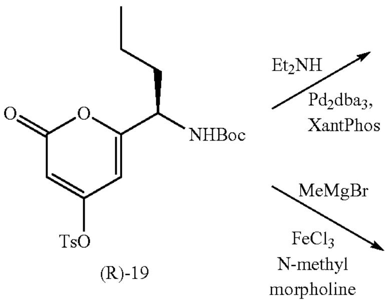

(R)-19

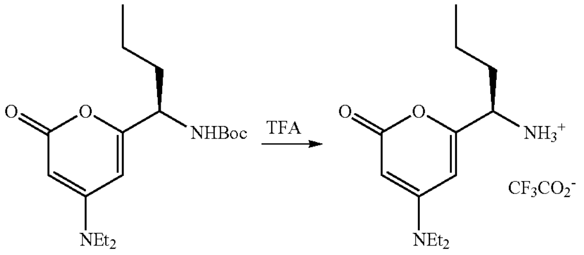

(R)-33 (R)-34

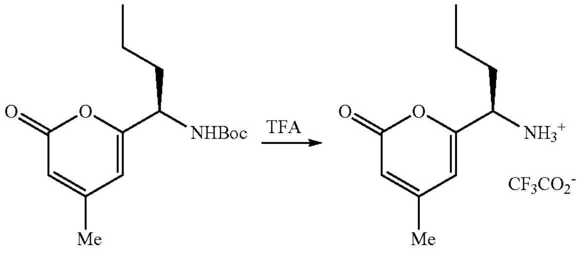

(R)-35 (R)-36

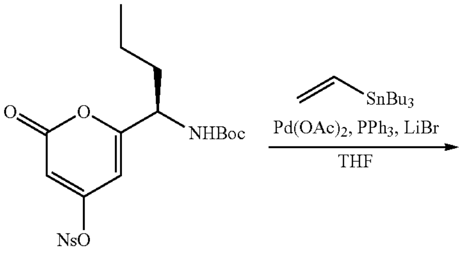

(R)-20

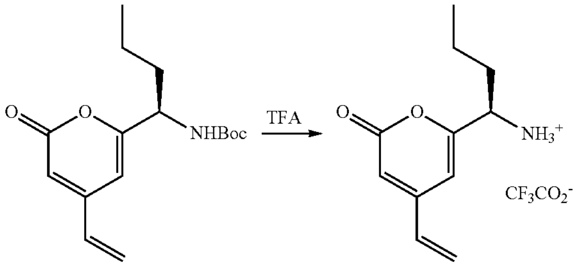

(R)-37 (R)-38

Synthesis of Intermediate (R)-33

(R)-33

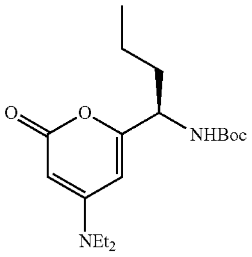

To a mixture of $Pd_2(dba)_3$ (10 mg, 0.115 mmol), XantPhos (13 mg, 0.023 mmol) and NaOtBu (33 mg, 0.34 mmol) was added (R)-19 (100 mg, 0.23 mmol) in 1,4-dioxane (2 mL) and diethylamine (0.034 mL, 0.69 mmol). The reaction was warmed to 105° C. for 4 h and then cooled to 23° C. and quenched with water. Extraction with $CH_2Cl_2$ gave a crude which was purified by flash chromatography over silica gel ($CH_2Cl_2/CH_3OH$ 98/2) to afford (R)-33 (36 mg, 47% yield).

$^1H$ NMR (300 MHz, $CDCl_3$) δ 5.88 (d, J=2.4 Hz, 1H), 4.99 (d, J=2.4 Hz, 1H), 4.34 (d, J=8.4 Hz, 1H), 3.32 (dt, J=12.0, 7.2 Hz, 4H), 1.89-1.55 (m, 6H), 1.42 (s, 9H), 1.19 (m, 3H), 0.92 (t, J=7.3 Hz, 3H).

Synthesis of Intermediate (R)-34

(R)-34

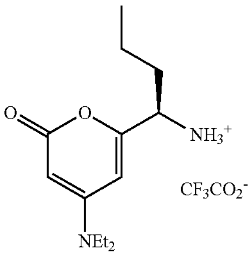

A solution of (R)-33 (44 mg, 0.13 mmol), $CH_2Cl_2$ (1.65 mL) and trifluoroacetic acid (0.5 mL) was stirred at 23° C. for 2 h and then evaporated to dryness. The crude was evaporated three times with toluene to remove trifluoroacetic acid. The crude contained (R)-34 (100% yield) was used in the next step without further purification.

$^1H$ NMR (300 MHz, $CD_3OD$) δ 6.55 (s, 1H), 4.89 (s, 1H), 4.17 (dd, J=9.0, 6.1 Hz, 1H), 3.46 (q, J=7.1 Hz, 4H), 3.02 (m, 1H), 2.06-1.74 (m, 2H), 1.49-1.25 (m, 2H), 1.21 (t, J=7.1 Hz, 6H), 0.99 (t, J=7.3 Hz, 3H).

Synthesis of intermediate (R)-35

(R)-35

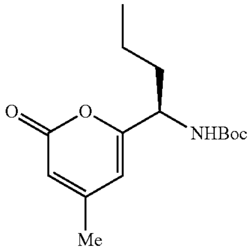

To a solution of (R)-19 (20 mg, 0.046 mmol), THF (0.2 mL), and $FeCl_3$ (0.4 mg, 0.0023 mmol), at −15° C., was added N-methyl-morpholine (0.04 mL, 0.41 mmol), and 1.4 M methylmagnesium bromide in THF/tol. The reaction was allowed to reach 23° C. in 3 h and then quenched with a saturated aqueous solution of ammonium chloride. The extraction with EtOAc gave a crude which was purified by flash chromatography on silica gel (Hexane/EtOAc 8/2) to afford (R)-35 (13 mg, 100% yield).

$^1$H NMR (300 MHz, $CDCl_3$) δ 5.99 (d, J=1.5 Hz, 2H), 4.91 (d, J=8.9 Hz, 1H), 4.37 (q, J=7.9 Hz, 1H), 2.13 (d, J=1.1 Hz, 3H), 1.84-1.54 (m, 4H), 1.42 (s, 9H), 0.92 (td, J=7.5, 2.0 Hz, 3H).

MS (ES): m/z 304.1 $[M+Na]^+$.

Synthesis of Intermediate (R)-36

(R)-36

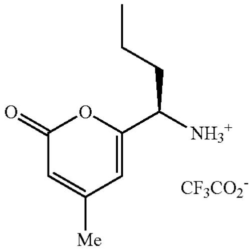

A solution of (R)-35 (15 mg, 0.053 mmol), $CH_2Cl_2$ (1.8 mL) and trifluoroacetic acid (0.36 mL) was stirred at 23° C. for 2 h and then evaporated to dryness. The crude was evaporated three times with toluene to remove trifluoroacetic acid. The crude contained (R)-36 (100% yield) was used in the next step without further purification.

$^1$H NMR (300 MHz, $CDCl_3$) δ 6.19 (d, J=1.4 Hz, 1H), 6.07 (s, 1H), 4.19-3.99 (m, 1H), 2.16 (d, J=1.4 Hz, 3H), 1.89 (t, J=7.8 Hz, 2H), 1.46-1.07 (m, 2H), 1.00-0.74 (m, 3H).

Synthesis of Intermediate (R)-37

(R)-37

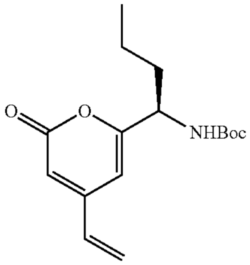

To a solution of (R)-20 (491 mg, 1.05 mmol) in THF (18 mL) was added palladium(II) acetate (12 mg, 0.05 mmol), triphenylphosphine (28 mg, 0.10 mmol) and lithium bromide (273 mg, 3.15 mmol) at 23° C. The reaction mixture was turned to a yellow-to-orange, stirred for 10 min at 23° C. and tri-n-butyl(vinyl)tin (0.52 mL, 3.15 mmol) was added at 23° C. The reaction mixture was refluxed for 1 h and concentrated under vacuum. An aqueous solution of KF 2M was added to the crude and the mixture was stirred for 30 min at 23° C. Filtration over Celite® and washing with $Et_2O$ gave a crude which was purified in an automatic system for flash chromatography ($SiO_2$) to yield (R)-37 (158 mg, 51% yield).

$^1$H NMR (400 MHz, $CDCl_3$): δ 6.53-6.41 (m, 1H), 6.28 (d, J=1.6 Hz, 1H), 6.05 (d, J=1.5 Hz, 1H), 5.92 (dd, J=17.5, 1.5 Hz, 1H), 5.63 (dd, J=10.8, 1.5 Hz, 1H), 4.94 (d, J=9.0 Hz, 1H), 4.43 (q, J=8.1 Hz, 1H), 1.88-1.72 (m, 2H), 1.43 (s, 9H), 1.34 (dt, J=15.8, 8.1 Hz, 2H), 0.94 (td, J=7.3, 2.5 Hz, 3H).

$^{13}$C NMR (100 MHz, $CDCl_3$): δ 163.1, 162.9, 155.1, 151.6, 133.5, 130.5, 128.7, 128.6, 122.9, 111.3, 110.1, 99.9, 80.3, 77.5, 77.4, 77.2, 76.8, 67.6, 52.9, 35.5, 29.8, 29.6, 28.5, 27.0, 24.0, 22.3, 19.3, 13.7, 1.2.

MS (ES+): m/z 316.3 $[M+Na]^+$.

$R_f$: 0.25 (Hex:EtOAc 4:1).

Synthesis of Intermediate (R)-38

(R)-38

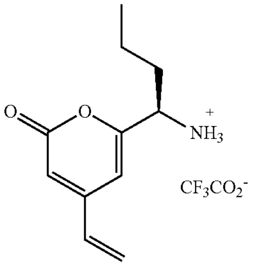

A solution of (R)-37 (1.01 g, 3.44 mmol) in $CH_2Cl_2$ (37 mL) and trifluoroacetic acid (11 mL) was stirred at 23° C. for 2 h and then evaporated to dryness. The crude was evaporated three times with toluene to remove trifluoroacetic acid. The crude containing (R)-38 (1.06 g, 100% yield) was used in the next step without further purification.

$^1$H NMR (400 MHz, $CDCl_3$): δ 6.79 (s, 3H), 6.62-6.44 (m, 2H), 6.18 (s, 1H), 6.01 (d, J=17.5 Hz, 1H), 5.74 (d,

J=10.8 Hz, 1H), 4.26 (t, J=7.5 Hz, 1H), 1.98 (q, J=7.8 Hz, 2H), 1.46-1.28 (m, 2H), 0.98-0.81 (m, 3H).

$^{13}$C NMR (100 MHz, $CDCl_3$): δ 163.9, 160.9, 160.5, 160.1, 159.7, 156.4, 152.6, 132.5, 125.0, 116.6, 113.7, 112.3, 104.1, 53.6, 33.2, 29.9, 18.8, 17.7, 13.3.

MS (ES+): m/z 194.3 $[M+H]^+$.

Example 6 Synthesis of Intermediates of Formula III

Scheme 5 provides some examples of the synthesis of an intermediate of formula III.

Scheme 5

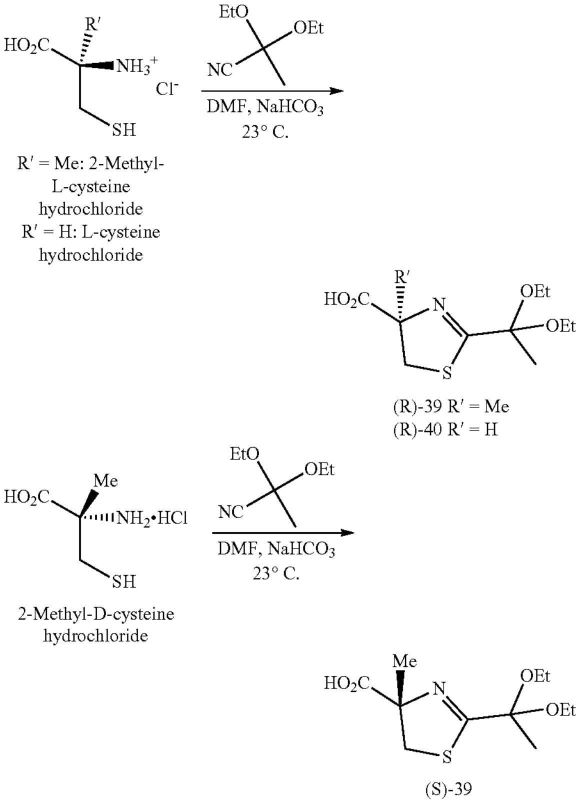

R' = Me: 2-Methyl-L-cysteine hydrochloride
R' = H: L-cysteine hydrochloride (R)-39 R' = Me
(R)-40 R' = H 2-Methyl-D-cysteine hydrochloride (S)-39

Synthesis of Intermediate (R)-39

(R)-39

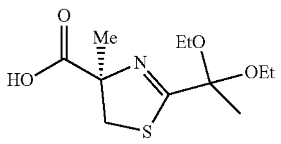

2-Methyl-L-cysteine hydrochloride (Obtained following the procedure described in Recent Res. Devel. Organic Chem. 2004, 8, 323-339) (13 g, 75.74 mmol) was dissolved in the minimum quantity of $H_2O$, cooled at 0° C. and basified with an aqueous saturated solution of $NaHCO_3$ until pH 8. Evaporation of the solvent under vacuum afforded the corresponding sodium salt which was dissolved in an aqueous saturated solution of $NaHCO_3$ (151 mL, 2 mL/mmol). The aqueous solution was cooled to 0° C. and was added DMF (151 mL, 2 mL/mmol) and 2,2-diethoxypropanenitrile (20 mL, 128 mmol, 1.7 equiv). The reaction mixture was stirred overnight at 23° C. After cooling at 0° C., HCl 0.5 M was added until pH 2. The aqueous layer was extracted with a mixture 50:50 of Hex:EtOAc (×3). The combined organic layers were dried over anhydrous $Na_2SO_4$, filtered, and concentrated under vacuum to afford crude (R)-39 (11.39 g, 57% yield) which was used in the next step without further purification.

$^1$H NMR (300 MHz, $CDCl_3$): δ 3.72 (d, J=11.6 Hz, 1H), 3.60-3.47 (m, 4H), 3.16 (d, J=11.6 Hz, 1H), 1.59 (d, J=1.9 Hz, 6H), 1.20 (t, J=7.1, 6H).

$^{13}$C NMR (100 MHz, $CDCl_3$): δ 175.6, 163.3, 100.5, 84.5, 57.9, 57.9, 40.7, 24.2, 23.9, 15.4.

Optical rotation: $[\alpha_D]$ −4.4 (c 0.098, MeOH).

Synthesis of Intermediate (R)-40

(R)-40

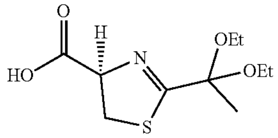

To a solution of L-cysteine (250 mg, 2.06 mmol) in water (27 mL) and $NaHCO_3$ (2 g) at 0° C., were added DMF (27 mL) and 2,2-diethoxypropionitrile (0.42 mL, 2.7 mmol). The reaction was stirred for 24 h at 23° C. and after cooling to 0° C. 1M HCl was added to pH=2. The aqueous layer was extracted with EtOAc and the combined organic layers were dried over anhydrous $Na_2SO_4$, filtered and concentrated under vacuum to give (R)-40 (191 mg, 37% yield).

$^1$H NMR (300 MHz, $CDCl_3$): δ 5.31 (dd, J=10.1, 7.5 Hz, 1H), 3.74-3.40 (m, 5H), 2.94 (d, J=26.1 Hz, 1H), 1.59 (s, 3H), 1.20 (q, J=7.0 Hz, 6H).

$^{13}$C NMR (75 MHz, $CDCl_3$): δ 182.2, 175.2, 165.8, 103.0, 80.1, 60.3, 60.0, 39.3, 37.1, 34.2, 26.2, 17.7.

Synthesis of Intermediate (S)-39

(S)-39

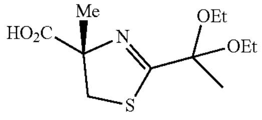

2-Methyl-D-cysteine hydrochloride (3.1 g, 17.9 mmol) was dissolved in the minimum quantity of $H_2O$, cooled at 0° C. and basified with an aqueous saturated solution of $NaHCO_3$ until pH 8. Evaporation of the solvent under vacuum afforded the corresponding sodium salt which was dissolved in a saturated aqueous solution of $NaHCO_3$ (35.8 mL, 2 mL/mmol). The aqueous solution was cooled to 0° C. and was added DMF (35.8 mL, 2 mL/mmol) and 2,2-diethoxypropanenitrile (4.7 mL, 30.4 mmol, 1.7 equiv). The reaction mixture was stirred overnight at 23° C. After cooling at 0° C., HCl 0.5 M was added until pH 2. The aqueous layer was extracted with a mixture 50:50 of Hex:EtOAc (×3). The combined organic layers were dried over anhydrous $Na_2SO_4$, filtered, and concentrated under vacuum to afford crude (S)-39 (3.34 g, 71% yield) which was used in the next step without further purification.

$^1$H NMR (400 MHz, $CDCl_3$): δ 3.69 (dd, J=11.5, 0.7 Hz, 1H), 3.54 (m, 4H), 3.12 (dd, J=11.6, 0.7 Hz, 1H), 1.57 (d, J=0.7 Hz, 3H), 1.56 (d, J=0.7 Hz, 3H), 1.19 (tt, J=7.1, 0.8 Hz, 6H).

$^{13}$C NMR (100 MHz, $CDCl_3$): δ 176.3, 164.0, 101.5, 85.7, 58.9, 58.8, 37.8, 32.7, 24.9, 16.5, 16.4.

MS (ES+): m/z 262.3 [M+H]$^+$.

Optical rotation: [$\alpha_D$] +4.6 (c 0.096, MeOH).

Example 7. Synthesis of Compounds 1 and 1a

Scheme 6 provides an example of the synthesis of compounds 1 and 1a

Scheme 6

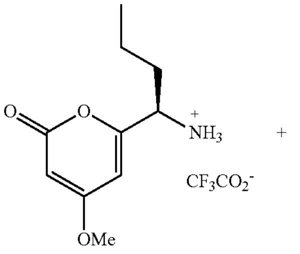

(R)-23

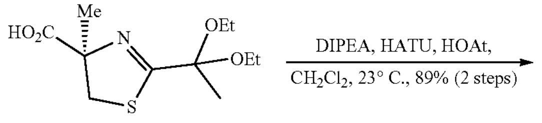

(S)-39

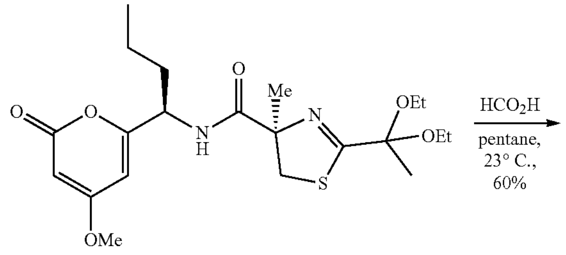

41

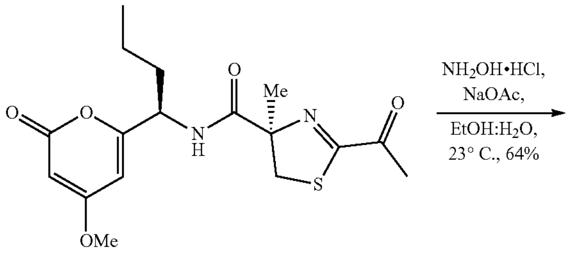

42

-continued

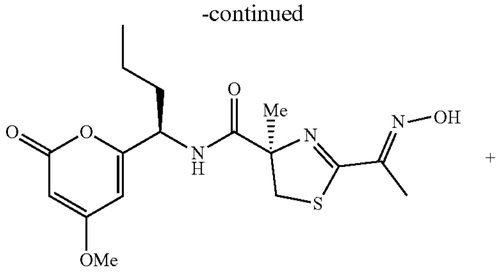

1

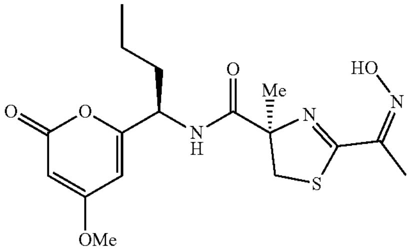

1a

Synthesis of Intermediate 41

41

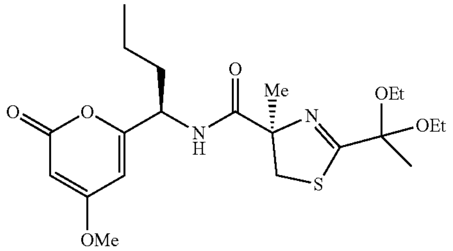

To a solution of (R)-23 (6.76 g, 21.7 mmol) and (R)-39 (5.68 g, 21.7 mmol) in $CH_2Cl_2$ (152 mL) was sequentially added at 23° C. O-(7-azabenzotriazol-1-yl)-N,N,N',N'-tetramethyluronium hexafluorophosphate (HATU) (17.02 g, 44.7 mmol, 2.06 equiv), 1-hydroxy-7-azabenzotriazole (HOAt) (6.2 g, 45.1 mmol, 2.08 equiv), and N,N-diisopropylethylamine (16.24 mL, 93 mmol, 4.29 equiv). The reaction mixture was stirred for 15 hours at 23° C., diluted with $CH_2Cl_2$ and washed with an aqueous saturated solution of $NaHCO_3$, HCl 0.5 M, and an aqueous saturated solution of NaCl. The combined organic layers were dried over anhydrous $Na_2SO_4$, filtered and concentrated under vacuum. The obtained crude was purified by column chromatography (Hex:EtOAc, from 8:2 to 6:4) to give pure 41 (8.5 g, 89% for two steps).

$^1$H NMR (400 MHz, $CDCl_3$): δ 7.02 (d, J=9.0 Hz, 1H), 5.96-5.70 (m, 1H), 5.45-5.33 (m, 1H), 4.72 (td, J=8.5, 6.2 Hz, 1H), 3.77 (s, 3H), 3.67-3.43 (m, 5H), 3.15 (d, J=11.7 Hz, 1H), 1.87 (ddt, J=13.1, 9.7, 6.4 Hz, 1H), 1.71 (ddd, J=9.6, 8.3, 5.5 Hz, 2H), 1.61 (s, 3H), 1.53 (s, 3H), 1.44-1.28 (m, 2H), 1.22 (q, J=7.2 Hz, 6H), 0.94 (t, J=7.3 Hz, 3H).

$^{13}$C NMR (75 MHz, $CDCl_3$): δ 177.1, 174.7, 171.0, 164.1, 163.2, 100.5, 99.8, 88.6, 85.4, 58.0, 56.1, 51.0, 40.6, 34.9, 25.5, 24.0, 19.3, 15.4, 13.8.

MS (ES+): m/z 463.3 [M+Na]$^+$.

$R_f$: 0.29 (Hex:EtOAc 1:1).

Synthesis of Intermediate 42

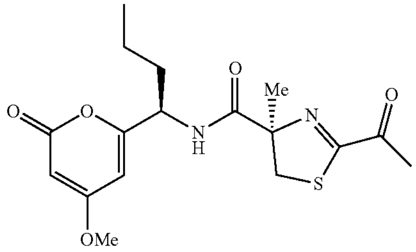

42

Over 41 (4.25 g, 9.6 mmol) was added at 23° C. pentane (255 mL, 60 mL/g) and formic acid (170 mL, 40 mL/g). The reaction mixture was stirred vigorously for 2 hours at 23° C. The solvent was removed under vacuum. The obtained crude was purified by column chromatography ($CH_2Cl_2$:EtOAc, from 9:1 to 8:2) to obtain pure 42 (4.25 g, 60% yield).

$^1$H NMR (400 MHz, $CDCl_3$): δ 7.01 (d, J=8.9 Hz, 1H), 5.91 (dd, J=2.2, 0.4 Hz, 1H), 5.42 (t, J=2.1 Hz, 1H), 4.74 (q, J=7.8 Hz, 1H), 3.82-3.75 (m, 3H), 3.63 (dd, J=12.0, 2.0 Hz, 1H), 3.28 (dd, J=11.9, 0.9 Hz, 1H), 2.56 (d, J=0.9 Hz, 3H), 1.95-1.73 (m, 1H), 1.54 (d, J=2.0 Hz, 3H), 1.46-1.29 (m, 1H), 0.96 (td, J=7.3, 1.7 Hz, 3H).

$^{13}$C NMR (75 MHz, $CDCl_3$): δ 193.1, 173.2, 170.8, 170.4, 164.0, 162.0, 100.3, 88.6, 86.1, 56.0, 51.1, 40.1, 34.8, 26.3, 24.5, 19.0, 13.5.

MS (ES+): m/z 367.1 $[M+H]^+$, 389.1 $[M+Na]^+$.

Synthesis of Compounds 1 and 1a

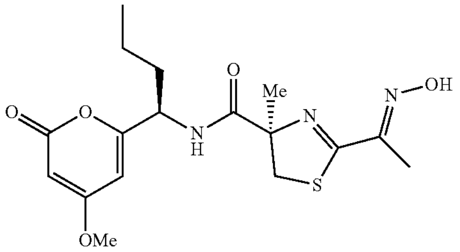

1

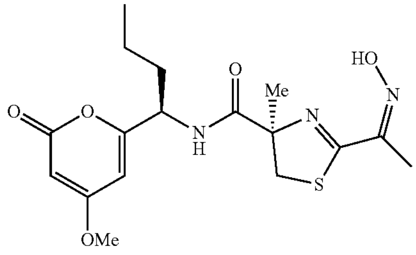

1a

To a solution of 42 (4.25 g, 11.6 mmol) in ethanol (127.6 mL, 11 mL/mmol) and $H_2O$ (127.6 mL, 11 mL/mmol) was added at 23° C. hydroxylamine hydrochloride (5.96 g, 84.7 mmol, 7.4 equiv) and sodium acetate (4.28 g, 52.2 mmol, 4.5 equiv). The reaction mixture was stirred for 24 hours at 23° C. The solvent was removed under vacuum, the residue obtained was dissolved in $H_2O$ and extracted with EtOAc. The combined organic layers were dried over anhydrous $Na_2SO_4$, filtered and concentrated under vacuum. The obtained crude was purified by semipreparative HPLC (X-Bridge Prep C18, 5 μm, 19×150 mm, isocratic $H_2O$:$CH_3CN$ (62:38) flow: 15 mL/min, UV detection) to yield 1a (320 mg, 7% yield, retention time: 6.0 min) and 1 (2.72 g, 64% yield, retention time: 9.3 min). Synthetic 1 exhibited physical, spectroscopic ($^1$H, $^{13}$C NMR and MS) and biological characteristics equivalent to those reported in Example 2.

Compound 1

$^1$H NMR (500 MHz, $CD_3OD$): δ 6.08 (dd, J=2.2, 0.7 Hz, 1H), 5.55 (d, J=2.2 Hz, 1H), 4.72 (dd, J=9.4, 5.4 Hz, 1H), 3.84 (s, 3H), 3.59 (d, J=11.7 Hz, 1H), 3.22 (d, J=11.6 Hz, 1H), 2.17 (s, 3H), 1.87 (dddd, J=13.7, 9.6, 6.6, 5.4 Hz, 1H), 1.82-1.69 (m, 1H), 1.55 (s, 3H), 1.53-1.32 (m, 2H), 0.98 (t, J=7.4 Hz, 3H).

$^{13}$C NMR (75 MHz, $CDCl_3$): δ 176.5, 173.4, 170.3, 166.7, 165.2, 152.9, 100.8, 88.9, 85.6, 57.0, 52.1, 40.6, 35.2, 25.0, 20.2, 13.8, 11.0.

MS (ES+): m/z 382.3 $[M+H]^+$, 404.1 $[M+Na]^+$.

$R_f$: 0.36 (Hex:EtOAc 1:1).

Compound 1a $^1$H NMR (500 MHz, $CD_3OD$): δ 6.08 (dd, J=2.2, 0.7 Hz, 1H), 5.55 (d, J=2.2 Hz, 1H), 4.72 (dd, J=9.4, 5.4 Hz, 1H), 3.84 (s, 3H), 3.59 (d, J=11.7 Hz, 1H), 3.22 (d, J=11.6 Hz, 1H), 2.17 (s, 3H), 1.87 (dddd, J=13.7, 9.6, 6.6, 5.4 Hz, 1H), 1.82-1.69 (m, 1H), 1.55 (s, 3H), 1.53-1.32 (m, 2H), 0.98 (t, J=7.4 Hz, 3H).

$^{13}$C NMR (125 MHz, $CDCl_3$): δ 173.5, 171.0, 164.6, 164.5, 162.4, 147.2, 100.1, 88.5, 83.6, 56.0, 51.0, 40.9, 35.0, 24.8, 19.2, 19.0, 13.5.

Example 8. Synthesis of Compounds Epi-1 and Epi-1a

Scheme 7 provides a comparative example of the synthesis of compounds epi-1 and epi-1a Scheme 7

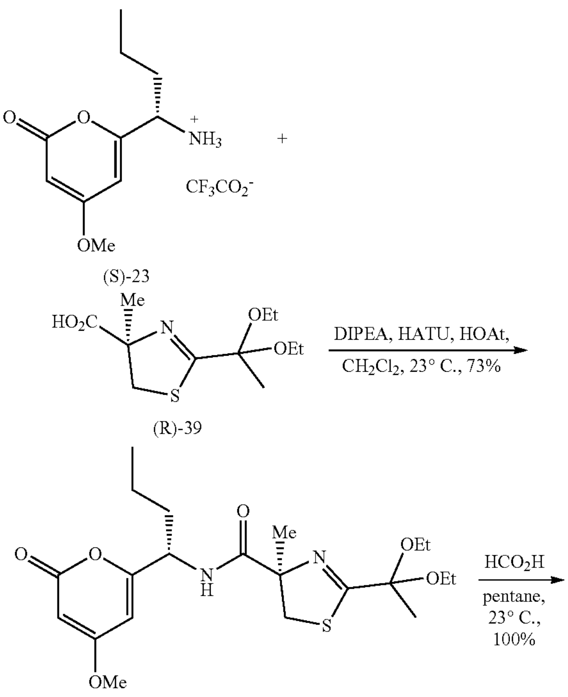

epi-41

-continued

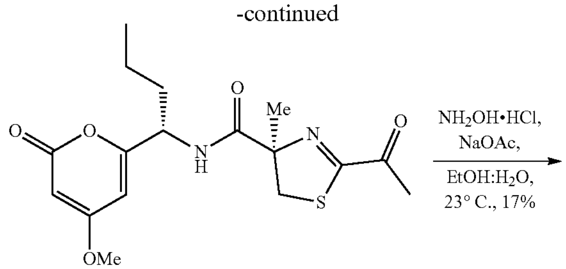

epi-42

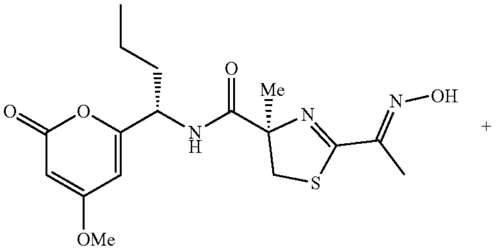

epi-1

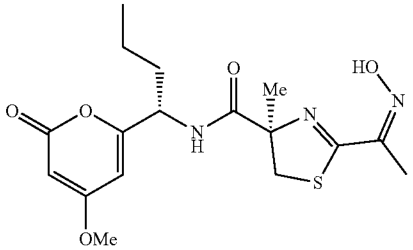

epi-1a

Synthesis of Analog Epi-41 epi-41

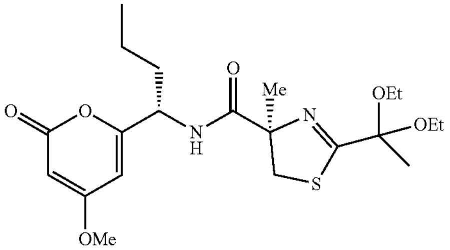

To a suspension of (S)-23 (24 mg, 0.076 mmol) and (R)-39 (19 mg, 0.076 mmol) in $CH_2Cl_2$ (0.5 mL) were added HATU (60 mg, 0.16 mmol), HOAt (22 mg, 0.16 mmol) and DIPEA (0.057 mL, 0.33 mmol) and the mixture was stirred at 23° C. overnight. Dilution with $CH_2Cl_2$, washing of the organic layer with 0.5M HCl, with brine and then dried over anhydrous $Na_2SO_4$. Evaporation of the solvent gave a crude which was purified by flash chromatography on silica gel (hexane/EtOAc from 9/1 to 7/3) to afford epi-41 (33 mg, 73% yield).

$^1H$ NMR (500 MHz, $CD_3OD$): δ 6.15 (d, J=2.1 Hz, 1H), 5.58 (d, J=2.2 Hz, 1H), 4.67 (dd, J=9.3, 5.5 Hz, 1H), 3.87 (s, 3H), 3.62 (d, J=11.7 Hz, 1H), 3.66-3.47 (m, 4H), 3.24 (d, J=11.7 Hz, 1H), 1.92-1.79 (m, 1H), 1.79-1.70 (m, 1H), 1.58 (s, 3H), 1.47 (s, 3H), 1.42-1.26 (m, 2H), 1.22 (t, J=7.1 Hz, 6H), 0.95 (t, J=7.4 Hz, 3H).

$^{13}C$ NMR (125 MHz, $CD_3OD$): δ 178.0, 176.6, 173.4, 166.6, 165.3, 111.4, 101.6, 100.8, 88.9, 86.2, 58.8, 58.8, 57.0, 52.3, 41.2, 35.3, 25.1, 24.2, 20.2, 15.5 (×2), 13.8.

Synthesis of Analog Epi-42 epi-42

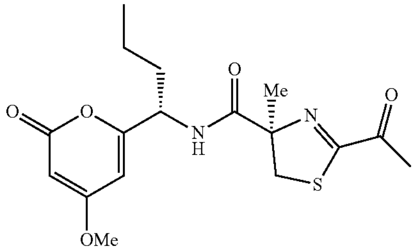

To a mixture of epi-41 (10 mg, 0.023 mmol) and pentane (0.6 mL) was added formic acid (0.4 mL). The reaction was stirred vigorously at 23° C. or 2 h and then evaporated to dryness with toluene to remove efficiently the formic acid giving epi-42 (100%).

$^1H$ NMR (500 MHz, $CD_3OD$): δ 6.15 (dd, J=2.2, 0.7 Hz, 1H), 5.59 (d, J=2.2 Hz, 1H), 4.71 (dd, J=9.3, 5.8 Hz, 1H), 3.87 (s, 3H), 3.71 (d, J=11.8 Hz, 1H), 3.32 (d, J=11.9 Hz, 1H), 1.96-1.67 (m, 2H), 1.55 (s, 3H), 1.49 (s, 3H), 1.47-1.27 (m, 2H), 0.95 (t, J=7.4 Hz, 3H).

$^{13}C$ NMR (125 MHz, $CD_3OD$): δ 194.9, 175.6, 173.5, 171.7, 166.8, 165.3, 100.9, 88.9, 87.4, 57.1, 52.4, 41.3, 35.0, 24.5, 20.3, 20.2, 13.8.

Synthesis of Analogs Epi-1 and Epi-1a epi-1

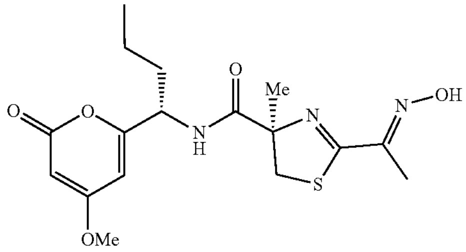

epi-1a

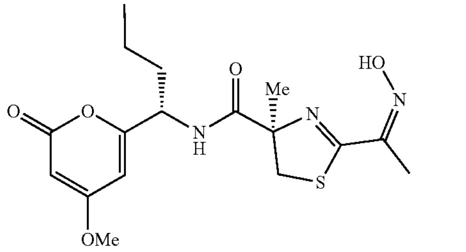

To a solution of epi-44 (8 mg, 0.023 mmol) in ethanol (0.5 mL) and water (0.5 mL), were added $NH_2OH{\cdot}HCl$ (11 mg, 0.16 mmol) and NaOAc (8 mg, 0.10 mmol). After stirring at 23° C. for 24 h the ethanol was evaporated under vacuum and the aqueous layer was extracted with EtOAc. The combined organic layers were dried over anhydrous $Na_2SO_4$, filtered and after evaporation of the solvent; the obtained crude was purified by HPLC method, using an XBridge C18 5 μm $H_2O/CH_3CN$ to give epi-1a (0.6 mg) and epi-1 (1.5 mg, 17% yield).

Analog Epi-1a $^1$H NMR (500 MHz, $CD_3OD$): δ 6.16 (dq, J=2.3, 0.8 Hz, 1H), 5.61-5.56 (m, 1H), 4.69 (dd, J=9.2, 5.8 Hz, 1H), 3.87 (t, J=0.8 Hz, 3H), 3.57 (dt, J=11.5, 0.8 Hz, 1H), 3.19 (dt, J=11.5, 0.8 Hz, 1H), 2.19 (t, J=0.8 Hz, 3H), 1.93-1.68 (m, 2H), 1.51 (t, J=0.9 Hz, 3H), 1.35 (m, 1H), 0.98-0.90 (m, 3H).

$^{13}$C NMR (125 MHz, $CD_3OD$): δ 176.5, 173.4, 170.1, 166.6, 165.2, 152.8, 100.7, 88.7, 85.4, 56.9, 52.2, 40.5, 35.0, 24.8, 20.1, 13.7, 10.8.

Analog epi-1

$^1$H NMR (500 MHz, $CD_3OD$) δ 6.13 (d, J=2.2 Hz, 1H), 5.57 (d, J=2.2 Hz, 1H), 4.68 (td, J=8.9, 5.6 Hz, 1H), 3.86 (s, 3H), 3.60 (d, J=11.7 Hz, 1H), 3.21 (d, J=11.6 Hz, 1H), 2.16 (s, 3H), 1.82 (dd, J=9.3, 6.0 Hz, 1H), 1.73 (dd, J=9.2, 4.8 Hz, 1H), 1.52 (s, 4H), 1.46-1.26 (m, 1H), 0.93 (t, J=7.4 Hz, 3H).

Example 9. Synthesis of More Compounds of Formula I

Scheme 8 provides another example of the synthesis of more compounds of formula I.

Scheme 8

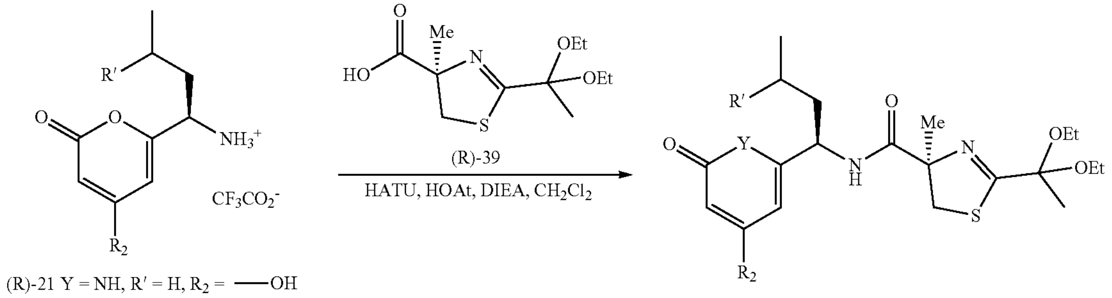

(R)-21 Y = NH, R′ = H, $R_2$ = —OH
(R)-22 Y = O, R′ = H, $R_2$ = —OH
(R)-24 Y = O, R′ = Me, $R_2$ = —OMe
(R)-25 Y = O, R′ = H, $R_2$ = —OEt
(R)-27 Y = O, R′ = H, $R_2$ = —On-Bu
(R)-28 Y = O, R′ = H, $R_2$ = n-heptyloxy
(R)-29 Y = O, R′ = H, $R_2$ = n-heptadecyloxy
(R)-30 Y = O, R′ = H, $R_2$ = —Oallyl
(R)-31 Y = O, R′ = H, $R_2$ = —Opropargyl
(R)-32 Y = O, R′ = H, $R_2$ = cyclopropylmethyloxy
(R)-34 Y = O, R′ = H, $R_2$ = —$NEt_2$
(R)-36 Y = O, R′ = H, $R_2$ = Me
(R)-38 Y = O, R′ = H, $R_2$ = vinyl 43 Y = NH, R′ = H, $R_2$ = —OH
44 Y = O, R′ = H, $R_2$ = —OH
45 Y = O, R′ = Me, $R_2$ = —OMe
46 Y = O, R′ = H, $R_2$ = —OEt
47 Y = O, R′ = H, $R_2$ = —On-Bu
48 Y = O, R′ = H, $R_2$ = n-heptyloxy
49 Y = O, R′ = H, $R_2$ = n-heptadecyloxy
50 Y = O, R′ = H, $R_2$ = —Oallyl
51 Y = O, R′ = H, $R_2$ = —Opropargyl
52 Y = O, R′ = H, $R_2$ = cyclopropylmethyloxy
53 Y = O, R′ = H, $R_2$ = —$NEt_2$
54 Y = O, R′ = H, $R_2$ = Me
55 Y = O, R′ = H, $R_2$ = vinyl

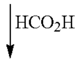

-continued

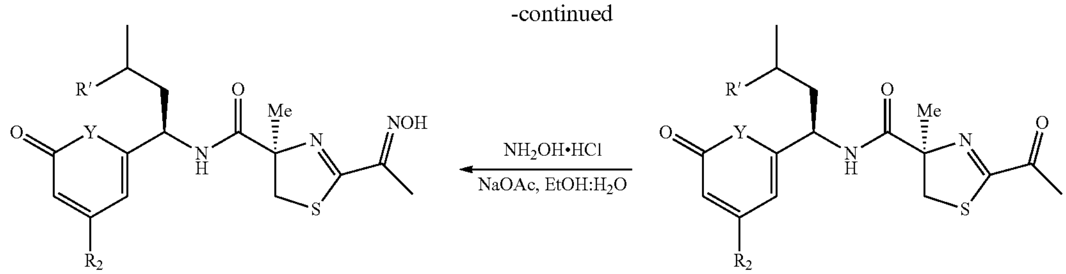

69 Y = O, R′ = Me, $R_2$ = —OMe, E-oxime
69a Y = O, R′ = Me, $R_2$ = —OMe, Z-oxime
70 Y = O, R′ = H, $R_2$ = —OEt, E-oxime
71 Y = O, R′ = H, $R_2$ = —On-Bu, E-oxime
71a Y = O, R′ = H, $R_2$ = —On-Bu, Z-oxime
72 Y = O, R′ = H, $R_2$ = n-heptyloxy, E-oxime
72a Y = O, R′ = H, $R_2$ = n-heptyloxy, Z-oxime
73 Y = O, R′ = H, $R_2$ = n-heptadecyloxy, E-oxime
73a Y = O, R′ = H, $R_2$ = n-heptadecyloxy, Z-oxime
74 Y = O, R′ = H, $R_2$ = —Oallyl, E-oxime
74a Y = O, R′ = H, $R_2$ = —Oallyl, Z-oxime
75 Y = O, R′ = H, $R_2$ = —Opropargyl, E-oxime
75a Y = O, R′ = H, $R_2$ = —Opropargyl, Z-oxime
76 Y = O, R′ = H, $R_2$ = cyclopropylmethyloxy, E-oxime
76a Y = O, R′ = H, $R_2$ = cyclopropylmethyloxy, Z-oxime
77 Y = O, R′ = H, $R_2$ = —$NEt_2$, E-oxime
78 Y = O, R′ = H, $R_2$ = Me, E-oxime
79 Y = O, R′ = H, $R_2$ = vinyl, E-oxime 56 Y = NH, R′ = H, $R_2$ = —OH
57 Y = O, R′ = H, $R_2$ = —OH
58 Y = O, R′ = Me, $R_2$ = —OMe
59 Y = O, R′ = H, $R_2$ = —OEt
60 Y = O, R′ = H, $R_2$ = —On-Bu
61 Y = O, R′ = H, $R_2$ = n-heptyloxy
62 Y = O, R′ = H, $R_2$ = n-heptadecyloxy
63 Y = O, R′ = H, $R_2$ = —Oallyl
64 Y = O, R′ = H, $R_2$ = —Opropargyl
65 Y = O, R′ = H, $R_2$ = cyclopropylmethyloxy
66 Y = O, R′ = H, $R_2$ = —$NEt_2$
67 Y = O, R′ = H, $R_2$ = Me
68 Y = O, R′ = H, $R_2$ = vinyl Compound 43

43

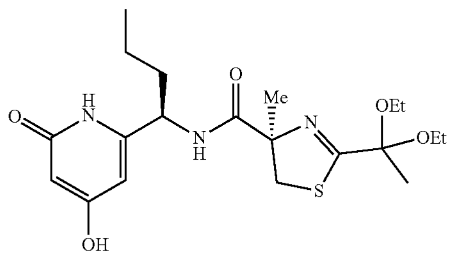

To a suspension of (R)-21 (20 mg, 0.11 mmol) and (R)-39 (27 mg, 0.11 mmol) in $CH_2Cl_2$ (1.3 mL) were added HATU (43 mg, 0.11 mmol), HOAt (16 mg, 0.11 mmol) and DIPEA (0.082 mL, 0.47 mmol) and the mixture was stirred at 23° C. overnight. Dilution with $CH_2Cl_2$, washing of the organic layer with 0.5M HCl, with brine and then dried over anhydrous $Na_2SO_4$. Evaporation of the solvent gave a crude which was purified by flash chromatography on silica gel ($CH_2Cl_2$/$CH_3OH$ 98/2) to afford 43 (46 mg, 100% yield).

$^1H$ NMR (300 MHz, $CD_3OD$): δ 5.90 (m, 1H), 5.66 (m, 1H), 4.76 (q, J=7.7 Hz, 1H), 3.71-3.45 (m, 5H), 3.26-3.17 (m, 1H), 1.79 (q, J=7.7 Hz, 2H), 1.59 (d, J=1.9 Hz, 3H), 1.50 (d, J=0.7 Hz, 3H), 1.37 (m, 2H), 1.28-1.14 (m, 6H), 1.06-0.89 (m, 3H).

MS (ES): m/z 448.3 $[M+Na]^+$, 851.4 $[2M+H]^+$.

Compound 44

44

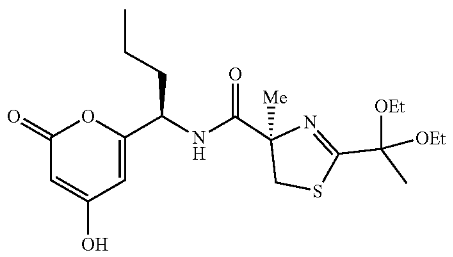

To a suspension of (R)-22 (12 mg, 0.067 mmol) and (R)-39 (16 mg, 0.0.067 mmol) in $CH_2Cl_2$ (0.8 mL) were added HATU (26 mg, 0.067 mmol), HOAt (10 mg, 0.067 mmol) and DIPEA (0.05 mL, 0.29 mmol) and the mixture was stirred at 23° C. overnight. Dilution with $CH_2Cl_2$, washing of the organic layer with 0.5M HCl, with brine and then dried over anhydrous $Na_2SO_4$. Evaporation of the solvent gave a crude which was purified by flash chromatography on silica gel ($CH_2Cl_2$/$CH_3OH$ 98/2) to afford 44 (31 mg, 100% yield).

$^1H$ NMR (400 MHz, $CDCl_3$): δ 7.21 (d, J=8.9 Hz, 1H), 6.04-5.98 (m, 1H), 5.51 (dd, J=2.2, 0.5 Hz, 1H), 4.71 (td, J=8.5, 6.7 Hz, 1H), 3.65-3.43 (m, 5H), 3.23-3.12 (m, 1H), 2.81 (s, 3H), 1.80 (dddd, J=51.2, 17.5, 9.1, 5.1 Hz, 1H), 1.52 (s, 3H), 1.51-1.25 (m, 3H), 1.22 (dtd, J=7.8, 7.1, 0.6 Hz, 4H), 0.94 (t, J=7.3 Hz, 3H).

$^{13}C$ NMR (100 MHz, $CDCl_3$): δ 177.6, 175.2, 170.7, 170.6, 165.9, 165.4, 163.3, 100.8, 100.4, 91.0, 85.1, 57.9 (×2), 55.7, 51.4, 43.7, 40.5, 38.8, 34.7, 25.2, 23.9, 19.2, 18.8, 17.4, 15.4, 13.7, 12.7.

MS (ES): m/z 449.1 $[M+Na]^+$.

Compound 45

45

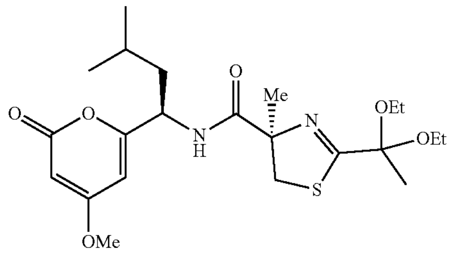

To a suspension of (R)-39 (63 mg, 0.24 mmol) and (R)-24 (74 mg, 0.24 mmol) in $CH_2Cl_2$ (2.2 mL) were added HATU (188 mg, 0.49 mmol), HOAt (69 mg, 0.49 mmol) and DIPEA (0.18 mL, 1.03 mmol) and the mixture was stirred at 23° C. overnight. Dilution with $CH_2Cl_2$, washing of the organic layer with 0.5 M HCl and brine and, finally, dried over anhydrous $Na_2SO_4$. Evaporation of the solvent gave a crude which was purified by flash chromatography on silica gel (hexane/EtOAc 9/1 to 7/3) to obtain 45 (50 mg, 47% yield).

$^1$H NMR (300 MHz, $CDCl_3$): δ 7.03 (d, J=8.9 Hz, 1H), 5.85 (d, J=2.3 Hz, 1H), 5.37 (d, J=2.2 Hz, 1H), 4.78 (td, J=8.9, 6.0 Hz, 1H), 3.76 (s, 3H), 3.67-3.41 (m, 5H), 3.14 (d, J=11.7 Hz, 1H), 1.74-1.62 (m, 1H), 1.60 (s, 2H), 1.59 (s, 3H), 1.51 (s, 3H), 1.29-1.14 (m, 6H), 0.93 (dd, J=6.2, 3.5 Hz, 6H).

Compound 46

46

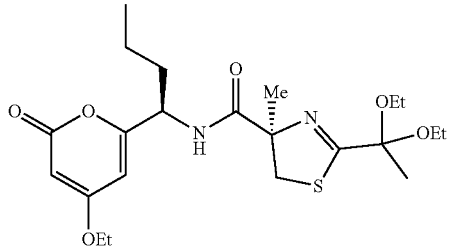

To a suspension of (R)-25 (24 mg, 0.112 mmol) and (R)-39 (29 mg, 0.112 mmol) in $CH_2Cl_2$ (1 mL) were added HATU (88 mg, 0.23 mmol), HOAt (32 mg, 0.23 mmol) and DIPEA (0.083 mL, 0.48 mmol) and the mixture was stirred at 23° C. overnight. Dilution with $CH_2Cl_2$, washing of the organic layer with 0.5M HCl, with brine and then dried over anhydrous $Na_2SO_4$. Evaporation of the solvent gave a crude which was purified by flash chromatography on silica gel (hexane/EtOAc from 9/1 to 7/3) to afford 46 (38 mg, 73% yield).

$^1$H NMR (300 MHz, $CDCl_3$) δ 7.00 (d, J=8.9 Hz, 1H), 5.81 (d, J=2.0 Hz, 1H), 5.34 (dd, J=2.3, 0.9 Hz, 1H), 4.70 (td, J=8.5, 6.2 Hz, 1H), 4.03-3.90 (m, 2H), 3.64-3.42 (m, 5H), 3.13 (dd, J=11.7, 0.9 Hz, 1H), 1.84 (m, 1H), 1.68 (m, 1H), 1.59 (d, J=0.9 Hz, 3H), 1.54-1.48 (m, 3H), 1.37 (td, J=7.0, 0.9 Hz, 3H), 1.24-1.14 (m, 6H), 0.97-0.88 (m, 3H).

MS (ES): m/z 477.2 $[M+Na]^+$.

Compound 47

47

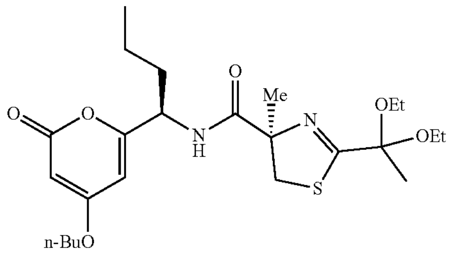

To a suspension of (R)-27 (24 mg, 0.1 mmol) and (R)-39 (26 mg, 0.11 mmol) in $CH_2Cl_2$ (1 mL) were added HATU (39 mg, 0.103 mmol), HOAt (14 mg, 0.104 mmol) and DIPEA (0.075 mL, 0.43 mmol) and the mixture was stirred at 23° C. overnight. Dilution with $CH_2Cl_2$, washing of the organic layer with 0.5 M HCl, with brine and then dried over anhydrous $Na_2SO_4$. Evaporation of the solvent gave a crude which was purified by flash chromatography on silica gel ($CH_2Cl_2$/EtOAc 9/1) to afford 47 (48 mg, 100% yield).

$^1$H NMR (300 MHz, $CDCl_3$) δ 7.02 (d, J=8.9 Hz, 1H), 5.82 (dt, J=2.2, 0.6 Hz, 1H), 5.35 (d, J=2.2 Hz, 1H), 4.72 (td, J=8.7, 6.2 Hz, 1H), 3.90 (t, J=6.4 Hz, 2H), 3.67-3.45 (m, 5H), 3.15 (dd, J=11.7, 0.6 Hz, 1H), 1.97-1.62 (m, 4H), 1.60 (d, J=0.6 Hz, 3H), 1.53 (s, 3H), 1.51-1.30 (m, 4H), 1.26-1.13 (m, 6H), 1.00-0.85 (m, 6H).

MS (ES): m/z 505.3 $[M+Na]^+$.

$R_f$: 0.62 (Hex:EtOAc 1:1).

Compound 48

48

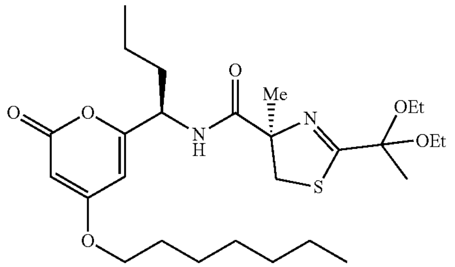

A mixture of (R)-28 (0.199 mmol) and (R)-39 (55 mg) was coevaporated with toluene and then HATU (82 mg) and HOAt (30 mg) were added. Reaction flask was evacuated and filled with $N_2$. $CH_2Cl_2$ (2 mL) and DIPEA (156 μL) were introduced via syringe. The mixture was stirred at 23° C. for 16 h. Then, it was diluted with $CH_2Cl_2$ before washing twice with HCl 0.5 N and once with brine. The organic layer was dried over anhydrous $Na_2SO_4$, filtered and evaporated to dryness. Crude residue was purified on a system for flash chromatography with a $SiO_2$ column eluting with mixtures of hexane/EtOAc from 100:0 to 50:50 in 15 min to afford 48 (71 mg, 68% yield).

$^1$H NMR (400 MHz, $CDCl_3$): δ 7.04 (d, J=8.9 Hz, 1H), 5.82 (dd, J=2.2, 0.6 Hz, 1H), 5.34 (d, J=2.2 Hz, 1H), 4.71 (td, J=8.5, 6.2 Hz, 1H), 3.88 (td, J=6.5, 1.1 Hz, 2H), 3.60 (d, J=11.7 Hz, 1H), 3.60-3.44 (m, 4H), 3.14 (d, J=11.7 Hz, 1H), 1.85 (ddt, J=13.6, 9.6, 6.3 Hz, 1H), 1.78-1.61 (m, 3H), 1.59 (s, 3H), 1.52 (s, 3H), 1.44-1.24 (m, 10H), 1.24-1.17 (m, 6H), 0.92 (t, J=7.3 Hz, 3H), 0.86 (t, J=6.9 Hz, 3H).

$^{13}C$ NMR (100 MHz, $CDCl_3$): δ 176.7, 174.4, 170.1, 164.0, 162.8, 100.2, 99.8, 88.6, 85.2, 69.0, 57.7, 57.6, 50.7, 40.3, 34.7, 31.6, 28.8, 28.3, 25.7, 25.3, 23.7, 22.5, 19.0, 15.2, 14.0, 13.5.

Compound 49

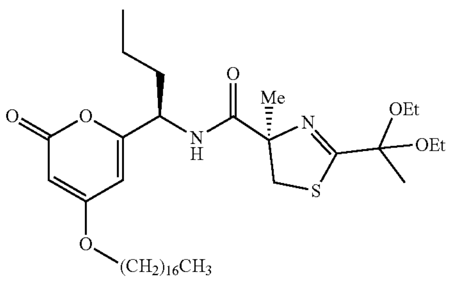

49

To a solution of (R)-29 (93 mg, 0.174 mmol) and (R)-39 (48 mg, 0.183 mmol) in $CH_2Cl_2$ (1.2 mL) was sequentially added O-(7-azabenzotriazol-1-yl)-N,N,N',N'-tetramethyluronium hexafluorophosphate (HATU) (72 mg, 0.188 mmol), 1-hydroxy-7-azabenzotriazole (HOAt) (26 mg, 0.190 mmol), and N,N-diisopropylethylamine (137 μL, 0.785 mmol) at 23° C. The reaction mixture was stirred overnight at 23° C., diluted with $CH_2Cl_2$ and washed HCl 0.5 M. The aqueous layer was extracted with $CH_2Cl_2$ (2×). The combined organic layers were dried over anhydrous $Na_2SO_4$, filtered and concentrated under vacuum. The obtained crude was purified in an automatic system for flash chromatography ($SiO_2$, Hex:EtOAc) to obtain 49 (91 mg, 78% yield for 2 steps).

$^1H$ NMR (400 MHz, $CDCl_3$): δ 7.03 (d, J=8.9 Hz, 1H), 5.83 (d, J=2.1 Hz, 1H), 5.35 (d, J=2.2 Hz, 1H), 4.72 (td, J=8.6, 6.2 Hz, 1H), 3.89 (td, J=6.6, 1.1 Hz, 2H), 3.61 (d, J=11.7 Hz, 1H), 3.61-3.45 (m, 4H), 3.15 (d, J=11.7 Hz, 1H), 1.93-1.79 (m, 1H), 1.79-1.62 (m, 3H), 1.60 (s, 3H), 1.53 (s, 3H), 1.44-1.23 (m, 32H), 1.24-1.18 (m, 6H), 0.93 (t, J=7.3 Hz, 3H), 0.86 (t, J=6.8 Hz, 3H).

$^{13}C$ NMR (100 MHz, $CDCl_3$): δ 176.8, 174.4, 170.1, 164.0, 162.8, 100.2, 99.9, 88.6, 85.2, 69.0, 57.7, 57.6, 50.8, 40.3, 34.7, 31.9, 29.7, 29.6, 29.5 (×2), 29.3, 29.2, 28.4, 25.8, 25.3, 23.7, 22.7, 19.0, 15.2, 14.1, 13.5.

Compound 50

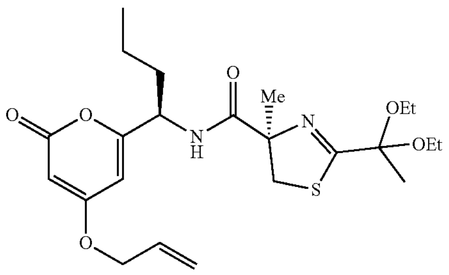

50

To a solution of (R)-30 (5.20 g, 15.42 mmol) and (R)-39 (4.03 g, 15.42 mmol) in $CH_2Cl_2$ (110 mL) was sequentially added O-(7-azabenzotriazol-1-yl)-N,N,N',N'-tetramethyluronium hexafluorophosphate (HATU) (5.86 g, 15.42 mmol), 1-hydroxy-7-azabenzotriazole (HOAt) (2.11 g, 15.42 mmol), and N,N-diisopropylethylamine (10.74 mL, 61.66 mmol) at 23° C. The reaction mixture was stirred overnight at 23° C., diluted with $CH_2Cl_2$ and washed HCl 0.5 M. The aqueous layer was extracted with $CH_2Cl_2$ (2×). The combined organic layers were dried over anhydrous $Na_2SO_4$, filtered and concentrated under vacuum. The obtained crude was purified by in an automatic system for flash chromatography ($SiO_2$, Hex:EtOAc 50:50) to obtain 50 (6.08 g, 85% yield).

$^1H$ NMR (400 MHz, $CDCl_3$): δ 7.02 (d, J=8.9 Hz, 1H), 6.01-5.88 (m, 1H), 5.86 (dd, J=2.2, 0.6 Hz, 1H), 5.46-5.24 (m, 3H), 4.72 (td, J=8.5, 6.3 Hz, 1H), 4.46 (dt, J=5.5, 1.5 Hz, 1H), 3.70-3.39 (m, 5H), 3.16 (d, J=11.6 Hz, 1H), 1.92-1.83 (m, 1H), 1.75-1.66 (m, 1H), 1.62 (s, 3H), 1.55 (s, 3H), 1.40-1.28 (m, 2H), 1.25-1.17 (m, 6H), 0.93 (td, J=7.4, 2.4 Hz, 3H).

$^{13}C$ NMR (100 MHz, $CDCl_3$): δ 176.8, 174.5, 169.6, 163.8, 163.1, 130.6, 119.5, 100.2, 99.7, 89.2, 85.2, 69.5, 57.8, 57.7, 50.8, 40.4, 34.7, 25.3, 23.7, 19.0, 15.2, 13.5.

MS (ES+): 489.2 $[M+Na]^+$.

Optical rotation: $[\alpha_D]$ +51.5 (c 0.037, MeOH).

$R_f$: 0.25 (Hex:EtOAc 7:3).

Compound 51

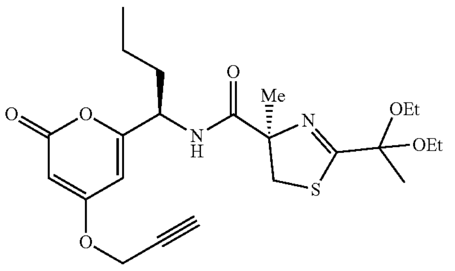

51

To a solution of (R)-31 (2.41 g, 7.18 mmol) and (R)-39 (1.98 g, 7.56 mmol) in $CH_2Cl_2$ (53 mL) was sequentially added O-(7-azabenzotriazol-1-yl)-N,N,N',N'-tetramethyluronium hexafluorophosphate (HATU) (2.96 g, 7.79 mmol), 1-hydroxy-7-azabenzotriazole (HOAt) (1.08 g, 7.87 mmol), and N,N-diisopropylethylamine (5.6 mL, 32.46 mmol) at 23° C. The reaction mixture was stirred overnight at 23° C., diluted with $CH_2Cl_2$ and washed HCl 0.5 M. The aqueous layer was extracted with $CH_2Cl_2$ (2×). The combined organic layers were dried over anhydrous $Na_2SO_4$, filtered and concentrated under vacuum. The obtained crude was purified in an automatic system for flash chromatography ($SiO_2$, Hex:EtOAc from 10:0 to 50:50) to obtain 51 (3.37 g, 100% yield for 2 steps).

$^1H$ NMR (400 MHz, $CDCl_3$): δ 7.04 (d, J=8.9 Hz, 1H), 5.86 (dd, J=2.3, 0.6 Hz, 1H), 5.52 (d, J 30=2.3 Hz, 1H), 4.72 (td, J=8.6, 6.2 Hz, 1H), 4.63 (d, J=2.5 Hz, 2H), 3.60 (d, J=11.8 Hz, 1H), 3.63-3.43 (m, 4H), 3.15 (d, J=11.8 Hz, 1H), 2.62 (t, J=2.4 Hz, 1H), 1.86 (ddt, J=13.6, 9.6, 6.3 Hz, 1H), 1.76-1.62 (m, 1H), 1.60 (s, 3H), 1.52 (s, 3H), 1.45-1.28 (m, 2H), 1.27-1.16 (m, 6H), 0.93 (t, J=7.3 Hz, 3H).

$^{13}C$ NMR (100 MHz, $CDCl_3$): δ 176.9, 174.5, 168.6, 163.4 (2×), 100.2, 99.3, 89.9, 85.1, 77.7, 75.6, 57.7, 57.6, 56.4, 50.8, 40.3, 34.6, 25.3, 23.7, 19.0, 15.2, 13.5.

MS (ES+): 487.3 $[M+Na]^+$.

$R_f$: 0.35 (Hex:EtOAc 50:50).

Compound 52

52

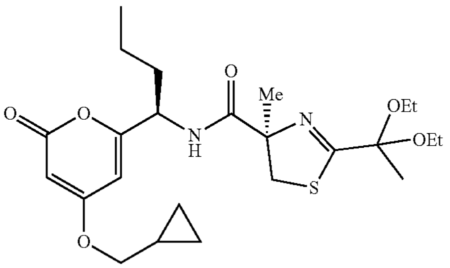

To a solution of (R)-32 (9.28 g, 26.41 mmol) and (R)-39 (6.90 g, 26.41 mmol) in $CH_2Cl_2$ (180 mL) was sequentially added O-(7-azabenzotriazol-1-yl)-N,N,N',N'-tetramethyluronium hexafluorophosphate (HATU) (10.04 g, 26.41 mmol), 1-hydroxy-7-azabenzotriazole (HOAt) (3.62 g, 26.41 mmol), and N,N-diisopropylethylamine (18.4 mL, 105.66 mmol) at 23° C. The reaction mixture was stirred overnight at 23° C., diluted with $CH_2Cl_2$ and washed HCl 0.5 M. The aqueous layer was extracted with $CH_2Cl_2$ (2×). The combined organic layers were dried over anhydrous $Na_2SO_4$, filtered and concentrated under vacuum. The obtained crude was purified by in an automatic system for flash chromatography ($SiO_2$, Hex:EtOAc 50:50) to obtain 52 (12.1 g, 95% yield).

$^1$H NMR (400 MHz, $CDCl_3$): δ 7.03 (d, J=8.9 Hz, 1H), 5.85 (dd, J=2.2, 0.5 Hz, 1H), 5.31 (d, J=2.2 Hz, 1H), 4.71 (td, J=8.5, 6.2 Hz, 1H), 3.80-3.67 (m, 2H), 3.61 (d, J=11.8 Hz, 1H), 3.61-3.42 (m, 4H), 3.14 (d, J=11.7 Hz, 1H), 1.86 (ddt, J=13.7, 9.5, 6.3 Hz, 1H), 1.75-1.62 (m, 1H), 1.60 (s, 3H), 1.52 (s, 3H), 1.45-1.15 (m, 2H), 1.22 (t, J=7.1 Hz, 3H), 1.20 (t, J=7.1 Hz, 3H), 0.92 (t, J=7.3 Hz, 3H), 0.74-0.58 (m, 2H), 0.38-0.27 (m, 2H).

$^{13}$C NMR (100 MHz, $CDCl_3$): δ 176.8, 174.4, 170.0, 163.9, 162.9, 100.2, 99.8, 88.6, 85.2, 73.7, 57.7, 57.6, 50.8, 40.3, 34.7, 25.3, 23.7, 19.0, 15.2, 13.5, 9.4, 3.3 (×2).

MS (ES+): 503.3 $[M+Na]^+$.

$R_f$: 0.49 (Hex:EtOAc 1:1).

53

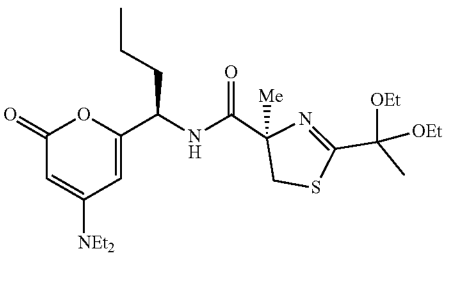

Compound 53

To a suspension of (R)-34 (31 mg, 0.13 mmol) and (R)-39 (34 mg, 0.13 mmol) in $CH_2Cl_2$ (1.5 mL) were added HATU (51 mg, 0.13 mmol), HOAt (19 mg, 0.13 mmol) and DIPEA (0.1 mL, 0.56 mmol) and the mixture was stirred at 23° C. overnight. Dilution with $CH_2Cl_2$, washing of the organic layer with 0.5 M HCl, with brine and then dried over anhydrous $Na_2SO_4$. Evaporation of the solvent gave a crude which was purified by flash chromatography on silica gel ($CH_2Cl_2$/$CH_3OH$ 98/2) to afford 53 (38 mg, 60% yield).

$^1$H NMR (300 MHz, $CDCl_3$) δ 7.04 (d, J=8.9 Hz, 1H), 5.85 (d, J=2.3 Hz, 1H), 4.96 (d, J=2.3 Hz, 1H), 4.67 (td, J=8.4, 6.8 Hz, 1H), 3.68-3.42 (m, 5H), 3.29 (qd, J=7.3, 3.5 Hz, 4H), 3.14 (d, J=11.7 Hz, 1H), 1.95-1.64 (m, 2H), 1.60 (s, 3H), 1.53 (s, 3H), 1.34 (dd, J=9.8, 6.8 Hz, 2H), 1.28-1.08 (m, 12H), 0.93 (t, J=7.3 Hz, 3H).

Compound 54

54

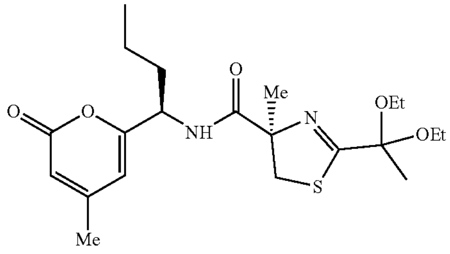

To a suspension of (R)-36 (10 mg, 0.053 mmol) and (R)-39 (14 mg, 0.053 mmol) in $CH_2Cl_2$ (0.4 mL) were added HATU (42 mg, 0.10 mmol), HOAt (15 mg, 0.10 mmol) and DIPEA (0.040 mL, 0.22 mmol) and the mixture was stirred at 23° C. overnight. Dilution with $CH_2Cl_2$, washing of the organic layer with 0.5 M HCl, with brine and then dried over anhydrous $Na_2SO_4$. Evaporation of the solvent gave a crude which was purified by flash chromatography on silica gel ($CH_2Cl_2$/EtOAc 6/4) to afford 54 (7 mg, 100% yield).

$^1$H NMR (300 MHz, $CDCl_3$) δ 7.08 (d, J=8.9 Hz, 1H), 5.96 (t, J=1.3 Hz, 1H), 5.93 (d, J=1.5 Hz, 1H), 4.72 (td, J=8.5, 6.6 Hz, 1H), 3.75-3.45 (m, 5H), 3.36 (d, J=11.8 Hz, 1H), 2.10 (d, J=1.2 Hz, 3H), 1.89-1.68 (m, 2H), 1.66 (s, 3H), 1.46-1.27 (m, 8H), 0.93 (t, J=7.3 Hz, 3H).

MS (ES): m/z 447.2 $[M+Na]^+$.

$R_f$: 0.33 (Hex:EtOAc 1:1).

Compound 55

55

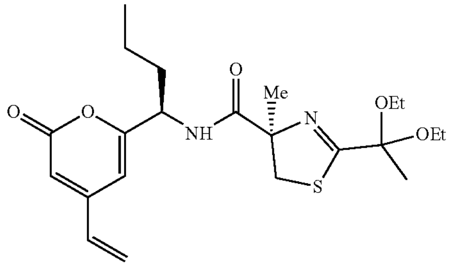

To a suspension of (R)-38 (1.06 g, 3.45 mmol) and (R)-39 (1.1 g, 3.45 mmol) in $CH_2Cl_2$ (24 mL) was sequentially added O-(7-azabenzotriazol-1-yl)-N,N,N',N'-tetramethyluronium hexafluorophosphate (HATU) (1.3 g, 3.45 mmol), 1-hydroxy-7-azabenzotriazole (HOAt) (473 mg, 3.45 mmol), and N,N-diisopropylethylamine (2.4 mL, 13.79 mmol) at 23° C. The reaction mixture was stirred overnight at 23° C., filtered through Celite® and the filtrate was concentrated under vacuum. The obtained crude was purified in an automatic system for flash chromatography ($SiO_2$, Hex:EtOAc) to obtain 55 (1.35 g, 90% yield).

$^1$H NMR (400 MHz, $CDCl_3$): δ 6.45 (dd, J=17.4, 10.8 Hz, 1H), 6.33 (d, J=1.5 Hz, 1H), 6.04-5.99 (m, 1H), 5.94 (d, J=17.5 Hz, 1H), 5.61 (d, J=10.8 Hz, 1H), 4.79 (td, J=8.5, 6.3 Hz, 1H), 3.81 (d, J=11.8 Hz, 1H), 3.64-3.45 (m, 4H), 3.19

(d, J=11.8 Hz, 1H), 1.94-1.83 (m, 1H), 1.82-1.70 (m, 1H), 1.64 (s, 6H), 1.45-1.29 (m, 2H), 1.23 (td, J=7.1, 2.6 Hz, 6H), 0.95 (t, J=7.4 Hz, 3H).

$^{13}$C NMR (75 MHz, $CDCl_3$): δ 162.6, 151.4, 133.5, 123.1, 111.4, 100.4, 99.7, 58.2, 58.1, 51.6, 40.5, 35.1, 25.5, 24.0, 19.3, 15.3, 13.7.

MS (ES+): m/z 459.2 $[M+Na]^+$.

$R_f$: 0.43 (Hex:EtOAc 1:1).

Compound 56

56

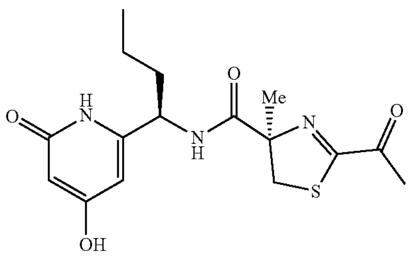

To a mixture of 43 (46 mg, 0.11 mmol) and pentane (3.4 mL) was added formic acid (2.3 mL). The reaction was stirred vigorously at 23° C. for 1.5 h and then evaporated to dryness with toluene to remove efficiently the formic acid giving crude 56 (100%) which was used in the next step without further purification.

MS (ES): m/z 352.2 $[M+H]^+$, 703.2 $[2M+H]^+$.

Compound 57

57

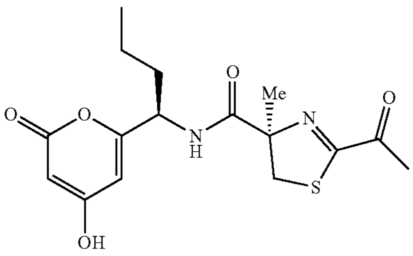

To a mixture of 44 (16 mg, 0.034 mmol) and pentane (0.96 mL) was added formic acid (0.64 mL). The reaction was stirred vigorously at 23° C. for 1.5 h and then evaporated to dryness with toluene to remove efficiently the formic acid giving crude 57 (13 mg, 100% yield) which was used in the next step without further purification.

$^1$H NMR (500 MHz, $CDCl_3$) δ 7.16 (d, J=8.4 Hz, 1H), 6.09 (d, J=2.0 Hz, 1H), 5.58 (d, J=2.1 Hz, 1H), 4.75 (td, J=8.5, 7.0 Hz, 1H), 3.60 (d, J=11.9 Hz, 1H), 3.30 (d, J=11.9 Hz, 1H), 2.57 (s, 3H), 1.98-1.76 (m, 2H), 1.56 (s, 3H), 1.51-1.31 (m, 2H), 0.98 (t, J=7.4 Hz, 3H).

MS (ES): m/z 375.1 $[M+Na]^+$, 727.1 $[2M+Na]^+$.

Compound 58

58

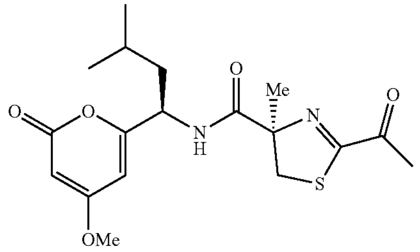

To a mixture of 45 (57 mg, 0.13 mmol) and pentane (3.4 mL) was added formic acid (2.3 mL). The reaction was stirred vigorously at 23° C. for 2 h and then evaporated to dryness with toluene to remove efficiently the formic acid. The crude was chromatographed on silica gel ($CH_2Cl_2$/EtOAc from 9/1 to 8/2) to give 58 (47 mg, 100% yield).

$^1$H NMR (300 MHz, $CDCl_3$) δ 6.98 (d, J=8.9 Hz, 1H), 5.93 (d, J=2.2 Hz, 1H), 5.43 (d, J=2.2 Hz, 1H), 4.81 (td, J=8.5, 6.9 Hz, 1H), 3.85-3.70 (m, 3H), 3.62 (d, J=11.9 Hz, 1H), 3.27 (d, J=11.9 Hz, 1H), 2.56 (s, 3H), 1.82-1.56 (m, 3H), 1.53 (s, 3H), 0.97 (t, J=6.4 Hz, 6H).

Compound 59

59

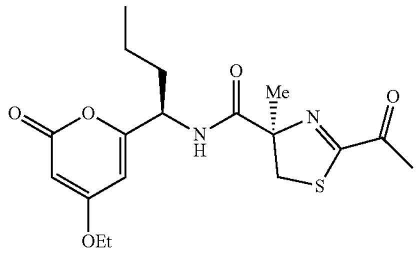

To a mixture of 46 (35 mg, 0.077 mmol) and pentane (2.1 mL) was added formic acid (1.4 mL). The reaction was stirred vigorously at 23° C. for 2 h and then evaporated to dryness with toluene to remove efficiently the formic acid giving crude 59 (30 mg, 100% yield) which was used in the next step without further purification.

$^1$H NMR (300 MHz, $CDCl_3$) δ 6.08 (d, J=2.0 Hz, 1H), 5.55 (d, J=2.1 Hz, 1H), 5.18 (d, J=8.4 Hz, 1H), 4.36 (d, J=7.9 Hz, 1H), 2.17 (d, J=1.1 Hz, 1H), 2.06 (s, 0H), 1.93-1.59 (m, 12H), 1.53 (d, J=1.1 Hz, 1H), 1.49-1.29 (m, 16H), 0.92 (t, J=7.3 Hz, 5H).

MS (ES): m/z 381.2 $[M+H]^+$, 403.3 $[M+Na]^+$.

$R_f$: 0.2 (Hex:EtOAc 6:4).

Compound 60

60

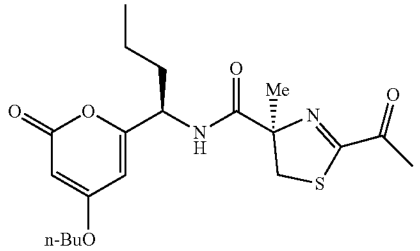

To a mixture of 47 (48 mg, 0.1 mmol) and pentane (3.2 mL) was added formic acid (2.2 mL). The reaction was stirred vigorously at 23° C. for 2 h and then evaporated to dryness with toluene to remove efficiently the formic acid giving crude 60 (100% yield) which was used in the next step without further purification.

$^1$H NMR (300 MHz, $CDCl_3$) δ 7.04 (d, J=8.9 Hz, 1H), 5.92 (d, J=2.2 Hz, 1H), 5.41 (d, J=2.2 Hz, 1H), 4.74 (q, J=7.8 Hz, 1H), 4.01-3.89 (m, 2H), 3.63 (d, J=11.9 Hz, 1H), 3.28 (d, J=11.9 Hz, 1H), 2.56 (d, J=1.4 Hz, 3H), 1.95-1.65 (m, 4H), 1.64-1.17 (m, 7H), 1.05-0.87 (m, 6H).

MS (ES): m/z 409.3 $[M+H]^+$, 431.1 $[M+Na]^+$.

$R_f$: 0.27 (Hex:EtOAc 6:4).

Compound 61

61

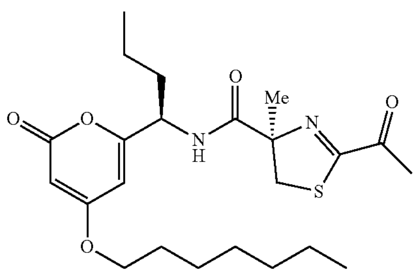

A mixture of 48 (69 mg) and pentane (3.6 mL) and formic acid (2.4 mL) was vigorously stirred for 2 h and the volatiles were evaporated to dryness. The crude was coevaporated few times with a mixture of $CH_2Cl_2$/toluene to eliminate the acid and give crude 61 (59 mg, 100% yield) which was used in the next step without further purification.

$^1$H NMR (400 MHz, $CDCl_3$): δ 7.04 (d, J=8.9 Hz, 1H), 5.91 (d, J=2.2 Hz, 1H), 5.40 (d, J=2.2 Hz, 1H), 4.73 (dt, J=8.8, 7.5 Hz, 1H), 3.91 (td, J=6.5, 1.7 Hz, 2H), 3.61 (d, J=12.0 Hz, 1H), 3.26 (d, J=11.9 Hz, 1H), 2.55 (s, 3H), 1.93-1.67 (m, 4H), 1.53 (s, 3H), 1.47-1.18 (m, 10H), 0.95 (t, J=7.3 Hz, 3H), 0.88 (t, J=6.8 Hz, 3H).

$^{13}$C NMR (100 MHz, $CDCl_3$): δ 193.2, 173.2, 170.4, 170.3, 164.3, 161.7, 100.8, 88.9, 86.0, 69.2, 51.0, 40.1, 34.8, 31.6, 29.6, 28.8, 28.3, 26.3, 25.7, 24.5, 22.5, 19.0, 14.0, 13.5.

Compound 62

62

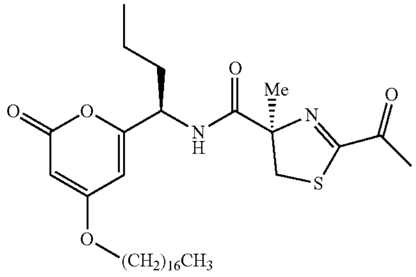

Over 49 (89 mg, 0.134 mmol) was added at 23° C. pentane (4.6 mL) and formic acid (3.1 mL). The reaction mixture was stirred vigorously for 2 hours at 23° C. and the volatiles were evaporated under vacuum. The obtained crude was evaporated few times with a mixture of $CH_2Cl_2$: toluene to eliminate formic acid to give crude 62 which was used in the next step without further purification.

$^1$H NMR (400 MHz, $CDCl_3$): δ 7.03 (d, J=9.0 Hz, 1H), 5.90 (d, J=2.1 Hz, 1H), 5.39 (d, J=2.2 Hz, 1H), 4.73 (dt, J=8.8, 7.6 Hz, 1H), 3.90 (td, J=6.5, 1.7 Hz, 2H), 3.61 (d, J=11.9 Hz, 1H), 3.26 (d, J=11.9 Hz, 1H), 2.55 (s, 3H), 1.93-1.66 (m, 4H), 1.53 (s, 3H), 1.46-1.18 (m, 32H), 0.95 (t, J=7.4 Hz, 3H), 0.85 (t, J=6.9 Hz, 3H).

$^{13}$C NMR (100 MHz, $CD_3OD$): δ 193.1, 173.2, 170.4, 170.2, 164.2, 161.7, 100.8, 88.9, 86.0, 69.2, 51.0, 40.1, 34.9, 31.9, 29.6 (×3), 29.5, 29.4, 29.3, 29.1, 28.3, 26.3, 25.7, 24.5, 22.6, 19.0, 14.1, 13.5.

Compound 63

63

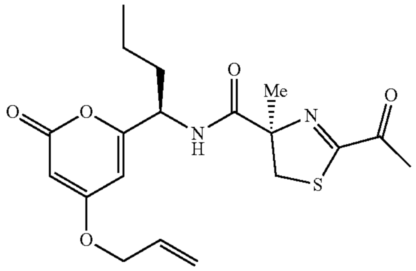

Over 50 (6.0 g, 12.92 mmol) was added at 23° C. pentane (314 mL) and formic acid (212 mL). The reaction mixture was stirred vigorously for 2 hours at 23° C. and the volatiles were evaporated under vacuum. The obtained crude was evaporated few times with a mixture of $CH_2Cl_2$:toluene to eliminate formic acid to give crude 63 (6.0 g, >100% yield) which was used in the next step without further purification.

$^1$H NMR (400 MHz, $CDCl_3$): δ 7.11 (d, J=8.9 Hz, 1H), 5.97 (d J=2.2 Hz, 1H), 5.99-5.89 (m, 1H), 5.48 (d, J=2.2 Hz, 1H), 5.44-5.28 (m, 2H), 4.75 (q, J=7.9 Hz, 1H), 4.49 (td, J=5.5, 1.5 Hz, 2H), 3.60 (d, J=11.9 Hz, 1H), 3.27 (d, J=11.9 Hz, 1H), 2.55 (s, 3H), 2.03-1.67 (m, 2H), 1.53 (s, 3H), 1.45-1.26 (m, 1H), 0.95 (t, J=7.4 Hz, 3H).

$^{13}$C NMR (100 MHz, $CDCl_3$): δ 193.3, 173.3, 170.6, 169.8, 164.1, 162.2, 130.7, 119.9, 100.8, 89.6, 86.3, 69.8, 51.2, 40.3, 35.1, 26.5, 24.8, 24.7, 19.3 (×2), 13.7.

MS (ES+): 393.2 $[M+H]^+$, 415.2 $[M+Na]^+$.

Optical rotation: $[\alpha_D]$ +51.0 (c 0.014, MeOH).

$R_f$: 0.39 (Hex:EtOAc 1:1).

Compound 64

64

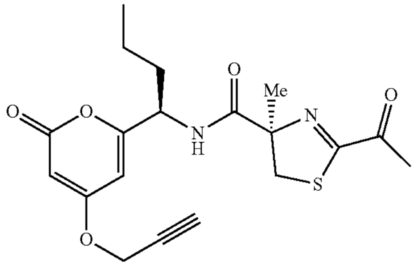

Over 51 (3.57 g, 7.68 mmol) was added at 23° C. pentane (186 mL) and formic acid (125 mL). The reaction mixture was stirred vigorously for 2 hours at 23° C. and the volatiles were evaporated under vacuum. The obtained crude was evaporated few times with a mixture of $CH_2Cl_2$:toluene to eliminate formic acid to give crude 64 which was used in the next step without further purification.

$^1H$ NMR (400 MHz, $CDCl_3$): δ 7.05 (d, J=8.9 Hz, 1H), 5.95 (d, J=2.2 Hz, 1H), 5.58 (d, J=2.3 Hz, 1H), 4.75 (q, J=8.1 Hz, 1H), 4.66 (d, J=2.5 Hz, 2H), 3.61 (d, J=11.9 Hz, 1H), 3.27 (d, J=11.9 Hz, 1H), 2.63 (t, J=2.4 Hz, 1H), 2.55 (s, 3H), 1.95-1.72 (m, 2H), 1.54 (s, 3H), 1.47-1.28 (m, 2H), 0.96 (t, J=7.4 Hz, 3H).

$^{13}C$ NMR (100 MHz, $CDCl_3$): δ 193.2, 173.3, 168.7, 163.8, 163.1, 162.3, 100.3, 90.1, 86.0, 77.8, 75.5, 56.5, 51.0, 40.1, 34.8, 26.3, 24.5, 19.0, 13.5.

MS (ES+): 391.2 $[M+H]^+$, 413.1 $[M+Na]^+$.

$R_f$: 0.26 (Hex:EtOAc 60:40).

Compound 65

65

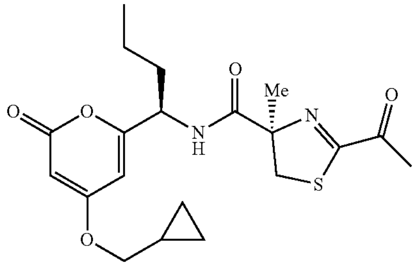

Over 52 (9.0 g, 18.73 mmol) was added at 23° C. pentane (460 mL) and formic acid (315 mL). The reaction mixture was stirred vigorously for 2 hours at 23° C. and the volatiles were evaporated under vacuum. The obtained crude was evaporated few times with a mixture of $CH_2Cl_2$:toluene to eliminate formic acid to give crude 65 (7.61 g, 100% yield) which was used in the next step without further purification.

$^1H$ NMR (400 MHz, $CDCl_3$): δ 7.05 (d, J=8.9 Hz, 1H), 5.94 (d, J=2.2 Hz, 1H), 5.37 (d, J=2.3 Hz, 1H), 4.73 (q, J=7.9 Hz, 1H), 3.76 (dd, J=7.1, 1.9 Hz, 2H), 3.61 (d, J=11.9 Hz, 1H), 3.27 (d, J=12.0 Hz, 1H), 2.55 (s, 3H), 1.94-1.73 (m, 1H), 1.66-1.53 (m, 1H), 1.53 (s, 3H), 1.52-1.16 (m, 2H), 0.95 (t, J=7.4 Hz, 3H), 0.70-0.61 (m, 2H), 0.33 (t, J=5.2 Hz, 2H).

$^{13}C$ NMR (100 MHz, $CDCl_3$): δ 193.2, 173.2, 170.4, 164.3, 163.0, 161.8, 100.8, 88.9, 86.0, 73.9, 51.0, 40.1, 34.8, 26.3, 24.5, 19.0, 13.5, 9.3, 3.4, 3.3.

MS (ES+): 407.1 $[M+H]^+$, 429.2 $[M+Na]^+$.

Optical rotation: $[\alpha_D]$ +56.2 (c 0.019, MeOH).

$R_f$: 0.47 (Hex:EtOAc 1:1).

Compound 66

66

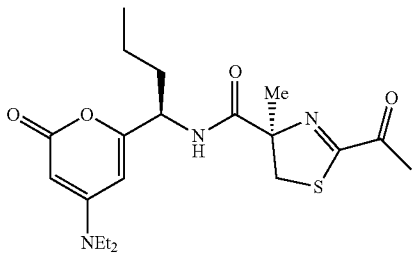

To a mixture of 53 (30 mg, 0.062 mmol) and pentane (1.8 mL) was added formic acid (1.2 mL). The reaction was stirred vigorously at 23° C. for 1.5 h and then evaporated to dryness with toluene to remove efficiently the formic acid giving crude 66 (100% yield) which was used in the next step without further purification.

$^1H$ NMR (300 MHz, $CDCl_3$) δ 7.16 (d, J=8.8 Hz, 1H), 5.94 (d, J=2.4 Hz, 1H), 5.04 (dd, J=5.5, 2.3 Hz, 1H), 4.80-4.60 (m, 1H), 3.63 (d, J=11.9 Hz, 1H), 3.38-3.18 (m, 5H), 2.56 (s, 3H), 1.95-1.63 (m, 2H), 1.55 (s, 3H), 1.37-1.05 (m, 8H), 0.96 (t, J=7.3 Hz, 3H).

MS (ES): m/z 408.2 $[M+H]^+$.

Compound 67

67

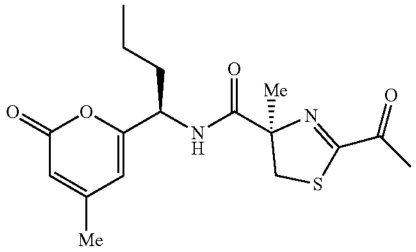

To a mixture of 54 (16 mg, 0.037 mmol) and pentane (0.96 mL) was added formic acid (0.64 mL). The reaction was stirred vigorously at 23° C. for 2 h and then evaporated to dryness with toluene to remove efficiently the formic acid giving crude 67 (100% yield) which was used in the next step without further purification.

$^1H$ NMR (400 MHz, $CDCl_3$) δ 7.03 (d, J=9.0 Hz, 1H), 6.04-5.93 (m, 2H), 4.75 (q, J=8.0 Hz, 1H), 3.68-3.60 (d, J=11.9 Hz, 1H), 3.28 (d, J=11.9 Hz, 1H), 2.57 (s, 3H), 2.14 (s, 3H), 1.94-1.74 (m, 2H), 1.55 (s, 3H), 1.46-1.27 (m, 2H), 1.04-0.90 (m, 3H).

MS (ES): m/z 351.2 $[M+H]^+$, 373.1 $[M+Na]^+$.

$R_f$: 0.42 (Hex:EtOAc 1:1).

Compound 68

68

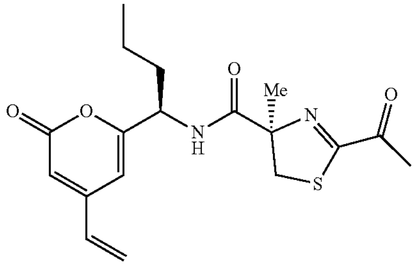

Over 55 (1.35 g, 3.1 mmol) was added at 23° C. pentane (70 mL) and formic acid (47 mL). The reaction mixture was stirred vigorously for 2 hours at 23° C. and the volatiles were evaporated under vacuum. The obtained crude was evaporated few times with a mixture of $CH_2Cl_2$:toluene to eliminate formic acid, The obtained crude was purified in an automatic system for flash chromatography ($SiO_2$) to yield 68 (454 mg, 40% yield).

$^1H$ NMR (400 MHz, $CDCl_3$): δ 7.04 (d, J=9.0 Hz, 1H), 6.45 (dd, J=17.5, 10.8 Hz, 1H), 6.26 (d, J=1.3 Hz, 1H), 6.04 (dd, J=1.5, 0.8 Hz, 1H), 5.89 (dd, J=17.6, 0.8 Hz, 1H), 5.61 (dd, J=10.8, 0.8 Hz, 1H), 4.84-4.68 (m, 1H), 3.62 (dd, J=11.9, 0.9 Hz, 1H), 3.25 (dd, J=11.9, 0.9 Hz, 1H), 2.54 (d, J=0.9 Hz, 3H), 1.94-1.72 (m, 2H), 1.54 (s, 1H), 1.53-1.20 (m, 2H), 0.99-0.80 (m, 3H).

MS (ES+): m/z 363.2 $[M+H]^+$, 385.1 $[M+Na]^+$.

$R_f$: 0.50 (Hex:EtOAc 1:1).

Compounds 69 and 69a

69

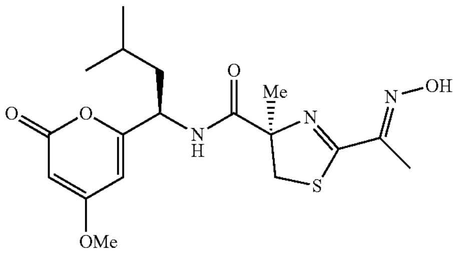

69a

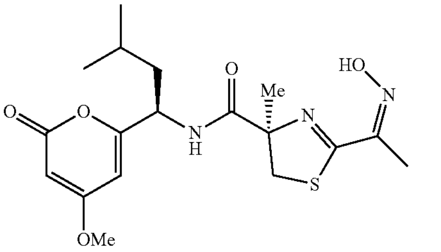

To a solution of 58 (47 mg, 0.13 mmol) in ethanol (1.32 mL) and water (1.32 mL), were added $NH_2OH{\cdot}HCl$ (61 mg, 0.95 mmol) and NaOAc (44 mg, 0.58 mmol). After stirring at 23° C. for 24 h the ethanol was evaporated under vacuum and the aqueous layer was extracted with EtOAc. The organic layers were dried over anhydrous $Na_2SO_4$ and after evaporation of the solvent the obtained crude was purified by HPLC method, using an XBridge C18 5 μm $H_2O/CH_3CN$ to obtain 69a (1.6 mg) and 69 (16.7 mg, 35% yield).

Compound 69a $^1H$ NMR (500 MHz, $CDCl_3$) δ 6.96 (d, J=8.9 Hz, 1H), 5.94 (dd, J=2.2, 0.6 Hz, 1H), 5.43 (d, J=2.2 Hz, 1H), 4.81 (td, J=8.7, 6.5 Hz, 1H), 3.80 (d, J=0.7 Hz, 3H), 3.69 (dd, J=11.7, 0.7 Hz, 1H), 3.22 (dd, J=11.7, 0.7 Hz, 1H), 2.20 (d, J=0.7 Hz, 3H), 1.82-1.51 (m, 3H), 1.63 (s, 3H), 0.96 (dd, J=8.4, 6.4 Hz, 6H).

Compound 69

$^1H$ NMR (500 MHz, $CDCl_3$) δ 8.70 (s, 1H), 7.08 (d, J=8.8 Hz, 1H), 5.93 (d, J=2.2 Hz, 1H), 5.43 (d, J=2.2 Hz, 1H), 4.81 (td, J=8.7, 6.6 Hz, 1H), 3.79 (s, 3H), 3.54 (d, J=11.6 Hz, 1H), 3.24 (d, J=11.6 Hz, 1H), 2.23 (s, 3H), 1.84-1.56 (m, 3H), 1.52 (s, 3H), 0.97 (dd, J=9.5, 6.5 Hz, 6H).

Compound 70

70

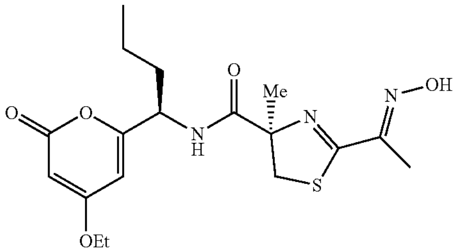

To a solution of 59 (35 mg, 0.077 mmol) in ethanol (0.85 mL) and water (0.85 mL), were added $NH_2OH{\cdot}HCl$ (40 mg, 0.57 mmol) and NaOAc (28 mg, 0.35 mmol). After stirring for 24 h the ethanol was evaporated under vacuum and the aqueous layer was extracted with EtOAc. The organic layers were dried over anhydrous $Na_2SO_4$ and after evaporation of the solvent the obtained crude was purified by HPLC method, using an XBridge C18 5 μm $H_2O/CH_3CN$ to give 70 (8 mg, 22% yield).

$^1H$ NMR (400 MHz, $CD_3OD$): δ 6.02 (dd, J=2.2, 0.7 Hz, 1H), 5.51 (d, J=2.2 Hz, 1H), 4.74 (dd, J=9.1, 5.8 Hz, 1H), 4.08 (q, J=7.0 Hz, 2H), 3.55 (d, J=11.5 Hz, 1H), 3.17 (d, J=11.5 Hz, 1H), 2.18 (s, 3H), 1.52 (s, 3H), 1.38 (t, J=7.0 Hz, 3H), 0.98 (t, J=7.4 Hz, 3H). MS (ES+): m/z 396.2 $[M+H]^+$, 418.2 $[M+Na]^+$.

$R_f$: 0.17 (Hex:EtOAc 6:4).

Compounds 71 and 71a

71

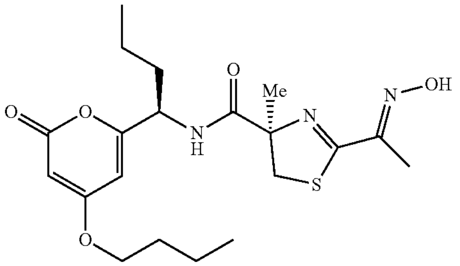

71a

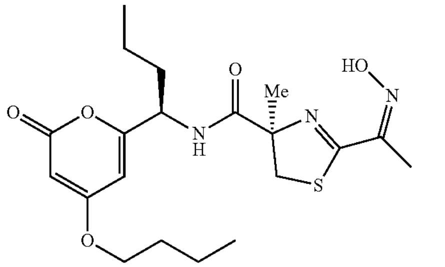

To a solution of 60 (45 mg, 0.11 mmol) in ethanol (1.2 mL) and water (1.2 mL), were added $NH_2OH{\cdot}HCl$ (56 mg, 0.81 mmol) and NaOAc (41 mg, 0.5 mmol). After stirring at 23° C. for 24 h the ethanol was evaporated under vacuum and the aqueous layer was extracted with EtOAc.

The organic layers were dried over anhydrous $Na_2SO_4$ and after evaporation of the solvent the obtained crude was purified by HPLC method, using an XBridge C18 5 lam $H_2O/CH_3CN$ to give 71a (2.5 mg) and 71 (15.9 mg, 34% yield).

Compound 71

$^1H$ NMR (400 MHz, $CD_3OD$): δ 6.03 (d, J=2.2 Hz, 1H), 5.52 (d, J=2.2 Hz, 1H), 4.74 (dd, J=9.2, 5.7 Hz, 1H), 4.02 (t, J=6.4 Hz, 2H), 3.56 (d, J=11.5 Hz, 1H), 3.17 (d, J=11.4 Hz, 1H), 2.18 (d, J=0.7 Hz, 3H), 1.92-1.70 (m, 4H), 1.53 (s, 3H), 1.49-1.35 (m, 3H), 0.98 (q, J=7.5 Hz, 6H).

MS (ES+): m/z 424.3 $[M+H]^+$, 446.1 $[M+Na]^+$.

$R_f$: 0.53 (Hex:EtOAc 6:4).

Compound 71a $^1H$ NMR (500 MHz, $CDCl_3$) δ 7.00 (d, J=8.9 Hz, 1H), 5.91 (d, J=2.2 Hz, 1H), 5.41 (d, J=2.2 Hz, 1H), 4.80-4.59 (m, 1H), 3.94 (td, J=6.5, 1.1 Hz, 2H), 3.70 (d, J=11.7 Hz, 1H), 3.23 (d, J=11.6 Hz, 1H), 2.20 (s, 3H), 1.88-1.67 (m, 4H), 1.64 (s, 3H), 1.56-1.29 (m, 4H), 0.96 (dt, J=8.1, 7.4 Hz, 6H).

Compounds 72 and 72a

72

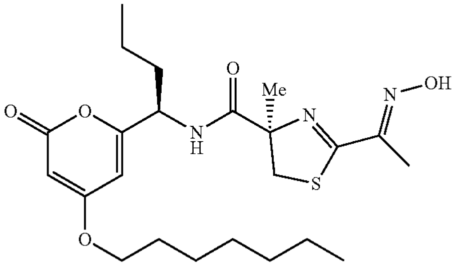

72a

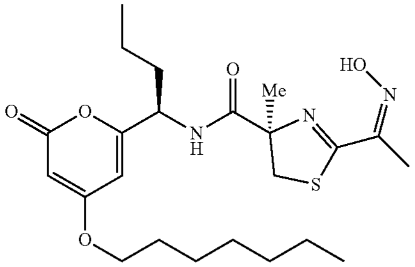

Compound 61 (0.131 mmol) was dissolved in ethanol (1.4 mL) prior to addition of water (1.4 mL), $NH_2OH{\cdot}HCl$ (67 mg, 0.963 mmol) and NaOAc (48 mg, 0.591 mmol). This mixture was stirred for 16 h and then ethanol was evaporated. Aqueous residue was diluted with brine and extracted with EtOAc. The combined organic layers were dried over $Na_2SO_4$, filtered and evaporated to dryness and the crude was chromatographed on a system for flash chromatography with a $SiO_2$ column eluting with mixtures of hexane/EtOAc from 100:0 to 60:40 in 40 min. This purification allowed to separate both stereoisomers.

Compound 72

$^1$H NMR (400 MHz, $CDCl_3$): δ 9.31 (s, 1H), 7.16 (d, J=8.8 Hz, 1H), 5.91 (d, J=2.2 Hz, 1H), 5.41 (d, J=2.1 Hz, 1H), 4.73 (q, J=7.9 Hz, 1H), 3.91 (t, J=6.5 Hz, 2H), 3.51 (d, J=11.6 Hz, 1H), 3.24 (dd, J=11.6, 0.5 Hz, 1H), 2.22 (s, 3H), 1.95-1.66 (m, 4H), 1.51 (s, 3H), 1.45-1.17 (m, 10H), 0.95 (t, J=7.3 Hz, 3H), 0.88 (t, J=6.8 Hz, 3H).

$^{13}$C NMR (100 MHz, $CDCl_3$): δ 174.2, 170.4, 167.9, 164.5, 162.1, 153.0, 100.7, 88.9, 84.3, 69.2, 51.0, 39.9, 34.7, 31.6, 28.8, 28.4, 25.7, 24.6, 22.5, 19.0, 14.0, 13.6, 11.2.

Compound 72a $^1$H NMR (400 MHz, $CDCl_3$): δ 7.05 (d, J=8.8 Hz, 1H), 5.91 (d, J=2.2 Hz, 1H), 5.40 (d, J=2.3 Hz, 1H), 4.73 (q, J=7.9 Hz, 1H), 3.91 (t, J=5.8 Hz, 2H), 3.68 (d, J=11.7 Hz, 1H), 3.22 (d, J=11.6 Hz, 1H), 2.19 (s, 3H), 1.89-1.66 (m, 4H), 1.63 (s, 3H), 1.43-1.17 (m, 10H), 0.94 (t, J=7.4 Hz, 3H), 0.89 (t, J=6.8 Hz, 3H).

$^{13}$C NMR (100 MHz, $CD_3OD$): δ 173.3, 172.4, 170.5, 164.7, 163.7, 162.1, 100.5, 88.9, 83.9, 69.2, 51.1, 40.9, 35.1, 31.6, 28.8, 28.4, 25.7, 24.9, 22.5, 19.1, 14.0, 13.6, 11.8.

Compounds 73 and 73a

73

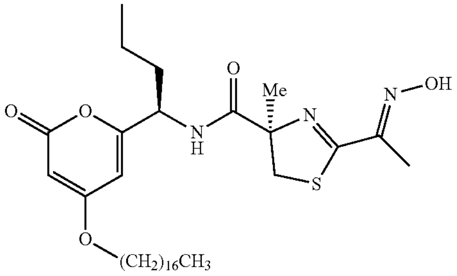

73a

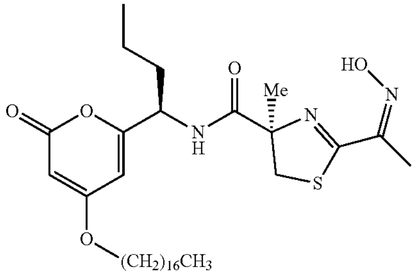

To a solution of crude 62 (79 mg, 0.134 mmol) in EtOH (1.5 mL) and $H_2O$ (1.5 mL) was added $NH_2OH{\cdot}HCl$ (69 mg, 0.992 mmol) and NaOAc (49 mg, 0.603 mmol) at 23° C. The reaction mixture was stirred overnight at 23° C. and concentrated under vacuum. The residue obtained was diluted with an aqueous saturated solution of NaCl and extracted with EtOAc (3×). The combined organic layers were dried over anhydrous $Na_2SO_4$, filtered and concentrated under vacuum. The obtained crude was purified in an automatic system for flash chromatography ($SiO_2$, Hex:EtOAc) to afford 73 (33 mg, 41% yield for 2 steps) and 73a (7 mg, 8% yield for 2 steps).

Compound 73

$^1$H NMR (400 MHz, $CDCl_3$): δ 9.32 (s, 1H), 7.16 (d, J=8.8 Hz, 1H), 5.91 (d, J=2.1 Hz, 1H), 5.40 (d, J=2.2 Hz, 1H), 4.73 (q, J=7.7 Hz, 1H), 3.91 (t, J=6.5 Hz, 2H), 3.51 (d, J=11.6 Hz, 1H), 3.24 (d, J=11.6 Hz, 1H), 2.22 (s, 3H), 1.95-1.66 (m, 4H), 1.51 (s, 3H), 1.46-1.15 (m, 30H), 0.95 (t, J=7.4 Hz, 3H), 0.86 (t, J=6.7 Hz, 3H).

$^{13}$C NMR (100 MHz, $CDCl_3$): δ 174.2, 170.3, 167.9, 164.5, 162.0, 153.0, 100.7, 88.9, 84.3, 69.2, 51.0, 39.9, 34.8, 31.9, 29.7, 29.6, 29.5 (×2), 29.3, 29.2, 28.4, 25.8, 24.6, 22.7, 19.1, 14.1, 13.6, 11.2.

Compound 73a $^1$H NMR (500 MHz, $CDCl_3$): δ 8.29 (s, 1H), 7.13 (d, J=8.8 Hz, 1H), 5.39 (d, J=2.2 Hz, 1H), 4.73 (q, J=7.9 Hz, 1H), 3.91 (td, J=6.6, 1.9 Hz, 2H), 3.55 (d, J=11.6 Hz, 1H), 3.23 (d, J=11.6 Hz, 1H), 2.24 (s, 3H), 1.94-1.68 (m, 4H), 1.52 (s, 3H), 1.45-1.18 (m, 32H), 0.96 (t, J=7.4 Hz, 3H), 0.88 (t, J=6.9 Hz, 3H).

$^{13}$C NMR (125 MHz, $CDCl_3$): δ 173.9, 170.3, 167.9, 164.4, 162.2, 153.4, 100.6, 88.9, 84.3, 69.2, 51.0, 39.9, 34.8, 31.9, 29.7, 29.6, 29.5 (×2), 29.3, 29.2, 28.4, 25.8, 24.7, 22.7, 19.1, 14.1, 13.6, 11.3.

Compounds 74 and 74a

74

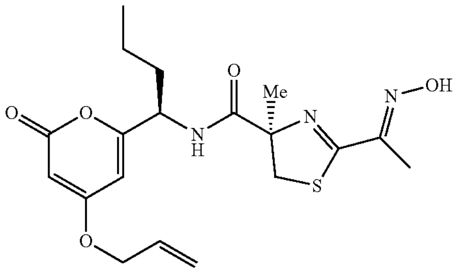

74a

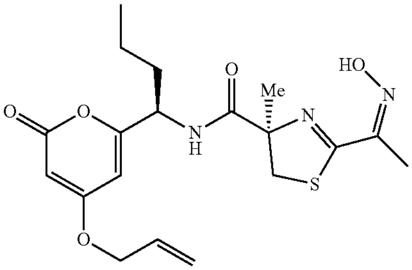

To a solution of crude 63 (700 mg, 1.78 mmol) in EtOH (20 mL) and $H_2O$ (20 mL) was added $NH_2OH{\cdot}HCl$ (920 mg, 13.23 mmol) and NaOAc (660 mg, 8.04 mmol) at 23° C. The reaction mixture was stirred for 24 h at 23° C. and concentrated under vacuum. The residue obtained was diluted with an aqueous saturated solution of NaCl and extracted with EtOAc (3×). The combined organic layers were dried over anhydrous $Na_2SO_4$, filtered and concentrated under vacuum. The obtained crude was purified was purified by flash chromatography on silica gel ($CH_2Cl_2$:EtOAc, from 90:10 to 70:30) to afford 74 (387 mg, 53% yield) and 74a (45 mg, 6% yield).

Compound 74

$^1H$ NMR (400 MHz, $CD_3OD$): δ 6.06 (d, J=2.2 Hz, 1H), 6.04-5.94 (m, 1H), 5.53 (d, J=2.2 Hz, 1H), 5.43-5.29 (m, 2H), 4.74 (dd, J=9.1, 5.8 Hz, 1H), 4.58 (td, J=5.5, 1.5 Hz, 2H), 3.55 (d, J=11.5 Hz, 1H), 3.17 (d, J=11.5 Hz, 1H), 2.17 (s, 3H), 1.92-1.77 (m, 2H), 1.52 (s, 3H), 1.50-1.34 (m, 2H), 0.98 (t, J=7.3 Hz, 3H).

$^{13}C$ NMR (100 MHz, $CDCl_3$): δ 174.4, 169.8, 168.2, 164.4, 162.3, 152.9, 130.6, 119.5, 100.5, 89.5, 84.3, 69.6, 51.0, 39.9, 34.7, 24.6, 19.0, 13.6, 11.2.

MS (ES+): m/z 408.2 $[M+H]^+$, 430.1 $[M+Na]^+$.

Optical rotation: $[\alpha_D]$ +53.7 (c 0.071, MeOH).

$R_f$: 0.29 (Hex:EtOAc 6:4).

Compound 74a $^1H$ NMR (400 MHz, $CDCl_3$): δ 10.44 (br s, 1H), 7.07 (d, J=8.9 Hz, 1H), 6.01-5.88 (m, 1H), 5.42 (dd, J=3.3, 1.7 Hz, 1H), 5.39-5.31 (m, 2H), 4.73 (td, J=8.3, 6.7 Hz, 1H), 4.48 (dt, J=5.5, 1.5 Hz, 2H), 3.65 (d, J=11.7 Hz, 1H), 3.21 (d, J=11.7 Hz, 1H), 2.19 (s, 3H), 1.89-1.65 (m, 2H), 1.60 (s, 3H), 1.41-1.28 (m, 2H), 0.93 (t, J=7.4 Hz, 3H).

$^{13}C$ NMR (100 MHz, $CDCl_3$): δ 173.5, 169.9, 164.6, 164.5, 162.5, 147.2, 130.5, 119.6, 100.3, 89.4, 83.6, 69.6, 51.0, 40.8, 35.0, 24.7, 19.2, 19.0, 13.5.

Compounds 75 and 75a

75

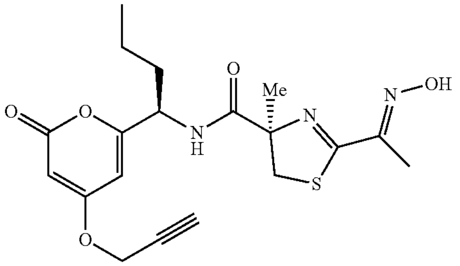

75a

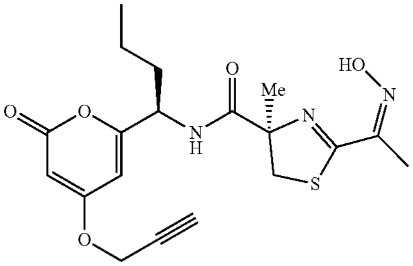

To a solution of crude 64 (3.0 g, 7.68 mmol) in EtOH (85 mL) and $H_2O$ (85 mL) was added $NH_2OH{\cdot}HCl$ (3.95 g, 56.86 mmol) and NaOAc (2.84 g, 34.58 mmol) at 23° C. The reaction mixture was stirred overnight at 23° C. and concentrated under vacuum. The residue obtained was diluted with an aqueous saturated solution of NaCl and extracted with EtOAc (3×). The combined organic layers were dried over anhydrous $Na_2SO_4$, filtered and concentrated under vacuum. The obtained crude was purified was purified by flash chromatography on silica gel (Hex:EtOAc, from 100:0 to 40:60) to afford 75 (1.44 mg, 46% yield for 2 steps) and 75a (392 mg, 12% yield for 2 steps).

Compound 75

$^1H$ NMR (400 MHz, $CD_3OD$): δ 6.07 (d, J=2.2 Hz, 1H), 5.64 (d, J=2.3 Hz, 1H), 4.81 (d, J=2.4 Hz, 2H), 4.78-4.69 (m, 1H), 3.54 (d, J=11.5 Hz, 1H), 3.18 (d, J=11.5 Hz, 1H), 3.15-3.13 (m, 1H), 2.18 (s, 3H), 1.92-1.76 (m, 2H), 1.52 (s, 3H), 1.49-1.35 (m, 2H), 0.99 (t, J=7.4 Hz, 3H).

$^{13}C$ NMR (125 MHz, $CDCl_3$): δ 174.3, 168.7, 168.0, 163.8, 162.7, 153.1, 100.1, 90.1, 84.3, 77.8, 75.6, 56.5, 51.0, 39.9, 34.8, 24.7, 19.0, 13.6, 11.3.

MS (ES+): m/z 406.1 $[M+H]^+$.

$R_f$: 0.29 (Hex:EtOAc 6:4).

Compound 75a $^1H$ NMR (400 MHz, $CDCl_3$): δ 7.02 (d, J=8.7 Hz, 1H), 5.94 (d, J=2.2 Hz, 1H), 5.56 (dd, J=2.3, 0.8 Hz, 1H), 4.74 (q, J=8.1 Hz, 1H), 4.66 (dt, J=2.4, 1.2 Hz, 2H), 3.69 (dd, J=11.7, 0.8 Hz, 1H), 3.22 (dd, J=11.7, 0.9 Hz, 1H), 2.63 (t, J=2.4 Hz, 1H), 2.20 (s, 3H), 1.91-1.64 (m, 2H), 1.63 (s, 3H), 1.46-1.32 (m, 2H), 0.94 (t, J=7.3 Hz, 3H).

$^{13}C$ NMR (100 MHz, $CDCl_3$): δ 173.9, 168.7, 167.5, 163.7, 162.8, 153.3, 100.0, 90.1, 84.2, 77.7, 75.6, 56.5, 51.0, 39.9, 34.8, 24.7, 19.1, 13.6, 11.3.

Compound 141

141

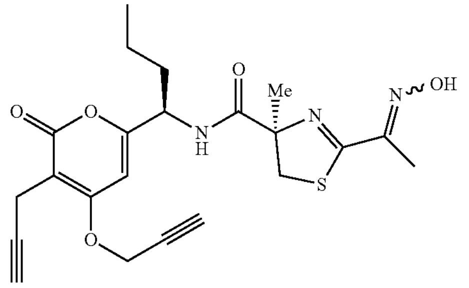

During the purification of one scale-up batch of compound 75 (1.44 g, HPLC: 78.8%) by preparative reversed phase HPLC (Sunfire C18, $CH_3CN$:$H_2O$ from 40% to 60% $CH_3CN$ in 30 minutes, UV detection, flow: 15 mL/min) it was obtained 141 ($t_R$ 16.8 min, 201 mg) and 75 ($t_R$ 14.6 min, 718 mg).

$^1$H NMR (400 MHz, $CDCl_3$): δ 8.71 (s, 1H), 7.13 (d, J=8.7 Hz, 1H), 6.28 (s, 1H), 4.85-4.71 (m, 2H), 3.57 (d, J=11.6 Hz, 1H), 3.33 (d, J=2.7 Hz, 2H), 3.24 (d, J=11.6 Hz, 1H), 2.62 (t, J=2.4 Hz, 1H), 2.23 (s, 3H), 1.99-1.72 (m, 2H), 1.54 (s, 3H), 1.48-1.25 (m, 1H), 1.29-1.23 (m, 1H), 0.97 (t, J=7.4 Hz, 3H), 0.92-0.80 (m, 1H).

$^{13}$C NMR (125 MHz, $CDCl_3$): δ 174.3, 168.6, 164.5, 162.5, 153.2, 102.9, 95.7, 84.4, 80.8, 77.9, 76.8, 67.6, 57.1, 51.6, 40.1, 34.9, 25.0, 19.2, 13.7, 13.3, 11.5.

MS (ES+): m/z 444.1 $[M+H]^+$.

$R_f$: 0.29 (Hex:EtOAc 6:4).

Compounds 76 and 76a

76

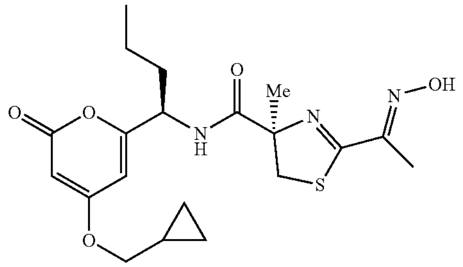

76a

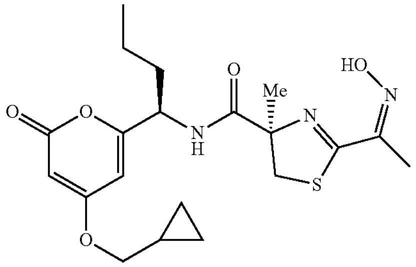

To a solution of crude 65 (33 mg, 0.08 mmol) in EtOH (0.9 mL) and $H_2O$ (0.9 mL) was added $NH_2OH·HCl$ (42 mg, 0.6 mmol) and NaOAc (30 mg, 0.36 mmol) at 23° C. The reaction mixture was stirred for 24 h at 23° C. and concentrated under vacuum. The residue obtained was diluted with an aqueous saturated solution of NaCl and extracted with EtOAc (3×). The combined organic layers were dried over anhydrous $Na_2SO_4$, filtered and concentrated under vacuum. The obtained crude was purified was purified by flash chromatography on silica gel (Hex:EtOAc, from 100:0 to 40:60) to afford 76 (15 mg, 44% yield) and 76a (3 mg, 9% yield).

Compound 76

$^1$H NMR (400 MHz, $CD_3OD$): δ 7.85 (d, J=8.6 Hz, 1H), 6.05 (s, 1H), 5.48 (s, 1H), 4.74 (q, J=6.8, 5.0 Hz, 1H), 3.86 (d, J=7.2 Hz, 2H), 3.56 (d, J=11.5 Hz, 1H), 3.17 (d, J=11.5 Hz, 1H), 2.19 (s, 3H), 1.96-1.72 (m, 2H), 1.52 (s, 3H), 1.43 (ddd, J=29.8, 14.7, 7.4 Hz, 4H), 1.31-1.16 (m, 1H), 0.99 (t, J=7.4 Hz, 3H), 0.63 (d, J=7.6 Hz, 2H), 0.35 (d, J=5.0 Hz, 2H).

$^{13}$C NMR (100 MHz, $CD_3OD$): δ 175.1, 171.2, 168.8, 165.3, 163.8, 151.5, 126.4, 99.7, 87.9, 84.2, 74.0, 50.7, 39.1, 33.9, 23.6, 18.8, 12.5, 9.6, 9.0, 2.3.

MS (ES+): m/z 422.1 $[M+H]^+$, 444.2 $[M+Na]^+$.

Optical rotation: $[\alpha_D]$ +55 (c 0.022, MeOH).

$R_f$: 0.42 (hexanes:EtOAc 1:1).

Compound 76a $^1$H NMR (400 MHz, $CDCl_3$): δ 8.32 (s, 1H), 7.19 (d, J=8.7 Hz, 1H), 5.94 (t, J=2.1 Hz, 1H), 5.41-5.33 (m, 1H), 4.73 (q, J=7.9 Hz, 1H), 3.76 (dd, J=7.2, 2.1 Hz, 3H), 3.57 (d, J=11.6 Hz, 1H), 3.23 (dd, J=11.7, 1.9 Hz, 1H), 2.24 (s, 3H), 2.20 (s, 1H), 1.95-1.65 (m, 2H), 1.64 (s, 1H), 1.54 (s, 2H), 1.45-1.31 (m, 2H), 1.23 (d, J=18.1 Hz, 2H), 0.95 (q, J=7.4 Hz, 3H), 0.83 (s, 1H), 0.67 (dd, J=7.9, 1.3 Hz, 3H), 0.38-0.29 (m, 1H).

$^{13}$C NMR (100 MHz, $CDCl_3$): δ 173.8, 170.1, 168.4, 164.3, 162.3, 153.3, 100.5, 88.9, 84.2, 73.8, 51.1, 39.9, 34.8, 24.7, 19.1, 13.6, 11.3, 9.4, 3.4 (×2).

MS (ES+): m/z 422.1 $[M+H]^+$.

Compound 77

77

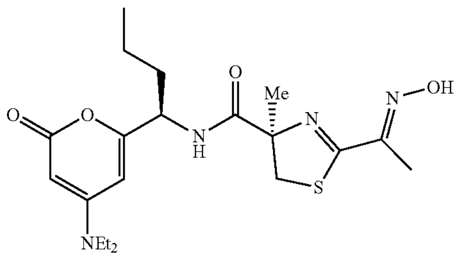

To a solution of 66 (25 mg, 0.062 mmol) in ethanol (0.7 mL) and water (0.7 mL), were added $NH_2OH·HCl$ (31 mg, 0.45 mmol) and NaOAc (23 mg, 0.28 mmol). After stirring at 23° C. for 24 h the ethanol was evaporated under vacuum and the aqueous layer was extracted with EtOAc. The organic layers were dried over anhydrous $Na_2SO_4$ and after evaporation of the solvent the obtained crude was purified by HPLC method, using an XBridge C18 5 μm $H_2O/CH_3CN$ to give 77 (2.9 mg, 12% yield).

$^1$H NMR (500 MHz, $CD_3OD$) δ 6.10 (dd, J=2.4, 0.7 Hz, 1H), 5.01 (d, J=2.4 Hz, 1H), 4.75 (dt, J=9.3, 5.8 Hz, 1H), 3.60 (d, J=11.5 Hz, 1H), 3.43-3.34 (m, 4H), 3.19 (d, J=11.5 Hz, 1H), 2.20 (s, 3H), 1.97-1.76 (m, 2H), 1.56 (s, 3H), 1.54-1.34 (m, 2H), 1.16 (t, J=7.1 Hz, 6H), 1.00 (t, J=7.4 Hz, 3H).

MS (ES): m/z 423.2 $[M+H]^+$, 445.2 $[M+Na]^+$.

Compound 78

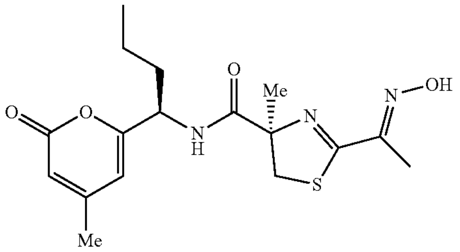

78

To a solution of 67 (16 mg, 0.045 mmol) in ethanol (0.4 mL) and water (0.4 mL), were added $NH_2OH \cdot HCl$ (19 mg, 0.33 mmol) and NaOAc (14 mg, 0.18 mmol). After stirring at 23° C. for 24 h the ethanol was evaporated under vacuum and the aqueous layer was extracted with EtOAc. The organic layers were dried over anhydrous $Na_2SO_4$ and after evaporation of the solvent the obtained crude was purified by HPLC method, using an XBridge C18 5 μm $H_2O/CH_3CN$ to give 78 (2.9 mg, 18% yield).

$^1$H NMR (400 MHz, $CD_3OD$): δ 7.81 (d, J=8.7 Hz, 1H), 6.14 (d, J=1.5 Hz, 1H), 6.02 (s, 1H), 4.75 (ddd, J=8.9, 5.9, 3.0 Hz, 1H), 3.54 (d, J=11.5 Hz, 1H), 3.17 (d, J=11.5 Hz, 1H), 2.18 (s, 3H), 2.15 (d, J=1.2 Hz, 3H), 1.90-1.78 (m, 2H), 1.53 (s, 3H), 1.49-1.36 (m, 2H), 0.99 (t, J=7.4 Hz, 3H).

MS (ES): m/z 366.2 $[M+H]^+$, 388.1 $[M+Na]^+$.

$R_f$: 0.35 (hexanes:EtOAc 6:4).

Compound 79

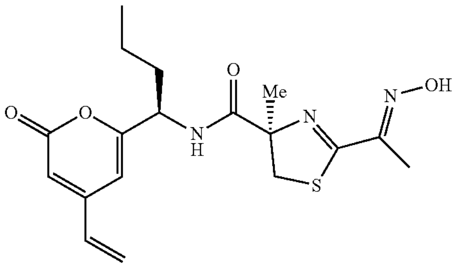

79

To a solution of crude 68 (453 mg, 1.25 mmol) in ethanol (5 mL) was added $NH_2OH \cdot HCl$ (131 mg, 1.88 mmol) at 23° C. The reaction mixture was stirred at 70° C. for 3 h and diluted with $H_2O$. The resulting precipitate was concentrated under vacuum. The obtained crude was purified in an automatic system for flash chromatography ($SiO_2$) to obtain 79 (217 mg, 46%).

$^1$H NMR (400 MHz, $CD_3OD$): δ 6.58 (dd, J=17.5, 10.8 Hz, 1H), 6.47 (d, J=1.5 Hz, 1H), 6.11 (d, J=1.4 Hz, 1H), 6.02 (d, J=17.5 Hz, 1H), 5.66 (d, J=10.8 Hz, 1H), 4.85-4.72 (m, 1H), 3.62-3.46 (m, 1H), 3.37-3.22 (m, 1H), 3.18 (dd, J=11.5, 0.9 Hz, 1H), 2.19 (s, 3H), 1.90-1.69 (m, 2H), 1.56 (s, 3H), 1.57-1.33 (m, 2H), 0.99 (td, J=7.4, 2.9 Hz, 3H).

$^{13}$C NMR (100 MHz, $CD_3OD$): δ 176.6, 170.3, 164.9, 164.5, 153.9, 152.9, 134.5, 124.0, 111.5, 100.5, 85.6, 52.3, 40.8, 35.4, 25.2, 20.2, 13.8, 11.0.

MS (ES+): m/z 378.2 $[M+H]^+$, 400.1 $[M+Na]^+$.

$R_f$: 0.39 (hexanes:EtOAc 1:1).

Scheme 9 provides further examples of the synthesis of more compounds of formula I.

Scheme 9

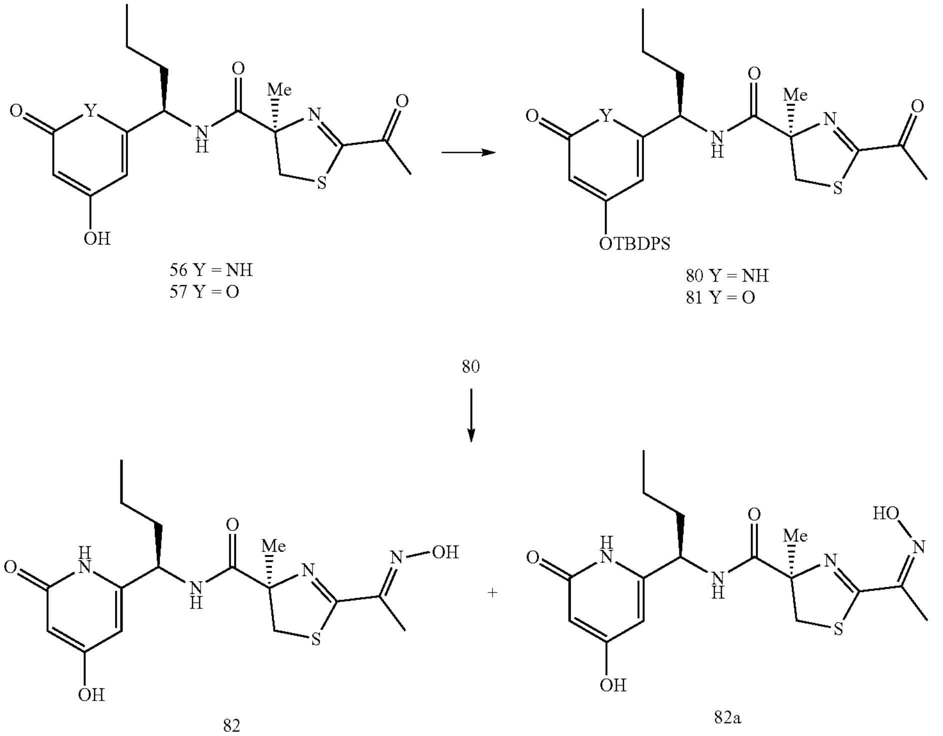

56 Y = NH
57 Y = O

80 Y = NH
81 Y = O

80

82

82a

Compound 80

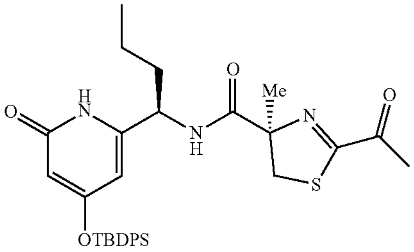

80

A solution of 56 (38 mg, 0.11 mmol), imidazole (16 mg, 2.2 mmol), ClTBDPS (0.066 mL, 2.2 mmol) in acetonitrile (1.0 mL) was stirred at 23° C. for 2 h. The reaction mixture was diluted with $CH_2Cl_2$ and washed with a saturated aqueous solution of $NH_4Cl$. The combined organic layers were dried over anhydrous $Na_2SO_4$, filtered and concentrated under vacuum. The crude obtained was purified by flash chromatography 80 over silica gel ($CH_2Cl_2$/EtOAc 1/1) to afford 80 (36 mg, 56% yield).

$^1H$ NMR (300 MHz, $CDCl_3$): δ 7.66 (m, 4H), 7.52-7.29 (m, 6H), 5.86 (d, J=2.2 Hz, 1H), 5.49 (d, J=2.2 Hz, 1H), 4.79-4.62 (m, 1H), 3.58 (d, J=11.8 Hz, 1H), 3.14 (d, J=11.7 Hz, 1H), 2.04 (d, J=0.6 Hz, 3H), 1.65 (m, 2H), 1.44 (s, 3H), 1.34-1.07 (m, 2H), 1.07 (s, 9H), 0.93-0.74 (m, 3H).

MS (ES): m/z 590.5 $[M+H]^+$.

Compound 81

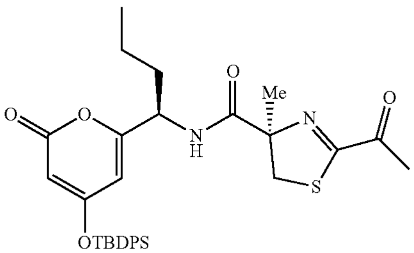

81

A solution of 57 (42 mg, 0.12 mmol), imidazole (10 mg, 0.14 mmol) and ClTBDPS (0.034 mL, 0.13 mmol) in acetonitrile (1.0 mL) was stirred at 23° C. for 2 h. The reaction mixture was diluted with $CH_2Cl_2$ and washed with a saturated aqueous solution of $NH_4Cl$. The combined organic layers were dried over anhydrous $Na_2SO_4$, filtered and concentrated under vacuum. The crude obtained was purified by flash chromatography over silica gel ($CH_2Cl_2$/EtOAc 1/1) to yield 81 (32 mg, 46% yield).

$^1H$ NMR (300 MHz, $CDCl_3$): δ 7.74-7.57 (m, 4H), 7.56-7.29 (m, 6H), 6.96 (d, J=9.0 Hz, 1H), 5.87 (d, J=2.2 Hz, 1H), 5.23 (d, J=2.2 Hz, 1H), 4.67 (q, J=7.8 Hz, 1H), 3.56 (d, J=12.0 Hz, 1H), 3.26 (d, J=11.9 Hz, 1H), 2.53 (d, J=0.5 Hz, 3H), 1.91-1.64 (m, 2H), 1.52 (s, 3H), 1.07 (s, 9H), 0.93 (t, J=7.3 Hz, 3H).

MS (ES): m/z 591.3 $[M+H]^+$, 613.2 $[M+Na]^+$.

Compounds 82 and 82a

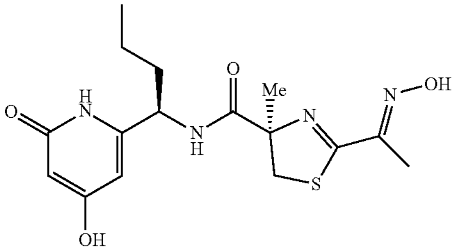

82

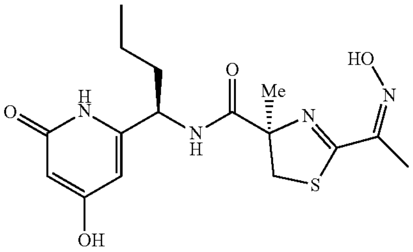

82a

To a solution of 80 (35 mg, 0.059 mmol) in ethanol (0.7 mL) and water (0.7 mL), were added $NH_2OH·HCl$ (30 mg, 0.45 mmol) and NaOAc (22 mg, 0.28 mmol). After stirring at 23° C. for 24 h the ethanol was evaporated under vacuum and the aqueous layer was extracted with EtOAc.

The organic layers were dried over anhydrous $Na_2SO_4$ and after evaporation of the solvent the obtained crude was purified by HPLC method, using an XBridge C18 5 lam $H_2O/CH_3CN$ to give 82a (1.5 mg) and 82 (5.6 mg, 26% yield).

Compound 82

$^1H$ NMR (500 MHz, $CDCl_3$): δ 5.87 (s, 1H), 5.28 (d, J=0.7 Hz, 1H), 4.69 (t, J=7.6 Hz, 1H), 3.55-3.44 (m, 1H), 3.14 (d, J=11.6 Hz, 1H), 2.12 (s, 3H), 1.77 (t, J=7.7 Hz, 2H), 1.50 (d, J=1.5 Hz, 3H), 1.35 (ddd, J=41.7, 14.0, 7.0 Hz, 2H), 0.93 (t, J=7.3 Hz, 3H).

Compound 82a $^1H$ NMR (500 MHz, $CD_3OD$): δ 6.01 (d, J=2.1 Hz, 1H), 5.67 (d, J=2.2 Hz, 1H), 4.69 (dd, J=8.6, 6.8 Hz, 1H), 3.58 (d, J=11.5 Hz, 1H), 3.18 (d, J=11.5 Hz, 1H), 2.21 (s, 3H), 1.85-1.69 (m, 2H), 1.50 (s, 3H), 1.45-1.22 (m, 3H), 0.94 (t, J=7.4 Hz, 3H).

Scheme 10 provides further examples of the synthesis of more compounds of formula I.

Scheme 10

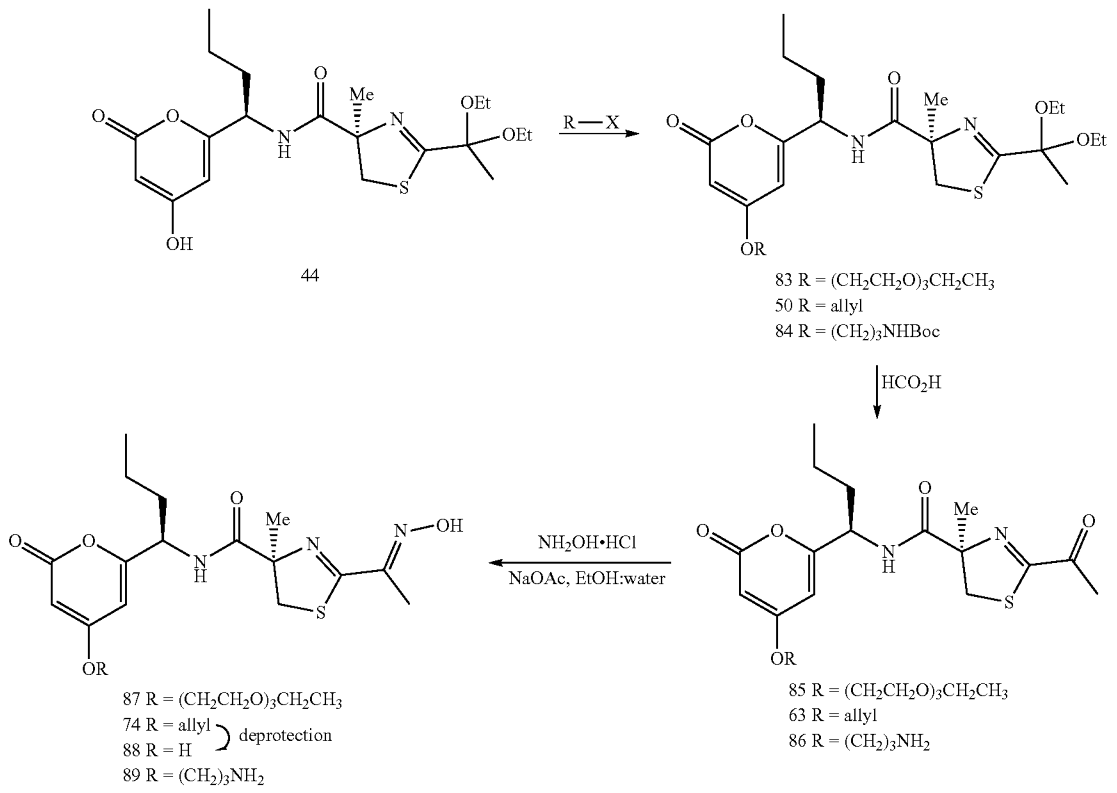

Compound 83

83

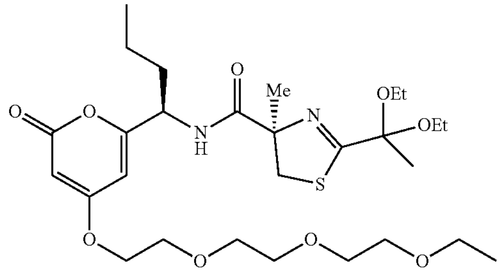

A mixture of 44 (31 mg, 0.085 mmol), $K_2CO_3$ (59 mg, 0.42 mmol), and 1-ethoxy-2-(2-(2-iodoethoxy)ethoxy)ethane (122 mg, 0.42 mmol) in acetone (0.85 mL) was stirred at 23° C. for 24 h and then filtered over Celite®. Evaporation of the solvent gave a crude which was chromatographed on silica gel ($CH_2Cl_2$/EtOAc 7/3) to afford 83 (11 mg, 83% yield).

$^1$H NMR (300 MHz, $CDCl_3$): δ 7.03 (d, J=8.8 Hz, 1H), 5.89 (d, J=2.2 Hz, 1H), 5.37 (d, J=2.2 Hz, 1H), 4.84-4.75 (m, 1H), 4.76-4.63 (m, 1H), 4.10-4.01 (m, 2H), 4.01-3.91 (m, 1H), 3.86-3.76 (m, 2H), 3.74-3.41 (m, 11H), 3.15 (d, J=11.7 Hz, 1H), 1.93-1.61 (m, 2H), 1.60 (s, 3H), 1.52 (s, 3H), 1.46-1.16 (m, 9H), 0.90 (dt, J=17.4, 7.2 Hz, 3H).

MS (ES): m/z 609.3 $[M+Na]^+$.

Compound 50

50

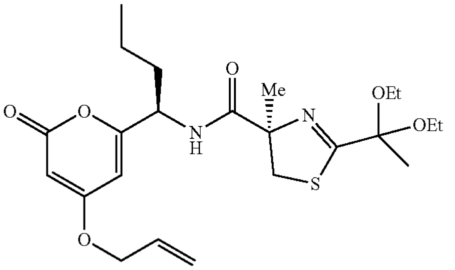

84

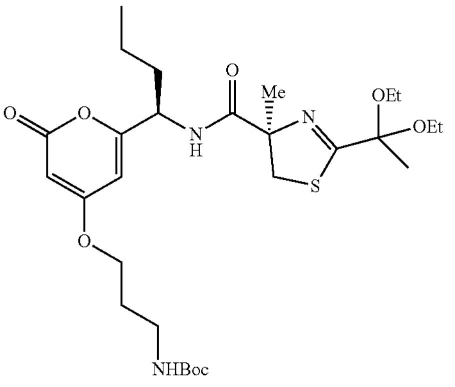

A mixture of 44 (30 mg, 0.07 mmol), $K_2CO_3$ (29 mg, 0.21 mmol), and allylbromide (0.18 mL, 2.1 mmol) in DMF (0.6 mL) was stirred at 23° C. for 5 h and then filtered over Celite®. Evaporation of the solvent gave a crude which was chromatographed on silica gel ($CH_2Cl_2$/EtOAc 8/1) to afford 50 (18 mg, 55% yield).

Compound 84

A mixture of 44 (50 mg, 0.12 mmol), $K_2CO_3$ (83 mg, 0.6 mmol), and t-butyl-(3-iodopropyl)carbamate (171 mg, 0.6 mmol) in acetone (1 mL) was stirred at 23° C. for 24 h and then filtered over Celite®. Evaporation of the solvent gave a crude which was chromatographed on silica gel ($CH_2Cl_2$/EtOAc) to afford 84 (40 mg, 57% yield).

$^1$H NMR (300 MHz, $CDCl_3$): δ 7.70 (s, 1H), 7.56-7.45 (m, 1H), 7.03 (d, J=8.8 Hz, 1H), 5.84 (d, J=2.1 Hz, 1H), 5.36 (d, J=2.1 Hz, 1H), 4.68 (dd, J=15.6, 7.8 Hz, 2H), 4.40-4.22 (m, 1H), 3.96 (t, J=6.1 Hz, 2H), 3.68-3.36 (m, 5H), 3.24 (d, J=6.5 Hz, 2H), 3.15 (d, J=11.8 Hz, 1H), 2.79 (d, J=1.6 Hz, 1H), 1.98-1.67 (m, 4H), 1.60 (s, 3H), 1.52 (s, 3H), 1.42 (s, 9H), 1.26-1.15 (m, 6H), 0.93 (t, J=7.3 Hz, 3H).

MS (ES): m/z 539.2 $[M+H]^+$, 606.2 $[M+Na]^+$.

Compound 85

85

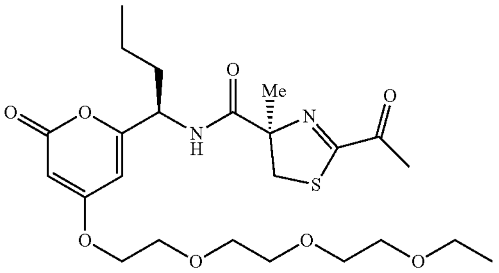

To a mixture of 83 (30 mg, 0.05 mmol) and pentane (1.8 mL) was added formic acid (1.2 mL). The reaction was stirred vigorously at 23° C. for 1.5 h and then evaporated to dryness with toluene to remove efficiently the formic acid giving 85 (100%).

$^1$H NMR (300 MHz, $CDCl_3$): δ 7.03 (d, J=8.9 Hz, 1H), 5.96 (d, J=2.2 Hz, 1H), 5.42 (d, J=2.2 Hz, 1H), 4.72 (m, 1H), 4.08 (m, 2H), 3.82 (m, 2H), 3.74-3.48 (m, 11H), 3.28 (d, J=12.0 Hz, 1H), 2.56 (s, 3H), 1.90-1.61 (m, 2H), 1.54 (s, 3H), 1.34 (m, 2H), 1.30-1.13 (m, 6H), 0.99 (t, 3H).

63

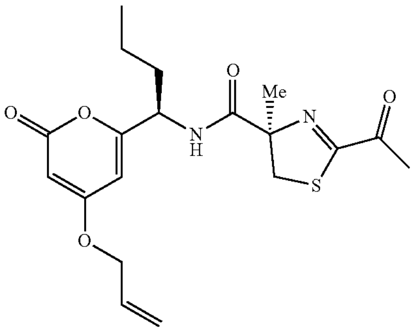

-continued

86

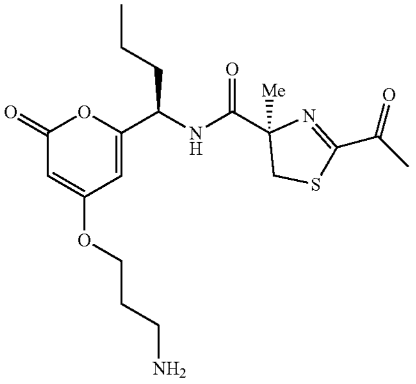

Compound 63

To a mixture of 50 (58 mg, 0.1 mmol) and pentane (2.9 mL) was added formic acid (2 mL). The reaction was stirred vigorously at 23° C. for 1.5 h and then evaporated to dryness with toluene to remove efficiently the formic acid giving 63 crude (100%) which was used immediately in the next step.

Compound 86

To a mixture of 84 (40 mg, 0.068 mmol) and pentane (2 mL) was added formic acid (1.4 mL). The reaction was stirred vigorously at 23° C. for 1.5 h and then evaporated to dryness with toluene to remove efficiently the formic acid giving crude 86 (100%) which was used in the next step without further purification.

MS (ES): m/z 410.1 $[M+H]^+$, 433.3 $[M+Na]^+$.

Compound 87

87

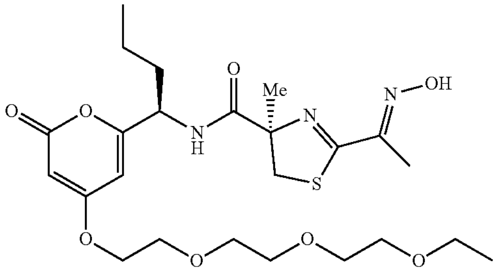

To a solution of 85 (26 mg, 0.051 mmol) in ethanol (0.6 mL) and water (0.6 mL), were added $NH_2OH \cdot HCl$ (26 mg, 0.45 mmol) and NaOAc (19 mg, 0.28 mmol). After stirring at 23° C. for 24 h the ethanol was evaporated under vacuum and the aqueous layer was extracted with EtOAc. The organic layers were dried over anhydrous $Na_2SO_4$ and after evaporation of the solvent 87 the obtained crude was purified by HPLC method, using an XBridge C18 5 μm $H_2O$/$CH_3CN$ to give 87 (12.2 mg, 46% yield).

$^1$H NMR (300 MHz, $CDCl_3$): δ 9.45 (s, 1H), 6.85 (d, J=9.0 Hz, 1H), 5.81 (dd, J=2.3, 0.7 Hz, 1H), 5.38 (d, J=2.2 Hz, 1H), 4.70 (m, 1H), 4.05 (m, 2H), 3.82 (m, 2H), 3.72-3.47 (m, 7H), 3.15 (d, J=11.5 Hz, 1H), 2.22 (d, J=0.4 Hz, 3H), 1.99-1.65 (m, 2H), 1.58 (s, 3H), 1.47-1.27 (m, 2H), 1.21 (td, J=7.0, 0.5 Hz, 3H), 0.95 (t, J=7.3 Hz, 3H).

MS (ES): m/z 528.3 $[M+H]^+$, 550.3 $[M+Na]^+$.

Compound 74

74

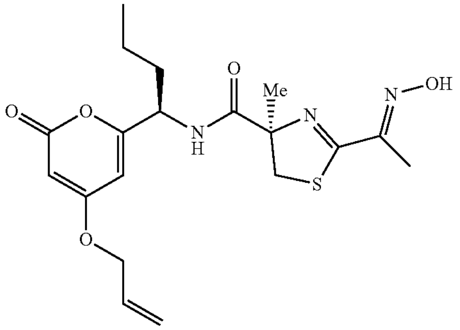

To a solution of 63 crude in ethanol (1.1 mL) and water (1.1 mL), were added $NH_2OH{\cdot}HCl$ (51 mg, 0.45 mmol) and NaOAc (19 mg, 0.45 mmol). After stirring at 23° C. for 24 h the ethanol was evaporated under vacuum and the aqueous layer was extracted with EtOAc. The organic layers were dried over anhydrous $Na_2SO_4$ and after evaporation of the solvent the obtained crude was purified by chromatography on silica gel ($CH_2Cl_2$/EtOAc 1/1) to afford 74 (17 mg, 34% yield).

Compound 88

88

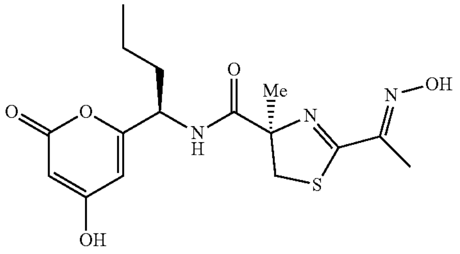

To a solution of 74 (15 mg, 0.04 mmol) in $CH_2Cl_2$ (1 mL) was added $PhSiH_3$ (0.09 mL, 0.74 mmol) followed by addition of $Pd(PPh_3)_4$ in one portion. The mixture was stirred at 23° C. for 20 min until disappeared of starting material (reaction followed by TLC). After removing of volatiles, the residue was purified by chromatography on silica gel ($CH_2Cl_2$:EtOAc 1/1) to afford 88 (4.2 mg, 34% yield).

$^1H$ NMR (400 MHz, $CDCl_3$): δ 10.74 (s, 1H), 10.17 (s, 1H), 7.30 (d, J=10.4 Hz, 1H), 6.17 (d, J=2.1 Hz, 1H), 5.78 (d, J=2.1 Hz, 1H), 4.80 (dt, J=10.2, 7.8 Hz, 1H), 3.47 (d, J=12.0 Hz, 1H), 3.24 (d, J=11.9 Hz, 1H), 2.22 (s, 3H), 1.83 (tt, J=15.1, 6.1 Hz, 2H), 1.51 (s, 3H), 1.45-1.23 (m, 2H), 0.98 (t, J=7.3 Hz, 3H).

$^{13}C$ NMR (100 MHz, $CD_3OD$): δ 175.9, 172.3, 169.5, 167.4, 162.1, 152.1, 103.2, 92.5, 84.1, 50.6, 40.3, 34.0, 24.6, 19.1, 13.5, 11.2.

MS (ES): m/z 368.1 $[M+H]^+$, 390.0 $[M+Na]^+$.

$R_f$: 0.12 ($CH_2Cl_2$:$CH_3OH$ 9:1).

Compound 89

89

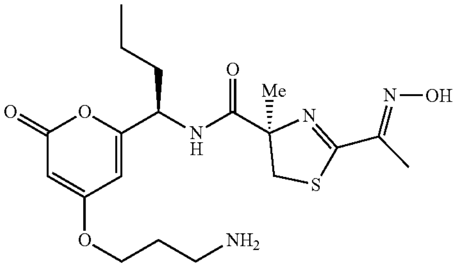

To a mixture of 86 (28 mg, 0.068 mmol) in ethanol (0.75 mL) and water (0.75 mL), were added $NH_2OH{\cdot}HCl$ (34 mg, 0.50 mmol) and NaOAc (25 mg, 0.31 mmol). After stirring at 23° C. for 24 h the ethanol was evaporated under vacuum and the aqueous layer was extracted with EtOAc.

The organic layers were dried over anhydrous $Na_2SO_4$ and after evaporation of the solvent the obtained crude was purified by HPLC method, using an Sunfire C18 5 μm, 10×150 mm; $CH_3CN/H_2O$, 28% isocratic to give 89 (0.7 mg).

$^1H$ NMR (500 MHz, $CD_3OD$): δ 6.06 (d, J=2.0 Hz, 1H), 5.56 (d, J=2.0 Hz, 1H), 4.74 (m, 1H), 4.14 (t, J=6.0 Hz, 2H), 3.54 (d, J=11.5 Hz, 1H), 3.18 (d, J=11.5 Hz, 1H), 3.01 (t, J=7.0 Hz, 2H), 2.19 (s, 3H), 2.09 (m, 2H), 1.86 (m, 2H), 1.54 (s, 3H), 1.51-1.36 (m, 2H), 0.99 (t, J=7.0 Hz, 3H).

MS (ES): m/z 425.1 $[M+H]^+$, 447.2 $[M+Na]^+$.

Scheme 11 provides further examples of the synthesis of more compounds of formula I.

Scheme 11

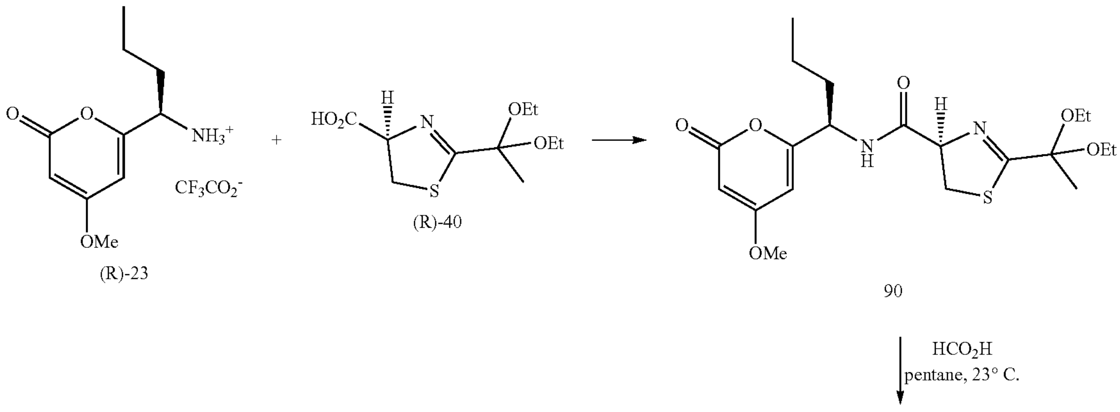

(R)-23

(R)-40

90

-continued

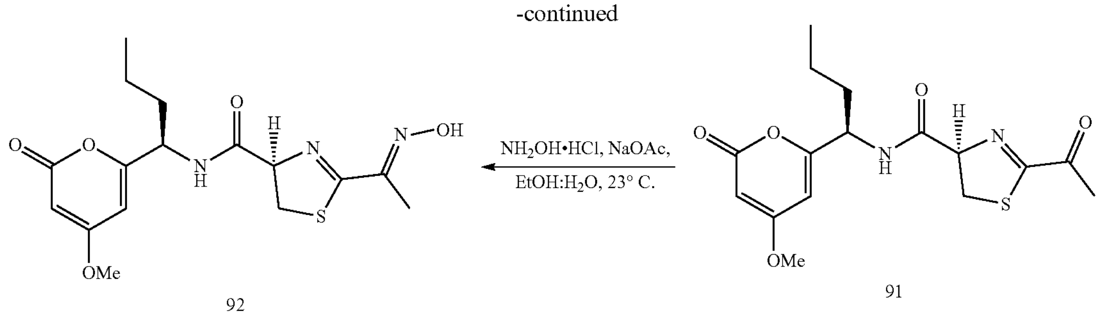

92

91

Compound 90

90

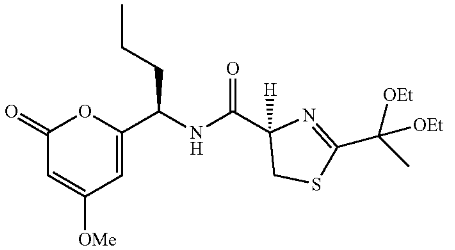

To a suspension of (R)-40 (30 mg, 0.19 mmol) and (R)-23 (37 mg, 0.19 mmol) in $CH_2Cl_2$ (1.3 mL) were added HATU (149 mg, 0.39 mmol), HOAt (54 mg, 0.39 mmol) and DIPEA (0.14 mL, 0.81 mmol) and the mixture was stirred at 23° C. overnight. Dilution with $CH_2Cl_2$, washing of the organic layer with 0.5M HCl and brine and, finally, dried over anhydrous $Na_2SO_4$. Evaporation of the solvent gave a crude which was purified by flash chromatography on silica gel (hexane/EtOAc 6/4) to afford 90 (26 mg, 33% yield).

$^1$H NMR (400 MHz, $CDCl_3$): δ 6.96 (d, J=8.7 Hz, 1H), 5.84 (t, J=1.9 Hz, 1H), 5.37 (d, J=2.1 Hz, 1H), 5.18-5.07 (m, 1H), 4.72 (td, J=8.4, 6.5 Hz, 1H), 3.75 (d, J=1.6 Hz, 3H), 3.66-3.38 (m, 6H), 1.90-1.69 (m, 2H), 1.59 (d, J=1.7 Hz, 3H), 1.39-1.29 (m, 2H), 1.27-1.12 (m, 6H).

$^{13}$C NMR (75 MHz, $CDCl_3$): δ 180.6, 172.1, 172.0, 165.2, 164.0, 101.6, 101.0, 89.6, 80.2, 59.1, 57.2, 52.2, 39.8, 35.8, 35.5, 25.0, 20.3, 16.4, 16.4, 14.8.

Compound 91

91

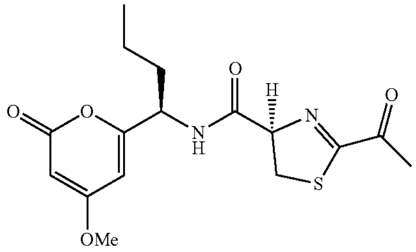

-continued

92

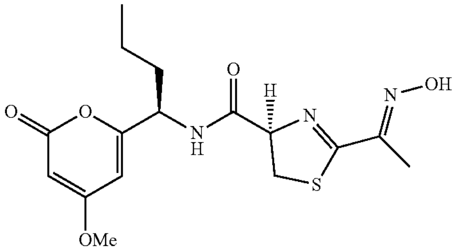

Over 90 (82 mg, 0.19 mmol) was added at 23° C. pentane (4.3 mL) and formic acid (2.9 mL). The reaction mixture was stirred vigorously for 1.5 hours at 23° C. The solvent was removed under vacuum to obtain crude 91 (75 mg) which was used in the next step without further purification.

MS (ES+): m/z 353.1 $[M+H]^+$.

Compound 92

A mixture of 91 (75 mg), ethanol (2.3 mL), water (2.3 mL), hydroxylamine hydrochloride (108 mg, 1.55 mmol) and NaOAc (77 mg, 0.94 mmol) was stirred overnight at 23° C. Then ethanol was evaporated, brine was added, and the aqueous phase was extracted with EtOAc. The combined organic phases were dried over anhydrous $Na_2SO_4$, filtered, and concentrated under vacuum. The resulting crude was chromatographed over silica gel (Hex:EtOAc, from 100:0 to 50:50) to give 92 (4.5 mg).

$^1$H NMR (500 MHz, $(CD_3)_2CO$): δ 11.25 (s, 1H), 7.64 (d, J=8.6 Hz, 1H), 6.03 (dd, J=2.2, 0.7 Hz, 1H), 5.43 (d, J=2.2 Hz, 1H), 5.24 (t, J=9.2 Hz, 1H), 4.75 (td, J=8.9, 5.5 Hz, 1H), 3.84 (s, 3H), 3.50 (d, J=9.2 Hz, 2H), 2.15 (d, J=0.6 Hz, 3H), 1.86 (ddt, J=13.6, 9.8, 6.2 Hz, 1H), 1.76 (dtd, J=14.0, 9.4, 5.2 Hz, 1H), 1.49 (dddd, J=15.5, 7.9, 6.2, 4.0 Hz, 1H), 1.40 (ddt, J=13.7, 9.8, 6.9 Hz, 1H), 0.95 (t, J=7.3 Hz, 3H).

$^{13}$C NMR (100 MHz, $(CD_3)_2CO$): δ 171.8, 170.8, 170.2, 165.2, 163.7, 152.9, 99.7, 99.5, 88.5, 79.9, 56.6, 51.7, 35.2, 33.9, 19.9, 13.9, 11.1.

MS (ES+): m/z 368.1 $[M+H]^+$.

Scheme 12 provides a further example of the synthesis of some compounds of formula I.

Scheme 12

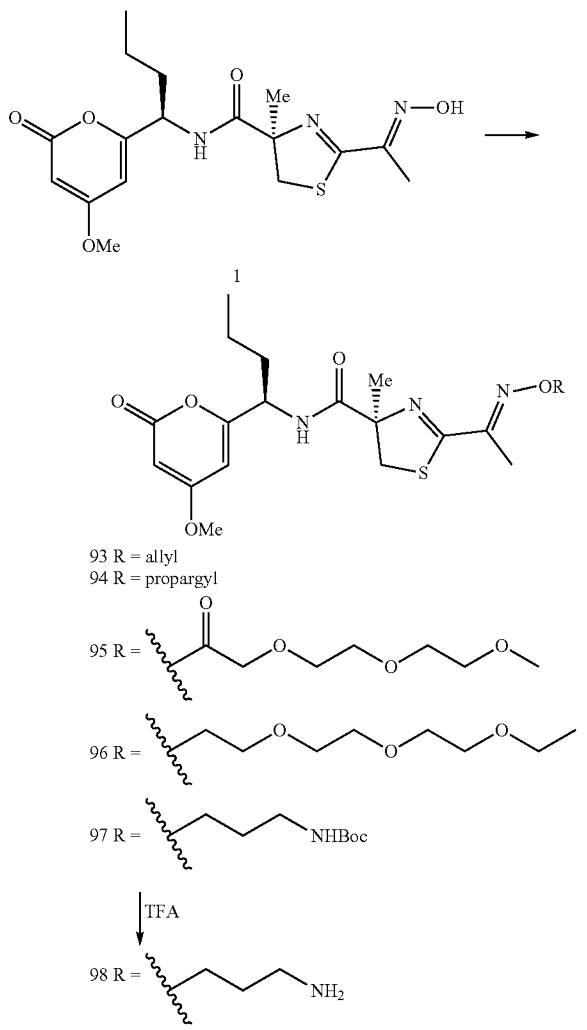

1

93 R = allyl
94 R = propargyl
95 R =
96 R =
97 R =
98 R =

Compound 93

93

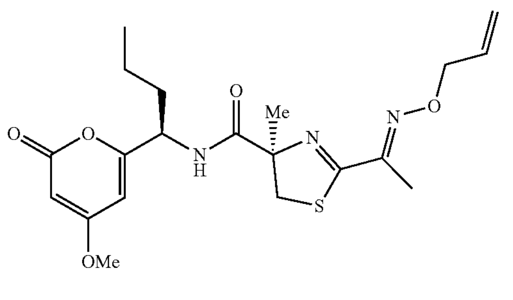

To a solution of 1 (11 mg, 0.029 mmol) in acetone (2 mL) was added $Cs_2CO_3$ (14 mg, 0.043 mmol) and allyl bromide (4 μL, 0.043 mmol) at 23° C. The reaction mixture was stirred for 2.5 h at 23° C., filtrated over Celite® and washed with EtOAc. The crude obtained was purified in an automatic system for flash chromatography ($SiO_2$, Hex:EtOAc from 95:5 to 50:50) to give 93 (7 mg, 58% yield).

$^1$H NMR (400 MHz, $CDCl_3$): δ 7.08 (d, J=8.8 Hz, 1H), 6.01 (dddd, J=17.3, 10.5, 6.1, 5.7 Hz, 1H), 5.88 (dd, J=2.3, 0.5 Hz, 1H), 5.41 (d, J=2.2 Hz, 1H), 5.38-5.22 (m, 2H), 4.78-4.67 (m, 3H), 3.78 (s, 3H), 3.51 (d, J=11.6 Hz, 1H), 3.19 (dd, J=11.6, 0.4 Hz, 1H), 2.20 (s, 3H), 1.89 (ddt, J=13.4, 9.5, 6.5 Hz, 1H), 1.76 (dddd, J=13.6, 9.7, 8.0, 5.6 Hz, 1H), 1.51 (s, 3H), 1.47-1.22 (m, 2H), 0.96 (t, J=7.3 Hz, 3H).

$^{13}$C NMR (100 MHz, $CDCl_3$): δ 174.1, 170.8, 167.8, 164.1, 162.4, 151.9, 133.3, 118.4, 100.1, 88.5, 84.3, 76.3, 55.9, 50.9, 39.8, 34.7, 24.7, 19.0, 13.6, 12.0.

Compound 94

94

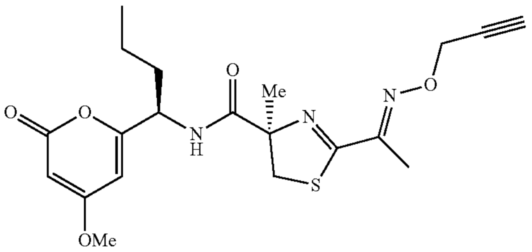

To a solution of 1 (11.6 mg, 0.03 mmol) in acetone (2.2 mL) was added $Cs_2CO_3$ (15 mg, 0.046 mmol) and propargyl bromide (5 μL, 0.046 mmol) at 23° C. The reaction mixture was stirred for 2.5 h at 23° C., filtrated over Celite® and washed with EtOAc. The crude obtained was purified in an automatic system for flash chromatography ($SiO_2$, Hex: EtOAc from 98:2 to 50:50) to yield 94 (11.7 mg, 91% yield).

$^1$H NMR (400 MHz, $CDCl_3$): δ 7.06 (d, J=8.8 Hz, 1H), 5.88 (d, J=2.2 Hz, 1H), 5.41 (d, J=2.5 Hz, 1H), 4.81 (d, J=2.4 Hz, 2H), 4.72 (q, J=7.9 Hz, 1H), 3.78 (s, 3H), 3.52 (d, J=11.7 Hz, 1H), 3.21 (d, J=11.6 Hz, 1H), 2.52 (t, J=2.5 Hz, 1H), 2.21 (s, 3H), 1.95-1.82 (m, 1H), 1.81-1.68 (m, 1H), 1.50 (s, 3H), 1.46-1.28 (m, 2H), 0.95 (t, J=7.6 Hz, 3H).

$^{13}$C NMR (100 MHz, $CD_3OD$): δ 174.0, 170.8, 167.4, 164.0, 162.4, 153.0, 100.1, 88.5, 84.3, 78.7, 75.2, 62.8, 55.9, 50.9, 39.9, 34.7, 24.7, 19.0, 13.6, 12.1.

Compound 95

95

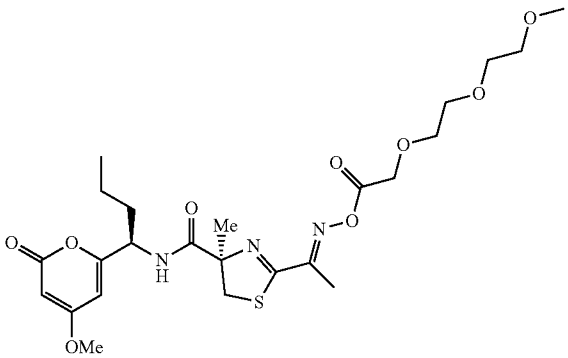

To a solution of 1 (12 mg, 0.031 mmol), $CH_2Cl_2$ (0.5 mL), EDC·HCl (12 mg, 0.062 mmol) and DIPEA (11 μL, 0.062 mmol) were added 2-[2-(2-methoxyethoxy)ethoxy]acetic acid (9 μL, 0.062 mmol) and catalytic DMAP. The reaction mixture was stirred for 24 h, diluted with $CH_2Cl_2$, and the organic layer was washed with 0.5 M HCl and an aqueous saturated solution of $HNaCO_3$ and then dried over anhydrous $Na_2SO_4$ to give a crude which was purified by HPLC method, using an XBridge C18 5 μm $H_2O/CH_3CN$ to give 95 (9 mg, 53% yield).

$^1H$ NMR (500 MHz, $CDCl_3$): δ 7.02 (d, J=8.9 Hz, 1H), 5.90 (m, 1H), 5.42 (d, J=2.2 Hz, 1H), 4.81-4.68 (m, 1H), 4.44 (s, 2H), 3.83-3.77 (m, 5H), 3.75-3.70 (m, 2H), 3.68-3.65 (m, 2H), 3.63 (d, J=11.7 Hz, 1H), 3.58-3.54 (m, 2H), 3.38 (s, 2H), 3.27 (d, J=11.7 Hz, 1H), 2.36 (s, 3H), 1.93-1.71 (m, 2H), 1.53 (s, 3H), 1.46-1.28 (m, 2H), 0.96 (t, J=7.4 Hz, 3H).

$^{13}C$ NMR (100 MHz, $CD_3OD$): δ 176.6, 173.5, 170.3, 166.7, 165.2, 152.9, 100.8, 88.9, 85.6, 72.9, 71.8, 71.6, 71.3, 69.1, 59.1, 57.0, 54.8, 52.1, 49.7, 40.6, 35.2, 34.8, 26.8, 26.1, 25.0, 20.2, 13.8, 11.0.

MS (ES): m/z 542.3 $[M+H]^+$, 564.2 $[M+Na]^+$.

$R_f$: 0.25 (hexanes:EtOAc 1:1).

Compound 96

96

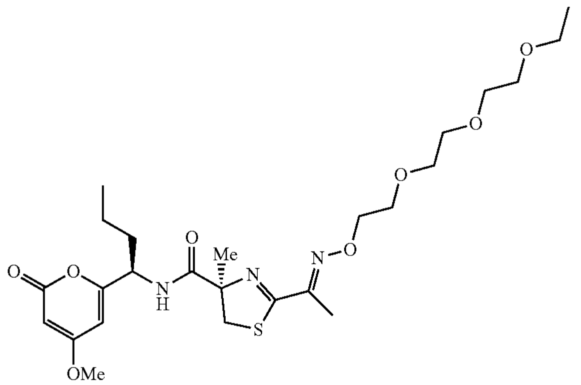

A mixture of 1 (9.3 mg, 0.024 mmol), $K_2CO_3$ (16 mg, 0.12 mmol), and 1-ethoxy-2-(2-(2-iodoethoxy)ethoxy)-ethane (34 mg, 0.12 mmol) in acetone (0.24 mL) was stirred at 23° C. for 24 h and then filtered over Celite®. Evaporation of the solvent gave a crude which was chromatographed on silica gel ($CH_2Cl_2$/EtOAc 1/1) to yield 96 (11 mg, 83% yield).

$^1H$ NMR (500 MHz, $CDCl_3$): δ 7.07 (d, J=8.7 Hz, 1H), 5.88 (d, J=2.2 Hz, 1H), 5.41 (d, J=2.2 Hz, 1H), 4.73 (td, J=8.4, 6.8 Hz, 1H), 4.43-4.32 (m, 2H), 3.79 (s, 5H), 3.69-3.63 (m, 6H), 3.62-3.57 (m, 2H), 3.56-3.47 (m, 3H), 3.20 (d, J=11.6 Hz, 1H), 2.19 (s, 3H), 1.95-1.73 (m, 2H), 1.51 (s, 3H), 1.44-1.28 (m, 2H), 1.21 (t, J=7.0 Hz, 3H), 0.96 (t, J=7.3 Hz, 3H).

MS (ES): m/z 542.3 $[M+H]^+$, 564.3 $[M+Na]^+$.

Compound 97

97

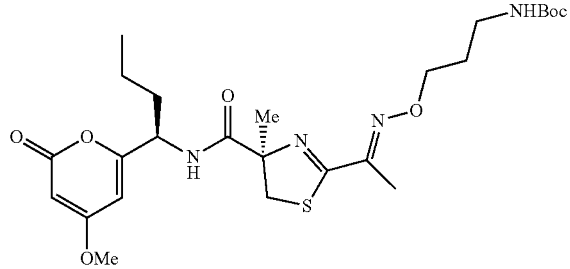

A mixture of 1 (16 mg, 0.042 mmol), potassium carbonate (29 mg, 0.21 mmol), and t-butyl-(3-iodopropyl)-carbamate (60 mg, 0.21 mmol) in acetone (0.4 mL) was stirred at 23° C. for 18 h and then filtered over Celite®. Evaporation of the solvent gave a crude which was chromatographed on silica gel ($CH_2Cl_2$/EtOAc 9/1) to afford 97 (22 mg, 100% yield).

$^1H$ NMR (500 MHz, $CDCl_3$): δ 7.06 (d, J=8.8 Hz, 1H), 5.88 (dd, J=2.3, 0.5 Hz, 1H), 5.41 (d, J=2.2 Hz, 1H), 4.83-4.58 (m, 1H), 4.28 (t, J=6.0 Hz, 2H), 3.78 (s, 3H), 3.51 (d, J=11.6 Hz, 1H), 3.30-3.11 (m, 3H), 2.17 (s, 3H), 1.98-1.61 (m, 4H), 1.50 (s, 3H), 1.43 (s, 9H), 1.41-1.15 (m, 2H), 0.95 (t, J=7.3 Hz, 3H).

MS (ES): m/z 539.3 $[M+H]^+$, 561.2 $[M+Na]^+$.

Compound 98

98

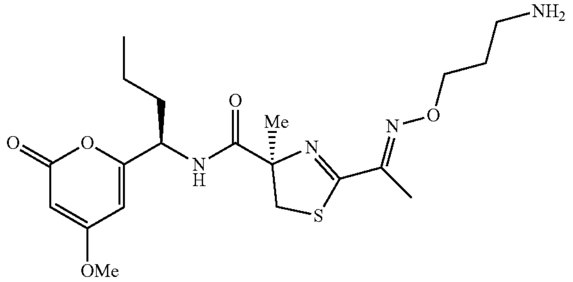

To a solution of 97 (30 mg, 0.055 mmol) in $CH_2Cl_2$ (0.6 mL) was added TFA (0.26 mL) dropwise. The mixture was stirred 2 h at 23° C. and then all volatiles were evaporated (co-evaporation with toluene 3 times). The crude oil was purified by chromatography on silica gel ($CH_2Cl_2/CH_3OH$ 15/1) to afford 98 (12.5 mg, 55% yield).

$^1H$ NMR (500 MHz, $CDCl_3$): δ 7.02 (d, J=8.8 Hz, 1H), 5.96 (d, J=2.2 Hz, 1H), 5.46 (d, J=2.2 Hz, 1H), 4.69 (q, J=7.9 Hz, 1H), 4.35 (dt, J=7.5, 4.9 Hz, 2H), 3.80 (s, 3H), 3.69 (d, J=11.6 Hz, 1H), 3.24-3.01 (m, 3H), 2.21 (s, 3H), 2.18-2.08 (m, 2H), 1.88-1.75 (m, 2H), 1.54 (s, 3H), 1.47-1.29 (m, 1H), 0.96 (t, J=7.4 Hz, 3H).

MS (ES): m/z 439.2 $[M+H]^+$, 461.1 $[M+Na]^+$.

Scheme 13 provides further examples of the synthesis of more compounds of formula I.

Scheme 13

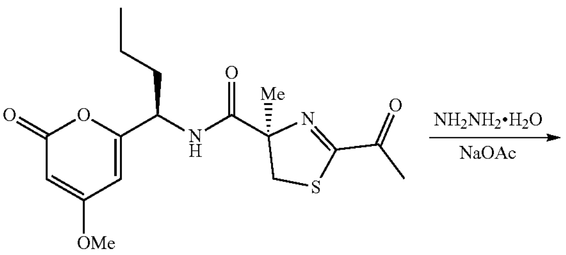

42

-continued

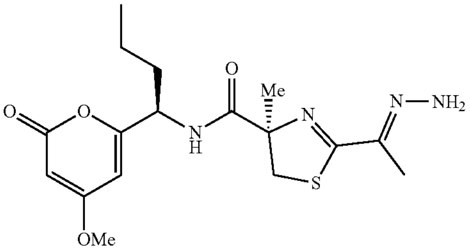

99

Compound 93

99

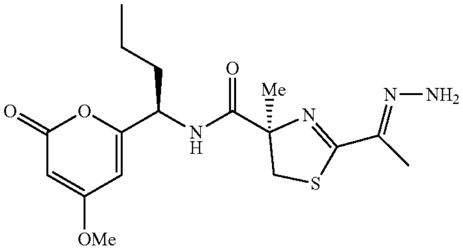

To a solution of 42 (11.6 mg, 0.032 mmol) in ethanol (0.3 mL) and water (0.3 mL), were added 50% hydrazine hydrate (0.015 mL) and NaOAc (12 mg, 0.14 mmol). After stirring at 23° C. for 24 h the solvents were evaporated under vacuum to dryness. The obtained crude was purified by chromatography on silica gel ($CH_2Cl_2$/EtOAc 1/1) to afford 99 (10 mg, 83% yield).

$^1$H NMR (500 MHz, $CDCl_3$): δ 7.14 (d, J=8.9 Hz, 1H), 5.90 (m, 1H), 5.41 (d, J=2.2 Hz, 1H), 4.82-4.62 (m, 1H), 3.79 (s, 3H), 3.50 (d, J=11.6 Hz, 1H), 3.17 (d, J=11.6 Hz, 1H), 2.11 (s, 3H), 1.88 (m, 1H), 1.76 (m, 1H), 1.52 (s, 3H), 1.48-1.21 (m, 2H), 0.96 (t, J=7.3 Hz, 3H).

MS (ES): m/z 381.2 $[M+H]^+$, 403.1 $[M+Na]^+$.

Example 10 Synthesis of Additional Compounds of Formula I

Scheme 14 provides an example of the synthesis of additional compounds of formula I.

Scheme 14

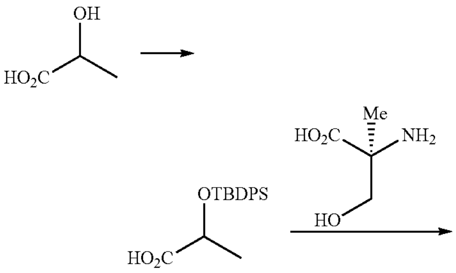

100

-continued

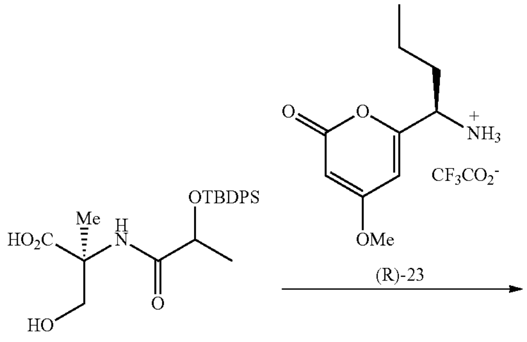

101

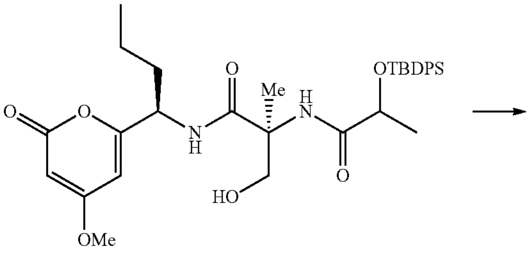

102

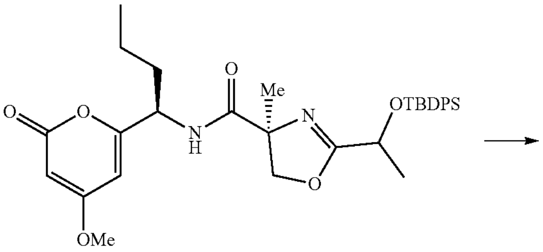

103

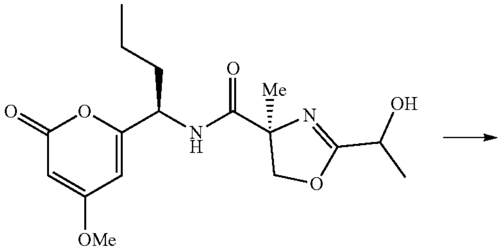

104

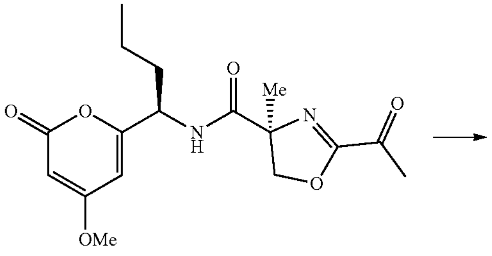

105

-continued

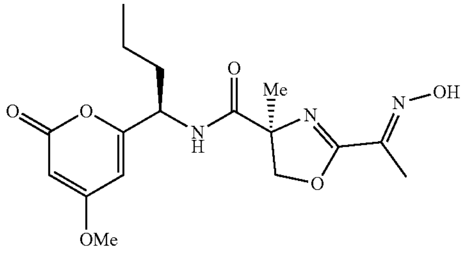

106

Compound 100

100

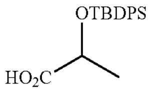

To a stirred solution of lactic acid (1.0 g, 11.1 mmol) with imidazole (1.13 g, 16.6 mmol) in anhydrous DMF (33 mL) was added in portions tert-butyldimethylsilyl chloride (2.8 mL; 11.1 mmol). After 48 h at 23° C. the solution was diluted with hexane and washed once with water, once with saturated $NaHCO_3$ and once with brine. The organic layer was dried over $Na_2SO_4$ and the solvent was removed under reduced pressure to yield 100 (3.1 g, 85% yield) as a colourless oil.

$^1$H NMR (500 MHz, $CDCl_3$): δ 7.65 (m, 4H), 7.40 (m, 6H), 4.32 (q, J=7.0 Hz, 1H), 1.32 (d, J=7.0 Hz, 3H), 1.11 (s, 9H).

$^{13}$C NMR (125 MHz, $CDCl_3$): δ 207.1, 135.7, 130.2, 130.1, 127.9, 127.8, 69.1, 30.9, 30.8, 26.8, 26.7, 21.0, 19.1.

MS (ES): m/z 351.2 $[M+Na]^+$.

Compound 101

101

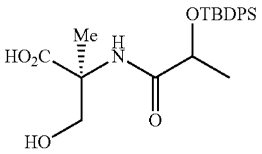

To a stirred solution of 100 (140 mg, 0.43 mmol) in anhydrous $CH_2Cl_2$ (3 mL), was added at 0° C. N-(3-Dimethylaminopropyl)-N'-ethylcarbodiimide hydrochloride (EDC·HCl) (89 mg, 0.47 mmol) and 1-Hydroxybenzotriazole hydrate (HOBt) (63 mg, 0.47 mmol). After 10 min at 0° C., (L)-α-methylserine (Across Organics) (50 mg, 0.43 mmol) and $Et_3N$ (0.06 mL) were added. The crude mixture was stirred 18 h at 23° C., diluted with $CH_2Cl_2$ and acidified with aqueous HCl (0.5 M) to pH~2 and extracted with $CH_2Cl_2$. The combined organic phase was dried over $Na_2SO_4$, filtrated and concentrated in vacuo to yield 101 (170 mg; 92% yield) that was used without further purification as a mixture of two diastereomers.

$^1$H NMR (300 MHz, $CDCl_3$) δ 7.96 (s, 1H), 7.86 (s, 1H), 7.66 (m, 8H), 7.61 (m, 1H), 4.27 (m, 2H), 3.98 (dd, J=11.4, 2.7 Hz, 2H), 3.78 (d, J=11.4, 1.7 Hz, 2H), 1.27 (d, J=7.2 Hz, 3H), 1.25 (d, J=7.2 Hz, 3H), 1.20 (s, 18H).

MS (ES): m/z 452.3 $[M+Na]^+$.

Compound 102

102

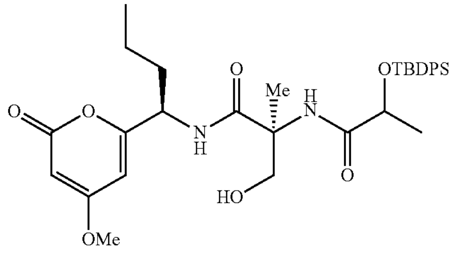

To a stirred solution of 101 (170 mg, 0.40 mmol) and (R)-23 (84 mg, 0.40 mmol) in anhydrous $CH_2Cl_2$ (3 mL) were added 1-[Bis(dimethylamino)methylene]-1H-1,2,3-triazolo[4,5-b]pyridinium-3-oxid hexafluorophosphate (HATU) (212 mg, 0.56 mmol), HO 1-Hydroxy-7-azabenzotriazole (HOAt) (76 mg, 0.56 mmol) and Diisopropylethylamine (DIPEA) (0.29 mL, 1.68 mmol) and the mixture was stirred at 23° C. overnight. After dilution with $CH_2Cl_2$, the organic layer was washed with 0.5 M HCl, brine and, finally, dried over $Na_2SO_4$. Filtration and evaporation of the solvent gave a crude which was purified by flash chromatography on silica gel (hexane/EtOAc) to afford 102 (102 mg, 46% yield) as a mixture of two diastereomers.

$^1$H NMR (300 MHz, $CDCl_3$): δ 8.06 (d, J=8.3 Hz, 2H), 7.82 (s, 2H), 7.66 (m, 8H), 7.40 (m, 12H), 5.88 (d, J=2.3 Hz, 1H), 5.85 (d, J=2.3 Hz, 1H), 5.38 (d, J=2.2 Hz, 1H), 5.36 (d, J=2.2 Hz, 1H), 4.69 (m, 2H), 4.28 (m, 6H), 4.0 (t, J=10.5 Hz, 2H), 3.76 (s, 3H), 3.72 (s, 3H), 1.89-1.62 (m, 4H), 1.50 (s, 3H), 1.43 (s, 3H), 1.35 (m, 4H), 1.30 (d, J=7.5 Hz, 3H), 1.23 (d, J=7.5 Hz, 3H), 1.12 (s, 9H), 1.09 (s, 9H), 0.92 (t, J=7.3 Hz, 6H).

MS (ES): m/z 609.2 $[M+H]^+$.

Compound 103

103

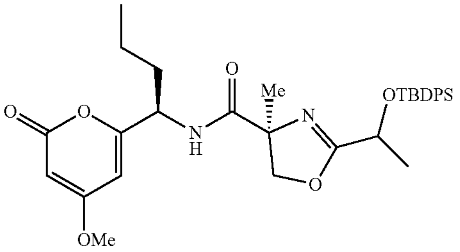

To a stirred solution of 102 (100 mg, 0.16 mmol) in anhydrous $CH_2Cl_2$ (1.5 mL) was added dropwise diethylaminosulfur trifluoride (DAST) (0.02 mL, 0.18 mmol) at −78° C. After 1.5 h, the reaction mixture was quenched by addition of $K_2CO_3$ (34 mg, 0.25 mmol) in one portion at −78° C. After warming to 23° C., the mixture was further diluted with saturated aqueous sodium bicarbonate and extracted with $CH_2Cl_2$. The combined organic layer was dried over $Na_2SO_4$, filtered, and concentrated to yield 103 (96 mg; 100% yield) that was used without further purification as a mixture of two diastereomers.

$^1$H NMR (300 MHz, $CDCl_3$): δ 7.66 (m, 8H), 7.38 (m, 12H), 6.87 (d, J=8.7 Hz, 1H), 6.81 (d, J=8.7 Hz, 1H), 5.81 (d, J=2.3 Hz, 1H), 5.78 (d, J=2.3 Hz, 1H), 5.40 (d, J=2.2 Hz, 1H), 5.37 (d, J=2.2 Hz, 1H), 4.66 (m, 2H), 4.50-4.25 (m, 4H), 3.97 (d, J=9.3 Hz, 1H), 3.90 (d, J=9.3 Hz, 1H), 3.77 (s,

3H), 3.75 (s, 3H), 1.90-1.57 (m, 4H), 1.40 (s, 3H), 1.38 (s, 3H), 1.28 (m, 10H), 1.06 (s, 18H), 0.92 (t, J=7.3 Hz, 6H).

MS (ES): m/z 591.2 $[M+H]^+$.

Compound 104

104

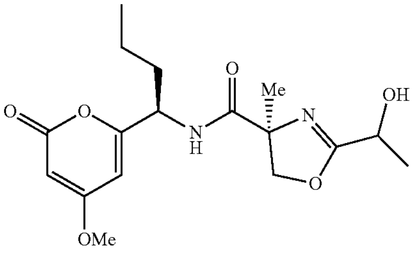

To a stirred solution of 103 (96 mg, 0.16 mmol) in anhydrous THF (1.5 ml) was added tetrabutylammonium fluoride (TBAF) (0.25 mL, 0.25 mmol) dropwise. After 1 h at 23° C. the reaction mixture was quenched with a saturated aqueous ammonium chloride and extracted with EtOAc. The combined organic layer was dried over $Na_2SO_4$, filtered, and concentrated to obtain crude 104 (55 mg; 99% yield) that was used without further purification as a mixture of two diastereomers.

$^1H$ NMR (300 MHz, $CDCl_3$): δ 7.05 (t, J=9.6 Hz, 2H), 5.89 (d, J=2.3 Hz, 1H), 5.87 (d, J=2.3 Hz, 1H), 5.40 (d, J=2.2 Hz, 2H), 4.67 (m, 2H), 4.58-4.22 (m, 4H), 4.10 (m, 2H), 3.76 (s, 6H), 1.86-1.60 (m, 4H), 1.5 (s, 6H), 1.46-1.30 (m, 10H), 0.92 (t, J=7.3 Hz, 6H).

MS (ES): m/z 353.1 $[M+H]^+$.

Compound 105

105

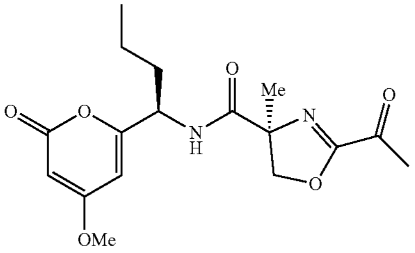

To a solution of 104 (57 mg, 0.16 mmol) in anhydrous $CH_2Cl_2$ (1.6 mL) at 23° C. was successively added $NaHCO_3$ (41 mg, 0.49 mmol) and Dess-Martin periodinane (DMP) (139 mg, 0.33 mmol) in portions. After 1 h at 23° C. (reaction followed by TLC (Hex:EtOAc 1:1), the reaction mixture was quenched with a 1:1 mixture of aqueous saturated solution of $NaHCO_3$ and 10% solution of $Na_2S_2O_3$. The mixture was stirred for 1 h at 23° C. and extracted with $CH_2Cl_2$. The combined organic phases were dried over $Na_2SO_4$, filtered and concentrated in vacuo to give an oil that was purified by flash chromatography on silica gel (hexane/EtOAc) to afford 105 (9 mg, 18% yield) as a white solid.

$^1H$ NMR (300 MHz, $CDCl_3$): δ 6.84 (d, J=9.3 Hz, 1H), 5.87 (d, J=2.3 Hz, 1H), 5.41 (d, J=2.3 Hz, 1H), 4.70 (m, 1H), 4.63 (d, J=9.3 Hz, 1H), 4.23 (d, J=9.3 Hz, 1H), 3.78 (s, 3H), 2.55 (s, 3H), 1.92-1.71 (m, 2H), 1.56 (s, 3H), 1.44-1.30 (m, 2H), 0.96 (t, J=7.2 Hz, 3H).

106

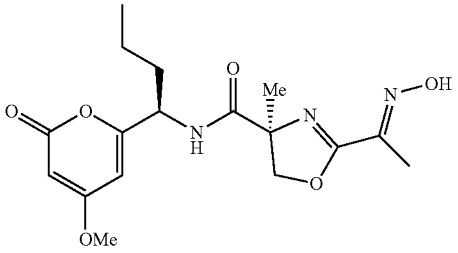

Compound 106

To a solution of 105 (7 mg, 0.02 mmol) in ethanol (0.22 mL) and water (0.22 mL), were added $NH_2OH{\cdot}HCl$ (10 mg, 0.146 mmol) and NaOAc (7 mg, 0.09 mmol). After stirring at 23° C. for 24 h, solvent was evaporated under vacuum and the aqueous layer was extracted with EtOAc. The combined organic layer was dried over $Na_2SO_4$, filtered, and concentrated to give a crude that was purified by chromatography on silica gel ($CH_2Cl_2$/EtOAc 1/1) to afford 106 (1.6 mg, 23% yield).

$^1H$ NMR (300 MHz, $CDCl_3$): δ 6.85 (d, J=9.3 Hz, 1H), 5.81 (d, J=2.3 Hz, 1H), 5.35 (d, J=2.3 Hz, 1H), 4.63 (m, 1H), 4.14 (d, J=9.3 Hz, 1H), 3.92 (d, J=9.3 Hz, 1H), 3.72 (s, 3H), 2.14 (s, 3H), 1.82-1.67 (m, 2H), 1.48 (s, 3H), 1.30 (m, 2H), 0.89 (t, J=7.2 Hz, 3H).

MS (ES): m/z 366.2 $[M+H]^+$.

Example 11 Synthesis of Additional Compounds of Formula I

Scheme 15 provides an example of the synthesis of additional compounds of formula I.

Scheme 15

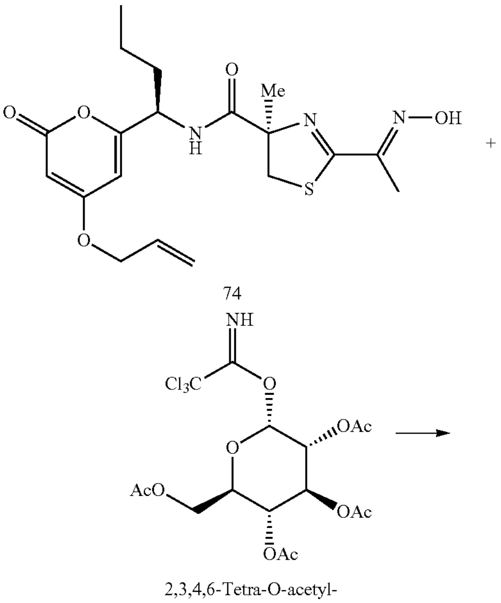

74

2,3,4,6-Tetra-O-acetyl-alpha-D-glucopyranosyl trichloroacetimidate

-continued

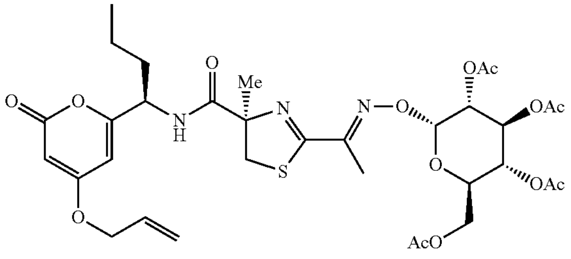

107

A mixture of 74 (37 mg; 0.091 mmol), 2,3,4,6-Tetra-O-acetyl-α-D-glucopyranosyl trichloroacetimidate (30 mg, 0.061 mmol) and freshly activated 4 Å MS (244 mg) were dissolved/suspended in $CH_2Cl_2$ (1.0 mL) and stirred for 1 h at 23° C. Then, the temperature was decreased to −20° C. and TMSOTf (12 μL; 0.064 mmol) was slowly added. The reaction was allowed to get into 23° C. and then stirred overnight. Subsequently, $Et_3N$ was added to quench the reacting mixture and the resulting suspension filtered through a by layer pad of Celite® (on top) and $Na_2SO_4$ (below). The solids were thoroughly washed with $CH_2Cl_2$ and the whole filtrate concentrated in vacuum, giving rise to a yellow-orange gel that was purified by flash chromatography on silica gel (Hex:EtOAc from 70:30 to 0:100) to afford pure 107 (23 mg, 51% yield).

$^1H$ NMR (400 MHz, $CDCl_3$): δ 7.08 (d, J=8.9 Hz, 1H), 6.00 (d, J=5.6 Hz, 1H), 5.98-5.92 (m, 1H), 5.41-5.36 (m, 3H), 5.15 (dd, J=2.8, 2.8 Hz, 1H), 4.92 (dd, J=9.3, 2.8 Hz, 1H), 4.73 (q, J=7.8, 1H), 4.65 (dd, J=5.6, 2.8 Hz, 1H), 4.49 (dt, J=5.6, 1.2 Hz, 2H), 4.23 (dd, J=4.0, 2.7, 2H), 3.93 (ddd, J=8.8, 5.0, 3.4, 1H), 3.53 (d, J=11.6, 1H), 3.21 (d, J=11.6, 1H), 2.17 (s, 3H), 2.10 (bs, 9H), 1.92-1.70 (m, 2H), 1.86 (s, 3H), 1.50 (s, 3H), 1.49-1.28 (m, 2H), 0.96 (t, J=7.3 Hz, 3H).

$^{13}C$ NMR (100 MHz, $CDCl_3$): δ 173.9, 170.8, 169.8, 169.8, 169.3, 167.5, 164.1, 162.4, 153.4, 130.7, 123.4, 119.8, 100.6, 98.7, 89.6, 84.88, 74.9, 70.2, 69.8, 67.9, 67.4, 63.3, 51.1, 40.0, 35.0, 24.9, 21.4, 21.0, 20.9, 20.9, 19.2, 13.7, 12.2.

MS (ES+): m/z 738 $[M+H]^+$, 760 $[M+Na]^+$.

$R_f$: 0.21 (Hex:EtOAc 50:50).

Scheme 16 provides an example of the synthesis of an additional compound of formula I.

Scheme 16

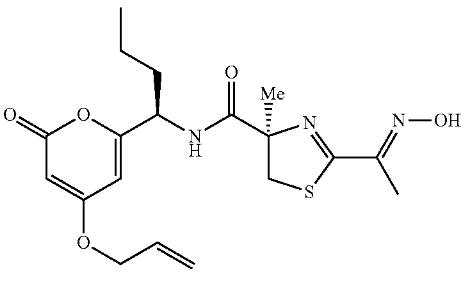

74

+

-continued

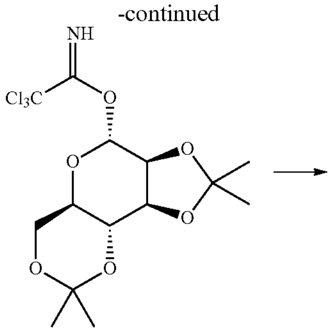

109

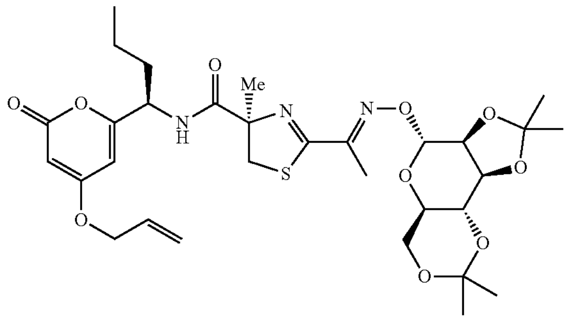

110 a) Synthesis of 109

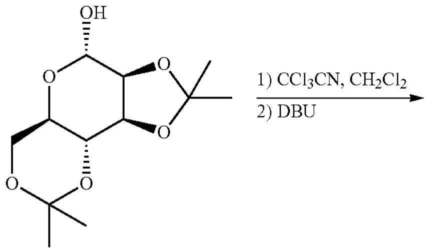

108

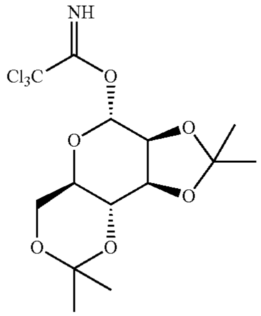

109

To a solution of 108 (570 mg, 2.190 mmol) [obtained as described in *Bioorg. Med. Chem.* 2013, 21, 4839-4845] in anhydrous $CH_2Cl_2$ (11 mL), $CCl_3CN$ (2.20 mL, 21.90 mmol) and DBU (66 μL, 0.44 mmol) were added dropwise in this order at 23° C. The reaction was stirred for 1 h and then, concentrated in vacuum. The resulting dark red crude was subjected to a chromatographic column ($SiO_2$, Hexane+1% $Et_3N$:EtOAc+1% $Et_3N$ from 80:20 to 50:50) giving rise to 109 (827 mg; 93% yield) as a white solid.

$^1H$ NMR (400 MHz): δ 8.59 (s, 1H), 6.26 (s, 1H), 4.92 (dd, J=5.9, 3.4 Hz, 1H), 4.86 (d, J=5.8 Hz, 1H), 4.43 (ddd, J=8.3, 6.2, 4.2 Hz, 1H), 4.14-4.09 (m, 2H), 4.03 (dd, J=8.9, 4.2 Hz, 1H), 1.50 (s, 3H), 1.45 (s, 3H), 1.38 (s, 3H), 1.37 (s, 3H).

$^{13}C$ NMR (100 MHz): δ 160.8, 113.6, 109.6, 104.9, 84.9, 83.0, 79.4, 72.8, 67.2, 27.1, 26.1, 25.3, 24.9.

MS (ES): m/z 426-428 $[M+Na]^+$.

$R_f$: 0.64 (Hex:EtOAc 2:1).

b) Synthesis of 110

A freshly-prepared stock solution (840 μL; 5% mol) of $Pd(PhCN)(OTf)_2$ catalyst in $CH_2Cl_2$, prepared by stirring $Pd(PhCN)_2Cl_2$ (10 mg; 0.026 mmol) and AgOTf (14 mg; 0.052 mmol) in $CH_2Cl_2$ (3.5 mL) at 23° C. for 5 min, was added to a solution of 109 (50 mg; 0.124 mmol) and 74 (61 mg; 0.161 mmol) in $CH_2Cl_2$, (700 μL) at 23° C. The reaction mixture was stirred at 23° C. overnight, then, treated with benzene (1 mL) and directly poured on a chromatographic column ($SiO_2$, $CH_2Cl_2$ to $CH_2Cl_2$:MeOH 98.2:1.8). According to this procedure, compound 110 (27.5 mg, 34% yield) was afforded as a foamy white solid (predominantly as a α anomer).

$^1H$ NMR (400 MHz, $CDCl_3$): δ 9.25 (s, 1H), 7.10 (d, J=8.9 Hz, 1H), 6.00-5.91 (m, 1H), 5.69 (bs, 1H), 5.42-5.30 (m, 3H), 4.93-4.91 (dd, J=6.0, 3.6 Hz, 1H), 4.87 (d, J=6.0 Hz, 1H), 4.73 (q, J=7.9 Hz, 1H), 4.49 (bd, J=6.6 Hz, 2H), 4.38 (m, 1H), 4.22 (dd, J=7.7, 3.9 Hz, 1H), 4.08 (bd, J=5.2 Hz, 2H), 3.52 (d, J=11.6 Hz, 1H), 3.20 (d, J=11.6 Hz 1H), 2.19 (s, 3H), 1.93-1.72 (m, 2H), 1.51 (s, 3H), 1.50 (s, 3H), 1.49-1.28 (m, 11H), 0.96 (t, J=7.4 Hz, 3H).

$^{13}C$ NMR (100 MHz, $CDCl_3$): δ 174.0, 169.8, 167.5, 164.1, 162.5, 153.8, 130.8, 119.8, 113.0, 109.3, 109.0, 100.6, 89.6, 84.8, 84.7, 83.3, 80.0, 73.5, 69.7, 66.8, 51.1, 40.0, 35.0, 27.1, 26.1, 25.3, 24.9, 24.6, 19.2, 13.7, 12.2.

MS (ES+): m/z 650 $[M+H]^+$, 672 $[M+Na]^+$.

$R_f$: 0.39 ($CH_2Cl_2$:MeOH 50:1).

Scheme 17 provides an example of the synthesis of an additional compound of formula I.

Scheme 17

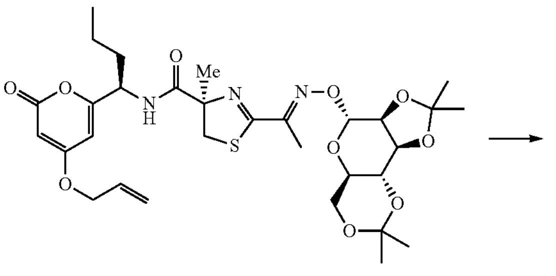

110

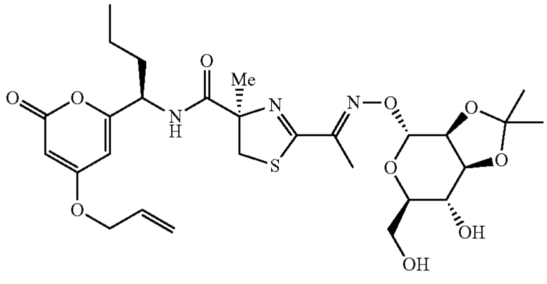

111

Compound 110 (31 mg, 0.048 mmol) was dissolved in aqueous AcOH (80%, 1.0 mL) and stirred at 65° C. for 4 h. Then, the solution was diluted with toluene (1.5 mL) and the volatiles vacuum evaporated, affording an oily beige crude. Co-evaporation of aqueous AcOH with toluene was repeated twice more. The obtained crude was purified by column chromatography ($SiO_2$, $CH_2Cl_2$ to $CH_2Cl_2$:MeOH 10:1) to obtain compound 111 (18 mg, 62% yield) as a waxy white solid.

$^1H$ NMR (500 MHz, $CDCl_3$): δ 7.04 (d, J=8.9 Hz, 1H), 5.99-5.92 (m, 1H), 5.72 (bs, 1H), 5.42-5.34 (m, 3H), 5.01 (dd, J=6.0, 4.3 Hz, 1H), 4.89 (d, J=6.0 Hz, 1H), 4.72 (q, J=8.0 Hz, 1H), 4.49 (bd, J=5.5 Hz, 2H), 4.25 (dd, J=8.0, 4.3 Hz, 1H), 3.97 (bd, J=8.3, 5.8, 3.4 Hz, 1H), 3.86 (d, J=11.5, 3.4 Hz, 1H), 3.74 (d, J=11.5, 5.8 Hz, 1H), 3.54 (d, J=11.6 Hz, 1H), 3.21 (d, J=11.6 Hz, 1H), 2.19 (s, 3H), 1.90-1.72 (m, 2H), 1.52 (s, 6H), 1.37 (s, 3H), 1.42-1.31 (m, 2H), 0.96 (t, J=7.4 Hz, 3H).

$^{13}C$ NMR (125 MHz, $CDCl_3$): δ 174.0, 169.9, 167.6, 164.2, 162.4, 153.9, 130.7, 119.8, 113.0, 108.7, 100.7, 89.6, 84.7, 84.6, 82.7, 80.7, 71.0, 69.8, 64.5, 51.2, 40.1, 35.0, 26.1, 25.0, 24.7, 19.2, 13.7, 12.2.

MS (ES+): m/z 610 $[M+H]^+$, 632 $[M+Na]^+$.

$R_f$: 0.12 ($CH_2Cl_2$:MeOH 50:1).

Scheme 18 provides an example of the synthesis of an additional compound of formula I.

Scheme 18

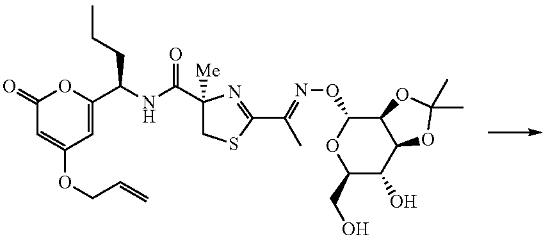

111

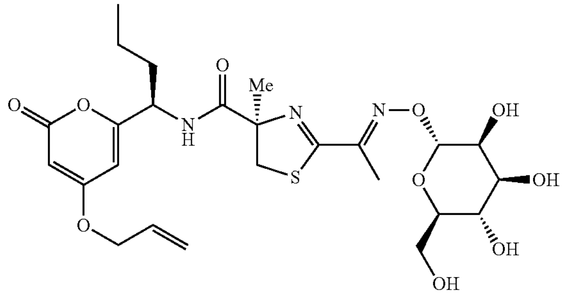

112

A solution of 111 (180 mg, 0.29 mmol) in aqueous AcOH (80%, 10 mL) was heated at 100° C. for 4 h. Then, the solution was diluted with toluene (10 mL) and the volatiles vacuum evaporated, affording an oily beige crude. Co-evaporation of aqueous AcOH with toluene was repeated (×5) to afford a beige crude that was purify by flash chromatography ($SiO_2$, $CH_2Cl_2$ to $CH_2Cl_2$:MeOH 90:10). Final purification was carried out by HPLC on a C18 Symmetry preparative column, flow rate 15 mL/min, $H_2O$:$CH_3CN$ mixtures to obtain compound 112 (60 mg, 36% yield).

$^1H$ NMR (500 MHz, $CDCl_3$): δ 7.07 (d, J=8.8 Hz, 1H), 6.00-5.92 (m, 1H), 5.72 (d, J=2.5, 1H), 5.44-5.34 (m, 3H), 4.72 (q, J=8.0 Hz, 1H), 4.61 (t, J=4.9 Hz, 1H), 4.50 (bd, J=5.6, 2H), 4.41 (dd, J=5.3, 2.5 Hz, 1H), 4.20 (dd, J=6.8, 4.5 Hz, 1H), 4.09 (td, J=6.4, 3.5 Hz, 1H), 3.87 (dd, J=11.6, 3.3 Hz, 1H), 3.77 (dd, J=11.6, 6.0 Hz, 1H), 3.55 (d, J=11.6 Hz, 1H), 3.20 (d, J=11.6 Hz, 1H), 2.20 (s, 3H), 1.92-1.73 (m, 2H), 1.52 (s, 3H), 1.42-1.28 (m, 2H), 0.96 (t, J=7.4 Hz, 3H).

$^{13}C$ NMR (100 MHz, $CDCl_3$): δ 174.2, 170.1, 167.9, 164.6, 162.5, 154.0, 130.7, 119.8, 110.5, 100.8, 89.6, 84.6, 80.8, 75.6, 71.9, 71.6, 69.9, 63.7, 51.2, 40.3, 34.9, 25.0, 19.2, 13.7, 12.5.

MS (ES+): m/z 570 $[M+H]^+$, 592 $[M+Na]^+$.

Compound 113

113

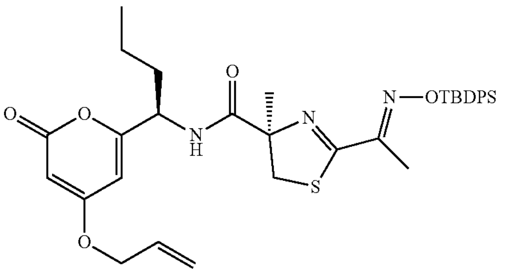

To a solution of 74 (121 mg) in dry DMF (3 mL) was added imidazole (47 mg), DMAP (1 mg) and TBDPSCl (85 μL) and reaction mixture was stirred overnight at 23° C. To quench the reaction, aqueous saturated solution of $NH_4Cl$ (10 mL) was added and mixture was extracted with EtOAc (3×10 mL). Combined organic phases were washed with water (3×10 mL) and brine (10 mL) and then dried over anhydrous $Na_2SO_4$, filtered and evaporated. Crude residue was purified on CombiFlash with a $SiO_2$ column and eluting with hexane/EtOAc from 100:0 to 0:100 in 30 min. to yield Compound 113 (108 mg, 56% yield).

$^1H$ NMR (400 MHz, $CDCl_3$): δ 7.75-7.66 (m, 2H), 7.48-7.33 (m, 8H), 7.14 (d, J=8.7 Hz, 1H), 6.03-5.87 (m, 1H), 5.94 (d, J=2.2 Hz, 1H), 5.42 (d, J=2.3 Hz, 1H), 5.43-5.36 (m, 1H), 5.34 (dq, J=10.5, 1.2 Hz, 1H), 4.73 (q, J=8.0 Hz, 1H), 4.48 (dt, J=5.6, 1.5 Hz, 2H), 3.46 (d, J=11.6 Hz, 1H), 3.15 (d, J=11.6 Hz, 1H), 2.35 (s, 3H), 1.89 (dq, J=9.5, 6.8 Hz, 1H), 1.78 (dddd, J=13.6, 9.6, 7.9, 5.7 Hz, 1H), 1.50 (s, 3H), 1.49-1.20 (m, 2H), 1.15 (s, 9H), 0.97 (t, J=7.3 Hz, 3H).

$^{13}C$ NMR (100 MHz, $CDCl_3$): δ 174.2, 169.7, 168.5, 164.1, 162.4, 157.2, 135.5, 132.8, 130.6, 129.9, 127.6, 119.6, 100.4, 89.4, 84.3, 69.6, 51.0, 39.7, 34.7, 27.1, 24.8, 19.6, 19.1, 13.6, 11.8.

Scheme 19 provides an example of the synthesis of additional compounds of formula I.

Scheme 19

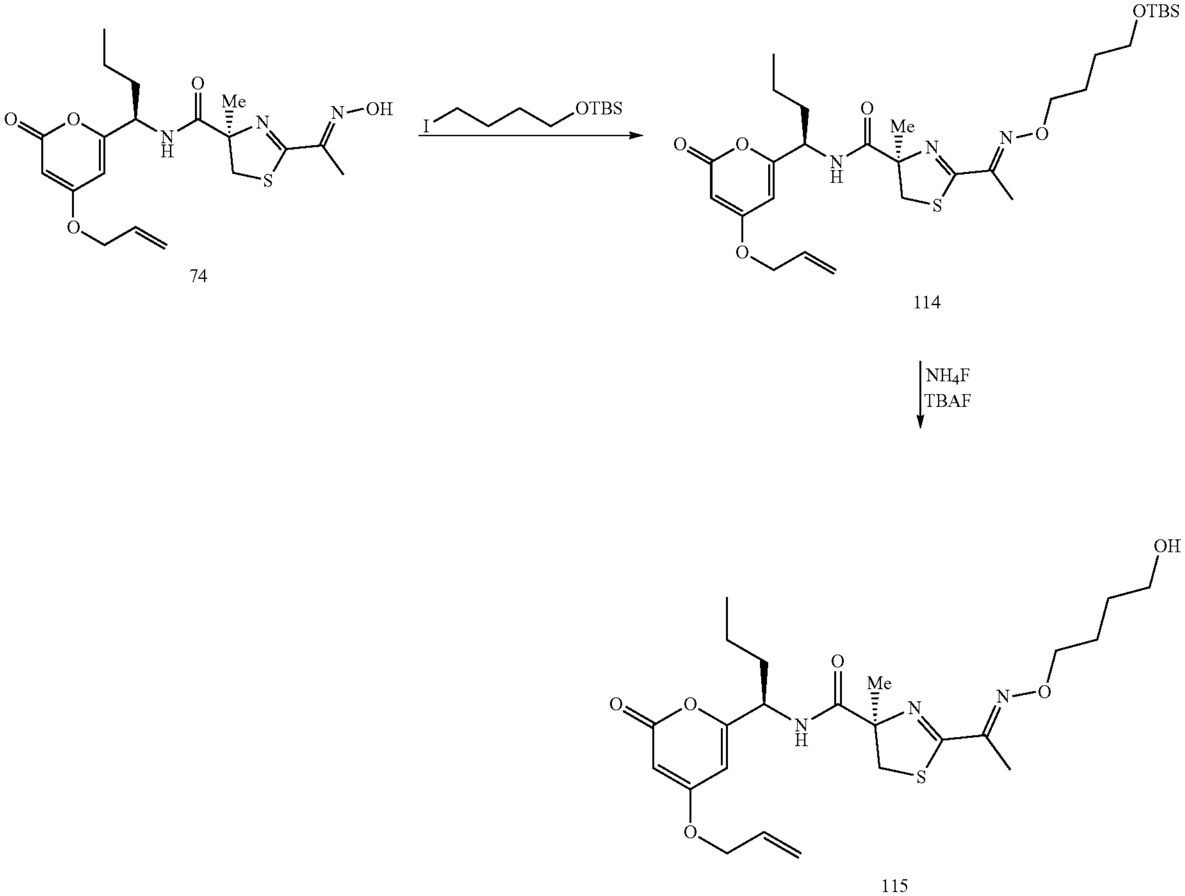

74

114

115

Compound 114

114

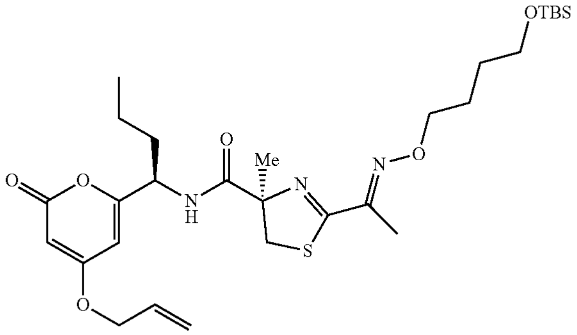

To a solution of 74 (77 mg, 0.190 mmol) in acetone (2 mL) $Cs_2CO_3$ (310 mg, 0.952 mmol) and tert-Butyl(4-iodobutoxy)dimethylsilane (0.25 mL, 0.952 mmol) were added at 23° C. The reaction mixture was stirred at 23° C. overnight, filtered, washed with EtOAc, and concentrated under reduced pressure. The resulting residue was purified by combiflash in $SiO_2$ ($CH_2Cl_2$:EtOAc from 100:0 to 90:10) to yield 114 (80 mg, 71% yield).

$^1$H NMR (400 MHz, $CD_3OD$): δ 7.85 (d, J=8.6 Hz, 1H), 6.06 (d, J=2.2 Hz, 1H), 6.05-5.92 (m, 1H), 5.53 (d, J=2.2 Hz, 1H), 5.46-5.27 (m, 2H), 4.75 (ddd, J=8.8, 7.3, 4.3 Hz, 1H), 4.58 (dt, J=5.6, 1.5 Hz, 2H), 4.22 (t, J=6.5 Hz, 2H), 3.67 (t, J=6.2 Hz, 2H), 3.58 (dd, J=11.5, 5.8 Hz, 1H), 3.19 (d, J=11.6 Hz, 1H), 2.19 (d, J=2.2 Hz, 3H), 1.97-1.70 (m, 4H), 1.60 (dd, J=8.7, 6.1 Hz, 2H), 1.52 (d, J=1.9 Hz, 3H), 1.49-1.34 (m, 4H), 0.98 (t, J=7.3 Hz, 3H), 0.89 (s, 9H), 0.06 (s, 6H).

$^{13}$C NMR (100 MHz, $CD_3OD$): δ 175.0, 170.7, 168.0, 165.1, 163.9, 151.4, 131.1, 118.0, 99.5, 88.4, 84.2, 74.9, 69.6, 62.5, 50.8, 39.3, 33.9, 28.8, 25.4, 25.0, 23.5, 18.8, 17.7, 12.5, 10.4, -6.5.

MS (ES+): m/z 594 $[M+H]^+$, 616 $[M+Na]^+$.

Compound 115

115

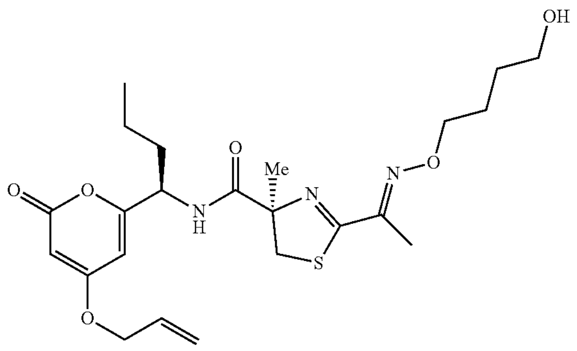

To a solution of 114 (70 mg, 0.118 mmol) in anhydrous THF (1 mL) ammonium fluoride (22 mg, 0.589 mmol) and TBAF (0.60 mL, 1.0 M in THF, 0.589 mmol) were added at 23° C. The reaction mixture was stirred for 4 h at 23° C., quenched with a saturated aqueous solution of NaCl, extracted with $CH_2Cl_2$ (2×10 mL), dried over anhydrous $Na_2SO_4$, filtered and concentrated under reduced pressure. The resulting residue was purified by combiflash in $SiO_2$ ($CH_2Cl_2$ to $CH_2Cl_2$:EtOAc 1:1) to yield 115 (40 mg, 71% yield).

$^1$H NMR (400 MHz, $CD_3OD$): δ 6.06 (d, J=2.2 Hz, 1H), 6.05-5.91 (m, 1H), 5.54 (d, J=2.2 Hz, 1H), 5.46-5.29 (m, 2H), 4.74 (dd, J=9.1, 5.8 Hz, 1H), 4.59 (dt, J=5.5, 1.6 Hz, 2H), 4.23 (t, J=6.5 Hz, 2H), 3.63-3.50 (m, 3H), 3.19 (d, J=11.5 Hz, 1H), 2.19 (s, 3H), 1.89-1.73 (m, 3H), 1.62 (dd, J=8.9, 6.2 Hz, 2H), 1.52 (s, 3H), 1.45-1.32 (m, 1H), 0.99 (q, J=8.1, 7.4 Hz, 3H).

$^{13}$C NMR (100 MHz, $CD_3OD$): δ 174.9, 170.7, 168.0, 165.1, 163.9, 151.5, 131.1, 118.0, 99.5, 88.4, 84.2, 74.9, 69.6, 61.2, 50.7, 39.3, 33.8, 28.6, 25.3, 23.5, 18.8, 12.4, 10.3.

MS (ES−): m/z 478 $[M-H]^-$.

Scheme 20 provides an example of the synthesis of an additional compound of formula I.

Scheme 20

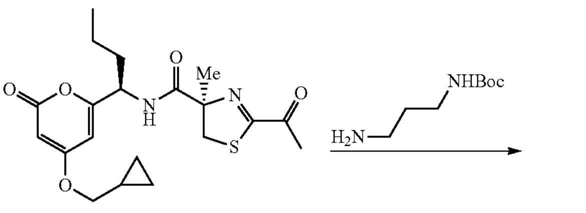

65

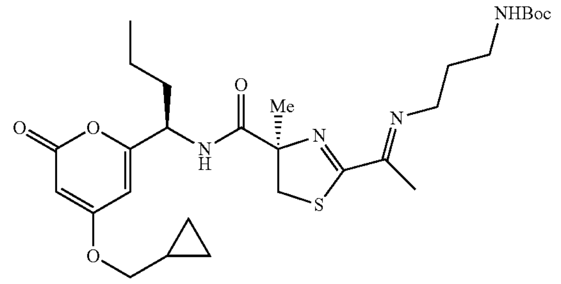

116

Compound 116

To a solution of 65 (42 mg, 0.103 mmol) in anhydrous toluene (1 mL), N-Boc-1,3-propanediamine (19 mg, 0.107 mmol), pTsOH (1 mg, 0.005 mmol) and molecular sieve were added and was refluxed for 2 h. Then, reaction mixture was filtered through Celite® and the filtrate was evaporated. The resulting residue was purified by combi flash in $SiO_2$ (from Hexane+1% $Et_3N$ to Hex:EtOAc:$Et_3N$ 1:1:0.01) to yield 116 (29 mg, 50% yield).

$^1$H NMR (500 MHz, $CDCl_3$): δ 7.10 (d, J=8.9 Hz, 1H), 5.92 (d, J=2.2 Hz, 1H), 5.34 (d, J=2.2 Hz, 1H), 5.22 (brs, 1H), 4.75-4.70 (m 1H), 3.76 (dd, J=7.1, 2.8 Hz, 2H), 3.53 (t, J=6.6 Hz, 2H), 3.50 (d, J=11.7 Hz, 1H), 3.30-3.26 (m, 2H), 3.16 (d, J=11.7 HZ, 1H), 2.20 (s, 3H), 1.914-1.84 (m, 3H), 1.80-1.73 (m, 1H), 1.52 (s, 3H), 1.42 (s, 9H), 1.45-1.33 (m, 1H), 1.24-1.19 (m, 1H), 0.98-0.94 (m, 4H), 0.68-0.64 (m, 2H), 0.34-0.31 (m, 2H).

$^{13}$C NMR (125 MHz, $CDCl_3$): δ 174.1, 173.7, 170.1, 170.0, 164.1, 162.3, 156.0, 100.5, 88.9, 88.8, 85.6, 73.8, 50.9, 30.6, 34.9, 30.1, 28.4, 28.3, 24.9, 19.0, 14.78, 13.6, 9.4, 3.4, 3.3.

MS (ES+): m/z 563 $[M+H]^+$.

$R_f$: 0.55 (Hex:EtOAc:$Et_3N$ 9:1:0.01).

Scheme 21 provides an example of the synthesis of an additional compound of formula I.

Scheme 21

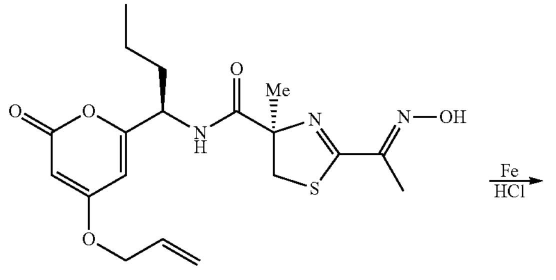

74

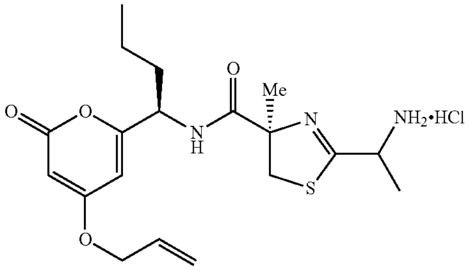

117

Compound 117

To a solution of 74 (50 mg, 0.123 mmol) in MeOH (1 mL) were added iron powder (14 mg, 0.24 mmol) and cone. HCl and the reaction mixture was stirred at 23° C. for 3 h. Then the reaction mixture was quenched with a saturated aqueous solution of $Na_2CO_3$ and was extracted with 10% MeOH in $CH_2Cl_2$. The organic layer was separated, dried over anhydrous $Na_2SO_4$, filtered, and concentrated under vacuum. The residue was purified by flash chromatography on silica gel ($CH_2Cl_2$:MeOH) to afford 117 (23 mg, 48% yield).

$^1H$ NMR (400 MHz, $CD_3OD$): δ 6.32-5.91 (m, 1H), 5.64-5.50 (m, 1H), 5.49-5.25 (m, 1H), 4.73 (dt, J=9.0, 6.3 Hz, 1H), 3.90-3.36 (m, 2H), 1.89-1.76 (m, 2H), 1.59-1.33 (m, 5H), 0.96 (ddd, J=8.6, 5.7, 1.8 Hz, 3H).

Example 12. Synthesis of Further Intermediates of Formula II

Scheme 22 provides further examples of the synthesis of intermediates of formula II Scheme 22

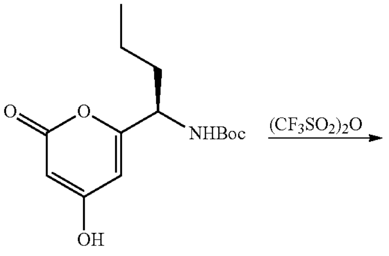

(R)-7

-continued

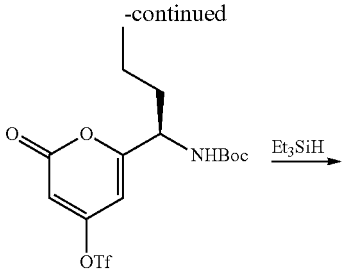

(R)-118

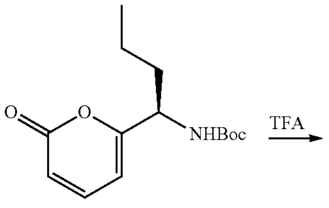

(R)-119

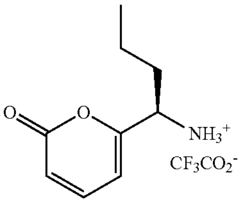

(R)-120

Compound (R)-118

(R)-118

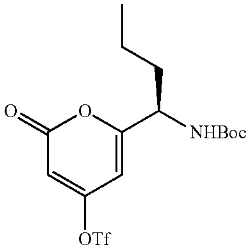

A solution of triflic anhydride (2.88 mL, 2.88 mmol) in $CH_2Cl_2$ (14 mL) was slowly added at −20° C. to a stirred solution (R)-7 (681 mg, 2.4 mmol) and triethylamine (0.4 mL, 2.88 mmol). Once the addition was complete, the cooling bath was removed and stirring continued for 2.5 h at 23° C. For work up, the mixture was washed with HCl (1 M) and the aqueous layer extracted with $CH_2Cl_2$ (×3). The combined organic phases were dried over anhydrous $MgSO_4$, filtered, concentrated under reduced pressure, and the residue was purified by flash chromatography (hexane/EtOAc) to give (R)-118 (730 mg, 73% yield) as a pale yellow oil.

$^1H$ NMR (400 MHz, $CDCl_3$): δ 6.19 (d, J=2.2 Hz, 1H), 6.15 (d, J=2.3 Hz, 1H), 4.83 (d, J=8.3 Hz, 1H), 4.46 (d, J=7.4 Hz, 1H), 1.83 (ddt, J=12.8, 9.6, 6.2 Hz, 1H), 1.73-1.61 (m, 1H), 1.44 (s, 9H), 1.42-1.24 (m, 2H), 0.96 (t, J=7.3 Hz, 3H).

$^{13}C$ NMR (100 MHz, $CDCl_3$): δ 167.7, 161.3, 161.0, 154.9, 118.5 (q, k=321.1 Hz), 103.4, 98.6, 80.9, 53.0, 35.1, 31.1, 28.4, 19.2, 13.7.

MS (ES+): m/z 438.0 $[M+Na]^+$.

$R_f$: 0.27 (Hex:EtOAc 9:1).

Compound (R)-119

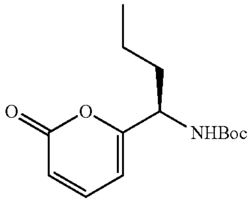

(R)-119

To a solution of (R)-118 (660 mg, 1.59 mmol) in degassed DMF (10.5 mL), was added successively $Pd(PPh_3)_4$ (0.367 mL, 0.32 mmol) and triethylsilane (0.5 mL, 3.18 mmol) and the resulting mixture was heated to 60° C. for 2 h. The reaction mixture was diluted with water and extracted with EtOAc. The combined organics were washed with water, (R)-119 dried over anhydrous $Na_2SO_4$, filtered, concentrated under reduced pressure and purified using flash column chromatography (hexane:EtOAc) to give (R)-119 (90 mg, 23% yield) as a colorless solid.

$^1$H NMR (400 MHz, $CDCl_3$): δ 7.32-7.26 (m, 1H), 6.20 (dd, J=9.4, 1.0 Hz, 1H), 6.13 (d, J=6.5 Hz, 1H), 4.90 (d, J=8.8 Hz, 1H), 4.41 (q, J=7.9 Hz, 1H), 1.79 (ddt, J=13.3, 9.5, 6.5 Hz, 1H), 1.66 (dq, J=13.9, 7.7 Hz, 1H), 1.42 (s, 9H), 1.38-1.24 (m, 1H), 0.93 (t, J=7.4 Hz, 3H).

$^{13}$C NMR (100 MHz, $CDCl_3$): δ 164.3, 162.3, 155.1, 143.7, 132.2, 129.7, 128.8, 128.6, 127.2, 123.5, 114.6, 102.7, 80.3, 52.8, 35.4, 29.8, 28.4, 19.2, 13.7.

MS (ES+): m/z 290.3 $[M+Na]^+$.

$R_f$: 0.13 (Hex:EtOAc 4:1).

Compound (R)-120

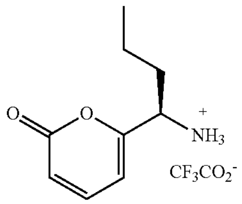

(R)-120

To a solution of (R)-119 (84 mg, 0.31 mmol) in $CH_2Cl_2$ (11.3 mL) was added TFA (3.46 mL) at 23° C. After being stirred for 2 hours, the mixture was concentrated to dryness to obtain crude (R)-120 which was used in the next without further purification.

$^1$H NMR (400 MHz, $CD_3OD$): δ 7.51 (ddd, J=9.6, 6.5, 1.0 Hz, 1H), 7.27-6.99 (m, 1H), 6.49 (dd, J=6.6, 1.0 Hz, 1H), 6.35 (dt, J=9.4, 1.0 Hz, 1H), 4.18 (dd, J=9.0, 6.1 Hz, 1H), 2.08-1.72 (m, 2H), 1.49-1.17 (m, 3H), 1.02-0.88 (m, 3H).

$^{13}$C NMR (100 MHz, $CD_3OD$): δ 162.6, 159.2, 145.1, 129.9, 129.2, 126.3, 117.2, 107.1, 53.5, 34.3, 19.6, 13.7.

Example 13. Synthesis of Intermediate 125

Scheme 23 provides an example of the synthesis of intermediate 125

Scheme 23

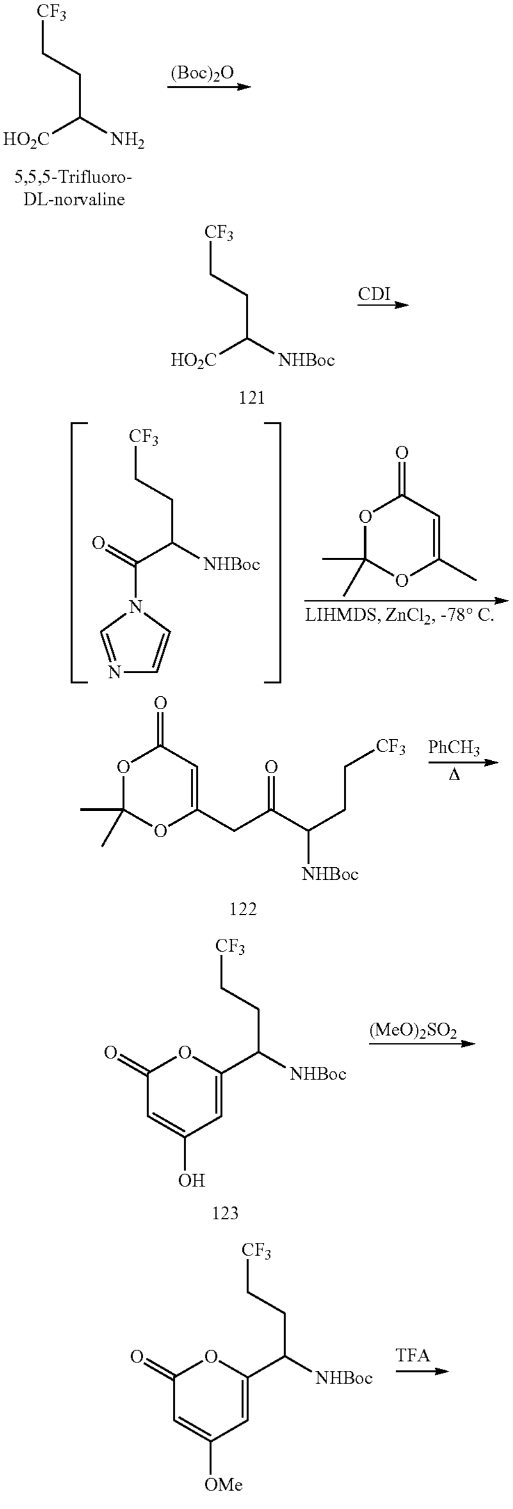

-continued

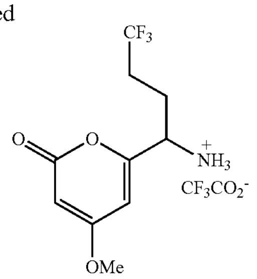

125

Compound 121

121

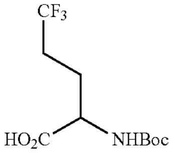

To a solution of 5,5,5-Trifluoro-DL-norvaline (206 mg, 1.2 mmol) and $Na_2CO_3$ (383 mg, 3.6 mmol) in $H_2O$ (2.4 mL) was dropwise added Boc anhydride (276 mg, 1.2 mmol) dissolved in 1,4-dioxane (2.4 mL) at 0° C. The reaction mixture was stirred at 23° C. for 5 hours and then, was diluted with EtOAc and washed with HCl 0.5 N (×2) and once with a saturated aqueous solution of NaCl (×1). The combined organic phases were dried over anhydrous $Na_2SO_4$, filtered, concentrated under reduced pressure to obtain crude 121 (326 mg, 100% yield) which was used in the next step without further purification.

$^1$H NMR (400 MHz, $CD_3OD$): δ 4.17 (dd, J=9.0, 4.9 Hz, 1H), 2.36-2.14 (m, 2H), 2.08 (ddt, J=16.2, 10.8, 5.4 Hz, 1H), 1.95-1.81 (m, 1H), 1.45 (s, 9H).

$^{13}$C NMR (100 MHz, $CD_3OD$): δ 174.9, 158.0, 129.8 (q, $J_{C-F}$=275 Hz, $CF_3$), 80.7, 53.7, 31.2 (q, $J_{C-F}$=29 Hz, $CH_2CF_3$), 28.7, 25.4.

Compound 122

122

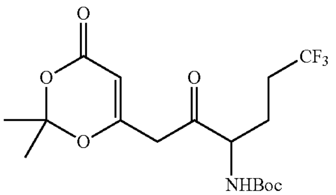

In a first flask, CDI (203 mg, 1.25 mmol) was added in portions to a solution of 121 (324 mg, 1.2 mmol) in 2-Me-THF (94.8 mL), with gas evolution. This mixture was stirred for 2 h at 23° C. In another flask, at −78° C., 2,2,6-trimethyl-4H-1,3-dioxin-4-one (0.53 mL, 3.6 mmol) in 2-Me-THF (3.6 mL) was added slowly to a solution of LiHMDS (3.6 mL, 1.0 M in THF, 3.6 mmol) in 2-Me-THF (4.8 mL).

After stirring at the same temperature for 1 h, $ZnCl_2$ (488 mg, 3.6 mmol) was added at −78° C. and the reaction mixture was stirred 30 minutes at −78° C. The first mixture was added via cannula. The reaction was stirring at −78° C. for 4 h and then quenched with saturated aqueous solution of $NH_4Cl$. Extraction with EtOAc, and dryness of the organic layers over $Na_2SO_4$ gave a crude which was purified by flash chromatography on silica gel (hexane/EtOAc 9/1 to 7/3) to afford 122 (256 mg, 54% yield).

$^1$H NMR (400 MHz, $CDCl_3$): δ 5.41 (d, J=8.2 Hz, 1H), 5.32 (s, 1H), 4.28 (t, J=7.2 Hz, 1H), 3.45 (d, J=3.3 Hz, 2H), 2.29-2.01 (m, 4H), 1.65 (s, 6H), 1.41 (s, 9H).

$^{13}$C NMR (100 MHz, $CDCl_3$): δ 201.7, 164.05, 160.6, 155.4, 126.6 (q, $J_{C-F}$=276 Hz, $CF_3$), 107.3, 96.9, 80.7, 58.3, 43.6, 29.9 (q, $J_{C-F}$=29 Hz, $CH_2CF_3$), 28.1, 24.9, 24.7, 23.1.

Compound 123

123

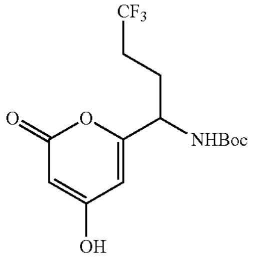

A solution of 122 (253 mg, 0.640 mmol) in toluene (6.4 mL) was refluxed for 30 min. After cooling to 23° C., it was evaporated to dryness and crude residue was purified in CombiFlash with hexane/EtOAc NHBoc 60:40 to 40:60 in 20 min. It was obtained 123 (121 mg, 56% yield) as a clear oil.

$^1$H NMR (400 MHz, $CDCl_3$): δ 6.05 (s, 1H), 5.51 (s, 1H), 5.30 (s, 1H), 5.22 (s, 1H), 2.30-1.75 (m, 4H), 1.36 (s, 9H).

Compound 124

124

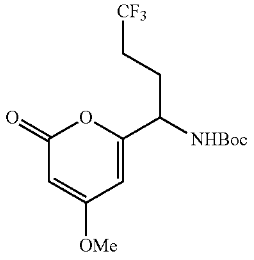

A mixture of 123 (119 mg, 0.353 mmol), acetone (3.5 mL), $K_2CO_3$ (244 mg, 1.76 mmol) and dimethyl sulfate (0.17 mL, 0.475 mmol) was stirred at 23° C. for 2 h. Filtration over Celite® and washing with EtOAc gave a crude which was purified In CombiFlash over silica gel with mixtures hexane/EtOAc 100:0 to 0:100 in 20 min to yield 124 (111 mg, 90% yield).

$^1$H NMR (400 MHz, $CDCl_3$): δ 5.96 (d, J=2.2 Hz, 1H), 5.44 (d, J=2.2 Hz, 1H), 5.12 (d, J=9.4 Hz, 1H), 4.45 (q, J=8.5 Hz, 1H), 3.79 (s, 3H), 2.24-1.79 (m, 4H), 1.41 (s, 9H).

$^{13}$C NMR (100 MHz, $CDCl_3$): δ 170.8, 163.8, 161.7, 154.8, 126.5 (q, $J_{C-F}$=276 Hz, $CF_3$), 100.3, 88.7, 80.6, 56.0, 51.5, 30.5 (q, $J_{C-F}$=29 Hz, $CH_2CF_3$), 28.2, 25.8.

Compound 125

125

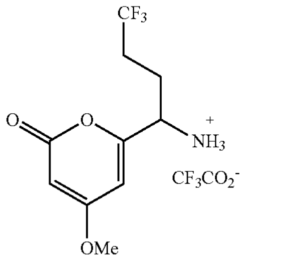

To a solution of 124 (109 mg, 0.310 mmol) in $CH_2Cl_2$ (4 mL) was added TFA (1.2 mL). After being stirred for 1 h at 23° C., the mixture was evaporated to dryness and then evaporated with toluene to eliminate TFA to obtain crude 125 (113 mg) which was used in the next step without further purification.

$^1$H NMR (400 MHz, $CD_3OD$): d 6.40 (d, J=2.2 Hz, 1H), 5.71 (d, J=2.2 Hz, 1H), 4.96 (s, 2H), 4.34-4.26 (m, 1H), 3.89 (s, 3H), 2.44-2.11 (m, 4H).

$^{13}$C NMR (100 MHz, $CD_3OD$): d 172.2, 165.1, 157.8, 127.9 (q, $J_{C-F}$=275 Hz, $\underline{C}F_3$), 105.3, 90.8, 57.3, 52.4, 30.5 (q, $J_{C-F}$=30 Hz, $\underline{C}H_2CF_3$), 24.8 (q, $J_{C-F}$=3.1 Hz, $\underline{C}H_2CH_2CF_3$).

Example 14. Synthesis of Additional Compounds of Formula I

Scheme 24 provides a further example of the synthesis of additional compounds of formula I.

Scheme 24

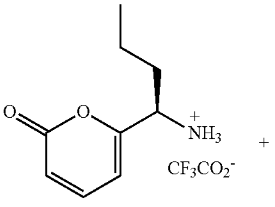

(R)-120

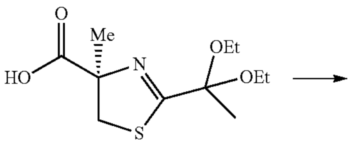

(R)-39

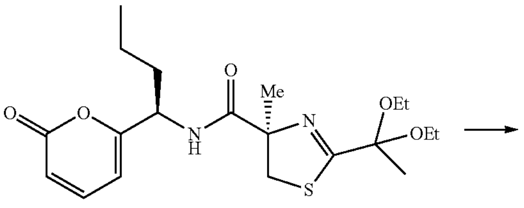

126

-continued

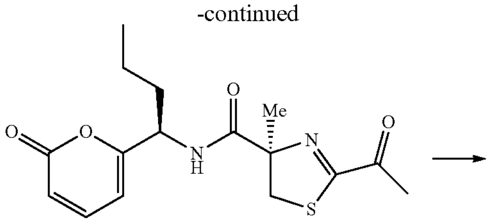

127

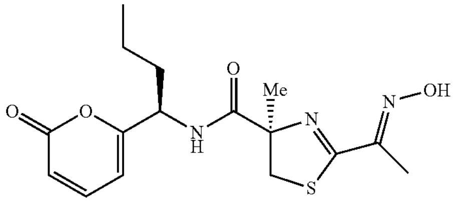

128

Compound 126

126

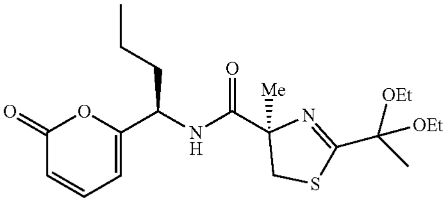

To a suspension of (R)-120 (90 mg, 0.0.32 mmol) and (R)-39 (84 mg, 0.32 mmol) were coevaporated 3 times with toluene to remove water, then the mixture was dissolved in $CH_2Cl_2$ (2.2 mL) were added HATU (122 mg, 0.32 mmol), HOAt (44 mg, 0.32 mmol) and DIPEA (0.22 mL, 0.1.28 mmol) and the mixture was stirred at 23° C. overnight. Dilution with $CH_2Cl_2$, washing of the organic layer with 0.5M HCl and a saturated aqueous solution of NaCl and, finally, dried over anhydrous $Na_2SO_4$, filtered, concentrated under reduced pressure. The crude obtained was purified by flash chromatography on silica gel (hexane/EtOAc 6/4) to afford 126 (100 mg, 77% yield).

$^1$H NMR (400 MHz, $CDCl_3$): δ 7.26-7.20 (m, 1H), 7.09 (d, J=8.8 Hz, 1H), 6.16 (dd, J=9.4, 1.0 Hz, 1H), 6.06 (dd, J=6.5, 1.1 Hz, 1H), 4.75 (q, J=7.9 Hz, 1H), 3.65-3.37 (m, 4H), 3.15 (dd, J=11.7, 1.0 Hz, 1H), 1.92-1.79 (m, 1H), 1.81-1.67 (m, 1H), 1.60 (d, J=0.9 Hz, 3H), 1.54 (d, J=0.9 Hz, 3H), 1.44-1.28 (m, 2H), 1.21 (qd, J=7.2, 1.0 Hz, 6H), 0.93 (td, J=7.3, 0.9 Hz, 3H).

$^{13}$C NMR (100 MHz, $CDCl_3$): δ 177.2, 174.4, 163.5, 161.5, 143.2, 114.7, 102.4, 100.2, 85.1, 57.8, 57.7, 51.0, 40.4, 34.8, 25.3, 23.7, 19.1, 15.2 (×2), 13.5.

MS (ES+): m/z 433.3 $[M+Na]^+$.

$R_f$: 0.33 (Hex:EtOAc 1:3).

Compound 127

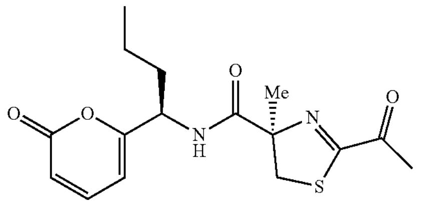

127

A mixture of 126 (100 mg, 0.24 mmol), pentane (7.3 mL) and formic acid (4.87 mL) was vigorously stirred for 2 h at 23° C. The volatiles were concentrated under vacuum with toluene to dryness to afford crude 127 (73 mg, 90% yield) which was used in the next step without purification.

$^{1}H$ NMR (400 MHz, $CDCl_3$): δ 7.40-7.17 (m, 1H), 7.04 (d, J=9.0 Hz, 1H), 6.30-6.07 (m, 2H), 4.79 (q, J=7.1, 6.0 Hz, 1H), 3.63 (dd, J=12.1, 3.2 Hz, 1H), 3.28 (dd, J=12.0, 3.1 Hz, 1H), 2.56 (d, J=3.8 Hz, 2H), 1.97-1.77 (m, 1H), 1.55 (d, J=3.6 Hz, 2H), 1.46-1.17 (m, 2H), 0.97 (q, J=5.7, 4.2 Hz, 3H).

$^{13}C$ NMR (100 MHz, $CDCl_3$): δ 193.2, 173.2, 170.4, 162.7, 161.7, 143.4, 114.9, 103.0, 86.1, 51.1, 40.1, 35.0, 26.3, 24.6, 19.1, 13.6.

Compound 128

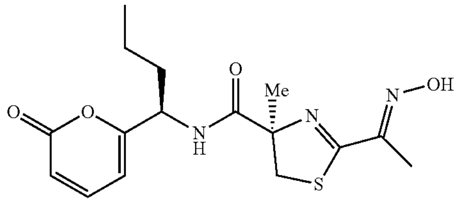

128

A mixture of 127 (70 mg, 0.21 mmol), ethanol (2.3 mL), water (2.3 mL), hydroxylamine hydrochloride (38 mg, 7.3 mmol) and NaOAc (77 mg, 0.94 mmol) was stirred for 24 h. Then ethanol was concentrated under vacuum, a saturated aqueous solution of NaCl was added, and the aqueous phase was extracted with EtOAc. The combined organic phases were dried over anhydrous $Na_2SO_4$, filtered, concentrated under reduced pressure. The crude was chromatographed over silica gel ($CH_2Cl_2$/EtOAc from 95/5 to 8/2) to afford 128 (29 mg, 40% yield).

$^{1}H$ NMR (400 MHz, $CD_3OD$): δ 7.84 (d, J=8.6 Hz, 1H), 7.46 (dd, J=9.4, 6.6 Hz, 1H), 6.31-6.16 (m, 2H), 4.77 (ddd, J=8.8, 7.3, 4.3 Hz, 1H), 3.52 (d, J=11.5 Hz, 1H), 3.18 (d, J=11.5 Hz, 1H), 2.18 (s, 3H), 1.94-1.75 (m, 2H), 1.52 (s, 3H), 1.49-1.34 (m, 1H), 0.99 (t, J=7.4 Hz, 3H).

MS (ES+): m/z 352.3 $[M+H]^+$, 374.1 $[M+Na]^+$.

Scheme 25 provides further examples of the synthesis of compounds of formula I:

Scheme 25

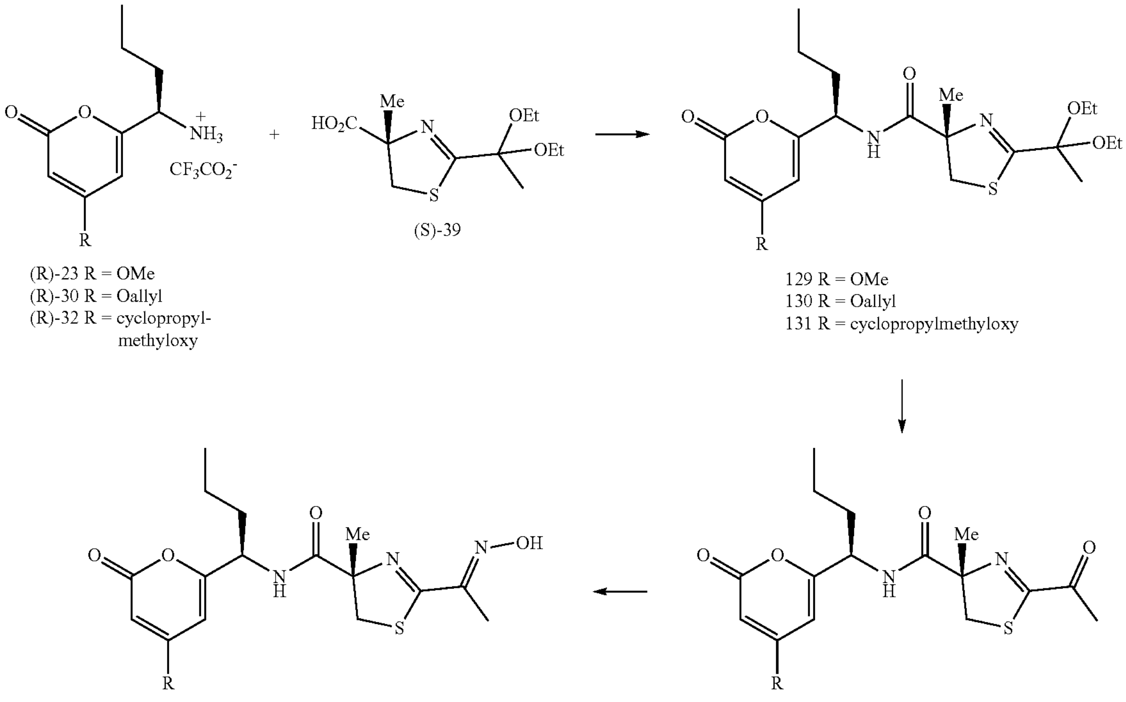

(R)-23 R = OMe
(R)-30 R = Oallyl
(R)-32 R = cyclopropyl-methyloxy (S)-39

129 R = OMe
130 R = Oallyl
131 R = cyclopropylmethyloxy

135 R = OMe
136 R = Oallyl
137 R = cyclopropylmethyloxy

132 R = OMe
133 R = Oallyl
134 R = cyclopropylmethyloxy

Compound 129

129

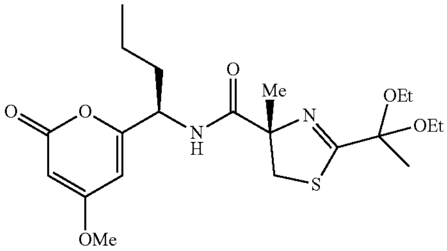

A mixture of (S)-39 (410 mg, 1.6 mmol) and (R)-23 (488 mg, 1.6 mmol) is coevaporated with toluene and then HATU (597 mg, 1.6 mmol) and HOAt (215 mg, 1.6 mmol) were added. Reaction flask is evacuated and filled with $N_2$ and $CH_2Cl_2$ (11 mL) and DIPEA (1.1 mL, 6.4 mmol) were introduced via syringe. The reaction mixture is stirred 16 h at 23° C. Then, it is diluted with $CH_2Cl_2$ before washing with HCl 0.5 N (×2) and with a saturated aqueous solution of NaCl. Combined organic layers were dried over anhydrous $Na_2SO_4$, filtered and evaporated to dryness. Crude residue is purified on a system for flash chromatography with a $SiO_2$ column eluting with mixtures of hexane/EtOAc from 100:0 to 50:50 in 15 min to obtain 129 (458 mg, 66% yield).

$^1$H NMR (400 MHz, $CDCl_3$): δ 7.02 (d, J=8.5 Hz, 1H), 5.93 (m, 1H), 5.41 (d, J=2.2 Hz, 1H), 4.65 (td, J=8.4, 6.2 Hz, 1H), 3.78 (d, J=0.7 Hz, 3H), 3.60 (m, 1H), 3.52 (m, 4H), 3.15 (dd, J=11.7, 0.7 Hz, 1H), 1.84 (ddd, J=13.4, 9.4, 6.7 Hz, 1H), 1.64 (dd, J=8.9, 5.5 Hz, 1H), 1.59 (d, J=0.7 Hz, 3H), 1.48 (s, 3H), 1.29 (m, 1H), 1.21 (m, 6H), 0.89 (t, J=7.3 Hz, 3H).

$^{13}$C NMR (100 MHz, $CDCl_3$): δ 177.7, 175.8, 172.2, 165.4, 164.2, 101.4, 101.0, 89.7, 86.4, 58.9, 58.8, 57.2, 52.1, 41.6, 35.8, 26.3, 24.9, 20.2, 16.5 (×2), 14.8.

MS (ES+): m/z 463.3 $[M+Na]^+$.

Compound 130

130

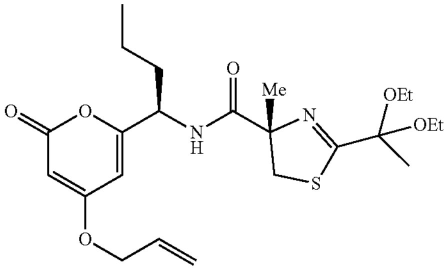

A mixture of (S)-39 (269 mg, 1.0 mmol) and (R)-30 (337 mg, 1.0 mmol) is coevaporated with toluene and then HATU (392 mg, 1.0 mmol) and HOAt (141 mg, 1.0 mmol) were added. Reaction flask is evacuated and filled with $N_2$ and $CH_2Cl_2$ (7.2 mL) and DIPEA (0.7 mL, 4.0 mmol) were introduced via syringe. The reaction mixture is stirred 16 h at 23° C. Then, it is diluted with $CH_2Cl_2$ before washing with HCl 0.5 N (×2) and with a saturated aqueous solution of NaCl. Combined organic layers were dried over anhydrous $Na_2SO_4$, filtered and evaporated to dryness. Crude residue is purified on a system for flash chromatography with a $SiO_2$ column eluting with mixtures of hexane/EtOAc from 100:0 to 50:50 in 15 min to obtain 130 (240 mg, 50% yield).

$^1$H NMR (400 MHz, $CDCl_3$): δ 6.94 (dd, J=8.6, 3.3 Hz, 1H), 5.80 (m, 2H), 5.22 (m, 3H), 4.51 (dq, J=11.6, 5.4, 4.0 Hz, 1H), 4.34 (d, J=4.4 Hz, 2H), 3.38 (m, 5H), 2.99 (dd, J=11.7, 3.6 Hz, 1H), 1.68 (dtd, J=11.2, 8.0, 7.4, 3.9 Hz, 1H), 1.50 (tq, J=8.4, 4.6, 3.9 Hz, 1H), 1.42 (d, J=3.4 Hz, 3H), 1.31 (d, J=3.4 Hz, 3H), 1.04 (ddt, J=11.0, 6.9, 3.0 Hz, 6H), 0.73 (td, J=7.5, 3.3 Hz, 3H).

$^{13}$C NMR (100 MHz, $CDCl_3$): δ 176.2, 174.3, 169.6, 163.8, 162.9, 130.6, 119.2, 100.0, 99.7, 89.1, 85.0, 69.4, 57.5, 57.4, 50.7, 40.2, 34.4, 24.9, 23.5, 18.8, 15.1, 13.4.

MS (ES+): m/z 489.2 $[M+Na]^+$.

Compound 131

131

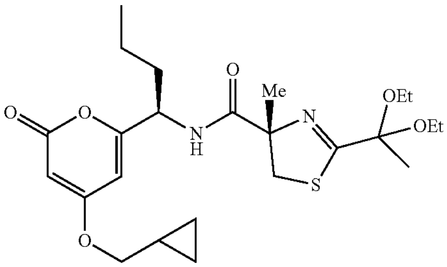

A mixture of (S)-39 (408 mg, 1.6 mmol) and (R)-32 (548 mg, 1.6 mmol) is coevaporated with toluene and then HATU (593 mg, 1.6 mmol) and HOAt (214 mg, 1.6 mmol) were added. Reaction flask is evacuated and filled with $N_2$ and $CH_2Cl_2$ (11 mL) and DIPEA (1.1 mL, 6.4 mmol) were introduced via syringe. The reaction mixture is stirred 16 h at 23° C. Then, it is diluted with $CH_2Cl_2$ before washing with HCl 0.5 N (×2) and with a saturated aqueous solution of NaCl. Combined organic layers were dried over anhydrous $Na_2SO_4$, filtered and evaporated to dryness. Crude residue is purified on a system for flash chromatography with a $SiO_2$ column eluting with mixtures of hexane/EtOAc from 100:0 to 50:50 in 15 min to obtain 131 (343 mg, 46% yield).

$^1$H NMR (400 MHz, $CDCl_3$): δ 6.92 (d, J=8.5 Hz, 1H), 5.81 (dt, J=2.2, 0.7 Hz, 1H), 5.21 (dd, J=2.2, 0.6 Hz, 1H), 4.51 (td, J=8.4, 6.1 Hz, 1H), 3.93 (qd, J=7.2, 0.6 Hz, 1H), 3.62 (m, 2H), 3.38 (m, 5H), 3.00 (dd, J=11.7, 0.7 Hz, 1H), 1.68 (m, 1H), 1.49 (m, 1H), 1.42 (d, J=0.6 Hz, 3H), 1.32 (s, 3H), 1.14 (m, 2H), 1.05 (m, 7H), 0.74 (t, J=7.3 Hz, 3H), 0.49 (m, 2H), 0.18 (m, 2H).

$^{13}$C NMR (100 MHz, $CDCl_3$): δ 176.1, 174.3, 170.0, 163.9, 162.7, 100.0, 99.8, 88.5, 85.0, 73.6, 57.5, 57.3, 50.7, 40.2, 34.4, 24.9, 23.5, 18.8, 15.1, 13.4, 9.3, 3.2 (×2).

MS (ES+): m/z 503.3 $[M+Na]^+$. PGP-231 ci

Compound 132

132

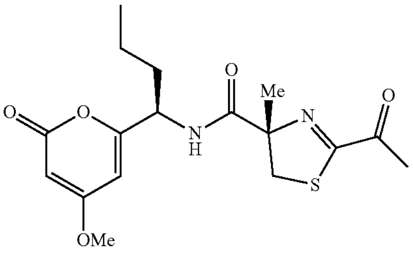

A mixture of 129 (458 mg, 1.07 mmol), pentane (24 mL) and formic acid (16 mL) was vigorously stirred for 2 h at 23° C. The volatiles were concentrated under vacuum with toluene to dryness to afford crude 132 (398 mg, 100% yield) which was used in the next step without purification.

$^1$H NMR (400 MHz, $CDCl_3$): δ 6.93 (d, J=8.5 Hz, 1H), 5.99 (dd, J=2.4, 1.1 Hz, 1H), 5.45 (dd, J=2.3, 1.1 Hz, 1H), 4.68 (q, J=7.8 Hz, 1H), 3.81 (d, J=1.2 Hz, 3H), 3.67 (dd, J=12.0, 1.3 Hz, 1H), 3.28 (dd, J=11.9, 1.2 Hz, 1H), 2.56 (d, J=1.2 Hz, 2H), 1.85 (m, 1H), 1.72 (m, 1H), 1.50 (d, J=1.3 Hz, 3H), 1.30 (m, 2H), 0.92 (td, J=7.3, 1.2 Hz, 3H).

$^{13}$C NMR (100 MHz, $CDCl_3$): δ 194.4, 174.5, 172.2, 171.5, 165.5, 163.3, 101.8, 89.9, 87.4, 57.3, 52.4, 41.5, 35.8, 27.6, 25.7, 20.3, 14.8.

MS (ES+): m/z 367.3 $[M+H]^+$.

Compound 133

133

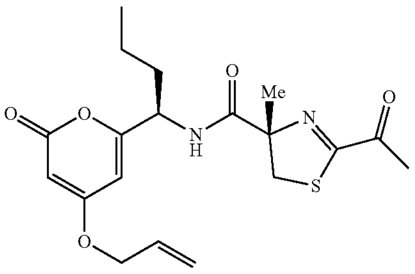

A mixture of 130 (240 mg, 0.6 mmol), pentane (12.5 mL) and formic acid (8.4 mL) was vigorously stirred for 2 h at 23° C. The volatiles were concentrated under vacuum with toluene to dryness to obtain crude 133 (252 mg, 100% yield) which was used in the next step without purification.

$^1$H NMR (400 MHz, $CDCl_3$): δ 6.94 (d, J=8.5 Hz, 1H), 5.99 (m, 3H), 5.41 (m, 4H), 4.69 (q, J=7.8 Hz, 1H), 4.51 (dq, J=5.8, 1.4 Hz, 2H), 3.67 (dd, J=12.0, 1.1 Hz, 1H), 3.28 (dd, J=11.9, 1.2 Hz, 1H), 2.56 (d, J=1.2 Hz, 3H), 1.86 (m, 1H), 1.72 (m, 1H), 1.50 (d, J=1.2 Hz, 3H), 1.30 (tt, J=14.3, 6.8 Hz, 3H), 0.92 (m, 3H).

$^{13}$C NMR (100 MHz, $CDCl_3$): δ 194.4, 174.5, 171.0, 166.2, 163.4, 159.6, 131.8, 120.9, 102.0, 90.7, 87.4, 70.9, 52.4, 41.5, 35.8, 27.6, 25.7, 20.3, 14.8.

MS (ES+): m/z 393.2 $[M+H]^+$.

Compound 134

134

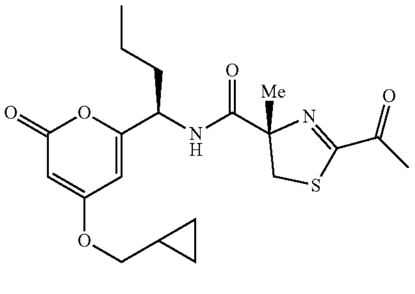

A mixture of 131 (343 mg, 1.07 mmol), pentane (18 mL) and formic acid (12 mL) was vigorously stirred for 2 h at 23° C. The volatiles were concentrated under vacuum with toluene to dryness to afford crude 134 (360 mg, 100% yield) which was used in the next step without purification.

$^1$H NMR (400 MHz, $CDCl_3$): δ 6.93 (d, J=8.6 Hz, 1H), 6.01 (d, J=2.2 Hz, 1H), 5.39 (d, J=2.3 Hz, 1H), 4.69 (q, J=7.8 Hz, 1H), 3.79 (dd, J=75, 2.7 Hz, 2H), 3.68 (d, J=11.9 Hz, 1H), 3.28 (dd, J=11.9, 0.6 Hz, 1H), 2.56 (d, J=0.6 Hz, 3H), 1.86 (ddt, J=14.0, 9.1, 7.1 Hz, 1H), 1.71 (m, 1H), 1.51 (s, 3H), 1.29 (m, 2H), 0.93 (t, J=7.4 Hz, 4H), 0.68 (m, 3H), 0.35 (dt, J=6.2, 4.9 Hz, 3H).

$^{13}$C NMR (100 MHz, $CDCl_3$): δ 194.4, 174.5, 173.6, 171.4, 165.5, 163.2, 102.1, 90.1, 87.4, 75.1, 52.4, 41.5, 35.8, 27.6, 25.7, 20.3, 14.8, 10.6, 4.7, 4.6.

MS (ES+): m/z 407.1 $[M+H]^+$.

Compound 135

135

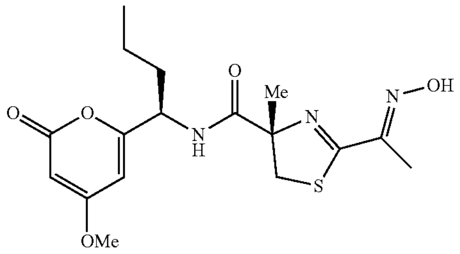

A mixture of 132 (392 mg, 1.07 mmol), ethanol (12 mL), water (12 mL), hydroxylamine hydrochloride (550 mg, 7.9 mmol) and NaOAc (395 mg, 4.8 mmol) was stirred overnight at 23° C. Then ethanol was concentrated under vacuum, a saturated aqueous solution of NaCl was added, and the aqueous phase was extracted with EtOAc. The combined organic phases were dried over anhydrous $Na_2SO_4$, filtered, concentrated under reduced pressure. The crude was chromatographed over silica gel (hexane/EtOAc from 100:0 to 50:50) to afford 135 (231 mg, 57% yield).

$^1$H NMR (400 MHz, $CDCl_3$): δ 11.10 (s, 1H), 7.06 (d, J=8.5 Hz, 1H), 5.92 (t, J=1.9 Hz, 1H), 5.40 (t, J=2.0 Hz, 1H), 4.61 (qd, J=7.4, 6.7, 1.5 Hz, 1H), 3.73 (d, J=1.7 Hz, 3H), 3.45 (dd, J=11.6, 1.8 Hz, 1H), 3.12 (dd, J=11.6, 1.6 Hz, 1H), 2.10 (m, 3H), 1.76 (m, 1H), 1.62 (dddt, J=13.6, 9.6, 5.7, 2.0 Hz, 1H), 1.40 (d, J=1.6 Hz, 3H), 1.19 (m, 2H), 0.81 (td, J=7.3, 1.6 Hz, 3H).

$^{13}$C NMR (100 MHz, $CDCl_3$): δ 174.4, 170.9, 168.4, 164.4, 162.3, 151.8, 100.0, 88.3, 84.0, 55.8, 50.7, 39.6, 34.2, 24.3, 18.7, 13.3, 10.8.

MS (ES+): m/z 382.3 $[M+H]^+$.

Compound 136

136

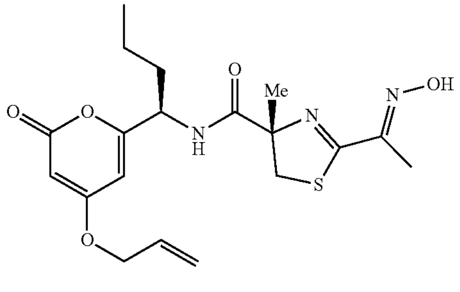

A mixture of 133 (239 mg, 0.61 mmol), ethanol (6.7 mL), water (6.7 mL), hydroxylamine hydrochloride (314 mg, 4.5 mmol) and NaOAc (225 mg, 2.7 mmol) was stirred overnight at 23° C. Then ethanol was concentrated under vacuum, a saturated aqueous solution of NaCl was added, and the aqueous phase was extracted with EtOAc. The combined organic phases were dried over anhydrous $Na_2SO_4$, filtered, concentrated under reduced pressure. The crude was chromatographed over silica gel (hexane/EtOAc from 100:0 to 50:50) to afford 136 (131 mg, 53% yield).

$^1H$ NMR (400 MHz, $CDCl_3$): δ 10.14 (s, 1H), 7.12 (m, 1H), 6.01 (t, J=1.7 Hz, 1H), 5.94 (dddd, J=16.0, 9.7, 6.3, 5.1 Hz, 1H), 5.46 (t, J=1.7 Hz, 1H), 5.39 (dq, J=17.2, 1.5 Hz, 1H), 5.33 (dp, J=10.5, 1.1 Hz, 1H), 4.69 (q, J=7.7 Hz, 1H), 4.49 (dt, J=5.6, 1.5 Hz, 2H), 3.54 (dt, J=11.6, 1.0 Hz, 1H), 3.24 (dd, J=11.6, 1.3 Hz, 1H), 2.19 (m, 3H), 1.83 (dtd, J=9.8, 7.7, 6.1 Hz, 1H), 1.70 (m, 1H), 1.47 (m, 3H), 1.25 (m, 3H), 0.88 (td, J=7.4, 1.2 Hz, 3H).

$^{13}C$ NMR (100 MHz, $CDCl_3$): δ 174.5, 169.9, 168.1, 164.6, 162.3, 152.6, 130.5, 119.6, 100.6, 89.4, 84.3, 69.6, 51.0, 40.0, 34.5, 24.4, 18.9, 13.5, 11.2.

MS (ES+): m/z 408.2 $[M+H]^+$.

Compound 137

137

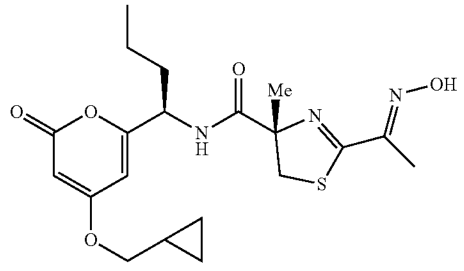

A mixture of 134 (341 mg, 0.84 mmol), ethanol (9.2 mL), water (9.2 mL), hydroxylamine hydrochloride (432 mg, 6.2 mmol) and NaOAc (310 mg, 3.8 mmol) was stirred overnight at 23° C. Then ethanol was concentrated under vacuum, a saturated aqueous solution of NaCl was added, and the aqueous phase was extracted with EtOAc. The combined organic phases were dried over anhydrous $Na_2SO_4$, filtered, concentrated under reduced pressure. The crude was chromatographed over silica gel (hexane/EtOAc from 100:0 to 50:50) to afford 137 (178 mg, 50% yield).

$^1H$ NMR (400 MHz, $CDCl_3$): δ 10.45 (s, 1H), 7.12 (d, J=8.6 Hz, 1H), 6.00 (d, J=2.1 Hz, 1H), 5.40 (dd, J=2.2, 0.7 Hz, 1H), 4.67 (q, J=7.7 Hz, 1H), 3.76 (m, 2H), 3.51 (d, J=11.6 Hz, 1H), 3.22 (dd, J=11.5, 0.7 Hz, 1H), 2.17 (d, J=0.7 Hz, 3H), 1.82 (ddt, J=13.7, 9.2, 6.8 Hz, 1H), 1.68 (m, 1H), 1.45 (s, 3H), 1.25 (m, 2H), 0.86 (m, 3H), 0.62 (m, 2H), 0.30 (m, 2H).

$^{13}C$ NMR (100 MHz, $CDCl_3$): δ 174.5, 170.3, 168.2, 164.8, 162.2, 152.4, 100.6, 88.8, 84.2, 73.8, 50.9, 39.9, 34.4, 24.3, 18.9, 13.4, 11.1, 9.3, 3.3 (x2).

MS (ES+): m/z 422.1 $[M+H]^+$.

Scheme 26 provides further examples of the synthesis of compounds of formula I:

Scheme 26

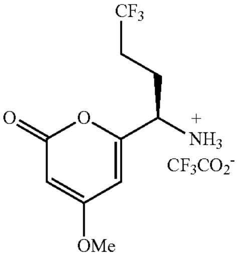

125

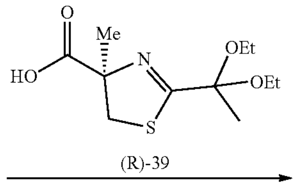

(R)-39

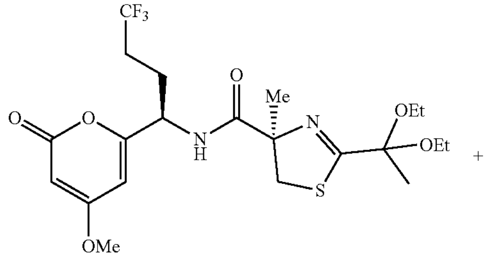

138

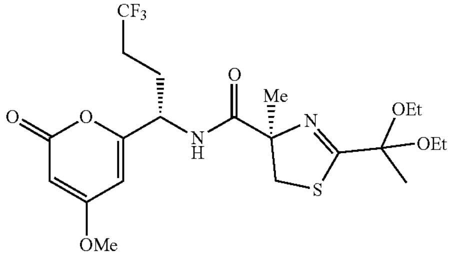

epi-138

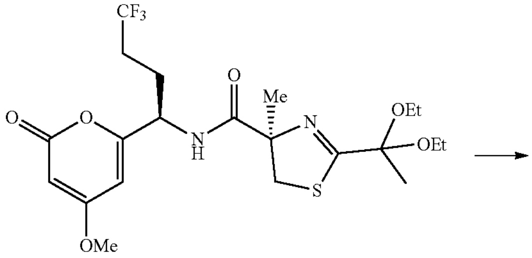

138

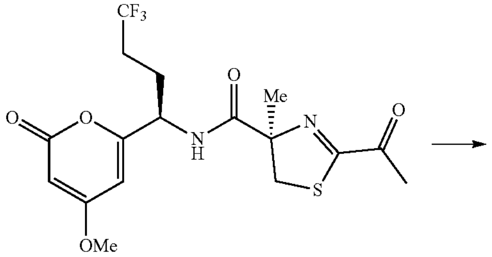

139

-continued

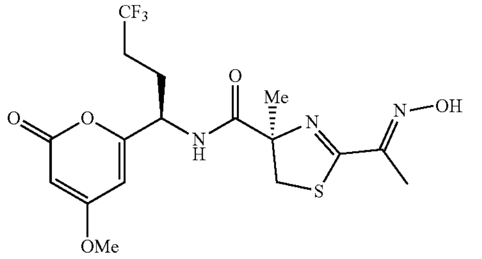

+

140

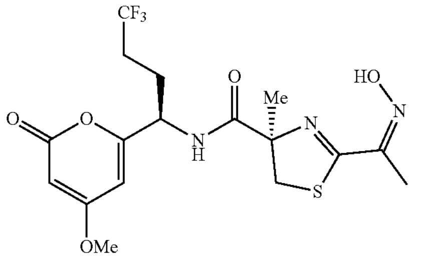

140a

Compound 138

138

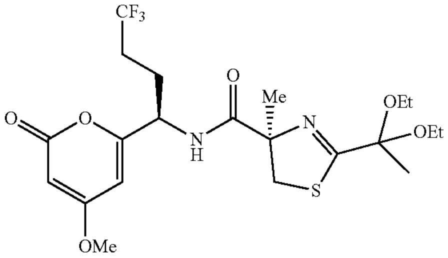

A mixture of 125 (113 mg, 0.310 mmol) and (R)-39 (85 mg) is coevaporated with toluene and then HATU (128 mg) and HOAt (47 mg) were added. Reaction flask is evacuated and filled with $N_2$ and $CH_2Cl_2$ (2.2 mL) and DIPEA (0.24 mL) were introduced via syringe. The reaction mixture is stirred 16 h at 23° C. Then, it is diluted with $CH_2Cl_2$ before washing with HCl 0.5 N (×2) and with a saturated aqueous solution of NaCl. Combined organic layers were dried over anhydrous $Na_2SO_4$, filtered and evaporated to dryness. Crude residue is purified on a system for flash chromatography with a $SiO_2$ column eluting with mixtures of hexane/EtOAc from 80:20 to 50:50 in 30 min to obtain 138 (47 mg, 31% yield). Compound epi-138 was also isolated with a similar yield.

Compound 138

$^1$H NMR (400 MHz, $CDCl_3$): δ 7.18 (d, J=9.3 Hz, 1H), 5.89 (d, J=2.2 Hz, 1H), 5.42 (d, J=2.2 Hz, 1H), 4.82 (td, J=9.0, 5.2 Hz, 1H), 3.79 (s, 3H), 3.65-3.42 (m, 5H), 3.17 (d, J=11.7 Hz, 1H), 2.24-2.07 (m, 3H), 2.09-1.95 (m, 1H), 1.60 (s, 3H), 1.54 (s, 3H), 1.22 (t, J=7.1 Hz, 3H), 1.21 (t, J=7.0 Hz, 3H).

$^{13}$C NMR (100 MHz, $CDCl_3$): δ 177.2, 174.7, 170.5, 163.2, 161.0, 126.4 (q, $J_{C-F}$=276 Hz, $\underline{C}F_3$), 100.3, 100.2, 88.8, 85.1, 57.8, 57.6, 56.0, 49.8, 40.2, 30.5 (q, $J_{C-F}$=30 Hz, $\underline{C}H_2CF_3$), 25.5, 25.3, 23.7, 15.12.

Compound 139

139

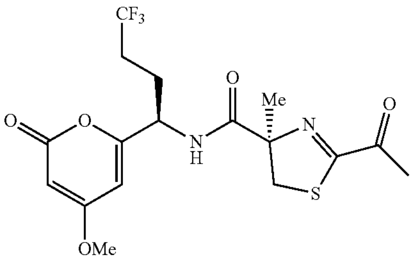

A mixture of 138 (47 mg, 0.095 mmol), pentane (2.4 mL) and formic acid (1.6 mL) was vigorously stirred for 2 h at 23° C. The volatiles were concentrated under vacuum with toluene to dryness to afford 139. The crude was used in the next step without purification.

$^1$H NMR (400 MHz, $CDCl_3$): δ 7.17 (d, J=9.1 Hz, 1H), 5.96 (d, J=2.2 Hz, 1H), 5.47 (d, J=2.2 Hz, 1H), 4.83 (q, J=7.4, 6.7 Hz, 1H), 3.81 (s, 3H), 3.62 (d, J=12.0 Hz, 1H), 3.28 (d, J=12.0 Hz, 1H), 2.55 (s, 3H), 2.23-2.04 (m, 4H), 1.56 (s, 3H).

$^{13}$C NMR (100 MHz, $CDCl_3$): δ 193.1, 173.6, 170.6, 163.5, 162.6, 160.0, 126.4 (q, $J_{C-F}$=276 Hz, $\underline{C}F_3$), 101.2, 89.1, 86.0, 56.2, 50.0, 40.0, 30.5 (q, $J_{C-F}$=30 Hz, $\underline{C}H_2CF_3$), 26.3, 25.8, 24.6.

Compounds 140 and 140a

140

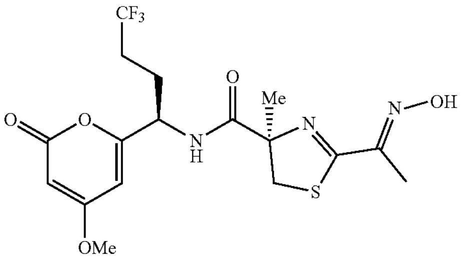

140a

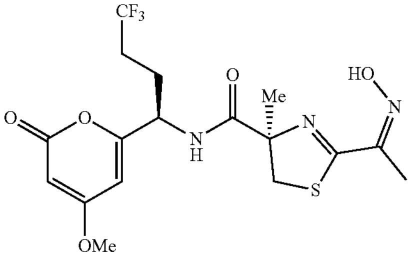

A mixture of 139 (40 mg, 0.095 mmol), ethanol (1.0 mL), water (1.0 mL), hydroxylamine hydrochloride (49 mg, 0.7 mmol) and NaOAc (35 mg, 0.43 mmol) was stirred for 16 h at 23° C. Then ethanol was concentrated under vacuum, a saturated aqueous solution of NaCl was added, and the aqueous phase was extracted with EtOAc. The combined organic phases were dried over anhydrous $Na_2SO_4$, filtered, concentrated under reduced pressure. The crude was chromatographed on a system for flash chromatography with a $SiO_2$ column eluting with mixtures of hexane/EtOAc from 100:0 to 50:50 in 50 min. This purification allowed to separate both stereoisomers, 140 (21.8 mg, 53% yield for 2 steps) and 140a (4.8 mg, 12% yield).

140

$^1$H NMR (400 MHz, $CDCl_3$): δ 8.91 (s, 1H), 7.25 (d, J=9.3 Hz, 1H), 5.95 (d, J=2.2 Hz, 1H), 5.46 (d, J=2.3 Hz, 1H), 4.82 (q, J=8.1 Hz, 1H), 3.80 (s, 3H), 3.53 (d, J=11.7 Hz, 1H), 3.23 (d, J=11.6 Hz, 1H), 2.22 (s, 3H), 2.22-2.02 (m, 4H), 1.53 (s, 3H).

$^{13}$C NMR (100 MHz, $CDCl_3$): δ 174.5, 170.6, 168.2, 163.7, 160.4, 153.2, 126.4 (q, $J_{C-F}$=276 HZ, $\underline{C}F_3$), 101.0, 89.1, 84.3, 56.1, 50.0, 39.8, 30.5 (q, $J_{C-F}$=30 Hz, $\underline{C}H_2CF_3$), 25.7, 24.8, 11.2.

140a $^1$H NMR (400 MHz, $CDCl_3$): δ 9.12 (s, 1H), 7.17 (d, J=8.8 Hz, 1H), 6.03 (d, J=2.2 Hz, 1H), 5.50 (d, J=2.2 Hz, 1H), 4.80 (q, J=8.1 Hz, 1H), 3.83 (s, 3H), 3.56 (d, J=11.6 Hz, 1H), 3.25 (d, J=11.5 Hz, 1H), 2.22 (s, 3H), 2.20-1.96 (m, 4H), 1.48 (s, 3H).

$^{13}$C NMR (100 MHz, $CDCl_3$): δ 174.4, 170.7, 168.3, 163.9, 160.5, 153.1, 126.4 (q, $J_{(C-F)}$=277 Hz, $\underline{C}F_3$), 101.1, 93.3, 89.0, 84.3, 56.2, 50.1, 40.1, 30.5 (q, $J_{(C-F)}$=30 Hz, $\underline{C}H_2CF_3$), 25.4, 24.4, 11.2.

Example 15. Synthesis of Additional Intermediates of Formula II

Scheme 27 provides further examples of the synthesis of intermediates of formula II Scheme 27

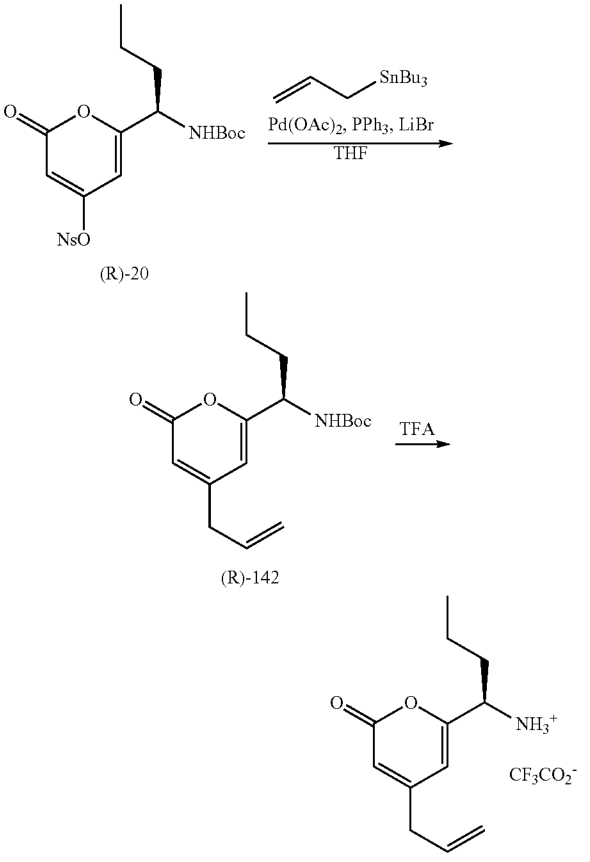

(R)-20

(R)-142

(R)-143

Synthesis of (R)-142

(R)-142

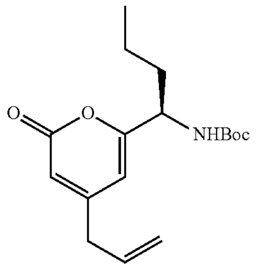

To a solution of (R)-20 (30 mg, 0.64 mmol) in THF (11 mL) was added palladium(II) acetate (7 mg, 0.032 mmol), triphenylphosphine (17 mg, 0.064 mmol) and lithium bromide (167 mg, 1.92 mmol) at 23° C. The reaction mixture was turned to a yellow-to-orange, stirred for 10 min at 23° C. and allyltributylstannane (0.34 mL, 1.088 mmol) was added at 23° C. The reaction mixture was refluxed for 2 h and concentrated under vacuum. An aqueous solution of KF 2M was added to the crude and the mixture was stirred for 30 min at 23° C. Filtration over Celite® and washing with $Et_2O$ gave a crude which was purified in an automatic system for flash chromatography ($SiO_2$) to yield (R)-142 (46.8 mg, 24% yield).

$^1$H NMR (400 MHz, $CDCl_3$): δ 6.48 (dq, J=15.7, 6.7 Hz, 1H), 6.24 (s, 1H), 6.18 (dd, J=16.3, 1.8 Hz, 1H), 5.94 (d, J=1.5 Hz, 1H), 4.92 (m, 1H), 4.46-4.31 (m, 1H), 1.93 (dd, J=6.8, 1.6 Hz, 2H), 1.86-1.63 (m, 2H), 1.39-1.23 (m, 2H), 0.98-0.86 (m, 3H).

MS (ES+): m/z 330.3 $[M+Na]^+$.

Synthesis of (R)-143

(R)-143

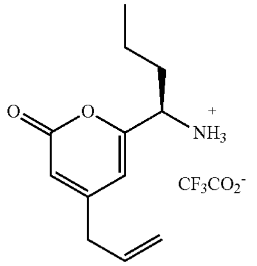

To a solution of (R)-142 (46.8 mg, 0.15 mmol) in $CH_2Cl_2$ (1.7 mL) was added TFA (0.5 mL). After being stirred for 2 h, the reaction mixture was evaporated to dryness to obtain crude (R)-143 (48.9 mg, 100% yield) which was used in the next step without further purification.

$^1$H NMR (400 MHz, $CDCl_3$): δ 8.24 (dd, J=12.9, 8.5 Hz, 2H), 5.81 (td, J=17.3, 7.3 Hz, 1H), 5.38 (d, J=10.1 Hz, 1H), 5.16 (d, J=17.1 Hz, 1H), 3o(d, J=7.3 Hz, 2H), 2.07-1.83 (m, 2H), 1.42-1.22 (m, 2H), 1.04-0.78 (m, 3H).

MS (ES+): m/z 230.3 $[M+Na]^+$, 208.3 $[M+H]^+$.

Example 16. Synthesis of Additional Compounds of Formula I

Scheme 28 provides further examples of the synthesis of compounds of formula I

Scheme 28

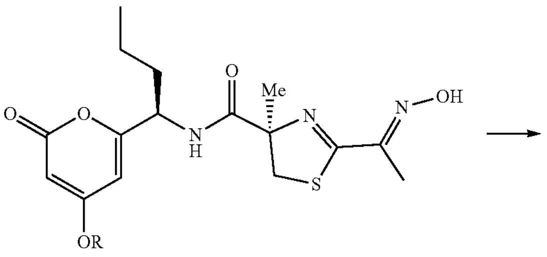

1 R = Me
74 R = allyl
75 R = propargyl
76 R = cyclopropylmethyl

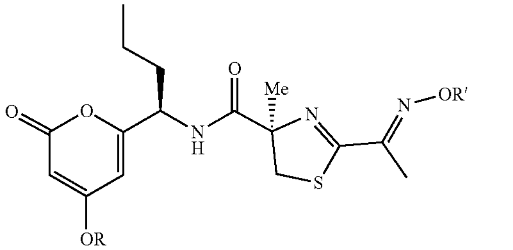

144 R = allyl, R′ = 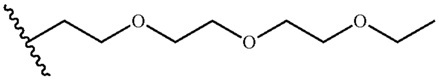

145 R = cyclopropylmethyl, R′ = 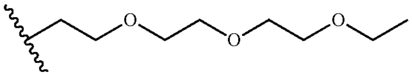

146 R = Me, R′ = 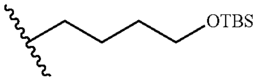

147 R = Me, R′ = 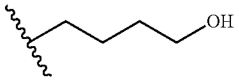

148 R = cyclopropylmethyl, R′ = 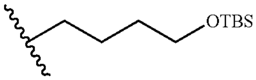

149 R = cyclopropylmethyl, R′ = 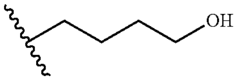

150 R = Me, R′ = 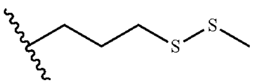

151 R =Me, R′ = 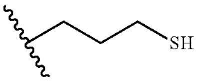

152 R = allyl, R′ = 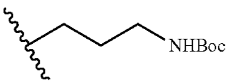

153 R = allyl, R′ = 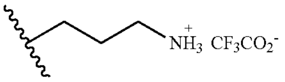

154 R = allyl, R′ = 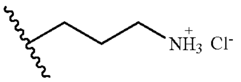

-continued

155 R = propargyl, R′ = 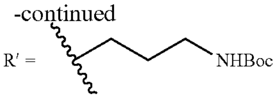

156 R = propargyl, R′ = 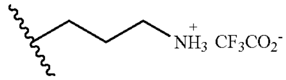

157 R = cyclopropylmethyl, R′ = 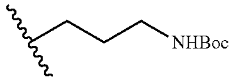

158 R = cyclopropylmethyl, R′ = 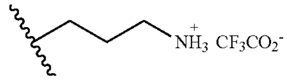

159 R = cyclopropylmethyl, R′ = 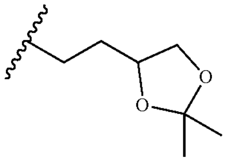

Synthesis of 144

144

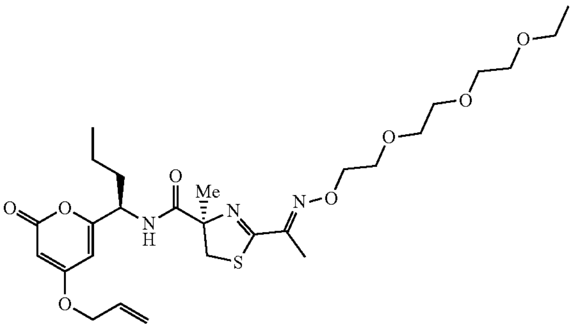

To a solution of 74 (75 mg, 0.184 mmol) in acetone (2 mL), $K_2CO_3$ (127 mg, 0.920 mmol) and 2-[2-(2-ethoxyethoxy)ethoxy]ethyl iodide (233 mg, 0.920 mmol) were added at 23° C. The reaction mixture was stirred at 23° C. overnight. The reaction mixture was filtered, washing with EtOAc and evaporated. The resulting residue was purified by combi flash in $SiO_2$ (from $CH_2Cl_2$ to $CH_2Cl_2$:EtOAc 4:4) to yield 144 (60 mg, 58% yield).

$^1H$ NMR (400 MHz, $CD_3OD$): δ 7.86 (d, J=8.5 Hz, 1H), 6.06 (d, J=2.1 Hz, 1H), 6.04-5.95 (m, 1H), 5.54 (d, J=2.2 Hz, 1H), 5.48-5.23 (m, 2H), 4.75 (dt, J=9.2, 5.8 Hz, 1H), 4.59 (d, J=5.4 Hz, 2H), 4.33 (t, J=4.7 Hz, 2H), 3.77 (t, J=4.7 Hz, 2H), 3.67-3.58 (m, 7H), 3.59-3.50 (m, 4H), 3.20 (d, J=11.5 Hz, 1H), 2.21 (s, 3H), 1.93-1.76 (m, 2H), 1.53 (s, 3H), 1.50-1.31 (m, 2H), 1.17 (t, J=7.0 Hz, 3H), 0.98 (t, J=7.3 Hz, 3H).

$^{13}C$ NMR (100 MHz, $CD_3OD$): δ 174.9, 170.7, 167.8, 165.1, 164.0, 152.1, 131.2, 118.0, 99.5, 88.4, 84.3, 74.3, 70.3, 70.2, 70.1, 69.6, 69.5, 69.0, 66.1, 50.8, 39.3, 33.8, 23.5, 18.8, 14.1, 12.5, 10.5.

MS (ES+): m/z 568.2 $[M+H]^+$, 590.2 $[M+Na]^+$.

Synthesis of 145

145

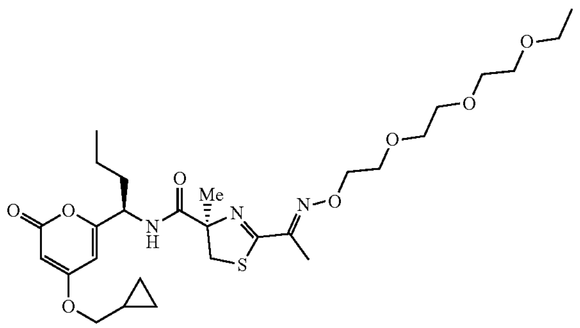

To a solution of 76 (74 mg, 0.176 mmol) in acetone (2 mL), $K_2CO_3$ (121 mg, 0.879 mmol) and 2-[2-(2-ethoxy-ethoxy)ethoxy]ethyl iodide (223 mg, 0.879 mmol) were added at 23° C. The reaction mixture was stirred at 23° C. overnight. The reaction mixture was filtered, washing with EtOAc and evaporated. The resulting residue was purified by combi flash in $SiO_2$ (from $CH_2Cl_2$ to $CH_2Cl_2$:EtOAc 6:4) to yield (79 mg, 79% yield).

$^1H$ NMR (400 MHz, $CD_3OD$): δ 7.86 (d, J=8.6 Hz, 1H), 6.05 (d, J=2.2 Hz, 1H), 5.48 (d, J=2.2 Hz, 1H), 4.75 (td, J=8.8, 5.8 Hz, 1H), 4.33 (t, J=4.7 Hz, 2H), 3.86 (d, J=7.2 Hz, 2H), 3.77 (t, J=4.7 Hz, 2H), 3.66-3.59 (m, 7H), 3.59-3.44 (m, 4H), 3.20 (d, J=11.6 Hz, 1H), 2.22 (s, 3H), 1.90-0.76 (m, 2H), 1.52 (s, 3H), 1.49-1.34 (m, 3H), 1.25-1.21 (m, 1H), 1.17 (t, J=7.0 Hz, 3H), 0.98 (t, J=7.4 Hz, 3H), 0.67-0.57 (m, 2H), 0.37-0.33 (m, 2H).

$^{13}C$ NMR (100 MHz, $CD_3OD$): δ 176.3, 176.2, 172.5, 169.1, 166.6, 165.2 (×2), 153.5, 101.0, 89.3, 85.7 (×2), 75.7, 75.3, 71.6 (×2), 71.5, 70.9, 70.4, 67.5, 52.2, 52.1, 40.7, 35.3, 35.2, 24.9, 20.2, 15.5, 13.9, 11.9, 10.4, 3.7.

MS (ES+): m/z 582.2 $[M+H]^+$, 604.2 $[M+Na]^+$.

$R_f$: 0.43 ($CH_2Cl_2$:EtOAc 6:4).

Synthesis of 146

146

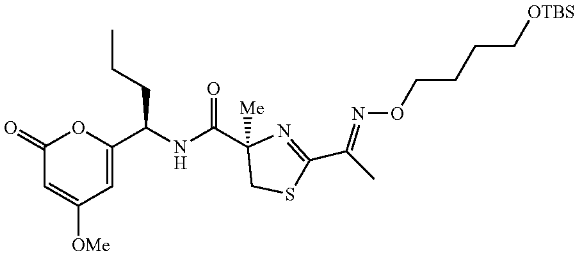

To a solution of 1 (85 mg, 0.22 mmol) in acetone (2 mL) was added $Cs_2CO_3$ (363 mg, 1.1 mmol) and tert-butyl(4-iodobutoxy)dimethylsilane (0.3 mL, 1.1 mmol) and the reaction was stirred at 23° C. overnight. Evaporation to dryness of the reaction mixture following by purification by flash chromatography on silica gel ($CH_2Cl_2$:EtOAc) gave 146 (100 mg, 30% yield).

$^1H$ NMR (400 MHz, $CDCl_3$): δ 7.07 (d, J=8.5 Hz, 1H), 5.86 (t, J=2.5 Hz, 1H), 5.39 (d, J=2.5 Hz, 1H), 4.70 (d, J=7.9 Hz, 1H), 4.21 (t, J=6.2 Hz, 2H), 3.76 (s, 3H), 3.62 (t, J=6.3 Hz, 2H), 3.48 (dd, J=11.8, 3.1 Hz, 1H), 3.18 (dd, J=14.5, 9.4 Hz, 2H), 2.15 (d, J=2.5 Hz, 3H), 1.96-1.50 (m, 6H), 1.48 (s, 3H), 1.42-1.26 (m, 2H), 0.94 (d, J=7.3 Hz, 3H), 0.86 (s, 6H), 0.02 (s, 3H).

$^{13}C$ NMR (100 MHz, $CDCl_3$): δ 174.2, 170.8, 167.9, 164.0, 162.5, 162.4, 151.4, 100.1, 100.0, 88.5, 84.3, 75.4, 74.1, 62.7, 55.9, 50.9, 39.8, 34.7, 30.0 (×2), 29.1, 25.9, 25.6, 24.7, 19.0, 18.3, 13.6, 11.8, 6.3, −5.3.

Synthesis of 147

147

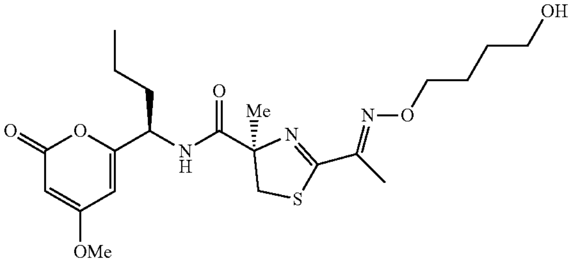

To a mixture of 146 (100 mg, 0.18 mmol) and $NH_4F$ (34 mg, 0.9 mmol) in THF (16 mL) was added TBAF (0.9 mL, 1.0 M in THF, 0.9 mmol) at 23° C. After being stirred for 4 h, 0.3 mL of TBAF was added to complete the reaction. After 2 h, the reaction was quenched with an aqueous saturated solution of NaCl and extracted with $CH_2Cl_2$. The organic layers were dried over anhydrous $Na_2SO_4$, filtered, and evaporation of the volatiles gave a crude which was purified by flash chromatography on silica gel ($CH_2Cl_2$:EtOAc) to afford 147 (54 mg, 37% yield).

$^1H$ NMR (400 MHz, $CDCl_3$): δ 7.06 (d, J=8.8 Hz, 1H), 5.87 (dd, J=2.2, 0.5 Hz, 1H), 5.40 (d, J=2.3 Hz, 1H), 4.71 (td, J=8.3, 6.8 Hz, 1H), 4.25 (td, J=6.4, 1.0 Hz, 2H), 3.77 (s, 3H), 3.68 (t, J=6.4 Hz, 2H), 3.51 (d, J=11.6 Hz, 1H), 3.41-3.27 (m, 3H), 3.18 (d, J=11.6 Hz, 1H), 2.17 (s, 3H), 1.92-1.62 (m, 6H), 1.50 (s, 3H), 1.48-1.29 (m, 2H), 1.29-1.17 (m, 3H), 0.95 (t, J=7.3 Hz, 3H).

$^{13}C$ NMR (100 MHz, $CDCl_3$): δ 174.1, 170.9, 167.9, 164.1, 162.4, 151.6, 100.1, 88.5, 84.3, 75.2, 62.5, 59.3, 55.9, 50.9, 39.9, 34.8, 29.7, 29.1, 25.6, 24.8, 24.3, 19.8, 19.0, 13.7, 13.6, 11.9.

Synthesis of 148

148

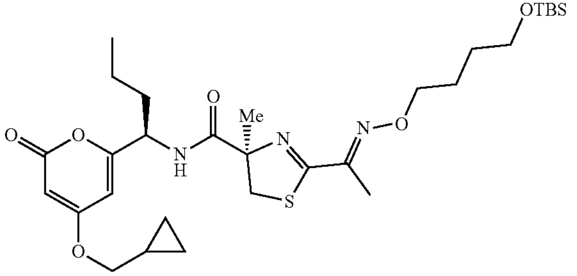

To a solution of 76 (458 mg, 1.08 mmol) in acetone (11 mL), $Cs_2CO_3$ (1.77 g, 5.43 mmol) and tert-butyl(4-iodobutoxy)dimethylsilane (1.41 mL, 5.43 mmol) were added and was stirred at 23° C. overnight. The reaction mixture was filtered washing with EtOAc. and evaporated. The resulting residue was purified by combi flash in $SiO_2$ (from $CH_2Cl_2$ to $CH_2Cl_2$:EtOAc 9:1) to yield 148 (587 mg, 89% yield).

$^1$H NMR (400 MHz, $CD_3OD$): δ 7.85 (d, J=8.6 Hz, 1H), 6.06 (d, J=2.2 Hz, 1H), 5.48 (s, 1H), 4.74 (td, J=8.8, 5.7 Hz, 1H), 4.23 (t, J=6.4 Hz, 2H), 3.86 (d, J=7.2 Hz, 2H), 3.67 (t, J=6.3 Hz, 2H), 3.58 (dd, J=11.5, 5.3 Hz, 1H), 3.19 (d, J=11.5 Hz, 1H), 2.20 (s, 3H), 1.94-1.71 (m, 4H), 1.64-1.57 (m, 2H), 1.52 (s, 3H), 1.51-1.32 (m, 2H), 1.28-1.20 (m, 1H), 0.98 (t, J=7.4 Hz, 3H), 0.89 (s, 9H), 0.72-0.57 (m, 2H), 0.37-0.33 (m, 2H), 0.05 (s, 6H).

$^{13}$C NMR (100 MHz, $CD_3OD$): δ 175.0, 171.2, 168.0, 165.3, 163.8, 151.5, 99.7, 87.9, 84.3, 74.9, 73.9, 62.5, 50.8, 39.2, 33.9, 28.8, 25.4, 25.0, 23.5, 18.8, 12.5, 10.4, 9.0, 2.3, −6.6.

MS (ES+): m/z 608.2 $[M+H]^+$, 630.2 $[M+Na]^+$.

$R_f$: 0.53 ($CH_2Cl_2$:EtOAc 9:1).

Synthesis of 149

149

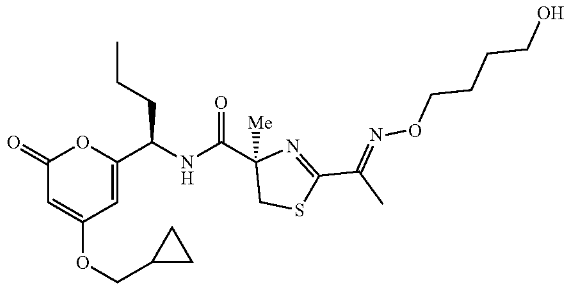

To a solution of 148 (95 mg, 0.156 mmol) in anhydrous MeOH (1 mL), PPTS (14 mg, 0.054 mmol) was added and was stirred at 23° C. for 3 h. Then, the solvent was removed under pressure and the resulting oil was dissolved in EtOAc and washed with an aqueous saturated solution of $NaHCO_3$ and $H_2O$. The combined organic layers were dried over anhydrous $Na_2SO_4$, filtered and evaporated. The resulting residue was purified by combi flash in $SiO_2$ (from $CH_2Cl_2$ to $CH_2Cl_2$:EtOAc 1:1) to obtain 149 (0.59 g, 77% yield).

$^1$H NMR (400 MHz, $CD_3OD$): δ 7.87 (d, J=8.6 Hz, 1H), 6.05 (d, J=2.2 Hz, 1H), 5.48 (d, J=2.2 Hz, 1H), 4.74 (td, J=8.9, 5.7 Hz, 1H), 4.23 (t, J=6.5 Hz, 2H), 3.86 (d, J=7.2 Hz, 2H), 3.70-3.49 (m, 3H), 3.19 (d, J=11.5 Hz, 1H), 2.20 (s, 3H), 1.88-1.74 (m, 4H), 1.68-1.57 (m, 2H), 1.52 (s, 3H), 1.50-1.32 (m, 2H), 1.25-1.20 (m, 1H), 0.98 (t, J=7.4 Hz, 3H), 0.70-0.54 (m, 2H), 0.37-0.33 (m, 2H).

$^{13}$C NMR (100 MHz, $CD_3OD$): δ 176.4, 172.6, 169.3, 166.7, 165.2, 152.9, 101.1, 89.2, 85.7, 76.3, 75.3, 62.6, 52.2, 40.7, 35.2, 30.0, 26.8, 24.9, 20.3, 13.9, 11.8, 10.4, 3.7.

MS (ES+): m/z 494.2 $[M+H]^+$, 516.2 $[M+Na]^+$.

$R_f$: 0.46 ($CH_2Cl_2$:EtOAc 1:1).

Synthesis of 150

150

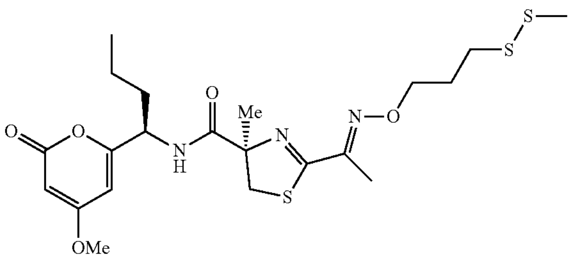

To a solution of 1 (60 mg, 0.16 mmol) in acetone (1.6 mL) was added $K_2CO_3$ (110 mg, 0.8 mmol) and 1-(3-iodopropyl)-2-methyldisulfane (200 mg, 0.8 mmol) at 23° C. After being stirred overnight, the reaction mixture was diluted with $CH_2Cl_2$ and $H_2O$ was added. Extraction with $CH_2Cl_2$, dryness over anhydrous $Na_2SO_4$, filtered, and evaporation of the organic layers gave a crude which was purified by flash chromatography on silica gel to afford 150 (15 mg, 19% yield).

$^1$H NMR (400 MHz, $CDCl_3$): δ 7.08 (d, J=8.8 Hz, 1H), 5.93-5.86 (m, 1H), 5.42 (d, J=2.2 Hz, 1H), 4.73 (q, J=7.9 Hz, 1H), 4.33 (t, J=6.1 Hz, 2H), 3.79 (s, 3H), 3.52 (d, J=11.6 Hz, 1H), 3.29 (t, J=6.7 Hz, 1H), 3.21 (d, J=11.6 Hz, 1H), 2.79 (td, J=7.0, 2.2 Hz, 3H), 2.19 (d, J=0.6 Hz, 3H), 2.13 (p, J=6.7 Hz, 2H), 1.95-1.70 (m, 2H), 1.52 (s, 3H), 0.97 (t, J=7.3 Hz, 3H).

$^{13}$C NMR (100 MHz, $CDCl_3$): δ 174.1, 170.9, 167.7, 164.1, 162.4, 152.0, 100.2, 88.6, 84.4, 73.4, 56.0, 50.9, 39.9, 38.7, 35.1, 34.8, 32.3, 29.7, 28.8, 24.8, 19.1, 13.6, 12.0, 4.6.

Synthesis of 151

151

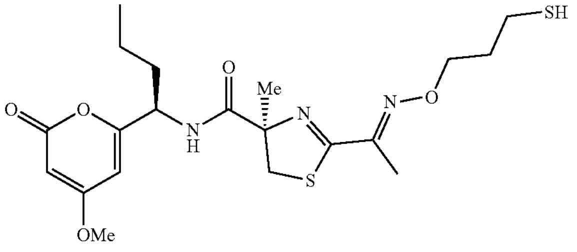

To a solution of 150 (15 mg, 0.03 mmol) in EtOAc (1.8 mL) and MeOH (2.7 mL) was added a mixture of DL-Dithiothreitol (DTT) (0.075 mL, 1.0 M in $H_2O$, 0.075 mmol) in 0.05 M $NaH_2PO_4$ in EDTA (1.8 mL) at 23° C. The reaction mixture was stirred for 7 h and the reaction was quenched with $H_2O$. Extraction with $CH_2Cl_2$, dryness over anhydrous $Na_2SO_4$, filtered, and evaporation of the organic layers gave a crude which was purified by flash chromatography on silica gel to afford 151 (7 mg, 26% yield).

$^1$H NMR (400 MHz, $CDCl_3$): δ 7.07 (d, J=8.8 Hz, 1H), 5.89 (d, J=2.2 Hz, 1H), 5.41 (d, J=2.2 Hz, 1H), 4.79-4.63 (m, 1H), 4.32 (dt, J=10.3, 6.1 Hz, 2H), 3.79 (s, 3H), 3.51 (d,

J=11.6 Hz, 1H), 3.19 (d, J=11.6 Hz, 1H), 2.83-2.57 (m, 5H), 2.18 (s, 3H), 2.08-1.66 (m, 4H), 1.56-1.48 (m, 2H), 0.96 (t, J=7.4 Hz, 3H).

Synthesis of 152

152

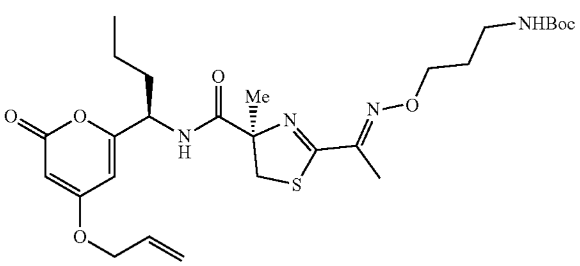

To a solution of 74 (1.03 g, 2.53 mmol) in acetone (25 mL) was added $Cs_2CO_3$ (1.24 g, 3.79 mmol) and tert-butyl (3-iodopropyl)carbamate (1.08 g, 3.79 mmol). The reaction mixture was refluxed for 30 min and, after allowed to cool to 23° C., filtrated through a Celite® plug that was washed with EtOAc. Organic filtrate was evaporated and crude residue was purified in a flash chromatography system over silica gel eluting with mixtures hexane:EtOAc from 80:20 to 60:40 in 20 min to yield pure 152 (1.47 g, 100% yield).

$^1H$ NMR (400 MHz, $CDCl_3$): δ 7.06 (d, J=8.7 Hz, 1H), 6.01-5.88 (m, 1H), 5.90 (d, J=2.1 Hz, 1H), 5.42-5.30 (m, 3H), 4.78-4.65 (m, 2H), 4.47 (dt, J=5.6, 1.5 Hz, 2H), 4.27 (t, J=6.0 Hz, 2H), 3.50 (d, J=11.6 Hz, 1H), 3.22 (q, J=7.9, 6.9 Hz, 2H), 3.18 (d, J=11.6 Hz, 1H), 2.16 (s, 3H), 1.94-1.68 (m, 4H), 1.49 (s, 3H), 1.42 (s, 9H), 1.39-1.29 (m, 2H), 0.94 (t, J=7.4 Hz, 3H).

$^{13}C$ NMR (100 MHz, $CDCl_3$): δ 174.0, 169.6, 167.7, 164.0, 162.4, 155.9, 151.8, 130.6, 119.5, 100.3, 89.3, 84.3, 79.1, 73.0, 69.5, 50.9, 39.8, 37.6, 34.7, 29.4, 28.3, 24.7, 19.0, 13.5, 11.8.

MS (ES+): m/z 587.3 $[M+Na]^+$, 565.3 $[M+H]^+$.

$R_f$: 0.16 (hexanes:EtOAc 7:3).

Synthesis of 153

153

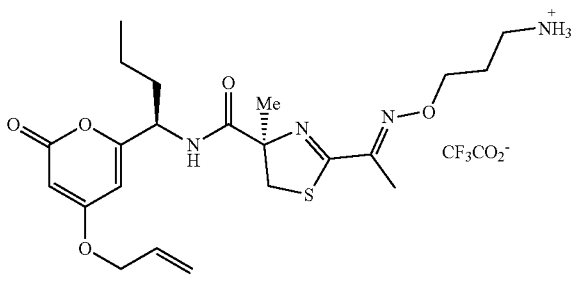

To a solution of 152 (1.47 g, 2.6 mmol) in $CH_2Cl_2$ (55 mL) was added TFA (16 mL). After being stirred for 2.5 hours, the reaction mixture was evaporated to dryness. Crude residue was purified in CombiFlash with $CH_2Cl_2$:MeOH mixtures from 100:0 to 90:10 in 20 min to give pure 153 (1.4 g, 100% yield).

$^1H$ NMR (400 MHz, $CDCl_3$): δ 8.07 (s, 2H), 7.01 (d, J=8.8 Hz, 1H), 5.95 (d, J=2.2 Hz, 1H), 6.01-5.86 (m, 1H), 5.43 (d, J=2.2 Hz, 1H), 5.41-5.28 (m, 2H), 4.69 (q, J=7.9 Hz, 1H), 4.47 (dd, J=5.6, 1.6 Hz, 2H), 4.28 (td, J=8.1, 7.3, 4.0 Hz, 2H), 3.55 (d, J=11.5 Hz, 1H), 3.14 (d, J=11.6 Hz, 1H), 3.09 (s, 2H), 2.16 (s, 3H), 2.14-2.05 (m, 2H), 1.78 (m, 2H), 1.52 (s, 3H), 1.48-1.21 (m, 2H), 0.94 (t, J=7.3 Hz, 3H).

$^{13}C$ NMR (100 MHz, $CDCl_3$): δ 174.0, 170.1, 167.7, 164.7, 162.4, 152.7, 130.5, 119.5, 100.7, 89.3, 84.3, 71.7, 69.7, 50.9, 40.1, 37.4, 34.6, 27.2, 24.7, 19.0, 13.5, 11.8.

MS (ES+): m/z 465.2 $[M+H]^+$.

$R_f$: 0.8 ($CH_2Cl_2$:MeOH 9:1).

Synthesis of 154

154

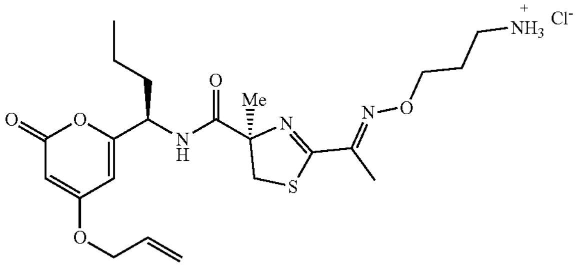

153 (424 mg) was treated with 2M NaOH and extracted with $CH_2Cl_2$ (×2). The organic layers were dried over anhydrous $Na_2SO_4$, filtered, and the volatiles were evaporated. 5-6 N of HCl in 2-propanol was added to the crude and then evaporated to dryness to give 154 (135 mg, 37% yield) as a foamed solid.

$^1H$ NMR (400 MHz, $CD_3OD$): δ 6.10 (s, 1H), 6.01 (m, 1H), 5.43 (s, 1H), 5.34 (m, 1H), 4.75 (m, 1H), 4.61 (m, 2H), 4.33 (m, 2H), 3.61 (d, J=11.6 Hz, 1H), 3.23 (d, J=11.6 Hz, 1H), 3.08 (m, 2H), 2.24 (s, 3H), 2.09 (m, 1H), 1.85 (m, 2H), 1.55 (m, 3H), 1.53-1.31 (m, 2H), 0.99 (m, 3H).

$^{13}C$ NMR (100 MHz, $CD_3OD$): δ 174.6, 170.8, 168.1, 165.2, 163.7, 152.5, 131.1, 118.0, 99.8, 88.5, 88.4, 84.1, 71.6, 69.6, 50.8, 39.3, 36.8, 33.8, 27.1, 23.4, 18.8, 12.4, 10.4.

MS (ES+): m/z 465.2 $[M+H]^+$.

Synthesis of 155

155

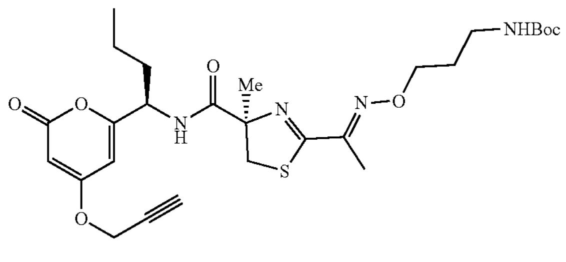

To a solution of 75 (53 mg, 0.131 mmol) in acetone (5 mL) was added $Cs_2CO_3$ (64 mg, 0.196 mmol) and tert-butyl (3-iodopropyl)carbamate (56 mg, 0.196 mmol). The reaction mixture was refluxed for 30 min and, after allowed to cool to 23° C., filtrated through a Celite® plug that was washed with EtOAc. Organic filtrate was evaporated and crude residue was purified in a flash chromatography system over silica gel eluting with mixtures hexane:EtOAc from 80:20 to 60:40 in 20 min to yield pure 155 (67 mg, 91% yield).

$^{1}$H NMR (400 MHz, $CDCl_3$): δ 7.05 (d, J=8.7 Hz, 1H), 5.89 (d, J=2.2 Hz, 1H), 5.53 (d, J=2.2 Hz, 1H), 4.76 (tt, J=3.8, 2.0 Hz, 1H), 4.71 (td, J=8.4, 6.8 Hz, 1H), 4.64 (d, J=2.4 Hz, 2H), 4.26 (t, J=6.1 Hz, 2H), 3.49 (d, J=11.6 Hz, 1H), 3.21 (q, J=9.6, 8.0 Hz, 2H), 3.18 (d, J=11.6 Hz, 1H), 2.62 (t, J=2.4 Hz, 1H), 2.16 (s, 3H), 1.95-1.78 (m, 3H), 1.81-1.66 (m, 1H), 1.49 (s, 3H), 1.41 (s, 9H), 1.46-1.25 (m, 2H), 0.94 (t, J=7.4 Hz, 3H).

$^{13}$C NMR (100 MHz, $CDCl_3$): δ 174.0, 168.6, 167.7, 163.6, 162.8, 155.9, 151.8, 99.9, 90.0, 84.3, 79.1, 77.7, 75.6, 73.0, 56.4, 50.9, 39.8, 37.6, 34.7, 29.4, 28.3, 24.7, 19.0, 13.5, 11.8.

Synthesis of 156

156

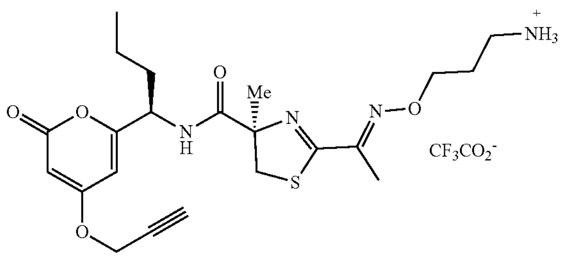

To a solution of 155 (67 mg, 0.119 mmol) in $CH_2Cl_2$, (2.5 mL) was added TFA (0.7 mL). After being stirred for 30 min, the reaction mixture was evaporated to dryness. Crude residue was purified in CombiFlash with $CH_2Cl_2$:MeOH mixtures from 100:0 to 90:1 to obtain pure 156 (55 mg, 80% yield).

$^{1}$H NMR (400 MHz, $CDCl_3$): δ 7.02 (d, J=8.8 Hz, 1H), 5.97 (d, J=2.2 Hz, 1H), 5.58 (d, J=2.2 Hz, 1H), 4.72 (q, J=7.9 Hz, 1H), 4.66 (d, J=2.5 Hz, 2H), 4.37-4.23 (m, 2H), 3.56 (d, J=11.6 Hz, 1H), 3.16 (d, J=11.6 Hz, 1H), 3.11 (t, J=7.4 Hz, 2H), 2.65 (t, J=2.4 Hz, 1H), 2.16 (s, 3H), 2.13-2.05 (m, 2H), 1.90-1.67 (m, 2H), 1.53 (s, 3H), 1.49-1.26 (m, 2H), 0.95 (t, J=7.3 Hz, 3H).

$^{13}$C NMR (100 MHz, $CDCl_3$): δ 174.2, 169.2, 167.8, 164.5, 162.8, 152.8, 100.5, 90.1, 84.3, 77.8, 75.6, 71.8, 56.6, 50.9, 40.1, 37.6, 34.6, 27.2, 24.7, 19.0, 13.5, 11.8.

157

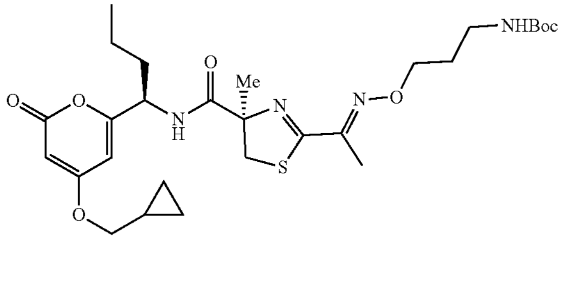

Synthesis of 157

To a solution of 76 (9 mg, 0.021 mmol) in acetone (5 mL) was added $Cs_2CO_3$ (10 mg, 0.031 mmol) and tert-butyl (3-iodopropyl)carbamate (9 mg, 0.031 mmol). The reaction mixture was refluxed for 30 min and, after allowed to cool to 23° C., filtrated through a Celite® plug that was washed with EtOAc. Organic filtrate was evaporated to obtain crude 157 (10 mg, 81% yield) which was used in the next without further purification.

$^{1}$H NMR (400 MHz, $CDCl_3$): δ 7.09 (t, J=8.0 Hz, 1H), 5.92 (d, J=2.2 Hz, 1H), 5.35 (t, J=1.7 Hz, 1H), 4.79-4.68 (m, 1H), 4.64 (s, 1H), 4.28 (t, J=6.0 Hz, 1H), 3.76 (dd, J=7.1, 1.9 Hz, 2H), 3.52 (dd, J=11.6, 8.6 Hz, 1H), 3.28-3.14 (m, 4H), 2.18 (s, 3H), 2.07-1.95 (m, 2H), 1.90 (dd, J=8.0, 4.9 Hz, 1H), 1.69 (s, 2H), 1.51 (d, J=2.9 Hz, 3H), 1.43 (s, 9H), 1.25 (d, J=2.2 Hz, 3H), 0.96 (td, J=7.3, 1.5 Hz, 3H), 0.66 (q, J=6.1 Hz, 1H), 0.33 (dt, J=6.1, 4.7 Hz, 1H).

Synthesis of 158

158

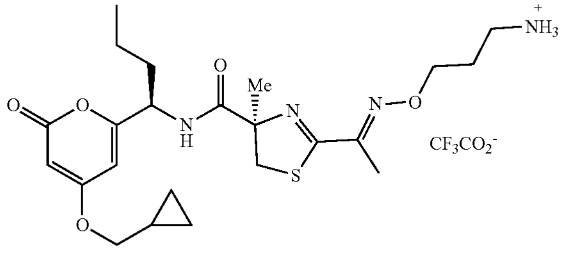

To a solution of 157 (12 mg, 0.021 mmol) in $CH_2Cl_2$ (0.4 mL) was added TFA (0.1 mL). After being stirred for 30 min, the reaction mixture was evaporated to dryness. Crude residue was purified in CombiFlash with $CH_2Cl_2$:MeOH mixtures from 100:0 to 85:15 to afford pure 158 (4.9 mg, 49% yield).

$^{1}$H NMR (400 MHz, $CDCl_3$): δ 7.85 (s, 1H), 7.03 (d, J=8.9 Hz, 1H), 6.01 (d, J=2.1 Hz, 1H), 5.44 (d, J=2.2 Hz, 1H), 4.72 (q, J=7.9 Hz, 1H), 4.30 (dt, J=12.0, 5.9 Hz, 2H), 3.76 (dd, J=7.2, 1.7 Hz, 2H), 3.58 (d, J=11.6 Hz, 1H), 3.15 (d, J=11.6 Hz, 1H), 2.36 (s, 1H), 2.17 (s, 3H), 2.10 (q, J=5.3, 4.3 Hz, 2H), 1.79 (m, 2H), 1.55 (s, 3H), 1.36 (m, 2H), 1.27-1.15 (m, 1H), 0.95 (t, J=7.3 Hz, 3H), 0.70-0.60 (m, 2H), 0.38-0.25 (m, 2H).

$^{13}$C NMR (100 MHz, $CDCl_3$): δ 174.2, 170.9, 167.9, 165.6, 162.2, 152.9, 101.4, 89.0, 84.3, 74.2, 72.0, 50.9, 40.2, 37.8, 34.5, 27.2, 24.7, 19.1, 13.5, 11.8, 9.3, 3.3 (×2).

Synthesis of 159

159

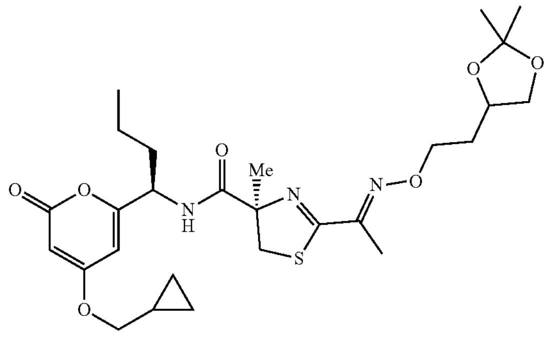

To a solution of 76 (50 mg, 0.121 mmol) in acetone (1.5 mL), $Cs_2CO_3$ (196 mg, 0.604 mmol) and 4-(2-iodoethyl)-2, 2-dimethyl-1,3-dioxolane (155 mg, 0.604 mmol) were added at 23° C. The reaction mixture was stirred at 23° C. overnight. Then was filtered washing with EtOAc. and evaporated. The resulting residue was purified by combi flash in $SiO_2$ (from $CH_2Cl_2$ to $CH_2Cl_2$:EtOAc 8:2) to afford 159 (60 mg, 91% yield).

$^1$H NMR (400 MHz, $CD_3OD$): δ 7 7.85 (d, J=8.6 Hz, 1H), 6.05 s, 1H), 5.48 (s, 1H), 4.75 (td, J=8.6, 5.8 Hz, 1H), 4.30 (t, J=6.3 Hz, 2H), 4.21 (p, J=6.3 Hz, 1H), 4.08 (dt, J=8.0, 4.8 Hz, 1H), 3.86 (d, J=7.2 Hz, 2H), 3.70-3.48 (m, 2H), 3.20 (d, J=11.5 Hz, 1H), 2.20 (s, 3H), 1.99-1.93 (m, 2H), 1.91-1.76 (m, 2H), 1.52 (s, 3H), 1.50-1.38 (m, 2H), 1.37 (s, 3H), 1.31 (s, 3H), 1.28-1.14 (m, 1H), 0.98 (t, J=7.3 Hz, 3H), 0.71-0.50 (m, 2H), 0.36-0.33 (m, 2H).

$^{13}$C NMR (100 MHz, $CD_3OD$): δ 174.9, 171.2, 167.8, 165.3, 163.8, 151.9, 108.5, 99.7, 87.9, 84.3, 73.9, 73.3, 71.9, 69.1, 50.8, 39.3, 33.9, 32.9, 25.9, 24.6, 23.5, 18.9, 12.5, 10.5, 8.98, 2.3.

MS (ES+): m/z 550.3 $[M+H]^+$, 572.3 $[M+Na]^+$.

$R_f$: 0.5 ($CH_2Cl_2$:EtOAc 8:2).

Example 17 Synthesis of Additional Compounds of Formula I

Scheme 29 provides further examples of the synthesis of compounds of formula I

Scheme 29

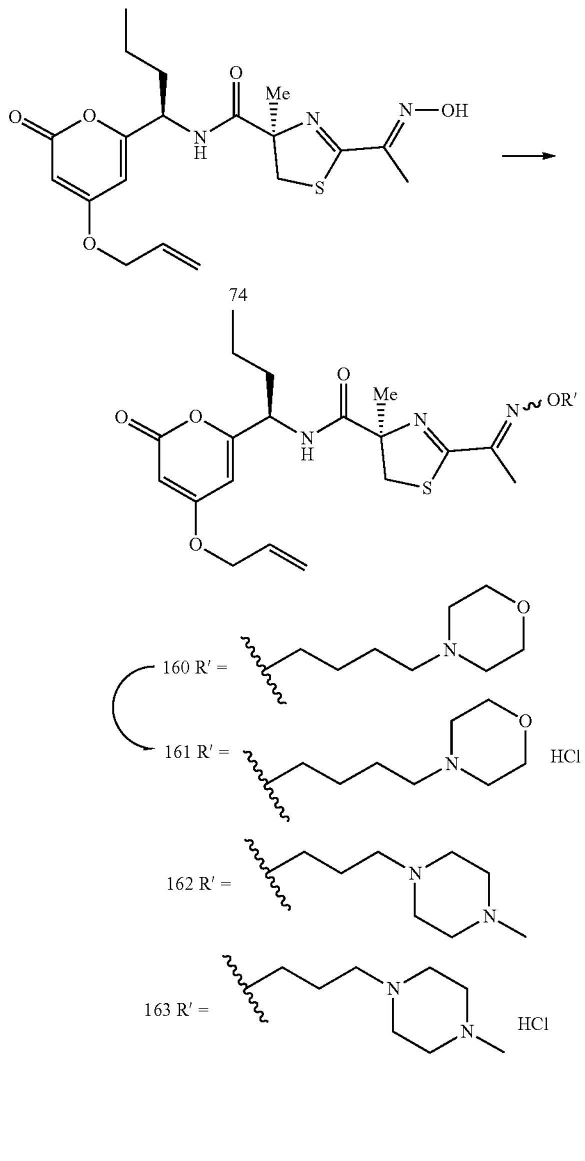

Synthesis of 160

160

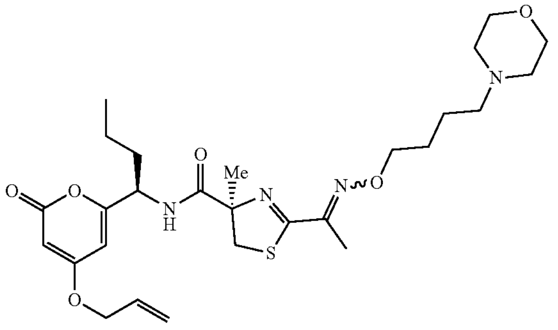

In a schlenk tube was poured anhydrous $Cs_2CO_3$ (88 mg, 0.269 mmol), 74 (43 mg, 0105 mmol) and 4-(4-chlorobutyl) morpholine hydrochloride (23 mg, 0.108 mol). Then, the solids were suspended in acetone (1.4 mL) and the mixture refluxed overnight. When cooled down, the suspension filtered through Celite®, washed with EtOAc and the filtrated was concentrated under vacuum. The resulting brown oily crude was subjected to a chromatographic purification ($SiO_2$, Hex:EtOAc from 50:50 to 0:100 followed by EtOAc: MeOH 95:5) to yield 160 (28 mg, 48% yield) as a ca. (50:50) mixture of geometrical estereoisomers and as pale orangish oil.

$^1$H NMR (500 MHz, $CDCl_3$): δ 7.08 (d, J=8.8 Hz, 1H) 7.02 (d, J=8.5 Hz, 1H), 5.99 (d, J=2.3 Hz, 1H), 5.98-5.91 (m, 2H), 5.90 (d, J=2.2 Hz, 1H), 5.43-5.38 (m, 6H), 4.71 (q, J=7.8, 6.9 Hz, 1H), 4.67 (q, J=7.8, 6.9 Hz, 1H), 4.49 (m, 4H), 4.23 (td, J=6.4, 5.3 Hz, 4H), 3.71 (t, J=4.9 Hz, 8H), 3.54 (d, J=11.6 Hz, 1H), 3.49 (d, J=11.6 Hz, 1H), 3.20 (d, J=2.3 Hz, 1H), 3.17 (d, J=2.3 Hz, 1H), 2.45 (bs, 8H), 2.39-2.36 (m, 4H), 2.15 (s, 6H), 1.92-1.80 (m, 2H), 1.79-1.64 (m, 6H), 1.59 (pd, J=6.8, 6.1, 3.4 Hz, 4H), 1.49 (s, 3H), 1.46 (s, 3H), 1.43-1.25 (m, 4H), 0.94 (t, J=7.4 Hz, 3H), 0.90 (t, J=7.4 Hz, 3H).

MS (ES+): m/z 571.3 $[M+Na]^+$, 549.2 $[M+H]^+$.

$R_f$: 0.15 (EtOAc).

Synthesis of 161

161

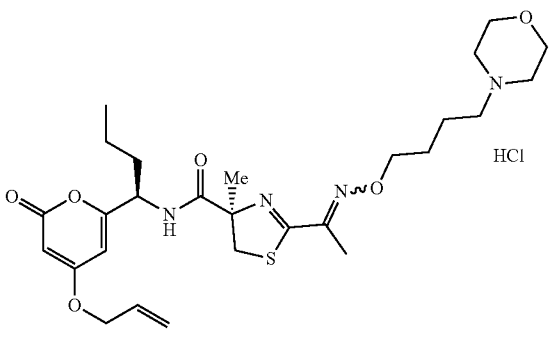

160 (160 mg, 0.292 mmol) was dissolved in a solution of HCl in 2-propanol (15 mL, 6 M) and stirred for 10 min.

Then, the volatiles were vacuum-evaporated and the brown residue treated twice more under the same conditions. When the starting compound was totally transformed, the resulting brown and dense residue was dried in a vacuum-assisted oven over overnight, resulting 161 (146 mg, 85% yield) as a pale brown solid and a ca. (50:50) mixture of geometrical estereoisomers.

$^1$H NMR (400 MHz, $CDCl_3$): δ 8.67 (brs, 1H), 8.58 (brs, 1H), 6.10-5.87 (m, 4H), 5.48-5.30 (m, 6H), 4.75-4.59 (m, 2H), 4.49 (brt, J=6.4 Hz, 4H), 4.44-3.40 (m, 16H), 2.38 (brs, 6H), 1.97-1.72 (m, 12H), 1.70-1.23 (m, 16H), 1.22 (s, 3H), 1.20 (s, 3H), 0.95 (t, J=7.4 Hz, 3H), 0.91 (t, J=7.2 Hz, 3H).

MS (ES+): m/z 549.3 $[M+H]^+$.

Synthesis of 162

162

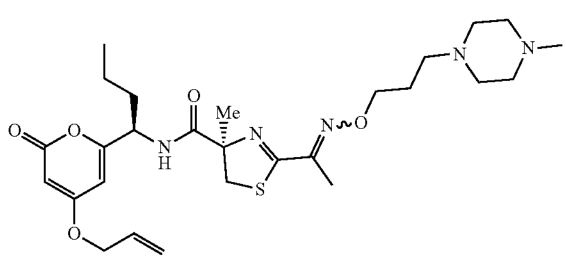

In a schlenk tube was poured anhydrous $K_2CO_3$ (36 mg, 0.258 mmol), 74 (35 mg, 0086 mmol) and 3-(4-methylpiperazin-1-yl)propyl methanesulfonate (26 mg, 0.086 mol). Then, the solids were suspended in acetone (1.4 mL) and the mixture refluxed overnight. When cooled down, the suspension was treated with a buffer solution $Na_2CO_3$:$NaHCO_3$ (pH=9.51) (20 mL), stirred and extracted with $CH_2Cl_2$ (4×25 mL). The combined organic layers were dried over anhydrous $Na_2SO_4$, filtered and concentrated in vacuum. The resulting brown oily crude was subjected to a chromatographic purification ($SiO_2$, EtOAc:MeOH from 90:0 to 0:100) to obtain 162 (42 mg, 97% yield) as a ca. (50:50) mixture of geometrical estereoisomers and as waxy solid.

$^1$H NMR (500 MHz, $(CD_3)_2SO$): δ 7.87 (m, 2H), 6.11 (d, J=2.1 Hz, 1H), 6.01 (d, J=2.2 Hz, 1H), 6.04-5.93 (m, 2H), 5.60 (d, J=2.2 Hz, 1H), 5.57 (d, J=2.2 Hz, 1H), 5.42 (ddd, J=12.4, 1.6, 0.7 Hz, 1H), 5.38 (ddd, J=12.3, 1.6, 0.7 Hz, 1H), 5.36-5.25 (m, 2H), 4.62 (d, J=5.5 Hz, 2H), 4.60 (d, J=5.6 Hz, 2H), 4.58-4.51 (m, 2H), 4.19 (td, J=6.4, 2.3 Hz, 4H), 3.60-3.52 (ddd, J=11.4, 7.9, 0.7 Hz, 2H), 3.19 (ddd, J=11.4, 7.9, 0.7 Hz, 2H), 2.45-2.20 (m, 20H), 2.15 (s, 6H), 2.13 (s, 6H), 1.82-1.70 (m, 10H), 1.45 (s, 3H), 1.43 (s, 3H), 1.42-1.16 (m, 16H), 0.89 (t, J=7.4 Hz, 3H), 0.85 (t, J=7.4 Hz, 3H).

MS (ES+): m/z 570.3 $[M+Na]^+$, 548.2 $[M+H]^+$.

Synthesis of 163

163

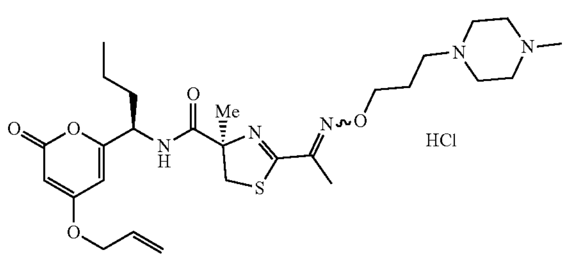

162 (77 mg, 0.14 mmol) was dissolved in a solution of HCl in 2-propanol (7 mL, 6 M) and stirred for 10 min. Then, the volatiles were vacuum-evaporated and the brown residue treated twice more under the same conditions. When the starting compound was totally transformed, the resulting brown and dense residue was dried in a vacuum-assisted oven over overnight, resulting 163 (75 mg, 91% yield) as a pale brown solid and a ca. (50:50) mixture of geometrical estereoisomers.

$^1$H NMR (400 MHz, $CDCl_3$): δ 8.30-8.50 (m, 1H), 6.07-5.88 (m, 4H), 5.48-5.30 (m, 6H), 4.75-4.60 (m, 2H), 4.49 (brt, J=6.4 Hz, 4H), 4.44-2.63 (m, 16H), 2.94 (brs, 6H), 2.51-2.15 (m, 3H), 2.33 (brs, 6H), 2.10-1.54 (m, 14H), 1.52-1.17 (m, 11H), 0.96 (t, J=7.4 Hz, 3H), 0.91 (t, J=7.2 Hz, 3H).

MS (ES+): m/z 548.2 $[M+H]^+$.

Example 18 Synthesis of Additional Compounds of Formula I

Scheme 30 provides further examples of the synthesis of compounds of formula I

Scheme 30

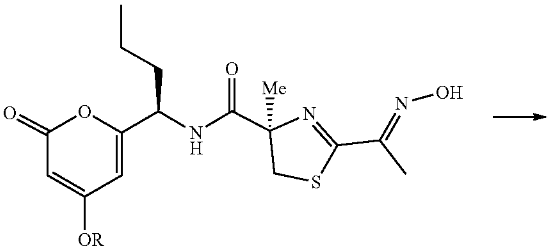

74 R = allyl
76 R = cyclopropylmethyl

-continued

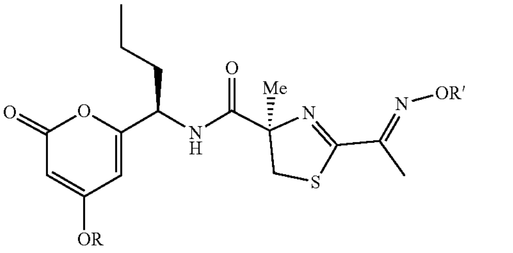

164 R = allyl, R' = 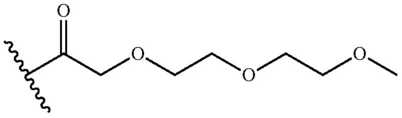

165 R = allyl, R' = 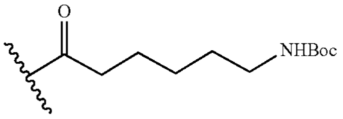

166 R = cyclopropylmethyl, R' = 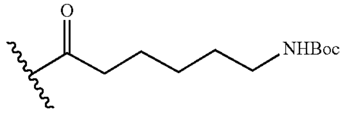

167 R = allyl, R' = 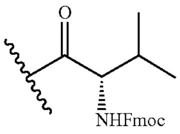

168 R = allyl, R' = 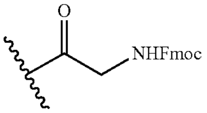

169 R = allyl, R' = 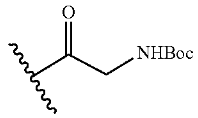

170 R = allyl, R' = 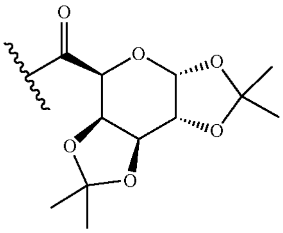

171 R = allyl, R' = 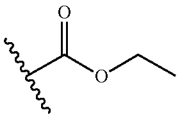

172 R = allyl, R' = 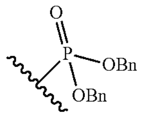

Synthesis of 164

164

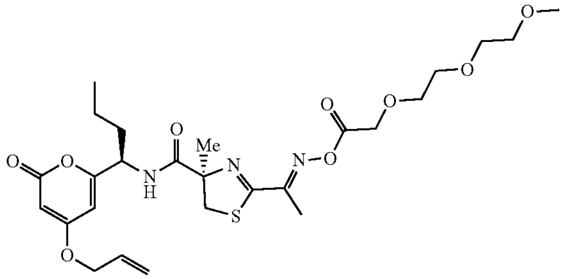

To a solution of 74 (51.1 mg, 0.125 mmol) $CH_2Cl_2$ (2 mL) was sequentially added EDC HCl (48 mg, 0.25 mmol), DIPEA (43.5 μL, 0.25 mmol), 2-(2-(2-methoxyethoxy) ethoxy)-acetic acid (38.37 μL, 0.25 mmol) and DMAP (cat) and the reaction mixture was stirred at 23° C. for 24 h. Once the reaction was finished, the solution was washed with HCl 0.5 N (previously cooled) and an aqueous saturated solution of $NaHCO_3$. Finally, the organic layer was dried over anhydrous $Na_2SO_4$, filtered and concentrated to give an oil crude. The crude was purificated with combiflash, using reverse phase column with this gradient: 5 min 10% $CH_3CN$; 20 min 50% $CH_3CN$ and 15 min 50% $CH_3CN$ to give 164 (22 mg, 31% yield).

$^1H$ NMR (400 MHz, $CD_3OD$): δ 8.10-8.03 (m, 1H), 6.74-6.67 (m, 1H), 6.13-5.95 (m, 2H), 5.55 (d, J=2.2 Hz, 1H), 5.49 (d, J=0.9 Hz, 1H), 5.42 (dd, J=17.3, 1.6 Hz, 1H), 5.33 (dt, J=10.5, 1.2 Hz, 1H), 5.05 (s, 2H), 4.75 (dd, J=9.2, 5.7 Hz, 1H), 4.63-4.56 (m, 2H), 3.69-3.51 (m, 4H), 3.40-3.28 (m, 11H), 3.18 (dd, J=11.5, 0.8 Hz, 1H), 3.08 (d, J=0.8 Hz, 3H), 2.19 (d, J=0.8 Hz, 3H), 1.94-1.75 (m, 1H), 1.53 (d, J=0.8 Hz, 3H), 1.47-1.32 (m, 1H), 1.29 (s, 1H), 1.04-0.95 (m, 3H).

$^{13}C$ NMR (100 MHz, $CD_3OD$): δ 152.9, 132.6, 119.4, 107.9, 100.9, 89.8, 85.6, 71.0, 52.2, 49.5, 49.0, 48.9, 40.6, 39.3, 35.2, 25.0, 20.3, 13.8, 11.0.

MS (ES+): m/z 590.2 $[M+Na]^+$, 568.3 $[M+H]^+$.

$R_f$: 0.27 ($CH_2Cl_2$:EtOAc 6:4).

Synthesis of 165

165

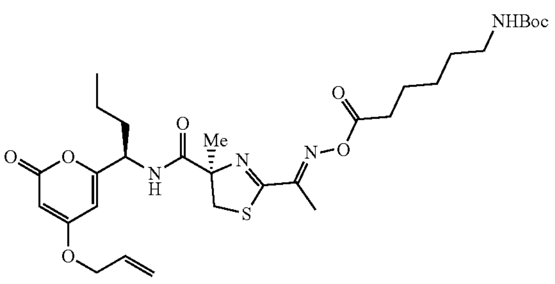

To a solution of 74 (20 mg, 0.048 mmol) in $CH_2Cl_2$ (1 mL), N-(tert-butoxycarbonyl)-6-aminohexanoic acid (12 mg, 0.053 mmol), DMAP (0.5 mg, 0.005 mmol) and a solution of DCC (11 mg, 0.053 mmol) in $CH_2Cl_2$ (0.5 mL)

were added at 0° C. The reaction mixture was 165 stirred at 0° C. for 1 h and at 23° C. overnight. Then was filtered and evaporated to yield crude 165 (30 mg, 99% yield) which was used in the next step without further purification.

$^1$H NMR (400 MHz, $(CD_3)_2CO$): δ 8.12 (d, J=5.7 Hz, 1H), 7.48 (d, J=8.6 Hz, 1H), 6.56 (d, J=5.8 Hz, 1H), 6.09-5.85 (m, 2H), 5.48-5.38 (m, 2H), 5.31 (d, J=10.5 Hz, 1H), 4.89-4.68 (m, 1H), 4.61 (d, J=5.5 Hz, 2H), 3.69 (d, J=11.6 Hz, 1H), 3.30 (d, J=11.6 Hz, 1H), 3.08 (q, J=6.7 Hz, 2H), 2.99 (s, 3H), 2.79 (s, 4H), 2.56 (t, J=7.4 Hz, 2H), 2.34 (s, 3H), 1.90-1.62 (m, 4H), 1.55 (s, 4H), 1.39 (s, 9H), 1.12 (dd, J=21.1, 11.4 Hz, 1H), 0.96 (t, J=7.4 Hz, 3H).

MS (ES+): m/z 621.2 $[M+H]^+$, 643.2 $[M+Na]^+$.

Synthesis of 166

166

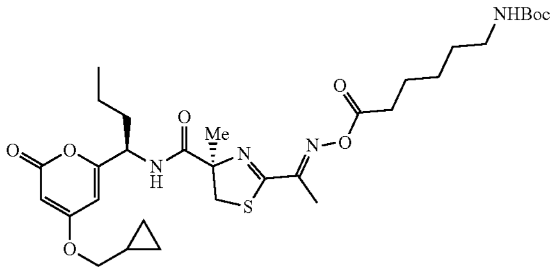

To a solution of 76 (50 mg, 0.118 mmol) in $CH_2Cl_2$ (2 mL), N-(tert-butoxycarbonyl)-6-aminohexanoic acid (30 mg, 0.130 mmol), DMAP (1.4 mg, 0.012 mmol) and a solution of DCC (27 mg, 0.130 mmol) in $CH_2Cl_2$ (0.5 mL) were added at 0° C. The reaction mixture was stirred at 0° C. for 1 h and at 23° C. overnight. Then was filtered and evaporated to yield crude 166 (75 mg, 99% yield) which was used in the next step without further purification.

$^1$H NMR (400 MHz, $(CD_3)_2CO$): δ 8.17-8.00 (m, 1H), 7.49 (d, J=8.6 Hz, 1H), 6.62-6.51 (m, 1H), 6.01 (d, J=2.3 Hz, 1H), 5.94 (s, 1H), 5.36 (d, J=2.2 Hz, 1H), 4.83-4.68 (m, 1H), 3.88 (dd, J=7.1, 2.3 Hz, 2H), 3.69 (d, J=11.6 Hz, 1H), 3.31 (d, J=11.6 Hz, 1H), 3.07 (q, J=6.6 Hz, 2H), 2.99 (s, 3H), 2.81 (d, J=12.4 Hz, 4H), 2.56 (t, J=7.4 Hz, 2H), 2.35 (s, 3H), 1.76 (m, 2H), 1.55 (s, 3H), 1.53-1.44 (m, 2H), 1.39 (s, 9H), 1.33-1.18 (m, 1H), 0.96 (t, J=7.3 Hz, 3H), 0.64-0.56 (m, 2H), 0.36 (dt, J=6.1, 4.4 Hz, 2H).

MS (ES+): m/z 657.2 $[M+Na]^+$.

Synthesis of 167

167

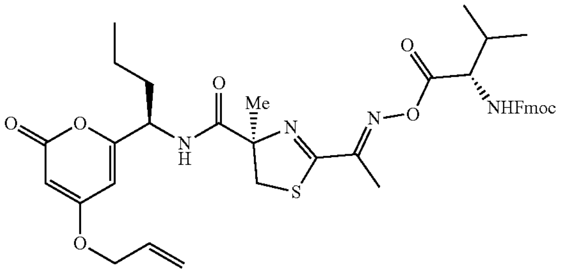

To a solution of 74 (43 mg, 0.106 mmol) in $CH_2Cl_2$ (1 mL) Fmoc-L-Val (40 mg, 0.117 mmol), DMAP (1 mg, 0.0106 mmol) and a solution of DCC (24 mg, 0.117 mmol) in $CH_2Cl_2$ (0.5 mL) were added at 0° C. The reaction mixture was stirred at 0° C. for 1 h and at 23° C. overnight. Then was filtered and evaporated to yield crude 167 (76 mg, 99% yield) which was used in the next step without further purification.

$^1$H NMR (400 MHz, $CD_3OD$): δ 8.03 (d, J=6.3 Hz, 1H), 7.76 (d, J=7.5 Hz, 2H), 7.65 (d, J=7.5 Hz, 2H), 7.35 (t, J=7.5 Hz, 2H), 7.27 (t, J=7.5 Hz, 2H), 6.69 (d, J=6.3 Hz, 1H), 6.05 (d, J=2.2 Hz, 1H), 5.97-5.87 (m, 1H), 5.48 (d, J=2.2 Hz, 1H), 5.39-5.18 (m, 2H), 4.75 (dd, J=9.1, 5.9 Hz, 1H), 4.50 (d, J=5.5 Hz, 2H), 4.41-4.32 (m, 2H), 4.27 (d, J=6.6 Hz, 1H), 4.20 (t, J=6.9 Hz, 1H), 3.67 (d, J=11.6 Hz, 1H), 3.27 (d, J=11.5 Hz, 1H), 2.34 (s, 3H), 2.26-2.14 (m, 1H), 1.91-1.75 (m, 2H), 1.53 (s, 3H), 1.51-1.17 (m, 2H), 1.07-0.89 (m, 9H).

$^{13}$C NMR (100 MHz, $CD_3OD$): δ 174.3, 170.7, 168.7, 165.1, 164.0, 163.4, 160.4, 157.4, 143.8, 141.2, 131.1, 127.2, 126.8, 124.8, 119.6, 118.0, 99.6, 88.6, 84.5, 69.6, 66.6, 59.1, 50.8, 39.9, 35.5, 33.8, 30.3, 23.4, 18.9, 18.2, 17.3, 12.5, 12.3.

MS (ES+): m/z 729.2 $[M+H]^+$, 751.2 $[M+Na]^+$.

Synthesis of 168

168

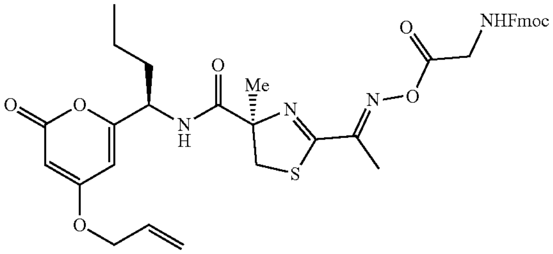

To a solution of 74 (42 mg, 0.102 mmol) in $CH_2Cl_2$ (1 mL) Fmoc-Gly (33 mg, 0.112 mmol), DMAP (1 mg, 0.0102 mmol) and a solution of DCC (23 mg, 0.112 mmol) in $CH_2Cl_2$ (0.5 mL) were added at 0° C. The reaction mixture was stirred at 0° C. for 1 h and at 23° C. overnight. Then was filtered and evaporated to yield crude 168 (69 mg, 99% yield) which was used in the next step without further purification.

$^1$H NMR (400 MHz, $CD_3OD$): δ 8.04-8.03 (m, 1H), 7.77 (d, J=7.5 Hz, 2H), 7.65 (d, J=7.5 Hz, 2H), 7.37 (t, J=7.5 Hz, 2H), 7.29 (t, J=7.4 Hz, 2H), 6.85 (d, J=6.8 Hz, 1H), 6.05 (d, J=2.2 Hz, 1H), 5.98-5.91 (m, 1H), 5.50 (d, J=2.3 Hz, 1H), 5.42-5.19 (m, 2H), 4.75 (dd, J=9.2, 5.7 Hz, 1H), 4.53 (d, J=5.8 Hz, 2H), 4.35 (d, J=7.1 Hz, 2H), 4.21 (t, J=7.2 Hz, 1H), 4.13 (s, 2H), 3.68 (d, J=11.6 Hz, 1H), 3.27 (d, J=11.5 Hz, 1H), 2.34 (s, 3H), 1.87-1.79 (m, 2H), 1.54 (s, 3H), 1.50-1.27 (m, 2H), 0.97 (t, J=7.3 Hz, 3H).

$^{13}$C NMR (100 MHz, $CD_3OD$): δ 174.3, 170.7, 168.7, 165.1, 164.0, 163.4, 160.4, 157.3, 143.8, 141.2, 131.1, 127.4, 126.8 (×2), 124.8, 119.6, 118.0, 99.5, 88.5, 84.5, 69.6, 66.6, 59.1, 50.8, 39.9, 35.6, 33.8, 30.3, 23.4, 18.9, 18.2, 17.3, 12.5, 12.3.

MS (ES+): m/z 687.2 $[M+H]^+$, 709.3 $[M+Na]^+$.

Synthesis of 169

169

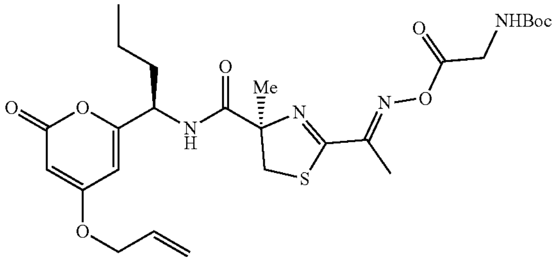

To a solution of 74 (25 mg, 0.062 mmol) in $CH_2Cl_2$ (1 mL) Boc-Gly (12 mg, 0.068 mmol), DMAP (0.7 mg, 0.061 mmol) and a solution of DCC (14 mg, 0.068 mmol) in $CH_2Cl_2$ (0.5 mL) were added at 0° C. The reaction mixture was stirred at 0° C. for 1 h and at 23° C. overnight. Then was filtered and evaporated to yield crude 169 (35 mg, 99% yield) which was used in the next step without further purification.

$^1H$ NMR (400 MHz, $(CD_3)_2CO$): δ 8.24-8.09 (m, 1H), 7.54 (d, J=8.7 Hz, 1H), 6.71-6.51 (m, 2H), 6.13-5.93 (m, 2H), 5.42 (dd, J=15.1, 2.0 Hz, 2H), 5.36-5.24 (m, 1H), 4.75 (dt, J=8.9, 4.5 Hz, 1H), 4.67-4.55 (m, 2H), 4.10 (d, J=6.0 Hz, 2H), 3.75-3.64 (m, 1H), 3.31 (d, J=11.6 Hz, 1H), 3.06 (s, 3H), 2.35 (s, 3H), 1.96-1.69 (m, 2H), 1.56 (s, 3H), 1.53-1.44 (m, 1H), 1.44 (s, 9H), 1.33-1.23 (m, 1H), 0.96 (t, J=7.4 Hz, 3H).

$^{13}C$ NMR (100 MHz, $(CD_3)_2CO$): δ 172.9, 169.7, 167.5, 164.3, 162.7, 159.6, 147.2, 131.7, 118.3, 106.6, 98.8, 88.5, 84.7, 78.7, 69.4, 50.8, 41.3, 40.1, 38.4, 34.2, 27.7 (×2), 24.0, 19.0, 13.0, 12.4. MS (ES+): m/z 565.2 $[M+H]^+$, 587.3 $[M+Na]^+$.

Synthesis of 170

170

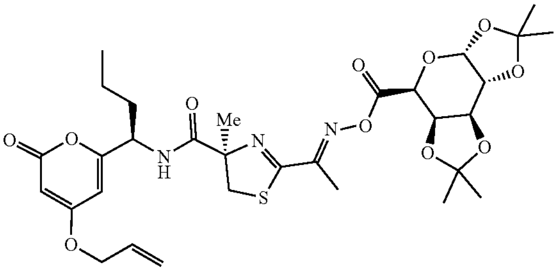

To a solution of 74 (32 mg, 0.079 mmol) in $CH_2Cl_2$ (1 mL), 1,2:3,4-di-O-isopropylidene-α-D-galacturonide (18 mg, 0.066 mmol), DMAP (1.6 mg, 0.0131 mmol) and a solution of DCC (27 mg, 0.131 mmol) in $CH_2Cl_2$ (0.5 mL) were added at 0° C. The reaction mixture was stirred at 0° C. for 1 h and at 23° C. overnight. Then was filtered and evaporated. The resulting residue was purified in preparative HPLC to yield 170 (25 mg, 57% yield).

$^1H$ NMR (500 MHz, $(CD_3)_2CO$): δ 7.51 (d, J=8.7 Hz, 1H), 6.05-5.99 (m, 1H), 6.02 (s, 1H), 5.63 (d, J=5.1 Hz, 1H), 5.52-5.36 (m, 2H), 5.31 (d, J=10.5 Hz, 1H), 4.85-4.67 (m, 4H), 4.61 (d, J=5.5 Hz, 2H), 4.50 (dd, J=5.1, 2.6 Hz, 1H), 3.70 (d, J=11.6 Hz, 1H), 3.33 (d, J=11.6 Hz, 1H), 2.37 (s, 3H), 1.95-1.69 (m, 2H), 1.56-1.29 (m, 2H), 1.56 (s, 3H), 1.52 (s, 3H), 1.39 (s, 3H), 1.36 (s, 3H), 1.33 (s, 3H), 0.97 (t, J=7.4 Hz, 3H).

$^{13}C$ NMR (125 MHz, $(CD_3)_2CO$): δ 173.8, 170.6, 167.1, 165.2, 163.6, 161.1, 132.7, 119.2, 109.7, 99.8, 97.4, 89.5, 85.7, 73.0, 71.9, 71.1, 70.3, 69.0, 51.8, 41.1, 35.2, 26.4, 26.2, 25.1, 25.0, 24.9, 20.0, 13.9, 13.5.

MS (ES+): m/z 664.2 $[M+H]^+$, 686.3 $[M+Na]^+$.

Synthesis of 171

171

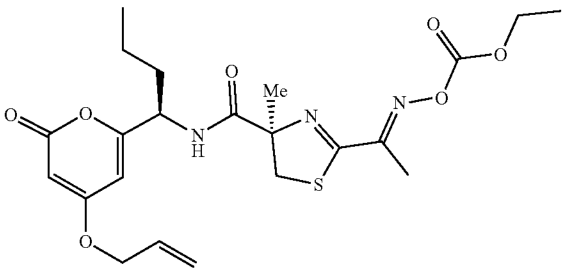

To a solution of 74 (50 mg, 0.124 mmol) in THF (1 mL) ethyl chloroformate (24 μL, 0.248 mmol) and $Et_3N$ (52 μL, 0.373 mmol) were added at 0° C. The reaction mixture was stirred at 0° C. for 1 h. Then was diluted with $H_2O$ and extracted with $CH_2Cl_2$. The combined organic layers were dried over anhydrous $Na_2SO_4$, filtered and evaporated to yield crude 171 (58 mg, 99% yield) which was used in the next step without further purification.

$^1H$ NMR (400 MHz, $(CD_3)_2CO$): δ 7.50 (d, J=8.7 Hz, 1H), 6.08-5.98 (m, 1H), 6.02 (s, 1H), 5.52-5.37 (m, 2H), 5.31 (d, J=10.6, 1H), 4.75 (td, J=8.9, 5.7 Hz, 1H), 4.61 (dt, J=5.5, 1.6 Hz, 2H), 4.32 (q, J=7.1 Hz, 2H), 3.70 (d, J=11.6 Hz, 1H), 3.31 (d, J=11.6 Hz, 1H), 2.34 (s, 3H), 1.96-1.68 (m, 2H), 1.55 (s, 3H), 1.68-1.16 (m, 5H), 0.96 (t, J=7.3 Hz, 3H).

MS (ES+): m/z 480.3 $[M+H]^+$, 502.2 $[M+Na]^+$.

Synthesis of 172

172

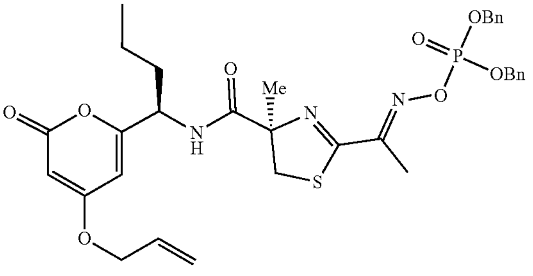

To a solution of 74 (50 mg, 0.124 mmol) in THF (1.50 mL), dibenzyl diisopropylphosphoramidite (62 μL, 0.185 mmol) and tetrazole (1.24 mL, 0.557 mmol) were added at 23° C. The reaction mixture was stirred at 23° C. for 2 h. The reaction mixture was cooled to −45° C., followed by dropwise addition of a solution of mCPBA (0.106 g, 0.618 mmol) in $CH_2Cl_2$ (1.5 mL). The reaction mixture was warmed to 23° C. and stirred for 1 h. The reaction was diluted an aqueous saturated solution of $Na_2S_2O_3$, extracted with EtOAc, and washed an aqueous saturated solution of $Na_2S_2O_3$ and with an aqueous saturated solution of $NaHCO_3$. The combined organic layers were dried over anhydrous $Na_2SO_4$, filtered and evaporated. The resulting residue was purified by combi flash in $SiO_2$ (hexane:EtOAc from 100:0 to 50:50) to afford 172 (26 mg, 32% yield).

$^1H$ NMR (400 MHz, $CD_3OD$): δ 7.92 (d, J=8.6 Hz, 1H), 7.40-7.32 (m, 10H), 6.07 (d, J=2.2 Hz, 1H), 6.05-5.89 (m, 1H), 5.51 (d, J=2.2 Hz, 1H), 5.38 (dd, J=17.3, 1.6 Hz, 1H), 5.29 (dd, J=10.5, 1.5 Hz, 1H), 5.21 (s, 2H), 5.19 (s, 2H), 4.80-4.74 (m, 1H), 4.54 (dt, J=5.6, 1.5 Hz, 2H), 3.70 (d, J=11.6 Hz, 1H), 3.36-3.17 (m, 1H), 2.22 (s, 3H), 1.97-1.71 (m, 2H), 1.55 (s, 3H), 1.55-1.21 (m, 2H), 0.98 (t, J=7.4 Hz, 3H).

$^{13}C$ NMR (125 MHz, $CD_3OD$): δ 175.6, 172.1, 167.2, 166.0, 165.3, 162.9, 162.8, 136.8, 136.7, 132.5, 129.8, 129.7, 129.6 (×3), 129.7, 129.3 (×3), 129.2, 119.5, 101.0, 89.8, 85.9, 72.1 (×2), 72.0 (×2), 71.0, 52.2, 41.2, 35.2, 24.7, 20.3, 13.8, 12.7.

MS (ES+): m/z 668.3 $[M+H]^+$, 690.2 $[M+Na]^+$.

Example 19 Synthesis of Additional Compounds of Formula I

Scheme 31 provides further examples of the synthesis of compounds of formula I

Synthesis of 173

173

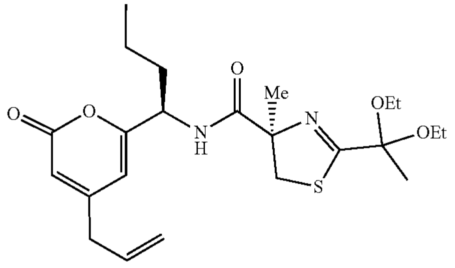

A mixture of (R)-143 (48 mg, 0.15 mmol) and (R)-39 (47 mg, 0.15 mmol) was evaporated with toluene and then HATU (58 mg, 0.15 mmol) and HOAt (21 mg, 0.15 mmol) were added. Reaction flask was evacuated, filled with $N_2$ and $CH_2Cl_2$ (1.1 mL) and DIPEA (0.1 mL, 0.6 mmol) were added via syringe at 23° C. The reaction mixture was stirred 16 h at 23° C. Then, it was diluted with $CH_2Cl_2$ before washing twice with HCl 0.5 N and once with an aqueous saturated solution of NaCl. The organic layer was dried over anhydrous $Na_2SO_4$, filtered and evaporated to dryness. The residue was purified on a system for flash chromatography on silica gel (Hex:EtOAc) to give 173 (20 mg, 68% yield).

$^1H$ NMR (400 MHz, $CDCl_3$): δ 7.12-7.04 (m, 1H), 6.45 (dq, J=15.8, 6.8 Hz, 1H), 6.19 (d, J=1.5 Hz, 1H), 6.18-6.10 (m, 1H), 5.92-5.88 (m, 1H), 4.75 (td, J=8.5, 6.5 Hz, 1H), 3.63 (d, J=11.7 Hz, 1H), 3.60-3.44 (m, 4H), 3.15 (dd, J=11.7, 0.8 Hz, 1H), 1.91 (dd, J=6.7, 1.6 Hz, 2H), 1.89-1.67 (m, 2H), 1.60 (s, 3H), 1.55 (s, 3H), 1.46-1.27 (m, 2H), 1.21 (m, 6H), 0.96-0.90 (m, 3H).

Scheme 31

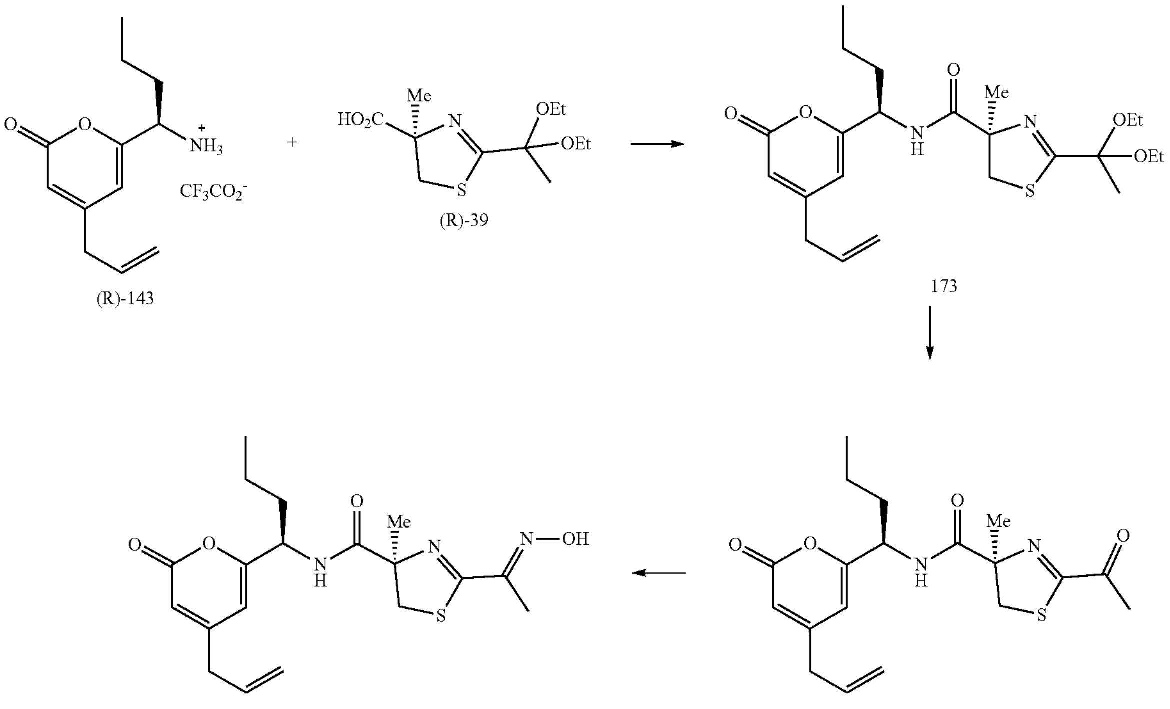

(R)-143

(R)-39

173

175

174

$^{13}C$ NMR (100 MHz, $CDCl_3$): δ 178.3, 174.1, 162.9, 161.8, 151.8, 136.2, 128.1, 109.5, 100.4, 100.3, 85.0, 58.0, 57.9, 51.3, 40.6, 35.0, 28.0, 27.0, 25.5, 23.9, 19.3, 19.0, 18.9, 17.7, 15.4, 15.3, 13.7 (×2).

MS (ES+): m/z 473.1 $[M+Na]^+$.

Synthesis of 174

174

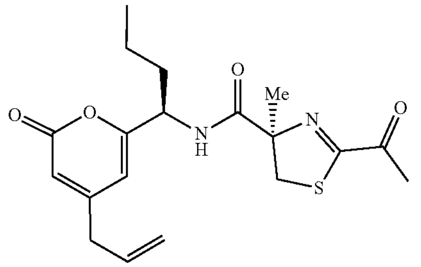

A mixture of 173 (20 mg, 0.044 mmol), pentane (1 mL) and formic acid (0.7 mL) was vigorously stirred for 2 h and the volatiles were evaporated. The crude was evaporated few times with a mixture of $CH_2Cl_2$/toluene to eliminate the acid. The crude obtained was purified by flash chromatography on silica gel (hex:EtOAc) to give 174 (6 mg, 17% yield).

$^1H$ NMR (400 MHz, $CDCl_3$): δ 7.04 (d, J=8.9 Hz, 1H), 6.46 (dq, J=15.8, 6.8 Hz, 1H), 6.31-6.08 (m, 3H), 5.94 (s, 1H), 4.85-4.70 (m, 1H), 3.64 (d, J=11.9 Hz, 1H), 3.27 (d, J=11.9 Hz, 1H), 2.56 (s, 3H), 1.93 (dd, J=6.7, 1.6 Hz, 3H), 1.90-1.59 (m, 4H), 1.55 (s, 3H), 1.49-1.23 (m, 2H), 0.97 (t, J=7.4 Hz, 3H).

MS (ES+): m/z 399.2 $[M+Na]^+$, 377.1 $[M+H]^+$.

Synthesis of 175

175

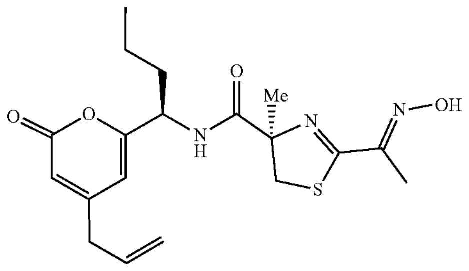

A mixture of 174 (6 mg, 0.015 mmol), EtOH (0.2 mL), $H_2O$ (0.2 mL), $NH_2OH·HCl$ (7 mg, 0.11 mmol) and NaOAc (5 mg, 0.06 mmol) was stirred at 23° C. for 24 h. Then ethanol was evaporated, a aqueous saturated solution of NaCl was added, and the aqueous phase was extracted with EtOAc. The combined organic phases were dried over anhydrous $Na_2SO_4$, filtered, an concentrated under vacuum. The crude was chromatographed over silica gel (hex:EtOAc) to afford 175 (2 mg, 34% yield).

$^1H$ NMR (400 MHz, $CD_3OD$): δ 6.66-6.52 (m, 1H), 6.41 (s, 1H), 6.29 (d, J=15.8 Hz, 1H), 5.98 (s, 1H), 4.80 (m, 1H), 3.61 (dd, J=11.5, 1.1 Hz, 1H), 3.17 (dd, J=11.5, 1.1 Hz, 1H), 2.20 (d, J=1.1 Hz, 3H), 1.92 (dt, J=6.8, 1.4 Hz, 3H), 1.92-1.79 (m, 2H), 1.57 (s, 3H), 1.34-1.13 (m, 2H), 1.00 (t, J=7.4, 3H).

$^{13}C$ NMR (100 MHz, $CD_3OD$): δ 176.5, 170.4, 165.3, 164.1, 154.5, 152.9, 138.4, 128.9, 109.5, 101.0, 85.7, 40.7, 35.4, 30.4, 25.3, 20.3, 19.0, 13.9, 11.0.

MS (ES+): m/z 399.2 $[M+Na]^+$, 377.1 $[M+H]^+$.

Example 20 Synthesis of Additional Compounds of Formula I

Scheme 32 provides further examples of the synthesis of compounds of formula I

Scheme 32

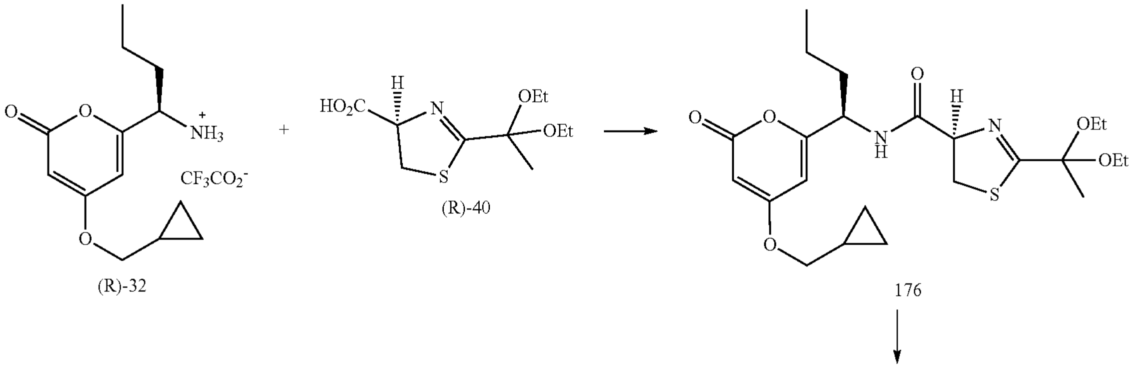

(R)-32

(R)-40

176

-continued

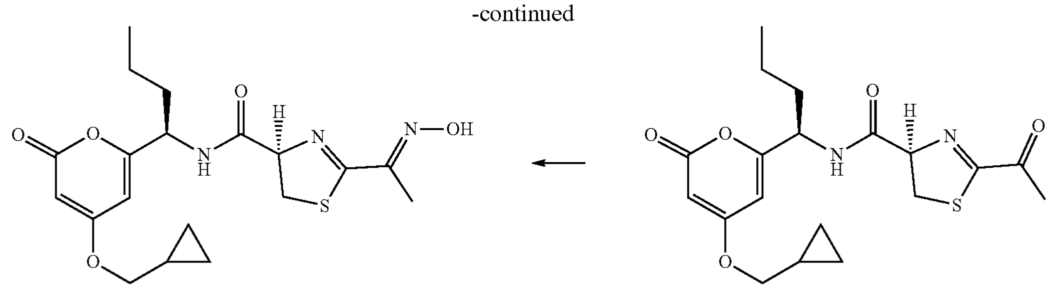

178 177

Synthesis of 176

176

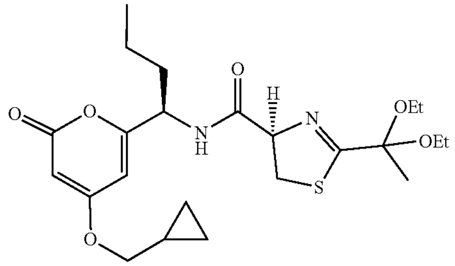

A mixture of (R)-32 (600 mg, 1.71 mmol) and (R)-40 (422 mg, 1.71 mmol) was evaporated with toluene and then HATU (649 mg, 1.71 mmol) and HOAt (234 mg, 1.71 mmol) were added. Reaction flask was evacuated, filled with $N_2$ and $CH_2Cl_2$ (12 mL) and DIPEA (1.2 mL, 6.84 mmol) were added via syringe at 23° C. The reaction mixture was stirred 16 h at 23° C. Then, it was diluted with $CH_2Cl_2$ before washing twice with HCl 0.5 N and once with an aqueous saturated solution of NaCl. The organic layer was dried over anhydrous $Na_2SO_4$, filtered and evaporated to dryness. The residue was purified on a system for flash chromatography on silica gel ($CH_2Cl_2$:EtOAc) to give 176 (660 mg, 63% yield).

$^1$H NMR (400 MHz, $CDCl_3$): δ 6.98 (d, J=8.8 Hz, 1H), 5.90-5.73 (m, 1H), 5.28 (dd, J=2.2, 1.2 Hz, 1H), 5.14 (ddd, J=10.1, 8.4, 1.3 Hz, 1H), 4.71 (td, J=8.4, 6.5 Hz, 1H), 3.71 (ddd, J=7.2, 3.2, 1.1 Hz, 2H), 3.61-3.38 (m, 5H), 1.89-1.75 (m, 1H), 1.74-1.59 (m, 1H), 1.57 (d, J=1.5 Hz, 3H), 1.42-1.25 (m, 2H), 1.24-1.11 (m, 6H), 0.89 (td, J=7.3, 1.3 Hz, 3H), 0.61 (dt, J=8.0, 1.0 Hz, 1H), 0.28 (dt, J=4.8, 1.2 Hz, 2H).

$^{13}$C NMR (100 MHz, $CDCl_3$): δ 170.8, 170.0, 164.0, 162.7, 88.7, 78.8, 77.4, 77.1, 76.8, 73.7, 57.8, 50.9, 34.6, 34.2, 23.8, 19.0, 15.2, 15.1, 13.5, 9.4, 3.3 (x2).

MS (ES+): m/z 489.2 $[M+Na]^+$.

Synthesis of 177

177

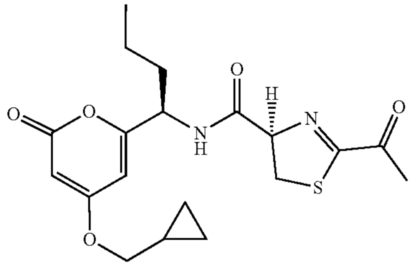

To 176 (75 mg, 0.16 mmol) was added pentane (8.4 mL) and formic acid (5.6 mL). The mixture was stirred for 1 h, and then toluene was added to quench the reaction. The volatiles were evaporated under vacuum and the crude was coevaporated with toluene twice. The crude was purified by flash chromatography on silica gel ($CH_2Cl_2$:EtOAc) to yield 177 (23 mg, 40% yield).

$^1$H NMR (400 MHz, $CDCl_3$): δ 6.99 (d, J=8.8 Hz, 1H), 5.95 (d, J=2.2 Hz, 1H), 5.35 (d, J=2.2 Hz, 1H), 5.24 (dd, J=10.9, 10.2 Hz, 1H), 4.77 (q, J=7.7 Hz, 1H), 3.77 (td, J=6.9, 1.8 Hz, 2H), 3.68-3.48 (m, 2H), 2.55 (s, 3H), 1.95-1.69 (m, 2H), 1.48-1.17 (m, 2H), 0.96 (t, J=7.3 Hz, 3H), 0.66 (dd, J=8.0, 1.2 Hz, 2H), 0.33 (td, J=4.7, 2.2 Hz, 2H).

$^{13}$C NMR (100 MHz, $CDCl_3$): δ 192.9, 172.8, 170.1, 169.4, 164.1, 161.8, 100.8, 88.9, 80.1, 73.9, 51.3, 34.8, 34.2, 26.3, 19.1, 13.6, 9.4, 3.4 (x2).

MS (ES+): m/z 393.2 $[M+H]^+$, 415.3 $[M+Na]^+$.

Synthesis of 178

178

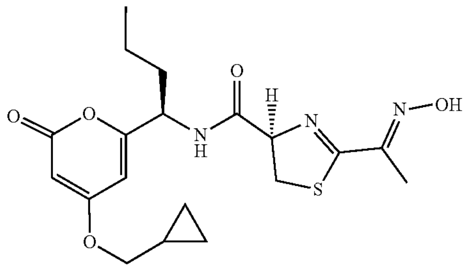

To a solution of 177 (22 mg, 0.056 mmol) in EtOH (0.6 mL) and $H_2O$ (0.6 mL), $NH_2OH·HCl$ (10 mg, 0.14 mmol)

and NaOAc (20 mg, 0.24 mmol) were added at 23° C. and was stirred at 23° C. overnight. Then ethanol was evaporated. The aqueous residue was diluted with brine and extracted with EtOAc. The combined organic layers were dried over anhydrous $Na_2SO_4$, filtered and evaporated. The resulting residue was purified by combi flash on silica gel ($CH_2Cl_2$:EtOAc) to afford 178 (14 mg, 61% yield).

$^1$H NMR (400 MHz, $CD_3OD$): δ 6.17 (dd, J=2.2, 0.8 Hz, 1H), 5.50 (d, J=2.2 Hz, 1H), 5.17 (d, J=9.4 Hz, 1H), 4.73 (dd, J=9.3, 5.5 Hz, 1H), 3.88 (dd, J=8.4, 7.2 Hz, 2H), 3.54-3.35 (m, 2H), 2.16 (d, J=3.1 Hz, 3H), 1.96-1.70 (m, 2H), 1.59-1.34 (m, 2H), 0.98 (dt, J=10.4, 7.3 Hz, 3H), 0.71-0.60 (m, 2H), 0.44-0.30 (m, 2H).

$^{13}$C NMR (100 MHz, $CD_3OD$): δ 171.4, 171.3, 170.9, 165.5, 164.0, 151.5, 99.7, 87.7, 78.7, 74.0, 73.9, 50.9, 33.8, 32.7, 18.8, 12.4, 9.6, 9.0, 2.2.

MS (ES+): m/z 408.2 $[M+H]^+$, 430.1 $[M+Na]^+$.

Example 21 Synthesis of Additional Compounds of Formula I

Scheme 33 provides further examples of the synthesis of compounds of formula I

Scheme 33

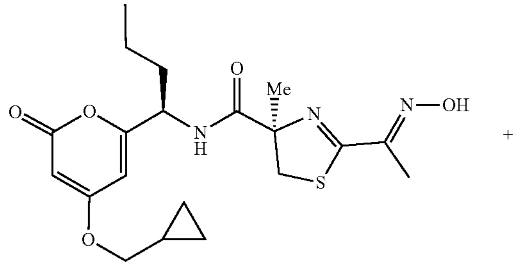

76

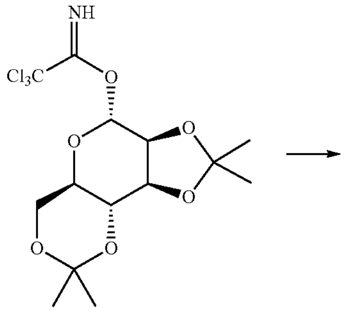

109

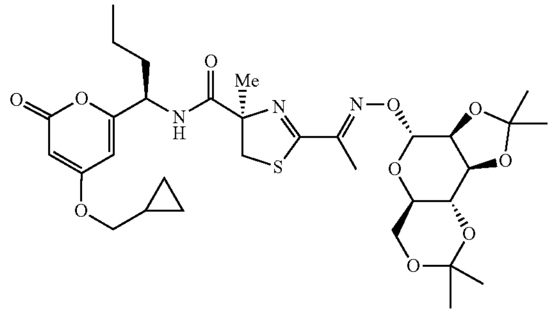

179

Synthesis of 179

A freshly-prepared stock solution (700 μL; 5% mol) of $Pd(PhCN)(OTf)_2$ catalyst in $CH_2Cl_2$, prepared by stirring $Pd(PhCN)_2Cl_2$ (9 mg; 0.024 mmol) and AgOTf (12 mg; 0.047 mmol) in $CH_2Cl_2$ (3.5 mL) at 23° C. for 5 min, was added to a solution of 109 (37 mg; 0.0091 mmol) and 76 (50 mg; 0.139 mmol) in $CH_2Cl_2$, (500 μL) at 23° C. The reaction mixture was stirred at 23° C. overnight, then, treated with benzene (1 mL) and directly poured on a chromatographic column ($SiO_2$, $CH_2Cl_2$:MeOH from 10:0 to 98.2:1.8). According to this procedure, 179 (31 mg, 51% yield) was afforded as a foamy white solid (predominantly as a α anomer).

$^1$H NMR (400 MHz, $CDCl_3$): δ 9.38 (s, 1H), 7.14 (dd, J=8.8, 2.9 Hz, 1H), 5.93 (dd, J=4.3, 2.1 Hz, 1H), 5.67 (s, 1H), 5.37 (t, J=2.2 Hz, 1H), 4.91 (dd, J=6.0, 3.9 Hz, 1H), 4.87 (d, J=5.9 Hz, 1H), 4.73 (q, J=8.5, 7.9 Hz, 1H), 4.38 (dt, J=7.8, 5.2 Hz, 1H), 4.22 (dd, J=7.7, 3.8 Hz, 1H), 4.08 (brs, 1H), 4.07 (s, 1H), 3.84-3.69 (m, 2H), 3.52 (d, J=11.6 Hz, 1H), 3.22 (dd, J=11.6, 2.3 Hz, 1H), 2.22 (s, 3H), 2.19 (s, 3H), 1.93-1.71 (m, 2H), 1.51 (s, 3H), 1.49 (s, 3H), 1.45 (s, 3H), 1.37 (s, 3H), 1.35 (s, 3H), 1.45-1.30 (m, 1H), 1.30-1.12 (m, 1H), 0.95 (t, J=7.3 Hz, 3H), 0.66 (m, 2H), 0.33 (dt, J=6.0, 4.7 Hz, 2H).

$^{13}$C NMR (100 MHz, $CDCl_3$): δ 174.3, 174.1, 170.3, 170.2, 168.2, 167.5, 164.5, 164.4, 162.4, 162.2, 153.8, 153.1, 112.9, 109.3, 109.0, 108.9, 100.9, 100.7 (×2), 100.6, 89.1 (×2), 89.0 (×2), 84.8, 84.6 (×2), 84.4, 83.3, 83.2, 80.1, 79.8, 74.1, 74.0, 73.8, 73.5, 66.8, 51.2, 51.1, 40.0, 39.9 (×2), 35.0, 34.9, 27.1, 27.0, 26.1, 26.0, 25.3, 25.2, 24.9, 24.8, 24.7, 24.6, 24.5, 19.2, 13.7 (×2), 12.2 (×2), 11.4, 11.3, 9.6, 9.5, 3.5 (×2).

MS (ES+): m/z 664.2 $[M+H]^+$, 686.3 $[M+Na]^+$.

Scheme 34 provides an example of the synthesis of an additional compound of formula I.

Scheme 34

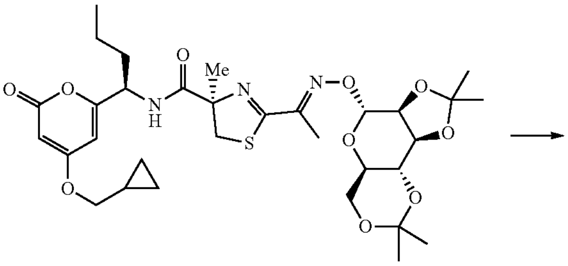

179

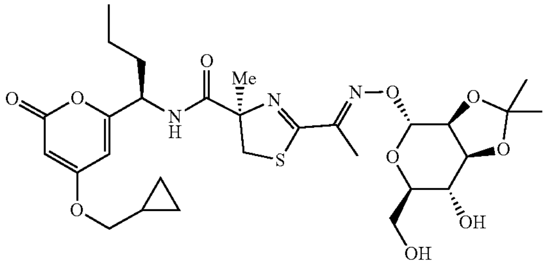

180

Synthesis of 180

179 (30 mg; 0.045 mmol) was dissolved in a mixture of TFA:$CHCl_3$:$H_2O$ (2.5:100:1, 1.1 mL) and stirred for 5 h at 23° C. Then, the solution was diluted with toluene (1.5 mL) and the volatiles vacuum co-evaporated, affording oily beige crude. 180 (18 mg, 66% yield) was obtained by purification over flash chromatography on silica gel ($CH_2Cl_2$:MeOH from 100:0 to 90:10) as a waxy solid.

$^{1}H$ NMR (500 MHz, $CDCl_3$): δ 7.07 (d, J=8.7 Hz, 1H), 5.94 (d, J=2.0 Hz, 1H), 5.72 (s, 1H), 5.36 (d, J=2.1 Hz, 1H), 5.01 (dd, J=5.9, 4.2 Hz, 1H), 4.89 (d, J=5.9 Hz, 1H), 4.72 (m, 1H), 4.25 (dd, J=8.7, 4.2 Hz, 1H), 3.97 (m, 1H), 3.86 (d, J=11.5, 3.4 Hz, 1H), 3.75 (m, 3H), 3.54 (d, J=11.6 Hz, 1H), 3.21 (d, J=11.6 Hz, 1H), 2.20 (s, 3H), 1.90-1.72 (m, 2H), 1.52 (s, 6H), 1.37 (s, 3H), 1.42-1.31 (m, 2H), 1.22 (m, 1H), 0.96 (t, J=7.4 Hz, 3H), 0.64 (m, 2H), 0.34 (m, 2H).

$^{13}C$ NMR (125 MHz, $CDCl_3$): δ 173.8, 170.1, 167.5, 164.3, 162.1, 153.8, 112.8, 108.6, 100.7, 88.9, 84.5, 84.4, 82.5, 80.5, 73.8, 70.7, 64.3, 51.0, 39.9, 34.8, 29.7, 25.9, 24.8, 24.5, 19.0, 13.6, 12.1, 9.4, 3.4 (×2).

MS (ES+): m/z 624.2 $[M+H]^+$, 646.3 $[M+Na]^+$.

$R_f$: 0.39 ($CH_2Cl_2$:MeOH 15:1).

Scheme 35 provides an example of the synthesis of an additional compound of formula I.

Scheme 35

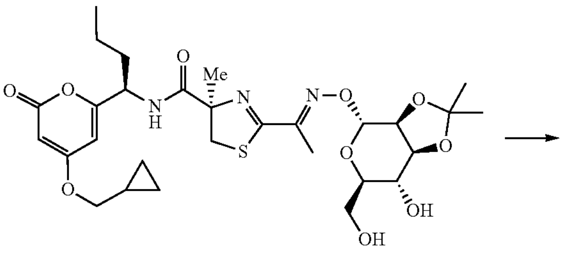

180

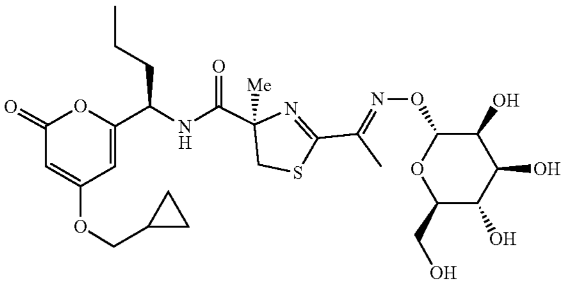

181

Synthesis of 181

A solution of 180 (17 mg; 0.027 mmol) in aqueous AcOH (80%, 1.0 mL) was heated for 4.5 h at 80° C. Then, when cooled down, diluted with toluene (1.5 mL) and the volatiles vacuum evaporated giving an oily beige crude. 181 (14.6 mg, 92% yield) was obtained by purification over flash chromatography on silica gel ($CH_2Cl_2$:MeOH from 100:0 to 90:10) as a pale yellow solid.

$^{1}H$ NMR (500 MHz, $(CD_3)_2SO$): δ 7.90 (d, J=8.5 Hz, 1H), 6.03 (d, J=2.2 Hz, 1H), 5.49 (d, J=2.2 Hz, 1H), 5.46 (d, J=4.8 Hz, 1H), 5.26 (bd, J=5.3 Hz, OH), 4.98 (bs, OH), 4.65 (bs, OH), 4.60 (q, J=7.8 Hz, 1H), 4.41 (bs, OH), 4.16 (m, 1H), 4.07 (bs, 1H), 3.92 (dd, J=8.3, 2.7 Hz, 1H), 3.85 (m, 1H), 3.71 (bs, 1H), 3.57-3.49 (m, 2H), 3.21 (d, J=11.6 Hz, 1H), 2.19 (s, 3H), 1.75 (q, J=7.6 Hz, 2H), 1.45 (s, 3H), 1.43-1.24 (m, 2H), 1.18 (m, 1H), 0.90 (t, J=7.4 Hz, 3H), 0.57 (dt, J=9.7, 3.1 Hz, 2H), 0.30 (dt, J=6.0, 4.2 Hz 2H).

$^{13}C$ NMR (100 MHz, $(CD_3)_2SO$): δ 172.6, 170.0, 165.9, 164.7, 163.1, 153.2, 111.0, 98.6, 88.0, 84.2, 81.0, 75.4, 73.5, 70.9, 69.1, 63.1, 50.3, 39.6, 33.5, 24.0, 18.8, 13.4, 12.3, 9.4, 3.1.

MS (ES+): m/z 584.2 $[M+H]^+$, 606.3 $[M+Na]^+$.

$R_f$: 0.16 ($CH_2Cl_2$:MeOH 15:1).

Example 22 Synthesis of Additional Compounds of Formula I

Scheme 36 provides further examples of the synthesis of compounds of formula I

Scheme 36

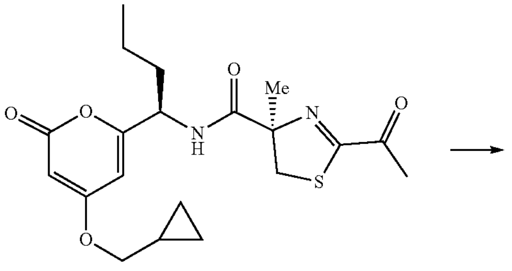

65

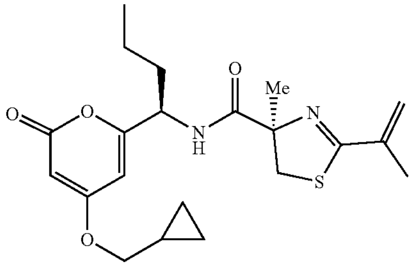

182

To a solution of Methyltriphenylphosphonium bromide (58 mg, 0.28 mmol) in THF (0.7 mL) was added nBuLi (0.175 mL, 1.6 M, 0.28 mmol) dropwise at 23° C. The yellow suspension was stirred for 2.5 h and a solution of 65 (55 mg, 0.14 mmol) in THF (0.4 mL) was added. After 2 h the reaction was refluxed for 3 h and then overnight at 23° C. The reaction was quenched with an aqueous saturated solution of $NH_4Cl$ and extracted with $CH_2Cl_2$. The crude was purified by flash chromatography on silica gel ($CH_2Cl_2$: EtOAc) to give a fraction (7 mg) that contained 182. This fraction was then purified by flash chromatography on silica gel (hexane:EtOAc) to give 182 (4 mg, 7% yield).

$^{1}H$ NMR (400 MHz, $CDCl_3$): δ 7.12 (d, J=8.6 Hz, 1H), 5.91 (dt, J=2.2, 0.5 Hz, 1H), 5.65 (d, J=1.4 Hz, 1H), 5.56 (d, J=1.6 Hz, 1H), 5.34 (d, J=2.2 Hz, 1H), 4.71 (q, J=7.8 Hz, 1H), 3.83-3.68 (m, 2H), 3.64-3.53 (m, 1H), 3.24 (dd, J=11.5, 0.6 Hz, 1H), 2.09 (dt, J=1.5, 0.7 Hz, 3H), 1.95-1.66 (m, 2H), 1.51 (s, 3H), 1.44-1.18 (m, 3H), 1.00-0.90 (m, 3H), 0.73-0.57 (m, 2H), 0.33 (q, J=5.2 Hz, 2H).

MS (ES+): m/z 405.2 $[M+H]^+$, 427.3 $[M+Na]^+$.

Scheme 37 provides a further example of the synthesis of compounds of formula I

Scheme 37

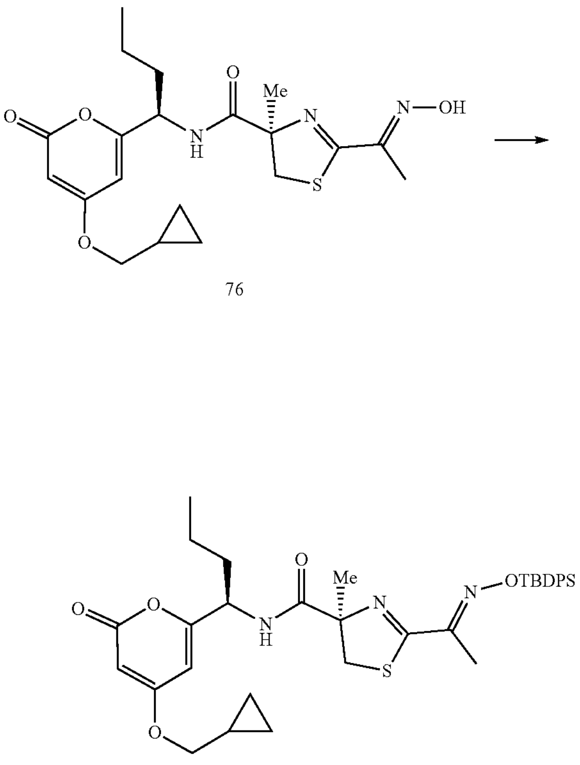

76

183

To a solution of 76 (80 mg, 0.19 mmol) in DMF (0.2 mL) was added slowly ClTBDPS (52 μL, 0.199 mmol) and then a crystal of DMAP at 23° C. The reaction mixture was stirred at 23° C. overnight. Then was quenched by dilution with $CH_2Cl_2$, washed with 0.5M HCl and an aqueous saturated solution of NaCl. The organic layers were dried over anhydrous $Na_2SO_4$, filtered and concentrated under vacuum. The crude obtained was purified by flash chromatography on silica gel ($CH_2Cl_2$:EtOAc) to afford 183 (119 mg, 91% yield).

$^1H$ NMR (400 MHz, $CD_3OD$): δ 7.73-7.64 (m, 4H), 7.46-7.30 (m, 6H), 6.06 (dd, J=2.2, 0.7 Hz, 1H), 5.46 (d, J=2.2 Hz, 1H), 4.80-4.70 (m, 1H), 3.80 (dd, J=7.2, 3.0 Hz, 2H), 3.57 (d, J=11.6 Hz, 1H), 3.15 (d, J=11.5 Hz, 1H), 2.40 (s, 3H), 1.90-1.75 (m, 2H), 1.53 (s, 3H), 1.51-1.16 (m, 2H), 1.12 (s, 9H), 0.97 (t, J=7.4 Hz, 3H), 0.72-0.39 (m, 2H), 0.30 (dt, J=4.7, 1.3 Hz, 2H).

$^{13}C$ NMR (100 MHz, $CD_3OD$): δ 176.2, 172.6, 166.7, 165.3, 159.1, 136.5, 134.1, 131.1, 128.8, 101.1, 89.3, 85.8, 75.3, 61.5, 52.3, 40.7, 35.3, 27.6, 25.0, 20.4, 20.3, 14.5, 13.9, 12.0, 10.4, 3.7.

MS (ES+): m/z 660.3 $[M+H]^+$, 682.3 $[M+Na]^+$.

Scheme 38 provides a further example of the synthesis of compounds of formula I

Scheme 38

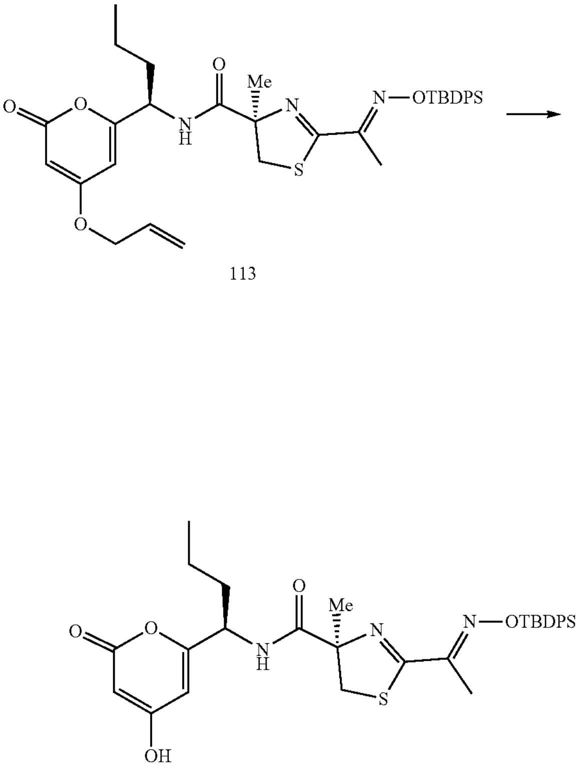

113

184

To a solution of 113 (106 mg) in $CH_2Cl_2$ (4.1 mL) was added tetrakis(triphenylphosphine)palladium(0) (9 mg), acetic acid (47 μL) and tributyltin hydride (265 μL). The reaction mixture was stirred for 30 minutes and poured over a silica gel column to purify. Elution with hexane:EtOAc from 100:0 to 0:100 gave 184 (>100% yield).

$^1H$ NMR (400 MHz, $CDCl_3$): δ 7.76-7.67 (m, 4H), 7.45-7.32 (m, 6H), 6.13 (d, J=2.1 Hz, 1H), 5.59 (d, J=2.1 Hz, 1H), 4.70 (q, J=7.9 Hz, 1H), 3.37 (d, J=11.6 Hz, 1H), 3.15 (d, J=11.6 Hz, 1H), 2.35 (s, 3H), 1.99-1.77 (m, 2H), 1.49 (s, 3H), 1.45-1.27 (m, 2H), 1.15 (s, 9H), 0.96 (t, J=7.3 Hz, 3H).

$^{13}C$ NMR (100 MHz, $CD_3OD$): δ 175.4, 170.5, 169.1, 165.7, 162.5, 157.1, 135.5, 132.8, 132.7, 129.9, 127.6 (×2), 101.4, 91.3, 83.9, 51.6, 39.5, 34.3, 27.1, 24.5, 19.5, 19.1, 13.6, 11.8.

Example 23 Synthesis of Additional Compounds of Formula I

Scheme 39 provides further examples of the synthesis of compounds of formula I

Scheme 39

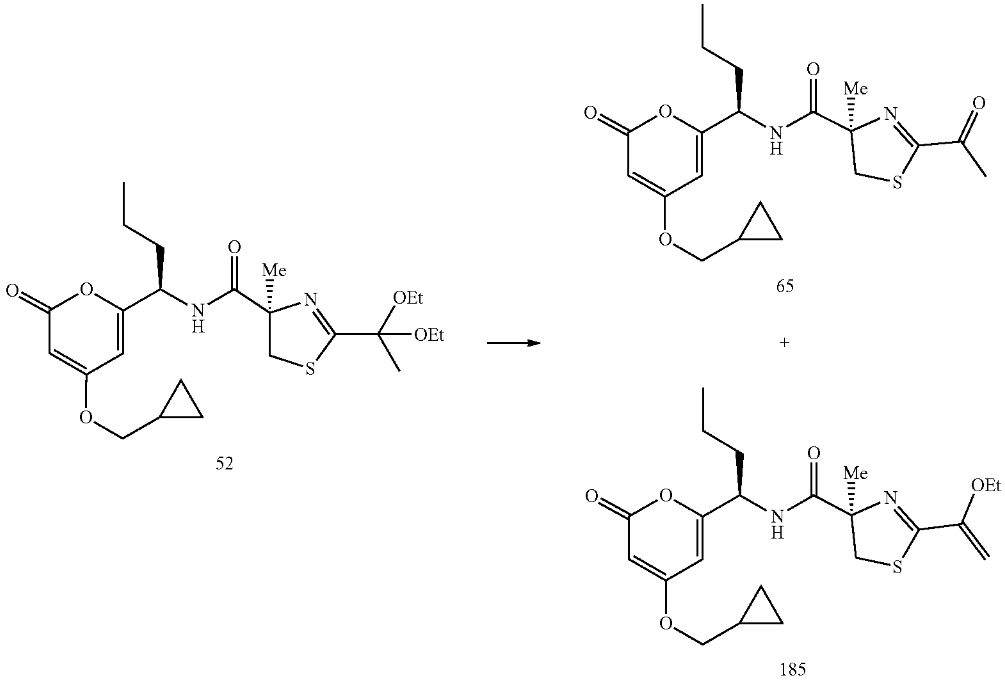

52

65

+

185

Synthesis of 185

A mixture of 52 (138 mg, 0.29 mmol) and HCl in 1,4-dioxane (4 mL, 4 M, 16 mmol) was stirred for 60 min at 23° C. and the volatiles were evaporated to dryness. The crude was coevaporated few times with toluene to eliminate the acid. The resulting residue was purified in preparative HPLC to yield 65 (30 mg, 25%) and 185 (15 mg, 12%), while 50 mg of starting material was recovered.

$^{1}$H NMR (500 MHz, $CDCl_3$): δ 7.07 (d, J=8.7 Hz, 1H), 5.91 (d, J=2.2 Hz, 1H), 5.35 (d, J=2.2 Hz, 1H), 5.10 (d, J=2.9 Hz, 1H), 4.72 (td, J=8.4, 6.6 Hz, 1H), 4.45 (d, J=2.9 Hz, 1H), 3.90 (q, J=7.0 Hz, 2H), 3.83-3.69 (m, 2H), 3.60 (d, J=11.6 Hz, 1H), 3.22 (d, J=11.6 Hz, 1H), 1.92-1.87 (m, 1H), 1.76-1.71 (m, 1H), 1.54 (s, 3H), 1.40 (t, J=7.0 Hz, 3H), 1.45-1.30 (m, 2H), 1.27-1.19 (m, 1H), 0.95 (t, J=7.4 Hz, 3H), 0.75-0.51 (m, 2H), 0.37-0.22 (m, 2H).

$^{13}$C NMR (125 MHz, $CDCl_3$): δ 174.4 170.1, 167.2, 164.3, 162.8, 153.5, 100.2, 90.4, 88.8, 84.8, 73.7, 64.5, 51.0, 40.7, 34.6, 29.7, 24.6, 19.0, 14.7, 13.6, 9.4, 3.4.

MS (ES+): m/z 435.2 $[M+H]^+$, 457.3 $[M+Na]^+$.

Example 24 Synthesis of Additional Intermediates of Formula II

Scheme 40 provides a further example of the synthesis of intermediates of formula II Scheme 40

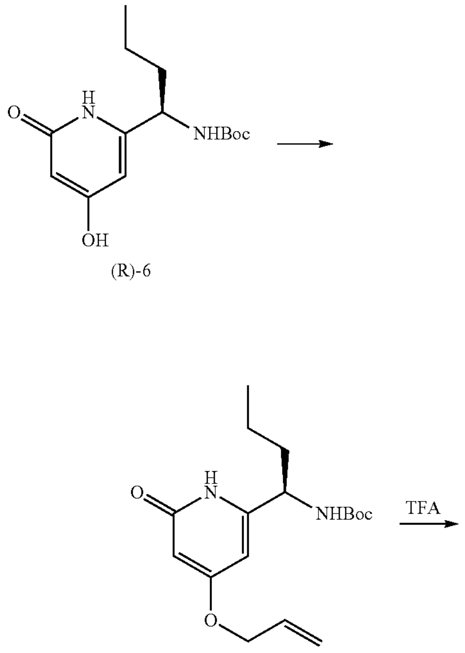

(R)-6

(R)-186

-continued

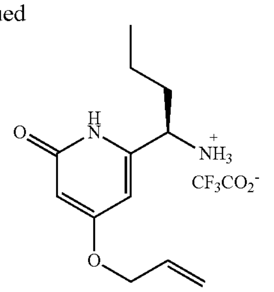

(R)-187

Synthesis of (R)-186

(R)-186

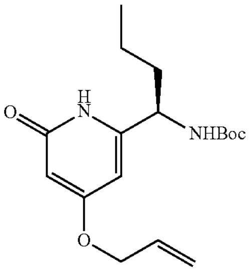

To a suspension of (R)-6 (50 mg, 0.2 mmol) in acetone (4 mL) and $K_2CO_3$ (37 mg, 0.3 mmol) was added 3-bromoprop-1-ene (15 μL, 0.2 mmol) dropwise at 23° C. The reaction mixture was stirred at 40° C. for 23 h, cooled to 23° C. and filtered. The filtrate was evaporated to dryness and the residue was dissolved in EtOAc, washed with $H_2O$ (2×100 mL) and an aqueous saturated solution of NaCl. The organic layer was dried over anhydrous $Na_2SO_4$, filtrated and concentrated under vacuum to give a crude, which upon column chromatography ($SiO_2$, EtOAc) gave (R)-186 (16 mg, 29% yield).

$^1$H NMR (400 MHz, $CD_3OD$): δ 7.16 (d, J=8.2 Hz, 1H), 6.10-5.95 (m, 2H), 5.78 (d, J=2.4 Hz, 1H), 5.41 (dq, J=17.3, 1.7 Hz, 1H), 5.30 (dq, J=10.5, 1.4 Hz, 1H), 5.04-4.94 (m, 2H), 4.56 (dt, J=5.5, 1.6 Hz, 1H), 4.39 (s, 1H), 1.62 (tt, J=13.7, 6.2 Hz, 2H), 1.44 (s, 9H), 1.32-1.20 (m, 2H), 0.95 (t, J=7.4 Hz, 3H).

$^{13}$C NMR (10 MHz, $CD_3OD$): δ 170.9, 167.9, 152.9, 136.6, 133.3, 118.6, 99.0, 96.6, 80.8, 70.2, 53.4, 37.7, 28.7, 20.5, 13.9.

MS (ES+): m/z 323.3 $[M+H]^+$.

$R_f$: 0.18 (EtOAc).

Synthesis of (R)-187

(R)-187

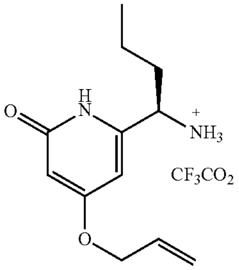

To a solution of (R)-146 (658 mg, 2.04 mmol) in $CH_2Cl_2$ (7.2 mL) was added TFA (24.5 mL). After being stirred for 2 h at 23° C., the reaction mixture was evaporated to dryness to obtain crude (R)-187 (652 mg, 95% yield) which was used in the next step without further purification.

$^1$H NMR (400 MHz, $CD_3OD$): δ 6.53 (s, 1H), 6.27 (d, J=1.9 Hz, 1H), 6.11-5.93 (m, 3H), 5.48-5.37 (m, 2H), 5.36-5.26 (m, 2H), 5.04-4.91 (m, 1H), 4.68 (d, J=4.9 Hz, 1H), 4.64-4.56 (m, 3H), 4.16 (dt, J=14.6, 7.3 Hz, 2H), 3.37-3.25 (m, 7H), 1.97-1.82 (m, 4H), 1.43 (dd, J=13.9, 7.1 Hz, 1H), 1.41-1.28 (m, 1H), 1.29 (s, 1H), 1.25-1.13 (m, OH), 1.05-0.84 (m, 7H).

Example 25 Synthesis of Additional Compounds of Formula I

Scheme 41 provides a further example of the synthesis of compounds of formula I

Scheme 41

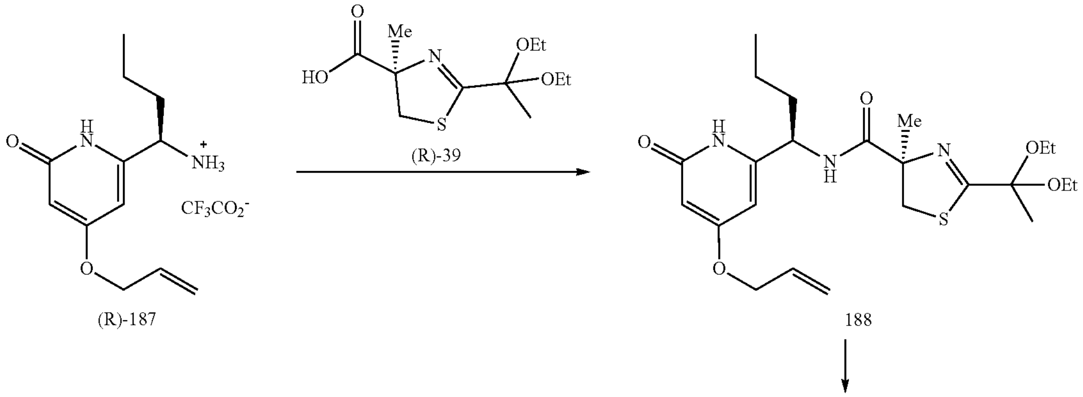

(R)-39

(R)-187

188

-continued

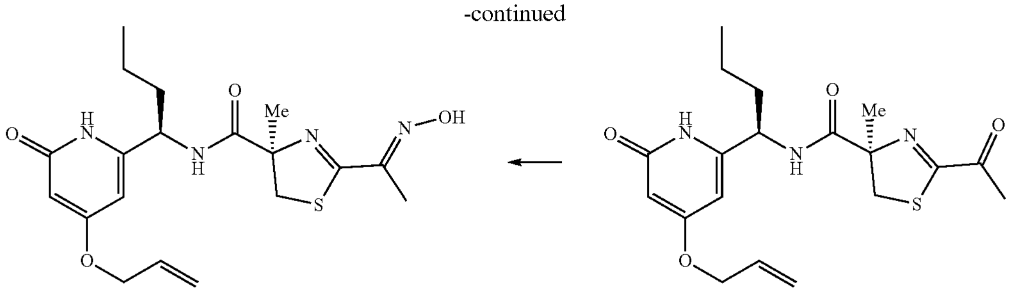

190 189

Synthesis of 188

188

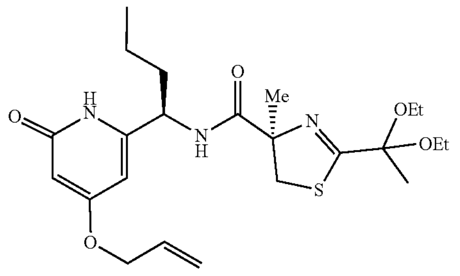

A mixture of (R)-187 (552 mg, 1.7 mmol) and (R)-39 (452 mg, 1.7 mmol) was evaporated with toluene and then HATU (657 mg, 1.7 mmol) and HOAt (237 mg, 1.7 mmol) were added. Reaction flask was evacuated, filled with $N_2$ and $CH_2Cl_2$ (12 mL) and DIPEA (1.2 mL, 6.9 mmol) were added via syringe. The mixture was stirred 16 h at 23° C. Then, it was diluted with $CH_2Cl_2$ before washing twice with HCl 0.5 N and once with an aqueous saturated solution of NaCl. The organic layer was dried over anhydrous $Na_2SO_4$, filtered and evaporated to dryness. The residue was purified on a system for flash chromatography on silica gel ($CH_2Cl_2$:EtOAc) to afford 188 (517 mg, 64% yield).

$^1H$ NMR (400 MHz, $CD_3OD$): δ 6.09 (dd, J=2.4, 0.5 Hz, 1H), 6.08-5.96 (m, 1H), 5.79 (d, J=2.3 Hz, 1H), 5.45-5.35 (m, 1H), 5.33-5.25 (m, 1H), 4.72-4.66 (m, 1H), 4.59-4.55 (m, 2H), 3.69-3.46 (m, 4H), 3.23 (d, J=11.8, 1H), 1.84-1.67 (m, 2H), 1.60 (s, 3H), 1.44 (s, 3H), 1.48-1.32 (m, 2H), 1.20 (m, 6H), (0.94 (t, J=7.4 Hz, 3H).

Synthesis of 189

189

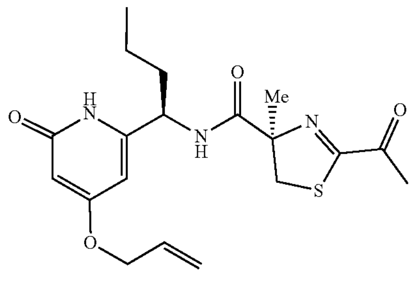

A mixture of 188 (517 mg, 1.11 mmol), pentane (27 mL) and formic acid (18 mL) was vigorously stirred for 2 h and the volatiles were evaporated. The crude was evaporated few times with a mixture of $CH_2Cl_2$/toluene to eliminate formic acid. The crude mixture was purified by silica gel column chromatography ($CH_2Cl_2$:EtOAc) to give 189 (350 mg. 80% yield).

$^1H$ NMR (400 MHz, $CD_3OD$): δ 6.08-5.93 (m, 2H), 5.77 (d, J=2.4 Hz, 1H), 5.45-5.34 (m, 1H), 5.34-5.24 (m, 1H), 4.78 (m, 1H), 4.54 (dt, J=5.5, 1.6 Hz, 2H), 3.66-3.60 (m, 1H), 3.31-3.27 (m, 1H), 2.56 (m, 2H), 1.56 (s, 3H), 1.49-1.25 (m, 2H), 1.01-0.96 (m, 3H).

Synthesis of 190

190

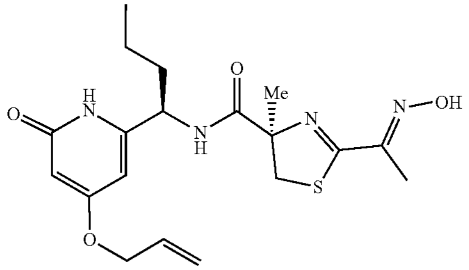

A mixture of 189 (346 mg, 0.88 mmol), ethanol (9.7 mL), $H_2O$ (9.7 mL), hydroxylamine hydrochloride (430 mg, 6.2 mmol) and NaOAc (290 mg, 3.5 mmol) was stirred at 23° C. for 24 h. Then ethanol was evaporated, an aqueous saturated solution of NaCl was added, and the aqueous phase was extracted with EtOAc. The combined organic phases were dried over anhydrous $Na_2SO_4$, filtered and concentrated under vacuum. The crude was chromatographed over silica gel ($CH_2Cl_2$:Methanol) to give 190 (242 mg, 67% yield).

$^1H$ NMR (400 MHz, $CD_3OD$): δ 6.13-5.94 (m, 2H), 5.77 (dd, J=2.4, 1.1 Hz, 1H), 5.39 (dp, J=17.2, 1.5 Hz, 1H), 5.29 (dp, J=10.6, 1.4 Hz, 1H), 4.76 (dd, J=9.0, 6.3 Hz, 1H), 4.54 (dt, J=5.3, 1.5 Hz, 2H), 3.48 (dd, J=11.5, 1.1 Hz, 1H), 3.18 (dd, J=11.5, 1.1 Hz, 1H), 2.20 (d, J=1.2 Hz, 3H), 1.92-1.73 (m, 2H), 1.52 (d, J=1.1 Hz, 3H), 1.52-1.36 (m, 1H), 1.40-1.27 (m, 2H), 0.99 (td, J=7.4, 1.1 Hz, 3H).

$^{13}C$ NMR (100 MHz, $CDCl_3$): δ 176.7, 170.7, 170.5, 167.9, 152.9, 151.1, 133.3, 118.6, 99.9, 97.0, 85.5, 70.2, 52.3, 40.7, 36.7, 24.8, 20.5, 13.8, 11.0.

MS (ES+): m/z 407.1 $[M+H]^+$.

$R_f$: 0.33 ($CH_2Cl_2$:MeOH 9:1).

Scheme 42 provides further examples of the synthesis of compounds of formula I.

Scheme 42

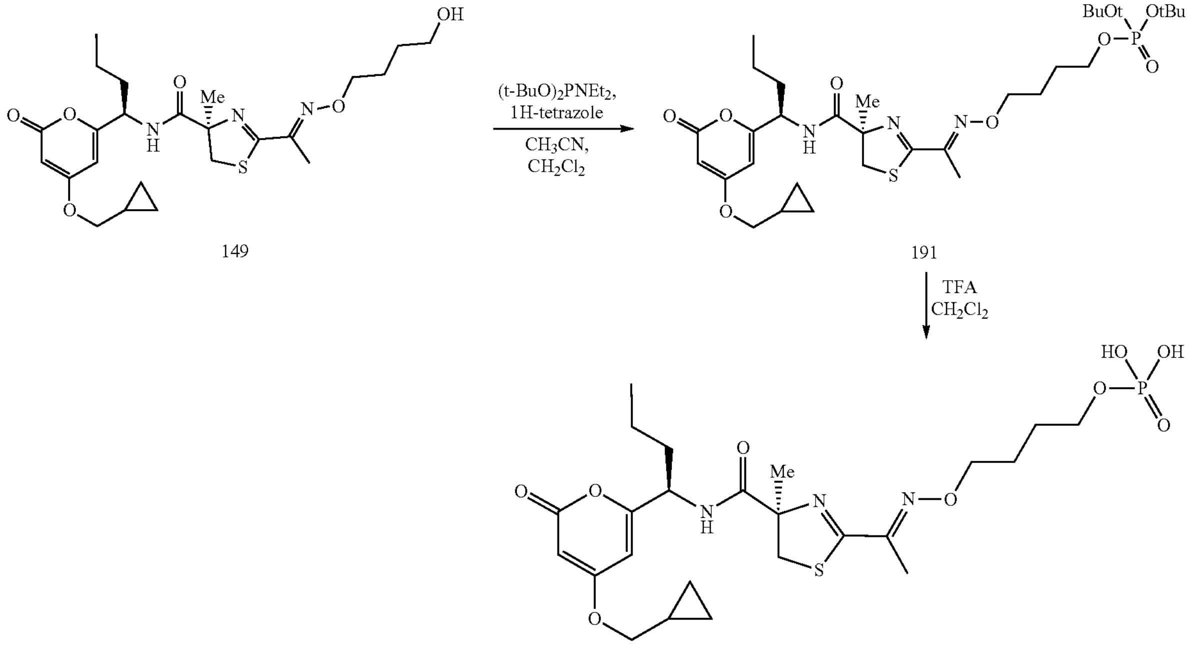

149 191 192

Synthesis of 191

To a solution of 149 (54 mg, 0.110 mmol) in anhydrous $CH_3CN$ (4.50 mL) and anhydrous $CH_2Cl_2$ (4.50 mL), 1H-tetrazole (3 mL, 1.317 mmol) and $(tBuO)_2PNEt_2$ (0.150 mL, 0.550 mmol) were added at 23° C. The reaction mixture was stirred at 23° C. for 1 h, then 70% tBuOOH solution (2.20 mL, 15.37 mmol) was added and the mixture was stirred at 23° C. overnight. An 10% aqueous solution of $NaHSO_3$ (5 mL) was added and the mixture was stirred for 15 min. The mixture was extracted with $CH_2Cl_2$ (3×10 mL) and washed with $H_2O$ (1×10 mL). The organic extract was dried over anhydrous $Na_2SO_4$, filtered and evaporated. The resulting residue was purified by combiflash in $SiO_2$ (from $CH_2Cl_2$ to $CH_2Cl_2$:EtOAc 1:1) to yield 191 (50 mg, 67% yield).

$^1H$ NMR (400 MHz, $CD_3OD$): δ 6.06 (d, J=2.2 Hz, 1H), 5.48 (d, J=2.2 Hz, 1H), 4.74 (dd, J=9.1, 5.9 Hz, 1H), 4.25 (t, J=5.9 Hz, 2H), 4.01 (q, J=6.2 Hz, 2H), 3.86 (d, J=7.1 Hz, 2H), 3.58 (d, J=11.5 Hz, 1H), 3.20 (d, J=11.6 Hz, 1H), 2.20 (s, 3H), 1.88-1.75 (m, 6H), 1.52 (s, 3H), 1.47 (s, 18H), 1.44-1.10 (m, 3H), 0.98 (t, J=7.4 Hz, 3H), 0.76-0.50 (m, 2H), 0.44-0.27 (m, 2H).

$^{13}C$ NMR (100 MHz, $CD_3OD$): δ 174.8, 171.2, 168.0, 165.3, 163.8, 151.6, 99.7, 87.9, 84.2, 82.8, 82.7, 74.5, 73.9, 66.7, 66.7, 50.7, 39.2, 33.9, 28.8 (×2), 26.5, 26.4, 25.3, 23.5, 18.9, 12.5, 10.4, 9.0, 2.3.

MS (ES+): m/z 686.2 $[M+H]^+$.

Synthesis of 192

To a solution of 191 (150 mg, 0.219 mmol) in $CH_2Cl_2$ (13 mL) TFA (0.385 mL, 5.03 mmol) was added. The reaction mixture was stirred at 23° C. for 1 h. The mixture was evaporated to dryness, and coevaporated several times with toluene. The resulting residue was purified in preparative HPLC (SunFire from 5% to 100% $CH_3CN$+0.04% TFA) to yield 192 (110 mg. 88% yield).

$^1H$ NMR (500 MHz, $CD_3OD$): δ 7.87 (d, J=8.6 Hz, 1H), 6.06 (d, J=2.2 Hz, 1H), 5.50 (d, J=2.3 Hz, 1H), 4.78-4.68 (m, 1H), 4.26 (t, J=6.2 Hz, 2H), 4.08-3.96 (m, 2H), 3.88 (d, J=7.1 Hz, 2H), 3.59 (d, J=11.5 Hz, 1H), 3.20 (d, J=11.5 Hz, 1H), 2.22 (s, 3H), 1.94-1.71 (m, 6H), 1.54 (s, 3H), 1.52-1.46 (m, 1H), 1.43-1.37 (m 1H), 1.28-1.21 (m, 1H), 0.99 (t, J=7.4 Hz, 3H), 0.70-0.60 (m, 2H), 0.41-0.32 (m, 2H).

$^{13}C$ NMR (125 MHz, $CD_3OD$): δ 174.9, 171.3, 168.0, 165.4, 163.8, 151.7, 99.7, 87.8, 84.3, 74.5, 73.9, 65.9 (×2), 50.7, 39.3, 33.8, 26.7, 26.6, 25.1, 23.5, 18.8, 12.4, 10.3, 8.9, 2.2.

MS (ES+): m/z 574.2 $[M+H]^+$, 596.2 $[M+Na]^+$.

Example 26. Bioassays for the Detection of Antitumor Activity

The aim of this assay is to evaluate the in vitro cytostatic (ability to delay or arrest tumor cell growth) or cytotoxic (ability to kill tumor cells) activity of the samples being tested.

Cell Lines

| Name | No ATCC (when applicable) | Species | Tissue | Characteristics |
|---|---|---|---|---|
| A549 | CCL-185 | human | lung | lung carcinoma (NSCLC) |
| HT29 | HTB-38 | human | colon | colorectal adenocarcinoma |
| MDA-MB-231 | HTB-26 | human | breast | breast adenocarcinoma |
| PSN-1 | Ref. 1 | human | pancreas | pancreatic adenocarcinoma |

Ref. 1 Yamada, T. et al. (1986) Estabilishment of a human pancreatic adenocarcinoma cell line (PSN-1) with amplifications of both c-myc and activated c-Ki-ras by a point mutation. Biochem. Biophys. Res. Commun. 140, 167-173.

Evaluation of Cytotoxic Activity Using the SRB Colorimetric Assay

A colorimetric assay, using sulforhodamine B (SRB) reaction has been adapted to provide a quantitative measurement of cell growth and viability (following the technique described by V. Vichai and K. Kirtikara (2006) Nature Protoc. 1, 1112-1116.)

This form of assay employs 96-well cell culture microplates. All the cell lines used in this study were obtained from the American Type Culture Collection (ATCC), unless otherwise indicated, and derive from different types of human cancer.

Cells were maintained in Dulbecco's Modified Eagle Medium (DMEM) (for A549, HT-29 and MDA-MB-231) or RPMI (for PSN-1) supplemented with 10% Fetal Bovine Serum (FBS), 2 mM L-glutamine, 100 U/mL penicillin and 100 U/mL streptomycin at 37° C., 5% $CO_2$ and 98% humidity. For the experiments, cells were harvested from subconfluent cultures using trypsinization and resuspended in fresh medium before counting and plating.

Cells were seeded in 96 well microtiter plates, at $5\times10^3$ cells per well in aliquots of 150 μL, and allowed to attach to the plate surface for 18 hours (overnight) in drug free medium. After that, one control (untreated) plate of each cell line was fixed (as described below) and used for time zero reference value. Culture plates were then treated with test compounds (50 μL aliquots of 4× concentrated compound stock solutions made in complete culture medium) using ten serial dilutions (concentrations ranging from 10 to 0.00262 μg/mL) and triplicate cultures (final concentration of DMSO being 1%). After 72 hours treatment, the antitumor effect was measured by using the SRB methodology: Briefly, cells were washed twice with PBS, fixed for 15 min in 1% glutaraldehyde solution at room temperature, rinsed twice in PBS, and stained in 0.4% SRB solution for 30 min at room temperature. Cells were then rinsed several times with 1% acetic acid solution and air-dried at room temperature. SRB was then extracted in 10 mM trizma base solution and the absorbance measured in an automated spectrophotometric plate reader at 490 nm. Effects on cell growth and survival were estimated by applying the NCI algorithm (Boyd M R and Pauli K D. *Drug Dev Res.* 1995, 34, 91-104).

Using the mean±SD of triplicates, a dose-response curve was automatically generated using nonlinear regression analysis to a 4-parameter logistic curve. Three reference parameters were calculated (NCI algorithm) by automatic interpolation: $GI_{50}$=compound concentration that produces 50% cell growth inhibition, as compared to control cultures; TGI=total cell growth inhibition (cytostatic effect), as compared to control cultures, and $LC_{50}$=compound concentration that produces 50% net cell killing (cytotoxic effect).

Table 3 illustrates data on the biological activity ($GI_{50}$) of compounds of the present invention ($GI_{50}$ value).

TABLE 3

Cytotoxicity assay-Activity Data ($GI_{50}$ Molar)

| | | $GI_{50}$ (M) | | | |
|---|---|---|---|---|---|
| | Compound | A549 | HT29 | MDA-MB-231 | PSN-1 |
| 1 | 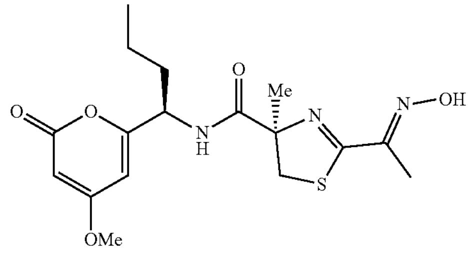 | 1.15E−08 | 1.44E−08 | 3.41E−08 | 2.88E−08 |
| 1a | 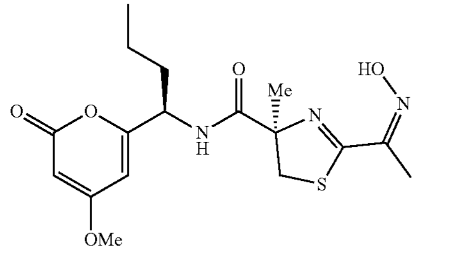 [SMILES: CCC[C@@H](NC(=O)[C@]1(C)CSC(/C(C)=N\O)=N1)c1cc(OC)cc(=O)o1] | 1.44E−07 | 1.52E−07 | 2.04E−07 | 3.41E−07 |
| epi-1 | 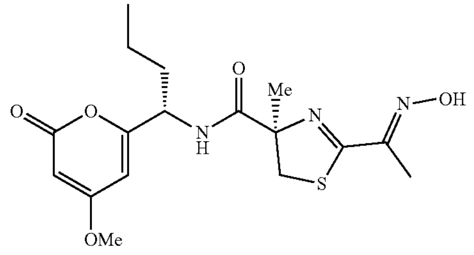 [SMILES: CCC[C@H](NC(=O)[C@]1(C)CSC(/C(C)=N/O)=N1)c1cc(OC)cc(=O)o1] | 2.88E−06 | 3.41E−06 | 3.93E−06 | 5.77E−06 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 2 | 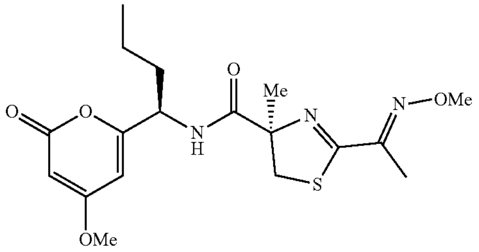 [SMILES: CCC[C@@H](NC(=O)[C@]1(C)CSC(/C(C)=N/OC)=N1)c1cc(OC)cc(=O)o1] | 2.53E−07 | 2.12E−07 | 4.30E−07 | 3.29E−07 |
| 42 | 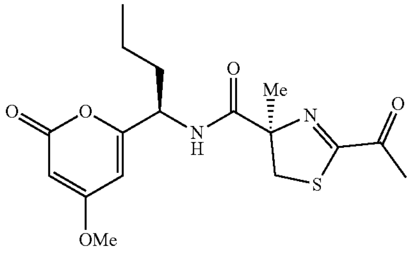 [SMILES: CCC[C@@H](NC(=O)[C@]1(C)CSC(C(C)=O)=N1)c1cc(OC)cc(=O)o1] | 2.46E−05 | 8.73E−06 | 4.64E−06 | 5.19E−06 |
| 46 | 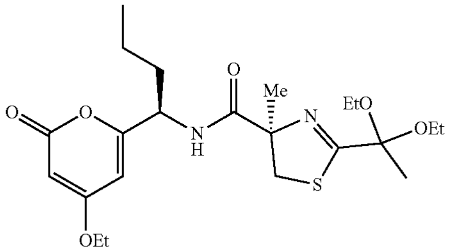 [SMILES: CCC[C@@H](NC(=O)[C@]1(C)CSC(C(C)(OCC)OCC)=N1)c1cc(OCC)cc(=O)o1] | 2.42E−06 | 2.18E−06 | 1.52E−06 | 4.62E−06 |
| 48 | 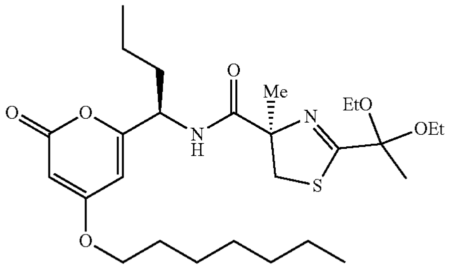 [SMILES: CCCCCCCOc1cc([C@@H](CCC)NC(=O)[C@]2(C)CSC(C(C)(OCC)OCC)=N2)oc(=O)c1] | 3.43E−06 | 2.29E−06 | 2.29E−06 | 2.10E−06 |
| 49 | 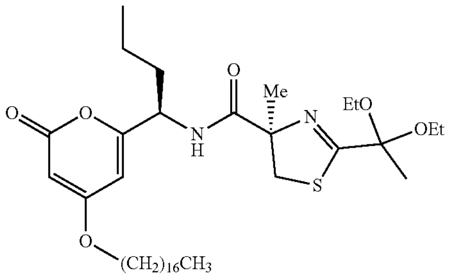 | 1.34E−06 | 9.32E−07 | 1.50E−06 | 1.46E−06 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 50 | 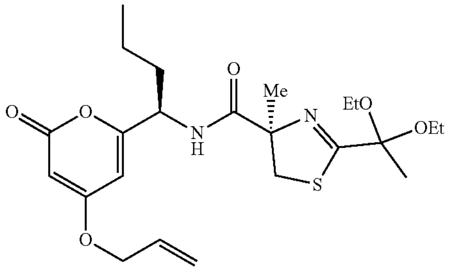 [SMILES: C=CCOc1cc([C@@H](CCC)NC(=O)[C@]2(C)CSC(C(C)(OCC)OCC)=N2)oc(=O)c1] | 6.43E−07 | 5.14E−07 | 5.36E−07 | 8.14E−07 |
| 51 | 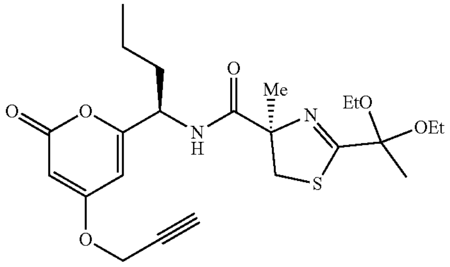 [SMILES: C#CCOc1cc([C@@H](CCC)NC(=O)[C@]2(C)CSC(C(C)(OCC)OCC)=N2)oc(=O)c1] | 3.44E−07 | 2.15E−07 | 3.23E−07 | 3.66E−07 |
| 52 | 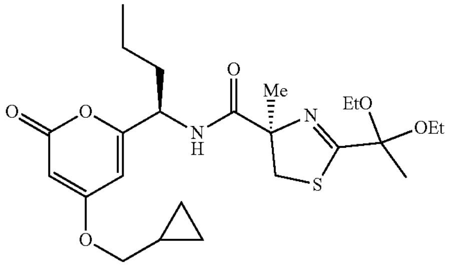 [SMILES: CCC[C@@H](NC(=O)[C@]1(C)CSC(C(C)(OCC)OCC)=N1)c1cc(OCC2CC2)cc(=O)o1] | 1.27E−06 | 1.21E−06 | 1.29E−06 | 1.77E−06 |
| 61 | 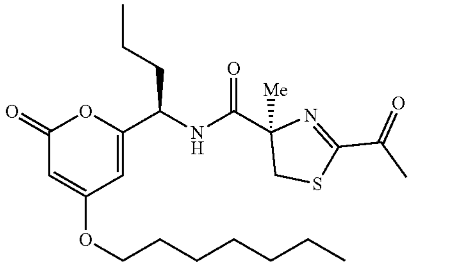 [SMILES: CCCCCCCOc1cc([C@@H](CCC)NC(=O)[C@]2(C)CSC(C(C)=O)=N2)oc(=O)c1] | 1.84E−06 | 1.40E−06 | 1.44E−06 | 1.73E−06 |
| 62 | 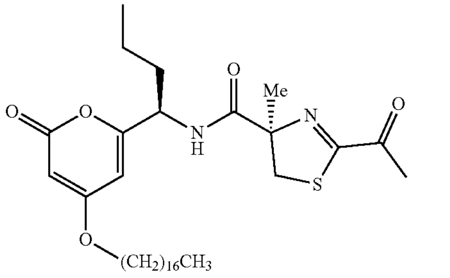 | 1.61E−06 | 1.10E−06 | 1.69E−06 | 1.64E−06 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 63 | 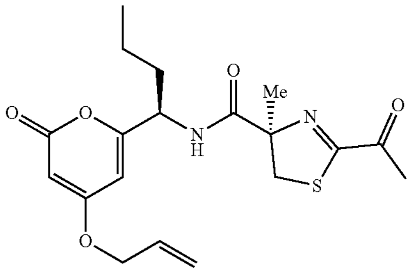 [SMILES: C=CCOc1cc([C@@H](CCC)NC(=O)[C@]2(C)CSC(C(C)=O)=N2)oc(=O)c1] | 8.15E−07 | 5.10E−07 | 4.84E−07 | 4.08E−07 |
| 64 | 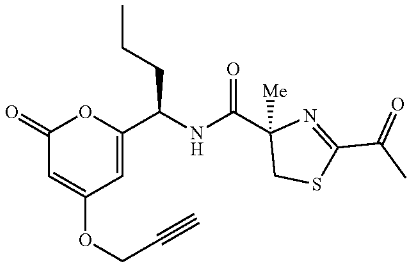 [SMILES: C#CCOc1cc([C@@H](CCC)NC(=O)[C@]2(C)CSC(C(C)=O)=N2)oc(=O)c1] | 9.99E−08 | 6.15E−08 | 5.38E−08 | 7.17E−08 |
| 65 | 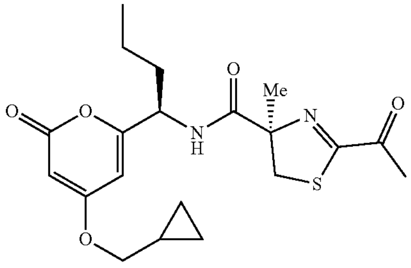 [SMILES: CCC[C@@H](NC(=O)[C@]1(C)CSC(C(C)=O)=N1)c1cc(OCC2CC2)cc(=O)o1] | 1.89E−06 | 1.08E−06 | 1.03E−06 | 1.25E−06 |
| 68 | 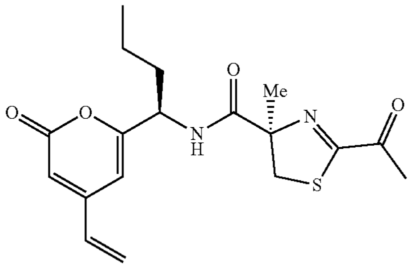 [SMILES: C=Cc1cc([C@@H](CCC)NC(=O)[C@]2(C)CSC(C(C)=O)=N2)oc(=O)c1] | 1.10E−05 | 9.10E−06 | 6.62E−06 | 4.69E−06 |
| 69 | 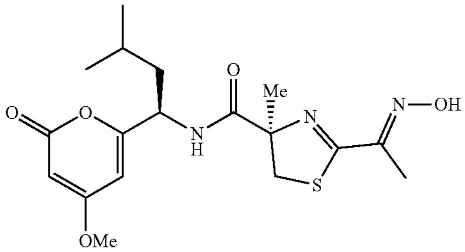 [SMILES: COc1cc([C@@H](CC(C)C)NC(=O)[C@]2(C)CSC(/C(C)=N/O)=N2)oc(=O)c1] | 2.20E−06 | 1.59E−06 | 1.62E−06 | 1.52E−06 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 69a | 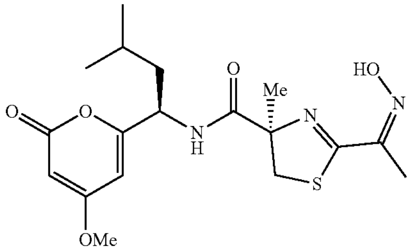 [SMILES: COc1cc([C@@H](CC(C)C)NC(=O)[C@]2(C)CSC(/C(C)=N\O)=N2)oc(=O)c1] | 5.06E−06 | 3.79E−06 | 4.55E−06 | 6.32E−06 |
| 70 | 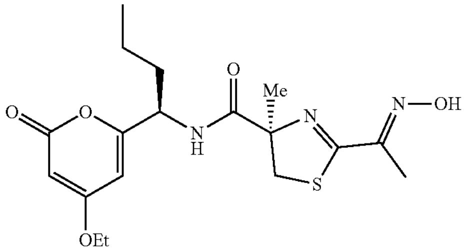 [SMILES: CCC[C@@H](NC(=O)[C@]1(C)CSC(/C(C)=N/O)=N1)c1cc(OCC)cc(=O)o1] | 1.44E−08 | 1.49E−08 | 2.38E−08 | 1.49E−08 |
| 71 | 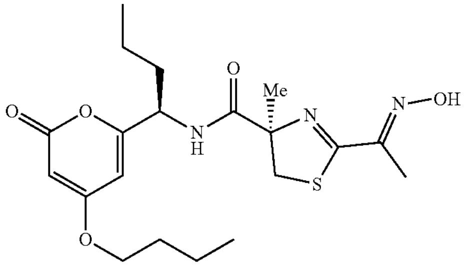 [SMILES: CCCCOc1cc([C@@H](CCC)NC(=O)[C@]2(C)CSC(/C(C)=N/O)=N2)oc(=O)c1] | 7.08E−09 | 7.56E−09 | 1.44E−08 | 1.04E−08 |
| 71a | 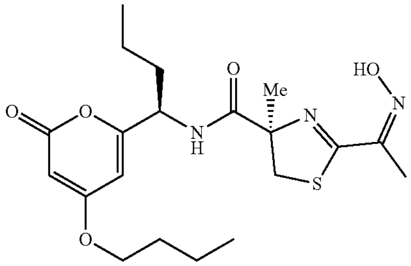 [SMILES: CCCCOc1cc([C@@H](CCC)NC(=O)[C@]2(C)CSC(/C(C)=N\O)=N2)oc(=O)c1] | 1.65E−08 | 1.70E−08 | 3.54E−08 | 3.07E−08 |
| 72 | 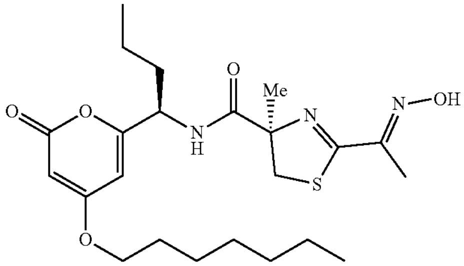 [SMILES: CCCCCCCOc1cc([C@@H](CCC)NC(=O)[C@]2(C)CSC(/C(C)=N/O)=N2)oc(=O)c1] | 2.58E−08 | 3.01E−08 | 3.01E−08 | 2.15E−08 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 72a | 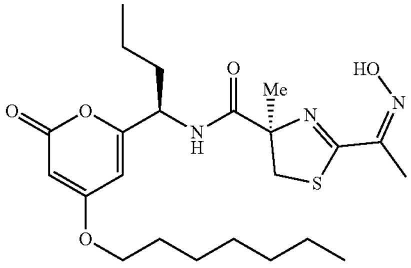 [SMILES: CCCCCCCOc1cc([C@@H](CCC)NC(=O)[C@]2(C)CSC(/C(C)=N\O)=N2)oc(=O)c1] | 1.10E−07 | 1.83E−07 | 1.03E−07 | 1.25E−07 |
| 73 | 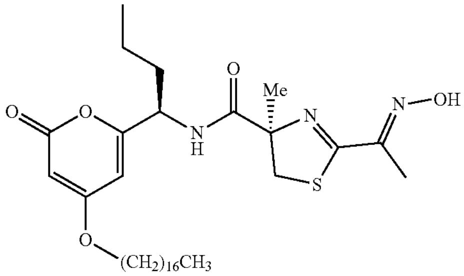 | 3.80E−07 | 3.96E−07 | 3.30E−07 | 3.47E−07 |
| 73a | 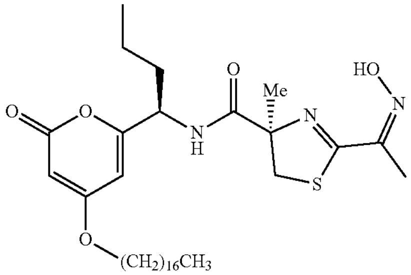 | 6.44E−08 | 6.27E−08 | 6.60E−08 | 5.94E−08 |
| 74 | 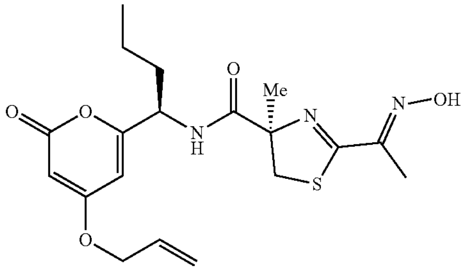 [SMILES: C=CCOc1cc([C@@H](CCC)NC(=O)[C@]2(C)CSC(/C(C)=N/O)=N2)oc(=O)c1] | 4.17E−09 | 2.94E−09 | 4.91E−09 | 3.19E−09 |
| 74a | 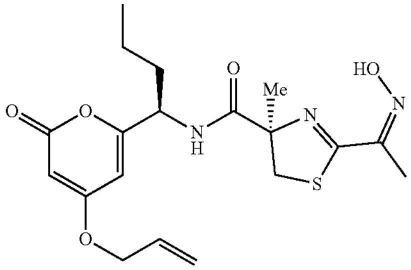 [SMILES: C=CCOc1cc([C@@H](CCC)NC(=O)[C@]2(C)CSC(/C(C)=N\O)=N2)oc(=O)c1] | 8.10E−09 | 7.61E−09 | 9.82E−09 | 1.25E−08 |

TABLE 3-continued
Cytotoxicity assay-Activity Data ($GI_{50}$ Molar)
| | | $GI_{50}$ (M) | | | |
|---|---|---|---|---|---|
| Compound | | A549 | HT29 | MDA-MB-231 | PSN-1 |
| 75 | 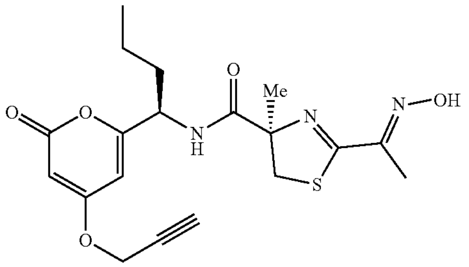 [SMILES: C#CCOc1cc([C@@H](CCC)NC(=O)[C@]2(C)CSC(/C(C)=N/O)=N2)oc(=O)c1] | 1.01E−09 | 9.62E−10 | 1.38E−09 | 1.18E−09 |
| 75a | 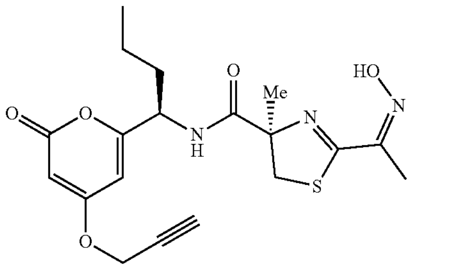 [SMILES: C#CCOc1cc([C@@H](CCC)NC(=O)[C@]2(C)CSC(/C(C)=N\O)=N2)oc(=O)c1] | 2.12E−09 | 1.18E−09 | 2.71E−09 | 2.00E−09 |
| 76 | 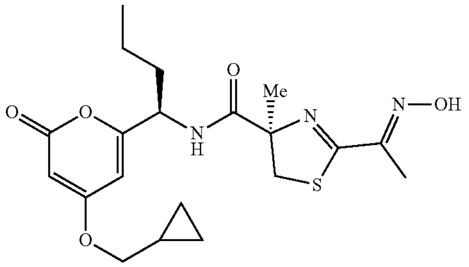 [SMILES: CCC[C@@H](NC(=O)[C@]1(C)CSC(/C(C)=N/O)=N1)c1cc(OCC2CC2)cc(=O)o1] | 3.56E−09 | 3.80E−09 | 3.80E−09 | 3.08E−09 |
| 76a | 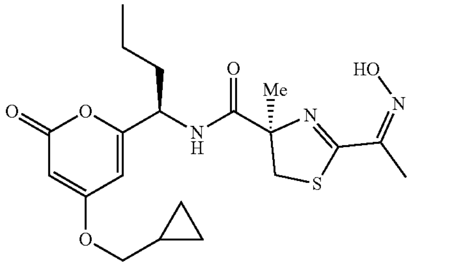 [SMILES: CCC[C@@H](NC(=O)[C@]1(C)CSC(/C(C)=N\O)=N1)c1cc(OCC2CC2)cc(=O)o1] | 3.80E−09 | 4.27E−09 | 4.51E−09 | 4.51E−09 |
| 77 | 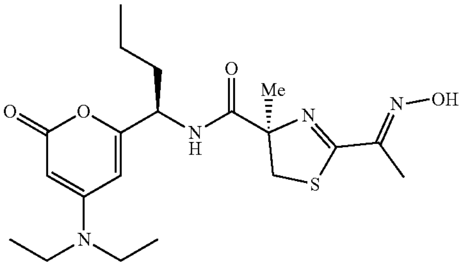 [SMILES: CCC[C@@H](NC(=O)[C@]1(C)CSC(/C(C)=N/O)=N1)c1cc(N(CC)CC)cc(=O)o1] | 2.15E−06 | 1.18E−06 | 1.96E−06 | 2.37E−06 |

TABLE 3-continued
| Cytotoxicity assay-Activity Data ($GI_{50}$ Molar) | | | | | |
|---|---|---|---|---|---|
| | | $GI_{50}$ (M) | | | |
| Compound | | A549 | HT29 | MDA-MB-231 | PSN-1 |
| 78 | 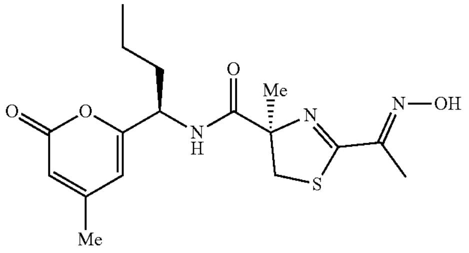 [SMILES: CCC[C@@H](NC(=O)[C@]1(C)CSC(/C(C)=N/O)=N1)c1cc(C)cc(=O)o1] | 2.49E−08 | 4.38E−08 | 4.38E−08 | 3.28E−08 |
| 79 | 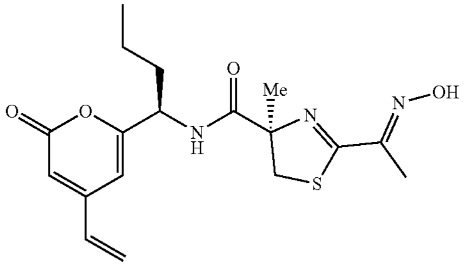 [SMILES: C=Cc1cc([C@@H](CCC)NC(=O)[C@]2(C)CSC(/C(C)=N/O)=N2)oc(=O)c1] | 4.24E−07 | 3.97E−07 | 3.44E−07 | 4.77E−07 |
| 82 | 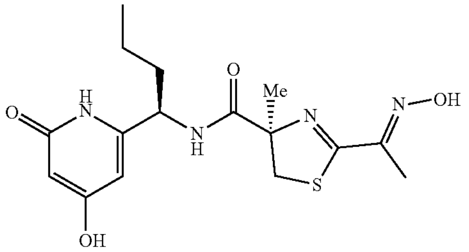 [SMILES: CCC[C@@H](NC(=O)[C@]1(C)CSC(/C(C)=N/O)=N1)c1cc(O)cc(=O)[nH]1] | 1.64E−06 | 4.91E−07 | 1.12E−06 | 3.55E−07 |
| 87 | 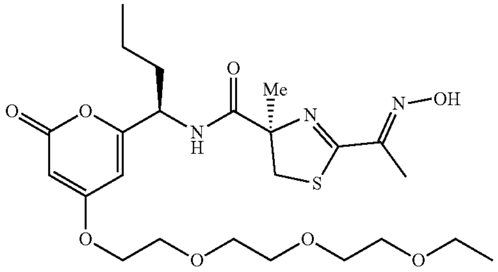 [SMILES: CCC[C@@H](NC(=O)[C@]1(C)CSC(/C(C)=N/O)=N1)c1cc(OCCOCCOCCOCC)cc(=O)o1] | 5.69E−06 | 5.50E−06 | 6.82E−06 | 7.01E−06 |
| 88 | 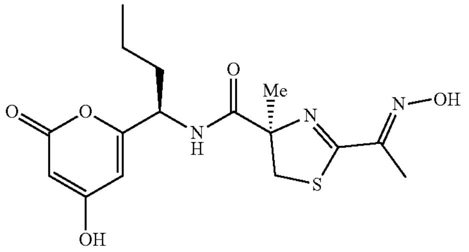 [SMILES: CCC[C@@H](NC(=O)[C@]1(C)CSC(/C(C)=N/O)=N1)c1cc(O)cc(=O)o1] | 2.04E−05 | 1.14E−05 | 2.18E−05 | 1.88E−05 |

TABLE 3-continued
| Compound | | GI$_{50}$ (M) A549 | HT29 | MDA-MB-231 | PSN-1 |
|---|---|---|---|---|---|
| Cytotoxicity assay-Activity Data (GI$_{50}$ Molar) | | | | | |
| 89 | 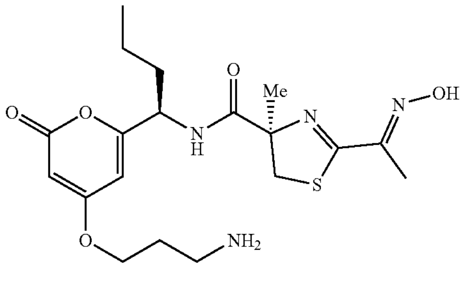 [SMILES: CCC[C@@H](NC(=O)[C@]1(C)CSC(/C(C)=N/O)=N1)c1cc(OCCCN)cc(=O)o1] | 1.65E−05 | 8.95E−06 | 5.89E−06 | 6.36E−06 |
| 92 | 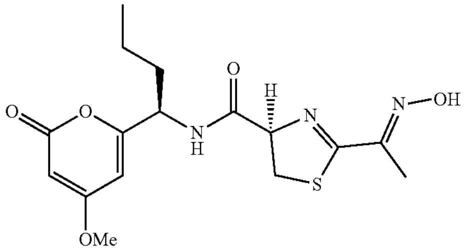 [SMILES: CCC[C@@H](NC(=O)[C@@H]1CSC(/C(C)=N/O)=N1)c1cc(OC)cc(=O)o1] | 1.55E−06 | 1.28E−06 | 9.53E−07 | 9.53E−07 |
| 93 | 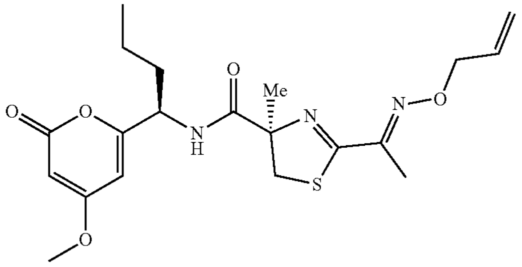 [SMILES: C=CCO/N=C(\C)C1=N[C@](C)(C(=O)N[C@H](CCC)c2cc(OC)cc(=O)o2)CS1] | 2.14E−08 | 2.35E−08 | 3.80E−08 | 2.85E−08 |
| 94 | 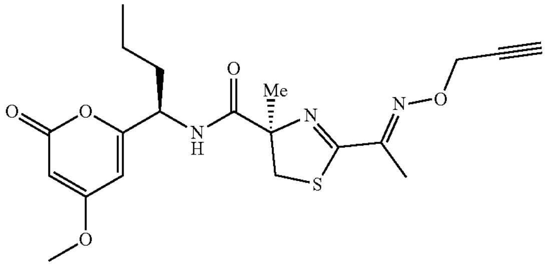 [SMILES: C#CCO/N=C(\C)C1=N[C@](C)(C(=O)N[C@H](CCC)c2cc(OC)cc(=O)o2)CS1] | 3.58E−08 | 2.26E−08 | 3.58E−08 | 3.58E−08 |
| 95 | 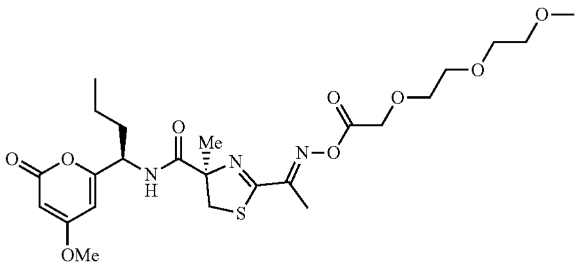 [SMILES: CCC[C@@H](NC(=O)[C@]1(C)CSC(/C(C)=N/OC(=O)COCCOCCOC)=N1)c1cc(OC)cc(=O)o1] | 2.03E−08 | 4.06E−08 | 4.43E−08 | 3.32E−08 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 96 | 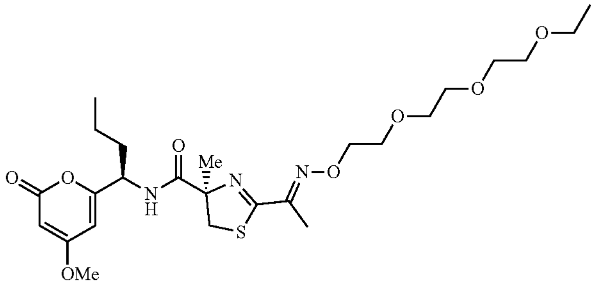 [SMILES: CCC[C@@H](NC(=O)[C@]1(C)CSC(/C(C)=N/OCCOCCOCCOCC)=N1)c1cc(OC)cc(=O)o1] | 1.77E−06 | 1.51E−06 | 2.95E−06 | 2.22E−06 |
| 97 | 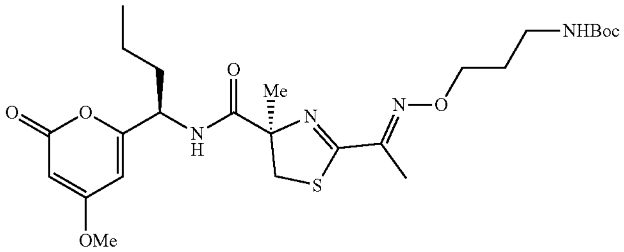 [SMILES: CCC[C@@H](NC(=O)[C@]1(C)CSC(/C(C)=N/OCCCNC(=O)OC(C)(C)C)=N1)c1cc(OC)cc(=O)o1] | 6.31E−07 | 5.94E−07 | 1.15E−06 | 8.35E−07 |
| 98 | 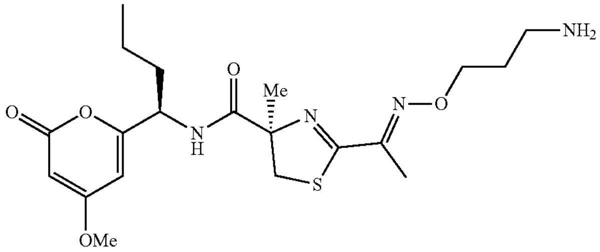 [SMILES: CCC[C@@H](NC(=O)[C@]1(C)CSC(/C(C)=N/OCCCN)=N1)c1cc(OC)cc(=O)o1] | 2.21E−08 | 2.51E−08 | 3.42E−08 | 2.74E−08 |
| 99 | 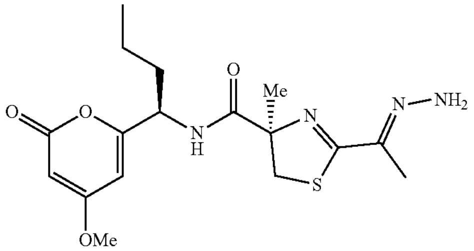 [SMILES: CCC[C@@H](NC(=O)[C@]1(C)CSC(/C(C)=N/N)=N1)c1cc(OC)cc(=O)o1] | 5.78E−07 | 4.47E−07 | 6.57E−07 | 9.20E−07 |
| 106 | 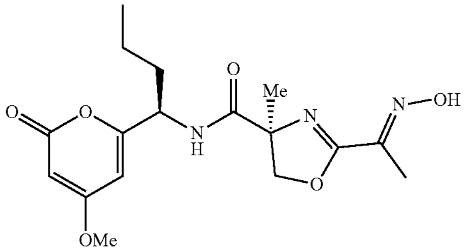 | 1.01E−06 | 7.12E−07 | 8.76E−07 | 1.56E−06 |

TABLE 3-continued
Cytotoxicity assay-Activity Data ($GI_{50}$ Molar)
| | | $GI_{50}$ (M) | | | |
|---|---|---|---|---|---|
| | Compound | A549 | HT29 | MDA-MB-231 | PSN-1 |
| 107 | 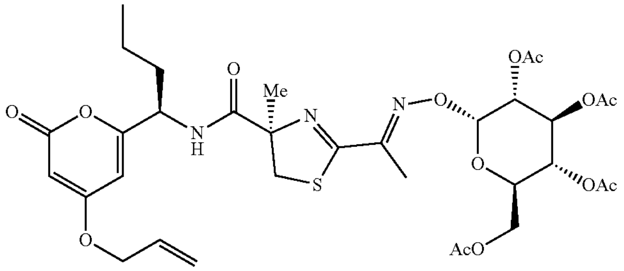 [SMILES: C=CCOc1cc([C@@H](CCC)NC(=O)[C@]2(C)CSC(/C(C)=N/O[C@H]3O[C@H](COC(C)=O)[C@@H](OC(C)=O)[C@H](OC(C)=O)[C@H]3OC(C)=O)=N2)oc(=O)c1] | 5.29E−08 | 5.29E−08 | 7.86E−08 | 6.10E−08 |
| 110 | 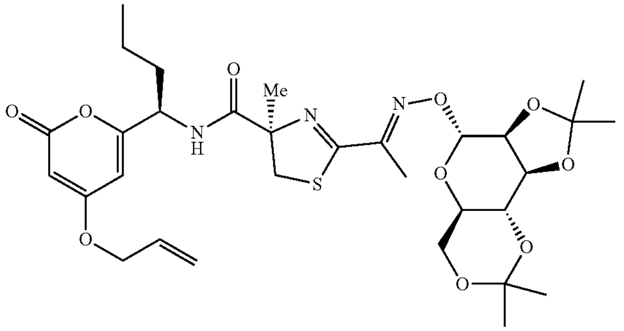 [SMILES: C=CCOc1cc([C@@H](CCC)NC(=O)[C@]2(C)CSC(/C(C)=N/O[C@H]3O[C@@H]4COC(C)(C)O[C@H]4[C@@H]4OC(C)(C)O[C@H]34)=N2)oc(=O)c1] | 4.31E−08 | 3.69E−08 | 7.85E−08 | 5.69E−08 |
| 111 | 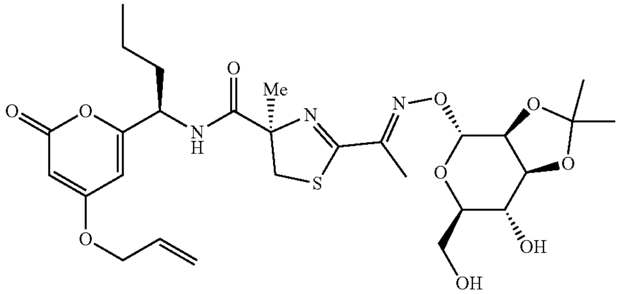 [SMILES: C=CCOc1cc([C@@H](CCC)NC(=O)[C@]2(C)CSC(/C(C)=N/O[C@H]3O[C@H](CO)[C@@H](O)[C@@H]4OC(C)(C)O[C@H]34)=N2)oc(=O)c1] | 2.62E−08 | 2.46E−08 | 2.95E−08 | 3.77E−08 |
| 112 | 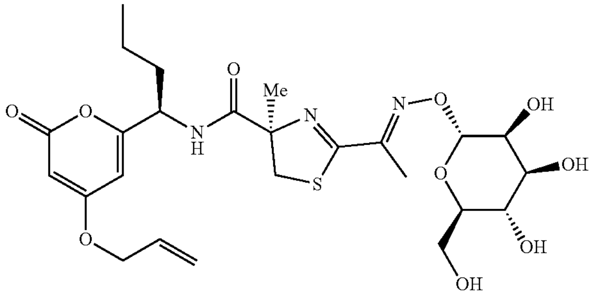 [SMILES: C=CCOc1cc([C@@H](CCC)NC(=O)[C@]2(C)CSC(/C(C)=N/O[C@H]3O[C@H](CO)[C@@H](O)[C@H](O)[C@@H]3O)=N2)oc(=O)c1] | 4.04E−06 | 1.11E−06 | 2.11E−06 | 1.23E−06 |
| 113 | 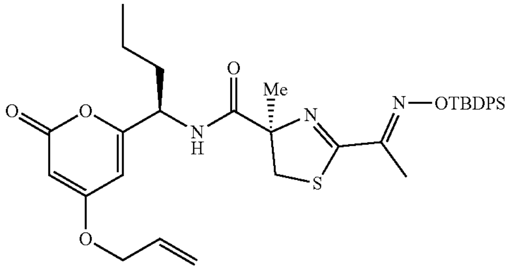 | 1.52E−08 | 5.57E−09 | 8.36E−09 | 1.47E−08 |

TABLE 3-continued
Cytotoxicity assay-Activity Data ($GI_{50}$ Molar)
| | Compound | $GI_{50}$ (M) A549 | HT29 | MDA-MB-231 | PSN-1 |
|---|---|---|---|---|---|
| 115 | 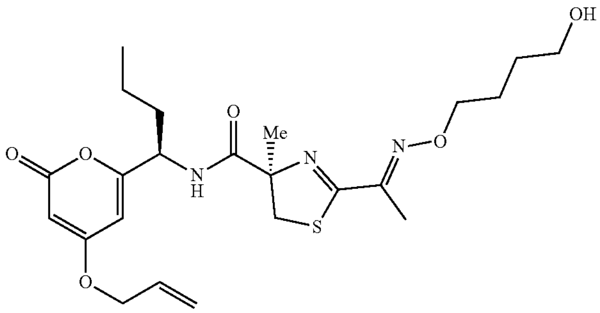 [SMILES: C=CCOc1cc([C@@H](CCC)NC(=O)[C@]2(C)CSC(/C(C)=N/OCCCCO)=N2)oc(=O)c1] | 1.11E−08 | 5.84E−09 | 1.19E−08 | 1.36E−08 |
| 116 | 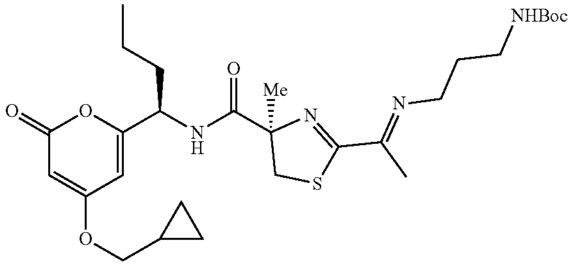 [SMILES: CCC[C@@H](NC(=O)[C@]1(C)CSC(/C(C)=N/CCCNC(=O)OC(C)(C)C)=N1)c1cc(OCC2CC2)cc(=O)o1] | 3.02E−07 | 2.49E−07 | 1.95E−07 | 3.02E−07 |
| 117 | 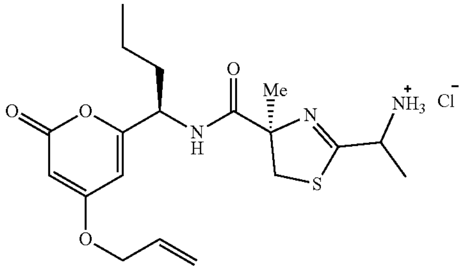 [SMILES: C=CCOc1cc([C@@H](CCC)NC(=O)[C@]2(C)CSC(C(C)[NH3+])=N2)oc(=O)c1 ; [Cl-]] | 3.02E−06 | 3.49E−06 | 4.65E−06 | 4.88E−06 |
| 127 | 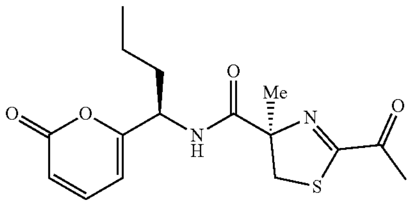 [SMILES: CCC[C@@H](NC(=O)[C@]1(C)CSC(C(C)=O)=N1)c1cccc(=O)o1] | >2.97E−05 | 1.40E−05 | 8.62E−06 | 1.87E−05 |
| 128 | 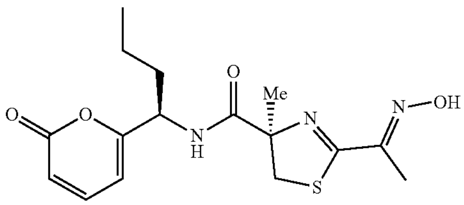 [SMILES: CCC[C@@H](NC(=O)[C@]1(C)CSC(/C(C)=N/O)=N1)c1cccc(=O)o1] | 9.11E−08 | 1.05E−07 | 2.85E−07 | 8.82E−08 |

TABLE 3-continued
Cytotoxicity assay-Activity Data ($GI_{50}$ Molar)
| | Compound | $GI_{50}$ (M) | | | |
|---|---|---|---|---|---|
| | | A549 | HT29 | MDA-MB-231 | PSN-1 |
| 129 | 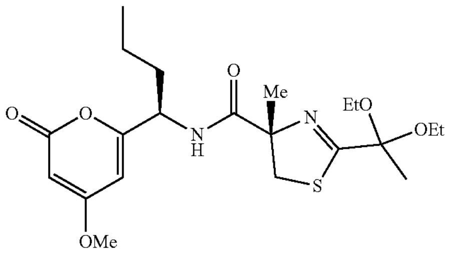 [SMILES: CCC[C@@H](NC(=O)[C@@]1(C)CSC(C(C)(OCC)OCC)=N1)c1cc(OC)cc(=O)o1] | 6.13E−06 | 3.63E−06 | 3.86E−06 | 5.45E−06 |
| 130 | 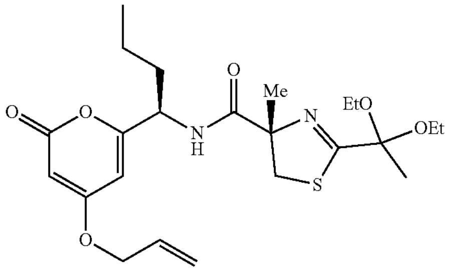 [SMILES: C=CCOc1cc([C@@H](CCC)NC(=O)[C@@]2(C)CSC(C(C)(OCC)OCC)=N2)oc(=O)c1] | 2.14E−07 | 2.06E−07 | 3.64E−07 | 3.64E−07 |
| 131 | 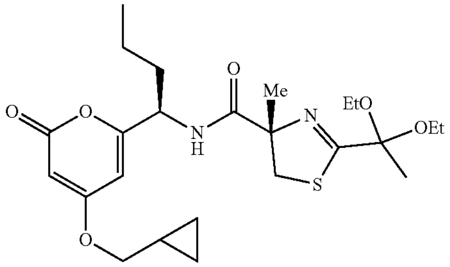 [SMILES: CCC[C@@H](NC(=O)[C@@]1(C)CSC(C(C)(OCC)OCC)=N1)c1cc(OCC2CC2)cc(=O)o1] | 2.08E−07 | 1.96E−07 | 3.33E−07 | 3.12E−07 |
| 133 | 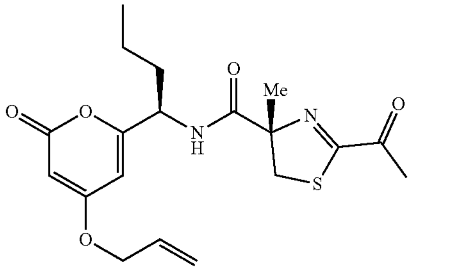 [SMILES: C=CCOc1cc([C@@H](CCC)NC(=O)[C@@]2(C)CSC(C(C)=O)=N2)oc(=O)c1] | 9.43E−06 | 4.59E−06 | 3.82E−06 | 5.61E−06 |
| 135 | 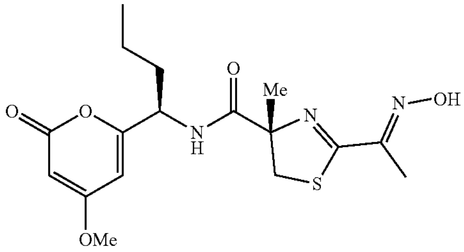 [SMILES: CCC[C@@H](NC(=O)[C@@]1(C)CSC(/C(C)=N/O)=N1)c1cc(OC)cc(=O)o1] | 2.46E−06 | 1.26E−06 | 2.33E−06 | 1.26E−06 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 136 | 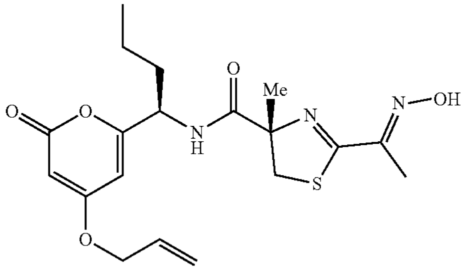 [SMILES: C=CCOc1cc([C@@H](CCC)NC(=O)[C@@]2(C)CSC(/C(C)=N/O)=N2)oc(=O)c1] | 7.12E−08 | 8.59E−08 | 7.85E−08 | 8.10E−08 |
| 137 | 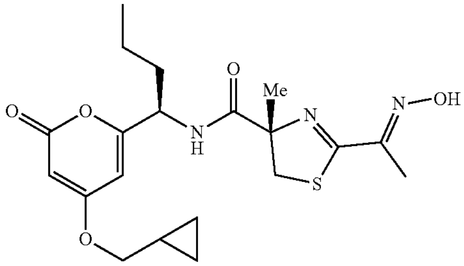 [SMILES: CCC[C@@H](NC(=O)[C@@]1(C)CSC(/C(C)=N/O)=N1)c1cc(OCC2CC2)cc(=O)o1] | 1.26E−07 | 1.09E−07 | 1.49E−07 | 1.45E−07 |
| 140 | 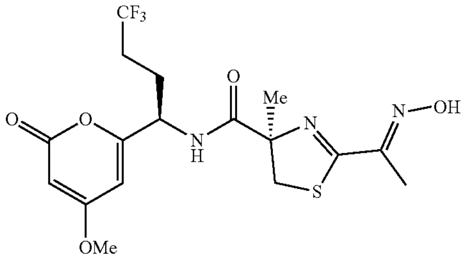 [SMILES: COc1cc([C@@H](CCC(F)(F)F)NC(=O)[C@]2(C)CSC(/C(C)=N/O)=N2)oc(=O)c1] | 6.66E−07 | 3.44E−07 | 4.59E−07 | 6.43E−07 |
| 140a | 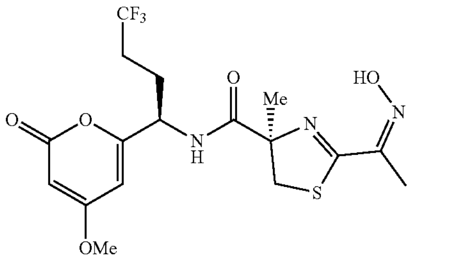 [SMILES: COc1cc([C@@H](CCC(F)(F)F)NC(=O)[C@]2(C)CSC(/C(C)=N\O)=N2)oc(=O)c1] | 2.53E−06 | 1.52E−06 | 2.27E−06 | 2.76E−06 |
| 141 | 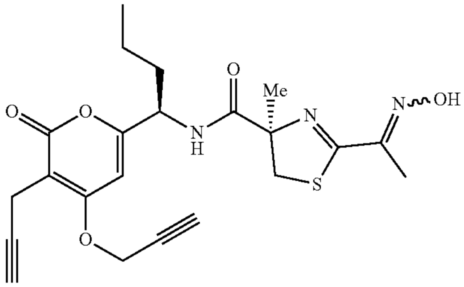 [SMILES: C#CCOc1cc([C@@H](CCC)NC(=O)[C@]2(C)CSC(C(C)=NO)=N2)oc(=O)c1CC#C] | 2.25E−07 | 1.78E−07 | 2.48E−07 | 3.38E−07 |

TABLE 3-continued
| Cytotoxicity assay-Activity Data ($GI_{50}$ Molar) | | | | |
|---|---|---|---|---|
| | $GI_{50}$ (M) | | | |
| Compound | A549 | HT29 | MDA-MB-231 | PSN-1 |
| 144 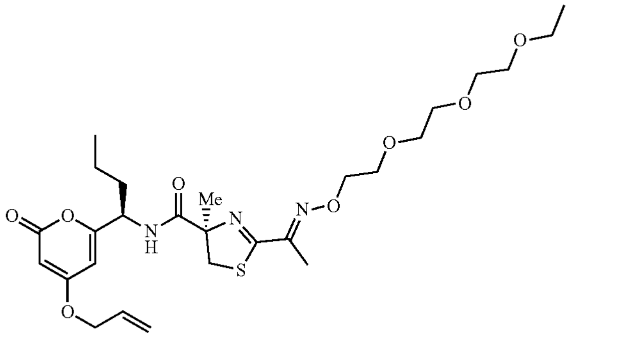 [SMILES: C=CCOc1cc([C@@H](CCC)NC(=O)[C@]2(C)CSC(/C(C)=N/OCCOCCOCCOCC)=N2)oc(=O)c1] | 7.22E−08 | 6.52E−08 | 1.62E−07 | 1.25E−07 |
| 145 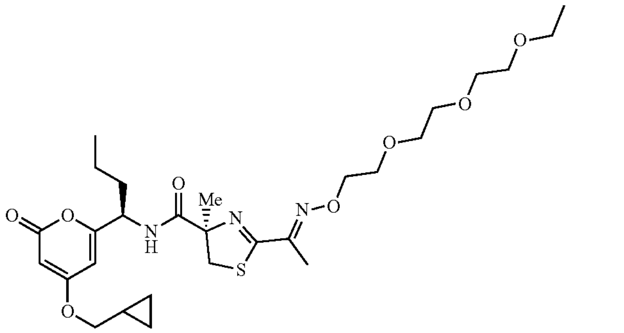 [SMILES: CCC[C@@H](NC(=O)[C@]1(C)CSC(/C(C)=N/OCCOCCOCCOCC)=N1)c1cc(OCC2CC2)cc(=O)o1] | 4.81E−08 | 6.19E−08 | 1.22E−07 | 1.12E−07 |
| 146 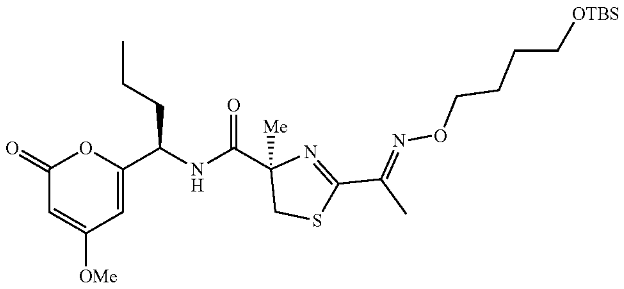 [SMILES: CCC[C@@H](NC(=O)[C@]1(C)CSC(/C(C)=N/OCCCCO[Si](C)(C)C(C)(C)C)=N1)c1cc(OC)cc(=O)o1] | 1.94E−06 | 1.02E−06 | 2.82E−06 | 2.11E−06 |
| 147 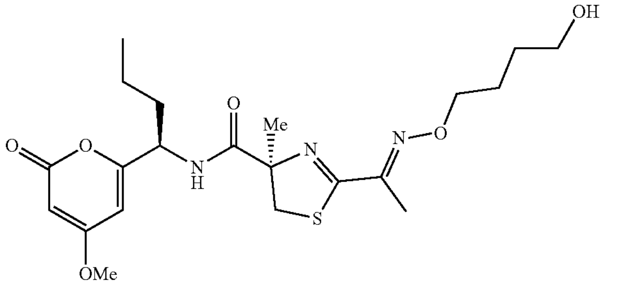 [SMILES: CCC[C@@H](NC(=O)[C@]1(C)CSC(/C(C)=N/OCCCCO)=N1)c1cc(OC)cc(=O)o1] | 1.48E−07 | 1.37E−07 | 2.87E−07 | 2.43E−07 |

TABLE 3-continued
Cytotoxicity assay-Activity Data ($GI_{50}$ Molar)
| | Compound | $GI_{50}$ (M) A549 | HT29 | MDA-MB-231 | PSN-1 |
|---|---|---|---|---|---|
| 148 | 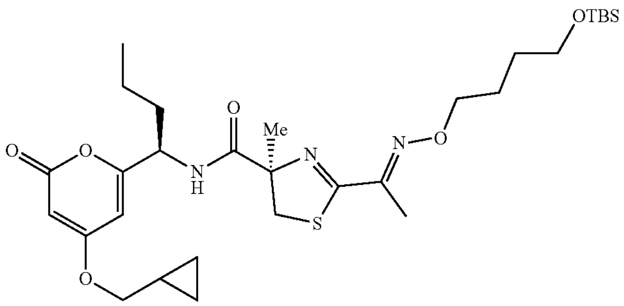 [SMILES: CCC[C@@H](NC(=O)[C@]1(C)CSC(/C(C)=N/OCCCCO[Si](C)(C)C(C)(C)C)=N1)c1cc(OCC2CC2)cc(=O)o1] | 2.63E−07 | 5.92E−08 | 2.47E−07 | 2.96E−07 |
| 149 | 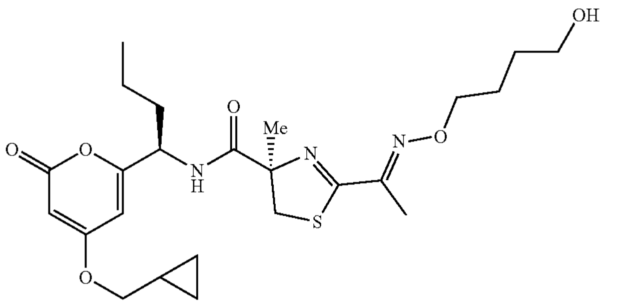 [SMILES: CCC[C@@H](NC(=O)[C@]1(C)CSC(/C(C)=N/OCCCCO)=N1)c1cc(OCC2CC2)cc(=O)o1] | 6.69E−09 | 6.28E−09 | 8.91E−09 | 1.36E−08 |
| 151 | 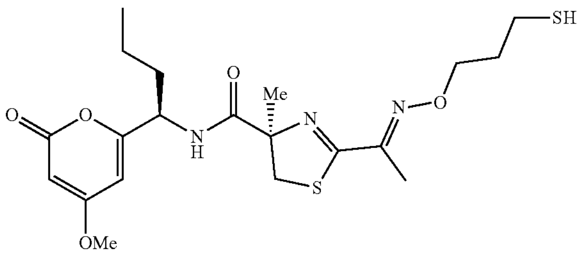 [SMILES: CCC[C@@H](NC(=O)[C@]1(C)CSC(/C(C)=N/OCCCS)=N1)c1cc(OC)cc(=O)o1] | 8.56E−07 | 5.05E−07 | 1.34E−06 | 1.21E−06 |
| 152 | 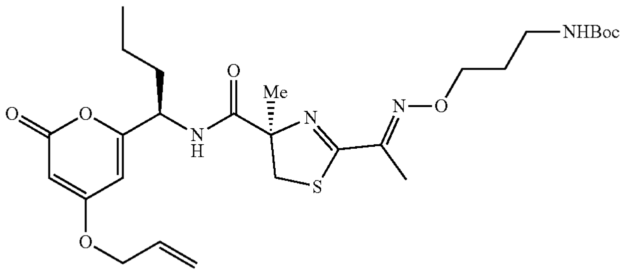 [SMILES: C=CCOc1cc([C@@H](CCC)NC(=O)[C@]2(C)CSC(/C(C)=N/OCCCNC(=O)OC(C)(C)C)=N2)oc(=O)c1] | 1.95E−08 | 1.95E−08 | 2.66E−08 | 2.13E−08 |
| 153 | 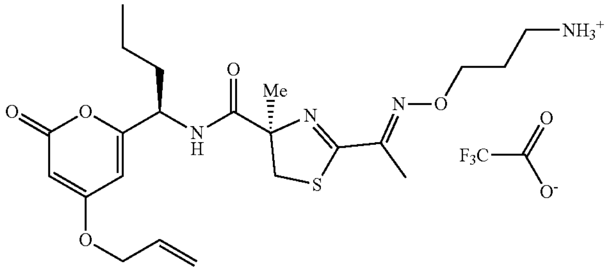 [SMILES: C=CCOc1cc([C@@H](CCC)NC(=O)[C@]2(C)CSC(/C(C)=N/OCCC[NH3+])=N2)oc(=O)c1 ; O=C([O-])C(F)(F)F] | 3.98E−09 | 3.380E−09 | 4.32E−09 | 3.98E−09 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 154 | 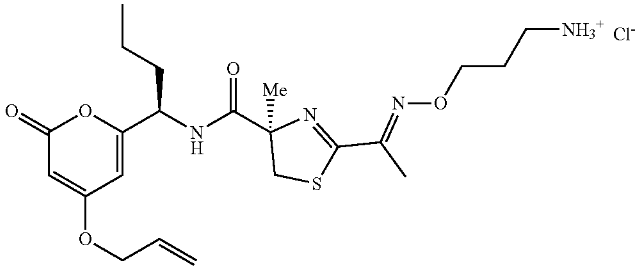 [SMILES: C=CCOc1cc([C@@H](CCC)NC(=O)[C@]2(C)CSC(/C(C)=N/OCCC[NH3+])=N2)oc(=O)c1 ; [Cl-]] | 4.79E−09 | 5.59E−09 | 6.79E−09 | 7.78E−09 |
| 155 | 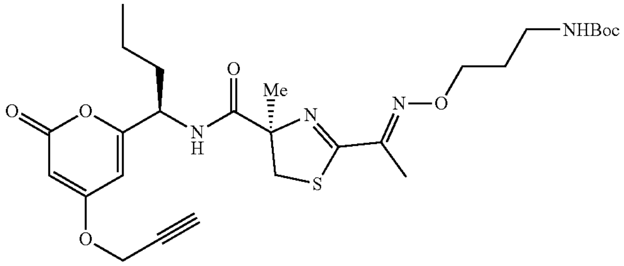 [SMILES: C#CCOc1cc([C@@H](CCC)NC(=O)[C@]2(C)CSC(/C(C)=N/OCCCNC(=O)OC(C)(C)C)=N2)oc(=O)c1] | 3.74E−08 | 4.09E−08 | 7.48E−08 | 7.30E−08 |
| 156 | 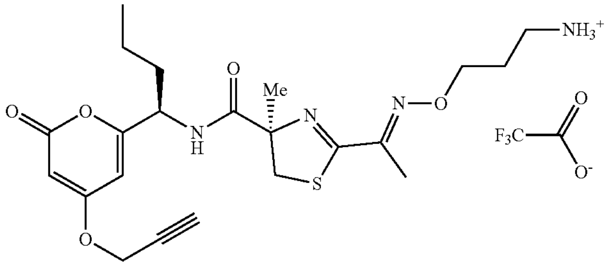 [SMILES: C#CCOc1cc([C@@H](CCC)NC(=O)[C@]2(C)CSC(/C(C)=N/OCCC[NH3+])=N2)oc(=O)c1 ; O=C([O-])C(F)(F)F] | 1.28E−09 | 2.43E−09 | 2.60E−09 | 2.43E−09 |
| 157 | 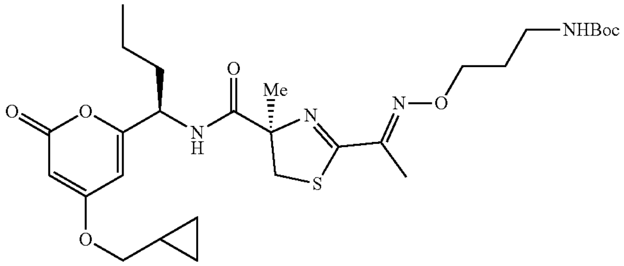 [SMILES: CCC[C@@H](NC(=O)[C@]1(C)CSC(/C(C)=N/OCCCNC(=O)OC(C)(C)C)=N1)c1cc(OCC2CC2)cc(=O)o1] | 5.37E−09 | 5.02E−09 | 5.37E−09 | 5.54E−09 |
| 158 | 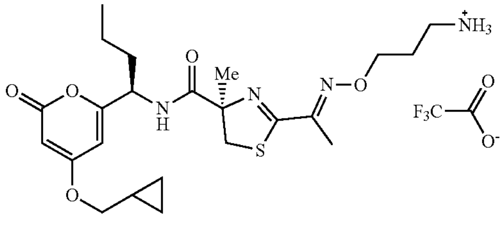 [SMILES: CCC[C@@H](NC(=O)[C@]1(C)CSC(/C(C)=N/OCCC[NH3+])=N1)c1cc(OCC2CC2)cc(=O)o1 ; O=C([O-])C(F)(F)F] | 5.43E−09 | 6.06E−09 | 1.21E−08 | 6.27E−09 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 159 | 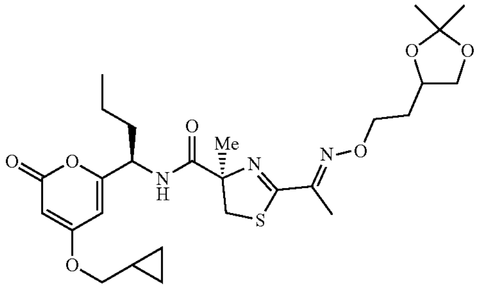 [SMILES: CCC[C@@H](NC(=O)[C@]1(C)CSC(/C(C)=N/OCCC2COC(C)(C)O2)=N1)c1cc(OCC2CC2)cc(=O)o1] | 4.91E−08 | 6.37E−08 | 6.73E−08 | 5.09E−08 |
| 161 | 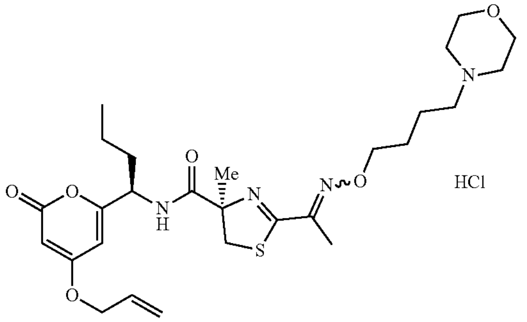 [SMILES: C=CCOc1cc([C@@H](CCC)NC(=O)[C@]2(C)CSC(C(C)=NOCCCCN3CCOCC3)=N2)oc(=O)c1 ; Cl] | 4.96E−09 | 5.47E−09 | 6.49E−09 | 5.13E−09 |
| 163 | 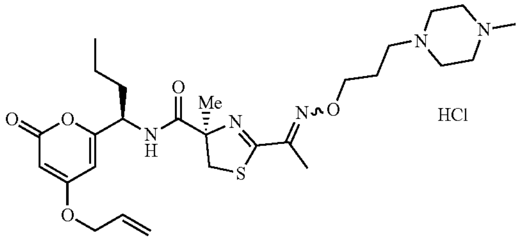 [SMILES: C=CCOc1cc([C@@H](CCC)NC(=O)[C@]2(C)CSC(C(C)=NOCCCN3CCN(C)CC3)=N2)oc(=O)c1 ; Cl] | 1.61E−08 | 1.56E−08 | 1.66E−08 | 1.64E−08 |
| 164 | 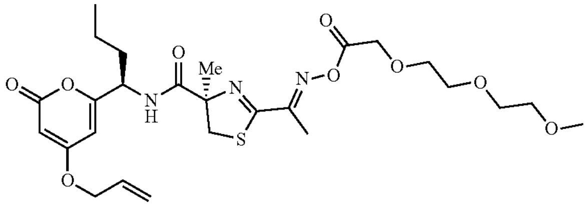 [SMILES: C=CCOc1cc([C@@H](CCC)NC(=O)[C@]2(C)CSC(/C(C)=N/OC(=O)COCCOCCOC)=N2)oc(=O)c1] | 6.52E−09 | 4.58E−09 | 7.22E−09 | 6.52E−09 |
| 165 | 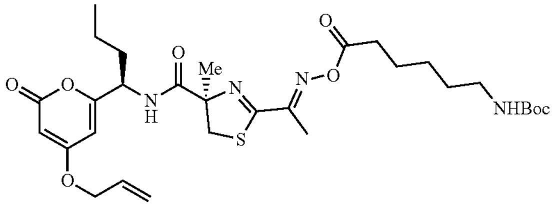 [SMILES: C=CCOc1cc([C@@H](CCC)NC(=O)[C@]2(C)CSC(/C(C)=N/OC(=O)CCCCCNC(=O)OC(C)(C)C)=N2)oc(=O)c1] | 5.48E−09 | 5.32E−09 | 7.41E−09 | 6.44E−09 |

TABLE 3-continued
Cytotoxicity assay-Activity Data ($GI_{50}$ Molar)
| | | $GI_{50}$ (M) | | | |
|---|---|---|---|---|---|
| | Compound | A549 | HT29 | MDA-MB-231 | PSN-1 |
| 166 | 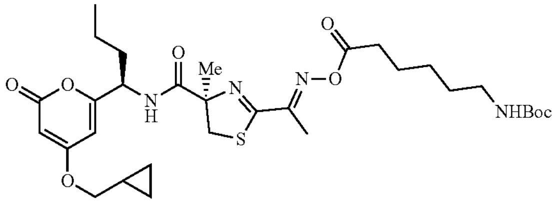 [SMILES: CCC[C@@H](NC(=O)[C@]1(C)CSC(/C(C)=N/OC(=O)CCCCCNC(=O)OC(C)(C)C)=N1)c1cc(OCC2CC2)cc(=O)o1] | 4.73E−09 | 4.57E−09 | 7.09E−09 | 6.30E−09 |
| 170 | 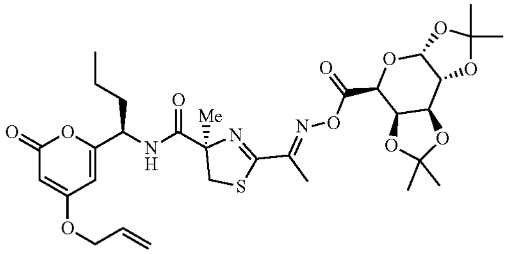 [SMILES: C=CCOc1cc([C@@H](CCC)NC(=O)[C@]2(C)CSC(/C(C)=N/OC(=O)[C@H]3O[C@@H]4OC(C)(C)O[C@@H]4[C@H]4OC(C)(C)O[C@H]43)=N2)oc(=O)c1] | 3.01E−09 | 2.41E−09 | 5.57E−09 | 2.71E−09 |
| 172 | 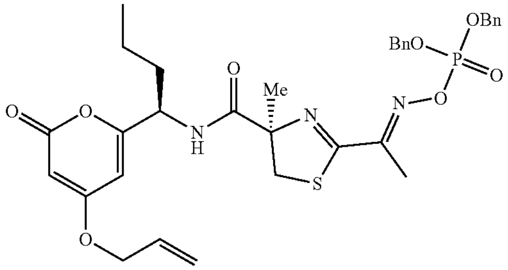 [SMILES: C=CCOc1cc([C@@H](CCC)NC(=O)[C@]2(C)CSC(/C(C)=N/OP(=O)(OCc3ccccc3)OCc3ccccc3)=N2)oc(=O)c1] | 8.09E−08 | 5.69E−08 | 1.08E−07 | 1.00E−07 |
| 175 | 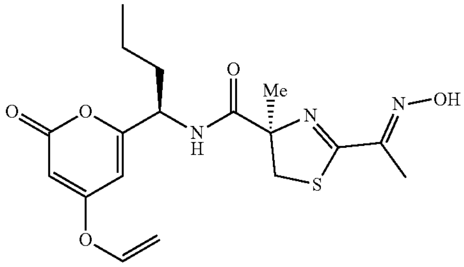 [SMILES: C=COc1cc([C@@H](CCC)NC(=O)[C@]2(C)CSC(/C(C)=N/O)=N2)oc(=O)c1] | 5.36E−08 | 1.10E−07 | 2.55E−07 | 3.83E−07 |
| 177 | 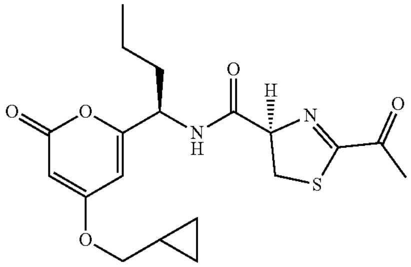 [SMILES: CCC[C@@H](NC(=O)[C@@H]1CSC(C(C)=O)=N1)c1cc(OCC2CC2)cc(=O)o1] | 2.27E−06 | 1.55E−06 | 1.61E−06 | >2.55E−05 |

TABLE 3-continued
| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 178 | 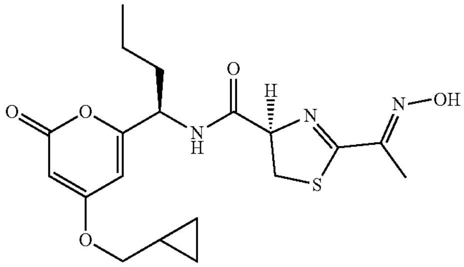 [SMILES: CCC[C@@H](NC(=O)[C@@H]1CSC(/C(C)=N/O)=N1)c1cc(OCC2CC2)cc(=O)o1] | 4.17E−08 | 7.61E−08 | 4.91E−08 | 3.68E−08 |
| 179 | 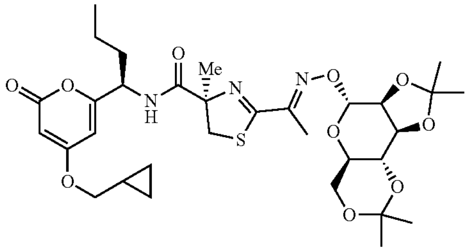 [SMILES: CCC[C@@H](NC(=O)[C@]1(C)CSC(/C(C)=N/O[C@H]2O[C@@H]3COC(C)(C)O[C@H]3[C@@H]3OC(C)(C)O[C@H]23)=N1)c1cc(OCC2CC2)cc(=O)o1] | 9.04E−09 | 6.48E−09 | 1.37E−08 | 1.43E−08 |
| 180 | 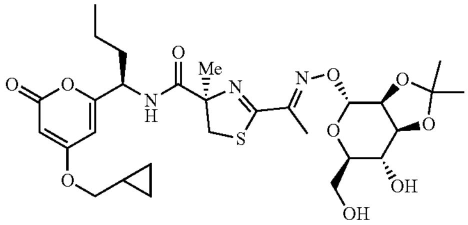 [SMILES: CCC[C@@H](NC(=O)[C@]1(C)CSC(/C(C)=N/O[C@H]2O[C@H](CO)[C@@H](O)[C@@H]3OC(C)(C)O[C@H]23)=N1)c1cc(OCC2CC2)cc(=O)o1] | 5.93E−07 | 3.69E−07 | 4.17E−07 | 5.29E−07 |
| 181 | 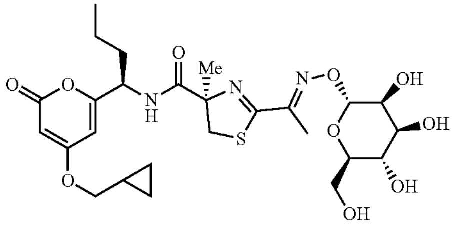 [SMILES: CCC[C@@H](NC(=O)[C@]1(C)CSC(/C(C)=N/O[C@H]2O[C@H](CO)[C@@H](O)[C@H](O)[C@@H]2O)=N1)c1cc(OCC2CC2)cc(=O)o1] | >1.71E−05 | 4.97E−06 | 6.34E−06 | 6.85E−06 |
| 182 | 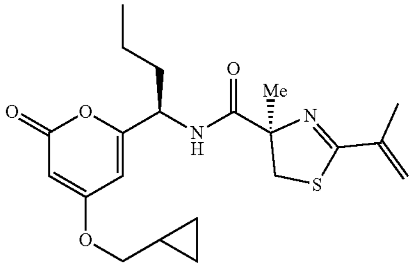 [SMILES: C=C(C)C1=N[C@](C)(C(=O)N[C@H](CCC)c2cc(OCC3CC3)cc(=O)o2)CS1] | 6.18E−08 | 7.42E−08 | 9.15E−08 | 8.16E−08 |

TABLE 3-continued
| Cytotoxicity assay-Activity Data (GI$_{50}$ Molar) | | | | | |
|---|---|---|---|---|---|
| | | GI$_{50}$ (M) | | | |
| | Compound | A549 | HT29 | MDA-MB-231 | PSN-1 |
| 183 | 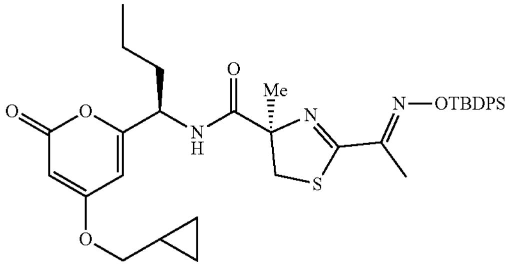 | 5.76E−09 | 5.46E−09 | 5.00E−09 | 8.18E−09 |
| 184 | 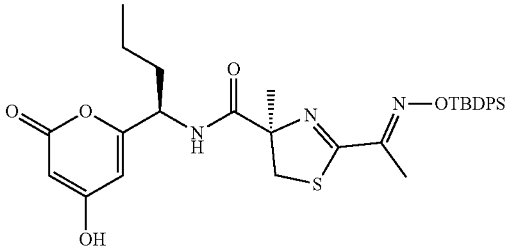 | 4.79E−06 | 2.97E−06 | 4.46E−06 | 4.13E−06 |
| 185 | 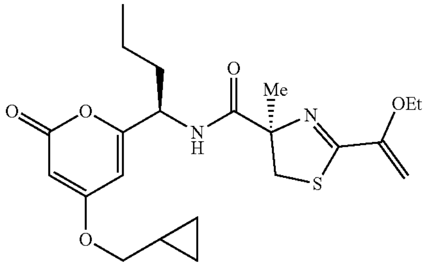 [SMILES: C=C(OCC)C1=N[C@](C)(C(=O)N[C@H](CCC)c2cc(OCC3CC3)cc(=O)o2)CS1] | 1.61E−07 | 2.07E−07 | 2.28E−07 | 1.40E−07 |
| 190 | 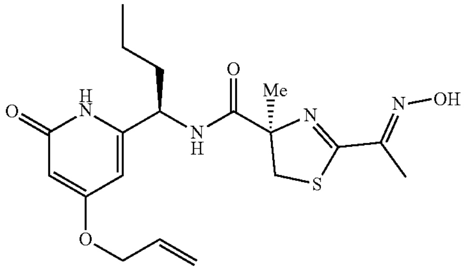 [SMILES: C=CCOc1cc([C@@H](CCC)NC(=O)[C@]2(C)CSC(/C(C)=N/O)=N2)[nH]c(=O)c1] | 5.90E−07 | 2.44E−07 | 2.39E−07 | 3.44E−07 |
| 191 | 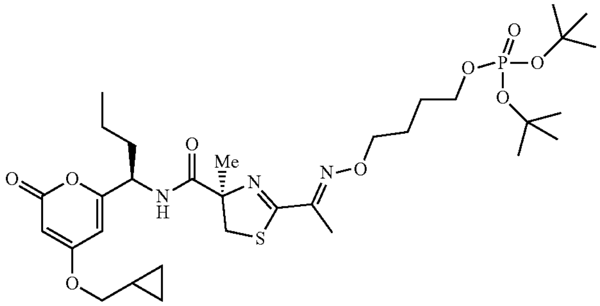 [SMILES: CCC[C@@H](NC(=O)[C@]1(C)CSC(/C(C)=N/OCCCCOP(=O)(OC(C)(C)C)OC(C)(C)C)=N1)c1cc(OCC2CC2)cc(=O)o1] | 4.96E−07 | 5.54E−07 | 6.12E−07 | 8.75E−07 |

TABLE 3-continued

| Cytotoxicity assay-Activity Data ($GI_{50}$ Molar) | | | | | |
|---|---|---|---|---|---|
| | | $GI_{50}$ (M) | | | |
| | Compound | A549 | HT29 | MDA-MB-231 | PSN-1 |
| 192 | 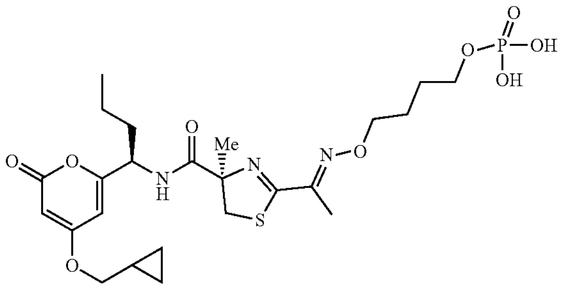 [SMILES: CCC[C@@H](NC(=O)[C@]1(C)CSC(/C(C)=N/OCCCCOP(=O)(O)O)=N1)c1cc(OCC2CC2)cc(=O)o1] | 9.07E−09 | 7.15E−09 | 1.64E−08 | 2.79E−08 |

The invention claimed is:

1. A compound of formula I or a pharmaceutically acceptable salt or ester thereof

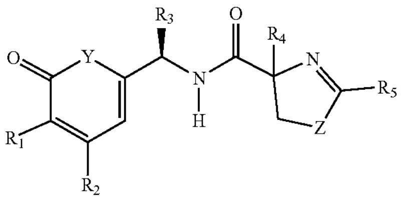

I wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, —$OSO_2R_b$, —$NR_cR_d$, —$NR_c$(C═O)$R_f$, and —$NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from —C($OR_e$)$_2R_g$, —C($SR_e$)$_2R_g$, —CH($OR_a$)$R_g$, —CH(O—(C═O)$R_f$)$R_g$, —CH($NR_cR_d$)$R_g$, —CH($NR_c$—(C═O)$R_f$)$R_g$, —CH($NR_c$—$OR_h$)$R_g$, —(C═O)$R_g$, —(C═$NR_c$)$R_g$, —(C═N—$OR_h$)$R_g$, —(C═N—O—(C═O)$R_f$)$R_g$, —(C═N—O—(C═O)$OR_a$)$R_g$, —(C═N—O—[(P═O)($OR_a$)$_2$])$R_g$, —(C═N—$NR_cR_d$)$R_g$, —(C═O)$OR_a$, —(C═O)$NR_c$—$OR_h$, —(C═O)$NR_cR_d$, —(C═$CH_2$)$R_g$, and —(C═$CH_2$)$OR_a$; or $R_5$ is a

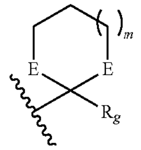

group where m is 0, 1 or 2 and each E group is independently selected from O and S;

Y is —O—;

Z is —S—;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $-CH_2O(CH_2CH_2O)_pCH_2CH_3$, $-CH_2O(CH_2CH_2O)_pCH_3$ wherein p is from 1 to about 25 and the optional substituents are one or more substituents $R_x$, and a group of formula:

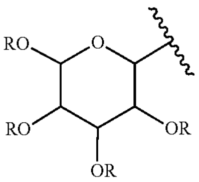
,
or
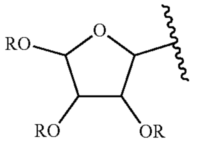

where each R group is, at each occurrence, independently selected from hydrogen, substituted or unsubstituted $C_1$-$C_6$ alkyl group, substituted or unsubstituted $-(C{=}O)-(C_1$-$C_6)$alkyl, and substituted or unsubstituted $-(C{=}O)NH(C_1$-$C_6)$alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene- acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, $-(CH_2CH_2O)_pCH_2CH_3$, $-(CH_2CH_2O)_pCH_3$ wherein p is from 1 to about 25, and substituted or unsubstituted monosaccharide residue, wherein the optional substituents are one or more substituents $R_x$; and substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, $S({=}O)R_y$, $SO_2R_y$, $OSO_2OR_y$, $SSR_y$, $P({=}O)(R_y)OR_z$, $OP({=}O)(OR_y)_2$, $NR_yR_z$, $NR_yC({=}O)R_z$, $NR_yC({=}O)OR_z$, $NR_yC({=}O)NR_yR_z$, $NR_yC({=}NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC({=}NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

wherein the compound of formula I is not a natural product.

2. The compound according to claim 1 which also has formula

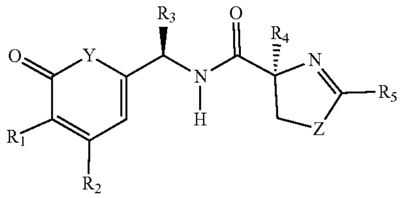

wherein $R_1$, $R_2$, $R_3$, $R_4$, $R_5$, Y, and Z are as defined in claim 1; or a pharmaceutically acceptable salt or ester thereof.

3. The compound according to claim 1 wherein $R_1$ is selected from hydrogen, halogen and substituted or unsubstituted $C_2$-$C_6$ alkynyl, wherein the optional substituents are one or more substituents $R_x$; or a pharmaceutically acceptable salt or ester thereof.

4. The compound according to claim 1, which also have formula Ia:

Ia

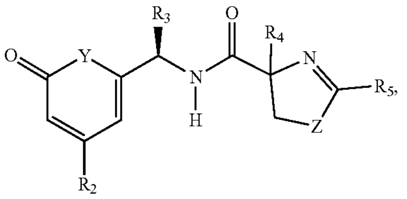

wherein $R_2$, $R_3$, $R_4$, $R_5$, Y, and Z are as defined in claim 1; or a pharmaceutically acceptable salt or ester thereof wherein the compound of formula Ia is not a natural product.

5. The compound according to claim 4, which also has formula Ib:

Ib

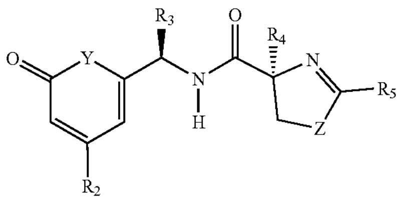

wherein $R_2$, $R_3$, $R_4$, $R_5$, Y and Z are as defined in claim 1; or a pharmaceutically acceptable salt or ester thereof wherein the compound of formula Ib is not a natural product.

6. The compound according to claim 1 wherein $R_2$ is selected from hydrogen, substituted or unsubstituted $C_1$-$C_6$ alkyl, substituted or unsubstituted $C_2$-$C_6$ alkenyl, wherein the optional substituents are one or more substituents $R_x$, —$OR_a$, and —$NR_cR_d$, where $R_a$ is selected from hydrogen, a silylether protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_6$alkyl, —$(CH_2CH_2O)_pCH_2CH_3$ where p is from 1 to about 15 and the optional substituents are one or more substituents $R_x$; and $R_c$ and $R_d$ are independently selected from substituted or unsubstituted $C_1$-$C_6$ alkyl wherein the optional substituents are one or more substituents $R_x$; or a pharmaceutically acceptable salt or ester thereof.

7. The compound according to claim 6, wherein $R_2$ is selected from hydrogen, methyl, vinyl, allyl, $NEt_2$, and $OR_a$ where $R_a$ is selected from hydrogen, methyl, ethyl, n-butyl, n-heptyl, allyl, propargyl, cyclopropylmethyl, —$(CH_2)_3$NH-Boc, —$(CH_2)_3NH_2$, and —$(CH_2CH_2O)_3CH_2CH_3$; or a pharmaceutically acceptable salt or ester thereof.

8. The compound according to claim 1, wherein $R_3$ is selected from halogen-substituted or unsubstituted $C_1$-$C_6$ alkyl and substituted or unsubstituted $C_3$-$C_4$ cycloalkyl-$C_1$-$C_4$ alkyl, wherein the optional substituents are one or more substituents $R_x$ and the halogen substituents are one or more substituents independently selected from F, Cl, Br, and I; or a pharmaceutically acceptable salt or ester thereof.

9. The compound according to claim 8, wherein $R_3$ is selected from n-propyl, 3,3,3-trifluoropropyl, and isobutyl; or pharmaceutically acceptable salt or ester thereof.

10. The compound according to claim 1, wherein $R_4$ is selected from hydrogen and substituted or unsubstituted $C_1$-$C_6$ alkyl, wherein the optional substituents are one or more substituents $R_x$; or a pharmaceutically acceptable salt or ester thereof.

11. The compound according to claim 10, wherein $R_4$ is hydrogen or methyl; or a pharmaceutically acceptable salt or ester thereof.

12. The compound according to claim 1, wherein $R_5$ is selected from —$C(OR_e)_2R_g$, —$CH(NR_cR_d)R_g$, —(C═O)$R_g$, —(C═$NR_c$)$R_g$, —(C═N—$OR_h$)$R_g$, —(C═N—O—(C═O)$R_f$)$R_g$, —(C═N—O—(C═O)$OR_a$)$R_g$, —(C═N—O—[(P═O)$(OR_a)_2$])$R_g$, —(C═N—$NR_cR_d$)$R_g$, —(C═$CH_2$)$R_g$, and —(C═$CH_2$)$OR_a$ wherein:

$R_h$ is selected from hydrogen, a protecting group for OH, substituted or unsubstituted $C_1$-$C_6$ alkyl, substituted or unsubstituted $C_2$-$C_6$ alkenyl, substituted or unsubstituted $C_2$-$C_6$ alkynyl, substituted or unsubstituted heterocyclo-$C_1$-$C_6$alkyl, —$(CH_2CH_2O)_pCH_2CH_3$ where p is from 1 to about 15 and a substituted or unsubstituted monosaccharide residue of formula:

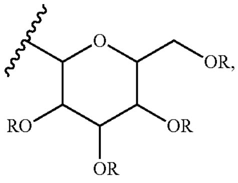

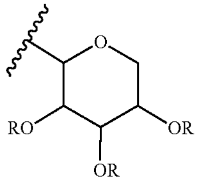

or

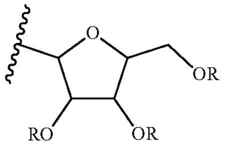

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl; wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

$R_g$ is substituted or unsubstituted $C_1$-$C_6$ alkyl, wherein the optional substituents are one or more substituents $R_x$;

$R_c$ and $R_d$ are independently selected from hydrogen and substituted or unsubstituted $C_1$-$C_6$ alkyl, wherein the optional substituents are one or more substituents $R_x$;

$R_a$ is substituted or unsubstituted $C_1$-$C_6$ alkyl, wherein the optional substituents are one or more substituents $R_x$;

$R_e$ is substituted or unsubstituted $C_1$-$C_6$ alkyl, wherein the optional substituents are one or more substituents $R_x$; and $R_f$ is selected from substituted or unsubstituted $C_1$-$C_6$ alkyl, —$CH_2O(CH_2CH_2O)_pCH_3$ where p is from 1 to about 15 and the optional substituents are one or more substituents $R_x$, and a group of formula:

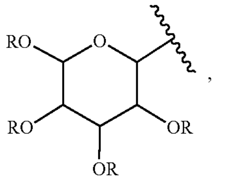

, or

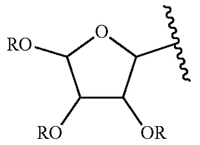

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

or a pharmaceutically acceptable salt or ester thereof.

13. The compound according to claim 12 wherein $R_5$ is selected from $—CH(NH_2)Me$, $—(C{=}O)Me$, $—(C{=}NR_c)Me$, $—(C{=}N—OR_h)Me$, $—(C{=}N—O—(C{=}O)R_f)Me$, $—(C{=}N—NH_2)Me$, $—(C{=}N—O—(C{=}O)OR_a)Me$, $—(C{=}N—O—[(P{=}O)(OR_a)_2])Me$, $—(C{=}CH_2)Me$, or $—(C{=}CH_2)OR_a$ where $R_a$ is ethyl or benzyl, $R_c$ is $—(CH_2)_3NHBoc$, $R_f$ is $—(CH_2)_5—NHBoc$, $—CH_2O(CH_2CH_2O)_2Me$ or a group of formula:

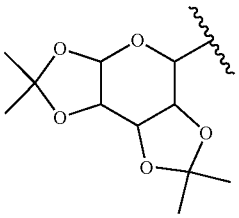
, and $R_h$ is selected from hydrogen, methyl, allyl, propargyl, $—(CH_2)_3NHBoc$, $—(CH_2)_3NH_2$, $—(CH_2)_3SH$, $—(CH_2)_4OH$, $—(CH_2)_4OP({=}O)(OH)_2$, $—(CH_2)_4OP({=}O)(O^t\text{-}Bu)_2$, $—(CH_2)_4\text{-}[4\lambda^2\text{-morpholine}]$, $—(CH_2)_3\text{-}[1\text{-methyl-}4\lambda^2\text{-piperazine}]$, $—(CH_2CH_2O)_3CH_2CH_3$, and a monosaccharide residue of formula:

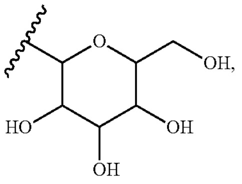

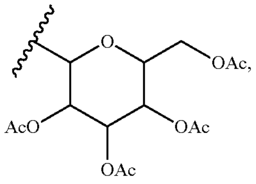

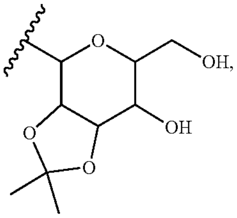

or

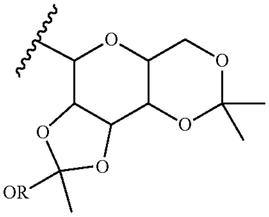
;

or a pharmaceutically acceptable salt or ester thereof.

14. The compound according to claim 1 selected from

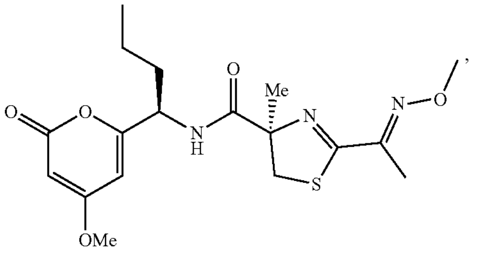

-continued

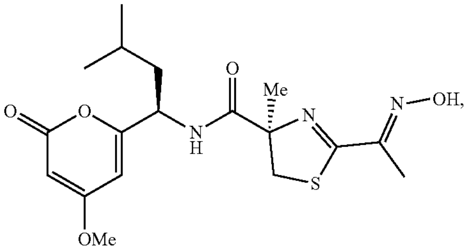

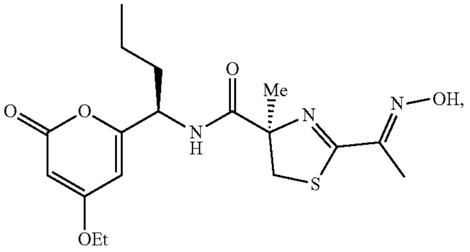

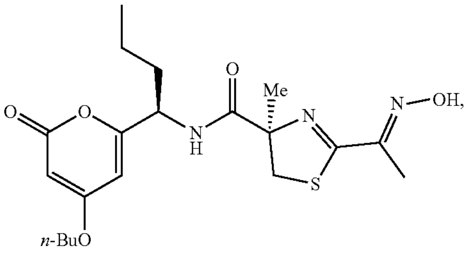

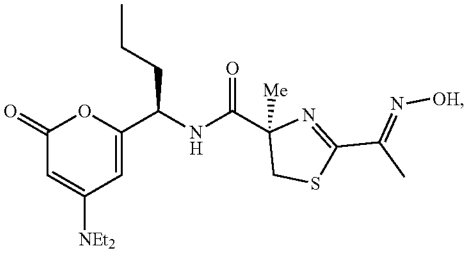

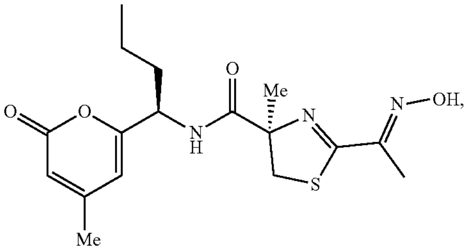

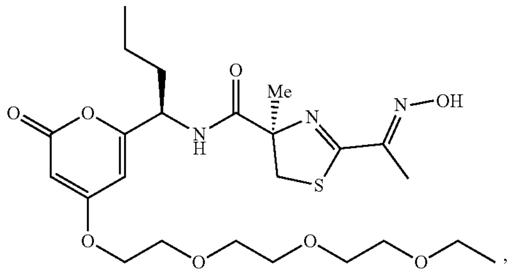

-continued
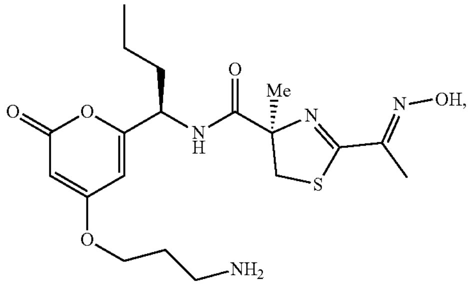
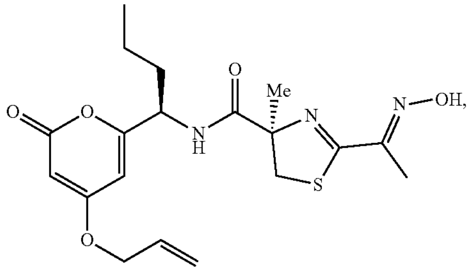
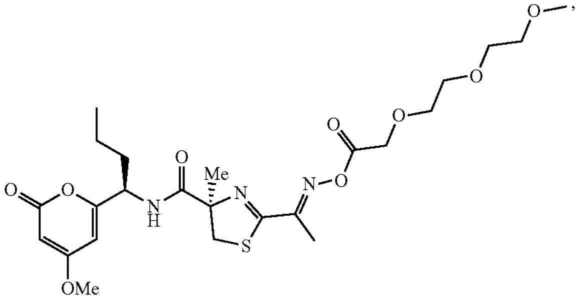
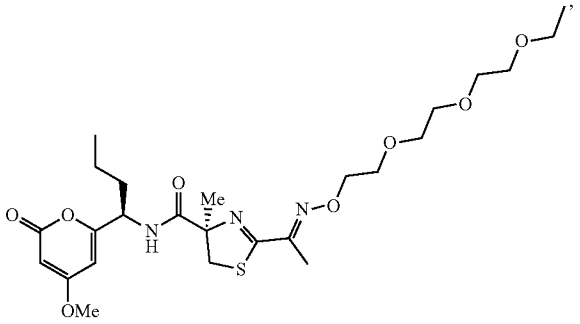
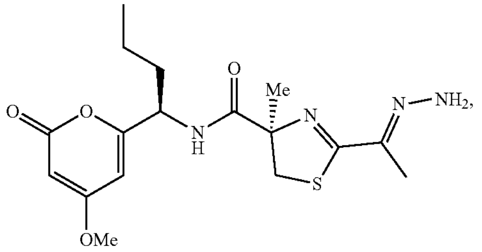
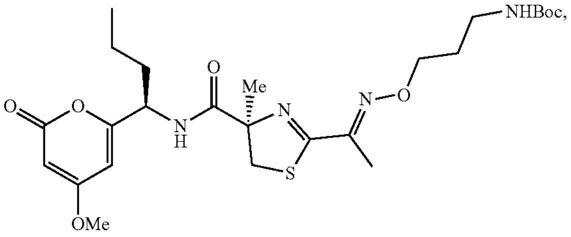
-continued
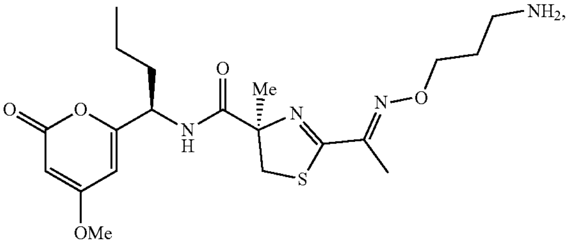
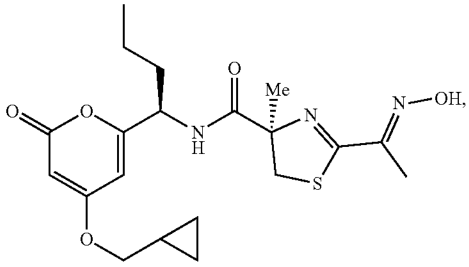
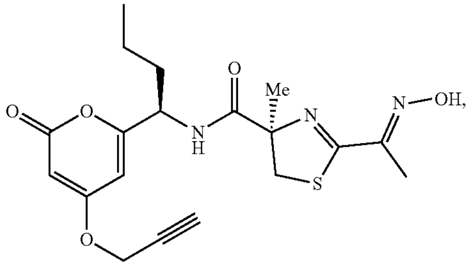
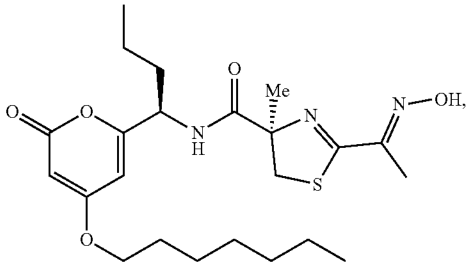
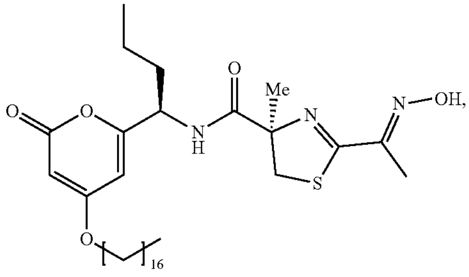
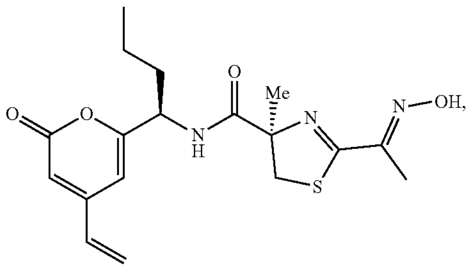

-continued
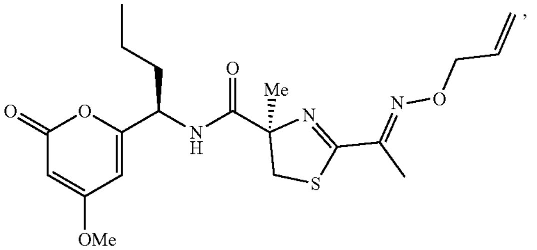
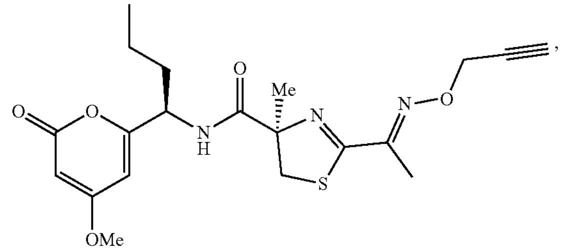
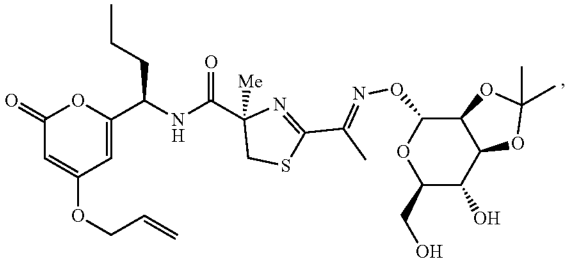
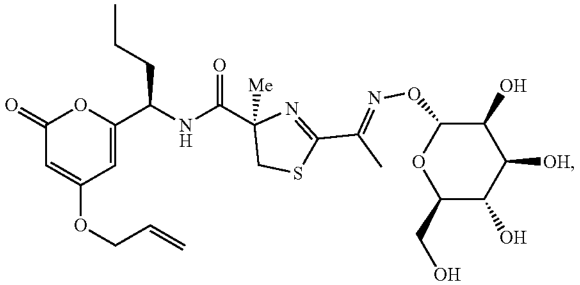
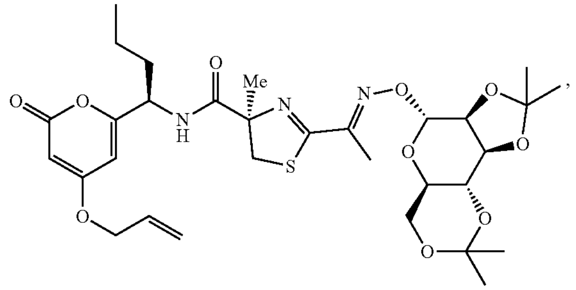
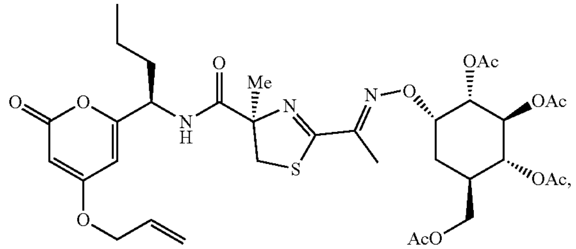
-continued
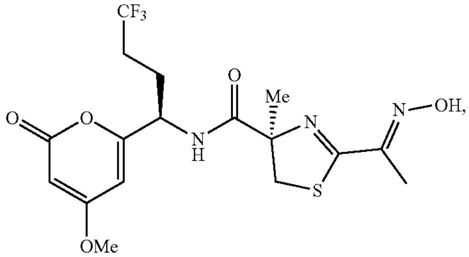
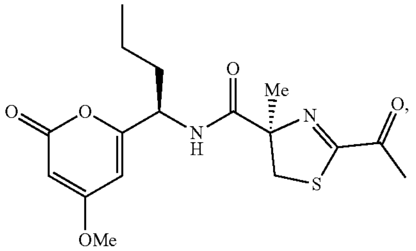
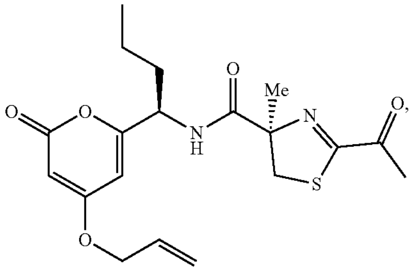
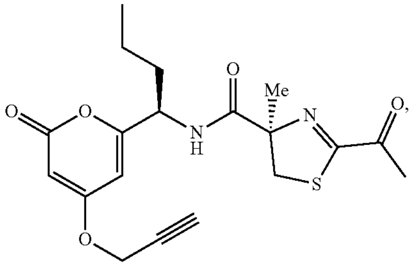
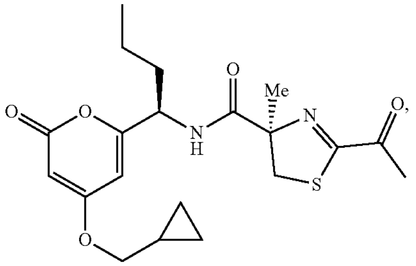
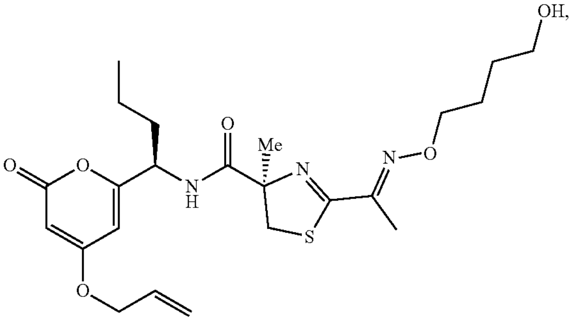

-continued
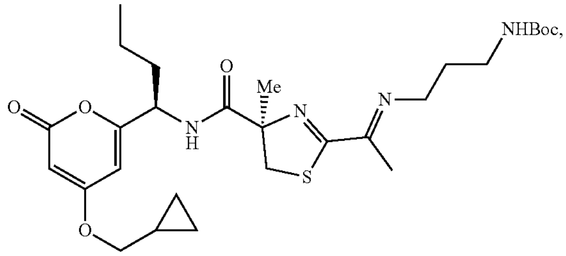
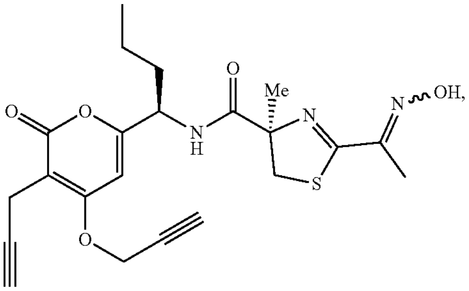
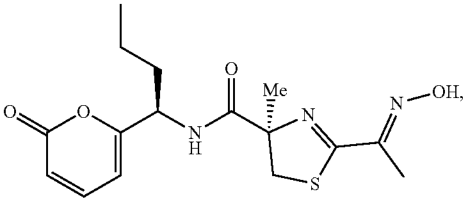
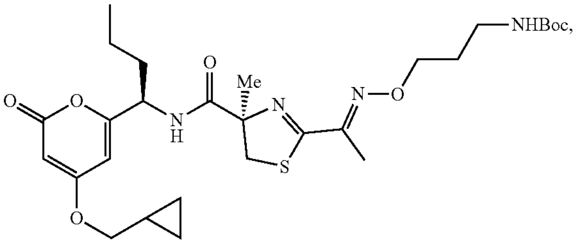
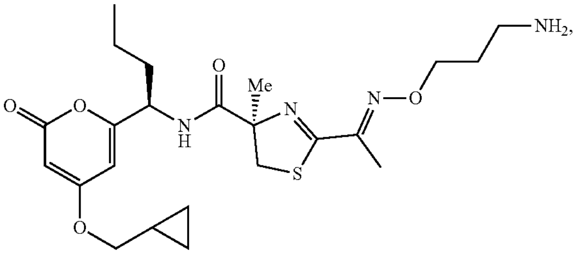
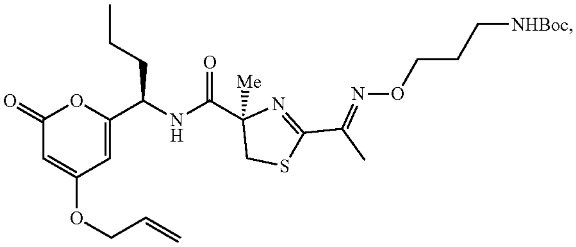
-continued
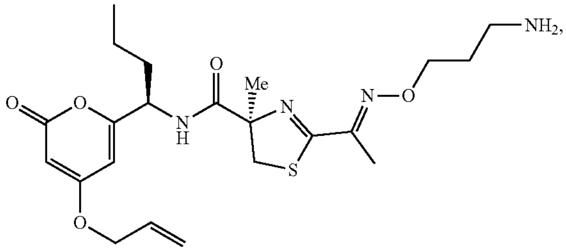
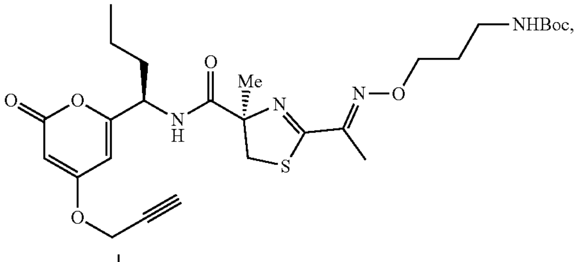
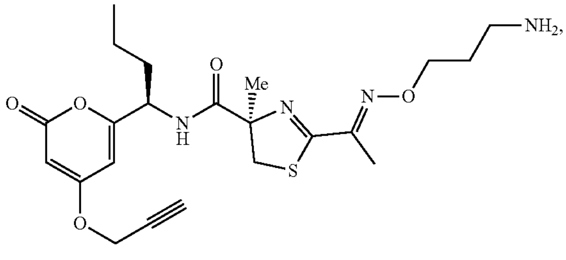
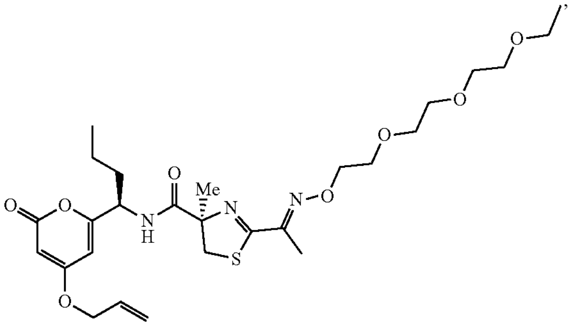
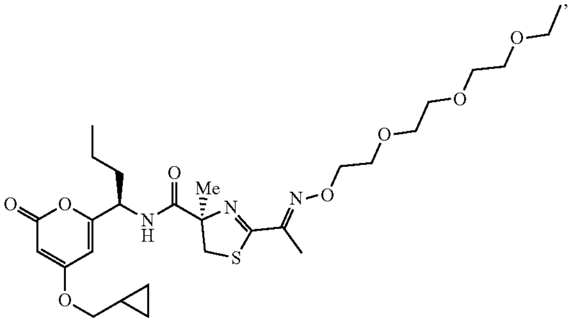
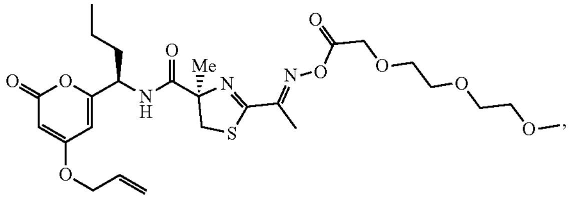

-continued
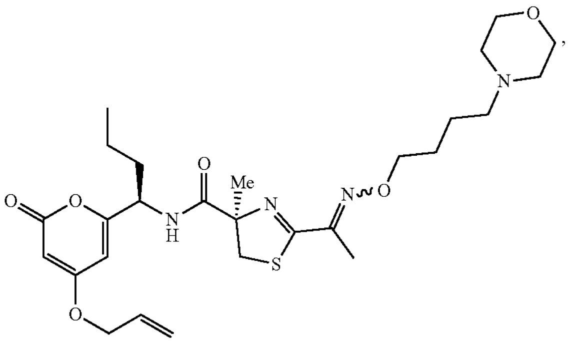
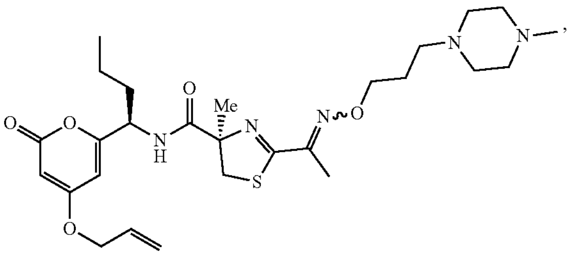
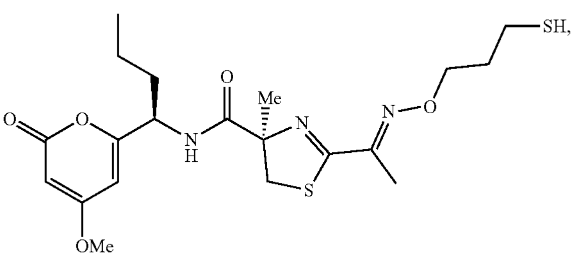
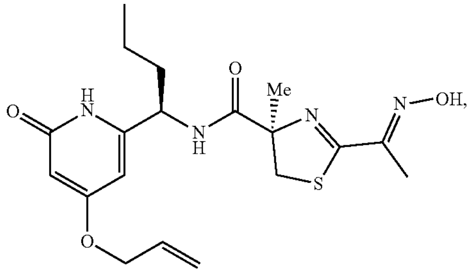
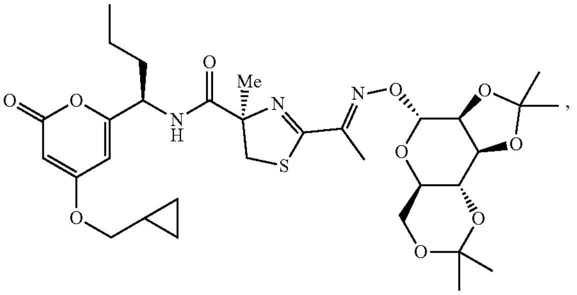
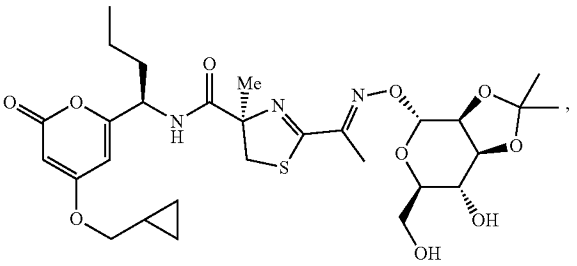
-continued
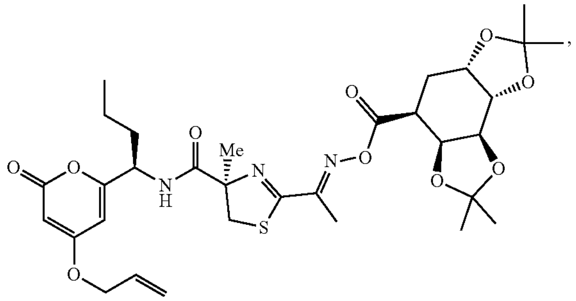
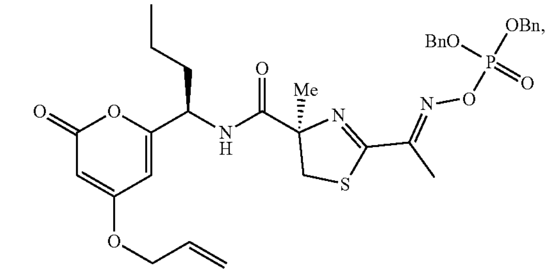
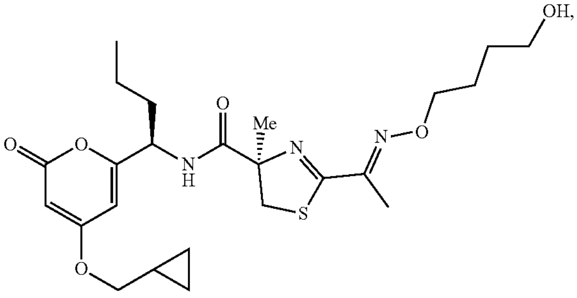
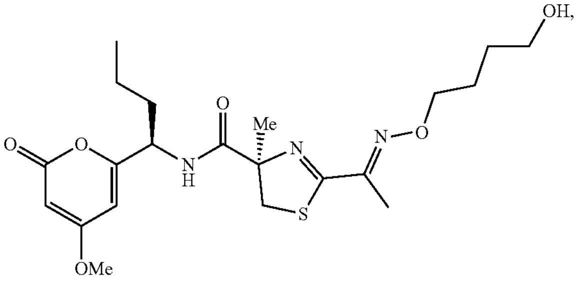
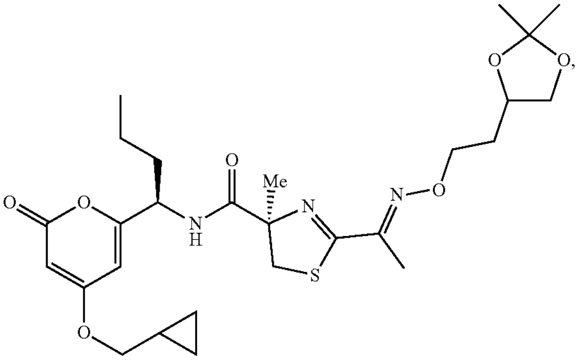
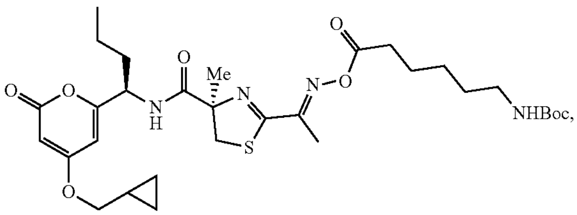

-continued

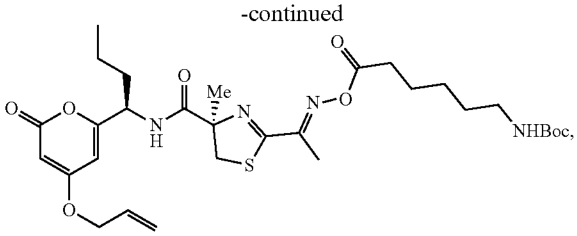

,

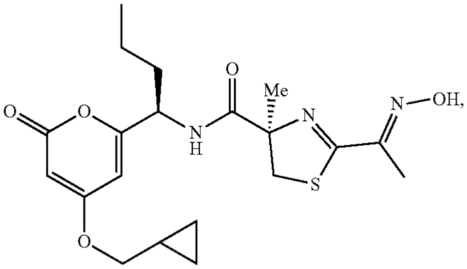

,

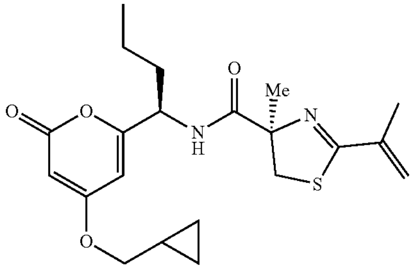

,

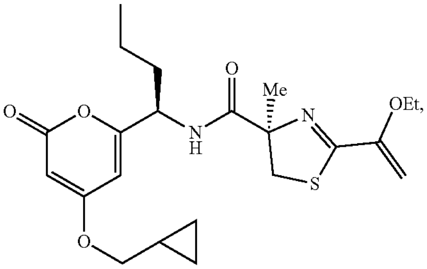

,

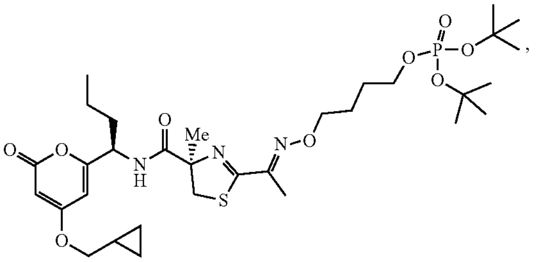

, and

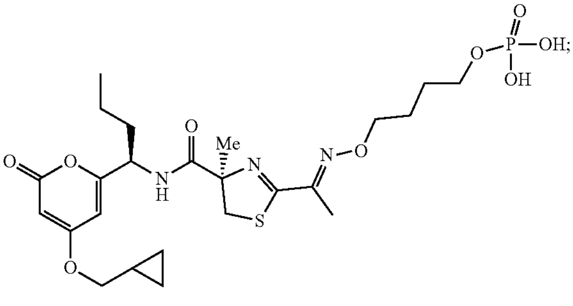

;

or a pharmaceutically acceptable salt or ester thereof.

15. The compound according to claim 1, wherein:

$R_5$ is selected from —$C(OR_e)_2R_g$, —$C(SR_e)_2R_g$, —CH$(OR_a)R_g$, —CH(O—(C═O)$R_f)R_g$, —CH$(NR_cR_d)R_g$, —CH$(NR_c$—(C═O)$R_f)R_g$, —CH$(NR_c$—$OR_h)R_g$, —(C═O)$R_g$, —(C═$NR_c)R_g$, —(C═N—$OR_h)R_g$, —(C═N—O—(C═O)$R_f)R_g$, —(C═N—$NR_cR_d)R_g$, —(C═O)$OR_a$, —(C═O)$NR_c$—$OR_h$, and —(C═O)$NR_cR_d$; or $R_5$ is a

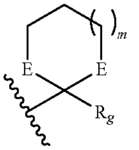

group where m is 0, 1 or 2 and each E group is independently selected from O and S;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$ and —$CH_2O(CH_2CH_2O)_pCH_3$ wherein p is from 1 to about 25 and the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$ wherein p is from 1 to about 25, and substituted or unsubstituted monosaccharide residue, wherein the optional substituents are one or more substituents $R_x$; and substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $SSR_y$, P(═O)$(R_y)OR_z$, $NR_yR_z$, $NR_yCOR_z$, $NR_yC$(═O)$NR_yR_z$, $NR_yC(═NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC(═NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different.

16. A pharmaceutical composition comprising a compound of formula I or a pharmaceutically acceptable salt or ester thereof

I

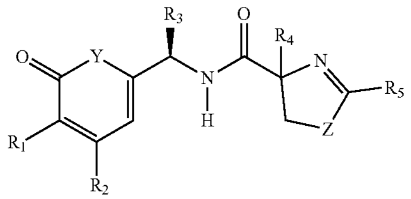

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, $—OR_a$, $—OSO_2R_b$, $—NR_cR_d$, $—NR_c(C{=}O)R_f$, and $—NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from $—C(OR_e)_2R_g$, $—C(SR_e)_2R_g$, $—CH(OR_a)R_g$, $—CH(O—(C{=}O)R_f)R_g$, $—CH(NR_cR_d)R_g$, $—CH(NR_c—(C{=}O)R_f)R_g$, $—CH(NR_c—OR_h)R_g$, $—(C{=}O)R_g$, $—(C{=}NR_c)R_g$, $—(C{=}N—OR_h)R_g$, $—(C{=}N—O—(C{=}O)R_f)R_g$, $—(C{=}N—O—(C{=}O)OR_a)R_g$, $—(C{=}N—O—[(P{=}O)(OR_a)_2])R_g$, $—(C{=}N—NR_cR_d)R_g$, $—(C{=}O)OR_a$, $—(C{=}O)NR_c—OR_h$, $—(C{=}O)NR_cR_d$, $—(C{=}CH_2)R_g$, and $—(C{=}CH_2)OR_a$; or $R_5$ is a

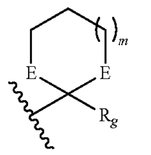

m is 0, 1 or 2 and each E group is independently selected from O and S;

group where

Y is —O—;

Z is —S—;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, $—(CH_2CH_2O)_pCH_2CH_3$, and $—(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $—CH_2O(CH_2CH_2O)_pCH_2CH_3$, $—CH_2O(CH_2CH_2O)_pCH_3$ wherein p is from 1 to about 25 and the optional substituents are one or more substituents $R_x$, and a group of formula:

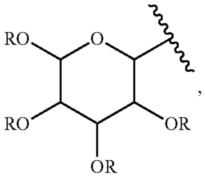

, or

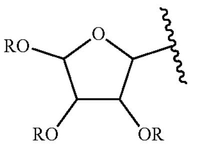

where each R group is, at each occurrence, independently selected from hydrogen, substituted or unsubstituted $C_1$-$C_6$ alkyl group, substituted or unsubstituted $—(C{=}O)—(C_1$-$C_6)$alkyl, and substituted or unsubstituted $—(C{=}O)NH(C_1$-$C_6)$alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, $—(CH_2CH_2O)_pCH_2CH_3$, $—(CH_2CH_2O)_pCH_3$ wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, $S(=O)R_y$, $SO_2R_y$, $OSO_2OR_y$, $SSR_y$, $P(=O)(R_y)OR_z$, $OP(=O)(OR_y)_2$, $NR_yR_z$, $NR_yC(=O)R_z$, $NR_yC(=O)OR_z$, $NR_yC(=O)NR_yR_z$, $NR_yC(=NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC(=NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

and a pharmaceutically acceptable carrier.

17. A dosage form comprising a pharmaceutical composition as defined in claim 16.

18. A method of treating cancer in a patient in need thereof, comprising administering a therapeutically acceptable amount of a compound of formula I or a pharmaceutically acceptable salt or ester thereof

I

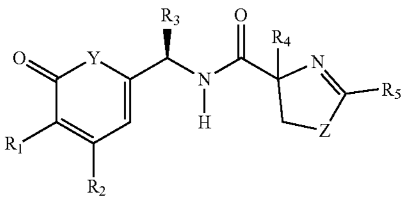

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, $—OR_a$, $—OSO_2R_b$, $—NR_cR_d$, $—NR_c(C{=}O)R_f$, and $—NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from $—C(OR_e)_2R_g$, $—C(SR_e)_2R_g$, $—CH(OR_a)R_g$, $—CH(O—(C{=}O)R_f)R_g$, $—CH(NR_cR_d)R_g$, $—CH(NR_c—(C{=}O)R_f)R_g$, $—CH(NR_c—OR_h)R_g$, $—(C{=}O)R_g$, $—(C{=}NR_c)R_g$, $—(C{=}N—OR_h)R_g$, $—(C{=}N—O—(C{=}O)R_f)R_g$, $—(C{=}N—O—(C{=}O)OR_a)R_g$, $—(C{=}N—O—[(P{=}O)(OR_a)_2])R_g$, $—(C{=}N—NR_cR_d)R_g$, $—(C{=}O)OR_a$, $—(C{=}O)NR_c—OR_h$, $—(C{=}O)NR_cR_d$, $—(C{=}CH_2)R_g$, and $—(C{=}CH_2)OR_a$; or $R_5$ is a

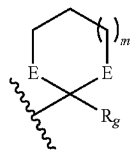

group where m is 0, 1 or 2 and each E group is independently selected from O and S;

Y is —O—;

Z is —S—;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, $—(CH_2CH_2O)_pCH_2CH_3$, and $—(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, —$CH_2O(CH_2CH_2O)_pCH_3$ wherein p is from 1 to about 25 and the optional substituents are one or more substituents $R_x$, and a group of formula:

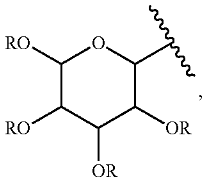

, or

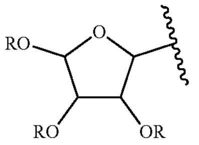

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_x$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$ wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $OSO_2OR_y$, $SSR_y$, P(═O)($R_y$)$OR_z$, OP(═O)$(OR_y)_2$, $NR_yR_z$, $NR_y$C(═O)$R_z$, $NR_y$C(═O)$OR_z$, $NR_y$C(═O)$NR_yR_z$, $NR_y$C(═$NR_y$)$NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_y$C(═$NR_y$)$NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s).

19. The method according to claim 18, wherein the cancer is selected from solid tumours, lung cancer, colon cancer, breast cancer and pancreas cancer.

20. A process for obtaining a compound of formula I or a pharmaceutically acceptable salt or ester thereof comprising the coupling of a compound of formula II with a compound of formula III in accordance to Scheme 1

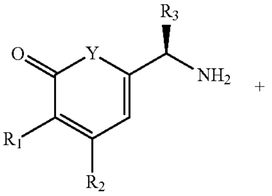

II

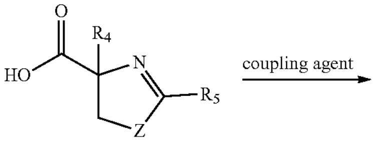

III

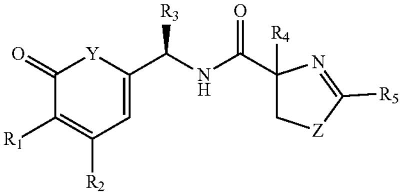

I wherein $R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, —$OSO_2R_b$, —$NR_cR_d$, —$NR_c$(C═O)

$R_f$, and $—NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br and I;

$R_4$ is selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

$R_5$ is selected from $—C(OR_e)_2R_g$, $—C(SR_e)_2R_g$, $—CH(OR_a)R_g$, $—CH(O—(C{=}O)R_f)R_g$, $—CH(NR_cR_d)R_g$, $—CH(NR_c—(C{=}O)R_f)R_g$, $—CH(NR_c—OR_h)R_g$, $—(C{=}O)R_g$, $—(C{=}NR_c)R_g$, $—(C{=}N—OR_h)R_g$, $—(C{=}N—O—(C{=}O)R_f)R_g$, $—(C{=}N—O—(C{=}O)OR_a)R_g$, $—(C{=}N—O—[(P{=}O)(OR_a)_2])R_g$, $—(C{=}N—NR_cR_d)R_g$, $—(C{=}O)OR_a$, $—(C{=}O)NR_c—OR_h$, $—(C{=}O)NR_cR_d$, $—(C{=}CH_2)R_g$, and $—(C{=}CH_2)OR_a$; or $R_5$ is a

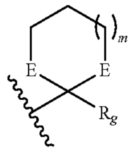

group where m is 0, 1 or 2 and each E group is independently selected from O and S;

Y is —O—;

Z is —S—;

each group $R_a$ is independently selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, $—(CH_2CH_2O)_pCH_2CH_3$, and $—(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, $—CH_2O(CH_2CH_2O)_pCH_2CH_3$, $—CH_2O(CH_2CH_2O),CH_3$ wherein p is from 1 to about 25 and the optional substituents are one or more substituents $R_x$, and a group of formula:

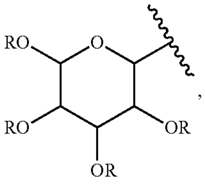, or 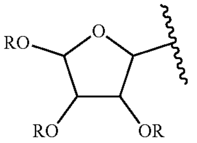

where each R group is, at each occurrence, independently selected from hydrogen, substituted or unsubstituted $C_1$-$C_6$ alkyl group, substituted or unsubstituted $—(C{=}O)—(C_1$-$C_6)$alkyl, and substituted or unsubstituted $—(C{=}O)NH(C_1$-$C_6)$alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, $—(CH_2CH_2O)_pCH_2CH_3$, $—(CH_2CH_2O)_pCH_3$ wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, $S({=}O)R_y$, $SO_2R_y$, $OSO_2OR_y$, $SSR_y$, $P({=}O)(R_y)OR_z$, $OP({=}O)(OR_y)_2$, $NR_yR_z$, $NR_yC({=}O)R_z$, $NR_yC({=}O)OR_z$, $NR_yC({=}O)NR_yR_z$, $NR_yC({=}NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC({=}NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

or an appropriately protected group as needed.

21. An intermediate compound of formula IIa

IIa

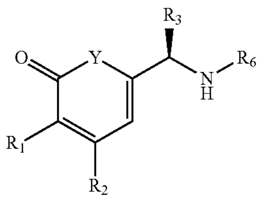

wherein:

$R_1$ is selected from hydrogen, halogen, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$;

$R_2$ is selected from hydrogen, halogen, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, —$OR_a$, $OSO_2R_b$, —$NR_cR_d$, —$NR_c(C{=}O)R_f$, and —$NR_cSO_2R_b$, wherein the optional substituents are one or more substituents $R_x$;

$R_3$ is selected from halogen-substituted or unsubstituted $C_1$-$C_{12}$ alkyl, halogen-substituted or unsubstituted $C_2$-$C_{12}$ alkenyl, halogen-substituted or unsubstituted $C_2$-$C_{12}$ alkynyl and substituted or unsubstituted $C_3$-$C_6$ cycloalkyl-$C_1$-$C_{12}$ alkyl, wherein the optional substituents are one or more substituents $R_x$ and the halogen substituents are one or more substituents independently selected from F, Cl, Br, and I;

$R_6$ is selected from hydrogen and a carbamate protecting group for amino;

Y is —O—;

$R_a$ is selected from hydrogen, a protecting group for OH, substituted or unsubstituted $C_1$-$C_{24}$ alkyl, substituted or unsubstituted $C_2$-$C_{24}$ alkenyl, substituted or unsubstituted $C_2$-$C_{24}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_b$ is independently selected from substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted aryl, and substituted or unsubstituted heterocyclic group, wherein the optional substituents are one or more substituents $R_x$;

each group $R_c$ and $R_d$ are independently selected from hydrogen, a protecting group for amino, substituted or unsubstituted $C_1$-$C_{12}$ alkyl, substituted or unsubstituted $C_2$-$C_{12}$ alkenyl, and substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

$R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, and —$CH_2O(CH_2CH_2O)_pCH_3$ wherein p is from 1 to about 25 and the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, $S({=}O)R_y$, $SO_2R_y$, $OSO_2OR_y$, $SSR_y$, $P({=}O)(R_y)OR_z$, $OP({=}O)(OR_y)_2$, $NR_yR_z$, $NR_yC({=}O)R_z$, $NR_yC({=}O)OR_z$, $NR_yC({=}O)NR_yR_z$, $NR_yC({=}NR_y)NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_yC({=}NR_y)NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

or a salt thereof.

22. An intermediate compound of formula IIIa

IIIa

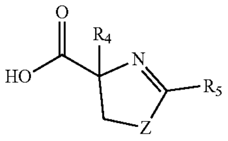

wherein $R_4$ is selected from unsubstituted $C_1$-$C_{12}$ alkyl, unsubstituted $C_2$-$C_{12}$ alkenyl and unsubstituted $C_2$-$C_{12}$ alkynyl;

$R_5$ is selected from —$C(OR_e)_2R_g$, —$C(SR_e)_2R_g$, —$CH(OR_a)R_g$, —CH(O—(C═O)$R_f$)$R_g$, —CH($NR_c$—(C═O)$R_f$)$R_g$, —CH($NR_c$—$OR_h$)$R_g$, —(C═O)$R_g$, —(C═$NR_c$)$R_g$, —(C═N—$OR_h$)$R_g$, —(C═N—O—(C═O)$R_f$)$R_g$, —(C═N—O—(C═O)$OR_a$)$R_g$, —(C═N—O—[(P═O)$(OR_a)_2$])$R_g$, —(C═N—$NR_cR_d$)$R_g$, —(C═O)$OR_a$, —(C═O)$NR_c$—$OR_h$, —(C═O)$NR_cR_d$, —(C═$CH_2$)$R_g$, and —(C═$CH_2$)$OR_a$; or $R_5$ is a

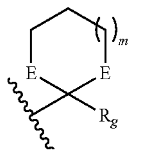

group where m is 0, 1, or 2 and each E group is independently selected from O and S;

Z is —S—;

each group $R_a$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted aryl, substituted or unsubstituted heterocyclic group, —$(CH_2CH_2O)_pCH_2CH_3$, and —$(CH_2CH_2O)_pCH_3$ wherein p is from 1 to about 25 and the optional substituents are one or more substituents $R_x$;

each group $R_c$ and $R_d$ is independently selected from hydrogen, a protecting group for amino, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, wherein the optional substituents are one or more substituents $R_x$; or $R_c$ and $R_d$ together with the nitrogen atom to which they are attached form a heterocyclic group;

each group $R_e$ is substituted or unsubstituted $C_1$-$C_{12}$ alkyl group, wherein the optional substituents are one or more substituents $R_x$;

each group $R_f$ is independently selected from hydrogen, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, —$CH_2O(CH_2CH_2O)_pCH_2CH_3$, —$CH_2O(CH_2CH_2O)_pCH_3$ wherein p is from 1 to about 25 and the optional substituents are one or more substituents $R_x$, and a group of formula:

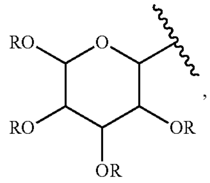

, or

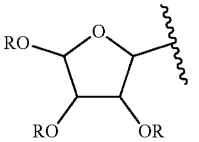

where each R group is, at each occurrence, independently selected from hydrogen, substituted or unsubstituted $C_1$-$C_6$ alkyl group, substituted or unsubstituted —(C═O)—($C_1$-$C_6$)alkyl, and substituted or unsubstituted —(C═O)NH($C_1$-$C_6$)alkyl, wherein the optional substituents are one or more substituents $R_x$; or two adjacent OR groups form an isopropylidene ketal or an acetal group selected from methylene-, methoxymethylene-, ethoxymethylene-, ethylidene-, benzylidene-, and p-methoxybenzylidene-acetals;

each group $R_g$ is independently selected from hydrogen, substituted or unsubstituted $C_1$-$C_{12}$ alkyl, substituted or unsubstituted $C_2$-$C_{12}$ alkenyl and substituted or unsubstituted $C_2$-$C_{12}$ alkynyl, wherein the optional substituents are one or more substituents $R_x$;

each group $R_h$ is independently selected from hydrogen, a protecting group for OH, substituted or unsubstituted $C_1$-$C_{12}$ alkyl, substituted or unsubstituted $C_2$-$C_{12}$ alkenyl, substituted or unsubstituted $C_2$-$C_{12}$ alkynyl, substituted or unsubstituted $C_3$-$C_6$cycloalkyl-$C_1$-$C_{12}$alkyl, substituted or unsubstituted heterocyclo-$C_1$-$C_{12}$alkyl, substituted or unsubstituted aryl, substituted or unsubstituted heterocyclic group, —$(CH_2CH_2O)_pCH_2CH_3$, —$(CH_2CH_2O)_pCH_3$, wherein p is from 1 to about 25, and substituted or unsubstituted monosaccharide residue, wherein the optional substituents are one or more substituents $R_x$;

substituents $R_x$ are selected from the group consisting of $C_1$-$C_{12}$ alkyl groups which may be optionally substituted with at least one group $R_y$, $C_2$-$C_{12}$ alkenyl groups which may be optionally substituted with at least one group $R_y$, $C_2$-$C_{12}$ alkynyl groups which may be optionally substituted with at least one group $R_y$, halogen atoms, oxo groups, thio groups, cyano groups, nitro groups, $OR_y$, $OCOR_y$, $OCOOR_y$, $COR_y$, $COOR_y$, $OCONR_yR_z$, $CONR_yR_z$, $SR_y$, S(═O)$R_y$, $SO_2R_y$, $OSO_2OR_y$, $SSR_y$, P(═O)($R_y$)$OR_z$, OP(═O)$(OR_y)_2$, $NR_yR_z$, $NR_y$C(═O)$R_z$, $NR_y$C(═O)$OR_z$, $NR_y$C(═O)$NR_yR_z$, $NR_y$C(═$NR_y$)$NR_yR_z$, aryl groups having from 6 to 18 carbon atoms in one or more rings which may optionally be substituted with one or more substituents which may be the same or different selected from the group consisting of $R_y$, $OR_y$, $OCOR_y$, $OCOOR_y$, $NR_yR_z$, $NR_yCOR_z$, and $NR_y$C(═$NR_y$)$NR_yR_z$, aralkyl groups comprising an alkyl groups having from 1 to 12 carbon atoms substituted with an optionally substituted aryl group as defined above, aralkyloxy groups comprising an alkoxy group having from 1 to 12 carbon atoms substituted with an optionally substituted aryl group as defined above, and a 5- to 14-membered saturated or unsaturated heterocyclic group having one or more rings and comprising at least one oxygen, nitrogen or sulphur atom in said ring(s), said heterocyclic group optionally being substituted with one or more substituents $R_y$, and where there is more than one optional substituents on any given group the optional substituents $R_y$ may be the same or different; and each $R_y$ and $R_z$ is independently selected from the group consisting of hydrogen, $C_1$-$C_{12}$ alkyl groups, $C_1$-$C_{12}$ alkyl groups that are substituted with at least one halogen atom, aralkyl groups comprising a $C_1$-$C_{12}$ alkyl group that is substituted with an aryl group having from 6 to 18 carbon atoms in one or more rings and heterocycloalkyl group comprising a $C_1$-$C_{12}$ alkyl group that is substituted with a 5- to 14-membered saturated or unsaturated heterocyclic group having one or more rings and comprising at least one oxygen, nitrogen or sulphur atom in said ring(s);

or a salt thereof.

23. The compound according to claim 1, of formula

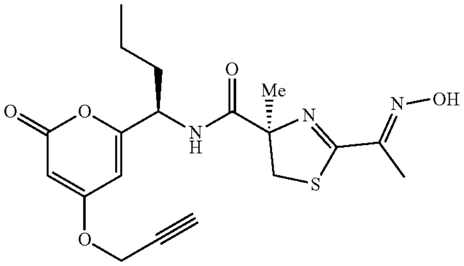 [SMILES: C#CCOc1cc([C@@H](CCC)NC(=O)[C@]2(C)CSC(/C(C)=N/O)=N2)oc(=O)c1]

or a pharmaceutically acceptable salt or ester thereof.

24. The compound according to claim 1, of formula

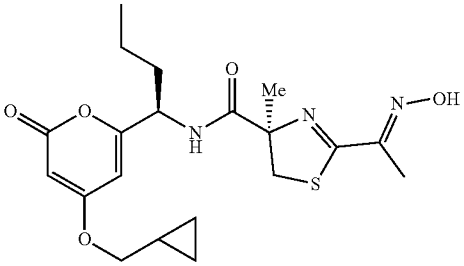 [SMILES: CCC[C@@H](NC(=O)[C@]1(C)CSC(/C(C)=N/O)=N1)c1cc(OCC2CC2)cc(=O)o1]

or a pharmaceutically acceptable salt or ester thereof.

25. The compound according to claim 1, of formula

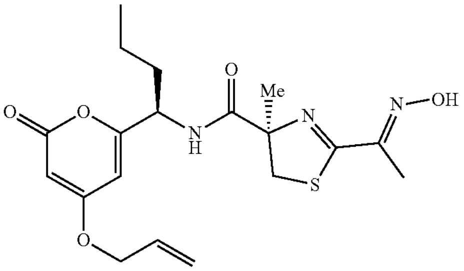 [SMILES: C=CCOc1cc([C@@H](CCC)NC(=O)[C@]2(C)CSC(/C(C)=N/O)=N2)oc(=O)c1]

or a pharmaceutically acceptable salt or ester thereof.

26. A method of inhibiting proliferation of cancer cells, comprising contacting cancer cells with an amount of a compound as defined in claim 1, wherein the amount is effective for inhibiting proliferation.

27. The method according to claim 26, wherein the cancer cells are cells of a cancer type selected from lung cancer, colon cancer, breast cancer and pancreas cancer.

28. A method of treating cancer in a patient in need thereof, comprising administering a pharmaceutical composition as defined in claim 16.

* * * * *